(12) United States Patent
Cheng et al.

(10) Patent No.: US 10,576,062 B2
(45) Date of Patent: Mar. 3, 2020

(54) CARBAMOYLOXYMETHYL TRIAZOLE CYCLOHEXYL ACIDS AS LPA ANTAGONISTS

(71) Applicant: Bristol-Myers Squibb Company, Princeton, NJ (US)

(72) Inventors: Peter Tai Wah Cheng, Princeton, NJ (US); Robert F. Kaltenbach, III, Holland, PA (US); Jun Li, Princeton, NJ (US); Jun Shi, Pennington, NJ (US); Yan Shi, Flourtown, PA (US); Shiwei Tao, Hillsborough, NJ (US); Hao Zhang, Belle Mead, NJ (US); Suresh Dhanusu, Hosur (IN); Kumaravel Selvakumar, Bangalore (IN); Ramesh Babu Reddigunta, Chittoor District (IN); Steven J. Walker, Pennington, NJ (US); Lawrence J. Kennedy, Titusville, NJ (US); James R. Corte, Yardley, PA (US); Tianan Fang, Newtown, PA (US); Sutjano Jusuf, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/038,739

(22) Filed: Jul. 18, 2018

(65) Prior Publication Data

US 2018/0333395 A1 Nov. 22, 2018

Related U.S. Application Data

(62) Division of application No. 15/628,104, filed on Jun. 20, 2017, now Pat. No. 10,071,078.

(60) Provisional application No. 62/352,792, filed on Jun. 21, 2016.

(51) Int. Cl.
| | | |
|---|---|---|
| *C07D 401/14* | (2006.01) | |
| *C07D 249/06* | (2006.01) | |
| *A61K 31/27* | (2006.01) | |
| *A61K 31/4192* | (2006.01) | |
| *A61K 31/454* | (2006.01) | |
| *C07D 401/04* | (2006.01) | |
| *A61K 31/41* | (2006.01) | |
| *C07C 62/10* | (2006.01) | |

(52) U.S. Cl.
CPC .......... *A61K 31/4192* (2013.01); *A61K 31/27* (2013.01); *A61K 31/454* (2013.01); *C07D 249/06* (2013.01); *C07D 401/04* (2013.01); *C07D 401/14* (2013.01); *A61K 31/41* (2013.01); *C07C 62/10* (2013.01)

(58) Field of Classification Search
CPC .......................... C07D 249/06; C07D 401/04
See application file for complete search history.

(56) References Cited

U.S. PATENT DOCUMENTS

| 8,742,097 B2 | 6/2014 | Hernandez et al. |
| 8,785,442 B2 | 7/2014 | An et al. |
| 10,071,078 B2 | 9/2018 | Cheng et al. |
| 2014/0329871 A1 | 11/2014 | Mishira et al. |
| 2019/0185446 A1 | 6/2019 | Shi et al. |

FOREIGN PATENT DOCUMENTS

| EP | 0 433 842 A2 | 6/1991 |
| WO | WO2005080379 A1 | 9/2005 |
| WO | WO2011/041694 A2 | 4/2011 |
| WO | WO2011041461 A2 | 4/2011 |
| WO | WO2012078593 A2 | 6/2012 |
| WO | WO2013189864 A1 | 12/2013 |
| WO | WO2013189865 A1 | 12/2013 |
| WO | WO2014/001279 A1 | 1/2014 |
| WO | WO2017220485 A1 | 12/2017 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Bakthadoss, M. et al., "Synthesis of highly diversified 1,2,3-trizole derivatives via domino [3+2] azide cycloaddition and denitration reaction sequence", The Royal Society of Chemistry, vol. 5, pp. 93447-93451 (2015).
Amishima, et al., "Expression of Epidermal Growth Factor and Epidermal Growth Factor Receptor Immunoreactivity in the Asthmatic Human Airway", Am. J. Respir. Critical Care Medicine, vol. 157, pp. 1907-1912 (1998 ).

(Continued)

*Primary Examiner* — Shawquia Jackson
(74) *Attorney, Agent, or Firm* — Jing G. Sun

(57) ABSTRACT

The present invention provides compounds of Formula (I):

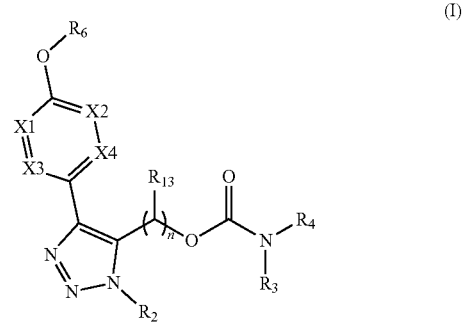

or stereoisomers, tautomers, pharmaceutically acceptable salts, solvates or prodrugs thereof, wherein all the variables are as defined herein. These compounds are selective LPA receptor inhibitors.

18 Claims, No Drawings

(56) References Cited

OTHER PUBLICATIONS

Boucharaba, et al., "Platelet-derived lysophosphatidic acid supports the progression of osteolytic bone metastases in breast cancer", J. Clin. Invest., vol. 114(12), pp. 1714-1725 (2004).
Boucharaba, et al., "The type 1 lysophosphatidic acid receptor is a target for therapy in bone metastases", PNAS, vol. 103(25), pp. 9643-9648 (2006).
Chen, et al., "Specific receptor subtype mediation of LPA-induced dual effects incardiac fibroblasts", FEBS Letters, vol. 580(19), pp. 4737-4745 (2006).
Contos, et al., "Lysophosphatidic Acid Receptors", Mol. Pharmacology, vol. 58(6), pp. 1188-1196 (2000).
Ediger, et al., "Transcription factor activation and mitogenic synergism in airway smooth muscle cells", Eur Respir Journal, vol. 21, pp. 759-769 (2003).
Gardell, et al., "Emerging medicinal roles for lysophospholipid signaling", Trends in Molecular Medicine, vol. 12(2), pp. 65-75 (2006).
Geoetzl, et al., "Lysophosphatidic Acid and Sphingosine 1-PhosphateProtection of T Cells from Apoptosis in Association with Suppression of Baxl", Journal of Immunology, vol. 162, pp. 2049-2056 (1999).
Guo, et al., "Mitogenic Signaling in Androgen Sensitive and Insensitive Prostate Cancer Cell Lines", Journal of Urology, vol. 163(3), pp. 1027-1032 (2000).
Holtsberg, et al., "Lysophosphatidic Acid Induces Necrosis and Apoptosis in Hippocampal Neurons", J. Neurochemistry, vol. 70, pp. 66-76 (1998).
Imamura, "Induction of in Vitro Tumor cell invasion of cellular monolayers by lysophosphatidic acid or phospholupase D", Biochem Biophys Res Commun., vol. 193(2), pp. 497-503 (1993).
Inoue, et al., "Initiation of neuropathic pain require lysophosphatidic acid receptor signaling" Nature Medicine, vol. 10, pp. 712-718 (2004).
Inoue, et al., "Lysophosphatidic acid and mesangial cells: implications for renal diseases", Clinical Science, vol. 96(4), pp. 431-436 (1999).
Ishii, et al., "Lysophospholipid Receptors:Signaling and Biology", Annu Rev Biochemistry, vol. 73, pp. 321-354 (2004).
Kantarci, et al., "Epithelial and connective tissue cell CTGF/CCN2 expression in gingival fibrosis", J Pathol., vol. 210, pp. 59-66 (2006).
Koh, et al., "Lysophosphatidic Acid is a Major Serum Noncytokine Survival Factor for Murine Macrophages Which Acts via the Phosphatidylinositol 3-Kinase Signaling Pathway", J Clin Invest., vol. 102, pp. 716-727 (1998).
Kropp, et al., "Characterization of Cultured Bladder Smooth Muscle Cells: Assessment of in Vitro Contractility", Journal of Urology, vol. 162(5), pp. 1779-1784 (1999).
Kuroda, et al., "Phospholipid Concentration in Lung Lavage Fluid as Biomarker for Pulmonary Fibrosis", Inhalation Toxicology, vol. 18(5), pp. 389-393 (2006).
Lin, et al., "Lysophosphatidic acid regulates inflammation-related genes in human endothelial cells through LPA1 and LPA3", Biochem Biophys Res Communication, vol. 363(4), pp. 1001-1008, (2007).
Maguire, et al., "Regulation of vascular reactivity by established and emerging GPCRs", Trends in Pharmacological Sciences, vol. 26(9), pp. 448-454 (2005).
Mills, et al., "The Emerging Role of Lysophosphatidic Acid in Cancer", Nat Rev Cancer, vol. 3, pp. 582-591 (2003).
Moolenaar, "Lysophosphatidic acid signalling", Curr. Opin. Cell Biology, vol. 7, pp. 203-210 (1995).
Mototani, et al., "A functional SNP in EDG2 increases susceptibilityto knee osteoarthritis in Japanese", Hum. Mol. Genetics, vol. 17(12), pp. 1790-1797 (2008).
Munger, et al., "The Integrin avb6 Binds and Activates Latent TGFb1:A Mechanism for Regulating Pulmonary Inflammation and Fibrosis", Cell, vol. 96, pp. 319-328 (1999).
Murph, et al., "Sharpening the edges of understanding the structure/function of the LPA1 receptor: Expression in cancer and mechanisms of regulation", Biochimica et Biophysica Acta, vol. 1781, pp. 547-557 (2008).
Osborne, et al., "Lipid Receptors in Cardiovascular Development", Annual Rev. Physiol., vol. 65, pp. 23-43 (2003).
Pradere, et al "LPA1 Receptor Activation Promotes Renal Interstitial Fibrosis", J Am Soc Nephrol, vol. 18, pp. 3110-3118 (2007).
Pradere, et al., "Lysophosphatidic acid and renal fibrosis", Biochimica et Biophysica Acta, vol. 1781, pp. 582-587 (2008).
Rother, et al., "Subtype-Selective Antagonists of Lysophosphatidic Acid Receptors Inhibit Platelet Activation Triggered by the LipidCore of Atherosclerotic Plaques", Circulation, vol. 108, pp. 741-747 (2003).
Saunders, et al., "Identification of small-molecule inhibitors of autotaxin that inhibit melanoma cell migration and invasion", Mol Cancer Ther., vol. 7(10), pp. 3352-3362 (2008).
Siess, "Athero- and thrombogenic actions of lysophosphatidic acid and sphingosine-1-phosphate", Biochimica et Biophysica Acta, vol. 1582, pp. 204-215 (2002).
Simon, et al., "Lysophosphatidic Acid 1 Receptor-dependent Downregulation of Peroxisome Proliferator-activated Receptor $\gamma 2$*" J.Biol. Chemistry, vol. 280(15) pp. 14656-14662 (2005).
Smalheiser, "Acute Neurite Retraction Elicited by Diverse Agents is Prevented by Genistein, a Tyrosine Kinase Inhibitor", J. Neurochemistry, vol. 61(1), pp. 340-343 (1993).
Sutphen, et al., "Lysophospholipids Are Potential Biomarkers of Ovarian Cancer", Cancer Epidemiol. Biomarkers Prev. 13, pp. 1185-1191 (2004).
Tager, et al., The lysophosphatidic acid receptor LPA1 links pulmonaryfibrosis to lung injury by mediating fibroblast recruitmentand vascular leak, Nature Medicine, vol. 14, pp. 45-54 (2008).
Watanabe, et al., "Both Plasma Lysophosphatidic Acid and Serum Autotaxin Levels are Increased in Chronic Hepatitis C", J Clinical Gastroenterology, vol. 41, pp. 616-623 (2007).
Watanabe, et al., "Plasma lysophosphatidic acid level and serum autotaxin activity are increased in liver injury in rats in relation to its severity", Life Science, vol. 81, pp. 1009-1015 (2007).
Wiedmaier, et al., "Bacteria induce CTGF and CYR61 expression in epithelial cells ina lysophosphatidic acid receptor-dependent manner", Int J Med Microbiology, vol. 298(3-4), pp. 231-243 (2008).
Xu, et al.,"Lysophosphatidic Acid Induces $\alpha v \beta 6$ Integrin-Mediated TGF-$\beta$ Activation via the LPA2 Receptor and the Small G Protein G$\alpha$q", Am J Pathology, vol. 174(4), pp. 1264-1279 (2009).
Yamada, et al., "Lysophosphatidic Acid (LPA) in Malignant Ascites Stimulates Motility of Human Pancreatic Cancer Cells through LPA1*", J Biol Chemistry, vol. 279, pp. 6596-6605 (2004).
Yamada, et al., "Lysophosphatidic acid stimulates the proliferation and motility of malignant pleural mesothelioma cells through lysophosphatidic acid receptors, LPA1 and LPA2", Cancer Science, vol. 99(8), pp. 1603-1610 (2008).
Yasuda, et al., "Phospholipid Analysis of Alveolar Macrophagesand Bronchoalveolar Lavage Fluid Following Bleomycin Administration to Rabbits", Lung, vol. 172, pp. 91-102 (1994).
Zhao, et al., "Regulation of Lysophosphatidic Acid Receptor Expression and Function in Human Synoviocytes: Implications for Rheumatoid Arthritis" Mol. Pharmacology, vol. 73(2), pp. 587-600 (2008).

* cited by examiner

CARBAMOYLOXYMETHYL TRIAZOLE CYCLOHEXYL ACIDS AS LPA ANTAGONISTS

CROSS-REFERENCE TO RELATED APPLICATIONS

This application is a Divisional of U.S. patent application Ser. No. 15/628,104, filed on Jun. 20, 2017, which claims priority to U.S. Provisional Application Ser. No. 62/352,792, filed Jun. 21, 2016, the entire content of which is incorporated herein by reference.

FIELD OF THE INVENTION

The present invention relates to novel substituted triazole compounds, compositions containing them, and methods of using them, for example, for the treatment or prophylaxis of disorders associated with one or more of the lysophosphatidic acid (LPA) receptors.

BACKGROUND OF THE INVENTION

Lysophospholipids are membrane-derived bioactive lipid mediators, of which one of the most medically important is lysophosphatidic acid (LPA). LPA is not a single molecular entity but a collection of endogenous structural variants with fatty acids of varied lengths and degrees of saturation (Fujiwara et al., *J Biol. Chem.*, 2005, 280, 35038-35050). The structural backbone of the LPAs is derived from glycerol-based phospholipids such as phosphatidylcholine (PC) or phosphatidic acid (PA).

The LPAs are bioactive lipids (signaling lipids) that regulate various cellular signaling pathways by binding to the same class of 7-transmembrane domain G protein-coupled (GPCR) receptors (Chun, J., Hla, T., Spiegel, S., Moolenaar, W., Editors, *Lysophospholipid Receptors: Signaling and Biochemistry*, 2013, Wiley; ISBN: 978-0-470-56905-4 & Zhao, Y. et al, Biochim. Biophys. *Acta (BBA)-Moil. Cell Biol. Of Lipids*. 2013, 1831, 86-92). The currently known LPA receptors are designated as LPA1, LPA2, LPA3, LPA4, LPA5 and LPA6 (Choi, J. W., *Annu. Rev. Pharmacol. Toxicol.*, 2010, 50, 157-186).

The LPAs have long been known as precursors of phospholipid biosynthesis in both eukaryotic and prokaryotic cells, but the LPAs have emerged only recently as signaling molecules that are rapidly produced and released by activated cells, notably platelets, to influence target cells by acting on specific cell-surface receptors (see, e.g., Moolenaar et al., *BioEssays*, 2004, 26, 870-881, and van Leewen et al., *Biochem. Soc. Trans.*, 2003, 31, 1209-1212). Besides being synthesized and processed to more complex phospholipids in the endoplasmic reticulum, LPAs can be generated through the hydrolysis of pre-existing phospholipids following cell activation; for example, the sn-2 position is commonly missing a fatty acid residue due to deacylation, leaving only the sn-1 hydroxyl esterified to a fatty acid. Moreover, a key enzyme in the production of LPA, autotaxin (lysoPLD/NPP2), may be the product of an oncogene, as many tumor types up-regulate autotaxin (Brindley, D., *J. Cell Biochem.* 2004, 92, 900-12). The concentrations of LPAs in human plasma & serum as well as human bronchoalveolar lavage fluid (BALF) have been reported, including determinations made using sensitive and specific LC/MS & LC/MS/MS procedures (Baker et al. *Anal. Biochem.*, 2001, 292, 287-295; Onorato et al., *J. LipidRes.*, 2014, 55, 1784-1796).

LPA influences a wide range of biological responses, ranging from induction of cell proliferation, stimulation of cell migration and neurite retraction, gap junction closure, and even slime mold chemotaxis (Goetzl, et al., *Scientific World J.*, 2002, 2, 324-338; Chun, J., Hla, T., Spiegel, S., Moolenaar, W., Editors, *Lysophospholipid Receptors: Signaling and Biochemistry*, 2013, Wiley; ISBN: 978-0-470-56905-4). The body of knowledge about the biology of LPA continues to grow as more and more cellular systems are tested for LPA responsiveness. For instance, it is now known that, in addition to stimulating cell growth and proliferation, LPAs promote cellular tension and cell-surface fibronectin binding, which are important events in wound repair and regeneration (Moolenaar et al., *BioEssays*, 2004, 26, 870-881). Recently, anti-apoptotic activity has also been ascribed to LPA, and it has recently been reported that PPARγ is a receptor/target for LPA (Simon et al., *J. Biol. Chem.*, 2005, 280, 14656-14662).

Fibrosis is the result of an uncontrolled tissue healing process leading to excessive accumulation and insufficient resorption of extracellular matrix (ECM) which ultimately results in end-organ failure (Rockey, D. C., et al., *New Engl. J. Med.*, 2015, 372, 1138-1149). Recently it was reported that the LPA1 receptor was over-expressed in idiopathic pulmonary fibrosis (IPF) patients. LPA1 receptor knockout mice were also protected from bleomycin-induced lung fibrosis (Tager et al., *Nature Med.*, 2008, 14, 45-54).

Thus, antagonizing the LPA1 receptor may be useful for the treatment of fibrosis such as pulmonary fibrosis, hepatic fibrosis, renal fibrosis, arterial fibrosis and systemic sclerosis, and thus the diseases that result from fibrosis (pulmonary fibrosis-Idiopathic Pulmonary Fibrosis [IPF], hepatic fibrosis-Non-alcoholic Steatohepatitis [NASH], renal fibrosis-diabetic nephropathy, systemic sclerosis-scleroderma, etc.)

SUMMARY OF THE INVENTION

The present invention provides novel substituted triazole compounds including stereoisomers, tautomers, pharmaceutically acceptable salts, solvates or prodrugs thereof, which are useful as antagonists against one or more of the lysophosphatidic acid (LPA) receptors, especially the LPA1 receptor.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, solvates or prodrugs thereof.

The compounds of the invention may be used in the treatment and/or prophylaxis of conditions in which LPA plays a role.

The compounds of the present invention may be used in therapy.

The compounds of the present invention may be used for the manufacture of a medicament for the treatment and/or prophylaxis of a condition in which inhibition of the physiological activity of LPA is useful, such as diseases in which an LPA receptor participates, is involved in the etiology or pathology of the disease, or is otherwise associated with at least one symptom of the disease.

In another aspect, the present invention is directed to a method of treating fibrosis of organs (liver, kidney, lung, heart and the like as well as skin), liver diseases (acute hepatitis, chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease [cancer (solid tumor, solid tumor metastasis, vascular fibroma, myeloma, multiple myeloma, Kaposi's sarcoma, leukemia, chronic lymphocytic leukemia (CLL) and the like) and invasive metastasis of cancer cell, and the like], inflammatory disease (psoriasis, nephropathy, pneumonia and the like), gastrointestinal tract disease (irritable bowel syndrome (IBS), inflammatory bowel disease (IBD), abnormal pancreatic secretion, and the like), renal disease, urinary tract-associated disease (benign prostatic hyperplasia or symptoms associated with neuropathic bladder disease, spinal cord tumor, hernia of intervertebral disk, spinal canal stenosis, symptoms derived from diabetes, lower urinary tract disease (obstruction of lower urinary tract, and the like), inflammatory disease of lower urinary tract, dysuria, frequent urination, and the like), pancreas disease, abnormal angiogenesis-associated disease (arterial obstruction and the like), scleroderma, brain-associated disease (cerebral infarction, cerebral hemorrhage, and the like), neuropathic pain, peripheral neuropathy, and the like, ocular disease (age-related macular degeneration (AMD), diabetic retinopathy, proliferative vitreoretinopathy (PVR), cicatricial pemphigoid, glaucoma filtration surgery scarring, and the like).

In another aspect, the present invention is directed to a method of treating diseases, disorders, or conditions in which activation of at least one LPA receptor by LPA contributes to the symptomology or progression of the disease, disorder or condition. These diseases, disorders, or conditions may arise from one or more of a genetic, iatrogenic, immunological, infectious, metabolic, oncological, toxic, surgical, and/or traumatic etiology.

In another aspect, the present invention is directed to a method of treating renal fibrosis, pulmonary fibrosis, hepatic fibrosis, arterial fibrosis and systemic sclerosis comprising administering to a patient in need of such treatment a compound of the present invention as described above.

In one aspect, the present invention provides methods, compounds, pharmaceutical compositions, and medicaments described herein that comprise antagonists of LPA receptors, especially antagonists of LPA1.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

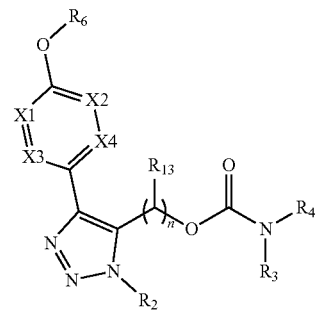

or stereoisomers, tautomers, pharmaceutically acceptable salts, solvates or prodrugs thereof, wherein
$R_2$ is independently selected from H and $C_{1-4}$ alkyl substituted with 1-5 $R_9$;
$R_{13}$ is independently selected from H, D, and $C_{1-4}$ alkyl substituted with 1-3 $R_9$;
$R_3$ and $R_4$ are independently selected from H, $C_{1-7}$ alkyl substituted with 1-3 $R_9$, —$(CR_7R_7)_r$—$C_{3-8}$ cycloalkyl substituted with 1-3 $R_8$, —$(CR_7R_7)_r$-aryl substituted with 1-3 $R_8$, $C_{2-7}$alkenyl substituted with 1-3 $R_9$, —$(CR_7R_7)_r$-5-6 membered heterocyclic ring substituted with 1-3 $R_8$, —$(CR_7R_7)_r$-5-6 membered heteroaryl ring substituted with 1-3 $R_8$, or $R_3$ and
$R_4$ combine with the N to which they are attached to form a 4-9 membered heterocyclic ring substituted with 1-3 $R_8$;
$X^1$, $X^2$, $X^3$, and $X^4$ are independently selected from $CR_5$ and N; provided no more than two of $X^1$, $X^2$, $X^3$, or $X^4$ are N;
$R_5$ is independently selected from H, F, Cl, $OR_7$, CN, $N(R_7)_2$, $C_{1-4}$ alkyl substituted with 1-5 $R_9$, $C_{1-4}$ alkoxy substituted with 1-5 $R_9$, and $C_{1-4}$ heteroalkyl substituted with 1-5 $R_9$;
$R_6$ is $C_{3-8}$ cycloalkyl which is substituted with $R_{10}$ and (—$CH_2$)$_{0-1}R_{11}$;
$R_7$ is independently selected from H, $C_{1-4}$ alkyl, and $C_{3-6}$ cycloalkyl; or $R_7$ and $R_7$, together with the carbon atom to which they both attach, form a $C_{3-6}$ cycloalkyl ring;
$R_8$ is independently selected from H, D, $C_{1-6}$ alkyl substituted with 1-5 $R_9$, $C_{2-6}$ alkenyl, $C_{2-6}$ alkynyl, phenyl, —$(CH_2)_r$—$C_{3-6}$ cycloalkyl, F, Cl, Br, CN, COOH, and $C_{1-4}$ alkoxy;
$R_9$ is independently selected from H, D, F, Cl, $NH_2$, OH, $OC_{1-5}$alkyl, $C_{1-5}$alkyl, $C_{1-5}$ heteroalkyl $C_{3-6}$ cycloalkyl, and phenyl, wherein when $R_9$ is Cl, $NH_2$ or OH it is not substituted on $C_1$ of the alkyl to which it is attached;
$R_{10}$ is independently selected from H, D, $C_{1-4}$ alkyl, F, Cl, Br, $OR_7$, NHC(=O)$OR_7$, and NHC(=O)$OR_7$;
$R_{11}$ is independently selected from H, CN, —C(=O)$R_{12}$, tetrazolyl,

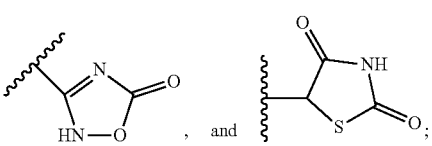 [SMILES: *c1nc(=O)o[nH]1 ; *C1SC(=O)NC1=O]

$R_{12}$ is independently selected from OH, $OC_{1-4}$ alkyl, $NH_2$, $NHCH_2CH_2SO_3H$, and $NHSO_2C_{1-4}$alky;
r is independently selected from zero, 1, 2, 3, and 4, and n is selected from 1, 2, 3, or 4.

In another embodiment, the present invention includes compounds of Formula (I), wherein
R$_3$ and R$_4$ are independently selected from H, C$_{1-7}$ alkyl substituted with 1-3 R$_9$, —(CR$_7$R$_7$)$_r$—C$_{3-8}$ cycloalkyl substituted with 1-3 R$_8$, —(CR$_7$R$_7$)$_r$-aryl substituted with 1-3 R$_8$, C$_{2-7}$alkenyl substituted with 1-3 R$_9$, —(CR$_7$R$_7$)$_r$-5-6 membered heterocyclic ring substituted with 1-3 R$_8$, —(CR$_7$R$_7$)$_r$-5-6 membered heteroaryl ring substituted with 1-3 R$_8$, and R$_3$ and
R$_4$ combine with the N to which they are attached to form the following:

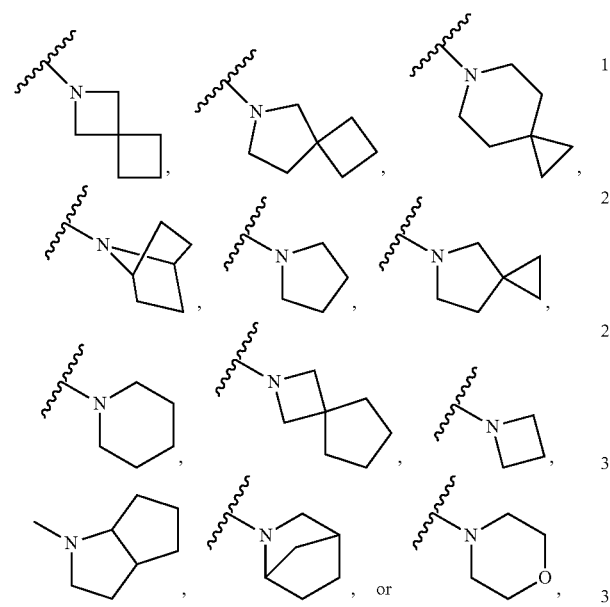

each of which may be substituted with 1-3 R$_8$, and n equals 1 or 2.

In another embodiment, the present invention includes compounds of Formula (I) wherein, R$_3$ and R$_4$ are independently selected from H, C$_{1-7}$ alkyl substituted with 1-3 R$_9$, —(CR$_7$R$_7$)$_r$—C$_{3-8}$ cycloalkyl substituted with 1-3 R$_8$, —(CR$_7$R$_7$)$_r$-aryl substituted with 1-3 R$_8$, C$_{2-7}$alkenyl substituted with 1-3 R$_9$,

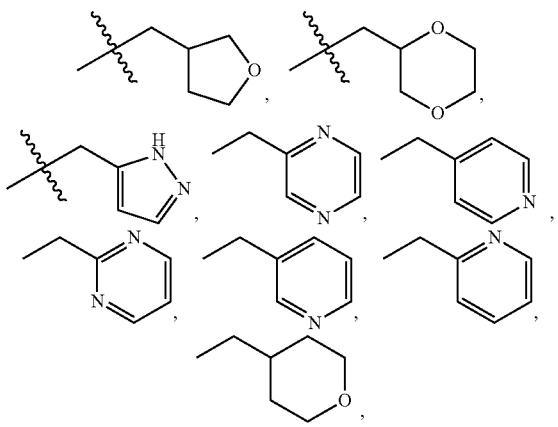

each of which can be substituted with 1-3 R$_8$, and R$_3$ and R$_4$ combine with the N to which they are attached to form a 4-9 membered heterocyclic ring substituted with 1-3 R$_8$; and n equals 1 or 2.

In another embodiment, the present invention includes compounds of Formula

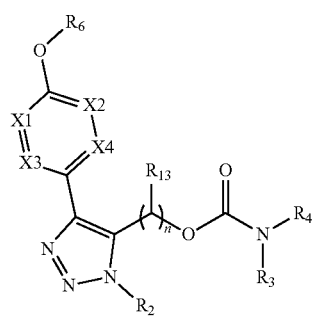

(II)

or stereoisomers, tautomers, pharmaceutically acceptable salts, solvates, or prodrugs thereof, wherein
R$_2$ is independently selected from H and C$_{1-4}$ alkyl substituted with 1-5 R$_9$;
R$_{13}$ is independently selected from H, D, and C$_{1-4}$ alkyl substituted with 1-3 R$_9$;
R$_3$ and R$_4$ are independently selected from H, C$_{1-7}$ alkyl substituted with 1-3 R$_9$, —(CR$_7$R$_7$)$_r$—C$_{3-6}$ cycloalkyl substituted with 1-3 R$_8$, and —(CR$_7$R$_7$)$_r$-aryl substituted with 1-3 R$_8$;
X$^1$, X$^2$, X$^3$, and X$^4$ are independently selected from CR$_5$ and N; provided no more than two of X$^1$, X$^2$, X$^3$, or X$^4$ are N;
R$_8$ is independently selected from H, F, Cl, OR$_7$, CN, N(R$_7$)$_2$, C$_{1-4}$ alkyl substituted with 1-5 R$_9$, C$_{1-4}$ alkoxy substituted with 1-5 R$_9$, and C$_{1-4}$ heteroalkyl substituted with 1-5 R$_9$;
R$_6$ is

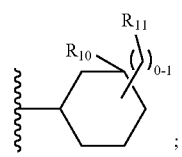

;

R$_7$ is independently selected from H, C$_{1-4}$ alkyl, and C$_{3-6}$ cycloalkyl; or R$_7$ and R$_7$, together with the carbon atom to which they both attach, form a C$_{3-6}$ cycloalkyl ring;
R$_8$ is independently selected from H, C$_{1-6}$ alkyl substituted with 1-5 R$_9$, C$_{2-6}$ alkenyl, C$_{2-6}$ alkynyl, —(CH$_2$)$_r$—C$_{3-6}$ cycloalkyl, F, Cl, Br, CN, =O, and CO$_2$H;
R$_9$ is independently selected from H, F, Cl, NH$_2$, OH, OC$_{1-5}$alkyl, C$_{1-5}$alkyl, C$_{1-5}$ heteroalkyl C$_{3-6}$ cycloalkyl, and phenyl, wherein when R$_9$ is Cl, NH$_2$ or OH it is not substituted on C$_1$ of the alkyl to which it is attached;
R$_{10}$ is independently selected from H, D, C$_{1-4}$ alkyl, F, Cl, Br, OR$_7$, NHC(=O)OR$_7$, and NHC(=O)R$_7$;
R$_{11}$ is independently selected from CN, —C(=O)R$_{12}$, tetrazolyl,

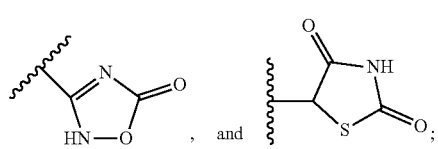 [SMILES: *c1nc(=O)o[nH]1 ; *C1SC(=O)NC1=O]

;

$R_{12}$ is independently selected from OH, $OC_{1-4}$ alkyl, $NH_2$, $NHCH_2CH_2SO_3H$, and $NHSO_2C_{1-4}$alky; and r is independently selected from zero, 1, 2, 3, and 4.

In another aspect, the present invention provides compounds of Formula (III):

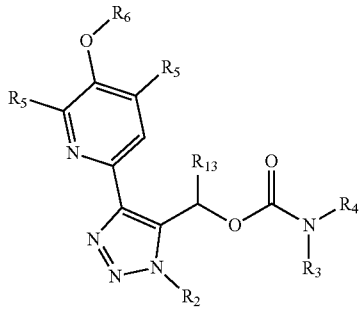

(III)

or stereoisomers, tautomers, pharmaceutically acceptable salts, solvates, or prodrugs thereof, wherein $R_2$ is independently selected from $CH_3$ and $CD_3$;

$R_{13}$ is independently selected from H and $C_{1-4}$ alkyl;

$R_3$ is independently selected from H and $C_{1-4}$ alkyl;

$R_4$ is independently selected from $C_{1-6}$ alkyl substituted with 1-3 $R_9$, —$(CR_7R_7)_r$—$C_{3-6}$ cycloalkyl substituted with 1-3 $R_8$, and —$(CR_7R_7)_r$-aryl substituted with 1-3 $R_8$;

$R_5$ is independently selected from H, F, Cl, CN and $C_{1-4}$ alkyl; provided one of $R_5$ is H;

$R_6$ is

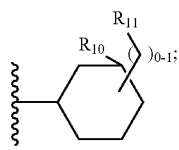

$R_7$ is independently selected from H, $C_{1-4}$ alkyl, and $C_{3-6}$ cycloalkyl; or $R_7$ and $R_7$, together with the carbon atom to which they both attach, form a $C_{3-6}$ cycloalkyl ring;

$R_8$ is independently selected from H, $C_{1-6}$ alkyl substituted with 1-5 $R_9$, $C_{3-6}$ cycloalkyl, F, Cl, Br, CN, =O, and COOH;

$R_9$ is independently selected from H, F, Cl, $NH_2$, OH, $OC_{1-5}$alkyl, $C_{1-5}$alkyl, $C_{3-6}$ cycloalkyl, and phenyl, wherein when $R_9$ is Cl, $NH_2$ or OH it is not substituted on $C_1$ of the alkyl to which it is attached;

$R_{10}$ is independently selected from H, D, $C_{1-4}$ alkyl, and F;

$R_{11}$ is independently selected from CN, —C(=O)$R_{12}$, and tetrazolyl;

$R_{12}$ is independently selected from OH, $OC_{1-4}$ alkyl, $NH_2$, and $NHSO_2C_{1-4}$alky; and r is independently selected from zero, 1, 2, 3, and 4.

In another aspect, the present invention provides compounds of Formula (IV):

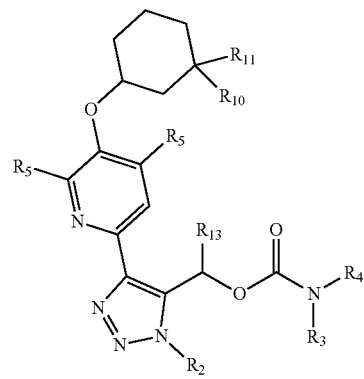

(IV)

or stereoisomers, tautomers, pharmaceutically acceptable salts, solvates, or prodrugs thereof, wherein $R_2$ is independently selected from $CH_3$ and $CD_3$;

$R_{13}$ is independently selected from H and $C_{1-4}$ alkyl;

$R_3$ is independently selected from H and $C_{1-4}$ alkyl;

$R_4$ is independently selected from $C_{1-6}$ alkyl,

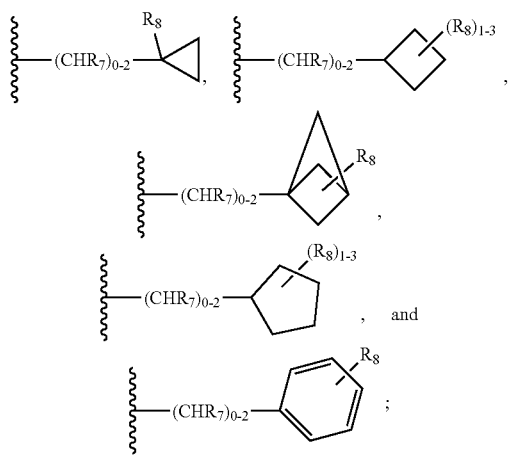

$R_5$ is independently selected from H, F, Cl, and $C_{1-4}$ alkyl; provided one of $R_5$ is H;

$R_7$ is independently selected from H, $C_{1-4}$ alkyl, and $C_{3-6}$ cycloalkyl;

$R_8$ is independently selected from H, $C_{1-6}$ alkyl substituted with 1-5 $R_9$, $C_{3-6}$ cycloalkyl, F, Cl, Br, CN, =O, and COOH;

$R_9$ is independently selected from H, F, Cl, $NH_2$, OH, $OC_{1-5}$alkyl, $C_{1-5}$alkyl, $C_{3-6}$ cycloalkyl, and phenyl, wherein when $R_9$ is Cl, $NH_2$ or OH it is not substituted on $C_1$ of the alkyl to which it is attached;

$R_{10}$ is independently selected from H, D, $C_{1-4}$ alkyl, and F;

$R_{11}$ is independently selected from CN, —C(=O)$R_{12}$, and

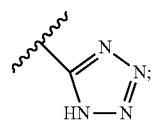

and $R_{12}$ is independently selected from OH, $NH_2$ and $NHSO_2C_{1-4}$ alky.

In another aspect, the present invention provides compounds of Formula (III) or stereoisomers, tautomers, pharmaceutically acceptable salts, solvates, or prodrugs thereof, wherein R₄ is independently selected from

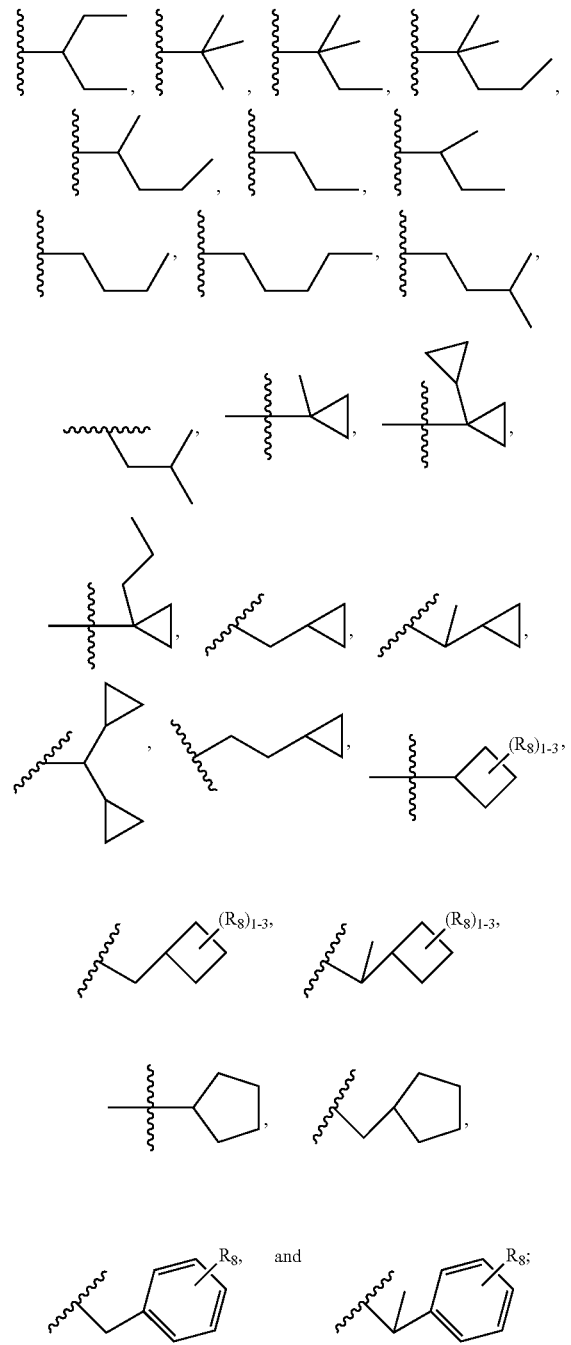

and

R₈ is independently selected from H, F, Cl, Br, CN, and C₁₋₄ alkyl; and other variables are as defined in Formula (IV).

In another aspect, the present invention provides compounds of Formula (V):

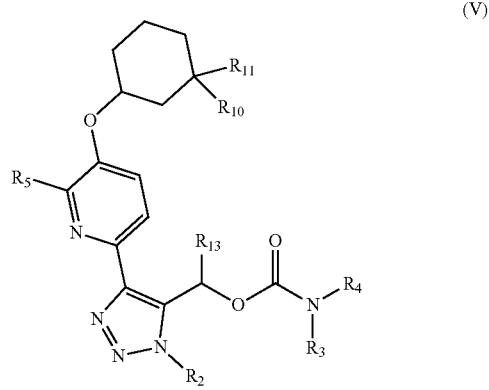

(V)

or stereoisomers, tautomers, pharmaceutically acceptable salts, solvates, or prodrugs thereof, wherein
R₂ is independently selected from CH₃ and CD₃;
R₁₃ is independently selected from H and CH₃;
R₃ is independently selected from H and CH₃;
R₄ is independently selected from

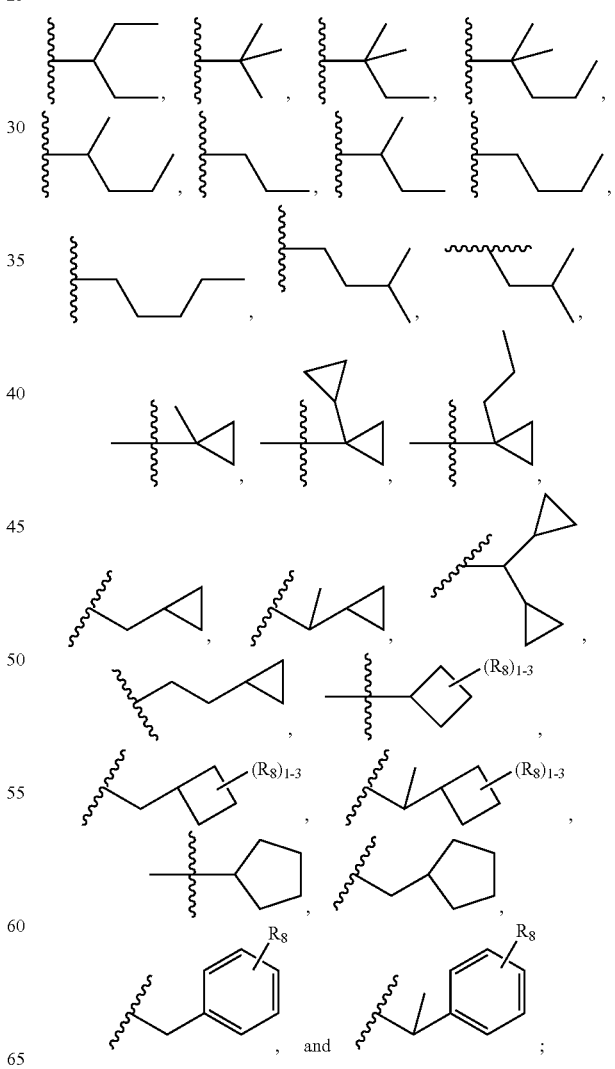

and
$R_5$ is independently selected from H, F, and $C_{1-4}$ alkyl;
$R_8$ is independently selected from H, F, Cl, Br, CN, and $C_{1-4}$ alkyl;
$R_{10}$ is independently selected from H, D, and F; and
$R_{11}$ is independently selected from —C(=O)OH, and —C(=O)NHSO$_2$Me.

In another aspect, the present invention provides compounds of Formula (VI):

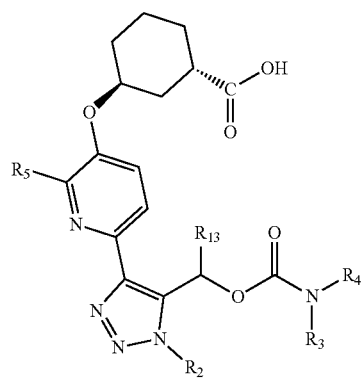

(VI)

or stereoisomers, tautomers, pharmaceutically acceptable salts, solvates, or prodrugs thereof, wherein
$R_2$ is independently selected from CH$_3$ and CD$_3$;
$R_{13}$ is independently selected from H and CH$_3$;
$R_3$ is independently selected from H and CH$_3$;
$R_4$ is independently selected from

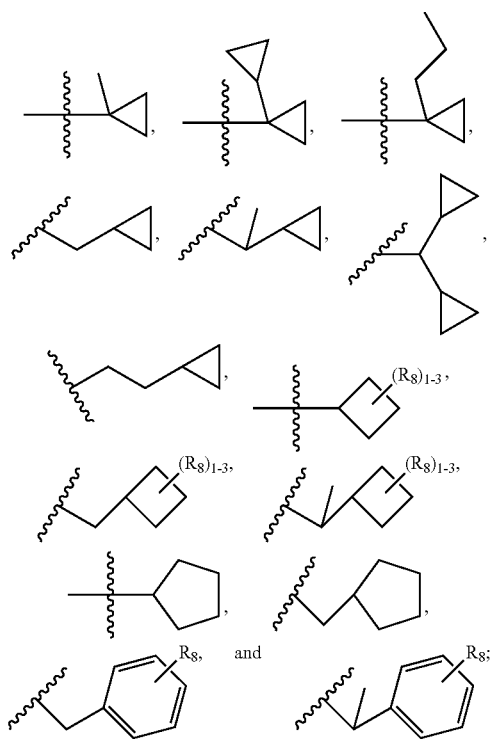

$R_5$ is independently selected from H and CH$_3$; and
$R_8$ is independently selected from H, F, Cl, Br, CN, and $C_{1-4}$ alkyl.

In another aspect, the present invention provides compounds of Formula (VII):

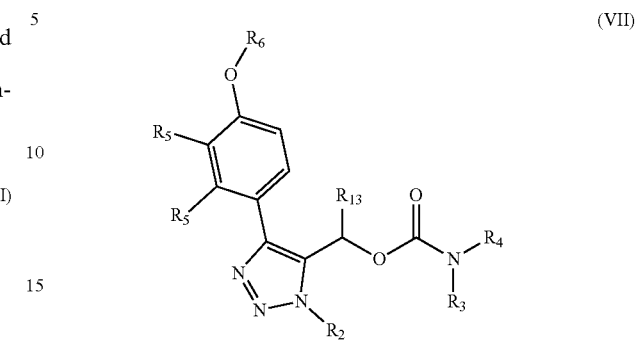

(VII)

or stereoisomers, tautomers, pharmaceutically acceptable salts, solvates, or prodrugs thereof, wherein
$R_2$ is independently selected from CH$_3$ and CD$_3$;
$R_{13}$ is independently selected from H and $C_{1-4}$ alkyl;
$R_3$ is independently selected from H and $C_{1-4}$ alkyl;
$R_4$ is independently selected from $C_{1-6}$ alkyl substituted with 1-3 $R_9$, $(CR_7R_7)_r$—$C_{3-6}$ cycloalkyl substituted with 1-3 $R_8$, and —$(CR_7R_7)_r$-aryl substituted with 1-3 $R_8$;
$R_5$ is independently selected from H, F, Cl, CN, and $C_{1-4}$ alkyl;
$R_6$ is

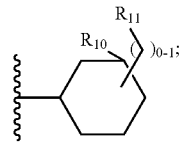

$R_7$ is independently selected from H, $C_{1-4}$ alkyl, and $C_{3-6}$ cycloalkyl; or $R_7$ and $R_7$, together with the carbon atom to which they both attach, form a $C_{3-6}$ cycloalkyl ring;
$R_8$ is independently selected from H, $C_{1-6}$ alkyl substituted with 1-5 $R_9$, $C_{3-6}$ cycloalkyl, F, Cl, Br, CN, =O, and COOH;
$R_9$ is independently selected from H, F, Cl, NH$_2$, OH, OC$_{1-5}$alkyl, C$_{1-5}$alkyl, C$_{3-6}$ cycloalkyl, and phenyl, wherein when $R_9$ is Cl, NH$_2$ or OH it is not substituted on $C_1$ of the alkyl to which it is attached;
$R_{10}$ is independently selected from H, $C_{1-4}$ alkyl, and F;
$R_{11}$ is independently selected from CN, —C(=O)R$_{12}$, tetrazolyl,

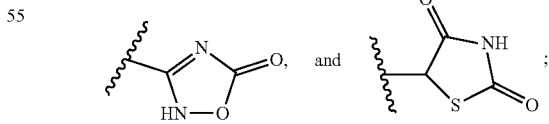

$R_{12}$ is independently selected from OH, OC$_{1-4}$ alkyl, NH$_2$, NHCH$_2$CH$_2$SO$_3$H, and NHSO$_2$C$_{1-4}$alky; and
r is independently selected from zero, 1, 2, 3, and 4.

In another aspect, the present invention provides compounds of Formula (VI) or stereoisomers, tautomers, pharmaceutically acceptable salts, solvates, or prodrugs thereof, wherein $R_1$ is independently selected from $CH_3$ and $CD_3$;
$R_2$ is independently selected from H and $CH_3$;
$R_3$ is independently selected from H and $CH_3$;
$R_4$ is independently selected from $C_{1-6}$ alkyl,

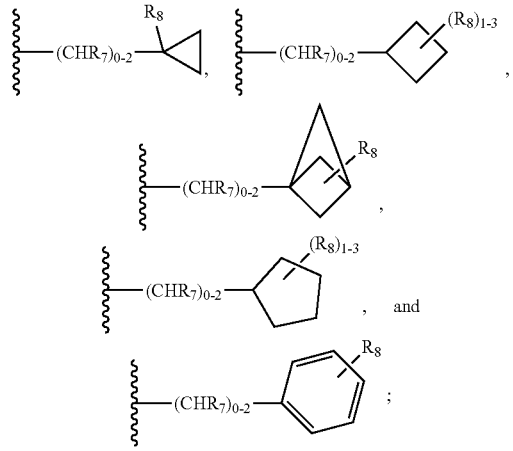

$R_5$ is independently selected from H, F, Cl, and $C_{1-4}$ alkyl;
$R_6$ is

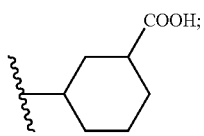 [SMILES: *C1CCCC(C(=O)O)C1]

$R_7$ is independently selected from H, $C_{1-4}$ alkyl, and $C_{1-6}$ cycloalkyl; and
$R_8$ is independently selected from H, F, Cl, Br, CN, and $C_{1-4}$ alkyl.

In another aspect, the present invention provides compounds of Formula (VIII):

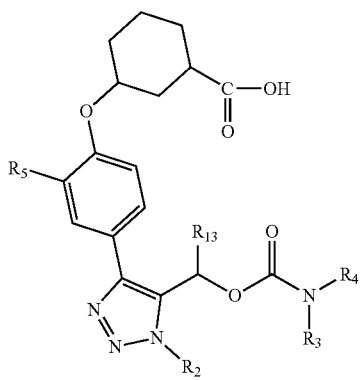

(VIII)

or stereoisomers, tautomers, pharmaceutically acceptable salts, solvates, or prodrugs thereof, wherein
$R_2$ is independently selected from $CH_3$ and $CD_3$;
$R_{13}$ is independently selected from H and $CH_3$;
$R_3$ is independently selected from H and $CH_3$;
$R_4$ is independently selected from

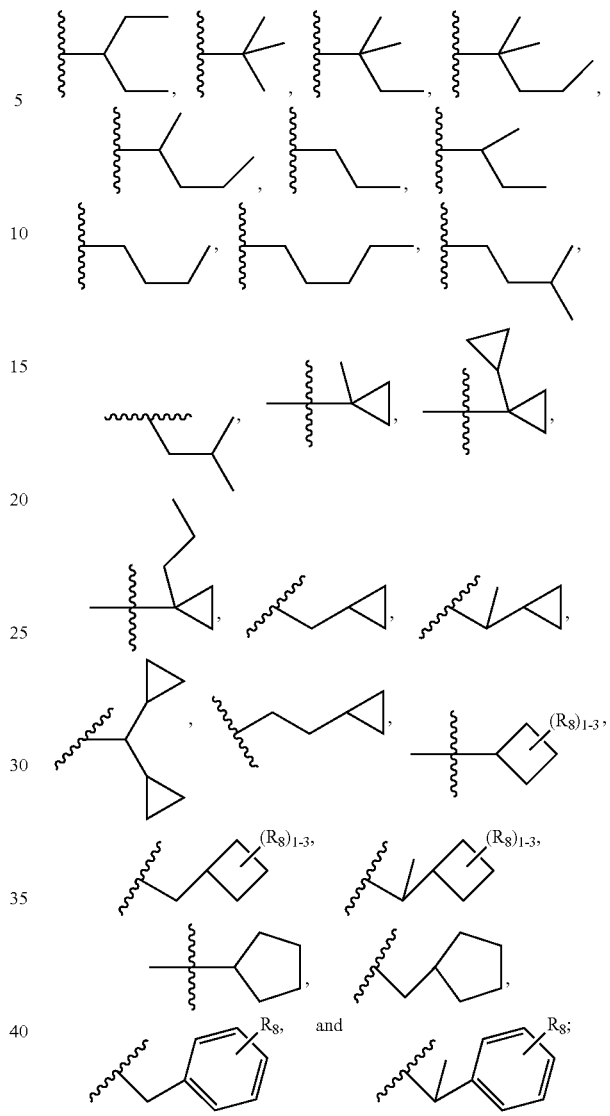

$R_5$ is independently selected from H, F, and $CH_3$; and
$R_8$ is independently selected from H, F, Cl, Br, CN, and $C_{1-4}$ alkyl.

In another aspect, the present invention provides compounds of Formula (IX):

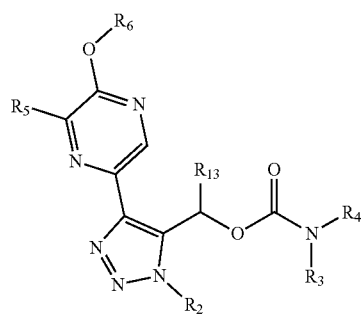

(IX)

or stereoisomers, tautomers, pharmaceutically acceptable salts, solvates, or prodrugs thereof, wherein R₂ is independently selected from CH₃ and CD₃;

R₁₃ is independently selected from H and C₁₋₄ alkyl;

R₃ is independently selected from H and C₁₋₄ alkyl;

R₄ is independently selected from C₁₋₆ alkyl substituted with 1-3 R₉, (CR₇R₇)ᵣ—C₃₋₆ cycloalkyl substituted with 1-3 R₈, and —(CR₇R₇)ᵣ-aryl substituted with 1-3 R₈;

R₅ is independently selected from H, F, Cl, CN, and C₁₋₄ alkyl;

R₆ is independently selected from

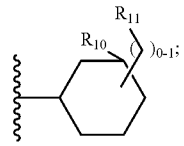

R₇ is independently selected from H, C₁₋₄ alkyl, and C₃₋₆ cycloalkyl; or R₇ and R₇, together with the carbon atom to which they both attach, form a C₃₋₆ cycloalkyl ring;

R₈ is independently selected from H, C₁₋₆ alkyl substituted with 1-5 R₉, C₃₋₆ cycloalkyl, F, Cl, Br, CN, =O, and COOH;

R₉ is independently selected from H, F, Cl, NH₂, OH, OC₁₋₅alkyl, C₁₋₅alkyl, C₃₋₆ cycloalkyl, and phenyl, wherein when R₉ is Cl, NH₂ or OH it is not substituted on C₁ of the alkyl to which it is attached;

R₁₀ is independently selected from H, and F,

R₁ is independently selected from CN, —C(=O)R₁₂, tetrazolyl,

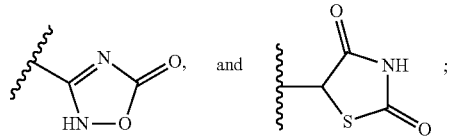 [SMILES: *c1nc(=O)o[nH]1 ; *C1SC(=O)NC1=O]

R₁₂ is independently selected from OH, OC₁₋₄ alkyl, NH₂, NHCH₂CH₂SO₃H, and NHSO₂C₁₋₄alky; and r is independently selected from zero, 1, 2, 3, and 4.

In yet another embodiment, the present invention includes a compound of Formula (I) or (II) selected from the group of:

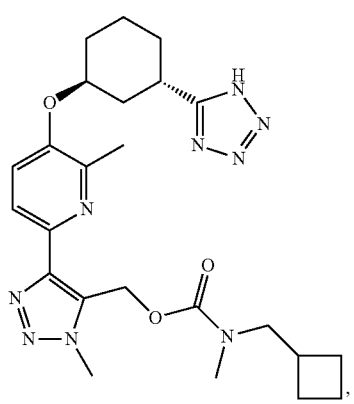 [SMILES: Cc1nc(-c2nnn(C)c2COC(=O)N(C)CC2CCC2)ccc1O[C@H]1CCC[C@H](c2nnn[nH]2)C1]

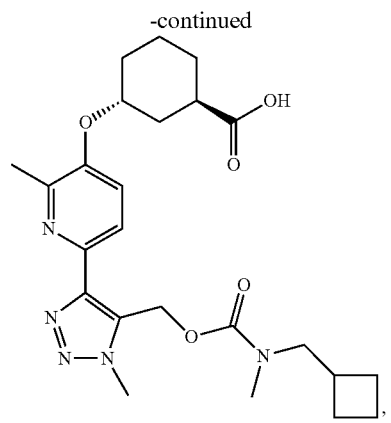

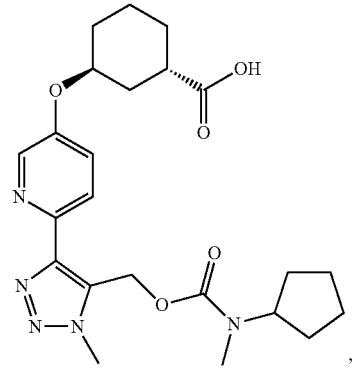

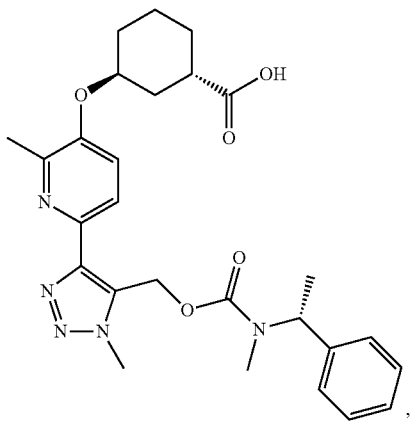

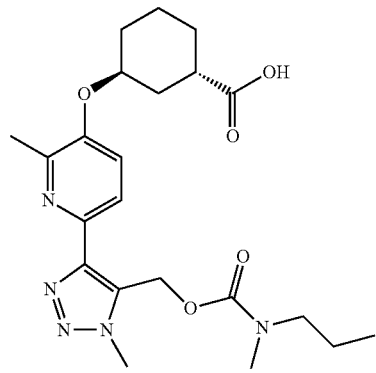

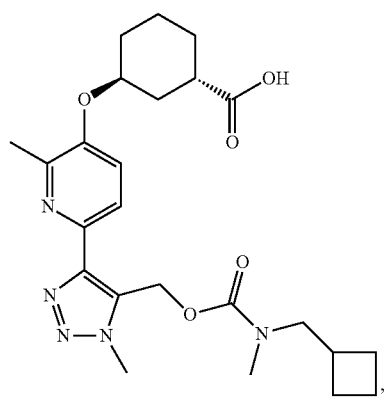
,
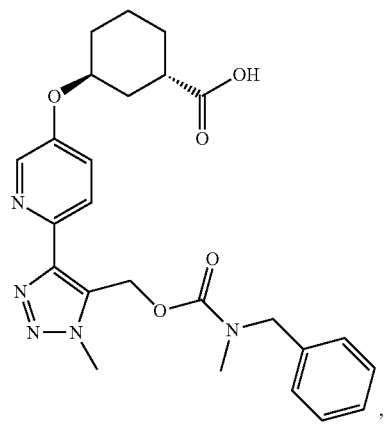
,
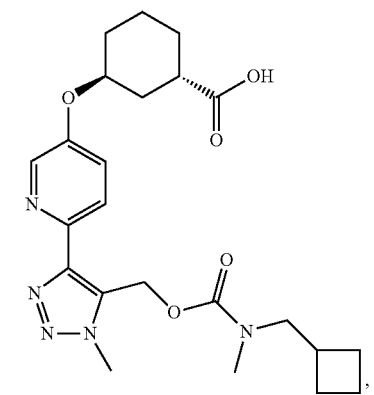
,
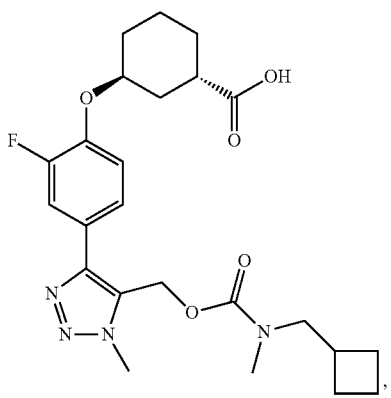
,
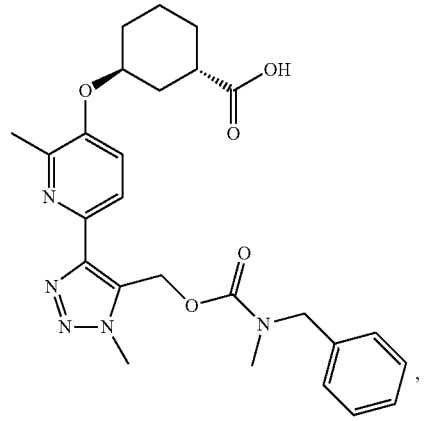
,
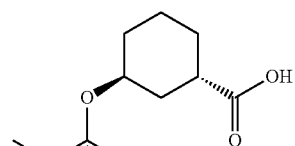
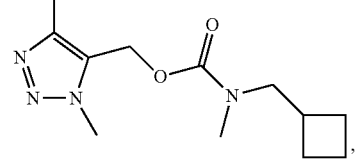
,
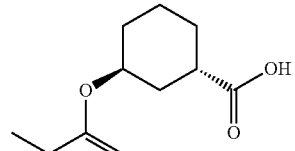
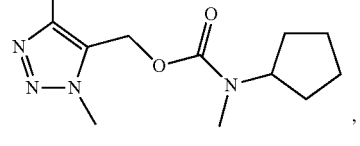
,
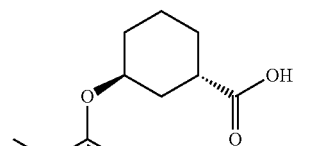
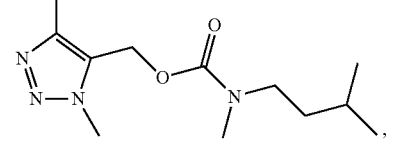
,

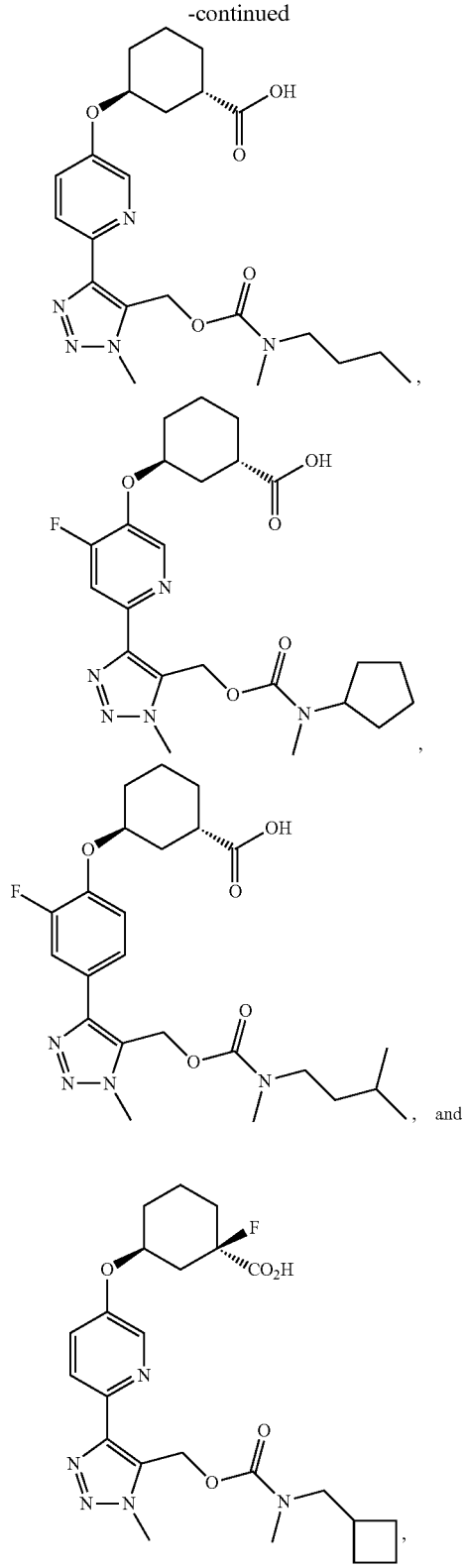
or an enantiomer, a diastereomer, a stereoisomer, or a pharmaceutically acceptable salt thereof.
In yet another embodiment, the present invention includes a compound of Formula (I) or (II) selected from the group of:
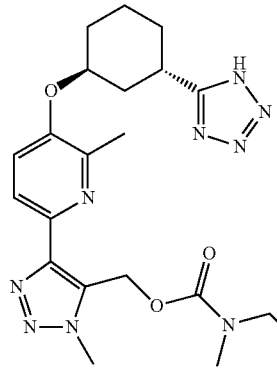
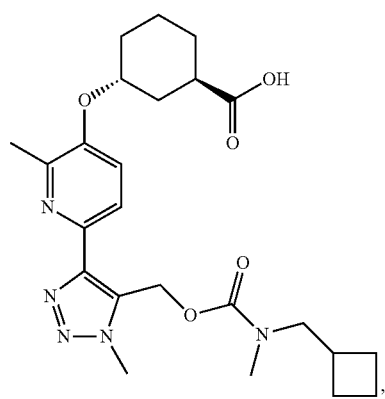
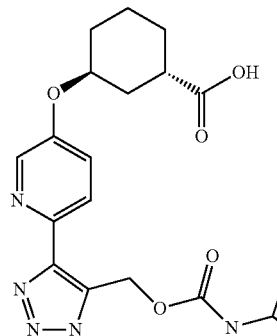
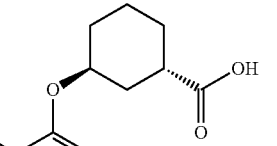
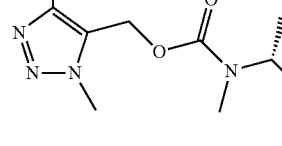
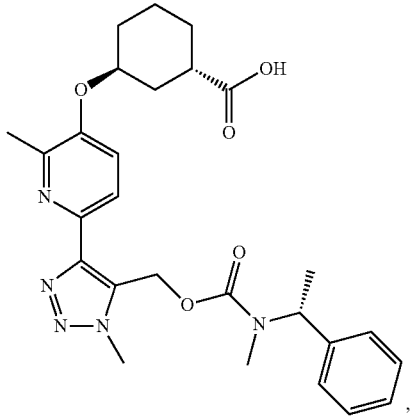

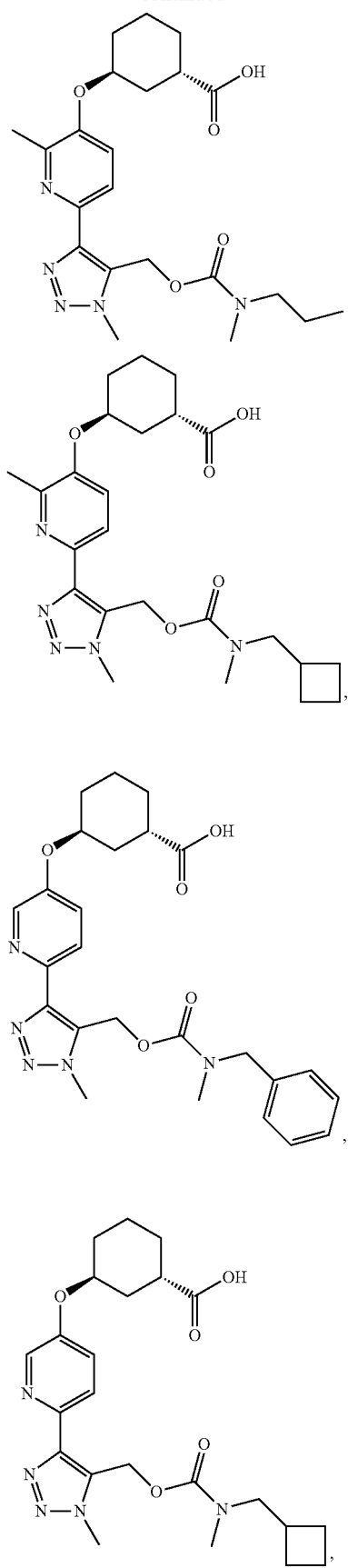
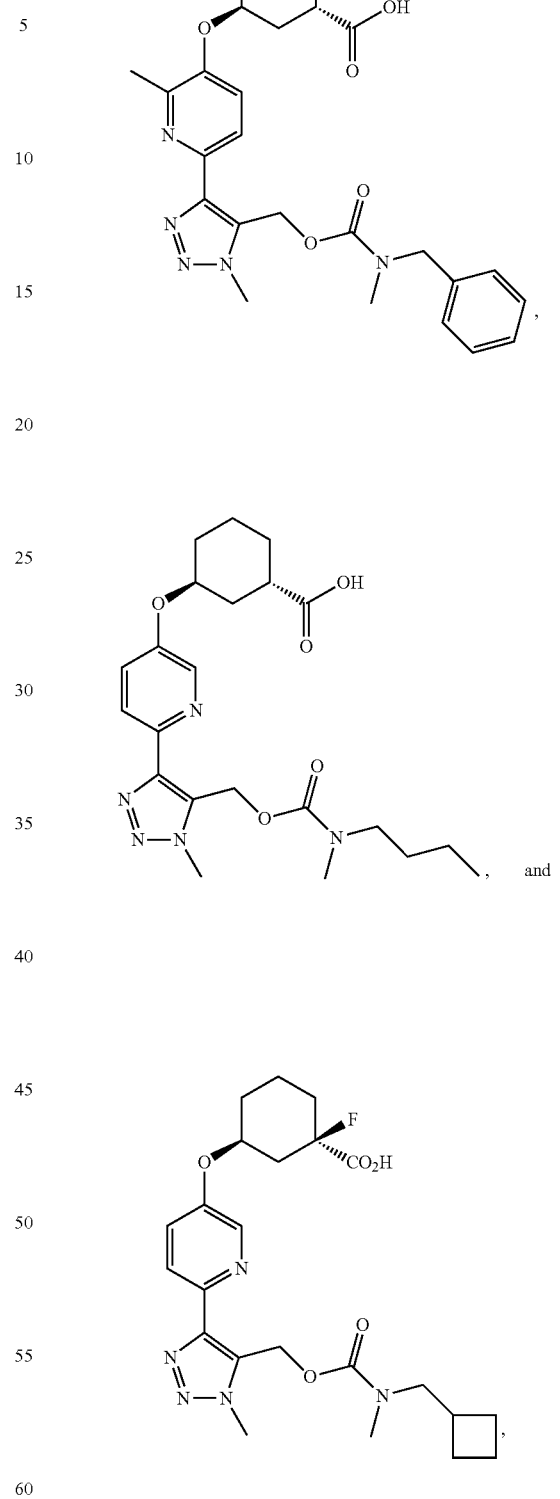
or an enantiomer, a diastereomer, a stereoisomer, or a pharmaceutically acceptable salt thereof.
In yet another embodiment, the present invention includes compound of Formula (I) or (II) wherein said compound has the formula:

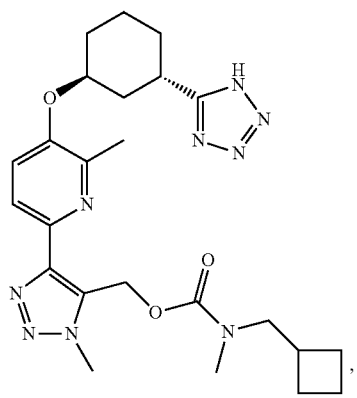

an enantiomer, a diastereomer, a stereoisomer, or a pharmaceutically acceptable salt thereof.

In yet another embodiment, the present invention includes compound of Formula (I) or (II) wherein said compound has the formula:

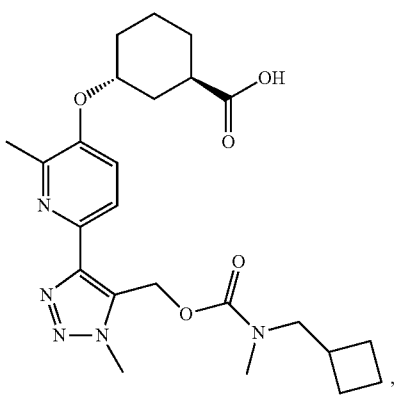 [SMILES: Cc1nc(-c2nnn(C)c2COC(=O)N(C)CC2CCC2)ccc1O[C@@H]1CCC[C@@H](C(=O)O)C1]

an enantiomer, a diastereomer, a stereoisomer, or a pharmaceutically acceptable salt thereof.

In yet another embodiment, the present invention includes compound of Formula (I) or (II) wherein said compound has the formula:

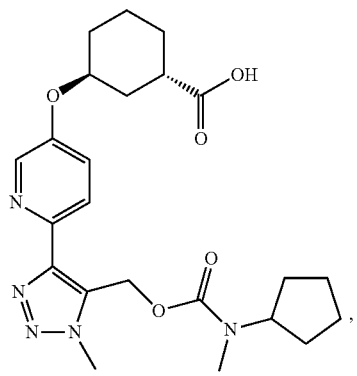 [SMILES: CN(C(=O)OCc1c(-c2ccc(O[C@H]3CCC[C@H](C(=O)O)C3)cn2)nnn1C)C1CCCC1]

an enantiomer, a diastereomer, a stereoisomer, or a pharmaceutically acceptable salt thereof.

In yet another embodiment, the present invention includes compound of Formula (I) or (II) wherein said compound has the formula:

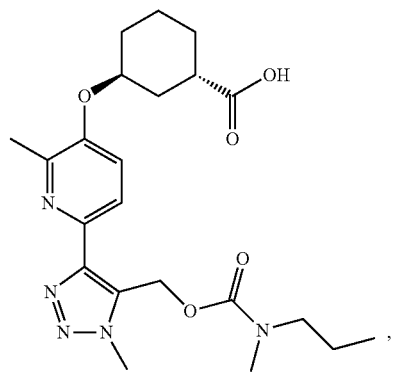 [SMILES: CCCN(C)C(=O)OCc1c(-c2ccc(O[C@H]3CCC[C@H](C(=O)O)C3)c(C)n2)nnn1C]

an enantiomer, a diastereomer, a stereoisomer, or a pharmaceutically acceptable salt thereof.

In yet another embodiment, the present invention includes compound of Formula (I) or (II) wherein said compound has the formula:

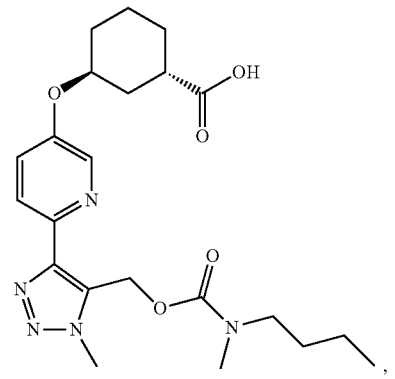 [SMILES: CCCCN(C)C(=O)OCc1c(-c2ccc(O[C@H]3CCC[C@H](C(=O)O)C3)cn2)nnn1C]

an enantiomer, a diastereomer, a stereoisomer, or a pharmaceutically acceptable salt thereof.

In yet another embodiment, the present invention includes compound of Formula (I) or (II) wherein said compound has the formula:

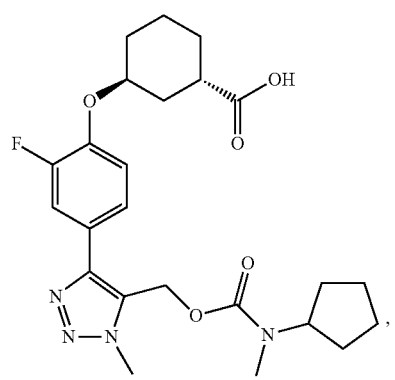 [SMILES: CN(C(=O)OCc1c(-c2ccc(O[C@H]3CCC[C@H](C(=O)O)C3)c(F)c2)nnn1C)C1CCCC1]

an enantiomer, a diastereomer, a stereoisomer, or a pharmaceutically acceptable salt thereof.

In yet another embodiment, the present invention includes compound of Formula (I) or (II) wherein said compound has the formula:

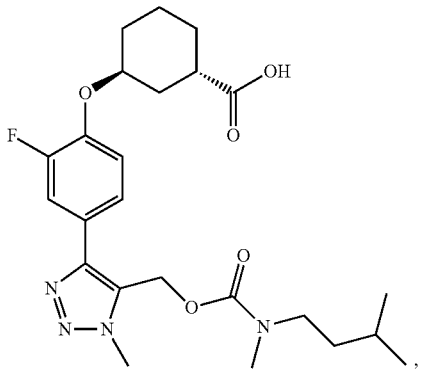 [SMILES: CC(C)CCN(C)C(=O)OCc1c(-c2ccc(O[C@H]3CCC[C@H](C(=O)O)C3)c(F)c2)nnn1C]

an enantiomer, a diastereomer, a stereoisomer, or a pharmaceutically acceptable salt thereof.

In yet another embodiment, the present invention includes compound of Formula (I) or (II) wherein said compound has the formula:

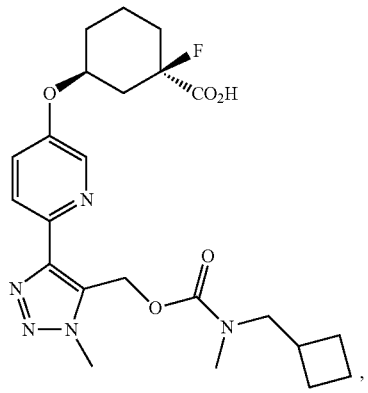 [SMILES: CN(CC1CCC1)C(=O)OCc1c(-c2ccc(O[C@H]3CCC[C@](F)(C(=O)O)C3)cn2)nnn1C]

or an enantiomer, a diastereomer, a stereoisomer, or a pharmaceutically acceptable salt thereof.

In yet another embodiment, the present invention includes compound of Formula (I) or (II) wherein said compound has the formula:

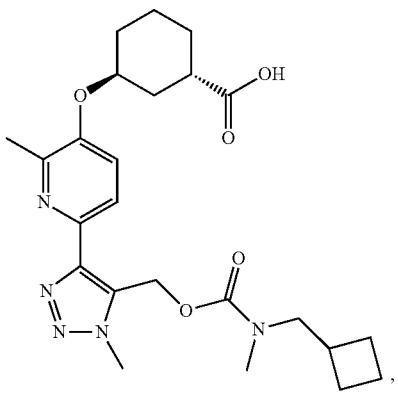 [SMILES: Cc1nc(-c2nnn(C)c2COC(=O)N(C)CC2CCC2)ccc1O[C@H]1CCC[C@H](C(=O)O)C1]

an enantiomer, a diastereomer, a stereoisomer, or a pharmaceutically acceptable salt thereof.

In yet another embodiment, the present invention includes compound of Formula (I) or (II) wherein said compound has the formula:

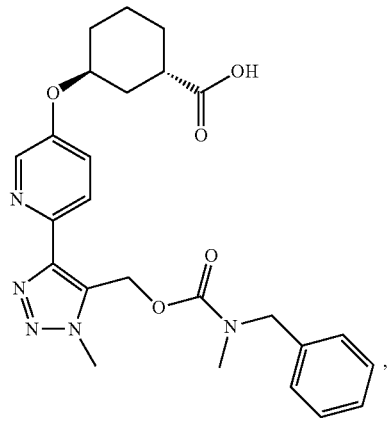 [SMILES: CN(Cc1ccccc1)C(=O)OCc1c(-c2ccc(O[C@H]3CCC[C@H](C(=O)O)C3)cn2)nnn1C]

an enantiomer, a diastereomer, a stereoisomer, or a pharmaceutically acceptable salt thereof.

For any and all of the embodiments, substituents are selected from among from a subset of the listed alternatives. For example, in some embodiments, $R_{12}$ is —OH, —O$C_{1-4}$ alkyl, or —NHSO$_2$$C_{1-4}$ alkyl. In some embodiments, $R_{12}$ is —OH or —O$C_{1-4}$ alkyl. In some embodiments, $R_{12}$ is —OH. In some embodiments, $R_{12}$ is —O$C_{1-4}$ alkyl. In some embodiments, $R_{12}$ is —OCH$_3$ or —OCH$_2$CH$_3$. In some embodiments, $R_{12}$ is —NHSO$_2$$C_{1-4}$alkyl.

In some embodiments, $R_3$ is $C_{1-4}$ alkyl; $R_5$ is H or $C_{1-4}$ alkyl. In some embodiments, $R_{12}$ is —OH, —OCH$_3$, —OCH$_2$CH$_3$, —NHSO$_2$CH$_3$ or —NHSO$_2$CH$_2$CH$_3$; $R_3$ is —CH$_3$, CD$_3$ or —CH$_2$CH$_3$. In some embodiments, $R_{12}$ is —OH, —OCH$_3$, —OCH$_2$CH$_3$, —NHSO$_2$CH$_3$ or —NHSO$_2$CH$_2$CH$_3$; $R_3$ is —CH$_3$, CD$_3$, or —CH$_2$CH$_3$; $R_5$ is H or $C_{1-4}$ alkyl.

In some embodiments, $R_4$ is

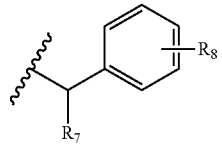

wherein

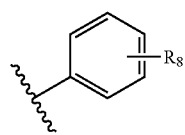

is 2-methylphenyl, 3-methylphenyl, 4-methylphenyl, 2-ethylphenyl, 3-ethylphenyl, 4-ethylphenyl, 2-deuteromethylphenyl, 3-deuteromethylphenyl, 4-deuteromethylphenyl, 2-monofluoromethylphenyl, 3-monofluoromethylphenyl, 4-monofluoromethylphenyl, 2-difluoromethylphenyl, 3-difluoromethylphenyl, 4-difluoromethylphenyl, 2-cyclopropylphenyl, 3-cyclopropylphenyl, 4-cyclopropylphenyl, 2-cyclobutylphenyl, 3-cyclobutylphenyl, 4-cyclobutylphenyl, 2-cyclopentylphenyl, 3-cyclopentylphenyl, 4-cyclopentylphenyl, 2-cyclohexylphenyl, 3-cyclohexylphenyl or 4-cyclohexylphenyl.

In some embodiments, $R_4$ is —$(CHR_7)_r$—$C_{3-6}$ cycloalkyl and r is 0, 1, or 2, and $R_7$ is H or methyl. In some embodiments, r is 0, $R_4$ is cyclopropyl, cyclobutyl, cyclopentyl, or cyclohexyl and $R_7$ is H or methyl. In some embodiments, r is 1, $R_4$ is cyclopropyl, cyclobutyl, cyclopentyl, or cyclohexyl, $R_7$ is H or methyl.

In some embodiments, $R_3$ is $C_{1-4}$ alkyl, $R_4$ is —$(CHR_7)_r$—$C_{3-6}$ cycloalkyl, and r is 0, 1, or 2, and $R_7$ is H or methyl. In some embodiments, $R_3$ is —$CH_3$, $CD_3$, or —$CH_2CH_3$, $R_4$ is cyclopropyl, cyclobutyl, cyclopentyl, or cyclohexyl, r is 0 or 1, and $R_7$ is H or methyl.

In some embodiments, $R_3$ is —$CH_3$, $R_4$ is cyclopropyl, cyclobutyl, cyclopentyl or cyclohexyl, r is 1, $R_7$ is H or methyl.

In some embodiments, $R_3$ is $C_{1-4}$ alkyl, $R_4$ is $C_{1-4}$ alkyl, and $R_7$ is H or methyl. In some embodiments, $R_3$ is —$CH_3$, $CD_3$, or —$CH_2CH_3$, $R_4$ is —$CH_3$, $CD_3$, —$CH_2CH_3$, —$CH_2CH_2CH_3$, —$CH(CH_3)_2$, —$CH_2CH_2CH_2CH_3$, —$CH_2CH(CH_3)_2$, or —$CH(CH_3)_3$, and $R_7$ is H or methyl. In some embodiments, $R_3$ is —$CH_3$, $R_4$ is —$CH_2CH_3$, —$CH_2CH_2CH_3$, —$CH(CH_3)_2$, —$CH_2CH_2CH_2CH_3$, —$CH_2CH(CH_3)_2$, or —$CH(CH_3)_3$, $R_7$ is H or methyl.

In some embodiments, $R_1$ is H or $C_{1-2}$ alkyl, $R_2$ is H or $C_{1-2}$ alkyl, $R_3$ is $C_{1-2}$ alkyl, $R_4$ is —$(CHR_7)_r$—$C_{3-6}$ cycloalkyl and r is 1, $R_5$ is H or $C_{1-2}$ alkyl, $R_6$ is cyclopentyl or cyclohexyl, $R_7$ is H or $C_{1-2}$ alkyl, $R_8$ is H, $R_9$ is H, $R_{10}$ is H, and $R_{11}$ is —C(=O)OH.

In some embodiments, $R_1$ is H or methyl, $R_2$ is H or methyl, $R_3$ is methyl, $R_4$ is —$CHR_7$-cyclopropyl, —$CHR_7$-cyclobutyl, —$CHR_7$-cyclopentyl, or —$CHR_7$-cyclohexyl, $R_5$ is H or methyl, $R_6$ is cyclohexyl, $R_7$ is H or methyl, $R_8$ is H, $R_9$ is H, $R_{10}$ is H, and $R_{11}$ is —C(=O)OH.

In some embodiments, the pharmaceutically acceptable salt of the compound of Formulas (I)-(IX) is a sodium salt.

Any combination of the groups described above for the various variables is contemplated herein. Throughout the specification, groups and substituents thereof are chosen by one skilled in the field to provide stable moieties and compounds.

In another aspect, the present invention provides a compound selected from any subset list of compounds exemplified in the present application.

In another embodiment, the present invention includes compounds of Formula (X):

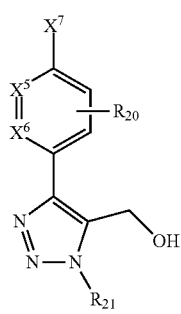

(X)

or an enantiomer, a diastereomer, or a stereoisomer thereof, wherein
$R_{20}$ is independently selected from $C_{1-6}$ alkyl or H;
$R_{21}$ is independently selected from $C_{1-6}$ alkyl or H;
$X^5$ and $X^6$ are independently selected from CH or N; and
$X^7$ is selected from Cl, Br, or F.

In another embodiment, the present invention includes compounds of Formula (XI):

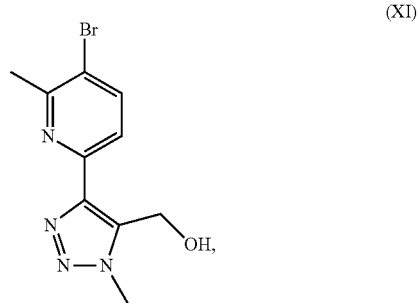 [SMILES: Cc1nc(-c2nnn(C)c2CO)ccc1Br]

(XI)

or an enantiomer, a diastereomer, or a stereoisomer thereof.

In another aspect, the present invention provides a compound selected from the list below:
(1S,3S)-3-((6-(5-(((cyclopentyl(methyl)carbamoyl)oxy) methyl)-1-methyl-1H-1,2,3-triazol-4-yl)pyridin-3-yl) oxy)cyclohexane-1-carboxylic acid (1)
(1S,3S)-3-((6-(5-(((((cyclobutylmethyl)(methyl)carbamoyl) oxy)methyl)-1-methyl-1H-1,2,3-triazol-4-yl)-2-methylpyridin-3-yl)oxy)cyclohexane-1-carboxylic acid (2)
(1S,3S)-3-((6-(5-(((((2-cyclopropylethyl)(methyl)carbamoyl)oxy)methyl)-1-methyl-1H-1,2,3-triazol-4-yl)pyridin-3-yl)oxy)cyclohexane-1-carboxylic acid (3) trans-3-(4-(5-(((cyclopentyl(methyl)carbamoyl)oxy)methyl)-1-methyl-1H-1,2,3-triazol-4-yl)phenoxy)cyclohexane-1-carboxylic acid (4)
(1S,3S)-3-(4-(5-(((Cyclopentyl(methyl)carbamoyl)oxy) methyl)-1-methyl-1H-1,2,3-triazol-4-yl)phenoxy)cyclohexanecarboxylic acid (5)
(1R,3R)-3-(4-(5-(((Cyclopentyl(methyl)carbamoyl)oxy) methyl)-1-methyl-1H-1,2,3-triazol-4-yl)phenoxy)cyclohexanecarboxylic acid (6)
(1-Methyl-4-(4-(((1S,3S)-3-((methylsulfonyl)carbamoyl) cyclohexyl)oxy)phenyl)-1H-1,2,3-triazol-5-yl)methyl cyclopentyl(methyl)carbamate (7) No names for (8) and (9)
(1S,3S)-3-(4-(1-Methyl-5-(((methyl(2-methylpentan-2-yl) carbamoyl)oxy)methyl)-1H-1,2,3-triazol-4-yl)phenoxy) cyclohexanecarboxylic acid (10)
3-((6-(5-(((((cyclobutylmethyl)(methyl)carbamoyl)oxy) methyl)-1-methyl-1H-1,2,3-triazol-4-yl)-2-methylpyridin-3-yl)oxy)-1-fluorocyclohexane-1-carboxylic acid (11)
(1S,3S)-3-(4-(5-(1-(((cyclobutylmethyl)(methyl)carbamoyl)oxy)ethyl)-1-methyl-1H-1,2,3-triazol-4-yl)phenoxy) cyclohexane-1-carboxylic acid (12)
3-((6-(5-(((((cyclobutylmethyl)(methyl)carbamoyl)oxy) methyl)-1-methyl-1H-1,2,3-triazol-4-yl)-2-methylpyridin-3-yl)oxy)-1-fluorocyclohexane-1-carboxylic acid (13)
(4-(5-(((1S,3S)-3-carbamoylcyclohexyl)oxy)-6-methylpyridin-2-yl)-1-methyl-1H-1,2,3-triazol-5-yl)methyl (cyclobutylmethyl)(methyl)carbamate (14)
(4-(5-(((1S,3S)-3-cyanocyclohexyl)oxy)-6-methylpyridin-2-yl)-1-methyl-1H-1,2,3-triazol-5-yl)methyl (cyclobutylmethyl)(methyl)carbamate (15)
(4-(5-(((1S,3S)-3-(1H-tetrazol-5-yl)cyclohexyl)oxy)-6-methylpyridin-2-yl)-1-methyl-1H-1,2,3-triazol-5-yl) methyl (cyclobutylmethyl)(methyl)carbamate (16)

(1-methyl-4-(6-methyl-5-((((1S,3S)-3-((methylsulfonyl)carbamoyl)cyclohexyl)oxy)pyridin-2-yl)-1H-1,2,3-triazol-5-yl)methyl (cyclobutylmethyl)(methyl)carbamate (17)

3-((6-(5-(((cyclopentyl(methyl)carbamoyl)oxy)methyl)-1-methyl-1H-1,2,3-triazol-4-yl)pyridin-3-yl)oxy)cyclohexane-1-carboxylic acid (18), (1S,3S)-3-((2-methyl-6-(1-methyl-5-(((methyl((R)-1-phenylethyl)carbamoyl)oxy)methyl)-1H-1,2,3-triazol-4-yl)pyridin-3-yl)oxy)cyclohexane-1-carboxylic acid (19), (1S,3S)-3-((6-(5-((((1-cyclobutylethyl)(methyl)carbamoyl)oxy)methyl)-1-methyl-1H-1,2,3-triazol-4-yl)-2-methylpyridin-3-yl)oxy)cyclohexane-1-carboxylic acid (20), (1S,3S)-3-((6-(1-methyl-5-(((methyl((R)-1-phenylethyl)carbamoyl)oxy)methyl)-1H-1,2,3-triazol-4-yl)pyridin-3-yl)oxy)cyclohexane-1-carboxylic acid (21), (1S,3S)-3-((6-(5-(((benzyl(methyl)carbamoyl)oxy)methyl)-1-methyl-1H-1,2,3-triazol-4-yl)pyridin-3-yl)oxy)cyclohexane-1-carboxylic acid (22), (1S,3S)-3-((6-(5-((((cyclobutylmethyl)(methyl)carbamoyl)oxy)methyl)-1-methyl-1H-1,2,3-triazol-4-yl)pyridin-3-yl)oxy)cyclohexane-1-carboxylic acid (23), (1S,3S)-3-((6-(1-methyl-5-(((methyl(pentan-2-yl)carbamoyl)oxy)methyl)-1H-1,2,3-triazol-4-yl)pyridin-3-yl)oxy)cyclohexane-1-carboxylic acid (24), (1S,3S)-3-((6-(5-(((((R)-1-cyclopropylethyl)(methyl)carbamoyl)oxy)methyl)-1-methyl-1H-1,2,3-triazol-4-yl)pyridin-3-yl)oxy)cyclohexane-1-carboxylic acid (25), (1S,3S)-3-(4-(5-(((benzyl(methyl)carbamoyl)oxy)methyl)-1-methyl-1H-1,2,3-triazol-4-yl)-2-fluorophenoxy)cyclohexane-1-carboxylic acid (26), (1S,3S)-3-(4-(5-((((cyclobutylmethyl)(methyl)carbamoyl)oxy)methyl)-1-methyl-1H-1,2,3-triazol-4-yl)-2-fluorophenoxy)cyclohexane-1-carboxylic acid (27), (1S,3S)-3-(2-fluoro-4-(1-methyl-5-(((methyl(pentan-2-yl)carbamoyl)oxy)methyl)-1H-1,2,3-triazol-4-yl)phenoxy)cyclohexane-1-carboxylic acid (28), (1S,3S)-3-((6-(5-(((((R)-1-cyclopropylethyl)(methyl)carbamoyl)oxy)methyl)-1-methyl-1H-1,2,3-triazol-4-yl)-2-methylpyridin-3-yl)oxy)cyclohexane-1-carboxylic acid (29), (1S,3S)-3-((6-(5-(((benzyl(methyl)carbamoyl)oxy)methyl)-1-methyl-1H-1,2,3-triazol-4-yl)-2-methylpyridin-3-yl)oxy)cyclohexane-1-carboxylic acid (30), (1S,3S)-3-((2-methyl-6-(1-methyl-5-(((methyl(pentan-2-yl)carbamoyl)oxy)methyl)-1H-1,2,3-triazol-4-yl)pyridin-3-yl)oxy)cyclohexane-1-carboxylic acid (31), (1S,3S)-3-((6-(5-(((butyl(methyl)carbamoyl)oxy)methyl)-1-methyl-1H-1,2,3-triazol-4-yl)-2-methylpyridin-3-yl)oxy)cyclohexane-1-carboxylic acid (32), (1S,3S)-3-((6-(5-(((cyclopentyl(methyl)carbamoyl)oxy)methyl)-1-methyl-1H-1,2,3-triazol-4-yl)-2-methylpyridin-3-yl)oxy)cyclohexane-1-carboxylic acid (33), (1S,3S)-3-((6-(5-(((isopentyl(methyl)carbamoyl)oxy)methyl)-1-methyl-1H-1,2,3-triazol-4-yl)-2-methylpyridin-3-yl)oxy)cyclohexane-1-carboxylic acid (34), (1S,3S)-3-((6-(5-((((4-chlorobenzyl)(methyl)carbamoyl)oxy)methyl)-1-methyl-1H-1,2,3-triazol-4-yl)-2-methylpyridin-3-yl)oxy)cyclohexane-1-carboxylic acid (35), (1S,3S)-3-(4-(5-(((((R)-1-cyclopropylethyl)(methyl)carbamoyl)oxy)methyl)-1-methyl-1H-1,2,3-triazol-4-yl)-2-methylphenoxy)cyclohexane-1-carboxylic acid (36), (1S,3S)-3-(4-(5-((((cyclobutylmethyl)(methyl)carbamoyl)oxy)methyl)-1-methyl-1H-1,2,3-triazol-4-yl)-2-methylphenoxy)cyclohexane-1-carboxylic acid (37), (1S,3S)-3-(4-(5-(((benzyl(methyl)carbamoyl)oxy)methyl)-1-methyl-1H-1,2,3-triazol-4-yl)-2-methylphenoxy)cyclohexane-1-carboxylic acid (38), (1S,3S)-3-(2-methyl-4-(1-methyl-5-(((methyl(pentan-2-yl)carbamoyl)oxy)methyl)-1H-1,2,3-triazol-4-yl)phenoxy)cyclohexane-1-carboxylic acid (39), (1S,3S)-3-(4-(5-(((butyl(methyl)carbamoyl)oxy)methyl)-1-methyl-1H-1,2,3-triazol-4-yl)-2-methylphenoxy)cyclohexane-1-carboxylic acid (40), (1S,3S)-3-(4-(5-(((cyclopentyl(methyl)carbamoyl)oxy)methyl)-1-methyl-1H-1,2,3-triazol-4-yl)-2-methylphenoxy)cyclohexane-1-carboxylic acid (41), (1S,3S)-3-((6-(5-(((isopentyl(methyl)carbamoyl)oxy)methyl)-1-methyl-1H-1,2,3-triazol-4-yl)-4-methylpyridin-3-yl)oxy)cyclohexane-1-carboxylic acid (42), (1S,3S)-3-((6-(5-(((butyl(methyl)carbamoyl)oxy)methyl)-1-methyl-1H-1,2,3-triazol-4-yl)pyridin-3-yl)oxy)cyclohexane-1-carboxylic acid (43), (1S,3S)-3-(4-(5-(((cyclopentyl(methyl)carbamoyl)oxy)methyl)-1-methyl-1H-1,2,3-triazol-4-yl)-2-fluorophenoxy)cyclohexane-1-carboxylic acid (44), (1S,3S)-3-(4-(5-((((1-cyclopropylethyl)(methyl)carbamoyl)oxy)methyl)-1-methyl-1H-1,2,3-triazol-4-yl)-2-fluorophenoxy)cyclohexane-1-carboxylic acid (45), (1S,3S)-3-(4-(5-(((butyl(methyl)carbamoyl)oxy)methyl)-1-methyl-1H-1,2,3-triazol-4-yl)-2-fluorophenoxy)cyclohexane-1-carboxylic acid (46), (1S,3 S)-3-(2-fluoro-4-(5-(((isopentyl(methyl)carbamoyl)oxy)methyl)-1-methyl-1H-1,2,3-triazol-4-yl)phenoxy)cyclohexane-1-carboxylic acid (47), (1S,3S)-3-(4-(5-((((1-cyclobutylethyl)(methyl)carbamoyl)oxy)methyl)-1-methyl-1H-1,2,3-triazol-4-yl)phenoxy)cyclohexane-1-carboxylic acid (isomer 1) (48), (1S,3S)-3-(4-(5-((((1-cyclobutylethyl)(methyl)carbamoyl)oxy)methyl)-1-methyl-1H-1,2,3-triazol-4-yl)phenoxy)cyclohexane-1-carboxylic acid (isomer 2) (49), (1S,3S)-3-((6-(5-(((isopentyl(methyl)carbamoyl)oxy)methyl)-1-methyl-1H-1,2,3-triazol-4-yl)pyridin-3-yl)oxy)cyclohexane-1-carboxylic acid (50), (1S,3S)-3-(4-(5-(((((R)-1-cyclopropylethyl)(methyl)carbamoyl)oxy)methyl)-1-methyl-1H-1,2,3-triazol-4-yl)phenoxy)cyclohexane-1-carboxylic acid (51), (1S,3S)-3-(4-(5-(((((S)-1-cyclopropylethyl)(methyl)carbamoyl)oxy)methyl)-1-methyl-1H-1,2,3-triazol-4-yl)phenoxy)cyclohexane-1-carboxylic acid (52), (1S,3S)-3-(4-(5-(((isobutyl(methyl)carbamoyl)oxy)methyl)-1H-1,2,3-triazol-4-yl)phenoxy)cyclohexane-1-carboxylic acid (53), (1S,3S)-3-(4-(5-((((1-cyclobutylethyl)(methyl)carbamoyl)oxy)methyl)-1-methyl-1H-1,2,3-triazol-4-yl)phenoxy)cyclohexane-1-carboxylic acid (54), (1S,3S)-3-(4-(5-((((2-cyclopropylethyl)(methyl)carbamoyl)oxy)methyl)-1-methyl-1H-1,2,3-triazol-4-yl)phenoxy)cyclohexane-1-carboxylic acid (55), (1S,3S)-3-(4-(5-(((isopentyl(methyl)carbamoyl)oxy)methyl)-1-methyl-1H-1,2,3-triazol-4-yl)-2-methylphenoxy)cyclohexane-1-carboxylic acid (56), (1S,3S)-3-(4-(1-methyl-5-(((methyl(pentan-2-yl)carbamoyl)oxy)methyl)-1H-1,2,3-triazol-4-yl)phenoxy)cyclohexane-1-carboxylic acid (57), (1S,3S)-3-(4-(1-methyl-5-(((methyl(pentyl)carbamoyl)oxy)methyl)-1H-1,2,3-triazol-4-yl)phenoxy)cyclohexane-1-carboxylic acid (58), (1S,3S)-3-(4-(1-methyl-5-(((methyl(propyl)carbamoyl)oxy)methyl)-1H-1,2,3-triazol-4-yl)phenoxy)cyclohexane-1-carboxylic acid (59), (1S,3S)-3-(4-(5-(((benzyl(methyl)carbamoyl)oxy)methyl)-1-methyl-1H-1,2,3-triazol-4-yl)phenoxy)cyclohexane-1-carboxylic acid (60), (1S,3S)-3-(4-(5-((((cyclopropylmethyl)(methyl)carbamoyl) oxy)methyl)-1-methyl-1H-1,2,3-triazol-4-yl)phenoxy)cyclohexane-1-carboxylic acid (61), (1R,3R)-3-(4-(5-(((isopentyl(methyl)carbamoyl)oxy) methyl)-1-methyl-1H-1,2,3-triazol-4-yl)phenoxy)cyclohexane-1-carboxylic acid (62), (1R,3R)-3-(4-(5-(((isopentyl(methyl)carbamoyl)oxy) methyl)-1-methyl-1H-1,2,3-triazol-4-yl)-2-methylphenoxy)cyclohexane-1-carboxylic acid (63), (1S,3S)-3-(4-(5-(((butyl(methyl)carbamoyl)oxy)methyl)-1-methyl-1H-1,2,3-triazol-4-yl)phenoxy)cyclohexane-1-carboxylic acid (64), (1S,3S)-3-(4-(5-((((1-cyclopropylethyl)(methyl)carbamoyl) oxy)methyl)-1-methyl-1H-1,2,3-triazol-4-yl)phenoxy)cyclohexane-1-carboxylic acid (65), (1S,3S)-3-(4-(5-((((cyclobutylmethyl)(methyl)carbamoyl) oxy)methyl)-1-methyl-1H-1,2,3-triazol-4-yl)phenoxy)cyclohexane-1-carboxylic acid (66), (1S,3S)-3-(4-(5-((((1-cyclobutylethyl)(methyl)carbamoyl) oxy)methyl)-1-methyl-1H-1,2,3-triazol-4-yl)phenoxy)cyclohexane-1-carboxylic acid (67), (1S,3S)-3-(4-(5-(((sec-butyl(methyl)carbamoyl)oxy) methyl)-1-methyl-1H-1,2,3-triazol-4-yl)phenoxy)cyclohexane-1-carboxylic acid (68), (3S)-3-((6-(5-((((cyclobutylmethyl)(methyl)carbamoyl) oxy)methyl)-1-methyl-1H-1,2,3-triazol-4-yl)-2-methylpyridin-3-yl)oxy)cyclohexane-1-carboxylic-1-d acid (69), (1S,3S)-3-(4-(5-(((((R)-1-cyclopropylethyl)(methyl)carbamoyl)oxy)methyl)-1-methyl-1H-1,2,3-triazol-4-yl)-2-fluorophenoxy)cyclohexane-1-carboxylic acid (70), (1S,3S)-3-(4-(5-(((isopentyl(methyl)carbamoyl)oxy) methyl)-1-methyl-1H-1,2,3-triazol-4-yl)phenoxy)cyclohexane-1-carboxylic acid (71), (1-Methyl-4-(4-(((1R,3R)-3-((methylsulfonyl)carbamoyl) cyclohexyl)oxy)phenyl)-1H-1,2,3-triazol-5-yl)methyl cyclopentyl(methyl)carbamate (72), (1S,3S)-3-(4-(5-(((cyclobutyl(methyl)carbamoyl)oxy) methyl)-1-methyl-1H-1,2,3-triazol-4-yl)phenoxy)cyclohexane-1-carboxylic acid (73), (1S,3S)-3-(4-(5-((((Dicyclopropylmethyl)(methyl)carbamoyl)oxy)methyl)-1-methyl-1H-1,2,3-triazol-4-yl)phenoxy)cyclohexanecarboxylic acid (74), (1S,3S)-3-(4-(1-methyl-5-(((methyl(1-propylcyclopropyl) carbamoyl)oxy)methyl)-1H-1,2,3-triazol-4-yl)phenoxy) cyclohexane-1-carboxylic acid (75), (1S,3S)-3-(4-(1-methyl-5-(((methyl(pentan-3-yl)carbamoyl)oxy)methyl)-1H-1,2,3-triazol-4-yl)phenoxy)cyclohexane-1-carboxylic acid (76), (1S,3S)-3-((6-(1-methyl-5-(((methyl(pentan-3-yl)carbamoyl)oxy)methyl)-1H-1,2,3-triazol-4-yl)pyridin-3-yl)oxy) cyclohexane-1-carboxylic acid (77), (1S,3S)-3-((6-(1-methyl-5-(((methyl(2-methylpentan-2-yl) carbamoyl)oxy)methyl)-1H-1,2,3-triazol-4-yl)pyridin-3-yl)oxy)cyclohexane-1-carboxylic acid (78), (1S,3S)-3-((6-(1-methyl-5-(((methyl(1-methylcyclopropyl) carbamoyl)oxy)methyl)-1H-1,2,3-triazol-4-yl)pyridin-3-yl)oxy)cyclohexane-1-carboxylic acid (79), (1S,3S)-3-((6-(5-((((Dicyclopropylmethyl)(methyl)carbamoyl)oxy)methyl)-1-methyl-1H-1,2,3-triazol-4-yl)pyridin-3-yl)oxy)cyclohexanecarboxylic acid (80), (1S,3S)-3-((6-(1-methyl-5-(((methyl(1-propylcyclopropyl) carbamoyl)oxy)methyl)-1H-1,2,3-triazol-4-yl)pyridin-3-yl)oxy)cyclohexane-1-carboxylic acid (81, 82), (1S,3S)-3-((2-Methyl-6-(1-methyl-5-(((methyl(pentan-3-yl) carbamoyl)oxy)methyl)-1H-1,2,3-triazol-4-yl)pyridin-3-yl)oxy)cyclohexanecarboxylic acid (83), (1S,3S)-3-((2-methyl-6-(1-methyl-5-(((methyl(2-methylpentan-2-yl)carbamoyl)oxy)methyl)-1H-1,2,3-triazol-4-yl)pyridin-3-yl)oxy)cyclohexanecarboxylic acid (84), (1S,3S)-3-((2-methyl-6-(1-methyl-5-(((methyl(1-methylcyclopropyl)carbamoyl)oxy)methyl)-1H-1,2,3-triazol-4-yl) pyridin-3-yl)oxy)cyclohexane-1-carboxylic acid (85), (1S,3S)-3-((6-(5-((((Dicyclopropylmethyl)(methyl)carbamoyl)oxy)methyl)-1-methyl-1H-1,2,3-triazol-4-yl)-2-methylpyridin-3-yl)oxy)cyclohexanecarboxylic acid (86), (1S,3S)-3-((2-methyl-6-(1-methyl-5-(((methyl(1-propylcyclopropyl)carbamoyl)oxy)methyl)-1H-1,2,3-triazol-4-yl) pyridin-3-yl)oxy)cyclohexane-1-carboxylic acid (87), (rac)-trans-3-((6-(5-(((cyclopentyl(methyl)carbamoyl)oxy) methyl)-1-methyl-1H-1,2,3-triazol-4-yl)-2-methylpyridin-3-yl)oxy)-1-fluorocyclohexane-1-carboxylic acid (88), trans-3-((6-(5-(((cyclopentyl(methyl)carbamoyl)oxy) methyl)-1-methyl-1H-1,2,3-triazol-4-yl)pyridin-3-yl) oxy)-1-fluorocyclohexane-1-carboxylic acid (89), trans-3-((6-(5-((((cyclobutylmethyl)(methyl)carbamoyl) oxy)methyl)-1-methyl-1H-1,2,3-triazol-4-yl)pyridin-3-yl)oxy)-1-fluorocyclohexane-1-carboxylic acid (90), trans-3-((6-(5-((((cyclobutylmethyl)(methyl)carbamoyl) oxy)methyl)-1-methyl-1H-1,2,3-triazol-4-yl)-2-methylpyridin-3-yl)oxy)cyclohexane-1-carboxylic acid (91), cis-3-((6-(5-(((((cyclobutylmethyl)(methyl)carbamoyl)oxy) methyl)-1-methyl-1H-1,2,3-triazol-4-yl)-2-methylpyridin-3-yl)oxy)cyclohexane-1-carboxylic acid (92), cis-3-((6-(5-(((((cyclobutylmethyl)(methyl)carbamoyl)oxy) methyl)-1-methyl-1H-1,2,3-triazol-4-yl)-2-methylpyridin-3-yl)oxy)cyclopentane-1-carboxylic acid (93), (1S,3S)-3-(4-(5-(1-((cyclopentyl(methyl)carbamoyl)oxy) ethyl)-1-methyl-1H-1,2,3-triazol-4-yl)phenoxy)cyclohexane-1-carboxylic acid (94), (Cis)-3-((6-(5-((((cyclobutylmethyl)(methyl)carbamoyl) oxy)methyl)-1-methyl-1H-1,2,3-triazol-4-yl)-2-methylpyridin-3-yl)oxy)cyclohexane-1-carboxylic acid (Enantiomer A, 95), (Cis)-3-((6-(5-((((cyclobutylmethyl)(methyl)carbamoyl) oxy)methyl)-1-methyl-1H-1,2,3-triazol-4-yl)-2-methylpyridin-3-yl)oxy)cyclohexane-1-carboxylic acid (Enantiomer B, 96), (1R,3R)-3-((6-(5-(((((cyclobutylmethyl)(methyl)carbamoyl) oxy)methyl)-1-methyl-1H-1,2,3-triazol-4-yl)-2-methylpyridin-3-yl)oxy)cyclohexane-1-carboxylic acid (97), (1S,3S)-3-((6-(5-((((2-fluorobenzyl)(methyl)carbamoyl) oxy)methyl)-1-methyl-1H-1,2,3-triazol-4-yl)-2-methylpyridin-3-yl)oxy)cyclohexane-1-carboxylic acid (98), (1S,3S)-3-((6-(5-((((1-cyclobutylpropyl)(methyl)carbamoyl)oxy)methyl)-1-methyl-1H-1,2,3-triazol-4-yl)-2-methylpyridin-3-yl)oxy)cyclohexane-1-carboxylic acid (99), (1S,3S)-3-((2-methyl-6-(1-methyl-5-(((methyl(1-phenylcyclopropyl)carbamoyl)oxy)methyl)-1H-1,2,3-triazol-4-yl) pyridin-3-yl)oxy)cyclohexane-1-carboxylic acid (100), (1S,3S)-3-((2-methyl-6-(1-methyl-5-(((methyl(3,3,3-trifluoropropyl)carbamoyl)oxy)methyl)-1H-1,2,3-triazol-4-yl)pyridin-3-yl)oxy)cyclohexane-1-carboxylic acid (101), (1S,3S)-3-((6-(5-(((bicyclo[1.1.1]pentan-1-yl(methyl)carbamoyl)oxy)methyl)-1-methyl-1H-1,2,3-triazol-4-yl)-2-methylpyridin-3-yl)oxy)cyclohexane-1-carboxylic acid (102), (1S,3S)-3-((2-methyl-6-(1-methyl-5-(((methyl(phenethyl) carbamoyl)oxy)methyl)-1H-1,2,3-triazol-4-yl)pyridin-3-yl)oxy)cyclohexane-1-carboxylic acid (103), (1S,3S)-3-((2-methyl-6-(1-methyl-5-(((methyl(propyl)carbamoyl)oxy)methyl)-1H-1,2,3-triazol-4-yl)pyridin-3-yl)oxy)cyclohexane-1-carboxylic acid (104), (1S,3S)-3-((6-(5-(((bicyclo[1.1.1]pentan-1-ylcarbamoyl)oxy)methyl)-1-methyl-1H-1,2,3-triazol-4-yl)-2-methylpyridin-3-yl)oxy)cyclohexane-1-carboxylic acid (105), (1S,3S)-3-((6-(5-((((1,3-dimethylcyclobutyl)(methyl)carbamoyl)oxy)methyl)-1-methyl-1H-1,2,3-triazol-4-yl)-2-methylpyridin-3-yl)oxy)cyclohexane-1-carboxylic acid (Enantiomer A, 106)

(1S,3S)-3-((6-(5-((((1,3-dimethylcyclobutyl)(methyl)carbamoyl)oxy)methyl)-1-methyl-1H-1,2,3-triazol-4-yl)-2-methylpyridin-3-yl)oxy)cyclohexane-1-carboxylic acid (Enantiomer B, 107), (1S,3S)-3-((6-(5-((((cyclobutylmethyl)carbamoyl)oxy)methyl)-1-methyl-1H-1,2,3-triazol-4-yl)-2-methylpyridin-3-yl)oxy)cyclohexane-1-carboxylic acid (108), (1S,3S)-3-((6-(5-((((cyclopentylmethyl)(methyl)carbamoyl)oxy)methyl)-1-methyl-1H-1,2,3-triazol-4-yl)-2-methylpyridin-3-yl)oxy)cyclohexane-1-carboxylic acid (109), (1S,3S)-3-((6-(5-((((cyclopropylmethyl)(methyl)carbamoyl)oxy)methyl)-1-(methyl-d3)-1H-1,2,3-triazol-4-yl)pyridin-3-yl)oxy)cyclohexane-1-carboxylic acid (110), (1S,3S)-3-((6-(5-(((cyclopentyl(methyl)carbamoyl)oxy)methyl)-1-(methyl-d3)-1H-1,2,3-triazol-4-yl)pyridin-3-yl)oxy)cyclohexane-1-carboxylic acid (111), (1S,3S)-3-((6-(5-(((butyl(methyl)carbamoyl)oxy)methyl)-1-(methyl-d3)-1H-1,2,3-triazol-4-yl)pyridin-3-yl)oxy)cyclohexane-1-carboxylic acid (112), (1S,3S)-3-((6-(5-((((cyclobutylmethyl)(methyl)carbamoyl)oxy)methyl)-1-(methyl-d3)-1H-1,2,3-triazol-4-yl)pyridin-3-yl)oxy)cyclohexane-1-carboxylic acid (113), (1S,3S)-3-((6-(5-((((cyclobutylmethyl)(methyl-d3)carbamoyl)oxy)methyl)-1-methyl-1H-1,2,3-triazol-4-yl)-2-methylpyridin-3-yl)oxy)cyclohexane-1-carboxylic acid (114), (3S)-3-((6-(5-((((cyclobutylmethyl)(methyl)carbamoyl)oxy)methyl)-1-methyl-1H-1,2,3-triazol-4-yl)-2-methylpyridin-3-yl)oxy)cyclohexane-1-carboxylic-1-d acid (115), (1S,3S)-3-((6-(5-(((isobutyl(methyl)carbamoyl)oxy)methyl)-1-methyl-1H-1,2,3-triazol-4-yl)-2-methylpyridin-3-yl)oxy)cyclohexane-1-carboxylic acid (116), (1S,3S)-3-((2-methyl-6-(1-methyl-5-(((methyl((tetrahydro-2H-pyran-4-yl)methyl)carbamoyl)oxy)methyl)-1H-1,2,3-triazol-4-yl)pyridin-3-yl)oxy)cyclohexane-1-carboxylic acid (117), (1S,3S)-3-((2-methyl-6-(1-methyl-5-(((methyl(pyridin-2-ylmethyl)carbamoyl)oxy)methyl)-1H-1,2,3-triazol-4-yl)pyridin-3-yl)oxy)cyclohexane-1-carboxylic acid (118), (1S,3S)-3-((6-(5-(((ethyl(methyl)carbamoyl)oxy)methyl)-1-methyl-1H-1,2,3-triazol-4-yl)-2-methylpyridin-3-yl)oxy)cyclohexane-1-carboxylic acid (119), (1S,3S)-3-((2-methyl-6-(1-methyl-5-(((methyl(pyridin-3-ylmethyl)carbamoyl)oxy)methyl)-1H-1,2,3-triazol-4-yl)pyridin-3-yl)oxy)cyclohexane-1-carboxylic acid (120), (1S,3S)-3-((2-methyl-6-(1-methyl-5-(((methyl(pyrimidin-2-ylmethyl)carbamoyl)oxy)methyl)-1H-1,2,3-triazol-4-yl)pyridin-3-yl)oxy)cyclohexane-1-carboxylic acid (121), (1S,3S)-3-((2-methyl-6-(1-methyl-5-(((methyl(pyridin-4-ylmethyl)carbamoyl)oxy)methyl)-1H-1,2,3-triazol-4-yl)pyridin-3-yl)oxy)cyclohexane-1-carboxylic acid (122), (1S,3S)-3-((2-methyl-6-(1-methyl-5-(((methyl(pyrazin-2-ylmethyl) carbamoyl)oxy)methyl)-1H-1,2,3-triazol-4-yl)pyridin-3-yl) oxy) cyclohexane-1-carboxylic acid (123), (1S,3S)-3-((2-methyl-6-(1-methyl-5-(((methyl((1-methyl-1H-pyrazol-5-yl)methyl)carbamoyl)oxy)methyl)-1H-1,2,3-triazol-4-yl)pyridin-3-yl)oxy)cyclohexane-1-carboxylic acid (124), (1S,3S)-3-((2-methyl-6-(1-methyl-5-(((methyl(morpholin-3-ylmethyl)carbamoyl)oxy)methyl)-1H-1,2,3-triazol-4-yl)pyridin-3-yl)oxy)cyclohexane-1-carboxylic acid (125), (1S,3S)-3-((2-methyl-6-(1-methyl-5-(((methyl((tetrahydrofuran-3-yl)methyl)carbamoyl)oxy)methyl)-1H-1,2,3-triazol-4-yl)pyridin-3-yl)oxy)cyclohexane-1-carboxylic acid (126), (1S,3S)-3-((6-(5-(((butyl(ethyl)carbamoyl)oxy)methyl)-1-methyl-1H-1,2,3-triazol-4-yl)-2-methylpyridin-3-yl)oxy)cyclohexane-1-carboxylic acid (127), (1S,3S)-3-((6-(5-(((ethyl(propyl)carbamoyl)oxy)methyl)-1-methyl-1H-1,2,3-triazol-4-yl)-2-methylpyridin-3-yl)oxy)cyclohexane-1-carboxylic acid (128), (1S,3S)-3-((6-(5-((((1-isopropylcyclopropyl)(methyl)carbamoyl)oxy)methyl)-1-methyl-1H-1,2,3-triazol-4-yl)-2-methylpyridin-3-yl)oxy)cyclohexane-1-carboxylic acid (129), (1S,3S)-3-((6-(5-((((1-isobutylcyclopropyl)(methyl)carbamoyl)oxy)methyl)-1-methyl-1H-1,2,3-triazol-4-yl)-2-methylpyridin-3-yl)oxy)cyclohexane-1-carboxylic acid (130), (1S,3S)-3-((6-(5-((((1-ethylcyclopropyl)(methyl)carbamoyl)oxy)methyl)-1-methyl-1H-1,2,3-triazol-4-yl)-2-methylpyridin-3-yl)oxy)cyclohexane-1-carboxylic acid (131), (1S,3S)-3-((2-methyl-6-(1-methyl-5-(((methyl(1-propylcyclobutyl)carbamoyl)oxy)methyl)-1H-1,2,3-triazol-4-yl)pyridin-3-yl)oxy)cyclohexane-1-carboxylic acid (132), (1S,3 S)-3-((6-(5-((((1-ethylcyclobutyl)(methyl)carbamoyl)oxy)methyl)-1-methyl-1H-1,2,3-triazol-4-yl)-2-methylpyridin-3-yl)oxy)cyclohexane-1-carboxylic acid (133), (1S,3S)-3-((6-(5-(((2-azaspiro[3.3]heptane-2-carbonyl)oxy)methyl)-1-methyl-1H-1,2,3-triazol-4-yl)-2-methylpyridin-3-yl)oxy)cyclohexane-1-carboxylic acid (134), (1S,3 S)-3-((6-(5-(((6-azaspiro[3.4]octane-6-carbonyl)oxy)methyl)-1-methyl-1H-1,2,3-triazol-4-yl)-2-methylpyridin-3-yl)oxy)cyclohexane-1-carboxylic acid (135), (1S,3S)-3-((6-(5-(((cyclobutyl(methyl)carbamoyl)oxy)methyl)-1-methyl-1H-1,2,3-triazol-4-yl)-2-methylpyridin-3-yl)oxy)cyclohexane-1-carboxylic acid (136), (1S,3S)-3-((6-(5-(((3,3-dimethylpiperidine-1-carbonyl)oxy)methyl)-1-methyl-1H-1,2,3-triazol-4-yl)-2-methylpyridin-3-yl)oxy)cyclohexane-1-carboxylic acid (137), (1S,3S)-3-((6-(5-(((isopropyl(methyl)carbamoyl)oxy)methyl)-1-methyl-1H-1,2,3-triazol-4-yl)-2-methylpyridin-3-yl)oxy)cyclohexane-1-carboxylic acid (138), (1S,3S)-3-((6-(5-((((3,3-difluorocyclobutyl)(methyl)carbamoyl)oxy)methyl)-1-methyl-1H-1,2,3-triazol-4-yl)-2-methylpyridin-3-yl)oxy)cyclohexane-1-carboxylic acid (139), (1S,3S)-3-((6-(5-(((3,3-dimethylpyrrolidine-1-carbonyl)oxy)methyl)-1-methyl-1H-1,2,3-triazol-4-yl)-2-methylpyridin-3-yl)oxy)cyclohexane-1-carboxylic acid (140), (1R,3S)-3-((6-(5-((((3,3-difluoro-cyclobutyl)(methyl)carbamoyl)oxy)methyl)-1-methyl-1H-1,2,3-triazol-4-yl)-2-methylpyridin-3-yl)oxy) cyclohexane-1-carboxylic acid; cis isomer from epimerization in final ester hydrolysis (141), (1S,3S)-3-((6-(5-(((cyclopropyl(methyl)carbamoyl)oxy)methyl)-1-methyl-1H-1,2,3-triazol-4-yl)-2-methylpyridin-3-yl)oxy)cyclohexane-1-carboxylic acid (142), (1S,3S)-3-((6-(5-(((3,3-difluoro-pyrrolidine-1-carbonyl)oxy)methyl)-1-methyl-1H-1,2,3-triazol-4-yl)-2-methyl-pyridin-3-yl)oxy)cyclohexane-1-carboxylic acid (143), (1S,3S)-3-((6-(5-(((5-azaspiro[2.4]heptane-5-carbonyl)oxy)methyl)-1-methyl-1H-1,2,3-triazol-4-yl)-2-methylpyridin-3-yl)oxy)cyclohexane-1-carboxylic acid (144), (1S,3S)-3-((6-(5-(((((3,3-difluoro-cyclobutyl)methyl)(methyl)carbamoyl)oxy)methyl)-1-methyl-1H-1,2,3-triazol-4-yl)-2-methylpyridin-3-yl)oxy)cyclohexane-1-carboxylic acid (145), (1R,3S)-3-((2-methyl-6-(1-methyl-5-(((methyl(spiro[2.3]hexan-1-yl)carbamoyl)oxy)methyl)-1H-1,2,3-triazol-4-yl)pyridin-3-yl)oxy)cyclohexane-1-carboxylic acid (cis isomer from epimerization in final ester hydrolysis) (146), (1S,3S)-3-((2-methyl-6-(1-methyl-5-(((3-methylpyrrolidine-1-carbonyl)oxy)methyl)-1H-1,2,3-triazol-4-yl)pyridin-3-yl)oxy)cyclohexane-1-carboxylic acid (mixture of diastereomers) (147), (1S,3S)-3-((6-(5-(((-2-azabicyclo[2.2.1]heptane-2-carbonyl)oxy)methyl)-1-methyl-1H-1,2,3-triazol-4-yl)-2-methylpyridin-3-yl)oxy)cyclohexane-1-carboxylic acid (mixture of diastereomers) (148), (1S,3S)-3-((2-methyl-6-(1-methyl-5-(((octahydrocyclopenta[b]pyrrole-1-carbonyl)oxy)methyl)-1H-1,2,3-triazol-4-yl)pyridin-3-yl)oxy)cyclohexane-1-carboxylic acid (mixture of diastereomers) (149), (1S,3 S)-3-((6-(5-(((3-(cyclopropylmethyl)pyrrolidine-1-carbonyl)oxy)methyl)-1-methyl-1H-1,2,3-triazol-4-yl)-2-methylpyridin-3-yl)oxy)cyclohexane-1-carboxylic acid (mixture of diastereomers) (150), (1S,3S)-3-((6-(5-(((3-isobutylpyrrolidine-1-carbonyl)oxy)methyl)-1-methyl-1H-1,2,3-triazol-4-yl)-2-methylpyridin-3-yl)oxy)cyclohexane-1-carboxylic acid (mixture of diastereomers) (151), (1S,3S)-3-((6-(5-(((2-ethylpyrrolidine-1-carbonyl)oxy)methyl)-1-methyl-1H-1,2,3-triazol-4-yl)-2-methylpyridin-3-yl)oxy)cyclohexane-1-carboxylic acid (mixture of diastereomers) (152), (1S,3S)-3-((6-(5-(((2-isobutylpyrrolidine-1-carbonyl)oxy)methyl)-1-methyl-1H-1,2,3-triazol-4-yl)-2-methylpyridin-3-yl)oxy)cyclohexane-1-carboxylic acid (mixture of diastereomers) (153), (1S,3S)-3-((2-methyl-6-(1-methyl-5-(((2-(trifluoromethyl)pyrrolidine-1-carbonyl)oxy)methyl)-1H-1,2,3-triazol-4-yl)pyridin-3-yl)oxy)cyclohexane-1-carboxylic acid (mixture of diastereomers) (154), (1S,3S)-3-((6-(5-(((3,3-dimethylazetidine-1-carbonyl)oxy)methyl)-1-methyl-1H-1,2,3-triazol-4-yl)-2-methylpyridin-3-yl)oxy)cyclohexane-1-carboxylic acid (155), (1S,3S)-3-((2-methyl-6-(1-methyl-5-(((3-methylazetidine-1-carbonyl)oxy)methyl)-1H-1,2,3-triazol-4-yl)pyridin-3-yl)oxy)cyclohexane-1-carboxylic acid (156), (1S,3 S)-3-((2-methyl-6-(1-methyl-5-(((2-methylazetidine-1-carbonyl)oxy)methyl)-1H-1,2,3-triazol-4-yl)pyridine-3-yl)oxy)cyclohexane-1-carboxylic acid (mixture of diastereomers) (157), (1R,3S)-3-((2-methyl-6-(1-methyl-5-(((methyl(spiro[3.3]heptan-2-yl)carbamoyl)oxy)methyl)-1H-1,2,3-triazol-4-yl)pyridin-3-yl)oxy)cyclohexane-1-carboxylic acid (158), (1S,3 S)-3-((6-(5-(((2-azaspiro[3.4]octane-2-carbonyl)oxy)methyl)-1-methyl-1H-1,2,3-triazol-4-yl)-2-methylpyridin-3-yl)oxy)cyclohexane-1-carboxylic acid (159), (1R,3S)-3-((6-(5-((((3,3-dimethylcyclobutyl)(methyl)carbamoyl)oxy)methyl)-1-methyl-1H-1,2,3-triazol-4-yl)-2-methylpyridin-3-yl)oxy)cyclohexane-1-carboxylic acid (cis isomer from epimerization in final ester hydrolysis step) (160), (1S,3S)-3-((2-methyl-6-(1-methyl-5-(((3-methylpiperidine-1-carbonyl)oxy)methyl)-1H-1,2,3-triazol-4-yl)pyridin-3-yl)oxy)cyclohexane-1-carboxylic acid (mixture of diastereomers) (161), (1S,3S)-3-((6-(5-((((2-cyclopropylethyl)(methyl)carbamoyl)oxy)methyl)-1-methyl-1H-1,2,3-triazol-4-yl)-2-methylpyridin-3-yl)oxy)cyclohexane-1-carboxylic acid (162), (1S,3S)-3-((6-(5-(((3-isopropylpyrrolidine-1-carbonyl)oxy)methyl)-1-methyl-1H-1,2,3-triazol-4-yl)-2-methylpyridin-3-yl)oxy)cyclohexane-1-carboxylic acid (mixture of diastereomers) (163), (1S,3S)-3-((6-(5-(((3-cyclopropylpyrrolidine-1-carbonyl)oxy)methyl)-1-methyl-1H-1,2,3-triazol-4-yl)-2-methyl-pyridin-3-yl)oxy)cyclohexane-1-carboxylic acid (mixture of diastereomers) (164), (1S,3S)-3-((6-(5-(((3-ethylpyrrolidine-1-carbonyl) oxy)methyl)-1-methyl-1H-1,2,3-triazol-4-yl)-2-methylpyridin-3-yl)oxy)cyclohexane-1-carboxylic acid (mixture of diastereomers) (165), (1S,3S)-3-((2-methyl-6-(1-methyl-5-(((3-propylpyrrolidine-1-carbonyl)oxy)methyl)-1H-1,2,3-triazol-4-yl)pyridin-3-yl)oxy) cyclohexane-1-carboxylic acid (mixture of diastereomers) (166), (1S,3S)-3-((6-(5-(((-7-azabicyclo[2.2.1]heptane-7-carbonyl)oxy) methyl)-1-methyl-1H-1,2,3-triazol-4-yl)-2-methylpyridin-3-yl)oxy) cyclohexane-1-carboxylic acid (167), (1S,3S)-3-((6-(5-((((3,3-dimethyl-cyclobutyl)(methyl)carbamoyl)oxy)methyl)-1-methyl-1H-1,2,3-triazol-4-yl)-2-methylpyridin-3-yl)oxy) cyclohexane-1-carboxylic acid (168), (1S,3S)-3-((2-methyl-6-(1-methyl-5-(((3-phenylpyrrolidine-1-carbonyl) oxy)methyl)-1H-1,2,3-triazol-4-yl)pyridin-3-yl)oxy)cyclohexane-1-carboxylic acid (mixture of diastereomers) (169), (1S,3S)-3-((6-(5-(((tert-butyl (methyl)carbamoyl)oxy)methyl)-1-methyl-1H-1,2,3-triazol-4-yl)-2-methylpyridin-3-yl)oxy)cyclohexane-1-carboxylic acid (170), (1S,3S)-3-((6-(5-(((6-azaspiro[2.5]octane-6-carbonyl)oxy)methyl)-1-methyl-1H-1,2,3-triazol-4-yl)-2-methylpyridin-3-yl)oxy)cyclohexane-1-carboxylic acid (171), (1R,3 S)-3-((2-methyl-6-(1-methyl-5-(((methyl(3-methylbut-2-en-1-yl)carbamoyl)oxy)methyl)-1H-1,2,3-triazol-4-yl)pyridin-3-yl)oxy) cyclohexane-1-carboxylic acid (cis isomer from epimerization during final hydrolysis step) (172), (1S,3S)-3-((6-(1-methyl-5-(((methyl(propyl)carbamoyl) oxy)methyl)-1H-1,2,3-triazol-4-yl)pyridin-3-yl)oxy)cyclohexane-1-carboxylic acid (173), (1S,3S)-3-((6-(5-(((cyclobutyl(methyl)carbamoyl)oxy) methyl)-1-methyl-1H-1,2,3-triazol-4-yl)pyridin-3-yl) oxy)cyclohexane-1-carboxylic acid (174), (1S,3S)-3-((6-(5-(((6-azaspiro[3.4]octane-6-carbonyl)oxy) methyl)-1-methyl-1H-1,2,3-triazol-4-yl)pyridin-3-yl) oxy) cyclohexane-1-carboxylic acid (175), (1S,3S)-3-((6-(5-(((2-azaspiro[3.3]heptane-2-carbonyl)oxy) methyl)-1-methyl-1H-1,2,3-triazol-4-yl)pyridin-3-yl) oxy) cyclohexane-1-carboxylic acid (176), (1S,3S)-3-((2-methyl-6-(1-methyl-5-(((methyl(3-methylbut-2-en-1-yl)carbamoyl)oxy)methyl)-1H-1,2,3-triazol-4-yl)pyridin-3-yl)oxy) cyclohexane-1-carboxylic acid (177), (1S,3S)-3-((6-(5-((((1-fluoro-2-methylpropan-2-yl)(methyl)carbamoyl)oxy)methyl)-1-methyl-1H-1,2,3-triazol-4-yl)-2-methyl-pyridin-3-yl)oxy)cyclohexane-1-carboxylic acid (178), (1S,3S)-3-((2-methyl-6-(1-methyl-5-(((methyl(spiro[2.3]hexan-5-yl)carbamoyl)oxy)methyl)-1H-1,2,3-triazol-4-yl)pyridin-3-yl)oxy) cyclohexane-1-carboxylic acid (179), (1S,3S)-3-((6-(1-methyl-5-(((methyl(spiro[3.3]heptan-2-yl)carbamoyl)oxy)methyl)-1H-1,2,3-triazol-4-yl)pyridin-3-yl)oxy) cyclohexane-1-carboxylic acid (180), (1S,3S)-3-((6-(5-((((3,3-dimethylcyclobutyl)(methyl)carbamoyl)oxy)methyl)-1-methyl-1H-1,2,3-triazol-4-yl)pyridin-3-yl)oxy)cyclohexane-1-carboxylic acid (181), (1S,3S)-3-((6-(5-((((3-fluorocyclobutyl)(methyl)carbamoyl)oxy)methyl)-1-methyl-1H-1,2,3-triazol-4-yl)-2-methylpyridin-3-yl)oxy)cyclohexane-1-carboxylic acid (mixture of diastereomers) (182), (1S,3S)-3-((6-(1-methyl-5-(((methyl(spiro[2.3]hexan-5-yl)carbamoyl)oxy)methyl)-1H-1,2,3-triazol-4-yl)pyridin-3-yl)oxy)cyclohexane-1-carboxylic acid (183), (1S,3S)-3-((6-(5-(((((2,2-dimethylcyclopropyl)methyl)(methyl)carbamoyl)oxy)methyl)-1-methyl-1H-1,2,3-triazol-4-yl)-2-methylpyridin-3-yl)oxy)cyclohexane-1-carboxylic acid (mixture of diastereomers) (184), (1S,3S)-3-((6-(5-(((((2,2-dimethylcyclopropyl)methyl)(methyl)carbamoyl)oxy)methyl)-1-methyl-1H-1,2,3-triazol-4-yl)pyridin-3-yl)oxy)cyclohexane-1-carboxylic acid (mixture of diastereomers) (185), (1S,3S)-3-((6-(5-(((((2,2-difluorocyclopropyl)methyl)(methyl)carbamoyl)oxy)methyl)-1-methyl-1H-1,2,3-triazol-4-yl)pyridin-3-yl)oxy)cyclohexane-1-carboxylic acid (mixture of diastereomers) (186), (1S,3S)-3-((6-(5-((((3-fluoro-3-methylbutyl)(methyl)carbamoyl)oxy)methyl)-1-methyl-1H-1,2,3-triazol-4-yl)-2-methylpyridin-3-yl)oxy)cyclohexane-1-carboxylic acid (187), (1S,3S)-3-((6-(5-((((3-fluoro-3-methylbutyl)(methyl)carbamoyl)oxy)methyl)-1-methyl-1H-1,2,3-triazol-4-yl)pyridin-3-yl)oxy)cyclohexane-1-carboxylic acid (188), (1S,3 S)-3-((6-(5-(((((1-fluorocyclobutyl)methyl)(methyl)carbamoyl)oxy)methyl)-1-methyl-1H-1,2,3-triazol-4-yl)-2-methylpyridin-3-yl)oxy)cyclohexane-1-carboxylic acid (189), (1S,3S)-3-((6-(5-((((3-fluoropropyl)(methyl)carbamoyl)oxy)methyl)-1-methyl-1H-1,2,3-triazol-4-yl)-2-methylpyridin-3-yl)oxy)cyclohexane-1-carboxylic acid (190), (1S,3S)-3-((6-(5-((((4-fluorobutyl)(methyl)carbamoyl)oxy)methyl)-1-methyl-1H-1,2,3-triazol-4-yl)-2-methylpyridin-3-yl)oxy)cyclohexane-1-carboxylic acid (191), (1S,3S)-3-((6-(5-((((4-fluorobutyl)(methyl)carbamoyl)oxy)methyl)-1-methyl-1H-1,2,3-triazol-4-yl)-2-methylpyridin-3-yl)oxy)cyclohexane-1-carboxylic acid (192), (1R,3R)-3-((2-methyl-6-(1-methyl-5-(((methyl(propyl)carbamoyl)oxy)methyl)-1H-1,2,3-triazol-4-yl)pyridin-3-yl)oxy)cyclohexane-1-carboxylic acid (193), (1S,3 S)-3-((6-(5-(((((cyclopropylmethyl)(methyl) carbamoyl)oxy)methyl)-1-methyl-1H-1,2,3-triazol-4-yl)-2-ethylpyridin-3-yl)oxy)cyclohexane-1-carboxylic acid (194), (1S,3S)-3-((6-(5-(((cyclopentyl(methyl)carbamoyl)oxy)methyl)-1-methyl-1H-1,2,3-triazol-4-yl)-2-ethylpyridin-3-yl)oxy)cyclohexane-1-carboxylic acid (195), (1S,3S)-3-((6-(5-((((cyclobutylmethyl)(methyl)carbamoyl)oxy)methyl)-1-methyl-1H-1,2,3-triazol-4-yl)-2-ethylpyridin-3-yl)oxy)cyclohexane-1-carboxylic acid (196), (1S,3S)-3-((2-ethyl-6-(5-(((isobutyl(methyl)carbamoyl)oxy)methyl)-1-methyl-1H-1,2,3-triazol-4-yl)pyridin-3-yl)oxy)cyclohexane-1-carboxylic acid (197), (1S,3S)-3-((6-(5-(((benzylcarbamoyl)oxy)methyl)-1-methyl-1H-1,2,3-triazol-4-yl)-2-ethylpyridin-3-yl)oxy)cyclohexane-1-carboxylic acid (198), (1S,3S)-3-((6-(5-(((butyl(methyl)carbamoyl)oxy)methyl)-1-methyl-1H-1,2,3-triazol-4-yl)-2-ethylpyridin-3-yl)oxy)cyclohexane-1-carboxylic acid (199), (1S,3S)-3-((2-ethyl-6-(1-methyl-5-(((methyl(propyl)carbamoyl)oxy)methyl)-1H-1,2,3-triazol-4-yl)pyridin-3-yl)oxy)cyclohexane-1-carboxylic acid (200), (1S,3S)-3-((6-(5-(((benzyl(methyl)carbamoyl)oxy)methyl)-1-methyl-1H-1,2,3-triazol-4-yl)-2-ethylpyridin-3-yl)oxy)cyclohexane-1-carboxylic acid (201), (1S,3S)-3-((2-ethyl-6-(5-(((ethyl(methyl)carbamoyl)oxy)methyl)-1-methyl-1H-1,2,3-triazol-4-yl)pyridin-3-yl)oxy)cyclohexane-1-carboxylic acid (202), (1S,3S)-3-((6-(5-(((cyclobutyl(methyl)carbamoyl)oxy)methyl)-1-methyl-1H-1,2,3-triazol-4-yl)-2-ethylpyridin-3-yl)oxy)cyclohexane-1-carboxylic acid (203), (1S,3S)-3-((6-(5-(((3,3-dimethylazetidine-1-carbonyl)oxy)methyl)-1-methyl-1H-1,2,3-triazol-4-yl)-2-ethylpyridin-3-yl)oxy)cyclohexane-1-carboxylic acid (204), (1S,3S)-3-((6-(5-(((bicyclo[1.1.1]pentan-1-ylcarbamoyl)oxy)methyl)-1-methyl-1H-1,2,3-triazol-4-yl)-2-ethylpyridin-3-yl)oxy) cyclohexane-1-carboxylic acid (205), (1S,3S)-3-((6-(5-(((bicyclo[1.1.1]pentan-1-yl(methyl)carbamoyl)oxy)methyl)-1-methyl-1H-1,2,3-triazol-4-yl)-2-ethylpyridin-3-yl)oxy)cyclohexane-1-carboxylic acid (206), (1S,3S)-3-((2-ethyl-6-(1-methyl-5-(((methyl(1-propylcyclopropyl) carbamoyl)oxy)methyl)-1H-1,2,3-triazol-4-yl)pyridin-3-yl)oxy) cyclohexane-1-carboxylic acid (207), (1S,3S)-3-((2-ethyl-6-(5-(((isopentyl(methyl)carbamoyl)oxy)methyl)-1-methyl-1H-1,2,3-triazol-4-yl)pyridin-3-yl)oxy)cyclohexane-1-carboxylic acid (208), (1S,3S)-3-((6-(5-((((2-cyclopropylethyl)(methyl)carbamoyl)oxy)methyl)-1-methyl-1H-1,2,3-triazol-4-yl)-2-ethylpyridin-3-yl)oxy)cyclohexane-1-carboxylic acid (209), (1S,3S)-3-((6-(5-(((2-azaspiro[3.3]heptane-2-carbonyl)oxy)methyl)-1-methyl-1H-1,2,3-triazol-4-yl)-2-ethylpyridin-3-yl)oxy)cyclohexane-1-carboxylic acid (210), (1S,3S)-3-((6-(5-(((5-azaspiro[2.4]heptane-5-carbonyl)oxy)methyl)-1-methyl-1H-1,2,3-triazol-4-yl)-2-ethylpyridin-3-yl)oxy)cyclohexane-1-carboxylic acid (211), (1S,3S)-3-((5-(5-(((butyl(methyl)carbamoyl)oxy)methyl)-1-methyl-1H-1,2,3-triazol-4-yl)pyrazin-2-yl)oxy)cyclohexane-1-carboxylic acid (212), (1S,3S)-3-((5-(5-(((((cyclopropylmethyl)(methyl)carbamoyl)oxy)methyl)-1-methyl-1H-1,2,3-triazol-4-yl)pyrazin-2-yl)oxy) cyclohexane-1-carboxylic acid (213), (1S,3 S)-3-((5-(5-(((((cyclobutylmethyl)(methyl)carbamoyl)oxy)methyl)-1-methyl-1H-1,2,3-triazol-4-yl)pyrazin-2-yl)oxy) cyclohexane-1-carboxylic acid (214), (1S,3S)-3-((5-(5-(((cyclopentyl(methyl)carbamoyl)oxy)methyl)-1-methyl-1H-1,2,3-triazol-4-yl)pyrazin-2-yl)oxy)cyclohexane-1-carboxylic acid (215), (1S,3S)-3-((3-methyl-5-(1-methyl-5-(((methyl(propyl)carbamoyl)oxy)methyl)-1H-1,2,3-triazol-4-yl)pyrazin-2-yl)oxy)cyclohexane-1-carboxylic acid (216), (1S,3S)-3-((5-(5-(((butyl (methyl)carbamoyl)oxy)methyl)-1-methyl-1H-1,2,3-triazol-4-yl)-3-methylpyrazin-2-yl)oxy) cyclohexane-1-carboxylic acid (219), (1S,3S)-3-((5-(5-(((((cyclopropyl-methyl)(methyl)carbamoyl) oxy)methyl)-1-methyl-1H-1,2,3-triazol-4-yl)-3-methyl-pyrazin-2-yl)oxy)cyclohexane-1-carboxylic acid (220), (1S,3S)-3-((5-(5-(((((cyclobutylmethyl)(methyl)carbamoyl)oxy)methyl)-1-methyl-1H-1,2,3-triazol-4-yl)-3-methyl-pyrazin-2-yl)oxy)cyclohexane-1-carboxylic acid (221), (1S,3S)-3-((5-(5-(((isopentyl (methyl)carbamoyl)oxy) methyl)-1-methyl-1H-1,2,3-triazol-4-yl)-3-methylpyrazin-2-yl)oxy) cyclohexane-1-carboxylic acid (222), (1S,3S)-3-((3-methyl-5-(1-methyl-5-(((methyl(pentyl)carbamoyl) oxy)methyl)-1H-1,2,3-triazol-4-yl)pyrazin-2-yl) oxy)cyclohexane-1-carboxylic acid (223), (1S,3S)-3-((5-(5-(((isobutyl(methyl)carbamoyl)oxy) methyl)-1-methyl-1H-1,2,3-triazol-4-yl)-3-methylpyrazin-2-yl)oxy) cyclohexane-1-carboxylic acid (224), (1S,3S)-3-((5-(5-((((2-cyclopropylethyl)(methyl)carbamoyl)oxy)methyl)-1-methyl-1H-1,2,3-triazol-4-yl)-3-methylpyrazin-2-yl) oxy)cyclohexane-1-carboxylic acid (225), (1S,3S)-3-((5-(5-(((cyclopentyl(methyl)carbamoyl)oxy) methyl)-1-methyl-1H-1,2,3-triazol-4-yl)-3-methylpyrazin-2-yl)oxy)cyclohexane-1-carboxylic acid (226), (1S,3S)-3-((5-(5-((((cyclopentylmethyl)(methyl)carbamoyl) oxy)methyl)-1-methyl-1H-1,2,3-triazol-4-yl)-3-methylpyrazin-2-yl)oxy)cyclohexane-1-carboxylic acid (227), (1S,3S)-3-((5-(5-(((benzyl(methyl)carbamoyl)oxy)methyl)-1-methyl-1H-1,2,3-triazol-4-yl)-3-methylpyrazin-2-yl) oxy) cyclohexane-1-carboxylic acid (228), (1S,3S)-3-((5-(5-(((cyclobutyl(methyl)carbamoyl)oxy) methyl)-1-methyl-1H-1,2,3-triazol-4-yl)-3-methylpyrazin-2-yl) oxy)cyclohexane-1-carboxylic acid (229), (1S,3S)-3-((5-(5-((((3-fluoropropyl)(methyl)carbamoyl) oxy)methyl)-1-methyl-1H-1,2,3-triazol-4-yl)-3-methylpyrazin-2-yl) oxy)cyclohexane-1-carboxylic acid (230), (1S,3S)-3-((3-methyl-5-(1-methyl-5-(((methyl(neopentyl) carbamoyl) oxy)methyl)-1H-1,2,3-triazol-4-yl)pyrazin-2-yl)oxy)cyclohexane-1-carboxylic acid (231), (1S,3 S)-3-((5-(5-((((2-fluoro-2-methylpropyl)(methyl)carbamoyl)oxy)methyl)-1-methyl-1H-1,2,3-triazol-4-yl)-3-methylpyrazin-2-yl) oxy)cyclohexane-1-carboxylic acid (232), (1S,3S)-3-((5-(5-((((((1-fluoro-cyclobutyl)methyl)(methyl) carbamoyl)oxy)methyl)-1-methyl-1H-1,2,3-triazol-4-yl)-3-methylpyrazin-2-yl)oxy)cyclohexane-1-carboxylic acid (233), (1S,3S)-3-((5-(5-(((((1-fluorocyclopentyl)methyl)(methyl) carbamoyl)oxy)methyl)-1-methyl-1H-1,2,3-triazol-4-yl)-3-methylpyrazin-2-yl)oxy)cyclohexane-1-carboxylic acid (234), (1S,3S)-3-((3-methyl-5-(1-methyl-5-(((methyl(((1R,2R)-2-methylcyclopropyl)methyl)carbamoyl)oxy)methyl)-1H-1,2,3-triazol-4-yl)pyrazin-2-yl)oxy)cyclohexane-1-carboxylic acid (235), (1S,3S)-3-((3-methyl-5-(1-methyl-5-(((methyl(((1S,2S)-2-methyl cyclopropyl)methyl)carbamoyl)oxy)methyl)-1H-1,2,3-triazol-4-yl)pyrazin-2-yl)oxy)cyclohexane-1-carboxylic acid (236), (1S,3S)-3-((5-(5-((((cyclopropylmethyl)(methyl)carbamoyl)oxy)methyl)-1-methyl-1H-1,2,3-triazol-4-yl)-3-(trifluoromethyl)pyridin-2-yl)oxy)cyclohexane-1-carboxylic acid (237), (1S,3 S)-3-((5-(5-(((cyclopentyl(methyl)carbamoyl)oxy) methyl)-1-methyl-1H-1,2,3-triazol-4-yl)-3-(trifluoromethyl)pyridin-2-yl)oxy)cyclohexane-1-carboxylic acid (238), (1S,3S)-3-((5-(5-((((cyclobutylmethyl)(methyl)carbamoyl) oxy)methyl)-1-methyl-1H-1,2,3-triazol-4-yl)-3-(trifluoromethyl)pyridin-2-yl)oxy)cyclohexane-1-carboxylic acid (239), (1S,3S)-3-((5-(5-(((cyclobutyl(methyl)carbamoyl)oxy) methyl)-1-methyl-1H-1,2,3-triazol-4-yl)-3-(trifluoromethyl)pyridin-2-yl)oxy)cyclohexane-1-carboxylic acid (240), (1S,3S)-3-((6-(5-(2-(((Cyclobutylmethyl)(methyl)carbamoyl)oxy)ethyl)-1-methyl-1H-1,2,3-triazol-4-yl)-2-methylpyridin-3-yl)oxy)cyclohexane-1-carboxylic acid (241), (1S,3S)-3-((2-Methyl-6-(1-methyl-5-(2-((methyl(propyl) carbamoyl)oxy)-ethyl)-1H-1,2,3-triazol-4-yl)pyridin-3-yl)oxy)cyclohexane-1-carboxylic acid, TFA salt (242), (1S,3 S)-3-((6-(5-(2-((Cyclopentyl-(methyl)carbamoyl)oxy) ethyl)-1-methyl-1H-1,2,3-triazol-4-yl)-2-methylpyridin-3-yl)oxy)cyclohexane-1-carboxylic acid (243), (1S,3S)-3-((6-(5-(2-((Benzyl(methyl)-carbamoyl)oxy) ethyl)-1-methyl-1H-1,2,3-triazol-4-yl)-2-methylpyridin-3-yl)oxy)cyclohexane-1-carboxylic acid (244), (1S,3S)-3-((6-(5-(2-((Isobutyl-(methyl)carbamoyl)oxy) ethyl)-1-methyl-1H-1,2,3-triazol-4-yl)-2-methylpyridin-3-yl)oxy)cyclohexane-1-carboxylic acid (245), (1S,3S)-3-((2-Methyl-6-(1-methyl-5-(2-((pyrrolidine-1-carbonyl)oxy)-ethyl)-1H-1,2,3-triazol-4-yl)pyridin-3-yl) oxy)cyclohexane-1-carboxylic acid, TFA salt (246), (1S,3S)-3-((6-(5-(2-((Cyclobutyl(methyl)carbamoyl)oxy) ethyl)-1-methyl-1H-1,2,3-triazol-4-yl)-2-methylpyridin-3-yl)oxy)cyclo-hexane-1-carboxylic acid, TFA salt (247), (1S,3S)-3-((6-(5-(2-(((Cyclobutyl-methyl)carbamoyl)oxy) ethyl)-1-methyl-1H-1,2,3-triazol-4-yl)-2-methylpyridin-3-yl)oxy)cyclohexane-1-carboxylic acid, TFA salt (248), (1S,3S)-3-((6-(5-(3-((Benzyl(methyl)carbamoyl)oxy)propyl)-1-methyl-1H-1,2,3-triazol-4-yl)-2-methylpyridin-3-yl)oxy)cyclohexane-1-carboxylic acid (249), (1S,3S)-3-((2-methyl-6-(1-methyl-5-(((methyl(2-propoxyethyl)carbamoyl)oxy)methyl)-1H-1,2,3-triazol-4-yl)pyridin-3-yl)oxy)cyclohexane-1-carboxylic acid (250), (1S,3S)-3-((6-(1-methyl-5-(((methyl(((1R,2R)-2-methylcyclopropyl)methyl)carbamoyl)oxy)methyl)-1H-1,2,3-triazol-4-yl)pyridin-3-yl)oxy)cyclohexane-1-carboxylic acid (251), (1S,3S)-3-((6-(1-methyl-5-(((methyl(((1S,2S)-2-methylcyclopropyl)methyl)carbamoyl)oxy)methyl)-1H-1,2,3-triazol-4-yl)pyridin-3-yl)oxy)cyclohexane-1-carboxylic acid (252), (1S,3S)-3-((6-(5-((((2-fluoro-2-methylpropyl)(methyl)carbamoyl)oxy)methyl)-1-methyl-1H-1,2,3-triazol-4-yl)-2-methylpyridin-3-yl)oxy) cyclohexane-1-carboxylic acid (253), (1S,3S)-3-((5-(5-((((2-fluorobutyl)(methyl)carbamoyl)oxy) methyl)-1-methyl-1H-1,2,3-triazol-4-yl)-3-methylpyrazin-2-yl)oxy)cyclohexane-1-carboxylic acid; mixture of diastereomers (254), (1S,3S)-3-((6-(5-((((2-fluorobutyl)(methyl)carbamoyl)oxy) methyl)-1-methyl-1H-1,2,3-triazol-4-yl)-2-methylpyridin-3-yl)oxy)cyclohexane-1-carboxylic acid; mixture of diastereomers (255), (1S,3S)-3-((6-(5-((((4-fluoropentyl)(methyl)carbamoyl) oxy)methyl)-1-methyl-1H-1,2,3-triazol-4-yl)-2-methylpyridin-3-yl)oxy)cyclohexane-1-carboxylic acid (256), (1R,3S)-3-((2-methyl-6-(1-methyl-5-(((methyl(((1R,2R)-2-methylcyclopropyl)methyl) carbamoyl)oxy)methyl)-1H-1,2,3-triazol-4-yl)pyridin-3-yl)oxy)cyclohexane-1-carboxylic acid (257), (1R,3 S)-3-((2-methyl-6-(1-methyl-5-(((methyl(((1S,2S)-2-methylcyclopropyl)methyl) carbamoyl)oxy)methyl)-1H-1,2,3-triazol-4-yl)pyridin-3-yl)oxy)cyclohexane-1-carboxylic acid (258), (1S,3S)-3-((6-(5-((((2,2-difluoropropyl)(methyl)carbamoyl) oxy)methyl)-1-methyl-1H-1,2,3-triazol-4-yl)-2-methylpyridin-3-yl)oxy)cyclohexane-1-carboxylic acid (259), (1S,3S)-3-((6-(5-((((3-fluorobutyl)(methyl)carbamoyl)oxy) methyl)-1-methyl-1H-1,2,3-triazol-4-yl)-2-methylpyridin-3-yl)oxy)cyclohexane-1-carboxylic acid (260), (1S,3S)-3-((6-(5-((((2-fluoropropyl)(methyl)carbamoyl)oxy)methyl)-1-methyl-1H-1,2,3-triazol-4-yl)-2-methylpyridin-3-yl)oxy)cyclohexane-1-carboxylic acid (261), (1S,3S)-3-((2-methyl-6-(1-methyl-5-(((methyl((2-methylcyclopropyl)methyl)carbamoyl)oxy)methyl)-1H-1,2,3-triazol-4-yl) pyridin-3-yl)oxy)cyclohexane-1-carboxylic acid; mixture of diastereomers (262), (1S,3S)-3-((2-methyl-6-(1-methyl-5-(((methyl((1-methyl-cyclo-propyl)methyl)carbamoyl)oxy)methyl)-1H-1,2,3-triazol-4-yl) pyridin-3-yl)oxy)cyclohexane-1-carboxylic acid (263), (1S,3S)-3-((2-methyl-6-(1-methyl-5-(((methyl(neopentyl)carbamoyl)oxy)methyl)-1H-1,2,3-triazol-4-yl)pyridin-3-yl)oxy) cyclohexane-1-carboxylic acid (264), (1S,3S)-3-((6-(5-((((cyclobutylmethyl)(methyl)carbamoyl)oxy)methyl)-1-methyl-1H-1,2,3-triazol-4-yl)-2-(hydroxymethyl)pyridin-3-yl)oxy)cyclohexane-1-carboxylic acid (265), (1S,3S)-3-((6-(5-((((cyclobutylmethyl)(methyl)carbamoyl)oxy)methyl)-1-methyl-1H-1,2,3-triazol-4-yl)-2-(fluoromethyl)pyridin-3-yl)oxy)cyclohexane-1-carboxylic acid (266), (1S,3S)-3-((6-(5-((((cyclobutylmethyl)(methyl)carbamoyl)oxy)methyl)-1-methyl-1H-1,2,3-triazol-4-yl)-2-(difluoromethyl)pyridin-3-yl)oxy)cyclohexane-1-carboxylic acid (267), (1S,3S)-3-((6-(5-((((cyclobutylmethyl)(methyl)carbamoyl)oxy)methyl)-1-methyl-1H-1,2,3-triazol-4-yl)-2-(methoxymethyl)pyridin-3-yl)oxy)cyclohexane-1-carboxylic acid (268), (1S,3S)-3-((6-(5-((((cyclobutylmethyl)(methyl)carbamoyl)oxy)methyl)-1-methyl-1H-1,2,3-triazol-4-yl)-2-(trifluoromethyl)pyridin-3-yl)oxy)cyclohexane-1-carboxylic acid (269), (1S,3S)-3-((2-cyano-6-(1-methyl-5-(((methyl(propyl)carbamoyl)oxy)methyl)-1H-1,2,3-triazol-4-yl)pyridin-3-yl)oxy)cyclohexane-1-carboxylic acid (270), (1S,3S)-3-((6-(5-((((cyclobutylmethyl)(methyl)carbamoyl)oxy)methyl)-1-methyl-1H-1,2,3-triazol-4-yl)-2-(2-hydroxypropan-2-yl)pyridin-3-yl)oxy)cyclohexane-1-carboxylic acid (271), (1S,3 S)-3-((2-Methoxy-6-(1-methyl-5-(((methyl(propyl)carbamoyl)oxy)methyl)-1H-1,2,3-triazol-4-yl)pyridin-3-yl)oxy)cyclohexane-1-carboxylic acid (272), (1S,3S)-3-((6-(5-((((cyclopropylmethyl)(methyl)carbamoyl)oxy)methyl)-1-methyl-1H-1,2,3-triazol-4-yl)-2-(trifluoromethyl)pyridin-3-yl)oxy)cyclohexane-1-carboxylic acid (273), (1S,3S)-3-((6-(1-methyl-5-(((methyl(propyl)carbamoyl)oxy)methyl)-1H-1,2,3-triazol-4-yl)-2-(trifluoromethyl)pyridin-3-yl) oxy)cyclohexane-1-carboxylic acid (274), (1S,3S)-3-((6-(5-(((butyl(methyl)carbamoyl)oxy)methyl)-1-methyl-1H-1,2,3-triazol-4-yl)-2-(trifluoromethyl)pyridin-3-yl)oxy)cyclohexane-1-carboxylic acid (275), (1S,3S)-3-((6-(5-(((cyclopentyl(methyl)carbamoyl)oxy) methyl)-1-methyl-1H-1,2,3-triazol-4-yl)-2-(trifluoro methyl)pyridin-3-yl)oxy) cyclohexane-1-carboxylic acid (276), (1S,3S)-3-((2-(difluoromethyl)-6-(1-methyl-5-(((methyl(propyl)carbamoyl)oxy)methyl)-1H-1,2,3-triazol-4-yl) pyridin-3-yl)oxy)cyclohexane-1-carboxylic acid (277), (1S,3S)-3-((6-(5-(((butyl(methyl)carbamoyl)oxy)methyl)-1-methyl-1H-1,2,3-triazol-4-yl)-2-(difluoromethyl)pyridin-3-yl)oxy)cyclohexane-1-carboxylic acid (278), (1S,3S)-3-((6-(5-((((cyclopropylmethyl)(methyl)carbamoyl)oxy)methyl)-1-methyl-1H-1,2,3-triazol-4-yl)-2-(difluoromethyl)pyridin-3-yl)oxy) cyclohexane-1-carboxylic acid (279), (1S,3S)-3-((6-(5-(((cyclobutyl(methyl)carbamoyl)oxy) methyl)-1-methyl-1H-1,2,3-triazol-4-yl)-2-(difluoromethyl) pyridin-3-yl)oxy)cyclohexane-1-carboxylic acid (280), (1S,3S)-3-((6-(5-(((cyclopentyl(methyl)carbamoyl)oxy) methyl)-1-methyl-1H-1,2,3-triazol-4-yl)-2-(difluoromethyl) pyridin-3-yl)oxy)cyclohexane-1-carboxylic acid (281), (1S,3S)-3-((6-(5-(((benzyl(methyl)carbamoyl)oxy)methyl)-1-methyl-1H-1,2,3-triazol-4-yl)-2-(difluoromethyl)pyridin-3-yl)oxy)cyclohexane-1-carboxylic acid (282), (1S,3 S)-3-((2-(methoxymethyl)-6-(1-methyl-5-(((methyl (propyl) carbamoyl)oxy)methyl)-1H-1,2,3-triazol-4-yl) pyridin-3-yl)oxy)cyclohexane-1-carboxylic acid (283), (1S,3S)-3-((6-(5-(((butyl(methyl)carbamoyl)oxy)methyl)-1-methyl-1H-1,2,3-triazol-4-yl)-2-(methoxymethyl)pyridin-3-yl)oxy)cyclohexane-1-carboxylic acid (284), (1S,3S)-3-((6-(5-((((cyclopropyl methyl)(methyl)carbamoyl)oxy)methyl)-1-methyl-1H-1,2,3-triazol-4-yl)-2-(methoxymethyl)pyridin-3-yl)oxy)cyclohexane-1-carboxylic acid (285), (1S,3S)-3-((6-(5-(((cyclobutyl (methyl)carbamoyl)oxy) methyl)-1-methyl-1H-1,2,3-triazol-4-yl)-2-(methoxymethyl) pyridin-3-yl) oxy)cyclohexane-1-carboxylic acid (286), (1S,3S)-3-((6-(5-(((cyclopentyl(methyl)carbamoyl)oxy) methyl)-1-methyl-1H-1,2,3-triazol-4-yl)-2-(methoxymethyl) pyridin-3-yl)oxy)cyclohexane-1-carboxylic acid (287), (1S,3S)-3-((2-methyl-6-(1-methyl-5-((((methyl-d3)(propyl) carbamoyl)oxy)methyl)-1H-1,2,3-triazol-4-yl)pyridin-3-yl)oxy) cyclohexane-1-carboxylic acid (288), (1S,3 S)-3-((2-cyano-6-(5-((((cyclopropylmethyl)(methyl) carbamoyl)oxy)methyl)-1-methyl-1H-1,2,3-triazol-4-yl) pyridin-3-yl)oxy)cyclohexane-1-carboxylic acid (289), (1S,3S)-3-((6-(5-(((benzyl(methyl)carbamoyl)oxy)methyl)-1-methyl-1H-1,2,3-triazol-4-yl)-2-cyanopyridin-3-yl) oxy)cyclohexane-1-carboxylic acid (290), (1S,3S)-3-((6-(5-(((butyl(methyl)carbamoyl)oxy)methyl)-1-methyl-1H-1,2,3-triazol-4-yl)-2-cyanopyridin-3-yl) oxy)cyclohexane-1-carboxylic acid (291), (1S,3 S)-3-((2-cyano-6-(5-((((cyclobutylmethyl)(methyl) carbamoyl)oxy)methyl)-1-methyl-1H-1,2,3-triazol-4-yl) pyridin-3-yl)oxy)cyclohexane-1-carboxylic acid (292), (1S,3S)-3-((2-cyano-6-(5-(((cyclobutyl(methyl)carbamoyl) oxy)methyl)-1-methyl-1H-1,2,3-triazol-4-yl)pyridin-3-yl)oxy)cyclohexane-1-carboxylic acid (293), (1S,3S)-3-((2-cyano-6-(5-(((cyclopentyl(methyl)carbamoyl)oxy)methyl)-1-methyl-1H-1,2,3-triazol-4-yl)pyridin-3-yl)oxy) cyclohexane-1-carboxylic acid (294).

In another embodiment, the compounds of the present invention have LPA1 IC$_{50}$ values ≤10 μM.

In another embodiment, the compounds of the present invention have LPA1 IC$_{50}$ values ≤1 μM.

In another embodiment, the compounds of the present invention have LPA1 IC$_{50}$ values ≤0.1 μM.

In another embodiment, the compounds of the present invention have LPA1 IC$_{50}$ values ≤0.05 μM.

In another embodiment, the compounds of the present invention have LPA1 IC$_{50}$ values ≤0.01 μM.

II. Other Embodiments of the Invention

In some embodiments, the compound of Formulas (I)-(IX), or a pharmaceutically acceptable salt thereof, is an antagonist of at least one LPA receptor. In some embodiments, the compound of Formulas (I)-(IX), or a pharmaceutically acceptable salt thereof, is an antagonist of $LPA_1$. In some embodiments, the compound of Formulas (I)-(IX), or a pharmaceutically acceptable salt thereof, is an antagonist of $LPA_2$. In some embodiments, the compound of Formulas (I)-(IX), or a pharmaceutically acceptable salt thereof, is an antagonist of $LPA_3$.

In some embodiments, presented herein are compounds selected from active metabolites, tautomers, pharmaceutically acceptable salts, solvates or prodrugs of a compound of Formulas (I)-(IX).

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with LPA receptor mediated fibrosis, comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1\text{-}10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2\text{-}6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2\text{-}6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1\text{-}6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1\text{-}6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluoroethoxy. Similarly, "haloalkylthio" or "thiohaloalkoxy" represents a haloalkyl group as defined above with the indicated number of carbon atoms attached through a sulphur bridge; for example, trifluoromethyl-S—, and pentafluoroethyl-S—.

The term "cycloalkyl" refers to cyclized alkyl groups, including mono-, bi- or poly-cyclic ring systems. "$C_3$ to $C_8$ cycloalkyl" or "$C_{3\text{-}8}$ cycloalkyl" is intended to include $C_3$, $C_4$, $C_5$, $C_6$, $C_7$, and $C_8$ cycloalkyl groups, including monocyclic, bicyclic, and polycyclic rings. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl and spiro and bridged cycloalkyl groups are included in the definition of "cycloalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6\text{-}10}$ aryl" refers to phenyl and naphthyl. Unless otherwise specified, "aryl", "$C_6$ or $C_{10}$ aryl" or "$C_{6\text{-}10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle", "heterocyclyl", or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent within the definition of the substitution of the heterocyclic ring). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocyclyl" is used, it is intended to include heteroaryl.

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group," "heteroaryl," or "heteroaryl ring" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent within the definition of the substitution of the heterocyclic ring). The nitrogen and sulfur heteroatoms may optionally be oxidized (i.e., N→O and S(O)$_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formulas (I)-(IX) may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5, "Design and Application of Prodrugs", *A Textbook of Drug Design and Development,* pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formulas (I)-(IX) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formulas (I)-(IX) include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl), glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

IV. Biology

Lysophospholipids are membrane-derived bioactive lipid mediators. Lysophospholipids include, but are not limited to, lysophosphatidic acid (1-acyl-2-hydroxy-sn-glycero-3-phosphate; LPA), sphingosine 1-phosphate (S1P), lysophosphatidylcholine (LPC), and sphingosylphosphorylcholine (SPC). Lysophospholipids affect fundamental cellular functions that include cellular proliferation, differentiation, survival, migration, adhesion, invasion, and morphogenesis. These functions influence many biological processes that include neurogenesis, angiogenesis, wound healing, immunity, and carcinogenesis.

LPA acts through sets of specific G protein-coupled receptors (GPCRs) in an autocrine and paracrine fashion. LPA binding to its cognate GPCRs (LPA$_1$, LPA$_2$, LPA$_3$, LPA$_4$, LPA$_5$, LPA$_6$) activates intracellular signaling pathways to produce a variety of biological responses.

Lysophospholipids, such as LPA, are quantitatively minor lipid species compared to their major phospholipid counterparts (e.g., phosphatidylcholine, phosphatidylethanolamine, and sphingomyelin). LPA has a role as a biological effector molecule, and has a diverse range of physiological actions such as, but not limited to, effects on blood pressure, platelet activation, and smooth muscle contraction, and a variety of cellular effects, which include cell growth, cell rounding, neurite retraction, and actin stress fiber formation and cell migration. The effects of LPA are predominantly receptor mediated.

Activation of the LPA receptors (LPA$_1$, LPA$_2$, LPA$_3$, LPA$_4$, LPA$_5$, LPA$_6$) with LPA mediates a range of downstream signaling cascades. These include, but are not limited to, mitogen-activated protein kinase (MAPK) activation, adenylyl cyclase (AC) inhibition/activation, phospholipase C (PLC) activation/Ca$^{2+}$ mobilization, arachidonic acid release, Akt/PKB activation, and the activation of small GTPases, Rho, ROCK, Rac, and Ras. Other pathways that are affected by LPA receptor activation include, but are not limited to, cyclic adenosine monophosphate (cAMP), cell division cycle 42/GTP-binding protein (Cdc42), proto-oncogene serine/threonine-protein kinase Raf (c-RAF), proto-oncogene tyrosine-protein kinase Src (c-src), extracellular signal-regulated kinase (ERK), focal adhesion kinase (FAK), guanine nucleotide exchange factor (GEF), glycogen synthase kinase 3b (GSK3b), c-jun amino-terminal kinase (JNK), MEK, myosin light chain II (MLC II), nuclear factor kB (NF-kB), N-methyl-D-aspartate (NMDA) receptor activation, phosphatidylinositol 3-kinase (PI3K), protein kinase A (PKA), protein kinase C (PKC), ras-related C$_3$ botulinum toxin substrate 1 (RAC1). The actual pathway and realized end point are dependent on a range of variables that include receptor usage, cell type, expression level of a receptor or signaling protein, and LPA concentration. Nearly all mammalian cells, tissues and organs co-express several LPA-receptor subtypes, which indicates that LPA receptors signal in a cooperative manner. LPA$_1$, LPA$_2$, and LPA$_3$ share high amino acid sequence similarity.

LPA is produced from activated platelets, activated adipocytes, neuronal cells, and other cell types. Serum LPA is produced by multiple enzymatic pathways that involve monoacylglycerol kinase, phospholipase A$_1$, secretory phospholipase A2, and lysophospholipase D (lysoPLD), including autotaxin. Several enzymes are involved in LPA degradation: lysophospholipase, lipid phosphate phosphatase, and LPA acyl transferase such as endophilin. LPA concentrations in human serum are estimated to be 1-5 µM. Serum LPA is bound to albumin, low-density lipoproteins, or other proteins, which possibly protect LPA from rapid degradation. LPA molecular species with different acyl chain lengths and saturation are naturally occurring, including 1-palmitoyl (16:0), 1-palmitoleoyl (16:1), 1-stearoyl (18:0), 1-oleoyl (18:1), 1-linoleoyl (18:2), and 1-arachidonyl (20:4) LPA. Quantitatively minor alkyl LPA has biological activities similar to acyl LPA, and different LPA species activate LPA receptor subtypes with varied efficacies.

LPA Receptors

LPA$_1$ (previously called VZG-1/EDG-2/mrec1.3) couples with three types of G proteins, $G_{i/o}$, $G_q$, and $G_{12/13}$. Through activation of these G proteins, LPA induces a range of cellular responses through LPA$_1$ including but not limited to: cell proliferation, serum-response element (SRE) activation, mitogen-activated protein kinase (MAPK) activation, adenylyl cyclase (AC) inhibition, phospholipase C (PLC) activation, $Ca^{2+}$ mobilization, Akt activation, and Rho activation.

Wide expression of LPA$_1$ is observed in adult mice, with clear presence in testis, brain, heart, lung, small intestine, stomach, spleen, thymus, and skeletal muscle. Similarly, human tissues also express LPA$_1$; it is present in brain, heart, lung, placenta, colon, small intestine, prostate, testis, ovary, pancreas, spleen, kidney, skeletal muscle, and thymus.

LPA$_2$ (EDG-4) also couples with three types of G proteins, $G_{i/o}$, $G_q$, and $G_{12/13}$, to mediate LPA-induced cellular signaling. Expression of LPA$_2$ is observed in the testis, kidney, lung, thymus, spleen, and stomach of adult mice and in the human testis, pancreas, prostate, thymus, spleen, and peripheral blood leukocytes. Expression of LPA$_2$ is upregulated in various cancer cell lines, and several human LPA$_2$ transcriptional variants with mutations in the 3'-untranslated region have been observed. Targeted deletion of LPA$_2$ in mice has not shown any obvious phenotypic abnormalities, but has demonstrated a significant loss of normal LPA signaling (e.g., PLC activation, $Ca^{2+}$ mobilization, and stress fiber formation) in primary cultures of mouse embryonic fibroblasts (MEFs). Creation of lpa1(−/−) lpa2 (−/−) double-null mice has revealed that many LPA-induced responses, which include cell proliferation, AC inhibition, PLC activation, $Ca^{2+}$ mobilization, JNK and Akt activation, and stress fiber formation, are absent or severely reduced in double-null MEFs. All these responses, except for AC inhibition (AC inhibition is nearly abolished in LPA$_1$ (−/−) MEFs), are only partially affected in either LPA$_1$ (−/−) or LPA$_2$ (−/−) MEFs. LPA$_2$ contributes to normal LPA-mediated signaling responses in at least some cell types (Choi et al, *Biochemica et Biophysica Acta* 2008, 1781, p 531-539).

LPA$_3$ (EDG-7) is distinct from LPA$_1$ and LPA$_2$ in its ability to couple with $G_{i/o}$ and $G_q$ but not $G_{12/13}$ and is much less responsive to LPA species with saturated acyl chains. LPA$_3$ can mediate pleiotropic LPA-induced signaling that includes PLC activation, $Ca^{2+}$ mobilization, AC inhibition/activation, and MAPK activation. Overexpression of LPA$_3$ in neuroblastoma cells leads to neurite elongation, whereas that of LPA$_1$ or LPA$_2$ results in neurite retraction and cell rounding when stimulated with LPA. Expression of LPA$_3$ is observed in adult mouse testis, kidney, lung, small intestine, heart, thymus, and brain. In humans, it is found in the heart, pancreas, prostate, testis, lung, ovary, and brain (frontal cortex, hippocampus, and amygdala). LPA$_4$ (p2y$_9$/GPR23) is of divergent sequence compared to LPA$_1$, LPA$_2$, and LPA$_3$ with closer similarity to the platelet-activating factor (PAF) receptor. LPA$_4$ mediates LPA induced $Ca^{2+}$ mobilization and cAMP accumulation, and functional coupling to the G protein Gs for AC activation, as well as coupling to other G proteins. The LPA$_4$ gene is expressed in the ovary, pancreas, thymus, kidney and skeletal muscle.

LPA$_5$ (GPR92) is a member of the purinocluster of GPCRs and is structurally most closely related to LPA$_4$. LPA$_5$ is expressed in human heart, placenta, spleen, brain, lung and gut. LPA$_5$ also shows very high expression in the CD$_8$+ lymphocyte compartment of the gastrointestinal tract.

LPA$_6$ (p2y$_5$) is a member of the purinocluster of GPCRs and is structurally most closely related to LPA$_4$. LPA$_6$ is an LPA receptor coupled to the G12/13-Rho signaling pathways and is expressed in the inner root sheaths of human hair follicles.

Illustrative Biological Activity

Wound Healing

Normal wound healing occurs by a highly coordinated sequence of events in which cellular, soluble factors and matrix components act in concert to repair the injury.

The healing response can be described as taking place in four broad, overlapping phases—hemostasis, inflammation, proliferation, and remodeling. Many growth factors and cytokines are released into a wound site to initiate and perpetuate wound healing processes.

When wounded, damaged blood vessels activate platelets. The activated platelets play pivotal roles in subsequent repair processes by releasing bioactive mediators to induce cell proliferation, cell migration, blood coagulation, and angiogenesis. LPA is one such mediator that is released from activated platelets; this induces platelet aggregation along with mitogenic/migration effects on the surrounding cells, such as endothelial cells, smooth muscle cells, fibroblasts, and keratinocytes.

Topical application of LPA to cutaneous wounds in mice promotes repair processes (wound closure and increased neoepithelial thickness) by increasing cell proliferation/migration without affecting secondary inflammation.

Activation of dermal fibroblasts by growth factors and cytokines leads to their subsequent migration from the edges of the wound into the provisional matrix formed by the fibrin clot whereupon the fibroblasts proliferate and start to restore the dermis by secreting and organizing the characteristic dermal extracellular matrix (ECM). The increasing number of fibroblasts within the wound and continuous precipitation of ECM enhances matrix rigidity by applying small tractional forces to the newly formed granulation tissue. The increase in mechanical stress, in conjunction with transforming growth factor β (TGFβ), induces α-smooth muscle actin (α-SMA) expression and the subsequent transformation of fibroblasts into myofibroblasts. Myofibroblasts facilitate granulation tissue remodeling via myofibroblast contraction and through the production of ECM components.

LPA regulates many important functions of fibroblasts in wound healing, including proliferation, migration, differentiation and contraction. Fibroblast proliferation is required in wound healing in order to fill an open wound. In contrast, fibrosis is characterized by intense proliferation and accumulation of myofibroblasts that actively synthesize ECM and proinflammatory cytokines. LPA can either increase or suppress the proliferation of cell types important in wound healing, such as epithelial and endothelial cells (EC), macrophages, keratinocytes, and fibroblasts. A role for LPA$_1$ in LPA-induced proliferation was provided by the observation that LPA-stimulated proliferation of fibroblasts isolated from LPA$_1$ receptor null mice was attenuated (Mills et al, *Nat Rev. Cancer* 2003; 3: 582-591). LPA induces cytoskeletal changes that are integral to fibroblast adhesion, migration, differentiation and contraction.

Fibrosis

Tissue injury initiates a complex series of host wound-healing responses; if successful, these responses restore normal tissue structure and function. If not, these responses can lead to tissue fibrosis and loss of function.

For the majority of organs and tissues the development of fibrosis involves a multitude of events and factors. Molecules involved in the development of fibrosis include proteins or peptides (profibrotic cytokines, chemokines, metalloproteinases etc.) and phospholipids. Phospholipids involved in the development of fibrosis include platelet activating factor (PAF), phosphatidyl choline, sphingosine-1 phosphate (S1P) and lysophosphatidic acid (LPA).

A number of muscular dystrophies are characterized by a progressive weakness and wasting of musculature, and by extensive fibrosis. It has been shown that LPA treatment of cultured myoblasts induced significant expression of connective tissue growth factor (CTGF). CTGF subsequently induces collagen, fibronectin and integrin expression and induces dedifferentiation of these myoblasts. Treatment of a variety of cell types with LPA induces reproducible and high level induction of CTGF (J. P. Pradere, et al., $LPA_1$ receptor activation promotes renal interstitial fibrosis, *J. Am. Soc. Nephrol.* 18 (2007) 3110-3118; N. Wiedmaier, et al., *Int J Med Microbiol;* 298(3-4):231-43, 2008). CTGF is a profibrotic cytokine, signaling down-stream and in parallel with TGFβ.

CTGF expression by gingival epithelial cells, which are involved in the development of gingival fibromatosis, was found to be exacerbated by LPA treatment (A. Kantarci, et al., *J Pathol.* 210 (2006) 59-66).

LPA is associated with the progression of liver fibrosis. In vitro, LPA induces stellate cell and hepatocyte proliferation. These activated cells are the main cell type responsible for the accumulation of ECM in the liver. Furthermore, LPA plasma levels rise during $CCl_4$-induced liver fibrosis in rodents, or in hepatitis C virus-induced liver fibrosis in humans (N. Watanabe, et al., Plasma lysophosphatidic acid level and serum autotaxin activity are increased in liver injury in rats in relation to its severity, *Life Sci.* 81 (2007) 1009-1015; N. Watanabe, et al., *J. Clin. Gastroenterol.* 41 (2007) 616-623).

An increase of phospholipid concentrations in the bronchoalveolar lavage fluid in rabbits and rodents injected with bleomycin has been reported (K. Kuroda, et al., Phospholipid concentration in lung lavage fluid as biomarker for pulmonary fibrosis, *Inhal. Toxicol.* 18 (2006) 389-393; K. Yasuda, et al., Lung 172 (1994) 91-102).

LPA is associated with heart disease and mycocardial remodeling. Serum LPA levels are increased after myocardial infarction in patients and LPA stimulates rat cardiac fibroblast proliferation and collagen production (Chen et al. *FEBS Lett.* 2006 Aug. 21; 580(19):4737-45).

Pulmonary Fibrosis

In the lung, aberrant wound healing responses to injury contribute to the pathogenesis of fibrotic lung diseases. Fibrotic lung diseases, such as idiopathic pulmonary fibrosis (IPF), are associated with high morbidity and mortality.

LPA is an important mediator of fibroblast recruitment in pulmonary fibrosis. LPA and $LPA_1$ play key pathogenic roles in pulmonary fibrosis. Fibroblast chemoattractant activity plays an important role in the lungs in patients with pulmonary fibrosis. Profibrotic effects of $LPA_1$-receptor stimulation is explained by $LPA_1$-receptor-mediated vascular leakage and increased fibroblast recruitment, both profibrotic events. The LPA-$LPA_1$ pathway has a role in mediating fibroblast migration and vascular leakage in IPF. The end result is the aberrant healing process that characterizes this fibrotic condition.

The $LPA_1$ receptor is the LPA receptor most highly expressed on fibroblasts obtained from patients with IPF. Furthermore, BAL obtained from IPF patients induced chemotaxis of human foetal lung fibroblasts that was blocked by the dual $LPA_1$-$LPA_3$ receptor antagonist Ki16425. In an experimental bleomycin-induced lung injury mouse model, it was shown that LPA levels were high in bronchoalveolar lavage samples compared with unexposed controls. $LPA_1$ knockout mice are protected from fibrosis after bleomycin challenge with reduced fibroblast accumulation and vascular leakage. In human subjects with IPF, high LPA levels were observed in bronchoalveolar lavage samples compared with healthy controls. Increased fibroblast chemotactic activity in these samples was inhibited by the Ki16425 indicating that fibroblast migration is mediated by the LPA-LPA receptor(s) pathway (Tager et al. *Nature Medicine*, 2008, 14, 45-54).

The LPA-$LPA_1$ pathway is crucial in fibroblast recruitment and vascular leakage in pulmonary fibrosis.

Activation of latent TGF-β by the αvβ6 integrin plays a critical role in the development of lung injury and fibrosis (Munger et al. Cell, vol. 96, 319-328, 1999). LPA induces αvβ6-mediated TGF-β activation on human lung epithelial cells (Xu et al. *Am. J. Pathology*, 2009, 174, 1264-1279). The LPA-induced αvβ6-mediated TGF-β activation is mediated by the $LPA_2$ receptor. Expression of the $LPA_2$ receptor is increased in epithelial cells and mesenchymal cells in areas of lung fibrosis from IPF patients compared to normal human lung tissue. The LPA-$LPA_2$ pathway contributes to the activation of the TGF-β pathway in pulmonary fibrosis. In some embodiments, compounds that inhibit $LPA_2$ show efficacy in the treatment of lung fibrosis. In some embodiments, compounds that inhibit both $LPA_1$ and $LPA_2$ show improved efficacy in the treatment of lung fibrosis compared to compounds which inhibit only $LPA_1$ or $LPA_2$.

Renal Fibrosis

LPA and $LPA_1$ are involved in the etiology of kidney fibrosis. LPA has effects on both proliferation and contraction of glomerular mesangial cells and thus has been implicated in proliferative glomerulonephritis (C. N. Inoue, et al., *Clin. Sci.* (Colch.) 1999, 96, 431-436). In an animal model of renal fibrosis [unilateral ureteral obstruction (UUO)], it was found that renal LPA receptors are expressed under basal conditions with an expression order of $LPA_2 > LPA_3 = LPA_1 \gg LPA_4$. This model mimics in an accelerated manner the development of renal fibrosis including renal inflammation, fibroblast activation and accumulation of extracellular matrix in the tubulointerstitium. UUO significantly induced $LPA_1$-receptor expression. This was paralleled by renal LPA production (3.3 fold increase) in conditioned media from kidney explants. Contra-lateral kidneys exhibited no significant changes in LPA release and LPA-receptors expression. This shows that a prerequisite for an action of LPA in fibrosis is met: production of a ligand (LPA) and induction of one of its receptors (the $LPA_1$ receptor) (J. P. Pradere et al., *Biochimica et Biophysica Acta*, 2008, 1781, 582-587).

In mice where the $LPA_1$ receptor was knocked out ($LPA_1$ (−/−), the development of renal fibrosis was significantly attenuated. UUO mice treated with the LPA receptor antagonist Ki16425 closely resembled the profile of $LPA_1$ (−/−) mice.

LPA can participate in intraperitonial accumulation of monocyte/macrophages and LPA can induce expression of the profibrotic cytokine CTGF in primary cultures of human fibroblasts (J. S. Koh, et al., *J. Clin. Invest.*, 1998, 102, 716-727).

LPA treatment of a mouse epithelial renal cell line, MCT, induced a rapid increase in the expression of the profibrotic cytokine CTGF. CTGF plays a crucial role in UUO-induced tubulointerstitial fibrosis (TIF), and is involved in the profibrotic activity of TGFβ. This induction was almost completely suppressed by co-treatment with the LPA-receptor antagonist Ki16425. In one aspect, the profibrotic activity of LPA in kidney results from a direct action of LPA on kidney cells involving induction of CTGF.

Hepatic Fibrosis

LPA is implicated in liver disease and fibrosis. Plasma LPA levels and serum autotaxin (enzyme responsible for LPA production) are elevated in hepatitis patients and animal models of liver injury in correlation with increased fibrosis. LPA also regulates liver cell function. $LPA_1$ and $LPA_2$ receptors are expressed by mouse hepatic stellate cells and LPA stimulates migration of hepatic myofibroblasts.

Ocular Fibrosis

LPA is in involved in wound healing in the eye. $LPA_1$ and $LPA_3$ receptors are detectable in the normal rabbit corneal epithelial cells, keratocytes and endothelial cells and $LPA_1$ and $LPA_3$ expression are increased in corneal epithelial cells following injury.

LPA and its homologues are present in the aqueous humor and the lacrimal gland fluid of the rabbit eye and these levels are increased in a rabbit corneal injury model.

LPA induces actin stress fiber formation in rabbit corneal endothelial and epithelial cells and promotes contraction corneal fibroblasts. LPA also stimulates proliferation of human retinal pigmented epithelial cells Cardiac Fibrosis LPA is implicated in myocardial infarction and cardiac fibrosis. Serum LPA levels are increased in patients following mycocardial infarction (MI) and LPA stimulates proliferation and collagen production (fibrosis) by rat cardiac fibroblasts. Both LPA1 and LPA3 receptors are highly expressed in human heart tissue.

Treatment of Fibrosis

In one aspect, a compound of Formulas (I)-(IX), or a pharmaceutically acceptable salt thereof, is used to treat or prevent fibrosis in a mammal. In one aspect, a compound of Formulas (I-(IX)), or a pharmaceutically acceptable salt thereof, is used to treat fibrosis of an organ or tissue in a mammal. In one aspect is a method for preventing a fibrosis condition in a mammal, the method comprising administering to the mammal at risk of developing one or more fibrosis conditions a therapeutically effective amount of a compound of Formulas (I-(IX)), or a pharmaceutically acceptable salt thereof. In one aspect, the mammal has been exposed to one or more environmental conditions that are known to increase the risk of fibrosis of an organ or tissue. In one aspect, the mammal has been exposed to one or more environmental conditions that are known to increase the risk of lung, liver or kidney fibrosis. In one aspect, the mammal has a genetic predisposition of developing fibrosis of an organ or tissue. In one aspect, a compound of Formulas (I)-(IX), or a pharmaceutically acceptable salt thereof, is administered to a mammal to prevent or minimize scarring following injury. In one aspect, injury includes surgery.

The terms "fibrosis" or "fibrosing disorder," as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Exemplary diseases, disorders, or conditions that involve fibrosis include, but are not limited to: Lung diseases associated with fibrosis, e.g., idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced); Chronic nephropathies associated with injury/fibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; Gut fibrosis, e.g., scleroderma, and radiation induced gut fibrosis; Liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis; Head and neck fibrosis, e.g., radiation induced; Corneal scarring, e.g., LASIK (laser-assisted in situ keratomileusis), corneal transplant, and trabeculectomy; Hypertrophic scarring and keloids, e.g., burn induced or surgical; and other fibrotic diseases, e.g., sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

In one aspect, a mammal suffering from one of the following non-limiting exemplary diseases, disorders, or conditions will benefit from therapy with a compound of Formulas (I)-(IX), or a pharmaceutically acceptable salt thereof: atherosclerosis, thrombosis, heart disease, vasculitis, formation of scar tissue, restenosis, phlebitis, COPD (chronic obstructive pulmonary disease), pulmonary hypertension, pulmonary fibrosis, pulmonary inflammation, bowel adhesions, bladder fibrosis and cystitis, fibrosis of the nasal passages, sinusitis, inflammation mediated by neutrophils, and fibrosis mediated by fibroblasts.

In one aspect, a compound of Formulas (I)-(IX), or a pharmaceutically acceptable salt thereof, is administered to a mammal with fibrosis of an organ or tissue or with a predisposition of developing fibrosis of an organ or tissue with one or more other agents that are used to treat fibrosis. In one aspect, the one or more agents include corticosteroids. In one aspect, the one or more agents include immunosuppressants. In one aspect, the one or more agents include B-cell antagonists. In one aspect, the one or more agents include uteroglobin.

In one aspect, a compound of Formulas (I)-(IX), or a pharmaceutically acceptable salt thereof, is used to treat a dermatological disorders in a mammal. The term "dermatological disorder," as used herein refers to a skin disorder. Such dermatological disorders include, but are not limited to, proliferative or inflammatory disorders of the skin such as, atopic dermatitis, bullous disorders, collagenoses, psoriasis, scleroderma, psoriatic lesions, dermatitis, contact dermatitis, eczema, urticaria, rosacea, wound healing, scarring, hypertrophic scarring, keloids, Kawasaki Disease, rosacea, Sjogren-Larsso Syndrome, urticaria. In one aspect, a compound of Formulas (I)-(IX), or a pharmaceutically acceptable salt thereof, is used to treat systemic sclerosis.

Pain

Since LPA is released following tissue injury, $LPA_1$ plays an important role in the initiation of neuropathic pain. $LPA_1$, unlike $LPA_2$ or $LPA_3$, is expressed in both dorsal root ganglion (DRG) and dorsal root neurons. Using the antisense oligodeoxynucleotide (AS-ODN) for $LPA_1$ and $LPA_1$-null mice, it was found that LPA-induced mechanical allodynia and hyperalgesia is mediated in an $LPA_1$-dependent manner. $LPA_1$ and downstream Rho-ROCK activation play a role in the initiation of neuropathic pain signaling. Pretreatment with *Clostridium botulinum* $C_3$ exoenzyme (BoTXC3, Rho inhibitor) or Y-27632 (ROCK inhibitor) completely abolished the allodynia and hyperalgesia in nerve-injured mice. LPA also induced demyelination of the dorsal root, which was prevented by BoTXC3. The dorsal root demyelination by injury was not observed in $LPA_1$-null mice or AS-ODN injected wild-type mice. LPA signaling appears to induce important neuropathic pain markers such as protein kinase Cγ (PKCγ) and a voltage-gated calcium channel α2δ1 subunit (Caα2δ1) in an $LPA_1$ and Rho-dependent manner (M. Inoue, et al., Initiation of neuropathic pain requires lysophosphatidic acid receptor signaling, *Nat. Med.* 10 (2004) 712-718).

In one aspect, a compound of Formulas (I)-(IX), or a pharmaceutically acceptable salt thereof, is used in the treatment of pain in a mammal. In one aspect, the pain is acute pain or chronic pain. In another aspect, the pain is neuropathic pain.

In one aspect, a compound of Formulas (I)-(IX), or a pharmaceutically acceptable salt thereof, is used in the treatment of fibromylagia. In one aspect, fibromyalgia stems from the formation of fibrous scar tissue in contractile (voluntary) muscles. Fibrosis binds the tissue and inhibits blood flow, resulting in pain.

Cancer

Lysophospholipid receptor signaling plays a role in the etiology of cancer.

Lysophosphatidic acid (LPA) and its G protein-coupled receptors (GPCRs) $LPA_1$, $LPA_2$, and/or $LPA_3$ play a role in the development of several types of cancers. The initiation, progression and metastasis of cancer involve several concurrent and sequential processes including cell proliferation and growth, survival and anti-apoptosis, migration of cells, penetration of foreign cells into defined cellular layers and/or organs, and promotion of angiogenesis. The control of each of these processes by LPA signaling in physiological and pathophysiological conditions underscores the potential therapeutic usefulness of modulating LPA signaling pathways for the treatment of cancer, especially at the level of the LPA receptors or ATX/lysoPLD. Autotaxin (ATX) is a prometastatic enzyme initially isolated from the conditioned medium of human melanoma cells that stimulates a myriad of biological activities, including angiogenesis and the promotion of cell growth, migration, survival, and differentiation through the production of LPA (*Mol Cancer Ther* 2008; 7(10):3352-62).

LPA signals through its own GPCRs leading to activation of multiple downstream effector pathways. Such downstream effector pathways play a role in cancer. LPA and its GPCRs are linked to cancer through major oncogenic signaling pathways.

LPA contributes to tumorigenesis by increasing motility and invasiveness of cells. LPA has been implicated in the initiation or progression of ovarian cancer. LPA is present at significant concentrations (2-80 μM) in the ascitic fluid of ovarian cancer patients. Ovarian cancer cells constitutively produce increased amounts of LPA as compared to normal ovarian surface epithelial cells, the precursor of ovarian epithelial cancer. Elevated LPA levels are also detected in plasma from patients with early-stage ovarian cancers compared with controls. LPA receptors ($LPA_2$ and $LPA_3$) are also overexpressed in ovarian cancer cells as compared to normal ovarian surface epithelial cells. LPA stimulates Cox-2 expression through transcriptional activation and post-transcriptional enhancement of Cox-2 mRNA in ovarian cancer cells. Prostaglandins produced by Cox-2 have been implicated in a number of human cancers and pharmacological inhibition of Cox-2 activity reduces colon cancer development and decreases the size and number of adenomas in patients with familial adenomatous polyposis. LPA has also been implicated in the initiation or progression of prostate cancer, breast cancer, melanoma, head and neck cancer, bowel cancer (colorectal cancer), thyroid cancer and other cancers (Gardell et al, *Trends in Molecular Medicine*, vol. 12, no. 2, p 65-75, 2006; Ishii et al, *Annu. Rev. Biochem*, 73, 321-354, 2004; Mills et al., *Nat. Rev. Cancer*, 3, 582-591, 2003; Murph et al., *Biochimica et Biophysica Acta*, 1781, 547-557, 2008).

The cellular responses to LPA are mediated through the lysophosphatidic acid receptors. For example, LPA receptors mediate both migration of and invasion by pancreatic cancer cell lines: an antagonist of $LPA_1$ and $LPA_3$ (Ki16425) and $LPA_1$-specific siRNA effectively blocked in vitro migration in response to LPA and peritoneal fluid (ascites) from pancreatic cancer patients; in addition, Ki16425 blocked the LPA-induced and ascites-induced invasion activity of a highly peritoneal metastatic pancreatic cancer cell line (Yamada et al, *J. Biol. Chem.*, 279, 6595-6605, 2004).

Colorectal carcinoma cell lines show significant expression of $LPA_1$ mRNA and respond to LPA by cell migration and production of angiogenic factors. Overexpression of LPA receptors has a role in the pathogenesis of thyroid cancer. $LPA_3$ was originally cloned from prostate cancer cells, concordant with the ability of LPA to induce autocrine proliferation of prostate cancer cells.

LPA has stimulatory roles in cancer progression in many types of cancer. LPA is produced from and induces proliferation of prostate cancer cell lines. LPA induces human colon carcinoma DLD1 cell proliferation, migration, adhesion, and secretion of angiogenic factors through $LPA_1$ signaling. In other human colon carcinoma cells lines (HT29 and WiDR), LPA enhances cell proliferation and secretion of angiogenic factors. In other colon cancer cell lines, $LPA_2$ and $LPA_3$ receptor activation results in proliferation of the cells. The genetic or pharmacological manipulation of LPA metabolism, specific blockade of receptor signaling, and/or inhibition of downstream signal transduction pathways, represent approaches for cancer therapies.

It has been reported that LPA and other phospholipids stimulate expression of interleukin-8 (IL-8) in ovarian cancer cell lines. In some embodiments, high concentrations of IL-8 in ovarian cancer correlate with poor initial response to chemotherapy and with poor prognosis, respectively. In animal models, expression of IL-8 and other growth factors such as vascular endothelial growth factor (VEGF) is associated with increased tumorigenicity, ascites formation, angiogenesis, and invasiveness of ovarian cancer cells. In some aspects, IL-8 is an important modulator of cancer progression, drug resistance, and prognosis in ovarian cancer. In some embodiments, a compound of Formulas (I)-(IX) inhibits or reduces IL-8 expression in ovarian cancer cell lines.

In one aspect, a compound of Formulas (I)-(IX), or a pharmaceutically acceptable salt thereof, is used in the treatment of cancer. In one aspect, a compound of Formulas (I)-(IX), or a pharmaceutically acceptable salt thereof, is used in the treatment of malignant and benign proliferative disease. In one aspect, a compound of Formula (I), or a pharmaceutically acceptable salt thereof, is used to prevent or reduce proliferation of tumor cells, invasion and metastasis of carcinomas, pleural mesothelioma (Yamada, Cancer Sci., 2008, 99(8), 1603-1610) or peritoneal mesothelioma, cancer pain, bone metastases (Boucharaba et al, *J Clin. Invest.*, 2004, 114(12), 1714-1725; Boucharaba et al, *Proc. Natl. acad. Sci.*, 2006, 103(25) 9643-9648). In one aspect is a method of treating cancer in a mammal, the method comprising administering to the mammal a compound of Formulas (I)-(IX), or a pharmaceutically acceptable salt thereof, and a second therapeutic agent, wherein the second therapeutic agent is an anti-cancer agent.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma or basal cell cancer) or hematological tumors (such as the leukemias) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, Wilms tumor.

The increased concentrations of LPA and vesicles in ascites from ovarian cancer patients and breast cancer effussions indicate that it could be an early diagnostic marker, a prognostic indicator or an indicator of response to therapy (Mills et al, *Nat. Rev. Cancer.*, 3, 582-591, 2003; Sutphen et al., *Cancer Epidemiol. Biomarkers Prev.* 13, 1185-1191, 2004). LPA concentrations are consistently higher in ascites samples than in matched plasma samples.

Respiratory and Allergic Disorders

In one aspect, LPA is a contributor to the pathogenesis of respiratory diseases. In one aspect the respiratory disease is asthma. Proinflammatory effects of LPA include degranulation of mast cells, contraction of smooth-muscle cells and release of cytokines from dendritic cells. Airway smooth muscle cells, epithelial cells and lung fibroblasts all show responses to LPA. LPA induces the secretion of IL-8 from human bronchial epithelial cells. IL-8 is found in increased concentrations in BAL fluids from patients with asthma, chronic obstructive lung disease, pulmonary sarcoidosis and acute respiratory distress syndrome and 11-8 has been shown to exacerbate airway inflammation and airway remodeling of asthmatics. $LPA_1$, $LPA_2$ and $LPA_3$ receptors have all been shown to contribute to the LPA-induced IL-8 production. Studies cloning multiple GPCRs that are activated by LPA allowed the demonstration of the presence of mRNA for the $LPA_1$, $LPA_2$ and $LPA_3$ in the lung (J. J. A. Contos, et al., *Mol. Pharmacol.* 58, 1188-1196, 2000).

The release of LPA from platelets activated at a site of injury and its ability to promote fibroblast proliferation and contraction are features of LPA as a mediator of wound repair. In the context of airway disease, asthma is an inflammatory disease where inappropriate airway "repair" processes lead to structural "remodeling" of the airway. In asthma, the cells of the airway are subject to ongoing injury due to a variety of insults, including allergens, pollutants, other inhaled environmental agents, bacteria and viruses, leading to the chronic inflammation that characterizes asthma.

In one aspect, in the asthmatic individual, the release of normal repair mediators, including LPA, is exaggerated or the actions of the repair mediators are inappropriately prolonged leading to inappropriate airway remodeling. Major structural features of the remodeled airway observed in asthma include a thickened lamina reticularis (the basement membrane-like structure just beneath the airway epithelial cells), increased numbers and activation of myofibroblasts, thickening of the smooth muscle layer, increased numbers of mucus glands and mucus secretions, and alterations in the connective tissue and capillary bed throughout the airway wall. In one aspect, LPA contributes to these structural changes in the airway. In one aspect, LPA is involved in acute airway hyperresponsiveness in asthma. The lumen of the remodeled asthmatic airway is narrower due to the thickening of the airway wall, thus decreasing airflow. In one aspect, LPA contributes to the long-term structural remodeling and the acute hyperresponsiveness of the asthmatic airway. In one aspect, LPA contributes to the hyper-responsiveness that is a primary feature of acute exacerbations of asthma.

In addition to the cellular responses mediated by LPA, several of the LPA signaling pathway components leading to these responses are relevant to asthma. EGF receptor upregulation is induced by LPA and is also seen in asthmatic airways (M. Amishima, et al., *Am. J. Respir. Crit. Care Med.* 157, 1907-1912, 1998). Chronic inflammation is a contributor to asthma, and several of the transcription factors that are activated by LPA are known to be involved in inflammation (Ediger et al., *Eur Respir J* 21:759-769, 2003).

In one aspect, the fibroblast proliferation and contraction and extracellular matrix secretion stimulated by LPA contributes to the fibroproliferative features of other airway diseases, such as the peribronchiolar fibrosis present in chronic bronchitis, emphysema, and interstitial lung disease. Emphysema is also associated with a mild fibrosis of the alveolar wall, a feature which is believed to represent an attempt to repair alveolar damage. In another aspect, LPA plays a role in the fibrotic interstitial lung diseases and obliterative bronchiolitis, where both collagen and myofibroblasts are increased. In another aspect, LPA is involved in several of the various syndromes that constitute chronic obstructive pulmonary disease.

Administration of LPA in vivo induces airway hyperresponsiveness, itch-scratch responses, infiltration and activation of eosinophils and neutrophils, vascular remodeling, and nociceptive flexor responses. LPA also induces histamine release from mouse and rat mast cells. In an acute allergic reaction, histamine induces various responses, such as contraction of smooth muscle, plasma exudation, and mucus production. Plasma exudation is important in the airway, because the leakage and subsequent airway-wall edema contribute to the development of airway hyperresponsiveness. Plasma exudation progresses to conjunctival swelling in ocular allergic disorder and nasal blockage in allergic rhinitis (Hashimoto et al., *J Pharmacol Sci* 100, 82-87, 2006). In one aspect, plasma exudation induced by LPA is mediated by histamine release from mast cells via one or more LPA receptors. In one aspect, the LPA receptor(s) include $LPA_1$ and/or $LPA_3$. In one aspect, a compound of Formulas (I)-(IX), or a pharmaceutically acceptable salt thereof, is used in the treatment of various allergic disorders in a mammal. In one aspect, a compound of Formulas (I)-(IX), or a pharmaceutically acceptable salt thereof, is used in the treatment of respiratory diseases, disorders or conditions in a mammal. In one aspect, a compound of Formulas (I)-(IX), or a pharmaceutically acceptable salt thereof, is used in the treatment of asthma in a mammal. In one aspect, a compound of Formulas (I)-(IX), or a pharmaceutically acceptable salt thereof, is used in the treatment of chronic asthma in a mammal.

The term "respiratory disease," as used herein, refers to diseases affecting the organs that are involved in breathing, such as the nose, throat, larynx, eustachian tubes, trachea, bronchi, lungs, related muscles (e.g., diaphram and intercostals), and nerves. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

In one aspect, presented herein is the use of a compound of Formulas (I)-(IX), or a pharmaceutically acceptable salt thereof, in the treatment or prevention of chronic obstructive pulmonary disease in a mammal comprising administering to the mammal at least once an effective amount of at least one compound of Formulas (I)-(IX), or a pharmaceutically acceptable salt thereof. In addition, chronic obstructive pulmonary disease includes, but is not limited to, chronic bronchitis or emphysema, pulmonary hypertension, interstitial lung fibrosis and/or airway inflammation, and cystic fibrosis.

Nervous System

The nervous system is a major locus for $LPA_1$ expression; there it is spatially and temporally regulated throughout brain development. Oligodendrocytes, the myelinating cells in the central nervous system (CNS), express $LPA_1$ in mammals. In addition, Schwann cells, the myelinating cells of the peripheral nervous system, also express $LPA_1$, which is involved in regulating Schwann cell survival and morphology. These observations identify important functions for receptor-mediated LPA signaling in neurogenesis, cell survival, and myelination.

Exposure of peripheral nervous system cell lines to LPA produces a rapid retraction of their processes resulting in cell rounding, which was, in part, mediated by polymerization of the actin cytoskeleton. In one aspect, LPA causes neuronal degeneration under pathological conditions when the blood-brain barrier is damaged and serum components leak into the brain (Moolenaar, *Curr. Opin. Cell Biol.* 7:203-10, 1995). Immortalized CNS neuroblast cell lines from the cerebral cortex also display retraction responses to LPA exposure through Rho activation and actomyosin interactions. In one aspect, LPA is associated with post-ischemic neural damage (*J. Neurochem.* 61, 340, 1993; *J. Neurochem.*, 70:66, 1998).

In one aspect, provided is a compound of Formulas (I)-(IX), or a pharmaceutically acceptable salt thereof, for use in the treatment or prevention of a nervous system disorder in a mammal. The term "nervous system disorder," as used herein, refers to conditions that alter the structure or function of the brain, spinal cord or peripheral nervous system, including but not limited to Alzheimer's Disease, cerebral edema, cerebral ischemia, stroke, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica.

In one aspect, provided is a compound of Formulas (I)-(IX), or a pharmaceutically acceptable salt thereof, for use in the treatment or prevention of a CNS disorder in a mammal. CNS disorders include, but are not limited to, multiple sclerosis, Parkinson's disease, Alzheimer's disease, stroke, cerebral ischemia, retinal ischemia, post-surgical cognitive dysfunction, migraine, peripheral neuropathy/neuropathic pain, spinal cord injury, cerebral edema and head injury.

Cardiovascular Disorders

Cardiovascular phenotypes observed after targeted deletion of lysophospholipid receptors reveal important roles for lysophospholipid signaling in the development and maturation of blood vessels, formation of atherosclerotic plaques and maintenance of heart rate (Ishii, I. et al. *Annu. Rev. Biochem.* 73, 321-354, 2004). Angiogenesis, the formation of new capillary networks from pre-existing vasculature, is normally invoked in wound healing, tissue growth and myocardial angiogenesis after ischemic injury. Peptide growth factors (e.g. vascular endothelial growth factor (VEGF)) and lysophospholipids control coordinated proliferation, migration, adhesion, differentiation and assembly of vascular endothelial cells (VECs) and surrounding vascular smooth-muscle cells (VSMCs). In one aspect, dysregulation of the processes mediating angiogenesis leads to atherosclerosis, hypertension, tumor growth, rheumatoid arthritis and diabetic retinopathy (Osborne, N. and Stainier, D. Y. *Annu. Rev. Physiol.* 65, 23-43, 2003).

Downstream signaling pathways evoked by lysophospholipid receptors include Rac-dependent lamellipodia formation (e.g. $LPA_1$) and Rho-dependent stress-fiber formation (e.g. $LPA_1$), which is important in cell migration and adhesion. Dysfunction of the vascular endothelium can shift the balance from vasodilatation to vasoconstriction and lead to hypertension and vascular remodeling, which are risk factors for atherosclerosis (Maguire, J. J. et al., *Trends Pharmacol. Sci.* 26, 448-454, 2005).

LPA contributes to both the early phase (barrier dysfunction and monocyte adhesion of the endothelium) and the late phase (platelet activation and intra-arterial thrombus formation) of atherosclerosis, in addition to its overall progression. In the early phase, LPA from numerous sources accumulates in lesions and activates its cognate GPCRs ($LPA_1$ and $LPA_3$) expressed on platelets (Siess, W. *Biochim. Biophys. Acta* 1582, 204-215, 2002; Rother, E. et al. *Circulation* 108, 741-747, 2003). This triggers platelet shape change and aggregation, leading to intra-arterial thrombus formation and, potentially, myocardial infarction and stroke. In support of its atherogenic activity, LPA can also be a mitogen and motogen to VSMCs and an activator of endothelial cells and macrophages. In one aspect, mammals with cardiovascular disease benefit from LPA receptor antagonists that prevent thrombus and neointima plaque formation.

In one aspect, a compound of Formulas (I)-(IX), or a pharmaceutically acceptable salt thereof, is used to treat or prevent cardiovascular disease in mammal.

The term "cardiovascular disease," as used herein refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

In one aspect, provided herein are methods for preventing or treating vasoconstriction, atherosclerosis and its sequelae myocardial ischemia, myocardial infarction, aortic aneurysm, vasculitis and stroke comprising administering at least once to the mammal an effective amount of at least one compound of Formulas (I)-(IX), or a pharmaceutically acceptable salt thereof, or pharmaceutical composition or medicament which includes a compound of Formulas (I)-(IX), or a pharmaceutically acceptable salt thereof.

In one aspect, provided herein are methods for reducing cardiac reperfusion injury following myocardial ischemia and/or endotoxic shock comprising administering at least once to the mammal an effective amount of at least one compound of Formulas (I)-(IX), or a pharmaceutically acceptable salt thereof.

In one aspect, provided herein are methods for reducing the constriction of blood vessels in a mammal comprising administering at least once to the mammal an effective amount of at least one compound of Formulas (I)-(IX), or a pharmaceutically acceptable salt thereof.

In one aspect, provided herein are methods for lowering or preventing an increase in blood pressure of a mammal comprising administering at least once to the mammal an effective amount of at least one compound of Formulas (I)-(IX), or a pharmaceutically acceptable salt thereof.

Inflammation

LPA has been shown to regulate immunological responses by modulating activities/functions of immune cells such as T-/B-lymphocytes and macrophages. In activated T cells, LPA activates IL-2 production/cell proliferation through $LPA_1$ (Gardell et al, *TRENDS in Molecular Medicine* Vol. 12 No. 2 Feb. 2006). Expression of LPA-induced inflammatory response genes is mediated by $LPA_1$ and $LPA_3$ (*Biochem Biophys Res Commun.* 363(4):1001-8, 2007). In addition, LPA modulates the chemotaxis of inflammatory cells (*Biochem Biophys Res Commun.*, 1993, 15; 193(2), 497). The proliferation and cytokine-secreting activity in response to LPA of immune cells (*J. Immunol.* 1999, 162, 2049), platelet aggregation activity in response to LPA, acceleration of migration activity in monocytes, activation of NF-κB in fibroblast, enhancement of fibronectin-binding to the cell surface, and the like are known. Thus, LPA is associated with various inflammatory/immune diseases.

In one aspect, a compound of Formulas (I)-(IX), or a pharmaceutically acceptable salt thereof, is used to treat or prevent inflammation in a mammal. In one aspect, antagonists of $LPA_1$ and/or $LPA_3$ find use in the treatment or prevention of inflammatory/immune disorders in a mammal. In one aspect, the antagonist of $LPA_1$ is a compound of Formulas (I)-(IX), or a pharmaceutically acceptable salt thereof.

Examples of inflammatory/immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

Other Diseases, Disorders or Conditions

In accordance with one aspect, are methods for treating, preventing, reversing, halting or slowing the progression of LPA-dependent or LPA-mediated diseases or conditions once it becomes clinically evident, or treating the symptoms associated with or related to LPA-dependent or LPA-mediated diseases or conditions, by administering to the mammal a compound of Formulas (I)-(IX), or a pharmaceutically acceptable salt thereof. In certain embodiments, the subject already has a LPA-dependent or LPA-mediated disease or condition at the time of administration, or is at risk of developing a LPA-dependent or LPA-mediated disease or condition.

In certain aspects, the activity of $LPA_1$ in a mammal is directly or indirectly modulated by the administration of (at least once) a therapeutically effective amount of at least one compound of Formulas (I)-(IX), or a pharmaceutically acceptable salt thereof.

Such modulation includes, but is not limited to, reducing and/or inhibiting the activity of $LPA_1$. In additional aspects, the activity of LPA in a mammal is directly or indirectly modulated, including reducing and/or inhibiting, by the administration of (at least once) a therapeutically effective amount of at least one compound of Formulas (I)-(IX), or a pharmaceutically acceptable salt thereof. Such modulation includes, but is not limited to, reducing and/or inhibiting the amount and/or activity of a LPA receptor. In one aspect, the LPA receptor is $LPA_1$.

In one aspect, LPA has a contracting action on bladder smooth muscle cell isolated from bladder, and promotes growth of prostate-derived epithelial cell (*J. Urology*, 1999, 162, 1779-1784; *J. Urology*, 2000, 163, 1027-1032). In another aspect, LPA contracts the urinary tract and prostate in vitro and increases intraurethral pressure in vivo (WO 02/062389).

In certain aspects, are methods for preventing or treating eosinophil and/or basophil and/or dendritic cell and/or neutrophil and/or monocyte and/or T-cell recruitment comprising administering at least once to the mammal an effective amount of at least one compound of Formulas (I)-(IX), or a pharmaceutically acceptable salt thereof.

In certain aspects, are methods for the treatment of cystitis, including, e.g., interstitial cystitis, comprising administering at least once to the mammal a therapeutically effective amount of at least one compound of Formulas (I)-(IX), or a pharmaceutically acceptable salt thereof.

In accordance with one aspect, methods described herein include the diagnosis or determination of whether or not a patient is suffering from a LPA-dependent or LPA-mediated disease or condition by administering to the subject a therapeutically effective amount of a compound of Formulas (I)-(IX), or a pharmaceutically acceptable salt thereof, and determining whether or not the patient responds to the treatment.

In one aspect provided herein are compounds of Formulas (I)-(IX), pharmaceutically acceptable salts, pharmaceutically acceptable prodrugs, and pharmaceutically acceptable solvates thereof, which are antagonists of $LPA_1$, and are used to treat patients suffering from one or more LPA-dependent or LPA-mediated conditions or diseases, including, but not limited to, lung fibrosis, kidney fibrosis, liver fibrosis, scarring, asthma, rhinitis, chronic obstructive pulmonary disease, pulmonary hypertension, interstitial lung fibrosis, arthritis, allergy, psoriasis, inflammatory bowel disease, adult respiratory distress syndrome, myocardial infarction, aneurysm, stroke, cancer, pain, proliferative disorders and inflammatory conditions. In some embodiments, LPA-dependent conditions or diseases include those wherein an absolute or relative excess of LPA is present and/or observed.

In any of the aforementioned aspects the LPA-dependent or LPA-mediated diseases or conditions include, but are not limited to, organ fibrosis, asthma, allergic disorders, chronic obstructive pulmonary disease, pulmonary hypertension, lung or pleural fibrosis, peritoneal fibrosis, arthritis, allergy, cancer, cardiovascular disease, ult respiratory distress syndrome, myocardial infarction, aneurysm, stroke, and cancer.

In one aspect, a compound of Formulas (I)-(IX), or a pharmaceutically acceptable salt thereof, is used to improve the corneal sensitivity decrease caused by corneal operations such as laser-assisted in situ keratomileusis (LASIK) or cataract operation, corneal sensitivity decrease caused by corneal degeneration, and dry eye symptom caused thereby.

In one aspect, presented herein is the use of a compound of Formulas (I)-(IX), or a pharmaceutically acceptable salt thereof, in the treatment or prevention of ocular inflammation and allergic conjunctivitis, vernal keratoconjunctivitis, and papillary conjunctivitis in a mammal comprising administering at least once to the mammal an effective amount of at least one compound of Formulas (I)-(IX), or a pharmaceutically acceptable salt thereof.

In one aspect, presented herein is the use of a compound of Formulas (I)-(IX), or a pharmaceutically acceptable salt thereof, in the treatment or prevention of Sjogren disease or inflammatory disease with dry eyes in a mammal comprising administering at least once to the mammal an effective amount of at least one compound of Formulas (I)-(IX), or a pharmaceutically acceptable salt thereof.

In one aspect, LPA and LPA receptors (e.g. $LPA_1$) are involved in the pathogenesis of osteoarthritis (Kotani et al, *Hum. Mol. Genet.*, 2008, 17, 1790-1797). In one aspect, presented herein is the use of a compound of Formula (I), or a pharmaceutically acceptable salt thereof, in the treatment or prevention of osteoarthritis in a mammal comprising administering at least once to the mammal an effective amount of at least one compound of Formulas (I)-(IX), or a pharmaceutically acceptable salt thereof.

In one aspect, LPA receptors (e.g. $LPA_1$, $LPA_3$) contribute to the pathogenesis of rheumatoid arthritis (Zhao et al, *Mol. Pharmacol.*, 2008, 73(2), 587-600). In one aspect, presented herein is the use of a compound of Formulas (I)-(IX), or a pharmaceutically acceptable salt thereof, in the treatment or prevention of rheumatoid arthritis in a mammal comprising administering at least once to the mammal an effective amount of at least one compound of Formulas (I)-(IX), or a pharmaceutically acceptable salt thereof.

In one aspect, LPA receptors (e.g. $LPA_1$) contribute to adipogenesis. (Simon et al, *J. Biol. Chem.*, 2005, vol. 280, no. 15, p. 14656). In one aspect, presented herein is the use of a compound of Formulas (I)-(IX), or a pharmaceutically acceptable salt thereof, in the promotion of adipose tissue formation in a mammal comprising administering at least once to the mammal an effective amount of at least one compound of Formulas (I)-(IX), or a pharmaceutically acceptable salt thereof.

a. In Vitro Assays

The effectiveness of compounds of the present invention as $LPA_1$ inhibitors can be determined in an $LPA_1$ functional antagonist assay as follows: Chinese hamster ovary cells overexpressing human $LPA_1$ were plated overnight (15,000 cells/well) in poly-D-lysine coated 384-well microplates (Greiner bio-one, Cat #781946) in DMEM/F12 medium (Gibco, Cat #11039). Following overnight culture, cells were loaded with calcium indicator dye (AAT Bioquest Inc, Cat #34601) for 30 minutes at 37° C. The cells were then equilibrated to room temperature for 30 minutes before the assay. Test compounds solubilized in DMSO were transferred to 384 well non-binding surface plates (Corning, Cat #3575) using the Labcyte Echo acoustic dispense and diluted with assay buffer [1×HBSS with calcium/magnesium (Gibco Cat #14025-092), 20 mM HEPES (Gibco Cat #15630-080) and 0.1% fatty acid free BSA (Sigma Cat #A9205)] to a final concentration of 0.5% DMSO. Diluted compounds were added to the cells by FDSS6000 (Hamamatsu) at final concentrations ranging from 0.08 nM to 5 µM. and were then incubated for 20 min at room temperature at which time LPA (Avanti Polar Lipids Cat #857130C) was added at final concentrations of 10 nM to stimulate the cells. The compound $IC_{50}$ value was defined as the concentration of test compound which inhibited 50% of the calcium flux induced by LPA alone. $IC_{50}$ values were determined by fitting data to a 4-parameter logistic equation (GraphPad Prism, San Diego Calif.).

b. In Vivo Assays

LPA Challenge with Plasma Histamine Evaluation.

Compound is dosed orally p.o. 2 hours to CD-1 female mice prior to the LPA challenge. The mice are then dosed via tail vein (IV) with 0.15 mL of LPA in 0.1% BSA/PBS (2 µg/L). Exactly 2 minutes following the LPA challenge, the mice are euthanized by decapitation and the trunk blood is collected. These samples are collectively centrifuged and individual 75 µL samples are frozen at −20° C. until the time of the histamine assay.

The plasma histamine analysis was run by standard EIA (Enzyme Immunoassay) methods. Plasma samples were thawed and diluted 1:30 in 0.1% BSA in PBS. The EIA protocol for histamine analysis as outlined by the manufacturer was followed (Histamine EIA, Oxford Biomedical Research, EA #31).

The LPA used in the assay is formulated as follows: LPA (1-oleoyl-2-hydroxy-sn-glycero-3-phosphate (sodium salt), 857130P, Avanti Polar Lipids) is prepared in 0.1% BSA/PBS for total concentration of 2 µg/µL. 13 mg of LPA is weighed and 6.5 mL 0.1% BSA added, vortexed and sonicated for ~1 hour until a clear solution is achieved.

V. Pharmaceutical Compositions, Formulations and Combinations

In some embodiments, provided is a pharmaceutical composition comprising a therapeutically effective amount of a compound of Formulas (I)-(IX), or a pharmaceutically acceptable salt thereof. In some embodiments, the pharmaceutical composition also contains at least one pharmaceutically acceptable inactive ingredient.

In some embodiments, provided is a pharmaceutical composition comprising a therapeutically effective amount of a compound of Formulas (I)-(IX), or a pharmaceutically acceptable salt thereof, and at least one pharmaceutically acceptable inactive ingredient. In one aspect, the pharmaceutical composition is formulated for intravenous injection, subcutaneous injection, oral administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the pharmaceutical composition further comprises one or more additional therapeutically active agents selected from: corticosteroids (e.g., dexamethasone or fluticasone), immunosuppresants (e.g., tacrolimus & pimecrolimus), analgesics, anti-cancer agent, anti-inflammatories, chemokine receptor antagonists, bronchodilators, leukotriene receptor antagonists (e.g., montelukast or zafirlukast), leukotriene formation inhibitors, monoacylglycerol kinase inhibitors, phospholipase $A_1$ inhibitors, phospholipase $A_2$ inhibitors, and lysophospholipase D (lysoPLD) inhibitors, autotaxin inhibitors, decongestants, antihistamines (e.g., loratidine), mucolytics, anticholinergics, antitussives, expectorants, anti-infectives (e.g., fusidic acid, particularly for treatment of atopic dermatitis), anti-fungals (e.g., clotriazole, particularly for atopic dermatitis), anti-IgE antibody therapies (e.g., omalizumab), β-2 adrenergic agonists (e.g., albuterol or salmeterol), other PGD2 antagonists acting at other receptors such as DP antagonists, PDE4 inhibitors (e.g., cilomilast), drugs that modulate cytokine production, e.g., TACE inhibitors, drugs that modulate activity of Th2 cytokines IL-4 & IL-5 (e.g., blocking monoclonal antibodies & soluble receptors), PPARγ agonists (e.g., rosiglitazone and pioglitazone), 5-lipoxygenase inhibitors (e.g., zileuton).

In some embodiments, the pharmaceutical composition further comprises one or more additional anti-fibrotic agents selected from pirfenidone, nintedanib, thalidomide, carlumab, FG-3019, fresolimumab, interferon alpha, lecithinized superoxide dismutase, simtuzumab, tanzisertib, tralokinumab, hu3G9, AM-152, IFN-gamma-1b, IW-001, PRM-151, PXS-25, pentoxifylline/N-acetyl-cysteine, pentoxifylline/vitamin E, salbutamol sulfate, [Sar9, Met (O2) 11]-Substance P, pentoxifylline, mercaptamine bitartrate, obeticholic acid, aramchol, GFT-505, eicosapentaenoic acid ethyl ester, metformin, metreleptin, muromonab-CD3, oltipraz, IMM-124-E, MK-4074, PX-102, RO-5093151. In some embodiments, provided is a method comprising administering a compound of Formulas (I)-(IX), or a pharmaceutically acceptable salt thereof, to a human with a LPA-dependent or LPA-mediated disease or condition. In some embodiments, the human is already being administered one or more additional therapeutically active agents other than a compound of Formulas (I)-(IX), or a pharmaceutically acceptable salt thereof. In some embodiments, the method further comprises administering one or more additional therapeutically active agents other than a compound of Formulas (I)-(IX), or a pharmaceutically acceptable salt thereof.

In some embodiments, the one or more additional therapeutically active agents other than a compound of Formulas (I)-(IX), or a pharmaceutically acceptable salt thereof, are selected from: corticosteroids (e.g., dexamethasone or fluticasone), immunosuppresants (e.g., tacrolimus & pimecrolimus), analgesics, anti-cancer agent, anti-inflammatories, chemokine receptor antagonists, bronchodilators, leukotriene receptor antagonists (e.g., montelukast or zafirlukast), leukotriene formation inhibitors, monoacylglycerol kinase inhibitors, phospholipase $A_1$ inhibitors, phospholipase $A_2$ inhibitors, and lysophospholipase D (lysoPLD) inhibitors, autotaxin inhibitors, decongestants, antihistamines (e.g., loratidine), mucolytics, anticholinergics, antitussives, expectorants, anti-infectives (e.g., fusidic acid, particularly for treatment of atopic dermatitis), anti-fungals (e.g., clotriazole, particularly for atopic dermatitis), anti-IgE antibody therapies (e.g., omalizumab), β-2 adrenergic agonists (e.g., albuterol or salmeterol), other PGD2 antagonists acting at other receptors such as DP antagonists, PDE4 inhibitors (e.g., cilomilast), drugs that modulate cytokine production, e.g. TACE inhibitors, drugs that modulate activity of Th2 cytokines IL-4 & IL-5 (e.g., blocking monoclonal antibodies & soluble receptors), PPARγ agonists (e.g., rosiglitazone and pioglitazone), 5-lipoxygenase inhibitors (e.g., zileuton).

In some embodiments, the one or more additional therapeutically active agents other than a compound of Formulas (I)-(IX), or a pharmaceutically acceptable salt thereof, are other anti-fibrotic agents selected from pirfenidone, nintedanib, thalidomide, carlumab, FG-3019, fresolimumab, interferon alpha, lecithinized superoxide dismutase, simtuzumab, tanzisertib, tralokinumab, hu3G9, AM-152, IFN-gamma-1b, IW-001, PRM-151, PXS-25, pentoxifylline/N-acetyl-cysteine, pentoxifylline/vitamin E, salbutamol sulfate, [Sar9, Met(O2)11]-Substance P, pentoxifylline, mercaptamine bitartrate, obeticholic acid, aramchol, GFT-505, eicosapentyl ethyl ester, metformin, metreleptin, muromonab-CD3, oltipraz, IMM-124-E, MK-4074, PX-102, RO-5093151.

In some embodiments, the one or more additional therapeutically active agents other than a compound of Formulas (I)-(IX), or a pharmaceutically acceptable salt thereof, are selected from ACE inhibitors, ramipril, AII antagonists, irbesartan, anti-arrythmics, dronedarone, PPARα activators, PPARγ activators, pioglitazone, rosiglitazone, prostanoids, endothelin receptor antagonists, elastase inhibitors, calcium antagonists, beta blockers, diuretics, aldosterone receptor antagonists, eplerenone, renin inhibitors, rho kinase inhibitors, soluble guanylate cyclase (sGC) activators, sGC sensitizers, PDE inhibitors, PDE5 inhibitors, NO donors, digitalis drugs, ACE/NEP inhibitors, statins, bile acid reuptake inhibitors, PDGF antagonists, vasopressin antagonists, aquaretics, NHE1 inhibitors, Factor Xa antagonists, Factor XIIIa antagonists, anticoagulants, anti-thrombotics, platelet inhibitors, profibroltics, thrombin-activatable fibrinolysis inhibitors (TAFI), PAI-1 inhibitors, coumarins, heparins, thromboxane antagonists, serotonin antagonists, COX inhibitors, aspirin, therapeutic antibodies, GPIIb/IIIa antagonists, ER antagonists, SERMs, tyrosine kinase inhibitors, RAF kinase inhibitors, p38 MAPK inhibitors, pirfenidone, multi-kinase inhibitors, nintedanib, sorafenib.

In some embodiments, the one or more additional therapeutically active agents other than a compound of Formulas (I)-(IX), or a pharmaceutically acceptable salt thereof, are selected from Gremlin-1 mAb, PAI-1 mAb, Promedior (PRM-151; recombinant human Pentraxin-2); FGF21, TGFβ antagonists, αvβ6 & αvβ pan-antagonists; FAK inhibitors, TG2 inhibitors, LOXL2 inhibitors, NOX4 inhibitors, MGAT2 inhibitors, GPR120 agonists.

Pharmaceutical formulations described herein are administrable to a subject in a variety of ways by multiple administration routes, including but not limited to, oral, parenteral (e.g., intravenous, subcutaneous, intramuscular), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compound of Formulas (I)-(IX), or a pharmaceutically acceptable salt thereof, is administered orally.

In some embodiments, the compound of Formulas (I)-(IX), or a pharmaceutically acceptable salt thereof, is administered topically. In such embodiments, the compound of Formulas (I)-(IX), or a pharmaceutically acceptable salt thereof, is formulated into a variety of topically administrable compositions, such as solutions, suspensions, lotions, gels, pastes, shampoos, scrubs, rubs, smears, medicated sticks, medicated bandages, balms, creams or ointments. Such pharmaceutical compounds can contain solubilizers, stabilizers, tonicity enhancing agents, buffers and preservatives. In one aspect, the compound of Formulas (I)-(IX), or a pharmaceutically acceptable salt thereof, is administered topically to the skin.

In another aspect, the compound of Formulas (I)-(IX), or a pharmaceutically acceptable salt thereof, is administered by inhalation. In one embodiment, the compound of Formulas (I)-(IX), or a pharmaceutically acceptable salt thereof, is administered by inhalation that directly targets the pulmonary system.

In another aspect, the compound of Formulas (I)-(IX), or a pharmaceutically acceptable salt thereof, is formulated for intranasal administration. Such formulations include nasal sprays, nasal mists, and the like.

In another aspect, the compound of Formulas (I)-(IX), or a pharmaceutically acceptable salt thereof, is formulated as eye drops.

In another aspect is the use of a compound of Formulas (I)-(IX), or a pharmaceutically acceptable salt thereof, in the manufacture of a medicament for treating a disease, disorder or conditions in which the activity of at least one LPA receptor contributes to the pathology and/or symptoms of the disease or condition. In one embodiment of this aspect, the LPA is selected from $LPA_1$, $LPA_2$, $LPA_3$, $LPA_4$, $LPA_5$ and $LPA_6$. In one aspect, the LPA receptor is $LPA_1$. In one aspect, the disease or condition is any of the diseases or conditions specified herein.

In any of the aforementioned aspects are further embodiments in which: (a) the effective amount of the compound of Formulas (I)-(IX), or a pharmaceutically acceptable salt thereof, is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration; and/or (i) the effective amount of the compound is administered rectally to the mammal; and/or (j) the effective amount is administered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Also provided is a method of inhibiting the physiological activity of LPA in a mammal comprising administering a therapeutically effective amount of a compound of Formulas (I)-(IX) or a pharmaceutically acceptable salt thereof to the mammal in need thereof.

In one aspect, provided is a medicament for treating a LPA-dependent or LPA-mediated disease or condition in a mammal comprising a therapeutically effective amount of a compound of Formulas (I)-(IX), or a pharmaceutically acceptable salt thereof.

In some cases disclosed herein is the use of a compound of Formulas (I)-(IX), or a pharmaceutically acceptable salt thereof, in the manufacture of a medicament for the treatment of a LPA-dependent or LPA-mediated disease or condition.

In some cases disclosed herein is the use of a compound of Formulas (I)-(IX), or a pharmaceutically acceptable salt thereof, in the treatment or prevention of a LPA-dependent or LPA-mediated disease or condition.

In one aspect, is a method for treating or preventing a LPA-dependent or LPA-mediated disease or condition in a mammal comprising administering a therapeutically effective amount of a compound of Formulas (I)-(IX), or a pharmaceutically acceptable salt thereof.

In one aspect, LPA-dependent or LPA-mediated diseases or conditions include, but are not limited to, fibrosis of organs or tissues, scarring, liver diseases, dermatological conditions, cancer, cardiovascular disease, respiratory diseases or conditions, inflammatory disease, gastrointestinal tract disease, renal disease, urinary tract-associated disease, inflammatory disease of lower urinary tract, dysuria, frequent urination, pancreas disease, arterial obstruction, cerebral infarction, cerebral hemorrhage, pain, peripheral neuropathy, and fibromyalgia.

In one aspect, the LPA-dependent or LPA-mediated disease or condition is a respiratory disease or condition. In some embodiments, the respiratory disease or condition is asthma, chronic obstructive pulmonary disease (COPD), pulmonary fibrosis, pulmonary arterial hypertension or acute respiratory distress syndrome.

In some embodiments, the LPA-dependent or LPA-mediated disease or condition is selected from idiopathic pulmonary fibrosis; other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease); radiation induced fibrosis; chronic obstructive pulmonary disease (COPD); scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; focal segmental glomerular sclerosis; IgA nephropathy; hypertension; Alport; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Duputren disease, keloids, cutaneous fibrosis; cutaneous scleroderma; spinal cord injury/fibrosis; myelofibrosis; vascular restenosis; atherosclerosis; arteriosclerosis; Wegener's granulomatosis; Peyronie's disease, chronic lymphocytic leukemia, tumor metastasis, transplant organ rejection, endometriosis, neonatal respiratory distress syndrome and neuropathic pain.

In one aspect, the LPA-dependent or LPA-mediated disease or condition is described herein.

In one aspect, provided is a method for the treatment or prevention of organ fibrosis in a mammal comprising administering a therapeutically effective amount of a compound of Formulas (I)-(IX) or a pharmaceutically acceptable salt thereof to a mammal in need thereof.

In one aspect, the organ fibrosis comprises lung fibrosis, renal fibrosis, or hepatic fibrosis.

In one aspect, provided is a method of improving lung function in a mammal comprising administering a therapeutically effective amount of a compound of Formula (I), or a pharmaceutically acceptable salt thereof to the mammal in need thereof. In one aspect, the mammal has been diagnosed as having lung fibrosis.

In one aspect, compounds disclosed herein are used to treat idiopathic pulmonary fibrosis (usual interstitial pneumonia) in a mammal.

In some embodiments, compounds disclosed herein are used to treat diffuse parenchymal interstitial lung diseases in mammal: iatrogenic drug induced, occupational/environmental (Farmer lung), granulomatous diseases (sarcoidosis, hypersensitivity pneumonia), collagen vascular disease (scleroderma and others), alveolar proteinosis, langerhans cell granulonleiomyomatosis, lymphangioleiomyomatosis, Hermansky-Pudlak Syndrome, Tuberous sclerosis, neurofibromatosis, metabolic storage disorders, familial interstitial lung disease.

In some embodiments, compounds disclosed herein are used to treat post-transplant fibrosis associated with chronic rejection in a mammal: Bronchiolitis obliterans for lung transplant.

In some embodiments, compounds disclosed herein are used to treat cutaneous fibrosis in a mammal: cutaneous scleroderma, Dupuytren disease, keloids.

In one aspect, compounds disclosed herein are used to treat hepatic fibrosis with or without cirrhosis in a mammal: toxic/drug induced (hemochromatosis), alcoholic liver disease, viral hepatitis (hepatitis B virus, hepatitis C virus, HCV), nonalcoholic liver disease (NAFLD, NASH), metabolic and auto-immune disease.

In one aspect, compounds disclosed herein are used to treat renal fibrosis in a mammal: tubulointerstitium fibrosis, glomerular sclerosis.

In any of the aforementioned aspects involving the treatment of LPA dependent diseases or conditions are further embodiments comprising administering at least one additional agent in addition to the administration of a compound having the structure of Formulas (I)-(IX), or a pharmaceutically acceptable salt thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

In some embodiments, compounds provided herein are used as antagonists of at least one LPA receptor. In some embodiments, compounds provided herein are used for inhibiting the activity of at least one LPA receptor or for the treatment of a disease or condition that would benefit from inhibition of the activity of at least one LPA receptor. In one aspect, the LPA receptor is $LPA_1$.

In other embodiments, compounds provided herein are used for the formulation of a medicament for the inhibition of $LPA_1$ activity.

Articles of manufacture, which include packaging material, a compound of Formulas (I)-(IX), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for inhibiting the activity of at least one LPA receptor, or for the treatment, prevention or amelioration of one or more symptoms of a disease or condition that would benefit from inhibition of the activity of at least one LPA receptor, are provided.

VI. General Synthesis Including Schemes

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, Fourth Edition, Wiley-Interscience (2006)).

The compounds of Formulas (I)-(IX) may be prepared by the exemplary processes described in the following schemes and working examples, as well as relevant published literature procedures that are used by one skilled in the art. Exemplary reagents and procedures for these reactions appear herein after and in the working examples. Protection and deprotection in the processes below may be carried out by procedures generally known in the art (see, for example, Wuts, P. G. M., *Greene's Protective Groups in Organic Synthesis,* 5th Edition, Wiley (2014)). General methods of organic synthesis and functional group transformations are found in: Trost, B. M. et al., Eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure.* 7th Edition, Wiley, New York, N.Y. (2013); Katritzky, A. R. et al., Eds., *Comprehensive Organic Functional Group Transformations II,* 2nd Edition, Elsevier Science Inc., Tarrytown, N.Y. (2004); Larock, R. C., *Comprehensive Organic Transformations,* $2^{nd}$ Edition, Wiley-VCH, New York, N.Y. (1999), and references therein.

Scheme 1 describes the synthesis of carbamoyloxymethyl triazole-aryloxy cyclohexyl acids 14. A dihalo (preferably dibromo) phenyl or azine (e.g. pyridine) derivative 1 is coupled with an appropriately protected (e.g. as a tetrahydropyranyl ether) propargyl alcohol 2 under Sonogashira conditions (e.g. Alper, P. et al, WO 2008097428) to give the corresponding bromo-aryl or bromo-heteroaryl protected propargyl alcohol 3. Thermal reaction of alkyne 3 with an alkyl azide 4 (with or without an appropriate catalyst; Qian, Y. et al, *J. Med. Chem.,* 2012, 55, 7920-7939 or Boren, B. C., et al., *J. Am. Chem. Soc.,* 2008, 130, 8923-8930) provides the corresponding regioisomeric protected hydroxylmethyltriazoles, from which the desired triazole regioisomer 5 can be isolated. Reaction of the bromoaryl- or bromoheteroaryl-triazoles 5 with pinacol diboronate in the presence of an appropriate palladium catalyst (Ishiyama, T. et al, *J. Org. Chem.* 1995, 60, 7508-7510) provides the corresponding pinacol boronate 6, which is then oxidized with hydrogen peroxide to give the corresponding phenol or hydroxyheteroarene 7 (Fukumoto, S. et al, WO 2012137982). Reaction of phenol/hydroxyheteroarene 7 with a 3-hydroxy cycloalkyl ester 8 under Mitsunobu reaction conditions (Kumara Swamy, K. C., *Chem. Rev.,* 2009, 109, 2551-2651) furnishes the corresponding triazole cycloalkyl ether ester 9. Deprotection of the hydoxytriazole 9 provides the triazole alcohol 10, which is then reacted with 4-nitrophenyl chloroformate in the presence of an appropriate base to give the corresponding triazole 4-nitrophenyl carbonate 11. The triazole 4-nitrophenyl carbonate 11 is then reacted with an amine 12 in the presence of an appropriate base to give the triazole carbamate 13, which then undergoes ester deprotection to give the desired carbamoyloxymethyltriazole-aryloxy cycloalkyl acids 14.

Scheme 1.

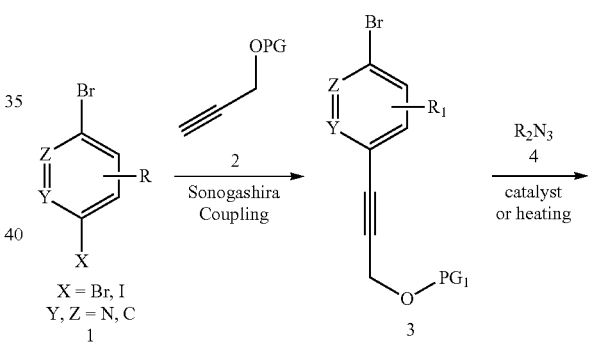

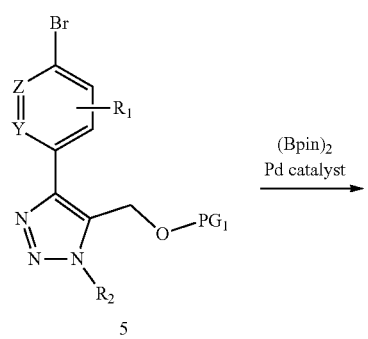

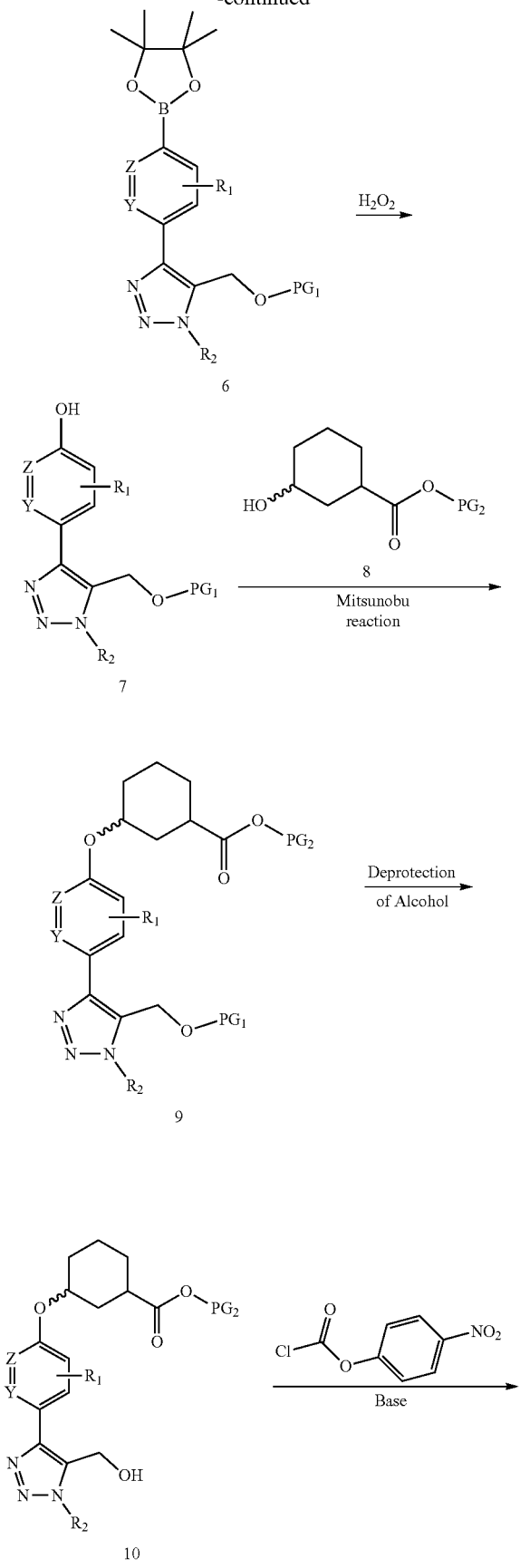
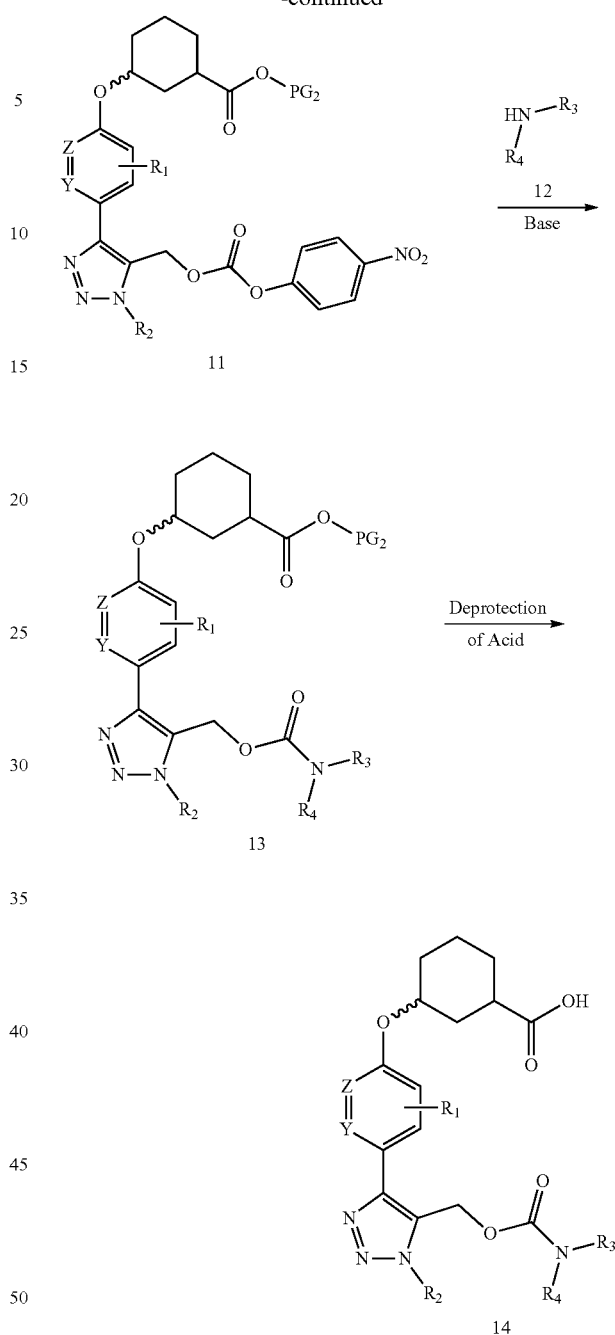

For the specific example of analogs 14, where R$_2$=CH$_3$ (Scheme 1A), instead of using an alkyl azide for the cycloaddition to the protected hydroxyalkyl alkyne 3, trimethylsilyl azide is a viable replacement reagent (Qian, Y. et al, *J Med. Chem.*, 2012, 55, 7920-7939) that can be used under either thermal or transition-metal catalyzed conditions (Boren, B. C. et. al., *J. Am. Chem. Soc.*, 2008, 130, 8923-8930). Under these conditions, the desired triazole regioisomer 15 is obtained as the major product of the 1,3-dipolar cycloaddition reaction, and the trimethylsilyl group is subsequently removed under standard desilylation conditions (e.g. Bu$_4$NF, as in Qian, Y. et al, *J. Med. Chem.*, 2012, 55, 7920-7939).

Scheme 1A.

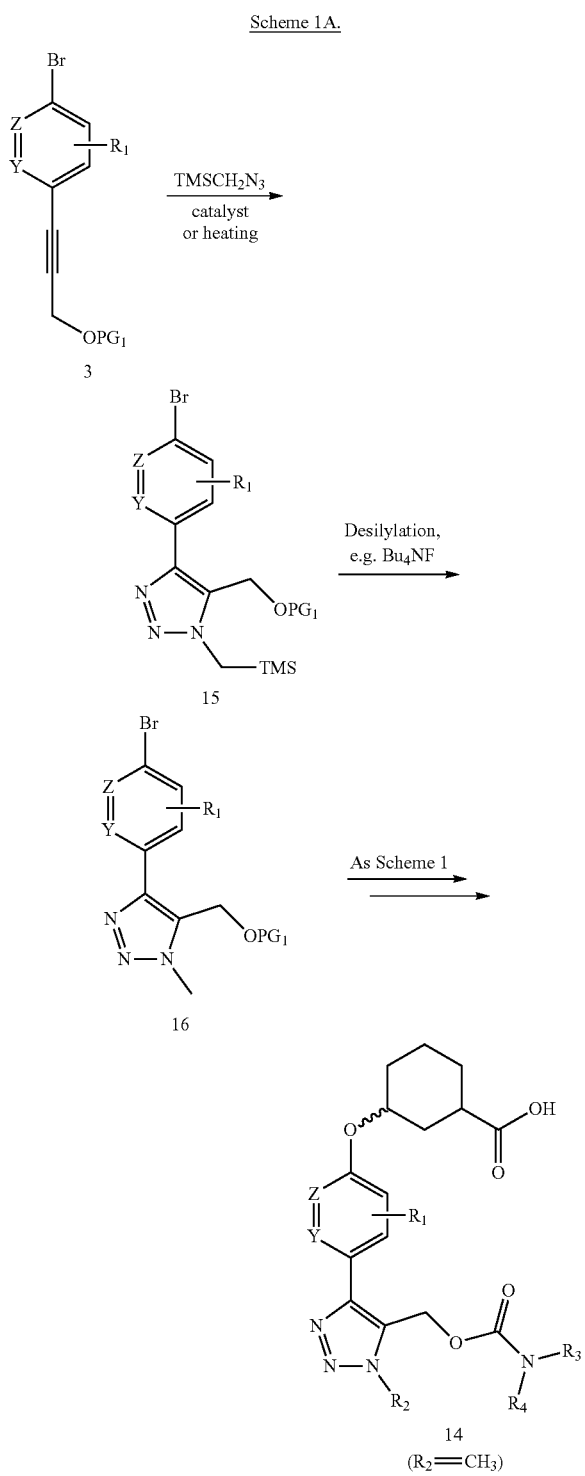

et. al., *J. Am. Chem. Soc.*, 2008, 130, 8923-8930) provides the corresponding regioisomeric hydroxymethyl-triazoles, from which the desired triazole regioisomer 18 can be isolated. Triazole alcohol 18 is then reacted with 4-nitrophenyl chloroformate in the presence of an appropriate base to give the corresponding triazole 4-nitrophenyl carbonate 19, which is then reacted with an amine 12 in the presence of an appropriate base to give the aryl/heteroaryl-triazole carbamate 20. The bromo-aryl/heteroaryl triazole 20 is then converted to the hydroxyaryl or hydroxy-heteroaryl triazole 21 via the corresponding boronate using the 2 step sequence [B(pin)$_2$/Pd-catalysis followed by treatment with H$_2$O$_2$] described in Scheme 1. Hydroxyaryl/heteroaryl triazole 22 is then reacted with a 3-hydroxy cycloalkylester 8 under Mitsunobu reaction conditions (Kumara Swamy, K. C., *Chem. Rev.*, 2009, 109, 2551-2651) to furnish the corresponding triazole cycloalkyl ether ester 13 which is then deprotected to give the desired carbamoyloxy methyltriazole-aryloxy cyclohexyl acids 14.

Scheme 2.

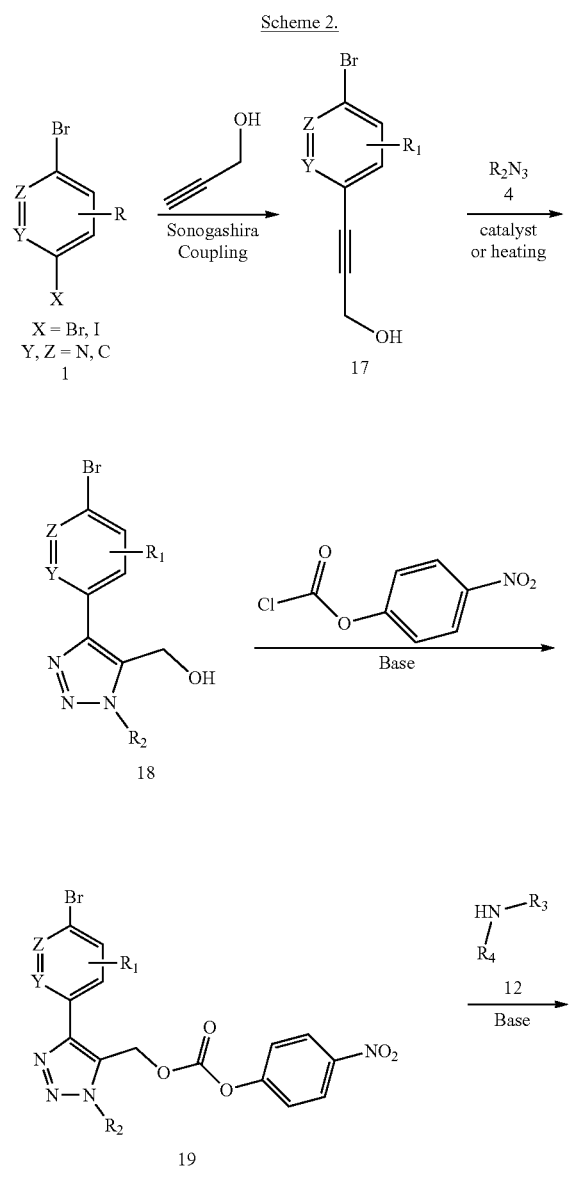

Scheme 2 describes an alternative synthetic route to the carbamoyloxymethyl triazole-aryloxy cyclohexyl acids 14. A dihalo (preferably dibromo) phenyl or azine (e.g. pyridine) derivative 1 is coupled with propargyl alcohol under Sonogashira conditions (Alper, P. et al, WO 2008097428) to give the corresponding bromo-aryl or bromo-heteroaryl propargyl alcohol 3. Thermal reaction of alkyne 3 with an alkyl azide 4 (with or without an appropriate catalyst, Qian, Y. et al, *J. Med. Chem.*, 2012, 55, 7920-7939; Boren, B. C.

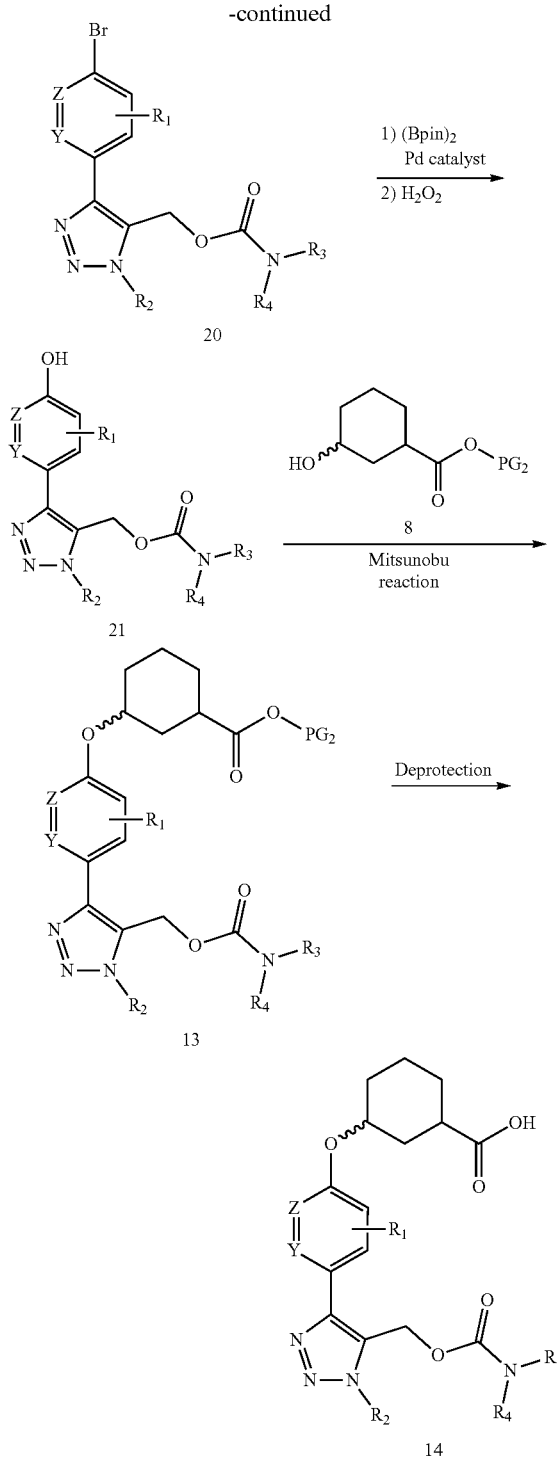

alkyl iodide 25 under basic conditions to give a mixture of regioisomeric alkylated triazoles, from which the desired triazole regioisomer 26 can be isolated. Lithiation of triazole 26 (Hemandez, M. et al, US 20120115844) followed by reaction with a formylating agent, e.g. dimethyl formamide, provided the triazole aldehyde 27. Deprotection of the alkoxy group of arene/heteroarene 27 followed by reprotection of the phenol/hydroxy-heteroarene with a more labile protecting group (e.g. t-butyldimethylsilyl ether) gives the protected aryl/heteroaryl triazole aldehyde 28, which is then reduced by standard methods (e.g. $NaBH_4$) to the corresponding triazole alcohol 29. Triazole alcohol 29 is reacted with 4-nitrophenyl chloroformate to give the corresponding triazole 4-nitrophenyl carbonate 30. This triazole carbonate 30 is then reacted with an amine 12 in the presence of an appropriate base to give the corresponding triazole carbamate, which subsequently undergoes deprotection to provide the hydroxy aryl/hetero-aryl triazole carbamate 21. The hydroxy aryl/heteroaryl triazole carbamate 21 then is subjected to a Mitsunobu reaction with 3-hydroxy cycloalkyl ester 8 to furnish the corresponding triazole cycloalkyl ether ester 13, followed by ester deprotection to give the desired carbamoyloxy methyltriazole-aryloxy cyclohexyl acids 14.

Scheme 3.

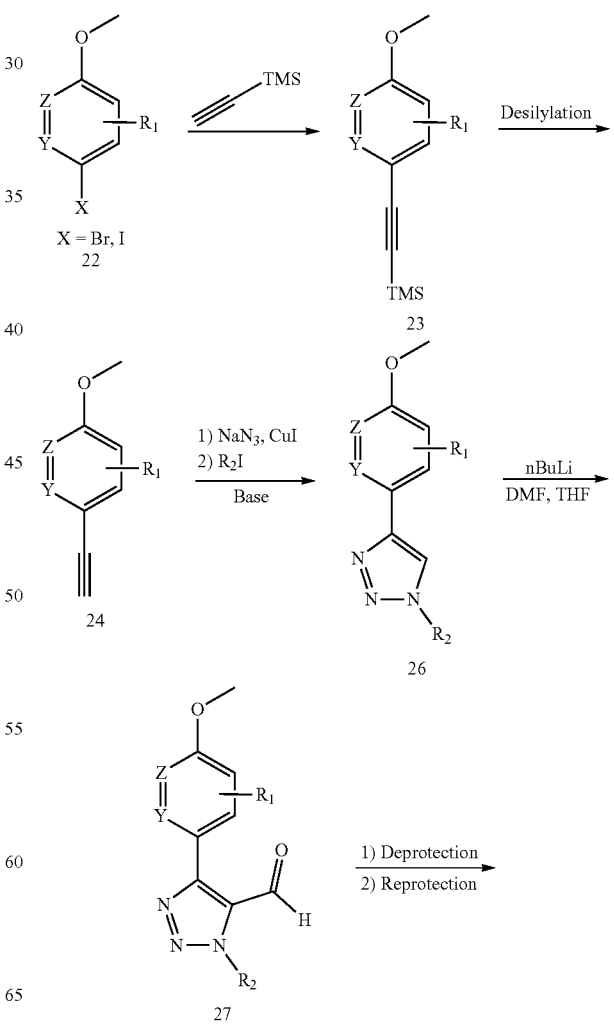

Another alternative synthesis of carbamoyloxymethyl triazole-aryloxy cyclohexyl acids 14 is described in Scheme 3. Reaction of an alkoxyphenyl or azine (e.g. pyridine) derivative 1 with trimethylsilyl acetylene under Sonogashira conditions (Alper, P. et al, WO 2008097428) gives the corresponding alkoxy-aryl or heteroaryl silyl acetylene 23, which is then desilylated under standard conditions (e.g. $Bu_4NF$) to give the alkyne 24. Thermal reaction of alkyne 24 with sodium azide gives the corresponding triazole (Roehrig, U. et al, WO 2009127669), which is then alkylated with an

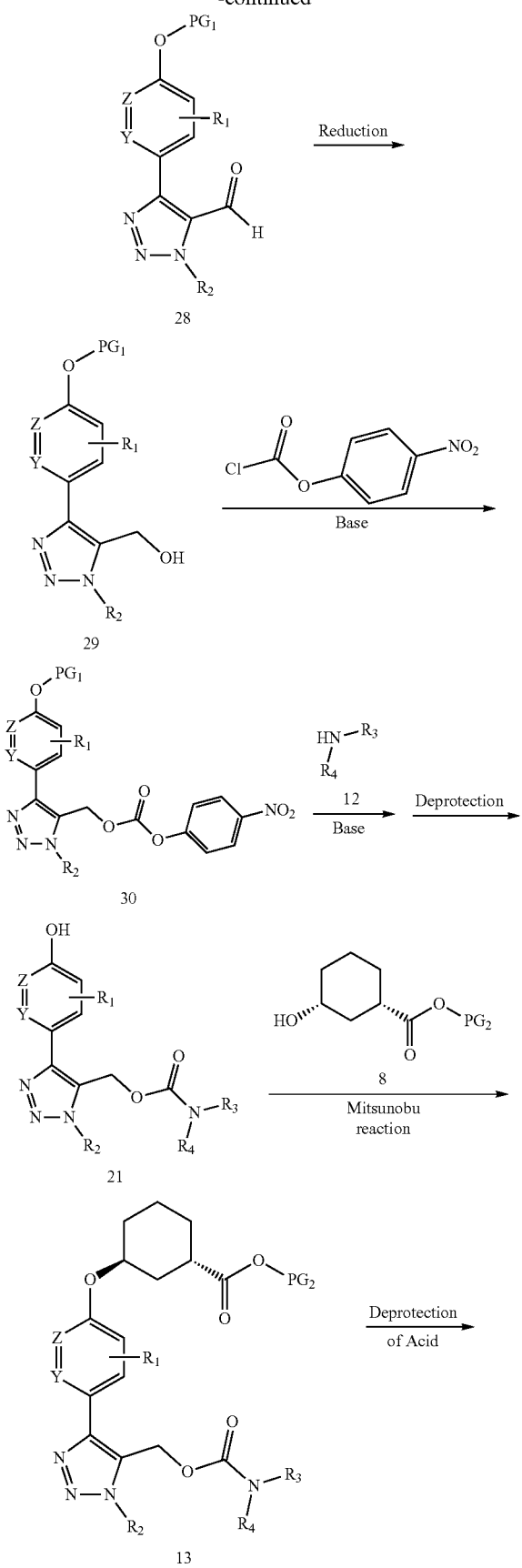

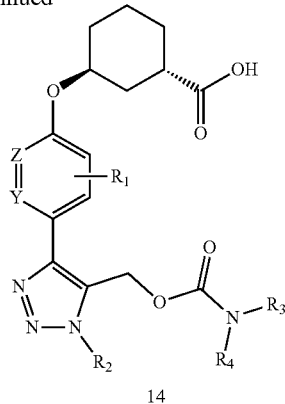

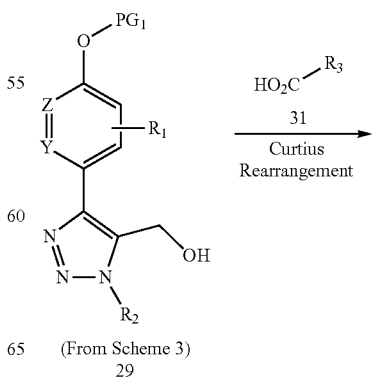

A different synthetic route for the preparation of triazole carbamate acids 14 is described in Scheme 4. The protected hydroxyaryl/heteroaryl triazole alcohol 29 is reacted with the intermediate isocyanate generated from a carboxylic acid 31 under Curtius reaction conditions (Seiders, T. et al, WO 2011041694A2) to give the monoalkyl NH-carbamate 32. Base-mediated reaction of NH-carbamate 32 with an appropriate alkyl iodide 33 provides the corresponding triazole N-disubstituted carbamate, which is then deprotected to provide the hydroxy aryl/heteroaryl triazole carbamate 21. Hydroxy aryl/heteroaryl triazole carbamate 21 then is subjected to a Mitsunobu reaction with 3-hydroxy cycloalky-lester 8 to furnish the corresponding triazole cycloalkyl ether ester 13 followed by ester deprotection to give the desired carbamoyloxy methyltriazole-aryloxy cyclohexyl acids 14. Alternatively, the triazole monoalkyl NH-carbamate 32 is deprotected to give the hydroxy aryl/heteroaryl triazole carbamate, which is then reacted with 3-hydroxy cycloalky-lester 8 under Mitsunobu reaction conditions to provide the triazole-aryloxy cyclohexyl ester NH-carbamate 34. Intermediate NH-carbamate 34 is then alkylated with alkyl iodide 33 under basic conditions; subsequent ester deprotection furnishes the desired carbamoyloxy methyltriazole-aryloxy cyclohexyl acids 14.

Scheme 4.

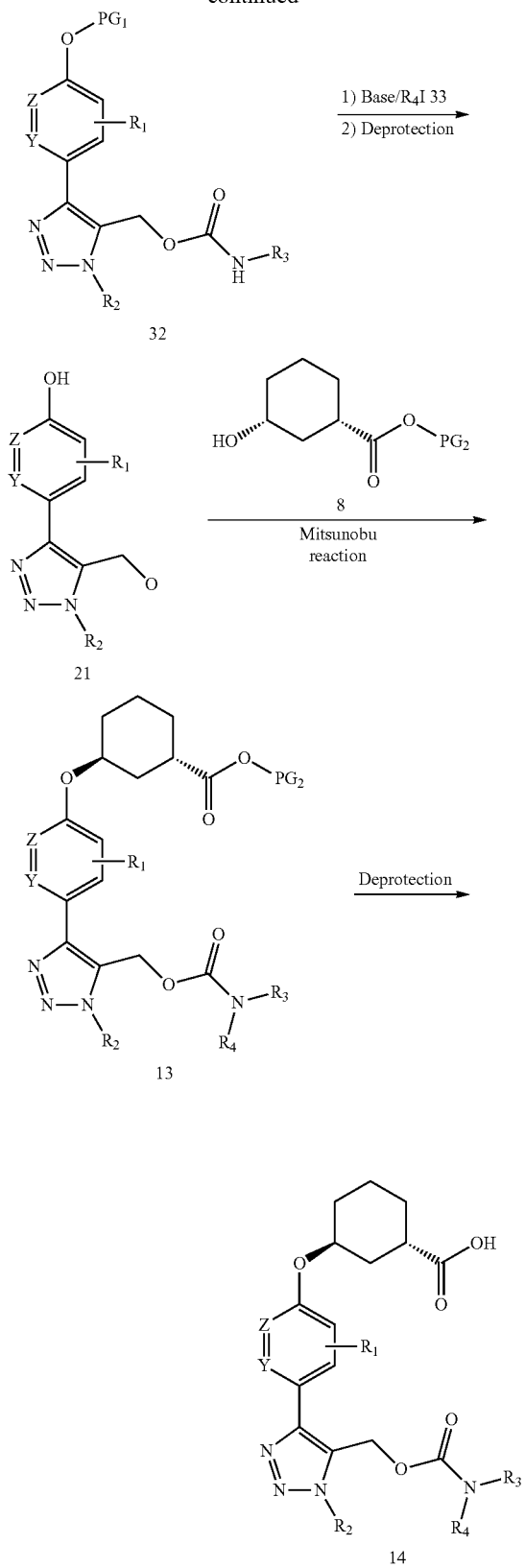
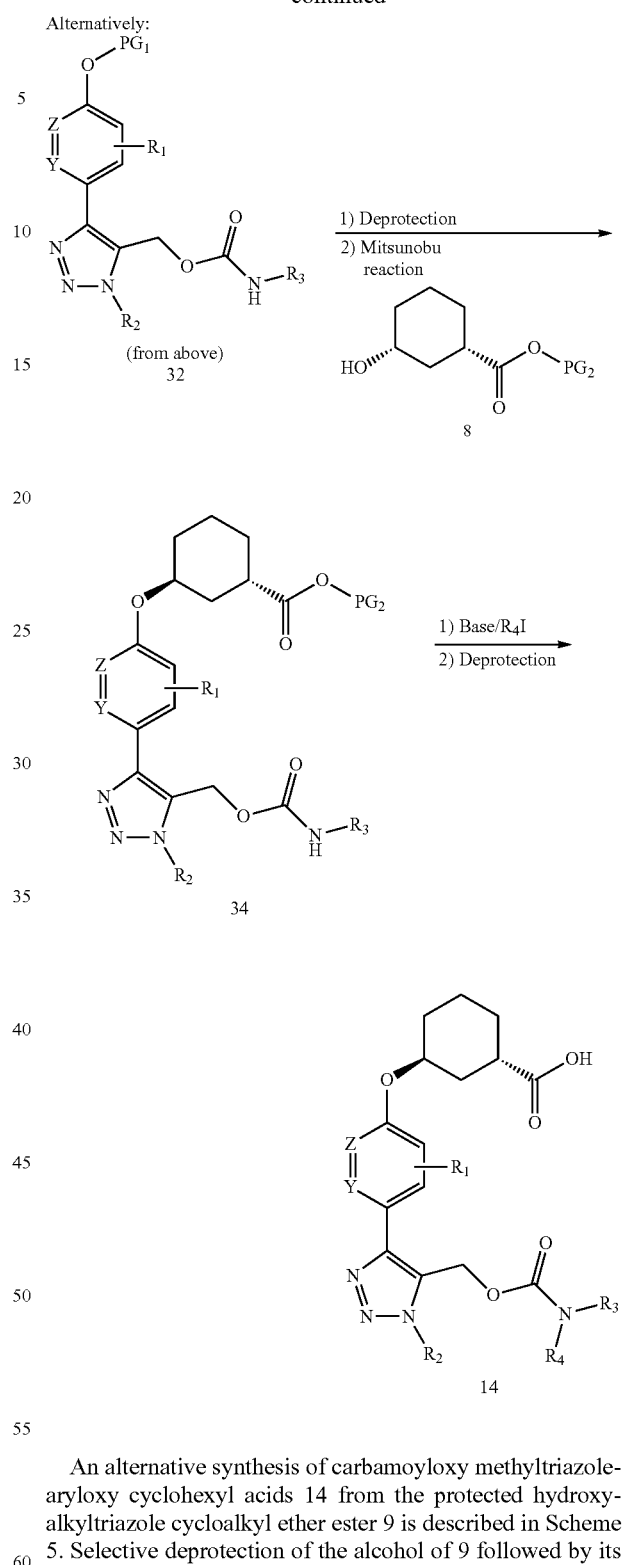

An alternative synthesis of carbamoyloxy methyltriazole-aryloxy cyclohexyl acids 14 from the protected hydroxy-alkyltriazole cycloalkyl ether ester 9 is described in Scheme 5. Selective deprotection of the alcohol of 9 followed by its reaction with the isocyanate generated from the Curtius rearrangement of an alkyl carboxylic acid 31 provides the triazole NH monoalkyl carbamate 34. The triazole NH-carbamate 34 is then alkylated with alkyl iodide 33 under basic conditions, followed by ester deprotection to give the desired carbamoyloxy methyltriazole-aryloxy cyclohexyl acids 14.

Scheme 5.

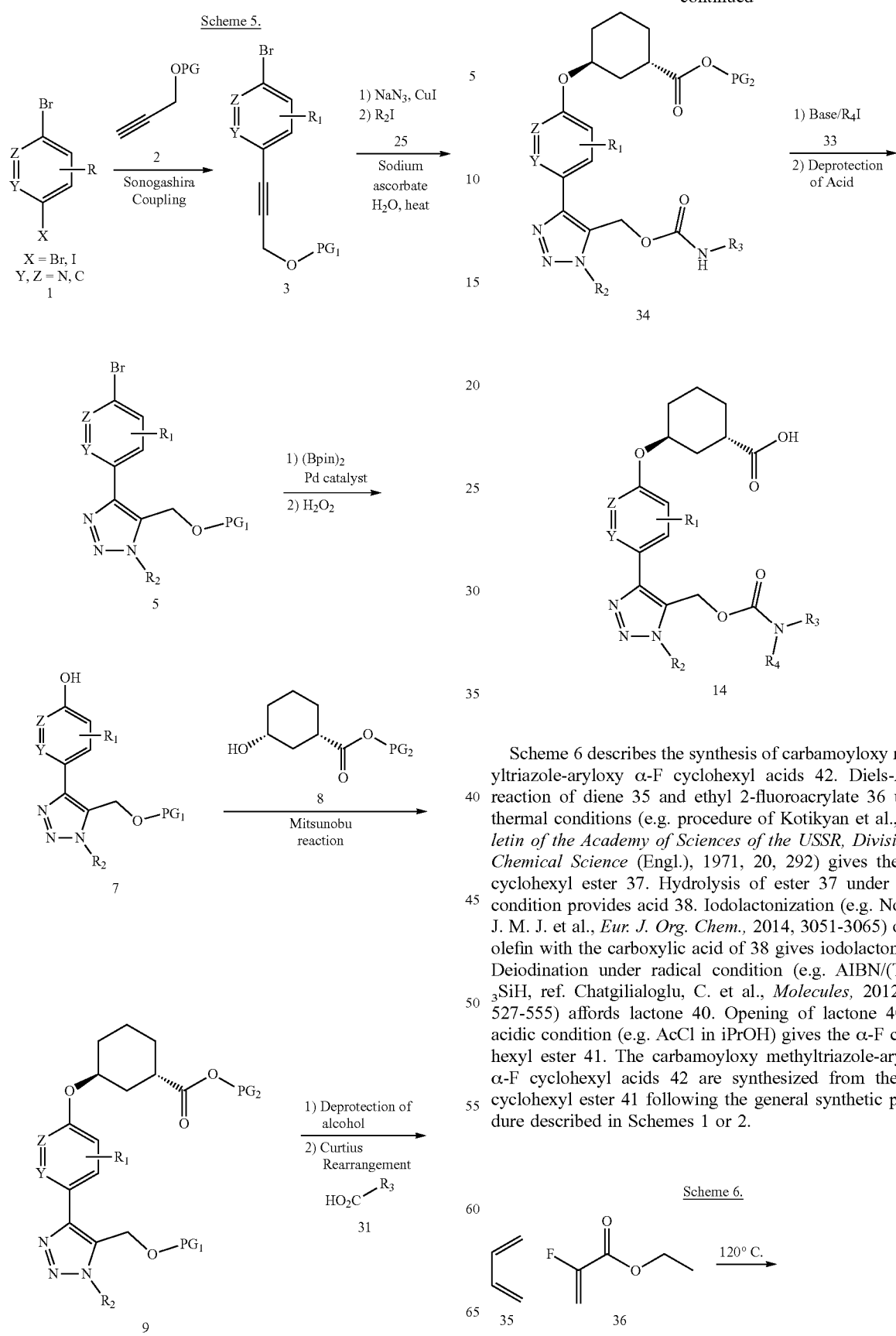

Scheme 6 describes the synthesis of carbamoyloxy methyltriazole-aryloxy α-F cyclohexyl acids 42. Diels-Alder reaction of diene 35 and ethyl 2-fluoroacrylate 36 under thermal conditions (e.g. procedure of Kotikyan et al., *Bulletin of the Academy of Sciences of the USSR, Division of Chemical Science* (Engl.), 1971, 20, 292) gives the α-F cyclohexyl ester 37. Hydrolysis of ester 37 under basic condition provides acid 38. Iodolactonization (e.g. Nolsoe, J. M. J. et al., *Eur. J. Org. Chem.*, 2014, 3051-3065) of the olefin with the carboxylic acid of 38 gives iodolactone 39. Deiodination under radical condition (e.g. AIBN/(TMS)$_3$SiH, ref. Chatgilialoglu, C. et al., *Molecules,* 2012, 17, 527-555) affords lactone 40. Opening of lactone 40 via acidic condition (e.g. AcCl in iPrOH) gives the α-F cyclohexyl ester 41. The carbamoyloxy methyltriazole-aryloxy α-F cyclohexyl acids 42 are synthesized from the α-F cyclohexyl ester 41 following the general synthetic procedure described in Schemes 1 or 2.

Scheme 6.

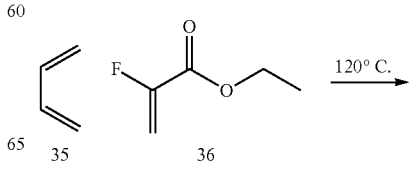

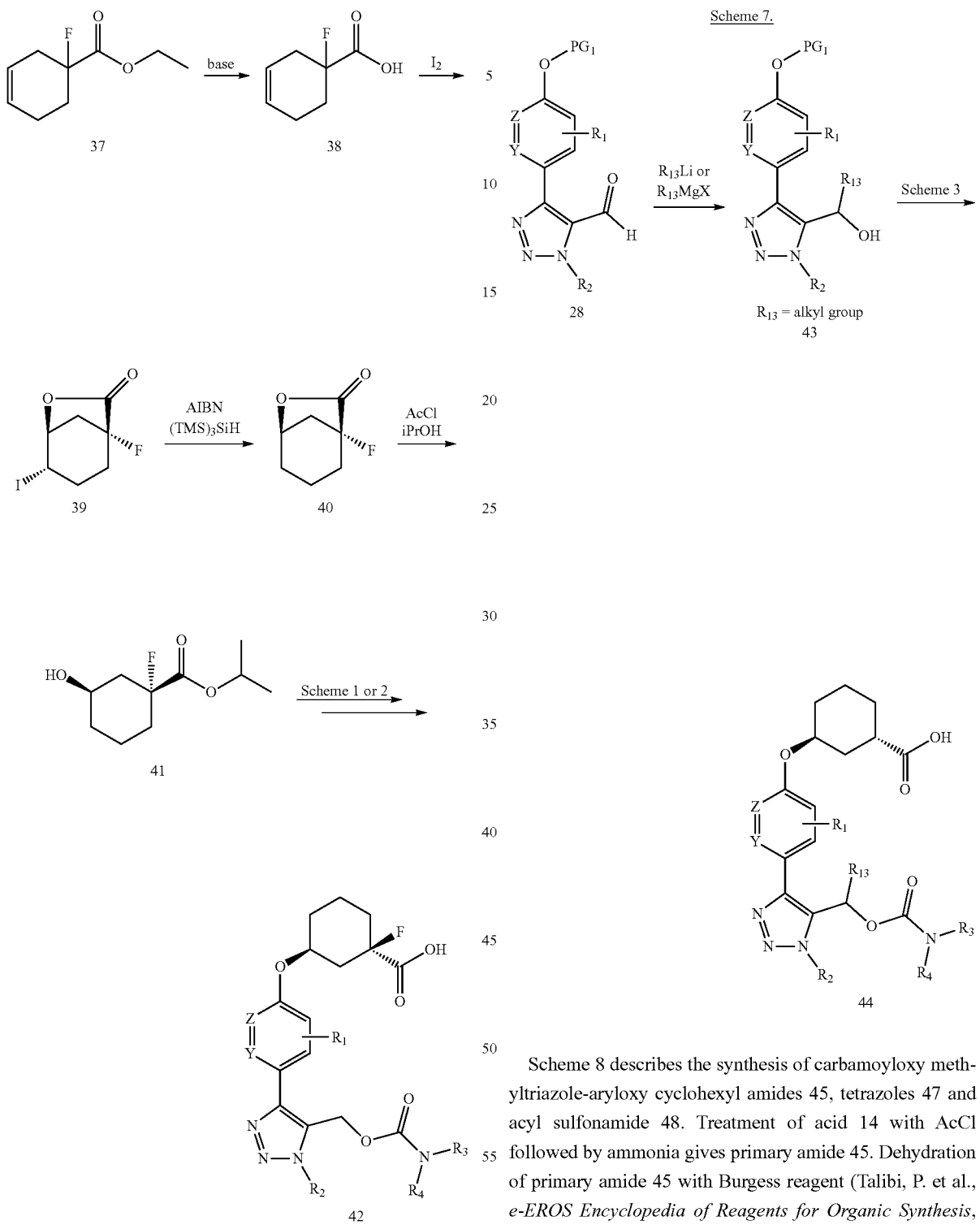

Scheme 7.

Scheme 7 describes the synthesis of carbamoyloxy methyltriazole-aryloxy cyclohexyl acids 44. Addition of an alkyl organometallic reagent (e.g R₁₃Li or R₁₃MgX) to aldehyde 28 gives triazole alcohol 43. The carbamoyloxy methyltriazole-aryloxy cyclohexyl acids 44 can then be synthesized from triazole alcohol 43 following the general synthetic procedure described in Scheme 3.

Scheme 8 describes the synthesis of carbamoyloxy methyltriazole-aryloxy cyclohexyl amides 45, tetrazoles 47 and acyl sulfonamide 48. Treatment of acid 14 with AcCl followed by ammonia gives primary amide 45. Dehydration of primary amide 45 with Burgess reagent (Talibi, P. et al., *e-EROS Encyclopedia of Reagents for Organic Synthesis*, published online 15 Sep. 2008, DOI: 10.1002/047084289X.rm095 m.pub2) furnishes nitrile 46. Cycloaddition of azide to nitrile 46 affords the tetrazole 47. In a similar manner to the preparation of amides 45, acyl sulfonamides 48 can be synthesized by the reaction of carboxylic acid 14 with methyl sulfonamide using standard coupling agents (e.g. EDC/DMAP).

Scheme 8

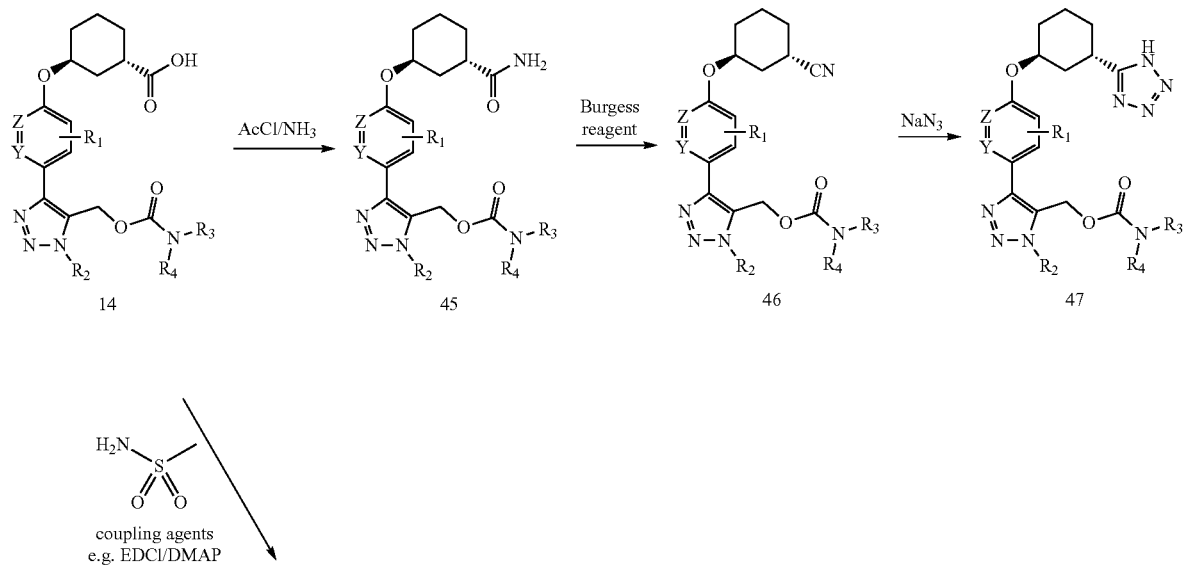

Scheme 9 describes the synthesis of carbamoyloxyethyl triazole-aryloxy cyclohexyl acids 53. The protected alcohol intermediate 9 is deprotected to the corresponding alcohol, which is then oxidized to the corresponding aldehyde (e.g. Dess-Martin periodinane or Swern oxidation) which is then subjected to an olefination reaction (e.g. Witting or Peterson olefination reaction) which provides the terminal olefin 49. Hydroboration of olefin 49 at the terminal carbon (e.g. with 9-BBN), followed by oxidative workup, provides the corresponding triazole ethyl alcohol 50. Triazole ethyl alcohol 50 is reacted with 4-nitrophenyl chloroformate in the presence of an appropriate base to give the corresponding triazole 4-nitrophenyl carbonate 51. The triazole 4-nitrophenyl carbonate 51 is then reacted with an amine 12 in the presence of an appropriate base to give the triazole carbamate 52, which then undergoes ester deprotection to give the desired carbamoyloxyethyltriazole-aryloxy cycloalkyl acids 53.

Scheme 9.

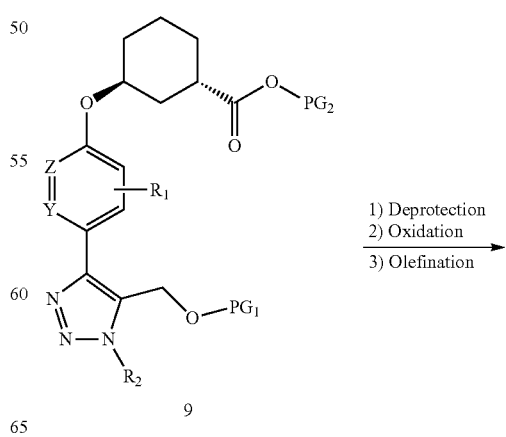

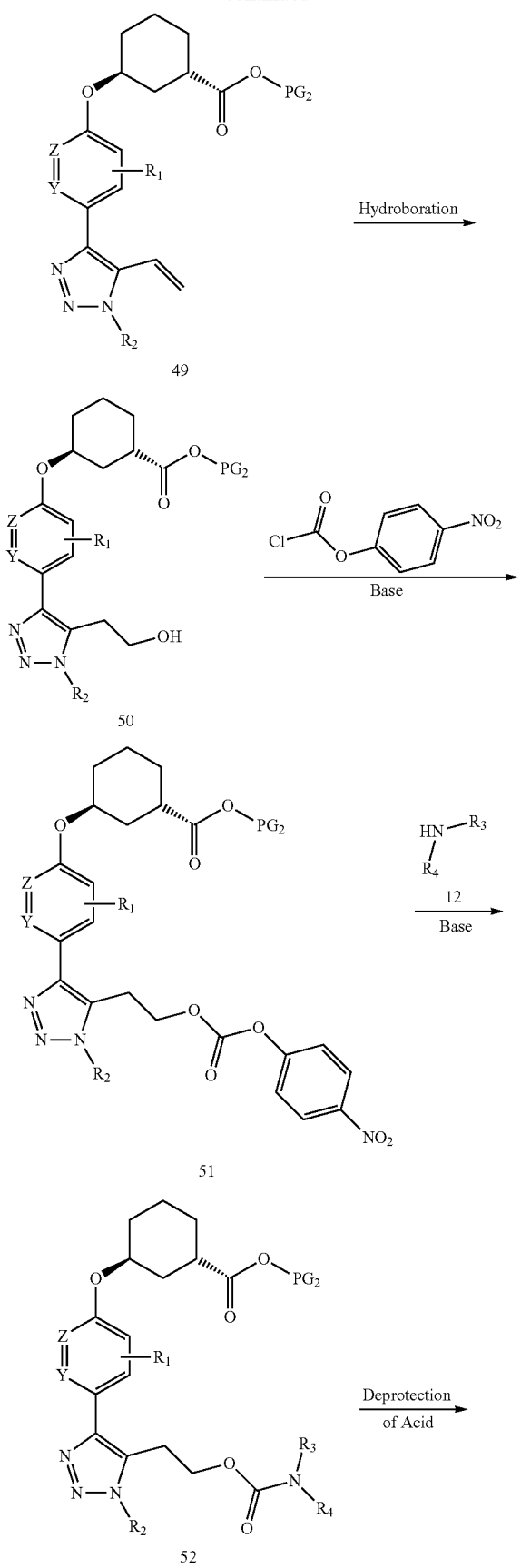
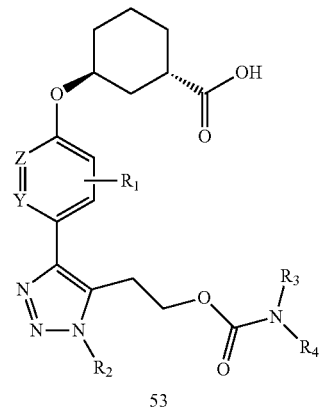
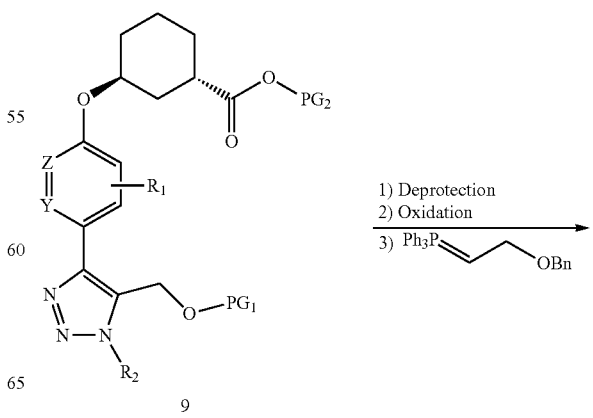

Scheme 10 describes the synthesis of carbamoyloxypropyl triazole-aryloxy cyclohexyl acids 58. The protected alcohol intermediate 9 is deprotected to the corresponding alcohol, then is oxidized to the corresponding aldehyde which is then subjected to olefination conditions (eg. Wittig reaction with a reagent with an appropriately protected alcohol such as 2-(benzyloxy) ethylidene) as shown) which provides olefin 54 as a mixture of cis/trans isomers. Hydrogenation of the olefin, followed by deprotection of the alcohol (e.g. using hydrogenolysis with $H_2$), provides the corresponding triazole alcohol 55. The triazole alcohol 55 is reacted with 4-nitrophenyl chloroformate in the presence of an appropriate base to give the corresponding triazole 4-nitrophenyl carbonate 56. The triazole 4-nitrophenyl carbonate 56 is then reacted with an amine 12 in the presence of an appropriate base to give the triazole carbamate 57, which then undergoes ester deprotection to give the desired carbamoyloxypropyltriazole-aryloxy cycloalkyl acids 58.

Scheme 10.

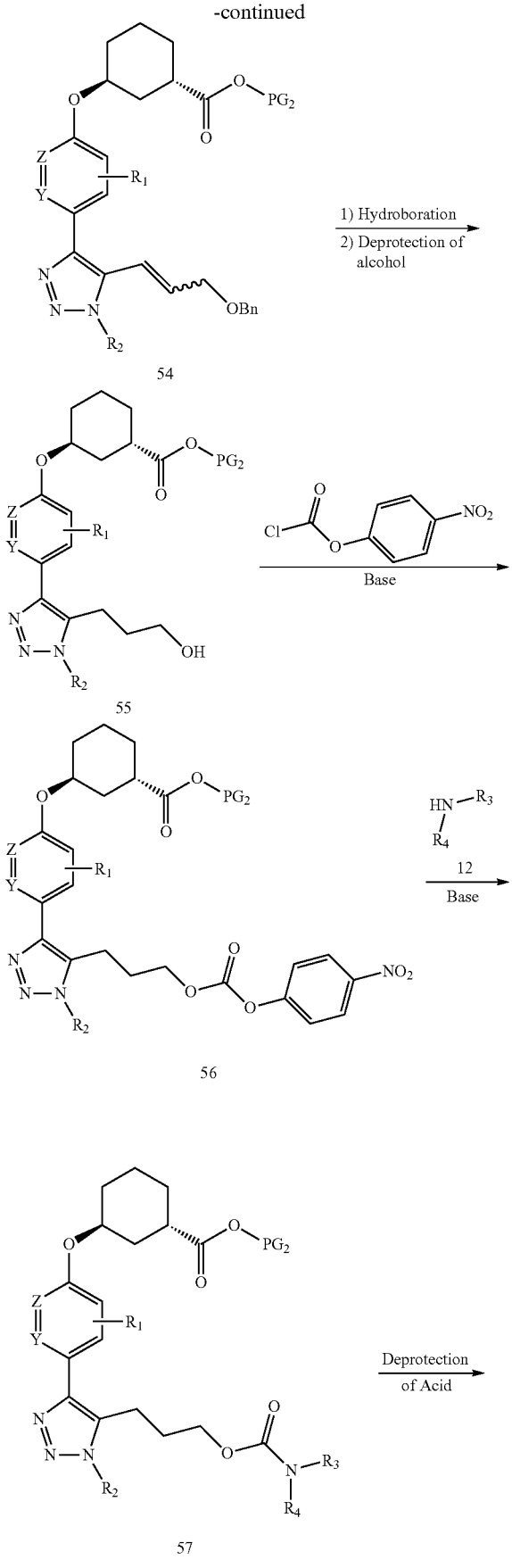
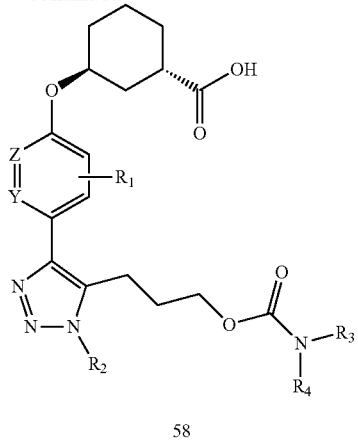

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "RBF" for round bottom flask, "atm" for atmosphere, "psi" for pounds per square inch, "conc." for concentrate, "RCM" for ring-closing metathesis, "sat" or "sat'd" for saturated, "SFC" for supercritical fluid chromatography "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "γ", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxycarbonyl
Boc$_2$O di-tert-butyl dicarbonate
AcOH or HOAc acetic acid
AlCl$_3$ aluminum trichloride
AIBN Azobis-isobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate Burgess reagent 1-methoxy-N-triethylammoniosulfonyl-methanimidate
CBz carbobenzyloxy
DCM or $CH_2Cl_2$ dichloromethane
$CH_3CN$ or ACN acetonitrile
$CDCl_3$ deutero-chloroform
$CHCl_3$ chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DEA diethylamine
Dess-Martin 1,1,1-tris(acetyloxy)-1,1-dihydro-1,2-benziodoxol-3-(1H)-one
DIC or DIPCDI diisopropylcarbodiimide
DIEA, DIPEA or Hunig's base diisopropylethylamine
DMAP 4-dimethylaminopyridine
DME 1,2-dimethoxyethane
DMF dimethyl formamide
DMSO dimethyl sulfoxide
cDNA complementary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH ethanol
GMF glass microfiber filter
Grubbs II (1,3-bis(2,4,6-trimethylphenyl)-2-imidazolidinylidene)dichloro (phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex hexane
HOBt or HOBT 1-hydroxybenzotriazole
$H_2O_2$ hydrogen peroxide
IBX 2-iodoxybenzoic acid
$H_2SO_4$ sulfuric acid
Jones reagent $CrO_3$ in aqueous $H_2SO_4$, 2 M solution
$K_2CO_3$ potassium carbonate
$K_2HPO_4$ potassium phosphate dibasic (potassium hydrogen phosphate)
KOAc potassium acetate
$K_3PO_4$ potassium phosphate tribasic
LAH lithium aluminum hydride
LG leaving group
LiOH lithium hydroxide
MeOH methanol
$MgSO_4$ magnesium sulfate
MsOH or MSA methylsulfonic acid/methanesulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ ammonia
$NH_4Cl$ ammonium chloride
$NH_4OH$ ammonium hydroxide
$NH_4HCO_2^{-1}$ ammonium formate
NMM N-methylmorpholine
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
PPTS pyridinium p-toluenesulfonate
i-PrOH or IPA isopropanol
PS Polystyrene
RT or rt room temperature
SEM-Cl 2-(trimethysilyl)ethoxymethyl chloride
$SiO_2$ silica oxide
$SnCl_2$ tin(II) chloride
TBAF tra-n-butylammonium fluoride
TBAI tetra-n-butylammonium iodide
TFA trifluoroacetic acid
THF tetrahydrofuran
THP tetrahydropyran
$TMSCHN_2$ Trimethylsilyldiazomethane
$TMSCH_2N_3$ Trimethylsilylmethyl azide
T3P propane phosphonic acid anhydride
TRIS tris (hydroxymethyl) aminomethane
pTsOH p-toluenesulfonic acid VII. Examples The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

HPLC/MS and Preparatory/Analytical HPLC Methods Employed in Characterization or Purification of Examples NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$HNMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

In the examples where $^1$H NMR spectra were collected in $d_6$-DMSO, a water-suppression sequence is often utilized. This sequence effectively suppresses the water signal and any proton peaks in the same region usually between 3.30-3.65 ppm which will affect the overall proton integration.

The term HPLC refers to a Shimadzu high performance liquid chromatography instrument with one of following methods:
HPLC-1: Sunfire C18 column (4.6×150 mm) 3.5 µm, gradient from 10 to 100% B:A for 12 min, then 3 min hold at 100% B.
Mobile phase A: 0.05% TFA in water:CH$_3$CN (95:5)
Mobile phase B: 0.05% TFA in CH$_3$CN:water (95:5)
TFA Buffer pH=2.5; Flow rate: 1 mL/min; Wavelength: 254 nm, 220 nm.
HPLC-2: XBridge Phenyl (4.6×150 mm) 3.5 µm, gradient from 10 to 100% B:A for 12 min, then 3 min hold at 100% B.
Mobile phase A: 0.05% TFA in water:CH$_3$CN (95:5)
Mobile phase B: 0.05% TFA in CH$_3$CN:water (95:5)
TFA Buffer pH=2.5; Flow rate: 1 mL/min; Wavelength: 254 nm, 220 nm.
HPLC-3: Chiralpak AD-H, 4.6×250 mm, 5 µm.
Mobile Phase: 30% EtOH-heptane (1:1)/70% CO$_2$
Flow rate=40 mL/min, 100 Bar, 35° C.; Wavelength: 220 nm
HPLC-4: Waters Acquity UPLC BEH C18, 2.1×50 mm, 1.7-µm particles;
Mobile Phase A: 5:95 CH$_3$CN:water with 10 mM NH$_4$OAc;
Mobile Phase B: 95:5 CH$_3$CN:water with 10 mM NH$_4$OAc;
Temperature: 50° C.; Gradient: 0-100% B over 3 min, then a 0.75-min hold at 100% B;
Flow: 1.11 mL/min; Detection: UV at 220 nm.
HPLC-5: Waters Acquity UPLC BEH C18, 2.1×50 mm, 1.7-µm particles;
Mobile Phase A: 5:95 CH$_3$CN:water with 0.1% TFA;
Mobile Phase B: 95:5 CH$_3$CN:water with 0.1% TFA;
Temperature: 50° C.; Gradient: 0-100% B over 3 min, then a 0.75-min hold at 100% B; Flow: 1.11 mL/min; Detection: UV at 220 nm.

Intermediate 1 (±)-cis-isopropyl 1-fluoro-3-hydroxycyclohexanecarboxylate

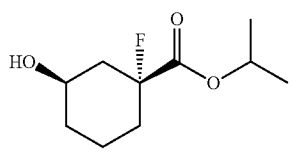

Intermediate 1A (±)-ethyl 1-fluorocyclohex-3-enecarboxylate

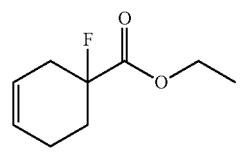

A mixture of 20% buta-1,3-diene in toluene (13.8 mL, 41.1 mmol) and ethyl 2-fluoroacrylate (3.07 mL, 27.4 mmol) was heated at 120° C. in a sealed tube for 7 days. The reaction was cooled to rt and concentrated in vacuo. The residue was chromatographed (80 g SiO$_2$) with EtOAc/Hexane (continuous gradient from 0% to 10% EtOAc over 20 min) to give Intermediate 1A (3.80 g, 22.1 mmol, 80% yield) as a clear oil. $^1$H NMR (500 MHz, CDCl$_3$) δ 5.79 (ddd, J=9.9, 4.7, 2.2 Hz, 1H), 5.64-5.58 (m, 1H), 4.26 (q, J=7.2 Hz, 2H), 2.73-2.57 (m, 1H), 2.45-2.23 (m, 2H), 2.20-1.91 (m, 3H), 1.32 (t, J=7.2 Hz, 3H); $^{19}$F NMR (471 MHz, CDCl$_3$) δ −162.69 (s, 1F).

Intermediate 1B (±)-1-fluorocyclohex-3-ene carboxylic Acid

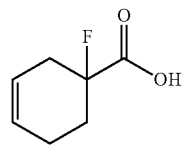

A mixture of Intermediate 1A (3.80 g, 22.1 mmol) and aq. LiOH (55.2 mL of a 2.0 M solution, 110 mmol) in THF (50 mL) was stirred at rt for 18 h. The reaction was acidified to pH=2 with conc. HCl (9.19 mL, 110 mmol), and then extracted with EtOAc (3×25 mL). The combined organic extracts were washed with water and concentrated in vacuo to give Intermediate 1B (3.0 g, 20.8 mmol, 94% yield) as a light yellowish oil. $^1$H NMR (500 MHz, CDCl$_3$) δ 5.81 (ddd, J=9.8, 4.6, 2.1 Hz, 1H), 5.66-5.58 (m, 1H), 2.76-2.59 (m, 1H), 2.49-2.37 (m, 1H), 2.35-2.23 (m, 1H), 2.22-1.92 (m, 3H); $^{19}$F NMR (471 MHz, CDCl$_3$) δ −163.02 (s, 1F).

Intermediate 1C (±)-1-fluoro-4-iodo-6-oxabicyclo [3.2.1]octan-7-one

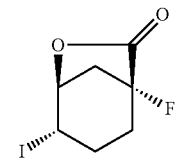 [SMILES: O=C1O[C@H]2C[C@]1(F)CC[C@@H]2I]

To a mixture of Intermediate 1B (3.0 g, 20.8 mmol) in water (20 mL) was added NaHCO$_3$ (5.25 g, 62.4 mmol) portionwise and the mixture was stirred until it became homogeneous. An aq. I2 solution (prepared by dissolving I2 (5.81 g, 22.0 mmol) and KI (20.7 g, 125 mmol) in 20 mL water) was added and the reaction was stirred overnight at rt in the dark. Water (100 mL) was then added and the mixture was extracted with DCM (3×25 mL), washed with 10% aq. Na$_2$S$_2$O$_3$ (20 mL×2) and water, dried (MgSO$_4$) and concentrated in vacuo. The residual crude oil was chromatographed (80 g SiO$_2$) with EtOAc/Hexane (continuous gradient from 0% to 50% EtOAc over 20 min) to give Intermediate 1C (3.53 g, 13.1 mmol, 62.8% yield) as a white solid. $^1$H NMR (500 MHz, CDCl$_3$) δ 4.89 (dt, J=6.5, 3.5 Hz, 1H), 4.44 (q, J=4.6 Hz, 1H), 3.08 (dd, J=11.6, 1.9 Hz, 1H), 2.75 (tddd, J=11.3, 6.5, 3.3, 1.1 Hz, 1H), 2.50-2.38 (m, 1H), 2.34-2.17 (m, 2H), 2.11-1.99 (m, 1H); $^{13}$C NMR (126 MHz, CDCl$_3$) δ 172.2, 172.0, 93.6, 91.9, 78.4, 78.3, 39.2, 39.0, 29.7, 29.6, 28.4, 28.2, 20.2; $^{19}$F NMR (471 MHz, CDCl$_3$) δ −167.97 (s, 1F)

Intermediate 1D (±)-1-fluoro-6-oxabicyclo[3.2.1]octan-7-one

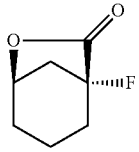

To a solution of intermediate 1C (350 mg, 1.30 mmol) and AIBN (21 mg, 0.130 mmol) in benzene (5 mL) was added tris(trimethylsilyl)silane (0.60 mL, 1.94 mmol) portionwise over 10 min at 60° C. The reaction was stirred at 70° C. for 2 h, cooled to rt and then concentrated in vacuo. The residue was dissolved in EtOAc, washed with sat. aq. NH$_4$Cl, dried (MgSO$_4$) and concentrated in vacuo. The crude oil was chromatographed (12 g SiO$_2$) with EtOAc/Hexane (continuous gradient from 0% to 30% EtOAc over 10 min) to give Intermediate 1D (124 mg, 0.860 mmol, 66.4% yield) as a white solid. $^{19}$F NMR (471 MHz, CDCl$_3$) δ −167.01 (s, 1F); $^1$H NMR (500 MHz, CDCl$_3$) δ 4.98-4.81 (m, 1H), 2.75 (dtdd, J=15.9, 6.8, 3.3, 1.7 Hz, 1H), 2.24-1.89 (m, 5H), 1.82-1.65 (m, 1H), 1.60-1.46 (m, 1H); $^{13}$C NMR (126 MHz, CDCl$_3$) δ 173.2, 173.0, 93.9, 92.3, 75.6, 75.5, 42.0, 41.9, 31.3, 31.1, 26.7, 17.7, 17.6

Intermediate 1

Acetyl chloride (0.061 mL, 0.860 mmol) was added portionwise to isopropanol (3 mL) at 0° C. and then stirred at rt for 30 min. Intermediate 1D (124 mg, 0.860 mmol) was added and the reaction was stirred overnight at rt, then was concentrated in vacuo. The residual crude oil was chromatographed (4 g SiO$_2$) with EtOAc/Hexane (continuous gradient from 0% to 50% EtOAc over 10 min) to give Intermediate 1 (140 mg, 0.685 mmol, 80% yield) as a clear oil. $^1$H NMR (500 MHz, CDCl$_3$) δ 5.08 (spt, J=6.3 Hz, 1H), 3.91 (tt, J=10.9, 4.4 Hz, 1H), 2.68 (br. s., 1H), 2.28 (dddt, J=13.5, 9.0, 4.6, 2.1 Hz, 1H), 2.06-1.98 (m, 1H), 1.96-1.87 (m, 1H), 1.82-1.62 (m, 4H), 1.37-1.22 (m, 7H); $^{19}$F NMR (471 MHz, CDCl$_3$) δ −162.93 (s, 1F); $^{13}$C NMR (126 MHz, CDCl$_3$) δ 170.9, 170.7, 95.7, 94.2, 69.3, 66.1, 40.7, 40.5, 33.9, 31.6, 31.4, 21.5, 19.1

Intermediate 2 isopropyl (3R)-3-hydroxycyclohexane-1-carboxylate-1-d

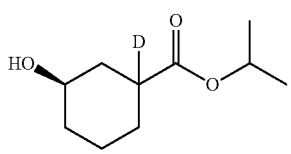

Intermediate 2A isopropyl (1S,3R)-3-((tert-butyldimethylsilyl)oxy)cyclohexane-1-carboxylate

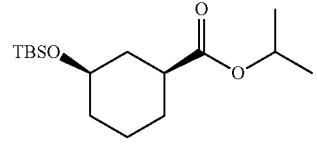 [SMILES: CC(C)OC(=O)[C@H]1CCC[C@@H](O[Si](C)(C)C(C)(C)C)C1]

To a solution of (1S,3R)-isopropyl 3-hydroxycyclohexanecarboxylate (0.5 g, 2.68 mmol) and imidazole (0.238 g, 3.49 mmol) in DCM (4 mL) was added tert-butylchlorodimethylsilane (0.486 g, 3.22 mmol) in DCM (1 mL) dropwise over 5 min, stirred at rt overnight. The reaction was diluted with Et$_2$O (20 mL). The mixture was washed with brine (10 mL); the white aqueous phase was separated and the organic phase was washed with water (10 mL), dried over Na$_2$SO$_4$ and concentrated in vacuo. The crude oil was chromatographed (80 g SiO$_2$) using a gradient of EtOAc/Hexane (0% to 20% over 15 min) to give (1S,3R)-isopropyl 3-((tert-butyldimethylsilyl)oxy)cyclohexanecarboxylate (0.60 g, 1.897 mmol, 70.7% yield) as a clear oil. $^1$H NMR (500 MHz, CDCl$_3$) δ 5.08-4.95 (m, 1H), 3.65-3.51 (m, 1H), 2.40-2.21 (m, 1H), 2.09 (d, J=12.7 Hz, 1H), 1.94-1.76 (m, 3H), 1.50-1.35 (m, 1H), 1.34-1.17 (m, 9H), 0.91 (s, 9H), 0.13-0.05 (m, 6H)

Intermediate 2B isopropyl (1S,3R)-3-((tert-butyldimethylsilyl)oxy)cyclohexane-1-carboxylate

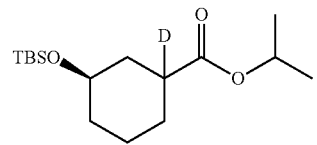 [SMILES: [2H]C1(C(=O)OC(C)C)CCC[C@@H](O[Si](C)(C)C(C)(C)C)C1]

A solution of LDA (1.664 ml, 3.33 mmol) was added under Ar to a solution of intermediate 2A (0.5 g, 1.66 mmol) in THF (6.66 mL) at −78° and the resultant mixture was stirred for 60 min. Then D2O (0.90 mL, 49.9 mmol) was added and the reaction was allowed to warm to rt. Saturated aq. NH$_4$Cl (3 mL) was added and the solution was allowed to warm to rt. The reaction mixture was extracted with EtOAc (10 mL), and the combined organic extracts were washed with aq. HCl (10 mL of a 2 M solution), saturated aq. NaHCO$_3$ and then brine. The organic layer was dried over MgSO$_4$, filtered, then concentrated in vacuo to give an oil as the crude product (used in the next step without further purification) (1S,3R)-isopropyl 3-((tert-butyldimethylsilyl)oxy)cyclohexanecarboxylate (0.50 g, 1.66 mmol). LCMS, [M+H]$^+$=302.1.

Intermediate 2

To a solution of intermediate 2B (0.53 g, 1.758 mmol) in THF (3 mL) was added Bu$_4$NF (3.52 mL of a 1 M solution, 3.52 mmol) at rt and stirred overnight. The reaction was then quenched with 1.5 M aq. potassium phosphate (10 mL) and extracted with EtOAc (10 mL). The organic extract was concentrated in vacuo and chromatographed (24 g SiO$_2$, continuous gradient from 0 to 100% EtOAc/Hexanes over 30 min, then at 100% EtOAc for 10 min) to give intermediate 2 (0.17 g, 0.908 mmol, 51.6% yield). $^1$H NMR (500 MHz, CDCl$_3$) δ 5.02 (dt, J=12.6, 6.2 Hz, 1H), 4.11 (t, J=4.3 Hz, 1H), 1.84 (d, J=4.1 Hz, 3H), 1.77-1.68 (m, 1H), 1.65-1.49 (m, 5H), 1.24 (d, J=6.3 Hz, 6H).

Example 1

(1S,3S)-3-((6-(5-((((cyclopentyl(methyl)carbamoyl)oxy)methyl)-1-methyl-1H-1,2,3-triazol-4-yl)-2-methylpyridin-3-yl)oxy)cyclohexane-1-carboxylic Acid

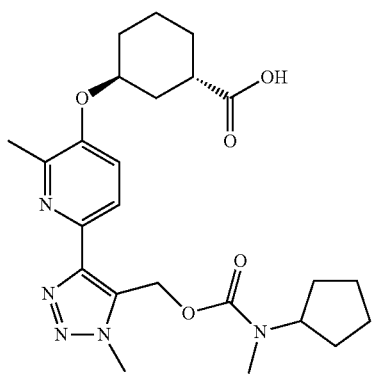 [SMILES: Cc1nc(-c2nnn(C)c2COC(=O)N(C)C2CCCC2)ccc1O[C@H]1CCC[C@H](C(=O)O)C1]

1A 3-bromo-2-methyl-6-(3-((tetrahydro-2H-pyran-2-yl)oxy)prop-1-yn-1-yl)pyridine

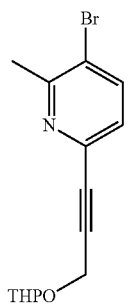

To a solution of 2,5-dibromo-6-methyl-pyridine (5 g, 21.11 mmol) and 2-(prop-2-yn-1-yloxy) tetrahydro-2H-pyran (4.44 g, 31.7 mmol) in MeCN (42.2 mL) was added Et$_3$N (8.83 mL, 63.3 mmol). The solution was degassed under N$_2$, then trans-dichlorobis (triphenylphosphine) palladium (II) chloride (0.74 g, 1.06 mmol) and CuI (0.20 g, 1.06 mmol) were added. The reaction was stirred at rt for 14 h, after which the reaction mixture was filtered through a Celite® plug and the plug was washed with EtOAc (2×10 mL). The filtrate was concentrated in vacuo and the residue was chromatographed (SiO$_2$; continuous gradient from 0% to 100% EtOAc in Hexanes for 20 min) to give the title compound as a white solid (6.0 g, 20.3 mmol, 96% yield). $^1$H NMR (400 MHz, CDCl$_3$) δ 8.65 (d, J=2.0 Hz, 1H), 7.80 (dd, J=8.3, 2.3 Hz, 1H), 7.35 (dd, J=8.4, 0.4 Hz, 1H), 4.91 (t, J=3.3 Hz, 1H), 4.61-4.45 (m, 2H), 3.98-3.81 (m, 1H), 3.66-3.44 (m, 1H), 1.92-1.73 (m, 2H), 1.72-1.52 (m, 2H). LCMS, [M+H]$^+$=298.0.

1B 3-bromo-2-methyl-6-(1-methyl-5-(((tetrahydro-2H-pyran-2-yl)oxy)methyl)-1H-1,2,3-triazol-4-yl)pyridine

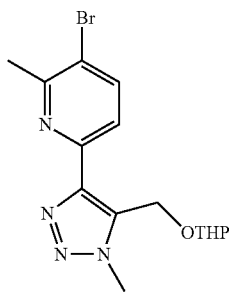

A solution of 1A (6.0 g, 20.3 mmol) in toluene (20 mL) and TMSCH$_2$N$_3$ (7.85 g, 60.8 mmol) was heated at 90° C. under Ar for 15 h, then was cooled to rt. Volatiles were removed in vacuo and the residue was dissolved in THF (20 mL). To the mixture was added TBAF (20.3 mL of a 1 M solution in THF, 20.3 mmol) at 0° C. After stirring for 10 min, the reaction was complete as determined by analytical HPLC. Volatiles were removed in vacuo and the residue was chromatographed (SiO$_2$, continuous gradient from 0% to 100% EtOAc in hexanes over 20 min) to give the title compound (2.1 g, 29% yield) as a white solid. $^1$H NMR (400 MHz, CHLOROFORM-d) δ 7.85 (d, J=8.4 Hz, 1H), 7.13 (d, J=8.4 Hz, 1H), 6.03 (br. s., 1H), 5.39-5.23 (m, 4H), 4.81-4.76 (m, 1H), 4.17 (s, 3H), 3.91 (ddd, J=11.3, 7.9, 3.3 Hz, 1H), 3.65-3.48 (m, 1H), 2.54 (s, 3H), 1.88-1.68 (m, 2H), 1.56 (br. s., 2H)

Alternatively, 1B can be synthesized by the following procedure:

To a stirred solution of 1A (4.0 g, 13.5 mmol) in DMF (45 mL) under N$_2$ was added NaN$_3$ (2.63 g, 40.5 mmol). The reaction mixture was stirred at 90° C. for 36 h, then was cooled to rt and filtered through Celite®. To the filtrate was added K$_2$CO$_3$ (3.73 g, 27.0 mmol) and the reaction mixture was stirred at rt for 10 min. CH$_3$I (1.27 mL, 20.3 mmol) was added dropwise and the reaction mixture was stirred at rt for 16 h, then was diluted with water (150 mL) and extracted with EtOAc (2×100 mL). The combined organic extracts were dried (Na$_2$SO$_4$), filtered and concentrated in vacuo. The residual mixture of products (the 2 N-methyl triazole regioisomers) were separated by flash chromatography (40 g Redisep® SiO$_2$ column, eluting with 21% EtOAc in hexanes). The desired regioisomer product, title compound 1B, was isolated as a white solid (1.0 g, 21%). LC-MS, [M+2]$^+$=355.2. $^1$H NMR (400 MHz, CDCl$_3$) δ ppm 8.64 (d, J=2.0 Hz, 1H), 8.10 (d, J=8.0 Hz, 1H), 7.83-7.92 (m, 1H), 5.27 (s, 2H), 4.68-4.77 (m, 1H), 4.17 (s, 3H), 3.80-3.90 (m, 1H), 3.49-3.57 (m, 1H), 1.67-1.80 (m, 1H), 1.56-1.62 (m, 2H), 1.49-1.55 (m, 2H).

1C 2-methyl-6-(1-methyl-5-((((tetrahydro-2H-pyran-2-yl)oxy)methyl)-1H-1,2,3-triazol-4-yl)pyridin-3-ol

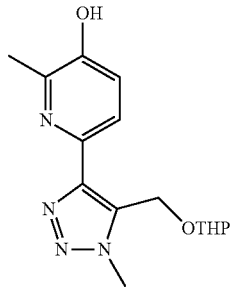

To a degassed solution (sparged with Ar 3×) of 1B (213 mg, 0.60 mmol), 4,4,4',4',5,5,5',5'-octamethyl-2,2'-bi(1,3,2-dioxaborolane (230 mg, 0.91 mmol) and KOAc (178 mg, 1.81 mmol) in THF was added Pd(dppf)Cl$_2$ (22 mg, 0.03 mmol). The reaction mixture was heated in a sealed tube at 80° C. for 16 h, then was cooled to rt and partitioned between water and EtOAc. The aqueous layer was extracted with EtOAc (3×20 mL). The combined organic extracts were washed with brine, dried (MgSO$_4$), filtered and concentrated in vacuo. The crude boronate product was carried on to the next step without further purification. To a solution of the crude product, 2-(1-methyl-5-((((tetrahydro-2H-pyran-2-yl)oxy)methyl)-1H-1,2,3-triazol-4-yl)-5-(4,4,5,5-tetramethyl-1,3,2-dioxaborolan-2-yl)pyridine (241 mg, 0.603 mmol) in EtOAc (2 mL) was added H$_2$O$_2$ (0.19 mL of a 30% aqueous solution, 6.0 mmol). The reaction mixture was stirred at rt for 1 h, then was cooled to 0° C. and quenched by slowly adding sat. aq. Na$_2$S$_2$O$_3$. The aqueous layer was extracted with EtOAc (3×20 mL). The combined organic extracts were washed with brine, dried (MgSO$_4$), filtered and concentrated in vacuo. The residue was chromatographed (SiO$_2$, continuous gradient from 0% to 100% EtOAc in Hexanes, 20 min) to give the title compound (150 mg, 86%) as a white solid. $^1$H NMR (400M Hz, CDCl$_3$) δ 8.27 (d, J=2.6 Hz, 1H), 8.06 (d, J=8.6 Hz, 1H), 7.29-7.21 (m, 1H), 5.33 (s, 1H), 5.28 (d, J=2.4 Hz, 2H), 4.76 (s, 1H), 4.18 (s, 3H), 3.90 (s, 1H), 3.63-3.48 (m, 1H), 1.72 (s, 2H), 1.65-1.51 (m, 2H). LCMS, [M+H]$^+$=291.2.

1D. isopropyl (1S,3S)-3-((2-methyl-6-(1-methyl-5-((((tetrahydro-2H-pyran-2-yl)oxy)methyl)-1H-1,2,3-triazol-4-yl)pyridin-3-yl)oxy)cyclohexane-1-carboxylate

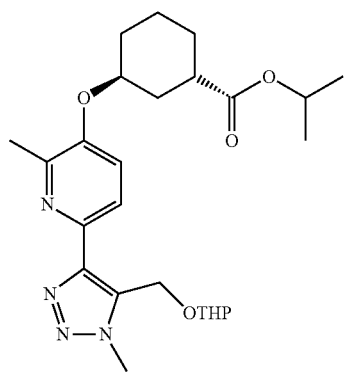

To a solution of 1C (1.18 g, 4.06 mmol) and (1S,3R)-isopropyl 3-hydroxy cyclohexanecarboxylate (synthesized according to the procedure described in US2007/0197788A1, 1.51 g, 8.13 mmol) in toluene (81 mL) was added Bu$_3$P (3.17 mL, 12.2 mmol). To this stirred mixture was added (E)-diazene-1,2-diylbis(piperidin-1-ylmethanone) (3.08 g, 12.2 mmol) portionwise, and the reaction mixture was heated at 50° C. for 120 min, then was cooled to rt. At this point an LC-MS of the reaction mixture showed the presence of the desired product. The mixture was filtered and the filtrate was concentrated in vacuo. The residue was chromatographed (SiO$_2$, continuous gradient from 0% to 100% EtOAc in Hexanes, 20 min) to give the title compound (1.20 g, 2.62 mmol, 64.4% yield) as a white foam. $^1$H NMR (400 MHz, CDCl$_3$) δ 7.95 (d, J=8.6 Hz, 1H), 7.22 (d, J=8.6 Hz, 1H), 5.45-5.24 (m, 2H), 5.04 (dt, J=12.5, 6.3 Hz, 1H), 4.83-4.64 (m, 2H), 4.16 (s, 3H), 3.91 (ddd, J=11.2, 7.9, 3.1 Hz, 1H), 3.64-3.48 (m, 1H), 2.93-2.71 (m, 1H), 2.52 (s, 3H), 2.23-1.45 (m, 14H), 1.26 (dd, J=6.4, 2.0 Hz, 6H).

1E. isopropyl (1S,3S)-3-((6-(5-(hydroxymethyl)-1-methyl-1H-1,2,3-triazol-4-yl)-2-methylpyridin-3-yl)oxy)cyclohexane-1-carboxylate

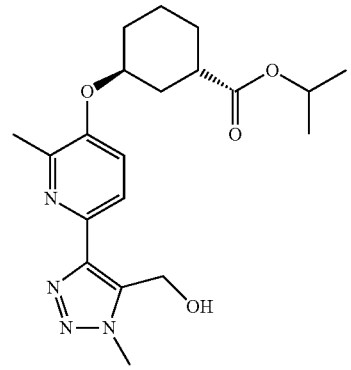

To a solution of 1D (1.7 g, 3.71 mmol) in MeOH (37 mL) added pyridinium p-toluenesulfonate (0.932 g, 3.71 mmol). The reaction mixture was heated to 60° C. for 2 h, then was cooled to rt, diluted with water and sat. aq. NaHCO$_3$, then extracted with EtOAc (3×10 mL). The combined organic extracts were concentrated in vacuo and chromatographed (SiO$_2$; continuous gradient from 0% to 100% EtOAc in Hexanes, 20 min) to give the title compound as a white foam (1.36 g, 3.63 mmol, 98% yield). $^1$H NMR (400 MHz, CDCl$_3$) δ 8.01 (d, J=8.6 Hz, 1H), 7.46 (d, J=5.1 Hz, 1H), 7.27-7.15 (m, 1H), 4.96 (dt, J=12.5, 6.3 Hz, 1H), 4.74 (s, 2H), 4.66-4.59 (m, 1H), 4.00 (s, 3H), 2.80-2.64 (m, 1H), 2.46 (s, 3H), 2.07-1.50 (m, 8H), 1.18 (dd, J=6.4, 2.2 Hz, 6H).

1F. isopropyl (1S,3S)-3-((2-methyl-6-(1-methyl-5-(((((4-nitrophenoxy)carbonyl)oxy)methyl)-1H-1,2,3-triazol-4-yl)pyridin-3-yl)oxy)cyclohexane-1-carboxylate

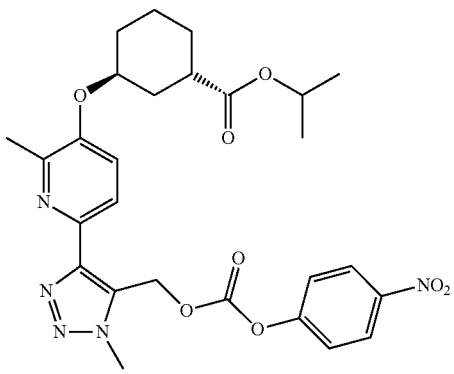

To a solution of 1E (1.36 g, 3.63 mmol) and 4-nitrophenyl chloroformate (2.20 g, 10.9 mmol) in DCM (36.3 mL) was added pyridine (1.47 mL, 18.2 mmol). The reaction mixture was stirred at rt for 2 h. LCMS showed the desired product at this point. The mixture was filtered and the filtrate was concentrated in vacuo. The residue was chromatographed (SiO$_2$, continuous gradient from 0% to 100% EtOAc in Hexanes, 20 min) to afford the title compound as a white solid (1.66 g, 3.08 mmol, 85% yield). $^1$H NMR (400 MHz, CDCl$_3$) δ 8.30 (d, J=9.2 Hz, 1H), 8.03 (d, J=8.4 Hz, 1H), 7.41 (d, J=9.2 Hz, 2H), 7.25 (d, J=8.6 Hz, 1H), 6.07 (s, 2H), 5.05 (quin, J=6.2 Hz, 1H), 4.72 (br. s., 1H), 4.22 (s, 3H), 2.91-2.73 (m, 1H), 2.52 (s, 3H), 2.21-1.61 (m, 9H), 1.27 (dd, J=6.3, 1.9 Hz, 6H).

1G. isopropyl (1S,3S)-3-((6-(5-((((cyclopentyl(methyl)carbamoyl)oxy)methyl)-1-methyl-1H-1,2,3-triazol-4-yl)-2-methylpyridin-3-yl)oxy)cyclohexane-1-carboxylate

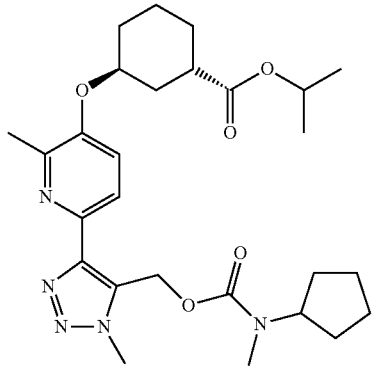

To a solution of 1F (5 g, 9 μmmol) and DIPEA (1.5 μL, 9 μmmol) in THF (0.5 mL) was added N-methylcyclopentanamine (1 mg, 9 μmmol). The reaction mixture was stirred at rt overnight, after which LC-MS showed the desired product. Volatiles were removed in vacuo and the residue was dissolved in EtOAc and washed with aq. 1N NaOH (5×10 mL) until the yellow color had disappeared. The organic layer was concentrated in vacuo. The residue was used for the next step without purification. LCMS, [M+H]+=514.4.

Example 1

To a stirred solution of 1G (4.6 mg, 9 μmol) in THF (0.5 mL), MeOH (0.1 mL) and water (0.1 mL) at rt was added aq LiOH.H$_2$O (0.023 mL of a 2.0 M solution, 0.045 mmol). The reaction mixture was stirred at 50° C. for 2 h, after which LC-MS showed that all starting material had been consumed. The mixture was acidified to pH=~1 by dropwise addition of 1M aq. HCl. The mixture was extracted with EtOAc (3×15 mL); the combined organic extracts were concentrated in vacuo. The residue was purified by preparative HPLC (PHENOMENEX®, Axia 5μ C18 30×100 mm column; detection at 220 nm; flow rate=40 mL/min; continuous gradient from 0% B to 100% B over 10 min+2 min hold time at 100% B, where A=90:10:0.1 H$_2$O:MeOH:TFA and B=90:10:0.1 MeOH:H$_2$O:TFA) (to give the title compound as an oil (3.2 mg, 75%). LCMS, [M+H]$^+$=472.3. $^1$H NMR (500 MHz, DMSO-d6) δ 7.84 (d, J=8.2 Hz, 1H), 7.49 (d, J=8.5 Hz, 1H), 5.64 (br. s., 2H), 4.79 (br. s., 1H), 4.10 (s, 3H), 2.66 (br. s., 4H), 2.42 (s, 3H), 2.10-1.31 (m, 17H). hLPA1 IC$_{50}$=24 nM. Acute in vivo histamine assay in CD-1 mice: −97% histamine at a 3 mg/kg dose of Example 1.

Example 2

(1S,3S)-3-((6-(5-(((cyclopentyl(methyl)carbamoyl)oxy)methyl)-1-methyl-1H-1,2,3-triazol-4-yl)pyridin-3-yl)oxy)cyclohexane-1-carboxylic Acid

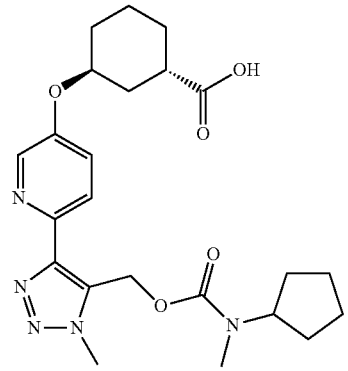 [SMILES: CN(C(=O)OCc1c(-c2ccc(O[C@H]3CCC[C@H](C(=O)O)C3)cn2)nnn1C)C1CCCC1]

2A. 3-(5-bromopyridin-2-yl)prop-2-yn-1-ol

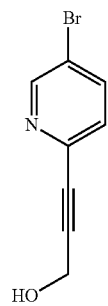

To a solution of 3,6-dibromopyridine (25.0 g, 100 mmol)) and prop-2-yn-1-ol (8.70 mL, 149 mmol) in MeCN (141 mL) was added Et₃N (33.2 mL, 240 mmol). The solution was degassed under Ar (sparged with Ar 3×), after which trans-dichlorobis(triphenlyphosphine) palladium (II) chloride (2.96 g, 4.22 mmol) and CuI (0.804 g, 4.22 mmol) were added. The reaction was stirred at rt under Ar for 14 h; the mixture was filtered through a Celite® plug, which was washed with EtOAc (3×50 mL). The combined filtrates were concentrated in vacuo. The residue was chromatographed (SiO₂; continuous gradient from 0% to 100% EtOAc in Hexanes, 20 min) to give the title compound as a white solid (16.6 g, 74% yield). $^1$H NMR (400 MHz, CD₃OD) δ 8.60 (d, J=2.2 Hz, 1H), 7.99 (dd, J=8.4, 2.2 Hz, 1H), 7.44 (d, J=8.4 Hz, 1H), 4.41 (s, 2H)

2B (4-(5-bromopyridin-2-yl)-1-methyl-1H-1,2,3-triazol-5-yl)methanol

To a degassed (sparged with Ar 3×) solution of 2A (1.9 g, 8.40 mmol) in dioxane (42.0 mL) was added chloro(pentamethylcyclopentadienyl)bis (triphenyl-phosphine) ruthenium (II) (0.402 g, 0.504 mmol). The mixture was degassed 3 times under Ar again and TMSCH₂N₃ (1.87 mL, 12.6 mmol) was added. The reaction was stirred at 50° C. for 15 h under Ar, then cooled to rt and concentrated in vacuo. The oily residue was dissolved in THF (90 mL) and cooled to 0° C. TBAF (5.40 mL of a 1.0 M solution in THF; 5.40 mmol) was added and the reaction was stirred at 0° C. for 10 min, after which solid NaHCO₃ (4 g) was added. The reaction mixture was stirred for 30 min at rt and then filtered. The filtrate was concentrated in vacuo. The residue was chromatographed (SiO₂; continuous gradient from 0% to 100% EtOAc in Hexanes, 20 min) to give the title compound (1.30 g, 4.59 mmol, 102% yield) as a white solid. $^1$H NMR (500 MHz, CDCl₃) δ 8.49 (dd, J=2.3, 0.7 Hz, 1H), 8.08 (dd, J=8.5, 0.6 Hz, 1H), 7.83 (dd, J=8.5, 2.2 Hz, 1H), 6.16 (t, J=6.9 Hz, 1H), 4.68 (d, J=6.9 Hz, 2H), 3.95 (s, 3H).

2C (4-(5-bromopyridin-2-yl)-1-methyl-1H-1,2,3-triazol-5-yl)methyl (4-nitrophenyl) carbonate

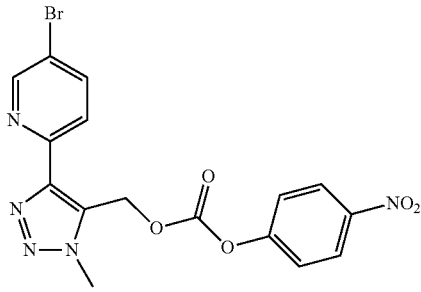 [SMILES: Cn1nnc(-c2ccc(Br)cn2)c1COC(=O)Oc1ccc([N+](=O)[O-])cc1]

To a solution of 2B (1.22 g, 4.31 mmol) in CH₂Cl₂ (50 mL) was added pyridine (1.74 mL, 21.55 mmol) and 4-nitrophenyl chloroformate (1.74 g, 8.62 mmol). The reaction was stirred at rt for 1 h, then was concentrated in vacuo. The residual solid was triturated with CH₂Cl₂ and filtered to give the pure title compound. The filtrate was concentrated in vacuo and the residue was chromatographed (SiO₂; continuous gradient from 0% to 100% EtOAc in DCM, 20 min); this purified material was combined with the previously triturated compound to give the title compound as a white solid (1.66 g, 86%). LCMS, [M+H]⁺=434.1.

2D. (4-(5-bromopyridin-2-yl)-1-methyl-1H-1,2,3-triazol-5-yl)methyl cyclopentyl(methyl)carbamate

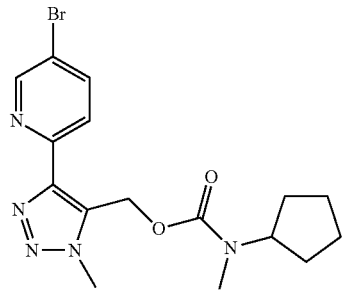 [SMILES: CN(C(=O)OCc1c(-c2ccc(Br)cn2)nnn1C)C1CCCC1]

To a solution of 2C (140 mg, 0.31 mmol) in THF (6.2 mL) was added iPr₂NEt (109 µL, 0.62 mmol) and 1-cyclobutyl-N-methylmethanamine (31 mg, 0.31 mmol). The reaction was stirred at rt for 2 h, then was concentrated in vacuo. The residue was chromatographed (SiO₂; continuous gradient from 0% to 100% EtOAc in Hexanes, 20 min) to give the title compound as a white solid (100 mg, 78%). $^1$H NMR (400 MHz, CDCl₃) δ 8.66 (dd, J=2.4, 0.7 Hz, 1H), 8.11 (dd, J=8.6, 0.7 Hz, 1H), 7.89 (dd, J=8.6, 2.4 Hz, 1H), 5.74 (s, 2H), 4.15 (s, 3H), 2.88-2.59 (m, 3H), 1.87-1.38 (m, 9H)

2E. (4-(5-Hydroxypyridin-2-yl)-1-methyl-1H-1,2,3-triazol-5-yl)methyl (cyclobutylmethyl)(methyl)carbamate

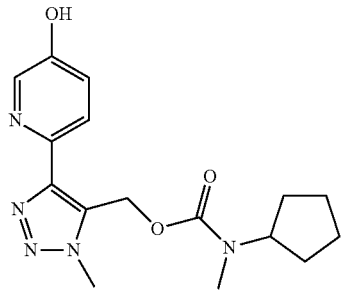 [SMILES: CN(C(=O)OCc1c(-c2ccc(O)cn2)nnn1C)C1CCCC1]

To a degassed (sparged with Ar 3×) solution of 2D (151 mg, 3.70 mmol), 4,4,4',4',5,5,5',5'-octamethyl-2,2'-bi(1,3,2-dioxaborolane) (1.41 g, 5.55 mmol), and potassium acetate (1.45 g, 14.8 mmol) in THF (25 mL) was added Pd(dppf)Cl$_2$ (0.271 g, 0.370 mmol) and the reaction was heated at 60° C. overnight under Ar, then cooled to rt. Water (10 mL) was added and the mixture was extracted with EtOAc (2×20 mL). The combined organic extracts were washed with water (10 mL) and brine (10 mL), dried (MgSO$_4$) and concentrated in vacuo. The residual crude boronate product was dissolved in EtOAc (15 mL) and H$_2$O$_2$ (1.62 mL of a 30% aq. solution, 18.5 mmol) was carefully added portionwise at 0° C. The reaction was allowed to warm to rt and stirred at rt for 1 h, then was cooled 0° C. and quenched with sat. aq. Na$_2$S$_2$O$_3$ (20 mL) and extracted with EtOAc (3×20 mL). The combined organic extracts were washed with water (20 mL) and brine (20 mL), dried (MgSO$_4$) and concentrated in vacuo. The residue was chromatographed (SiO$_2$; continuous gradient from 0% to 100% EtOAc in Hexanes, 20 min) to give the title compound as a white solid (962 mg, 75%). $^1$H NMR (400 MHz, CD$_3$OD) δ 8.22 (dd, J=3.0, 0.6 Hz, 1H), 7.87 (dd, J=8.6, 0.7 Hz, 1H), 7.30 (dd, J=8.7, 3.0 Hz, 1H), 5.68 (s, 2H), 4.19 (s, 3H), 2.76 (br. s., 3H), 1.92-1.43 (m, 8H). LCMS, [M+H]$^+$=332.3.

1G. isopropyl (1S,3S)-3-((6-(5-(((cyclopentyl(methyl)carbamoyl)oxy)methyl)-1-methyl-1H-1,2,3-triazol-4-yl)pyridin-3-yl)oxy)cyclohexane-1-carboxylate

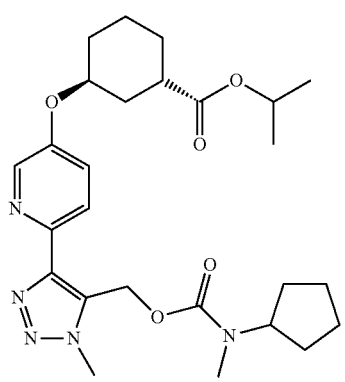

To a solution of 2E (962 mg, 2.79 mmol), (1S,3R)-isopropyl 3-hydroxy-cyclohexanecarboxylate (934 mg, 5.01 mmol), and Bu$_3$P (1.74 mL, 6.96 mmol) in toluene (55 mL) was added (E)-diazene-1,2-diylbis(piperidin-1-ylmethanone) (1.76 g, 6.96 mmol). The reaction was heated at 50° C. for 7 h, then was cooled to rt. The mixture was diluted with CH$_2$Cl$_2$ (20 mL) and filtered through Celite®, which was washed with additional CH$_2$Cl$_2$ (3×20 mL). The combined filtrates were concentrated in vacuo, and the residue was chromatographed (SiO$_2$; continuous gradient from 0% to 100% EtOAc in Hexanes, 20 min) to give the title compound as a white solid (786 mg, 55%). $^1$H NMR (400 MHz, CDCl$_3$) δ 8.33 (d, J=2.6 Hz, 1H), 8.12 (d, J=8.6 Hz, 1H), 7.34 (dd, J=8.8, 2.9 Hz, 1H), 5.78 (s, 2H), 5.05 (dt, J=12.5, 6.3 Hz, 1H), 4.77-4.66 (m, 1H), 4.16 (s, 3H), 2.95-2.64 (m, 4H), 2.12-2.08 (m, 1H), 2.03-1.87 (m, 4H), 1.82-1.41 (m, 12H), 1.29-1.19 (m, 6H). LCMS, [M+H]$^+$=500.4.

Example 2

To a solution of 2F (786 mg, 1.53 mmol) in THF (3 mL) and MeOH (3 mL) added aq. LiOH (3.06 mL of a 2N solution, 6.12 mmol). The reaction mixture was stirred at rt overnight, after which the pH was adjusted to ~5 and water (10 mL) was added. The mixture was extracted with EtOAc (3×30 mL), washed with water (30 mL) and brine (30 mL), dried (MgSO$_4$) and concentrated in vacuo. The resulting solid was dissolved in 3 mL of EtOAc and allowed to stand overnight to give the title compound as a white crystalline solid (600 mg, 83%). LCMS, [M+H]$^+$=458.2. $^1$H NMR (500 MHz, CD$_3$CN) δ 8.34 (d, J=2.5 Hz, 1H), 8.08-8.00 (m, 1H), 7.45 (dd, J=8.8, 2.8 Hz, 1H), 5.66 (s, 2H), 4.88-4.73 (m, 1H), 4.11 (s, 3H), 2.87-2.77 (m, 1H), 2.72 (br. s., 3H), 2.10-2.01 (m, 1H), 1.92-1.80 (m, 3H), 1.79-1.57 (m, 9H), 1.56-1.43 (m, 4H). HPLC-1: RT=7.99 min, purity=100%; HPLC-2: RT=7.81 min, purity=100%. hLPA1 IC$_{50}$=19 nM.

Example 3

(1S,3S)-3-((6-(5-((((2-cyclopropylethyl)(methyl)carbamoyl)oxy)methyl)-1-methyl-1H-1,2,3-triazol-4-yl)pyridin-3-yl)oxy)cyclohexane-1-carboxylic Acid

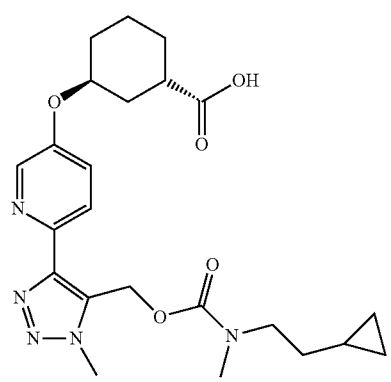

3A. Isopropyl (1S,3S)-3-((6-(1-methyl-5-((((4-nitrophenoxy)carbonyl)oxy)methyl)-1H-1,2,3-triazol-4-yl)pyridin-3-yl)oxy)cyclohexane-1-carboxylate

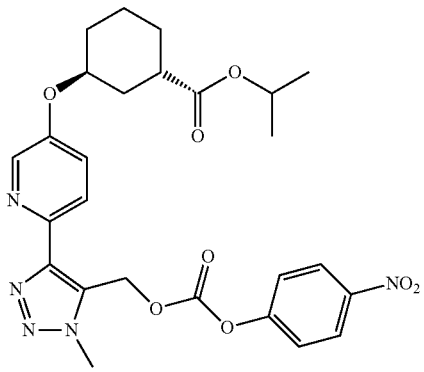

The title compound was prepared by the same synthetic sequence as for Example 1F, except that 2,5-dibromopyridine was used as starting material instead of 2,5-dibromo-6-methyl-pyridine. $^1$H NMR (400 MHz, CDCl$_3$) δ 8.43-8.25 (m, 3H), 8.23-8.10 (m, 1H), 7.47-7.31 (m, 3H), 6.11-5.77 (m, 2H), 5.20-4.95 (m, 1H), 4.79-4.63 (m, 1H), 4.31-4.19 (m, 3H), 2.92-2.71 (m, 1H), 2.12-1.54 (m, 8H), 1.35-1.20 (m, 6H). LCMS, [M+H]+=540.2.

3B. isopropyl (1S,3S)-3-((6-(5-((((2-cyclopropylethyl)carbamoyl)oxy)methyl)-1-methyl-1H-1,2,3-triazol-4-yl)pyridin-3-yl)oxy)cyclohexane-1-carboxylate

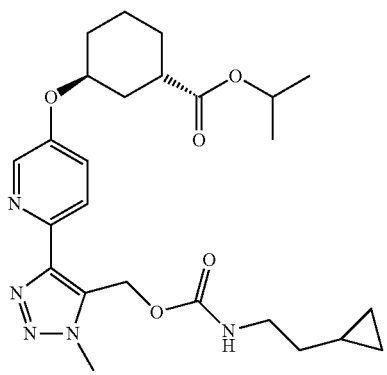

To a solution of Example 3A (10 mg, 9.3 μmol) and iPr$_2$NEt (6.5 μL, 0.037 mmol) in THF (0.5 mL) was added 2-cyclopropyl ethanamine (0.8 mg, 9.3 μmol). The reaction mixture was stirred at rt overnight, then was concentrated in vacuo. The residue was chromatographed (SiO$_2$; continuous gradient from 0% to 100% EtOAc in Hexanes, 20 min) to give the title compound as a white solid (8 mg, 80%). LCMS, [M+H]+=486.4.

3B. isopropyl (1S,3S)-3-((6-(5-((((2-cyclopropylethyl)(methyl)carbamoyl)oxy)methyl)-1-methyl-1H-1,2,3-triazol-4-yl)pyridin-3-yl)oxy)cyclohexane-1-carboxylate To a solution of 3A (50 mg, 0.103 mmol) and MeI (0.129 mL, 0.257 mmol) in DMF (0.5 mL) was added NaH (10 mg of a 40% suspension in oil, 0.25 mmol). The reaction was stirred at rt for 1 h, then was quenched with water (5 mL) and extracted with EtOAc (3×10 mL). The combined organic extracts were washed with water (10 mL) and brine (10 mL), dried (MgSO$_4$) and concentrated in vacuo to give the crude product, which was used in the next step without further purification. LCMS, [M+H]+=500.4.

Example 3

To a stirred solution of 3B (5 mg, 10 μmol) in THF (1.5 mL), MeOH (0.10 mL) and water (0.15 mL) at rt was added aq. LiOH (0.015 mL of a 2 M solution, 0.030 mmol). The reaction mixture was stirred at 50° C. for 1 h, then was cooled to rt. The mixture was acidified to pH 2.3 by dropwise addition of 1M aq. HCl, then was concentrated in vacuo. The residue was purified by preparative HPLC (PHENOMENEX®, Axia 5μ C18 30×100 mm column; detection at 220 nm; flow rate=40 mL/min; continuous gradient from 0% B to 100% B over 10 min+2 min hold time at 100% B, where A=90:10:0.1 H$_2$O:MeOH:TFA and B=90:10:0.1 MeOH:H$_2$O:TFA) (to give the title compound as an oil (4.2 mg, 92%). $^1$H NMR (500 MHz, DMSO-d$_6$) δ 8.13 (br. s., 1H), 7.78 (d, J=8.2 Hz, 1H), 7.33 (d, J=6.4 Hz, 1H), 5.48-5.30 (m, 2H), 4.57 (br. s., 1H), 3.89 (br. s., 3H), 3.09-2.88 (m, 2H), 2.56 (d, J=16.8 Hz, 4H), 2.46 (br. s., 1H), 1.80-1.53 (m, 5H), 1.51-1.25 (m, 5H), 1.20-0.93 (m, 4H). LCMS, [M+H]+=458.4. HPLC-4: RT=1.42 min, purity=100%. hLPA1 IC$_{50}$=19 nM.

Example 4

(rac)-trans-3-(4-(5-(((cyclopentyl(methyl)carbamoyl)oxy)methyl)-1-methyl-1H-1,2,3-triazol-4-yl)phenoxy)cyclohexane-1-carboxylic Acid

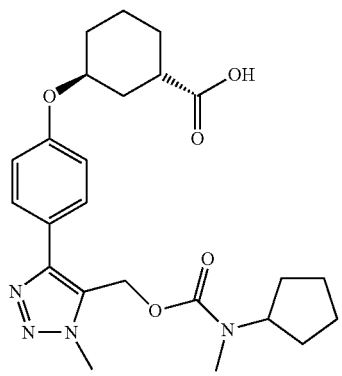

4A Methyl 4-(4-bromophenyl)-1H-1,2,3-triazole-5-carboxylate

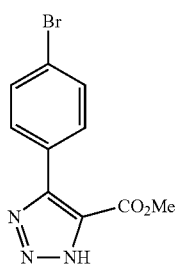 [SMILES: COC(=O)c1[nH]nnc1-c1ccc(Br)cc1]

To a stirred solution of 4-bromobenzaldehyde (1.0 g, 5.40 mmol), methyl 2-cyanoacetate (0.536 g, 5.40 mmol) and Et$_3$N.HCl (2.23 g, 16.2 mmol) in DMF (20 mL) under N$_2$ was added NaN$_3$ (1.12 g, 17.3 mmol) and the reaction mixture was stirred at 70° C. for 16 h, then was cooled to rt. The reaction mixture was slowly poured into water (100 mL) and extracted with EtOAc (2×50 mL). The combined organic layer was washed with brine (100 mL), dried (Na$_2$SO$_4$), filtered and concentrated in vacuo. The crude product was chromatographed (12 g Redisep® SiO$_2$ column, eluting with 40% EtOAc in n-hexanes) to afford the title compound (0.24 g, 16%) as a yellow solid. LCMS, [M+H]$^+$ =284.0. $^1$H NMR (400 MHz, DMSO-d6) δ ppm 15.91 (br. s., 1H), 7.75-7.85 (m, 4H), 3.82 (m, 3H).

4B Methyl 4-(4-bromophenyl)-1-methyl-1H-1,2,3-triazole-5-carboxylate

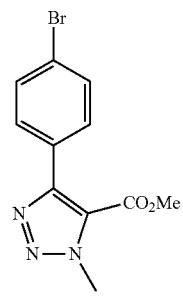 [SMILES: COC(=O)c1c(-c2ccc(Br)cc2)nnn1C]

To a stirred solution of 4A (250 mg, 0.886 mmol) in MeCN (5 mL) was added K$_2$CO$_3$ (122 mg, 0.886 mmol) and the reaction mixture was allowed to stir at rt for 30 min. CH$_3$I (0.06 mL, 0.886 mmol) was added and the reaction was stirred at rt under N$_2$ for 16 h. The reaction mixture was diluted with water, extracted with EtOAc (3×15 mL). The combined organic extracts were dried (Na$_2$SO$_4$), filtered and concentrated in vacuo. The residue was chromatographed (12 g Redisep® SiO$_2$ column, eluting with 30% EtOAc in n-hexanes) to afford the title compound (200 mg, 70%) as an off white solid. $^1$H NMR and LCMS showed the presence of a 3:1 ratio of a mixture of triazole regioisomers (with the title compound the as major isomer), which was carried onto the next step without further purification. LC-MS, [M+H]$^+$ =296.0.

4C (4-(4-Bromophenyl)-1-methyl-1H-1,2,3-triazol-5-yl)methanol

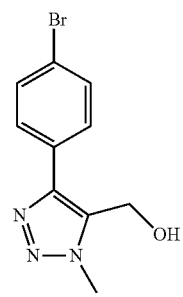

To a solution of mixture of 4B (250 mg, 0.844 mmol) in THF (10 mL) under nitrogen was added dropwise LiAlH (0.93 mL of a 1M solution in THF; 0.93 mmol) at 0° C. and the reaction mixture was allowed to stir at 0° C. for 1 h. The reaction was slowly quenched with water (0.5 mL) and aq. NaOH (0.5 mL of a 10% solution). The reaction mixture was diluted with water (30 mL) and extracted with EtOAc (2×20 mL). The combined organic extracts were washed with brine (25 mL), dried (Na$_2$SO$_4$), filtered and concentrated in vacuo. The residue was chromatographed (12 g Redisep® SiO$_2$ column, eluting with 55% EtOAc in n-hexanes) to afford the title compound (60 mg, 26%) as an off-white solid. The two regioisomers were separated by preparative HPLC (Column: Symmetry C8 (300×19) mm 5 μm; M. Phase A: 0.1% HCO$_2$H in water; M. Phase B: MeCN, flow rate: 17.0 mL/min; time (min)/% B: 0/45, 35/60). The desired triazole N-methyl regioisomer 4C was isolated as white solid (60 mg 26%) and structurally identified by proton NMR NOE studies on the N-methyl group. LC-MS, [M+H]+=270.0. ¹H NMR (300 MHz, DMSO-d6) δ ppm 7.80-7.60 (m, 4H), 5.59 (t, J=6.0 Hz, 1H) 4.66 (d, J=3 Hz, 2H), 4.08 (s, 3H).

4D (4-(4-Bromophenyl)-1-methyl-1H-1,2,3-triazol-5-yl)methyl cyclopentylcarbamate

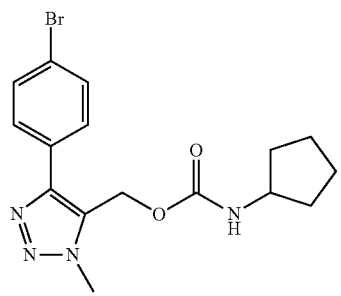 [SMILES: Cn1nnc(-c2ccc(Br)cc2)c1COC(=O)NC1CCCC1]

To a stirred solution of cyclopentanecarboxylic acid (63.9 mg, 0.559 mmol) and 4C (150 mg, 0.559 mmol) in toluene (4 mL) were added Et₃N (0.10 mL, 0.84 mmol) and Ph₂PON₃ (0.2 mL, 0.671 mmol), and the resultant solution was stirred at 110° C. for 20 h under N₂. The reaction mixture was cooled to rt, volatiles were removed in vacuo and the crude product was chromatographed (12 g Redisep® SiO₂ column, eluting with 38% EtOAc in n-hexanes) to afford the title compound (150 mg, 71%) as an off white solid. LC-MS, [M+H]+=379.0. ¹H NMR (400 MHz, CDCl₃) δ ppm 7.66 (d, J=8.8 Hz, 2H), 7.60 (d, J=8.8 Hz, 2H), 5.24 (s, 2H), 4.18 (s, 3H), 3.90-4.00 (m, 1H), 2.02-1.90 (m, 2H), 1.50-1.80 (m, 3H), 1.30-1.50 (m, 4H).

4E (4-(4-Bromophenyl)-1-methyl-1H-1,2,3-triazol-5-yl)methyl cyclopentyl(methyl)carbamate

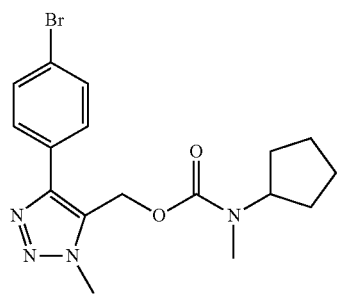 [SMILES: CN(C(=O)OCc1c(-c2ccc(Br)cc2)nnn1C)C1CCCC1]

To a stirred solution of 4D (200 mg, 0.527 mmol) and DMF (4 mL) was added NaH (19 mg of a 60% suspension in mineral oil, 0.79 mmol) portionwise at 0° C. and the reaction was stirred at 0° C. for 30 min. Iodomethane (0.049 mL, 0.79 mmol) was added at 0° C. and the reaction was allowed to warm to rt and stirred at rt for 1 h. The reaction mixture was slowly quenched with aq. HCl (5 mL of a 1.5 N solution), diluted with water (25 mL) and extracted with EtOAc (2×25 mL). The combined organic extracts were washed with brine (50 mL), dried (Na₂SO₄), filtered and concentrated in vacuo. The crude product was chromatographed (12 g Redisep® SiO₂ column, eluting with 40% EtOAc in n-hexanes) to afford the title compound (200 mg, 96%) as a pale yellow oily liquid. LC-MS, [M+H]+=395.0.

4F (1-Methyl-4-(4-(4,4,5,5-tetramethyl-1,3,2-dioxaborolan-2-yl)phenyl)-1H-1,2,3-triazol-5-yl)methyl cyclopentyl(methyl)carbamate

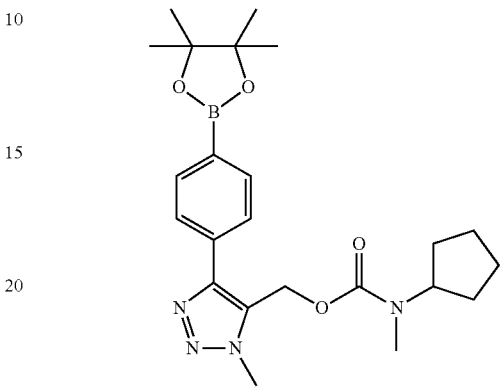

To a stirred solution of 4E (700 mg, 1.78 mmol) and bis(pinacolato)diboron (678 mg, 2.67 mmol) in 1,4-dioxane (7 mL) was added KOAc (349 mg, 3.56 mmol) and the reaction mixture was degassed with N₂ for 5 min. 1,1'-Bis (diphenylphosphino) ferrocenepalladium (II) dichloride-toluene adduct (73 mg, 0.089 mmol) was added and the reaction mixture was stirred at 90° C. for 16 h under N₂. The reaction mixture was cooled to rt, filtered through a Celite® pad, washed with EtOAc (50 mL) and the combined organic filtrates were concentrated in vacuo. The residue was chromatographed (24 g Redisep® SiO₂ column, eluting with 75% EtOAc in n-hexanes) to afford the title compound (700 mg, 89%) as a pale yellow oily liquid. LC-MS, [M+H]+= 441.2.

4G (4-(4-Hydroxyphenyl)-1-methyl-1H-1,2,3-triazol-5-yl)methyl cyclopentyl(methyl)carbamate

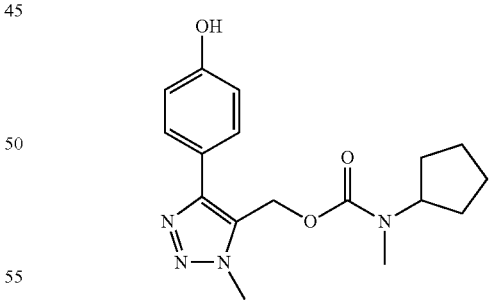

To a solution of 4F (700 mg, 1.590 mmol) in THF (20 mL) and water (7 mL) mixture was added sodium perborate monohydrate (317 mg, 3.18 mmol) and the reaction mixture was stirred at rt for 30 min. The reaction mixture was diluted with sat'd aq. NH₄Cl (50 mL) and extracted with EtOAc (2×50 mL). The combined organic extracts were dried (Na₂SO₄), filtered and concentrated in vacuo. The crude product was chromatographed (12 g Redisep® SiO₂ column, eluting with 60% EtOAc in n-hexanes) to afford the title compound (400 mg, 76%) as a white solid. LC-MS, [M+H]+

=331.2. $^1$H NMR (300 MHz, DMSO-$d_6$) δ ppm 9.63 (s, 1H), 7.55 (d, J=8.7 Hz, 2H), 6.86 (d, J=8.7 Hz, 2H), 5.26 (s, 2H), 4.20-4.50 (m, 1H), 4.09 (s, 3H), 2.67 (s, 3H), 1.60-1.80 (m, 4H), 1.40-1.60 (m, 4H).

4H (rac)-trans-Ethyl 3-(4-(5-((((cyclopentyl(methyl) carbamoyl)oxy)methyl)-1-methyl-1H-1,2,3-triazol-4-yl)phenoxy)cyclohexanecarboxylate

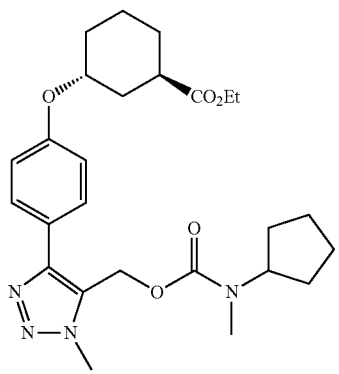 [SMILES: CN(C(=O)OCc1c(-c2ccc(O[C@@H]3CCC[C@@H](C(=O)O)C3)cc2)nnn1C)C1CCCC1]

To a stirred solution of 4G (300 mg, 0.908 mmol) and di-tert-butyl azodicarboxylate (627 mg, 2.72 mmol) and Ph$_3$P (714 mg, 2.72 mmol) in THF (10 mL) under N$_2$ was added ethyl 3-hydroxycyclohexanecarboxylate (racemic cis isomer; 313 mg, 1.82 mmol) and the reaction mixture was stirred at 60° C. for 16 h under N$_2$, then was cooled to rt and concentrated in vacuo. The residue was chromatographed (24 g Redisep® SiO$_2$ column, eluting with 40% EtOAc in n-hexanes) to afford the title compound (260 mg, 56%) as a colorless oil. LC-MS, [M+H]$^+$=485.2. $^1$H NMR (400 MHz, CD$_3$OD) δ ppm 7.67 (d, J=8.8 Hz, 2H), 7.09 (d, J=8.8 Hz, 2H), 5.35 (s, 2H), 4.70-4.80 (m, 1H), 4.18 (s, 3H), 4.12 (q, J=7.2 Hz, 2H), 2.70-2.90 (m, 1H), 2.75 (s, 3H), 1.80-2.10 (m, 4H), 1.40-1.80 (m, 13H), 1.10-1.30 (t, J=7.2 Hz, 3H).

Example 4

(rac)-trans-3-(4-(5-((((Cyclopentyl(methy)carbamoyl) oxy)methyl)-1-methyl-1H-1,2,3-triazol-4-yl)phenoxy)cyclohexanecarboxylic Acid

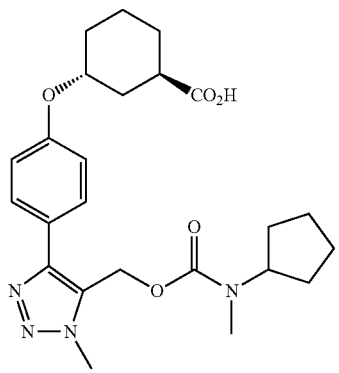

To a stirred solution of 4H (260 mg, 0.429 mmol) in THF (4 mL) and MeOH (4 mL) was added a solution of LiOH.H$_2$O (31 mg, 1.29 mmol) in water (4 mL) and the reaction mixture was stirred at rt for 16 h. The mixture was diluted with water (20 mL) and washed with Et$_2$O (20 mL) to remove traces of non-polar impurities. The aqueous layer was neutralized with aq. HCl (2.0 mL of a 1.5N solution) and extracted with 5% MeOH in CHCl$_3$ (25 mL). The organic layer was washed with brine (25 mL), dried (Na$_2$SO$_4$), filtered and concentrated in vacuo. The crude product was purified by preparative HPLC (Column: Symmetry C8 (300×19) mm 10 μm; M. Phase A: 0.1% HCOOH in water; M. Phase B: MeCN, flow rate: 17.0 mL/min; time (min)/% B: 0/30, 20/100) to afford the title compound (120 mg, 45%) as a white solid. LC-MS, [M+H]$^+$=457.2. $^1$H NMR (400 MHz, CD$_3$OD) δ 7.66 (d, J=8.40 Hz, 2H), 7.09 (d, J=8.80 Hz, 2H), 5.37 (s, 2H), 4.75-4.76 (m, 1H), 4.31-4.50 (m, 1H), 4.20 (s, 3H), 2.77-2.81 (m, 4H), 2.07-2.10 (m, 1H), 1.82-1.97 (m, 3H), 1.49-1.79 (m, 12H). hLPA1 IC$_{50}$=18 nM.

Example 5 and Example 6

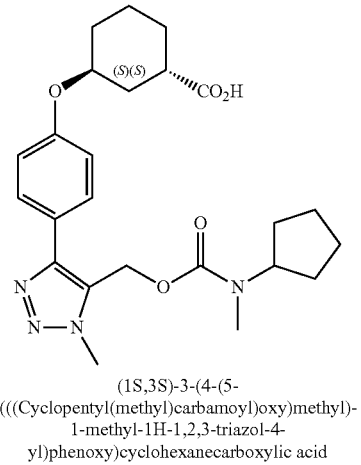

Example 5

(1S,3S)-3-(4-(5-((((Cyclopentyl(methyl)carbamoyl)oxy)methyl)-1-methyl-1H-1,2,3-triazol-4-yl)phenoxy)cyclohexanecarboxylic acid

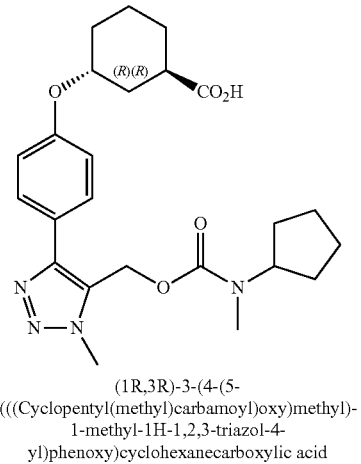

Example 6

(1R,3R)-3-(4-(5-((((Cyclopentyl(methyl)carbamoyl)oxy)methyl)-1-methyl-1H-1,2,3-triazol-4-yl)phenoxy)cyclohexanecarboxylic acid Individual enantiomers of Example 4 was separated by chiral SFC (Column/dimensions: Chiralpak IC (250×21) mm, 5 μm; % CO$_2$: 60%; % Co solvent: 40%(0.25% DEA in MeOH); Total Flow: 60 g/min; Back Pressure: 100 bars; Temperature: 25° C.; UV: 250 nm). Example 5 (37 mg, 18%) was isolated as a white solid. LC-MS, [M+H]$^+$=457.2. OR

[α]$^{24.8}_D$=(+)14.0 (c 0.10, MeOH). $^1$H NMR (400 MHz, CD$_3$OD) δ ppm 7.66 (d, J=8.40 Hz, 2H), 7.09 (d, J=8.40 Hz, 2H), 5.37 (s, 2H), 4.75-4.76 (m, 1H), 4.31-4.50 (m, 1H), 4.20 (s, 3H), 2.77-2.81 (m, 4H), 2.07-2.10 (m, 1H), 1.82-1.97 (m, 3H), 1.49-1.79 (m, 12H). hLPA1 IC$_{50}$=6 nM. Acute mouse in vivo histamine assay: −90% histamine at a 3 mg/kg dose of Example 5. Example 6 (35 mg, 17%) was isolated as a white solid. LC-MS, [M+H]$^+$=457.2. OR [α]$^{25.2}_D$=(−) 14.0 (c 0.10, MeOH). $^1$H NMR (400 MHz, CD$_3$OD) δ 7.66 (d, J=8.40 Hz, 2H), 7.09 (d, J=8.40 Hz, 2H), 5.37 (s, 2H), 4.75-4.76 (m, 1H), 4.31-4.50 (m, 1H), 4.20 (s, 3H), 2.77-2.81 (m, 4H), 2.07-2.10 (m, 1H), 1.82-1.97 (m, 3H), 1.49-1.79 (m, 12H). hLPA1 IC$_{50}$=1314 nM.

Example 7

(1-Methyl-4-(4-(((1S,3S)-3-((methylsulfonyl)carbamoyl)cyclohexyl)oxy)phenyl)-1H-1,2,3-triazol-5-yl)methyl cyclopentyl(methyl)carbamate

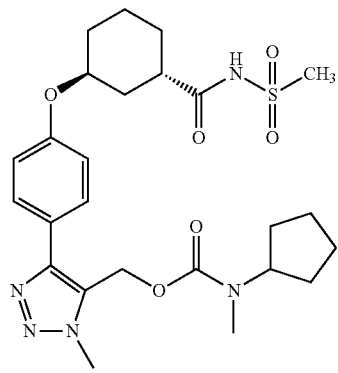 [SMILES: CN(C(=O)OCc1c(-c2ccc(O[C@H]3CCC[C@H](C(=O)NS(C)(=O)=O)C3)cc2)nnn1C)C1CCCC1]

To a stirred solution of Example 5 (10 mg, 0.022 mmol) and methane sulfonamide (3 mg, 0.033 mmol) in DCM (0.5 mL) and DMF (0.5 mL) mixture was added 4-dimethylaminopyridine (3.21 mg, 0.026 mmol) and 1-(3-dimethylaminopropyl)-3-ethylcarbodiimide hydrochloride (6.30 mg, 0.033 mmol) and the reaction mixture was stirred at rt for 16 h under N$_2$. The reaction mixture was concentrated in vacuo and the crude product was purified by preparative HPLC (Column: Sunfire C18 (150×19) mm 5 micron; M. Phase A: 0.1% HCO$_2$H in water; M. Phase B: MeCN, flow rate: 16.0 mL/min; time (min)/% B: 0/30, 30/100) to afford the title compound (4 mg, 33%) as a white solid. LC-MS, [M+H]$^+$=534.4. $^1$H NMR (400 MHz, CD$_3$OD) δ 7.67 (d, J=8.8 Hz, 2H), 7.09 (d, J=8.8 Hz, 2H), 5.37 (s, 2H), 4.20 (s, 3H), 3.20 (s, 3H), 2.78-2.89 (m, 5H), 1.59-2.10 (m, 17H). hLPA1 IC$_{50}$=3750 nM.

Example 8 & Example 9

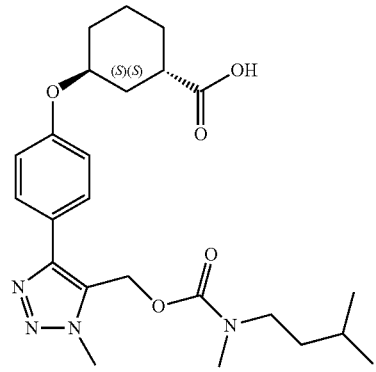

Example 8

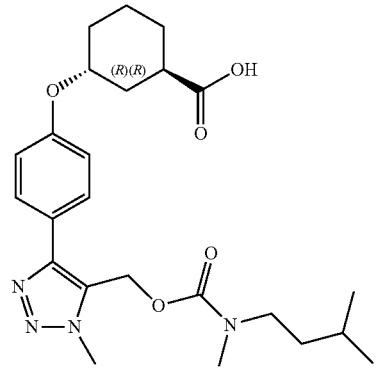

Example 9

8A 4-(4-Methoxyphenyl)-1-methyl-1-1H-1,2,3-triazole-5-carbaxaldehyde

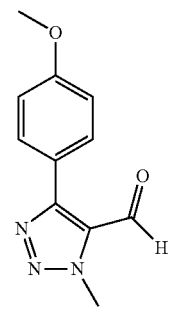 [SMILES: COc1ccc(-c2nnn(C)c2C=O)cc1]

To a stirred solution of 4-(4-methoxyphenyl)-1-methyl-1H-1,2,3-triazole (35 g, 185 mmol) in THF (860 mL) under N$_2$ was added n-BuLi (111 mL of a 2.5 M solution in hexanes, 277 mmol) dropwise at −78° C. and the reaction mixture was stirred at −78° C. for 1 h. DMF (22 mL, 277 mmol) was added at −78° C. and the reaction mixture was allowed to slowly warm to rt and stirred for 2 h at rt. The reaction mixture was cooled to 0° C., then was slowly quenched with sat'd aq. NH$_4$Cl and extracted with DCM (3×250 mL). The combined organic extracts were washed with brine (500 mL), dried (Na$_2$SO$_4$), filtered and concentrated in vacuo. The residue was chromatographed (330 g Redisep® SiO$_2$ column, eluting with 20% EtOAc in n-hexanes) to afford the title compound (18.0 g, 48%) as a yellow solid. LC-MS, [M+H]+=218.2. ¹H NMR (400 MHz, DMSO-d₆) δ ppm 10.04 (s, 1H), 7.84 (d, J=9.0 Hz, 2H), 7.10 (d, J=9.0 Hz, 2H), 4.31 (s, 3H), 3.84 (s, 3H).

8B 4-(4-Hydroxyphenyl)-1-methyl-1H-1,2,3-triazole-5-carbaldehyde

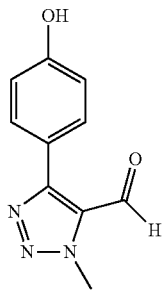

To a stirred solution of 8A (8.4 g, 38.7 mmol) in DCM (160 mL) was added dropwise BBr₃ (11 mL, 116 mmol) at 0° C. and the reaction mixture was stirred at 0° for 1 h. The reaction mixture was quenched carefully with ice-cold water and neutralized with 10% aq. NaHCO₃ and extracted with DCM (3×150 mL). The combined organic extracts were washed with brine (250 mL), dried (Na₂SO₄), filtered and concentrated in vacuo. The residue was diluted with DCM and the resulting solid that formed was filtered and dried in vacuo to afford the title compound (5.7 g, 73%) as a white solid. ¹H NMR (300 MHz, DMSO-d₆) δ ppm 10.04 (s, 1H), 9.88 (s, 1H), 7.71 (d, J=13.0 Hz, 2H), 6.92 (d, J=13.0 Hz, 2H), 4.28 (s, 3H).

8C 4-(4-((tert-Butyldimethylsilyl)oxy)phenyl)-1-methyl-1H-1,2,3-triazole-5-carbaldehyde

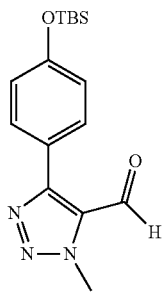 [SMILES: Cn1nnc(-c2ccc(O[Si](C)(C)C(C)(C)C)cc2)c1C=O]

To a stirred solution of 8B (1.0 g, 4.92 mmol) and imidazole (0.670 g, 9.84 mmol) in DMF (20 mL) was added TBSCl (0.890 g, 5.91 mmol) and the reaction mixture was stirred at rt for 16 h under N₂. Water (100 mL) was added to the mixture, which was extracted with EtOAc (2×75 mL). The combined organic extracts were washed with brine (150 mL), dried (Na₂SO₄), filtered and concentrated in vacuo. The crude product was chromatographed (24 g Redisep® SiO₂ column, eluting with 25% EtOAc in n-hexanes) to afford the title compound (1.2 g, 77%) as a white solid. ¹H NMR (300 MHz, CDCl₃) δ ppm 10.07 (s, 1H), 7.63 (d, J=8.7 Hz, 2H), 6.99 (d, J=8.7 Hz, 2H), 4.36 (s, 3H), 1.01 (s, 9H), 0.24 (s, 6H).

8D (4-(4-((tert-Butyldimethylsilyl)oxy)phenyl)-1-methyl-1H-1,2,3-triazol-5-yl)methanol

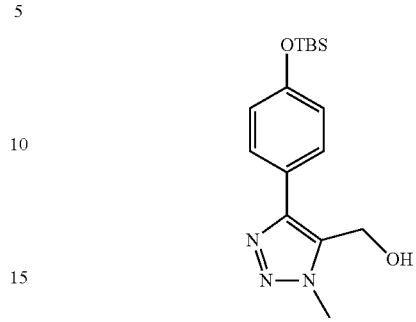

To a 0° C. solution of 8C (1.25 g, 3.94 mmol) in THF (30 mL) was added NaBH₄ (0.223 g, 5.91 mmol) and the reaction mixture was stirred at 0° C. for 1 h. The reaction mixture was diluted with water (75 mL) and extracted with EtOAc (2×75 mL). The combined organic extracts were washed with brine (150 mL), dried (Na₂SO₄), filtered and concentrated in vacuo. The crude product was chromatographed (24 g Redisep® SiO₂ column, eluting with 60% EtOAc in n-hexanes) to afford the title compound (0.7 g, 56%) as a white solid. LC-MS, [M+H]+=320.3. ¹H NMR (300 MHz, CD₃OD) δ ppm 7.59 (d, J=8.7 Hz, 2H), 6.97 (d, J=8.7 Hz, 2H), 4.77 (s, 2H), 4.15 (s, 3H), 1.02 (s, 9H), 0.24 (s, 6H).

8E (4-(4-((tert-Butyldimethylsilyl)oxy)phenyl)-1-methyl-1H-1,2,3-triazol-5-yl)methyl (4-nitrophenyl) carbonate

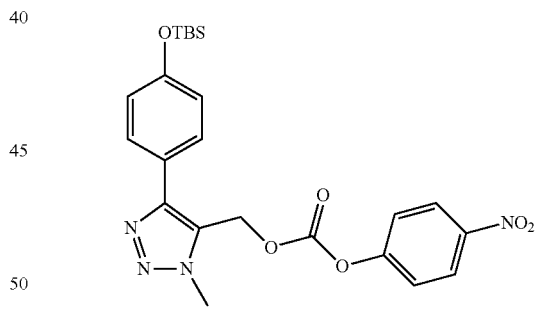

To a stirred solution of 8D (500 mg, 1.565 mmol) and iPr₂NEt (0.50 mL, 3.13 mmol) in DCM (10 mL) was added 4-nitrophenyl chloroformate (379 mg, 1.88 mmol) at 0° C. and the resultant pale yellow solution was stirred at rt for 16 h under N₂. The reaction mixture was diluted with water (50 mL) and extracted with DCM (2×50 mL). The combined organic extracts were dried (Na₂SO₄), filtered and concentrated in vacuo. The crude product was chromatographed (24 g Redisep® SiO₂ column, eluting with 40% EtOAc in n-hexanes) to afford the title compound (260 mg, 35%) as a white solid. LC-MS, [M+H]+=485.2. ¹H NMR (400 MHz, CDCl₃) δ ppm 8.30 (d, J=9.0 Hz, 2H), 7.64 (d, J=9.0 Hz, 2H), 7.40 (d, J=9.0 Hz, 2H), 6.96 (d, J=8.5 Hz, 2H), 5.47 (s, 2H), 4.22 (s, 3H), 1.00 (s, 9H), 0.23 (s, 6H).

8F (4-(4-((tert-Butyldimethylsilyl)oxy)phenyl)-1-methyl-1H-1,2,3-triazol-5-yl)methyl isopentylcarbamate

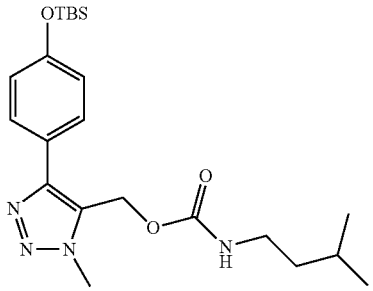 [SMILES: CC(C)CCNC(=O)OCc1c(-c2ccc(O[Si](C)(C)C(C)(C)C)cc2)nnn1C]

To a stirred solution of 8E (240 mg, 0.496 mmol) and Et₃N (0.20 mL, 1.49 mmol) in THF (10 mL) was added 3-methylbutan-1-amine (86 mg, 0.991 mmol) and the reaction mixture was stirred at rt for 16 h under N₂, then was concentrated in vacuo. The crude product was chromatographed (12 g Redisep® SiO₂ column, eluting with 65% EtOAc in n-hexanes) to afford the title compound (150 mg, 70%) as a pale yellow liquid. LC-MS, [M+H]⁺=433.4. ¹H NMR (400 MHz, CDCl₃) δ ppm 7.62 (d, J=8.5 Hz, 2H), 6.92 (d, J=8.5 Hz, 2H), 5.24 (s, 2H), 4.72 (br. s., 1H), 4.16 (s, 3H), 3.27-3.19 (m, 2H), 1.30-1.50 (m, 3H), 0.97-1.00 (s, 9H), 0.91-0.96 (m, 6H), 0.23 (s, 6H).

8G (4-(4-Hydroxyphenyl)-1-methyl-1H-1,2,3-triazol-5-yl)methyl isopentylcarbamate

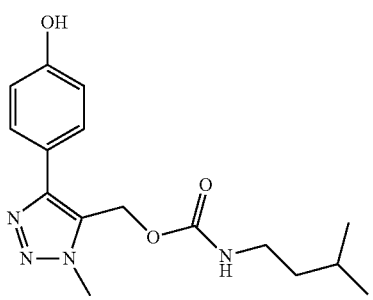 [SMILES: CC(C)CCNC(=O)OCc1c(-c2ccc(O)cc2)nnn1C]

To a stirred solution of 8F (150 mg, 0.347 mmol) in THF (6 mL) was added TBAF (0.52 mL of a 1M solution in THF; 0.52 mmol) at 0° C. and the reaction mixture was stirred at 0° C. for 30 min. The reaction mixture was diluted with water (25 mL) and extracted with EtOAc (2×25 mL). The combined organic extracts were dried (Na₂SO₄), filtered and concentrated in vacuo. The crude product was chromatographed (12 g Redisep® SiO₂ column, eluting with 85% EtOAc in n-hexanes) to afford the title compound (90 mg, 82%) as a white solid. LC-MS, [M+H]⁺=319.2. ¹H NMR (400 MHz, CD₃OD) δ ppm 7.56 (d, J=8.4 Hz, 2H), 6.91 (d, J=8.4 Hz, 2H), 5.28 (s, 2H), 4.19 (s, 3H), 3.15 (t, J=7.3 Hz, 2H), 1.55-1.70 (m, 1H), 1.40 (q, J=7.0 Hz, 2H), 0.94 (d, J=6.4 Hz, 6H).

8H (rac)-trans-(Ethyl 3-(4-(5-(((isopentylcarbamoyl)oxy)methyl)-1-methyl-1H-1,2,3-triazol-4-yl)phenoxy)cyclohexanecarboxylate

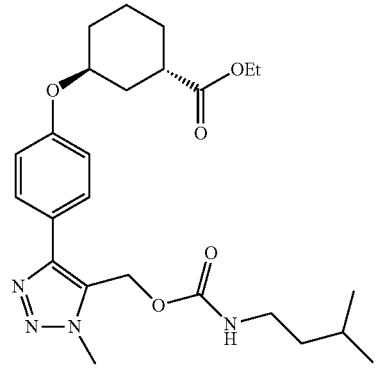 [SMILES: CCOC(=O)[C@H]1CCC[C@H](Oc2ccc(-c3nnn(C)c3COC(=O)NCCC(C)C)cc2)C1]

To a stirred solution of 8G (100 mg, 0.314 mmol), di-tert-butyl azodicarboxylate (217 mg, 0.942 mmol) and Ph₃P (247 mg, 0.942 mmol) in THF (10 mL) under N₂ was added ethyl 3-hydroxycyclohexanecarboxylate (racemic cis isomer; 135 mg, 0.785 mmol) and the reaction mixture was stirred at 60° C. for 16 h under N₂, then was cooled to rt. The reaction mixture was concentrated in vacuo and the crude product was chromatographed (12 g Redisep® SiO₂ column, eluting with 22% EtOAc in n-hexanes) to afford the title compound (90 mg, 60%) as a pale yellow liquid. LC-MS, [M+H]⁺=473.2. ¹H NMR (400 MHz, CD₃OD) δ ppm 7.66 (d, J=9.0 Hz, 2H), 7.09 (d, J=9.0 Hz, 2H), 5.29 (s, 2H), 4.75 (br. s., 1H), 4.20 (s, 3H), 4.13 (q, J=6.4 Hz, 2H), 3.15 (t, J=7.3 Hz, 2H), 2.80-2.90 (m, 1H), 1.60-2.00 (m, 6H), 1.20-1.35 (m, 9H), 0.93 (d, J=6.4 Hz, 6H).

8I (rac)-trans-Ethyl 3-(4-(5-(((isopentyl(methyl)carbamoyl)oxy)methyl)-1-methyl-1H-1,2,3-triazol-4-yl)phenoxy)cyclohexanecarboxylate

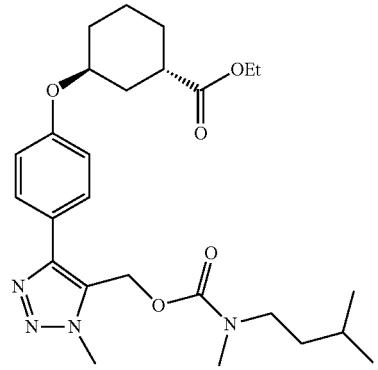 [SMILES: CCOC(=O)[C@H]1CCC[C@H](Oc2ccc(-c3nnn(C)c3COC(=O)N(C)CCC(C)C)cc2)C1]

To a stirred solution of 8H (90 mg, 0.190 mmol) in DMF (3 mL) under N₂ was added NaH (9 mg of a 60% mineral suspension, 0.38 mmol) portionwise at 0° C. and stirred at 0° C. for 30 min. Iodomethane (0.020 mL, 0.29 mmol) was then added and the reaction mixture was allowed to warm to rt & stirred at rt for 1 h. The reaction mixture was diluted with water (30 mL) and extracted with EtOAc (2×25 mL). The combined organic extracts were washed with brine (50 mL), dried (Na$_2$SO$_4$), and filtered. The combined filtrates were concentrated in vacuo. The crude product was purified by combiflash chromatography (12 g Redisep® SiO$_2$ column, eluting with 75% EtOAc in n-hexanes) to afford the title compound (60 mg, 64%) as a pale yellow liquid. LC-MS, [M+H]$^+$=487.2.

Example 8 & Example 9

To a stirred solution of 81 (50 mg, 0.103 mmol) in THF (2 mL) and MeOH (2 mL) mixture was added a solution of LiOH.H$_2$O (7.0 mg, 0.308 mmol) in water (2 mL) and the reaction mixture was stirred at rt for 16 h under N$_2$. The reaction mixture was diluted with water (20 mL) and washed with Et$_2$O (20 mL) to remove non-polar impurities. The aqueous layer was neutralized with aq. HCl (2.0 mL of a 1.5 N solution) and extracted with MeOH in CHCl$_3$ (5% of a 25 mL mixture). The organic layer was washed with brine (25 mL), dried (Na$_2$SO$_4$), filtered, and concentrated in vacuo. The crude product was purified by preparative HPLC (Column: Sunfire C18 (250×30) mm 5 µm; M. Phase A: 10 mM NH$_4$OAc in water; M. Phase B: MeCN, flow rate: 15.0 mL/min; time (min)/% B: 0/30, 8/40) followed by separation of individual enantiomers by chiral SFC. Example 8 (17 mg, 28%) was obtained as a gummy solid. LC-MS, [M+H]$^+$=459.2. OR [α]$^{25.1}_D$=(+)10.0 (c 0.10, MeOH). 1H NMR (400 MHz, CD$_3$OD) δ ppm 7.64-7.70 (m, 2H), 7.09 (d, J=8.8 Hz, 2H), 5.36-5.38 (m, 2H), 4.72-4.75 (m, 1H), 4.21 (s, 3H), 3.23-3.26 (m, 1H), 2.82-2.90 (m, 4H), 2.06-2.11 (m, 1H), 1.92-1.94 (m, 3H), 1.57-1.80 (m, 4H), 1.31-1.45 (m, 4H), 0.82-0.96 (m, 6H). hLPA1 IC$_{50}$=87 nM. Example 9 (14 mg, 24%) was obtained as a gummy solid. LC-MS, [M+H]$^+$=459.2. OR [α]$^{25.1}_D$=(−)2.0 (c 0.10, MeOH). $^1$H NMR (400 MHz, CD$_3$OD) δ ppm 7.64-7.70 (m, 2H), 7.09 (d, J=8.4 Hz, 2H), 5.36-5.38 (m, 2H), 4.72-4.75 (m, 1H), 4.21 (s, 3H), 3.23-3.26 (m, 1H), 2.82-2.90 (m, 4H), 2.06-2.11 (m, 1H), 1.92-1.94 (m, 3H), 1.57-1.80 (m, 4H), 1.31-1.45 (m, 4H), 0.82-0.96 (m, 6H). hLPA1 IC$_{50}$=65 nM.

Example 10

(1S,3S)-3-(4-(1-Methyl-5-(((methyl(2-methylpentan-2-yl)carbamoyl)oxy)methyl)-1H-1,2,3-triazol-4-yl)phenoxy)cyclohexanecarboxylic Acid

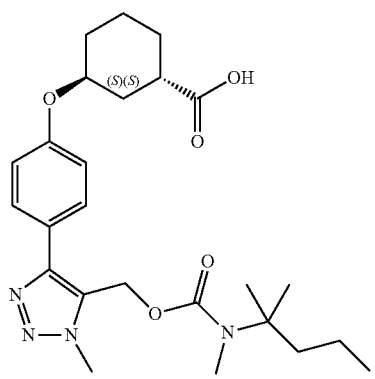

10A 4-(4-(Benzyloxy)phenyl)-1-methyl-1H-1,2,3-triazole-5-carbaldehyde

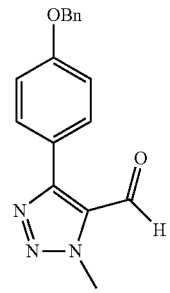 [SMILES: Cn1nnc(-c2ccc(OCc3ccccc3)cc2)c1C=O]

To a stirred mixture of compound 8B (5.5 g, 27.1 mmol) and K$_2$CO$_3$ (5.61 g, 40.6 mmol) in MeCN (60 mL) was added benzyl bromide (3.54 mL, 29.8 mmol) at rt and the reaction mixture was stirred at 70° C. for 3 h under N$_2$, then was cooled to rt. The reaction mixture was filtered through a Celite® pad, which was washed with DCM (200 mL). The combined filtrates was concentrated in vacuo to afford the title compound (7.50 g, 80%) as a pale yellow solid, which was carried onto to the next step without further purification. LC-MS, [M+H]$^+$=294.2. $^1$H NMR (400 MHz, CDCl$_3$) δ ppm 10.06 (s, 1H), 7.71 (d, J=8.8 Hz, 2H), 7.33-7.49 (m, 5H), 7.12 (d, J=8.8 Hz, 2H), 5.15 (s, 2H), 4.37 (s, 3H).

10B (4-(4-(Benzyloxy) phenyl)-1-methyl-1H-1,2,3-triazol-5-yl)methanol

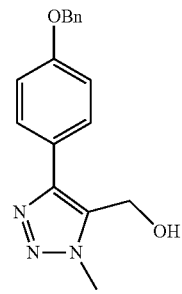 [SMILES: Cn1nnc(-c2ccc(OCc3ccccc3)cc2)c1CO]

To a stirred solution of 10A (8 g, 27.3 mmol) in THF (60 mL) and MeOH (60 mL) was added portionwise NaBH$_4$ (1.14 g, 30.0 mmol) at 0° C. under N$_2$ and the reaction mixture was stirred at rt for 1 h. The reaction mixture was diluted with sat'd. aq. NH$_4$Cl (200 mL) and extracted with EtOAc (2×200 mL). The combined organic extracts were washed with brine (400 mL), dried (Na$_2$SO$_4$), filtered and concentrated in vacuo to afford the title compound (7.0 g, 83%) as a white solid. This crude product was carried on to the next step without further purification. LC-MS, [M+H]$^+$=296.2. $^1$H NMR (300 MHz, CDCl$_3$) δ ppm 7.57 (d, J=9.0 Hz, 2H), 7.47-7.33 (m, 5H), 7.04 (d, J=9.0 Hz, 2H), 5.10 (s, 2H), 4.81 (d, J=4.2 Hz, 2H), 4.08 (s, 3H), 2.77 (t, J=5.4 Hz, 1H).

10C 4-(4-(Benzyloxy) phenyl)-5-(((tert butyldimethylsilyl) oxy) methyl)-1-methyl-1H-1,2,3-triazole

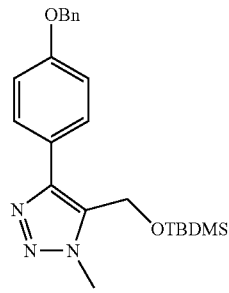 [SMILES: Cn1nnc(-c2ccc(OCc3ccccc3)cc2)c1CO[Si](C)(C)C(C)(C)C]

To a stirred solution of 10B (7 g, 23.70 mmol) and imidazole (4.84 g, 71.1 mmol) in DMF (100 mL) was added TBSCl (4.29 g, 28.4 mmol) and the reaction mixture was stirred at rt for 3 h under $N_2$. The reaction mixture was diluted with water (200 mL) and extracted with EtOAc (2×200 mL). The combined organic extracts were washed with brine (400 mL), dried ($Na_2SO_4$), filtered and concentrated in vacuo to afford the title compound (8.0 g, 77%) as a pale yellow solid. This crude product 10c was used in the next step without further purification. LC-MS, $[M+H]^+$ =410.2. $^1$H NMR (300 MHz, $CDCl_3$) δ ppm 8.03 (s, 1H), 7.61 (d, J=9.0 Hz, 2H), 7.33-7.50 (m, 5H), 7.12 (d, J=9.0 Hz, 2H), 5.11 (s, 2H), 4.81 (s, 2H), 4.13 (s, 3H), 0.91 (s, 9H), 0.07 (s, 6H).

10D 4-(5-(((tert-Butyldimethylsilyl) oxy) methyl)-1-methyl-1H-1,2,3-triazol-4-yl)phenol

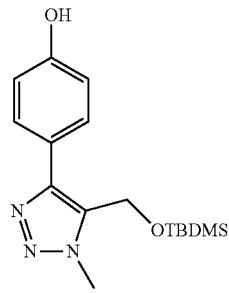 [SMILES: Cn1nnc(-c2ccc(O)cc2)c1CO[Si](C)(C)C(C)(C)C]

To a degassed ($N_2$ was bubbled in for 10 min) solution of 10C (8.0 g, 19.53 mmol) in MeOH (150 mL) was added 10% Pd/C (1 g, 0.940 mmol) at rt. The reaction mixture was degassed with $H_2$ for 5 min. then was stirred at rt under 1 atm of $H_2$ for 5 h, then the $H_2$ atmosphere was evacuated and replaced with $N_2$. The reaction mixture was filtered through a Celite® pad and washed with MeOH (200 mL). The combined filtrates was concentration in vacuo to afford the title compound (5.0 g, 76%) as a white solid.

This crude product 10D was used in the next step without further purification. LC-MS, $[M+H]^+$=320.2.

10E (rac)-trans-Ethyl 3-(4-(5-(((tert-butyldimethylsilyl) oxy)methyl)-1-methyl-1H-1,2,3-triazol-4-yl) phenoxy)cyclohexanecarboxylate

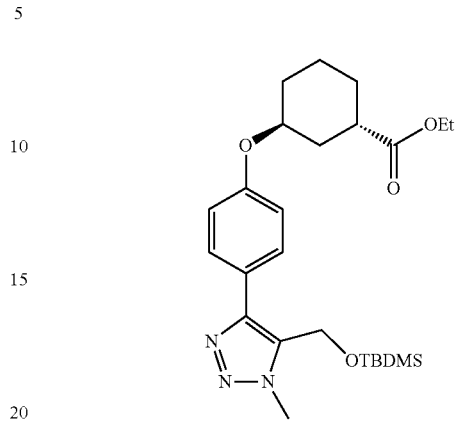

To a stirred solution of 10D (2.75 g, 8.61 mmol), di-tert-butyl azodicarboxylate (7.93 g, 34.4 mmol) and $Ph_3P$ (9.03 g, 34.4 mmol) in THF (80 mL) was added (rac)-cis-ethyl 3-hydroxycyclohexanecarboxylate (5.93 g, 34.4 mmol) and the reaction mixture was stirred at 60° C. for 16 h under $N_2$, then was cooled to rt. The reaction mixture was concentrated in vacuo. The crude product was chromatographed (120 g Redisep® $SiO_2$ column, eluting with 40% EtOAc in n-hexanes) to afford the title compound (2.7 g, 65%) as a colorless liquid. LC-MS, $[M+H]^+$=474.2.

10F (1S,3S)-ethyl 3-(4-(5-(hydroxymethyl)-1-methyl-1H-1,2,3-triazol-4-yl)phenoxy)cyclohexanecarboxylate

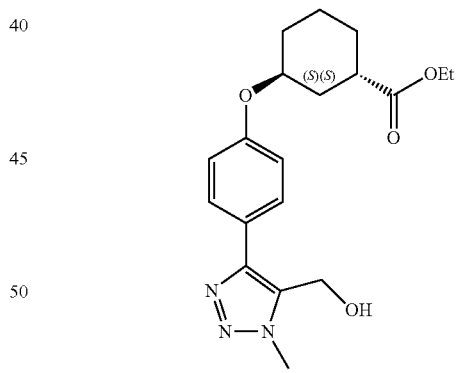

To a stirred solution 10E (200 mg, 0.211 mmol) in THF (6 mL) was added TBAF (0.317 mL of a 1M solution in THF; 0.317 mmol) at 0° C. and the reaction mixture was stirred at rt under $N_2$ for 30 min. The reaction mixture was diluted with water (25 mL) and extracted with EtOAc (2×25 mL). The combined organic extracts were washed with brine (40 mL), dried ($Na_2SO_4$), filtered and concentrated in vacuo. The crude product was chromatographed (12 g Redisep® $SiO_2$ column, eluting with 75% EtOAc in n-hexanes). The racemic product thus obtained was separated by chiral SFC (Luxcellulose-2 (250×21.5) mm, 5 μm; % $CO_2$: 70%; % Co-solvent: 30% (0.25% DEA in MeOH); Total Flow: 70 g/min; Back Pressure: 100 bars; Temperature: 35° C.; UV:

230 nm). The desired S,S enantiomer 10F was isolated (40 mg, 50%) as an off-white solid: LC-MS, [M+H]$^+$=360.2. Optical rotation [α]$^{25.2}_D$=(+)30 (c 0.10, MeOH). $^1$H NMR (400 MHz, CD$_3$OD) δ ppm 7.63 (d, J=8.4 Hz, 2H), 7.09 (d, J=8.4 Hz, 2H), 4.79 (s, 2H), 4.72-4.76 (m, 1H), 4.18 (s, 3H), 4.16 (q, J=7.0 Hz, 2H), 2.80-2.88 (m, 1H), 2.03-2.11 (m, 1H), 1.88-1.98 (m, 3H), 1.57-1.82 (m, 4H), 1.25-1.30 (m, 3H).

10G (1S,3S)-Ethyl-3-(4-(1-methyl-5-((((2-methyl-pentan-2-yl) carbamoyl)oxy)methyl)-1H-1,2,3-tri-azol-4-yl)phenoxy)cyclohexanecarboxylate

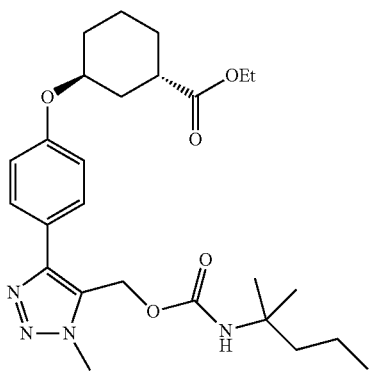 [SMILES: CCCC(C)(C)NC(=O)OCc1c(-c2ccc(O[C@H]3CCC[C@H](C(=O)OCC)C3)cc2)nnn1C]

To a solution of 10F (50 mg, 0.14 mmol), 2,2-dimethyl-pentanoic acid (18 mg, 0.139 mmol) and Et$_3$N (0.029 mL, 0.21 mmol) in toluene (3 mL) was added Ph$_2$PON$_3$ (0.036 mL, 0.167 mmol) and the resultant pale yellow solution was stirred at 110° C. for 16 h under N$_2$, then was cooled to rt. The reaction mixture was concentrated in vacuo and the crude product was chromatographed (12 g Redisep® SiO$_2$ column, eluting with 50% EtOAc in n-hexanes) to afford the title compound (40 mg, 50%) as a white solid. LC-MS, [M+H]$^+$=487.2. $^1$H NMR (400 MHz, CD$_3$OD) δ ppm 7.65 (d, J=9.2 Hz, 2H), 7.08 (d, J=9.2 Hz, 2H), 5.24 (s, 2H), 4.75 (br. s., 1H), 4.19 (s, 3H), 4.16 (q, J=7.2 Hz, 2H), 3.15 (s, 1H), 2.86 (d, J=11.0 Hz, 2H), 2.07 (br. s., 1H), 1.89-1.99 (m, 3H), 1.60-1.80 (m, 4H), 1.20-1.40 (m, 8H), 0.95-0.88 (m, 6H).

10H (1S,3S)-Ethyl 3-(4-(1-methyl-5-(((methyl(2-methylpentan-2-yl)carbamoyl)oxy)methyl)-1H-1,2,3-triazol-4-yl)phenoxy)cyclohexanecarboxylate

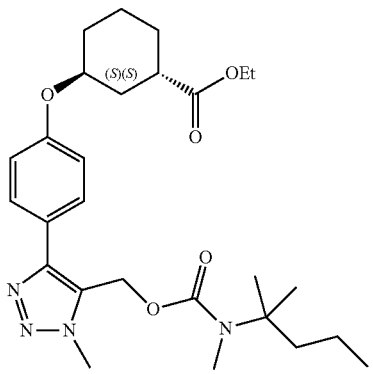

To a stirred solution of 10G (40.0 mg, 0.082 mmol) in DMF (3 mL) under N$_2$ was added NaH (4 mg of a 60% mineral suspension, 0.16 mmol) portionwise at 0° C. and stirred for 30 min. Iodomethane (7.71 µl, 0.123 mmol) was then added and the reaction mixture was stirred at rt for 1 h, then was diluted with water (20 mL). The mixture was extracted with EtOAc (2×20 mL) and the combined organic extracts were washed with brine (25 mL), dried (Na$_2$SO$_4$), filtered and concentrated in vacuo. The crude product was chromatographed (12 g Redisep® SiO$_2$ column, eluting with 75% EtOAc in n-hexanes) to afford the title compound (30 mg, 73%) as a pale yellow liquid. LC-MS, [M+H]$^+$=501.2.

Example 10

To a stirred solution of 10H (30.0 mg, 0.060 mmol) in THF (1.5 mL) and MeOH (1.5 mL) was added a solution of LiOH.H$_2$O (4.3 mg, 0.18 mmol) in water (1.5 mL) and the reaction mixture was stirred at rt for 16 h under N$_2$. The reaction mixture was diluted with water (20 mL) and washed with Et$_2$O (20 mL) to remove traces of nonpolar impurities. The aqueous layer was neutralized with aq. HCl (2.0 mL of a 1.5 N solution) and extracted with 5% MeOH in CHCl$_3$ (25 mL). The organic layer was washed with brine (25 mL), dried (Na$_2$SO$_4$), filtered and concentrated in vacuo. The residual crude product was purified by preparative HPLC (Kinetex Biphenyl 100A (2500×21.1) mm 5 µm; Mobile Phase A: 0.1% HCO$_2$H in water; Mobile Phase B: MeCN, flow rate: 18.0 mL/min; time (min)/% B: 0/40, 32/75, 35/95) to afford the title compound (8 mg, 28%) as a white solid. LC-MS, [M+H]$^+$=473.2. $^1$H NMR (400 MHz, CD$_3$OD) δ ppm 7.63 (d, J=8.80 Hz, 2H), 7.07 (d, J=8.80 Hz, 2H), 5.31 (s, 2H), 4.83-4.89 (m, 1H), 4.18 (s, 3H), 2.85 (s, 3H), 2.72-2.76 (m, 1H), 2.06-2.10 (m, 1H), 1.82-1.95 (m, 3H), 1.40-1.77 (m, 6H), 1.29 (s, 6H), 1.11-1.24 (m, 2H), 0.08-0.84 (m, 3H). hLPA1 IC$_{50}$=23 nM.

Example 11

(rac)-3-((6-(5-(((cyclobutylmethyl)(methyl)carbam-oyl)oxy)methyl)-1-methyl-1H-1,2,3-triazol-4-yl)-2-methylpyridin-3-yl)oxy)-1-fluorocyclohexane-1-carboxylic Acid

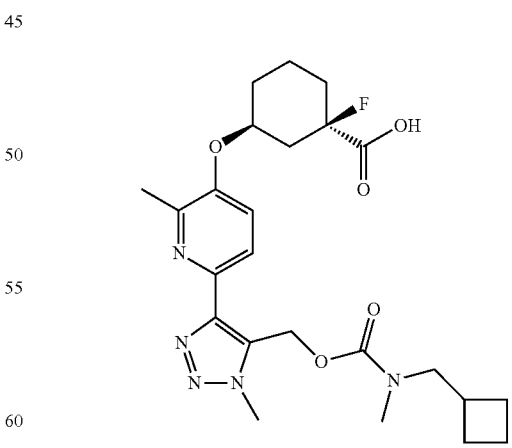

Example 11 was prepared according to the procedure of Example 2 by using Intermediate 1 instead of (1S,3R)-isopropyl 3-hydroxy-cyclohexanecarboxylate in the procedure (Mitsunobu reaction) to synthesize Example 2F. $^1$H NMR (400 MHz, CDCl$_3$) δ 8.15 (d, J=8.8 Hz, 1H), 8.00-

7.89 (m, 1H), 5.53-5.32 (m, 2H), 5.00 (br. s., 1H), 4.21 (d, J=2.4 Hz, 3H), 3.32 (dd, J=10.8, 7.5 Hz, 2H), 2.92 (d, J=13.6 Hz, 3H), 2.75 (d, J=2.6 Hz, 3H), 2.55 (dt, J=15.5, 7.8 Hz, 1H), 2.47-2.27 (m, 1H), 2.24-1.77 (m, 10H), 1.76-1.58 (m, 3H); $^{19}$F NMR (377 MHz, CDCl$_3$) δ −76.0 (s, F from TFA), −154.4 (s, 1F). LC-MS, [M+H]$^+$=490.4. hLPA1 IC$_{50}$=12 nM.

Example 12 (1S,3S)-3-(4-(5-(1-(((cyclobutylmethyl)(methyl)carbamoyl)oxy)ethyl)-1-methyl-1H-1,2,3-triazol-4-yl)phenoxy)cyclohexane-1-carboxylic Acid (Diastereomeric Mixture)

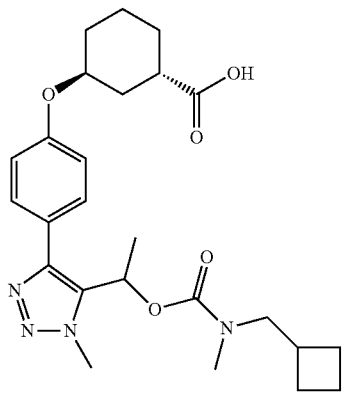 [SMILES: CC(OC(=O)N(C)CC1CCC1)c1c(-c2ccc(O[C@H]3CCC[C@H](C(=O)O)C3)cc2)nnn1C]

12A 1-(4-(4-((tert-butyldimethylsilyl)oxy)phenyl)-1-methyl-1H-1,2,3-triazol-5-yl)ethan-1-ol

To a −40° C. solution of 8C (279 mg, 0.879 mmol) in THF (18 mL) was added CH$_3$MgBr (439 μL of a 3 M solution in THF, 1.32 mmol). The reaction mixture was allowed to warm to rt and stirred at rt for 1 h. Water (15 mL) was added and the mixture was extracted with EtOAc (2×30 mL). The combined organic extracts were concentrated in vacuo and chromatographed (SiO$_2$; continuous gradient from 0% to 100% EtOAc in Hexanes, 20 min) to give 12A (230 mg, 78%) as an oil. $^1$H NMR (400 MHz, CDCl$_3$) δ 7.42 (d, J=8.8 Hz, 2H), 6.91 (d, J=8.8 Hz, 2H), 5.33 (dd, J=6.8, 3.5 Hz, 1H), 4.23 (s, 3H), 1.96 (d, J=3.3 Hz, 1H), 1.64 (d, J=6.8 Hz, 3H), 1.00 (s, 9H), 0.22 (s, 6H)

Example 12 was prepared according to the procedure for the synthesis of Example 8 by using 12A instead of 8D. $^1$H NMR (500 MHz, DMSO-d$_6$) δ 7.57 (br. s., 2H), 7.06 (d, J=6.6 Hz, 2H), 6.19-5.87 (m, 1H), 4.69 (br. s., 1H), 4.13 (d, J=5.6 Hz, 3H), 3.21-3.09 (m, 2H), 2.76 (d, J=15.7 Hz, 3H), 2.45-2.37 (m, 1H), 2.01-1.45 (m, 18H). LC-MS, [M+H]$^+$= 471.0. hLPA1 IC$_{50}$=384 nM.

Example 13

3-((6-(5-((((cyclobutylmethyl)(methyl)carbamoyl)oxy)methyl)-1-methyl-1H-1,2,3-triazol-4-yl)-2-methylpyridin-3-yl)oxy)-1-fluorocyclohexane-1-carboxylic Acid (Single Enantiomer)

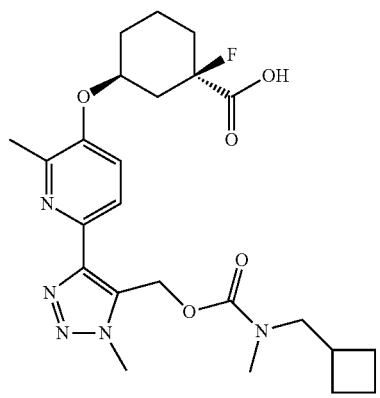 [SMILES: Cc1nc(-c2nnn(C)c2COC(=O)N(C)CC2CCC2)ccc1O[C@H]1CCC[C@](F)(C(=O)O)C1]

Example 13 was subjected to chiral SFC (Column: Chiralpak IC, 21×250 mm, 5 micron Mobile Phase: 40% MeOH/60% CO$_2$ Flow Conditions: 45 mL/min, 150 Bar, 40° C. Detector Wavelength: 254 nm Injection Details: 0.5 mL of 5 mg/mL solution in MeOH) to afford Example 13. $^1$H NMR (500 MHz, CDCl$_3$) δ 8.11-7.96 (m, 1H), 7.29 (d, J=8.5 Hz, 1H), 5.75 (d, J=9.6 Hz, 2H), 4.79 (d, J=3.3 Hz, 1H), 4.15 (d, J=7.7 Hz, 3H), 3.38-3.11 (m, 2H), 2.93-2.75 (m, 3H), 2.65-2.51 (m, 1H), 2.25 (br. s., 1H), 2.10-1.47 (m, 7H). LC-MS, [M+H]$^+$=490.4. hLPA1 IC$_{50}$=95 nM.

Example 14

(4-(5-(((1S,3S)-3-carbamoylcyclohexyl)oxy)-6-methylpyridin-2-yl)-1-methyl-1H-1,2,3-triazol-5-yl)methyl (cyclobutylmethyl)(methyl)carbamate

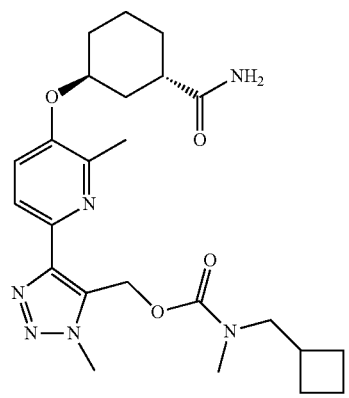 [SMILES: Cc1nc(-c2nnn(C)c2COC(=O)N(C)CC2CCC2)ccc1O[C@H]1CCC[C@H](C(N)=O)C1]

To a solution of Example 2 (100 mg, 0.21 mmol) and DMF (0.8 μL, 11 μmol) in CH$_2$Cl$_2$ (2 mL) was slowly added oxalyl chloride (0.21 mL, 0.42 mmol); the mixture was stirred at rt for 30 min. The mixture was concentrated in vacuo to give the acid chloride. To the acid chloride in CH$_2$Cl$_2$ (1.0 mL) was added ammonia (6.36 mL of a 0.5 N solution in dioxane, 3.18 mmol). The mixture was stirred at rt for 30 min, then was concentrated in vacuo. The residual crude product was chromatographed (SiO$_2$; 12 g; A=DCM, B=EtOAc; 12 min gradient from 0% B to 100% B; flow rate=30 mL/min) to afford the title compound (77 mg, 0.17 mmol, 89% yield) as a white solid. LCMS, [M+H]$^+$=471.2. $^1$H NMR (500 MHz, DMSO-d$_6$) [rotamer, ratio 53:47] [major rotamer-underline; minor rotamer~Italic]: 8 ppm 7.81 (d, J=8.5 Hz, 1H), 7.45 (d, J=8.6 Hz, 1H), 7.35 (s, 1H), 6.72 (s, 1H), 5.62 (s, 2H), 5.59 (s, 2H), 4.81 (br-s, 1H), 4.08 (br-s, 3H), 3.21 (br-s, 2H), 3.08 (br-s, 2H), 2.77-2.65 (m, 4H), 2.55 (s, 3H), 2.43 (s, 3H), 2.37-1.36 (m, 12H). HPLC-6: RT=1.36 min, purity=98%. hLPA1 IC$_{50}$=824 nM.

Example 15

(4-(5-(((1S,3S)-3-cyanocyclohexyl)oxy)-6-methyl-pyridin-2-yl)-1-methyl-1H-1,2,3-triazol-5-yl)methyl (cyclobutylmethyl)(methyl)carbamate

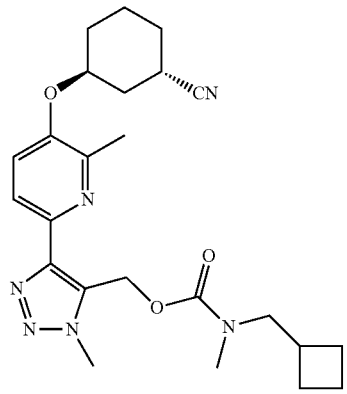 [SMILES: Cc1nc(-c2nnn(C)c2COC(=O)N(C)CC2CCC2)ccc1O[C@H]1CCC[C@H](C#N)C1]

A mixture of Example 14 (90 mg, 0.19 mmol) and Burgess reagent (137 mg, 0.57 mmol) in DCM (1 mL) and THF (1 mL) was stirred at rt for 48 h, then was concentrated in vacuo. The residue was chromatographed (SiO$_2$; 12 g; A=DCM, B=EtOAc; 12 min gradient from 0% B to 100% B; flow rate=30 mL/min) to afford the title compound (85 mg, 0.18 mmol, 95% yield) as a white solid. LCMS, [M+H]$^+$=453.0. $^1$H NMR (500 MHz, DMSO-d$_6$) [rotamer, ratio 53:47] [major rotamer~underline; minor rotamer-Italic]: δ ppm 7.83 (d, J=8.5 Hz, 1H), 7.47 (d, J=8.7 Hz, 1H), 5.62 (s, 2H), 5.58 (s, 2H), 4.71 (s, 1H), 4.08 (br-s, 3H), 3.22 (br-s, 2H), 3.08 (br-s, 2H), 2.77-2.65 (m, 4H), 2.55 (s, 3H), 2.40 (s, 3H), 2.34-1.34 (m, 12H). HPLC-6: RT=1.68 min, purity=97%. hLPA1 IC$_{50}$=3750 nM.

Example 16

(4-(5-(((1S,3 S)-3-(1H-tetrazol-5-yl)cyclohexyl)oxy)-6-methylpyridin-2-yl)-1-methyl-1H-1,2,3-triazol-5-yl)methyl (cyclobutylmethyl)(methyl)carbamate

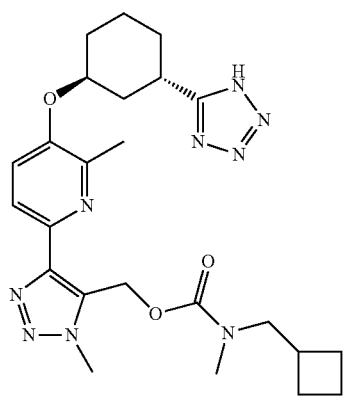 [SMILES: Cc1nc(-c2nnn(C)c2COC(=O)N(C)CC2CCC2)ccc1O[C@H]1CCC[C@H](c2nnn[nH]2)C1]

A mixture of Example 15 (69 mg, 0.15 mmol), TEA (0.32 mL, 2.3 mmol), NaN$_3$ (149 mg, 2.3 mmol) and HOAc (0.13 mL, 2.3 mmol) in toluene (1.0 mL) in a sealed tube was stirred at 100° C. for 18 h, then was cooled to rt. The mixture was diluted with EtOAc (5 mL), quenched with sat'd. aq. NaHCO$_3$ (3 mL). The mixture was extracted with EtOAc (5×5 mL). The combined organic extracts were dried (MgSO$_4$), filtered, and concentrated in vacuo. The crude material was purified by preparative LC/MS using the following conditions: Column: XBridge C18, 19×200 mm, 5-µm particles; Mobile Phase A: 5:95 MeCN: water with 10 mM NH$_4$OAc; Mobile Phase B: 95:5 MeCN: water with 10 mM NH$_4$OAc; Gradient: 10-60% B over 20 min, then a 5-min hold at 100% B; Flow: 20 mL/min. Fractions containing the desired product were combined and dried via centrifugal evaporation to afford the title compound (54 mg, 70% yield) as a white solid. LCMS, [M+H]$^+$=496.0. $^1$H NMR (500 MHz, DMSO-d$_6$) [rotamer, ratio 53:47] [major rotamer~underline; minor rotamer—Italic]: δ ppm 7.82 (d, J=8.5 Hz, 1H), 7.49 (d, J=8.6 Hz, 1H), 5.61 (s, 2H), 5.57 (s, 2H), 4.88 (s, 1H), 4.07 (br-s, 3H), 3.37 (m, 1H), 3.20 (br-s, 2H), 3.06 (br-s, 2H), 2.76-2.65 (m, 3H), 2.54 (s, 3H), 2.44 (s, 3H), 2.37-1.33 (m, 12H). HPLC-6: RT=1.50 min, purity=96%. hLPA1 IC$_{50}$=22 nM.

Example 17

(1-methyl-4-(6-methyl-5-(((1S,3S)-3-((methylsulfonyl)carbamoyl)cyclohexyl)oxy)pyridin-2-yl)-1H-1,2,3-triazol-5-yl)methyl (cyclobutylmethyl)(methyl)carbamate

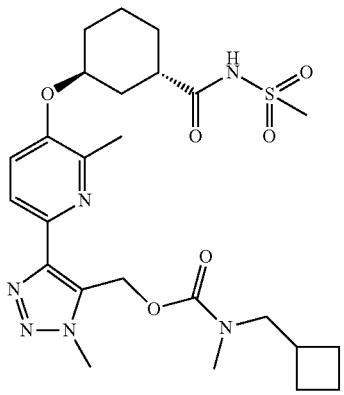 [SMILES: Cc1nc(-c2nnn(C)c2COC(=O)N(C)CC2CCC2)ccc1O[C@H]1CCC[C@H](C(=O)NS(C)(=O)=O)C1]

To a clear solution of Example 2 (15 mg, 0.032 mmol) and methanesulfonamide (5 mg, 0.048 mmol) and DMAP (6 mg, 0.048 mmol) in DMF (0.2 mL) and DCM (1 mL) was added EDC (9.4 mg, 0.048 mmol). The mixture was stirred at rt for 62 h, then was diluted with water (2 mL) and DCM (5 mL). The organic layer was washed with brine (5 mL), dried (MgSO$_4$) and concentrated in vacuo to afford a white solid, which was purified via preparative LC/MS with the following conditions: Column: XBridge C18, 19×200 mm, 5 m particles; Mobile Phase A: 5:95 MeCN: water with 10 mM NH$_4$OAc; Mobile Phase B: 95:5 MeCN: water with 10 mM NH$_4$OAc; Gradient: 20-70% B over 20 min, then a 3-min hold at 100% B; Flow: 20 mL/min. Fractions containing the desired product were combined and dried via centrifugal evaporation to afford the title compound (14 mg, 78% yield) as a white solid. LCMS, [M+H]$^+$=549.3. $^1$H NMR (500 MHz, DMSO-d$_6$) [rotamer, ratio 53:47] [major~underlined; minor~Italic]: δ ppm 7.82 (d, J=8.6 Hz, 1H), 7.46 (d, J=8.6 Hz, 1H), 5.62 (s, 2H), 5.58 (s, 2H), 4.85 (s, 1H), 4.08 (br-s, 3H), 3.60 (m, 1H), 3.24-3.08 (m, 2H), 2.79-2.67 (m, 4H), 2.54 (s, 6H), 2.44 (s, 3H), 2.35-1.35 (m, 12H). HPLC-6: RT=1.56 min, purity=97%. hLPA1 IC$_{50}$=352 nM.

TABLE 1

| Example | Structure & Name | Analytical & Biology Data | Method |
|---|---|---|---|
| 18 | (rac)-3-((6-(5-(((cyclopentyl(methyl)carbamoyl)oxy)methyl)-1-methyl-1H-1,2,3-triazol-4-yl)pyridin-3-yl)oxy)cyclohexane-1-carboxylic acid | LCMS, [M + H]$^+$ = 458.3. $^1$H NMR (500 MHz, CD$_3$CN) δ 8.26 (dd, J = 3.0, 0.6 Hz, 1H), 8.00-7.96 (m, 1H), 7.38 (dd, J = 8.8, 2.8 Hz, 1H), 5.58 (s, 2H), 4.70 (br. s., 1H), 4.03 (s, 3H), 2.79-2.69 (m, 1H), 2.64 (br. s., 3H), 2.01-1.93 (m, 2H), 1.84-1.73 (m, 3H), 1.71-1.49 (m, 8H), 1.48-1.36 (m, 4H) hLPA1 IC$_{50}$ = 21 nM. | Example 2 |
| 19 |  | LCMS, [M + H]$^+$ = 508.2 $^1$H NMR (500 MHz, DMSO-d$_6$) δ 7.83 (br d, J = 8.5 Hz, 1H), 7.46 (d, J = 8.6 Hz, 1H), 7.38-6.97 (m, 5H), 5.68 (br s, 2H), 5.36 (br s, 1H), 5.10 (br s, 1H), 4.76 (br s, 1H), 4.14-3.98 (m, 2H), 3.69 (br d, J = 7.7 Hz, 1H), 2.63-2.55 (m, 2H), 2.49-2.44 (m, 1H), 2.38 (br s, 3H), 1.99 (br d, J = 14.4 Hz, 1H), 1.87-1.70 (m, 3H), 1.67-1.28 (m, 7H) hLPA1 IC$_{50}$ = 17 nM | Example 3 |

TABLE 1-continued

| Example | Structure & Name | Analytical & Biology Data | Method |
|---|---|---|---|
| | (1S,3S)-3-((2-methyl-6-(1-methyl-5-(((methyl((R)-1-phenylethyl)carbamoyl)oxy)methyl)-1H-1,2,3-triazol-4-yl)pyridin-3-yl)oxy)cyclohexane-1-carboxylic acid | | |
| 20 | (1S,3S)-3-((6-(5-((((1-cyclobutylethyl)(methyl)carbamoyl)oxy)methyl)-1-methyl-1H-1,2,3-triazol-4-yl)-2-methylpyridin-3-yl)oxy)cyclohexane-1-carboxylic acid (diastereomeric mixture) | LCMS, [M + H]$^+$ = 486.2. $^1$H NMR (500 MHz, DMSO-d$_6$) δ 7.83 (br d, J = 8.3 Hz, 1H), 7.48 (br d, J = 8.6 Hz, 1H), 5.85-5.43 (m, 2H), 4.77 (br s, 1H), 4.28-3.96 (m, 3H), 2.55 (s, 6H), 2.42 (br d, J = 8.6 Hz, 3H), 1.97 (br s, 1H), 1.87-1.17 (m, 13H), 1.00-0.75 (m, 3H) hLPA1 IC$_{50}$ = 28 nM. | Example 1 |
| 21 | (1S,3S)-3-((6-(1-methyl-5-(((methyl((R)-1-phenylethyl)carbamoyl)oxy)methyl)-1H-1,2,3-triazol-4-yl)pyridin-3-yl)oxy)cyclohexane-1-carboxylic acid | LCMS, [M + H]$^+$ = 494.4 $^1$H NMR (500 MHz, DMSO-d$_6$) δ 8.43-8.29 (m, 1H), 8.07-7.94 (m, 1H), 7.66-7.51 (m, 1H), 7.42-7.04 (m, 5H), 5.78-5.57 (m, 2H), 5.45-5.03 (m, 1H), 4.87-4.73 (m, 1H), 4.22-3.95 (m, 3H), 2.74-2.63 (m, 1H), 2.60-2.56 (m, 3H), 2.00-1.91 (m, 1H), 1.90-1.71 (m, 3H), 1.70-1.59 (m, 2H), 1.57-1.33 (m, 5H) hLPA1 IC$_{50}$ = 21 nM. | Example 1 |

TABLE 1-continued

| Example | Structure & Name | Analytical & Biology Data | Method |
|---|---|---|---|
| 22 | (1S,3S)-3-((6-(5-((((benzyl(methyl)carbamoyl)oxy)methyl)-1-methyl-1H-1,2,3-triazol-4-yl)pyridin-3-yl)oxy)cyclohexane-1-carboxylic acid | LCMS, [M + H]$^+$ = 480.1.<br>$^1$H NMR (500 MHz, DMSO-d$_6$) δ 8.34 (br. s., 1H), 8.01 (d, J = 8.5 Hz, 1H), 7.55 (d, J = 7.0 Hz, 1H), 7.41-6.96 (m, 5H), 5.77-5.56 (m, 2H), 4.78 (br. s., 1H), 4.50-4.25 (m, 2H), 4.18-3.91 (m, 3H), 3.50 (br. s., 1H), 2.84-2.62 (m, 3H), 2.02-1.74 (m, 4H), 1.71-1.45 (m, 4H)<br>hLPA1 IC$_{50}$ = 18 nM. | Example 1 |
| 23 | (1S,3S)-3-((6-(5-(((((cyclobutylmethyl)(methyl)carbamoyl)oxy)methyl)-1-methyl-1H-1,2,3-triazol-4-yl)pyridin-3-yl)oxy)cyclohexane-1-carboxylic acid | LCMS, [M + H]$^+$ = 458.3<br>$^1$H NMR (500 MHz, DMSO-d$_6$) δ 8.35 (br. s., 1H), 7.99 (d, J = 8.5 Hz, 1H), 7.57 (d, J = 7.6 Hz, 1H), 5.62 (d, J = 19.2 Hz, 2H), 4.77 (br. s., 1H), 4.11 (d, J = 6.1 Hz, 3H), 3.56-3.41 (m, 1H), 3.28-3.04 (m, 2H), 2.80-2.67 (m, 3H), 2.02-1.40 (m, 15H)<br>hLPA1 IC$_{50}$ = 12 nM. | Example 1 |
| 24 | | LCMS, [M + H]$^+$ = 460.3<br>$^1$H NMR (500 MHz, DMSO-d$_6$) δ 8.44-8.29 (m, 1H), 8.07-7.95 (m, 1H), 7.55 (br d, J = 7.3 Hz, 1H), 5.73-5.52 (m, 2H), 4.78 (br s, 1H), 4.20-4.03 (m, 3H), 2.70-2.59 (m, 2H), 1.99-1.71 (m, 6H), 1.68-1.49 (m, 4H), 1.43-1.09 (m, 4H), 1.06-0.78 (m, 6H), 0.82-0.58 (m, 1H)<br>hLPA1 IC$_{50}$ = 47 nM. | Example 1 |

TABLE 1-continued

| Example | Structure & Name | Analytical & Biology Data | Method |
|---|---|---|---|
| | (1S,3S)-3-((6-(1-methyl-5-(((methyl(pentan-2-yl)carbamoyl)oxy)methyl)-1H-1,2,3-triazol-4-yl)pyridin-3-yl)oxy)cyclohexane-1-carboxylic acid (diastereomeric mixture) | | |
| 25 | (1S,3S)-3-((6-(5-(((((R)-1-cyclopropylethyl)(methyl)carbamoyl)oxy)methyl)-1-methyl-1H-1,2,3-triazol-4-yl)pyridin-3-yl)oxy)cyclohexane-1-carboxylic acid | LCMS, [M + H]$^+$ = 458.3<br>$^1$H NMR (400 MHz, CD$_3$CN) δ 8.24 (br. s., 1H), 8.12 (d, J = 8.1 Hz, 1H), 7.93 (dd, J = 9.1, 2.5 Hz, 1H), 5.17 (br. s., 2H), 4.80-4.59 (m, 1H), 3.97 (d, J = 15.8 Hz, 3H), 3.31-3.07 (m, 1H), 2.72-2.54 (m, 4H), 2.02-1.76 (m, 3H), 1.70-1.33 (m, 5H), 1.09-0.87 (m, 3H), 0.84-0.65 (m, 1H), 0.46-0.13 (m, 4H)<br>hLPA1 IC$_{50}$ = 20 nM. | Example 3 |
| 26 | (1S,3S)-3-(4-(5-(((benzyl(methyl)carbamoyl)oxy)methyl)-1-methyl-1H-1,2,3-triazol-4-yl)-2-fluorophenoxy)cyclohexane-1-carboxylic acid | LCMS, [M + H]$^+$ = 497.3<br>$^1$H NMR (500 MHz, DMSO-d$_6$) δ 7.73-7.41 (m, 2H), 7.38-6.98 (m, 6H), 5.43-5.26 (m, 2H), 4.72 (br. s., 1H), 4.39 (d, J = 8.9 Hz, 2H), 4.20-3.95 (m, 3H), 3.67-3.42 (m, 3H), 2.69-2.60 (m, 1H), 1.96 (br. s., 1H), 1.82 (t, J = 11.1 Hz, 3H), 1.69-1.45 (m, 5H)<br>hLPA1 IC$_{50}$ = 34 nM.<br>LCMS, [M + H]+ =475.1 | Example 1 |

TABLE 1-continued

| Example | Structure & Name | Analytical & Biology Data | Method |
|---|---|---|---|
| 27 | 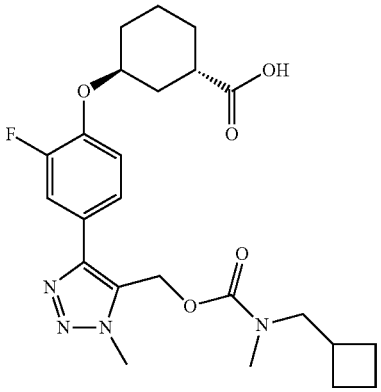 [SMILES: CN(CC1CCC1)C(=O)OCc1c(-c2ccc(O[C@H]3CCC[C@H](C(=O)O)C3)c(F)c2)nnn1C]<br>(1S,3S)-3-(4-(5-(((((cyclobutylmethyl)(methyl)carbamoyl)oxy)methyl)-1-methyl-1H-1,2,3-triazol-4-yl)-2-fluorophenoxy)cyclohexane-1-carboxylic acid | LCMS, [M + H]$^+$ = 475.1<br>$^1$H NMR (500 MHz, DMSO-d$_6$) δ 7.70-7.48 (m, 2H), 7.33 (t, J = 8.7 Hz, 1H), 5.32 (d, J = 7.9 Hz, 2H), 4.75 (br. s., 1H), 4.12 (br. s., 3H), 3.65-3.44 (m, 4H), 3.26-3.07 (m, 2H), 2.69-2.60 (m, 1H), 2.01-1.41 (m, 14H)<br>hLPA1 IC$_{50}$ = 14 nM. | Example 1 |
| 28 | 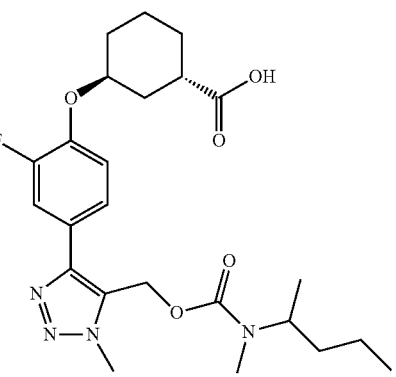<br>(1S,3S)-3-(2-fluoro-4-(1-methyl-5-(((methyl(pentan-2-yl)carbamoyl)oxy)methyl)-1H-1,2,3-triazol-4-yl)phenoxy)cyclohexane-1-carboxylic acid (diastereomeric mixture) | LCMS, [M + H]$^+$ = 477.1<br>$^1$H NMR (500 MHz, DMSO-d$_6$) δ 7.70-7.43 (m, 2H), 7.32 (br t, J = 8.5 Hz, 1H), 5.33 (br s, 2H), 4.75 (br s, 1H), 4.12 (s, 3H), 3.90 (br s, 1H), 3.52 (br d, J = 16.5 Hz, 2H), 2.71-2.59 (m, 2H), 1.97 (br s, 1H), 1.88-1.76 (m, 3H), 1.71-1.45 (m, 4H), 1.43-1.18 (m, 2H), 1.14-0.91 (m, 5H), 0.82 (br t, J = 6.9 Hz, 2H), 0.76-0.66 (m, 1H)<br>hLPA1 IC$_{50}$ = 25 nM. | Example 1 |
| 29 | 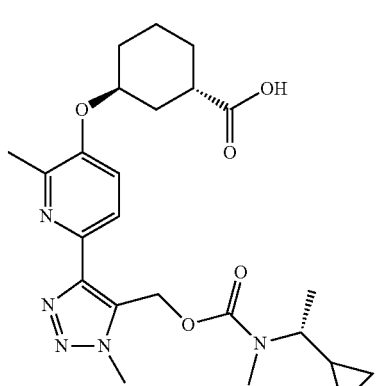<br>(1S,3S)-3-((6-(5-(((((R)-1-cyclopropylethyl)(methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 472.1<br>$^1$H NMR (500 MHz, DMSO-d$_6$) δ 7.69 (d, J = 8.2 Hz, 1H), 7.33 (d, J = 8.2 Hz, 1H), 5.74-5.34 (m, 2H), 4.64 (br. s., 1H), 3.95 (s, 3H), 3.27 (br. s., 1H), 2.67-2.44 (m, 4H), 2.27 (s, 3H), 1.88 (d, J = 14.0 Hz, 1H), 1.79-1.59 (m, 3H), 1.56-1.27 (m, 4H), 1.05-0.63 (m, 4H), 0.44--0.39 (m, 4H)<br>hLPA1 IC$_{50}$ = 41 nM. | Example 3 |

TABLE 1-continued

| Example | Structure & Name | Analytical & Biology Data | Method |
|---|---|---|---|
| 30 | 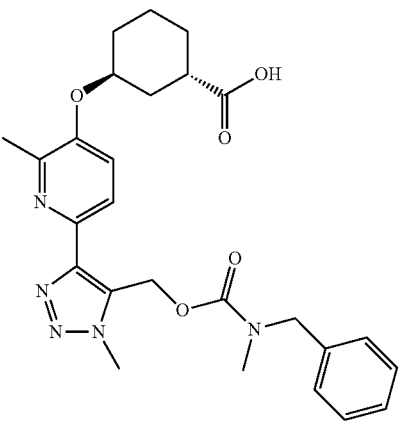<br>(1S,3S)-3-((6-(5-(((benzyl(methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 494.3<br>$^1$H NMR (500 MHz, DMSO-d$_6$) δ 7.86 (d, J = 8.5 Hz, 1H), 7.49 (d, J = 8.5 Hz, 1H), 7.39-6.97 (m, 5H), 5.79-5.63 (m, 2H), 4.79 (br. s., 1H), 4.49-4.26 (m, 2H), 4.17-3.91 (m, 3H), 2.86-2.69 (m, 3H), 2.68-2.59 (m, 1H), 2.41 (d, J = 14.3 Hz, 3H), 2.07-1.98 (m, 1H), 1.92-1.74 (m, 3H), 1.71-1.45 (m, 4H)<br>hLPA1 IC$_{50}$ = 16 nM. | Example 1 |
| 31 | 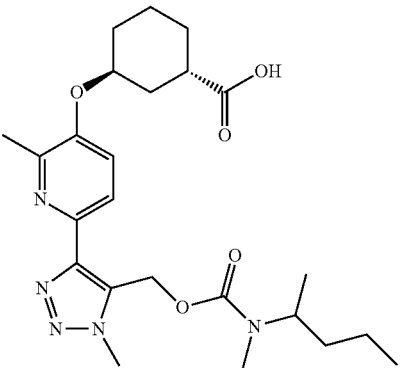 [SMILES: CCCC(C)N(C)C(=O)OCc1c(-c2ccc(O[C@H]3CCC[C@H](C(=O)O)C3)c(C)n2)nnn1C]<br>(1S,3S)-3-((2-methyl-6-(1-methyl-5-(((methyl(pentan-2-yl)carbamoyl)oxy)methyl)-1H-1,2,3-triazol-4-yl)pyridin-3-yl)oxy)cyclohexane-1-carboxylic acid<br>(diastereomeric mixture) | LCMS, [M + H]$^+$ = 474.3<br>$^1$H NMR (500 MHz, DMSO-d$_6$) δ 7.84 (d, J = 8.2 Hz, 1H), 7.48 (d, J = 7.0 Hz, 1H), 5.66 (br. s., 2H), 4.79 (br. s., 1H), 4.10 (s, 4H), 2.63 (br. s., 3H), 2.42 (s, 3H), 2.10-1.97 (m, 1H), 1.91-1.71 (m, 4H), 1.67-1.10 (m, 6H), 1.06-0.80 (m, 4H), 0.64 (br. s., 2H)<br>hLPA1 IC$_{50}$ = 36 nM. | Example 1 |
| 32 | 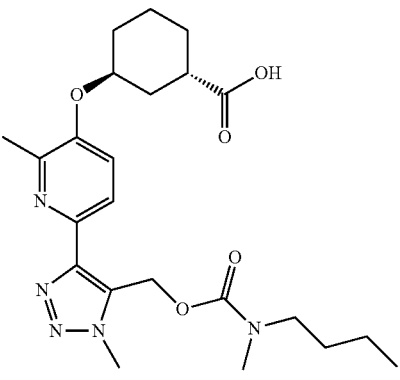<br>(1S,3S)-3-((6-(5-(((butyl(methyl)carbamoyl)oxy)methyl)-1-methyl-1H-1,2,3-triazol-4-yl)- | LCMS, [M + H]$^+$ = 460.3<br>$^1$H NMR (500 MHz, DMSO-d$_6$) δ 7.85 (d, J = 8.5 Hz, 1H), 7.48 (d, J = 8.5 Hz, 1H), 5.64 (d, J = 15.9 Hz, 2H), 4.79 (br. s., 1H), 4.10 (s, 3H), 3.53-3.32 (m, 2H), 3.23-3.02 (m, 1H), 2.85-2.69 (m, 3H), 2.42 (s, 3H), 1.81 (br. s., 3H), 1.63 (d, J = 9.8 Hz, 6H), 1.31-0.96 (m, 3H), 0.66 (br. s., 3H)<br>hLPA1 IC$_{50}$ = 10 nM. | Example 1 |

TABLE 1-continued

| Example | Structure & Name | Analytical & Biology Data | Method |
|---|---|---|---|
| | 2-methylpyridin-3-yl)oxy)cyclohexane-1-carboxylic acid | | |
| 33 | (1S,3S)-3-((6-(5-(((((cyclobutylmethyl)(methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 472.4<br>$^1$H NMR (400 MHz, CD$_3$CN) δ 7.96-7.79 (m, 1H), 7.35 (d, J = 8.8 Hz, 1H), 5.67 (br s, 2H), 4.86-4.62 (m, 1H), 4.19-3.97 (m, 4H), 3.39-3.01 (m, 2H), 2.88-2.63 (m, 4H), 2.60-2.29 (m, 4H), 2.18-2.04 (m, 1H), 1.91-1.44 (m, 12H), 1.29-1.15 (m, 1H)<br>hLPA1 IC$_{50}$ = 7 nM. | Example 1 |
| 34 | (1S,3S)-3-((6-(5-((((isopentyl(methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 474.3<br>$^1$H NMR (500 MHz, DMSO-d$_6$) δ 7.85 (d, J = 8.5 Hz, 1H), 7.48 (d, J = 8.5 Hz, 1H), 5.63 (d, J = 15.3 Hz, 2H), 4.79 (br. s., 1H), 4.10 (br. s., 3H), 3.44 (br. s., 1H), 3.22 (br. s., 1H), 3.06 (br. s., 1H), 2.84-2.69 (m, 3H), 2.63 (t, J = 10.4 Hz, 1H), 2.42 (s, 3H), 2.09-1.97 (m, 2H), 1.92-1.70 (m, 2H), 1.70-1.42 (m, 4H), 1.40-1.19 (m, 2H), 1.14 (br. s., 1H), 0.88 (br. s., 3H), 0.62 (d, J = 4.6 Hz, 3H)<br>hLPA1 IC$_{50}$ = 16 nM. | Example 1 |
| 35 | | LCMS, [M + H]$^+$ = 528.3<br>$^1$H NMR (500 MHz, DMSO-d$_6$) δ 7.85 (d, J = 8.5 Hz, 1H), 7.49 (d, J = 8.5 Hz, 1H), 7.44-6.99 (m, 4H), 5.83-5.59 (m, 2H), 4.79 (br. s., 1H), 4.49-4.25 (m, 2H), 4.18-3.93 (m, 3H), 2.86-2.68 (m, 3H), 2.67-2.60 (m, 1H), 2.45-2.29 (m, 3H), 2.03 (d, J = 13.7 Hz, 1H), 1.94-1.73 (m, 3H), 1.71-1.44 (m, 4H)<br>hLPA1 IC$_{50}$ = 284 nM. | Example 1 |

TABLE 1-continued

| Example | Structure & Name | Analytical & Biology Data | Method |
|---------|------------------|---------------------------|--------|
| 36 | (1S,3S)-3-((6-(5-((((4-chlorobenzyl)(methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 471.3<br>$^1$H NMR (400 MHz, CD$_3$CN) δ 7.48-7.31 (m, 2H), 6.87 (d, J = 8.4 Hz, 1H), 5.11 (s, 2H), 4.62 (br. s., 1H), 3.95 (s, 3H), 2.70-2.56 (m, 4H), 2.13 (s, 3H), 2.02-1.92 (m, 1H), 1.65-1.33 (m, 8H), 0.99 (br. s., 3H), 0.83-0.68 (m, 1H), 0.37 (br. s., 1H), 0.26--0.22 (m, 3H)<br>hLPA1 IC$_{50}$ = 6 nM. | Example 3 |
| 37 | (1S,3S)-3-(4-(5-(((((R)-1-cyclopropylethyl)(methyl)carbamoyl)oxy)methyl)-1-methyl-1H-1,2,3-triazol-4-yl)-2-methylphenoxy)cyclohexane-1-carboxylic acid | LCMS, [M − H]$^+$ = 471.3<br>$^1$H NMR (500 MHz, DMSO-d$_6$) δ 7.66-7.42 (m, 2H), 7.06 (d, J = 8.5 Hz, 1H), 5.28 (br. s., 2H), 4.74 (br. s., 1H), 4.10 (br. s., 3H), 3.48-3.34 (m, 2H), 2.76 (br. s., 2H), 2.65-2.58 (m, 1H), 2.22 (br. s., 3H), 2.02-1.40 (m, 15H)<br>hLPA1 IC$_{50}$ = 14 nM. | Example 1 |

(1S,3S)-3-(4-(5-(((((cyclobutylmethyl)(methyl)carbamoyl)oxy)methyl)-1-methyl-1H-1,2,3-triazol-4-yl)-2-methylphenoxy)cyclohexane-1-carboxylic acid TABLE 1-continued

| Example | Structure & Name | Analytical & Biology Data | Method |
|---|---|---|---|
| 38 | 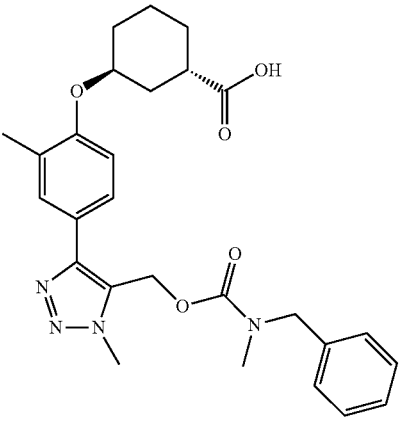 [SMILES: Cc1cc(-c2nnn(C)c2COC(=O)N(C)Cc2ccccc2)ccc1O[C@H]1CCC[C@H](C(=O)O)C1]<br>(1S,3S)-3-(4-(5-(((benzyl(methyl)carbamoyl)oxy)methyl)-1-methyl-1H-1,2,3-triazol-4-yl)-2-methylphenoxy)cyclohexane-1-carboxylic acid | LCMS, $[M - H]^+$ = 493.0<br>$^1$H NMR (500 MHz, DMSO-$d_6$) δ 7.65-7.39 (m, 2H), 7.37-6.94 (m, 7H), 5.32 (d, J = 19.5 Hz, 2H), 4.72 (br. s., 1H), 4.39 (d, J = 13.4 Hz, 2H), 4.18-3.95 (m, 3H), 2.89-2.70 (m, 3H), 2.62 (br. s., 1H), 2.24-2.10 (m, 3H) 2.00 (d, J = 11.9 Hz, 1H), 1.90-1.71 (m, 3H), 1.69-1.39 (m, 4H)<br>hLPA1 $IC_{50}$ = 32 nM. | Example 1 |
| 39 | 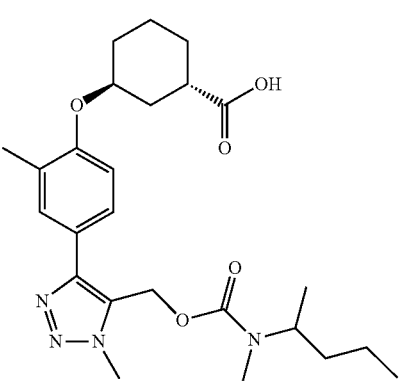 [SMILES: CCCC(C)N(C)C(=O)OCc1c(-c2ccc(O[C@H]3CCC[C@H](C(=O)O)C3)c(C)c2)nnn1C]<br>(1S,3S)-3-(2-methyl-4-(1-methyl-5-(((methyl(pentan-2-yl)carbamoyl)oxy)methyl)-1H-1,2,3-triazol-4-yl)phenoxy)cyclohexane-1-carboxylic acid<br>(diastereomeric mixture) | LCMS, $[M + H]^+$ = 473.3.<br>$^1$H NMR (500 MHz, DMSO-$d_6$) δ 7.62-7.42 (m, 2H), 7.05 (d, J = 8.5 Hz, 1H), 5.27 (br. s., 2H), 4.74 (br. s., 1H), 4.09 (s, 3H), 3.43 (br. s., 2H), 2.68-2.54 (m, 4H), 2.21 (s, 3H), 2.01 (d, J = 13.7 Hz, 1H), 1.88-1.71 (m, 3H), 1.69-1.18 (m, 6H), 1.16-0.66 (m, 6H)<br>hLPA1 $IC_{50}$ = 23 nM. | Example 1 |
| 40 | 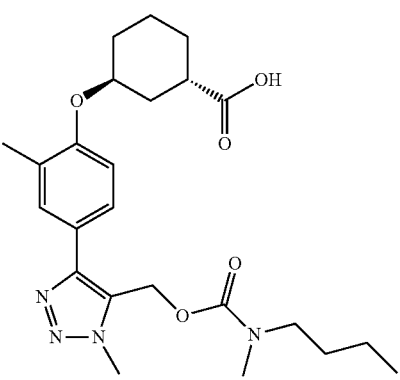 [SMILES: CCCCN(C)C(=O)OCc1c(-c2ccc(O[C@H]3CCC[C@H](C(=O)O)C3)c(C)c2)nnn1C]<br>(1S,3S)-3-(4-(5-(((butyl(methyl)carbamoyl)oxy)methyl)-1-methyl-1H-1,2,3-triazol-4-yl)-2-methylphenoxy)cyclohexane-1-carboxylic acid | LCMS, $[M + H]^+$ = 459.3<br>$^1$H NMR (500 MHz, DMSO-$d_6$) δ 7.52 (d, J = 13.1 Hz, 2H), 7.05 (d, J = 7.6 Hz, 1H), 5.27 (d, J = 5.5 Hz, 2H), 4.74 (br. s., 1H), 4.09 (s, 3H), 3.23-3.04 (m, 2H), 2.77 (d, J = 6.4 Hz, 3H), 2.61 (br. s., 1H), 2.22 (s, 3H), 2.00 (d, J = 12.8 Hz, 1H), 1.90-1.69 (m, 3H), 1.67-1.04 (m, 8H), 0.91-0.61 (m, 3H)<br>hLPA1 $IC_{50}$ = 28 nM. | Example 1 |

TABLE 1-continued

| Example | Structure & Name | Analytical & Biology Data | Method |
|---|---|---|---|
| 41 | 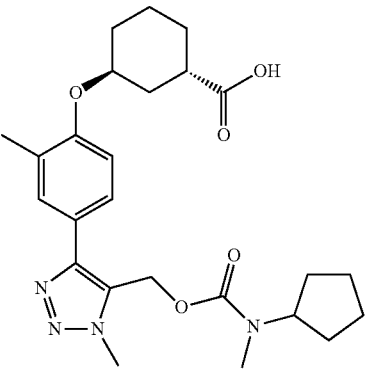<br>(1S,3S)-3-(4-(5-(((cyclopentyl(methyl)carbamoyl)oxy)methyl)-1-methyl-1H-1,2,3-triazol-4-yl)-2-methylphenoxy)cyclohexane-1-carboxylic acid | LCMS, $[M + H]^+$ = 471.3, $^1$H NMR (500 MHz, DMSO-$d_6$) δ 7.60-7.44 (m, 2H), 7.04 (d, J = 8.5 Hz, 1H), 5.28 (s, 2H), 4.74 (br. s., 1H), 4.09 (s, 3H), 3.42 (br. s., 1H), 2.72-2.58 (m, 4H), 2.27-2.17 (m, 3H), 2.01 (d, J = 13.4 Hz, 1H), 1.89-1.71 (m, 3H), 1.69-1.32 (m, 12H)<br>hLPA1 $IC_{50}$ = 14 nM. | Example 1 |
| 42 | 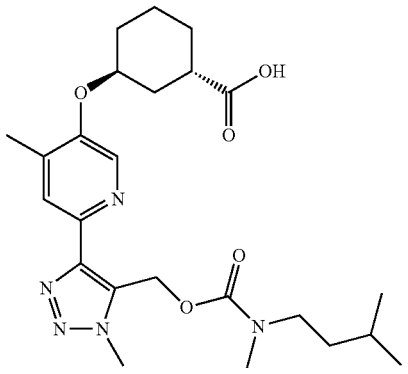 [SMILES: Cc1cc(-c2nnn(C)c2COC(=O)N(C)CCC(C)C)ncc1O[C@H]1CCC[C@H](C(=O)O)C1]<br>(1S,3S)-3-((6-(5-(((isopentyl(methyl)carbamoyl)oxy)methyl)-1-methyl-1H-1,2,3-triazol-4-yl)-4-methylpyridin-3-yl)oxy)cyclohexane-1-carboxylic acid | LCMS, $[M + H]^+$ = 474.3. $^1$H NMR (500 MHz, DMSO-$d_6$) δ 8.32 (s, 1H), 7.90 (s, 1H), 5.62 (d, J = 18.0 Hz, 2H), 4.88 (br. s., 1H), 4.10 (br. s., 3H), 3.26-3.04 (m, 2H), 2.76 (d, J = 17.7 Hz, 3H), 2.65 (br. s., 1H), 2.28 (s, 3H), 2.03 (d, J = 12.8 Hz, 1H), 1.93-1.77 (m, 3H), 1.70-1.06 (m, 7H), 0.88 (d, J = 4.6 Hz, 3H), 0.67 (d, J = 5.2 Hz, 3H)<br>hLPA1 $IC_{50}$ = 3750 nM. | Example 1 |
| 43 | 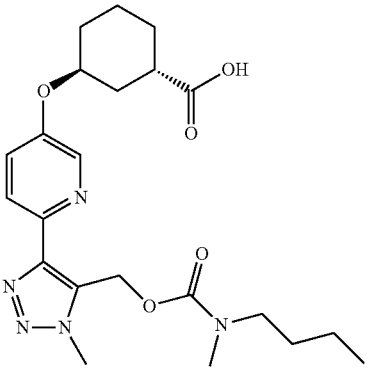 [SMILES: CCCCN(C)C(=O)OCc1c(-c2ccc(O[C@H]3CCC[C@H](C(=O)O)C3)cn2)nnn1C]<br>(1S,3S)-3-((6-(5-(((butyl(methyl)carbamoyl)oxy)methyl)-1-methyl-1H-1,2,3-triazol-4-yl)pyridin-3-yl)oxy)cyclohexane-1-carboxylic acid | LCMS, $[M + H]^+$ = 446.3. $^1$H NMR (500 MHz, DMSO-$d_6$) δ 8.35 (d, J = 2.4 Hz, 1H), 8.00 (d, J = 8.9 Hz, 1H), 7.55 (d, J = 8.2 Hz, 1H), 5.62 (d, J = 18.0 Hz, 2H), 4.79 (br. s., 1H), 4.11 (s, 3H), 3.24-3.04 (m, 2H), 2.82-2.62 (m, 4H), 1.98 (d, J = 14.0 Hz, 1H), 1.89-1.73 (m, 3H), 1.72-1.37 (m, 5H), 1.26 (br. s., 2H), 1.05 (br. s., 1H), 0.88 (br. s., 2H), 0.69 (br. s., 2H)<br>hLPA1 $IC_{50}$ = 7 nM. | Example 1 |

TABLE 1-continued

| Example | Structure & Name | Analytical & Biology Data | Method |
|---|---|---|---|
| 44 | 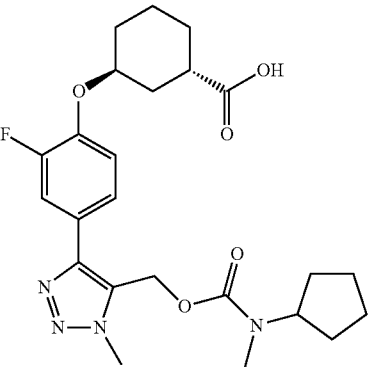 [SMILES: CN(C(=O)OCc1c(-c2ccc(O[C@H]3CCC[C@H](C(=O)O)C3)c(F)c2)nnn1C)C1CCCC1]<br>(1S,3S)-3-(4-(5-(((cyclopentyl(methyl)carbamoyl)oxy)methyl)-1-methyl-1H-1,2,3-triazol-4-yl)-2-fluorophenoxy)cyclohexane-1-carboxylic acid | LCMS, $[M + H]^+$ = 475.2<br>$^1$H NMR (500 MHz, DMSO-$d_6$) δ 7.61 (d, J = 12.2 Hz, 1H), 7.53 (d, J = 8.5 Hz, 1H), 7.35 (t, J = 8.5 Hz, 1H), 5.34 (s, 2H), 4.75 (br. s., 1H), 4.13 (s, 3H), 3.46-3.30 (m, 1H), 2.73-2.59 (m, 4H), 2.01-1.30 (m, 16H)<br>hLPA1 IC$_{50}$ = 6 nM. | Example 1 |
| 45 | 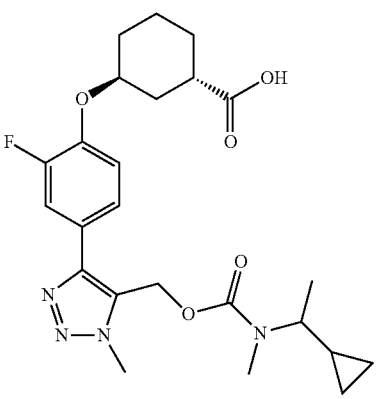 [SMILES: CC(C1CC1)N(C)C(=O)OCc1c(-c2ccc(O[C@H]3CCC[C@H](C(=O)O)C3)c(F)c2)nnn1C]<br>(1S,3S)-3-(4-(5-((((1-cyclopropylethyl)(methyl)carbamoyl)oxy)methyl)-1-methyl-1H-1,2,3-triazol-4-yl)-2-fluorophenoxy)cyclohexane-1-carboxylic acid<br>(diastereomeric mixture) | LCMS, $[M + H]^+$ = 475.4<br>$^1$H NMR (500 MHz, DMSO-$d_6$) δ 7.61-7.39 (m, 2H), 7.30-7.19 (m, 1H), 5.23 (s, 2H), 4.66 (br. s., 1H), 4.02 (s, 3H), 3.29 (br. s., 1H), 2.65 (br. s., 3H), 2.60-2.52 (m, 1H), 1.94-1.85 (m, 1H), 1.73 (d, J = 11.0 Hz, 3H), 1.56 (d, J = 8.5 Hz, 2H), 1.44 (br. s., 2H), 0.98 (d, J = 16.2 Hz, 4H), 0.51--0.31 (m, 4H)<br>hLPA1 IC$_{50}$ = 20 nM. | Example 1 |
| 46 | 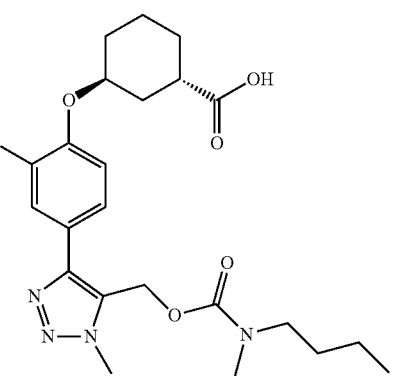<br>(1S,3S)-3-(4-(5-(((butyl(methyl)carbamoyl)oxy)methyl)-1-methyl-1H-1,2,3-triazol-4-yl)-2-fluorophenoxy)cyclohexane-1-carboxylic acid | LCMS, $[M + H]^+$ = 463.0<br>$^1$H NMR (500 MHz, DMSO-$d_6$) δ 7.69-7.45 (m, 2H), 7.35 (br. s., 1H), 5.34 (br. s., 2H), 4.75 (br. s., 1H), 4.13 (s, 3H), 3.23-3.06 (m, 2H), 2.78 (d, J = 8.9 Hz, 3H), 2.63 (br. s., 1H), 1.99-1.04 (m, 12H), 0.93-0.70 (m, 3H)<br>hLPA1 IC$_{50}$ = 6 nM. | Example 1 |

TABLE 1-continued

| Example | Structure & Name | Analytical & Biology Data | Method |
|---|---|---|---|
| 47 | 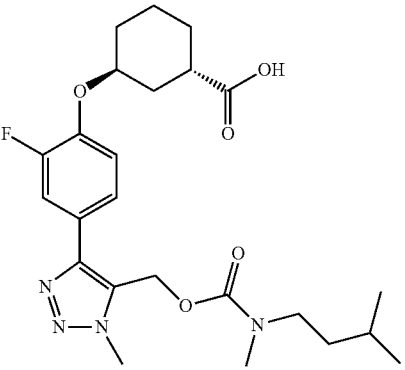 [SMILES: CC(C)CCN(C)C(=O)OCc1c(-c2ccc(O[C@H]3CCC[C@H](C(=O)O)C3)c(F)c2)nnn1C]<br>(1S,3S)-3-(2-fluoro-4-(5-(((isopentyl(methyl)carbamoyl)oxy)methyl)-1-methyl-1H-1,2,3-triazol-4-yl)phenoxy)cyclohexane-1-carboxylic acid | LCMS, $[M + H]^+$ = 477.1<br>$^1$H NMR (500 MHz, DMSO-$d_6$) δ 7.77-7.43 (m, 2H), 7.33 (br. s., 1H), 5.34 (d, J = 7.9 Hz, 2H), 4.75 (br. s., 1H), 4.13 (br. s., 3H), 3.23-3.06 (m, 2H), 2.78 (d, J = 14.6 Hz, 3H), 2.67 (br. s., 1H), 1.98 (br. s., 1H), 1.89-1.11 (m, 10H), 0.96-0.65 (m, 6H)<br>hLPA1 IC$_{50}$ = 3 nM. | Example 1 |
| 48 | 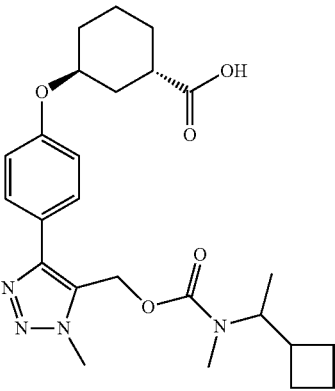 [SMILES: CC(C1CCC1)N(C)C(=O)OCc1c(-c2ccc(O[C@H]3CCC[C@H](C(=O)O)C3)cc2)nnn1C]<br>(1S,3S)-3-(4-(5-((((1-cyclobutylethyl)(methyl)carbamoyl)oxy)methyl)-1-methyl-1H-1,2,3-triazol-4-yl)phenoxy)cyclohexane-1-carboxylic acid (isomer 1) | LCMS, $[M + H]^+$ = 471.3<br>$^1$H NMR (400 MHz, CDCl$_3$) δ 7.73 (br s, 2H), 7.04 (br d, J = 7.5 Hz, 2H), 5.32 (s, 2H), 4.72 (br s, 1H), 4.19 (br s, 3H), 2.94 (br d, J = 3.1 Hz, 1H), 2.67 (s, 3H), 2.47-1.58 (m, 16H), 1.02 (br s, 3H)<br>hLPA1 IC$_{50}$ = 8 nM. | Example 1 |
| 49 | 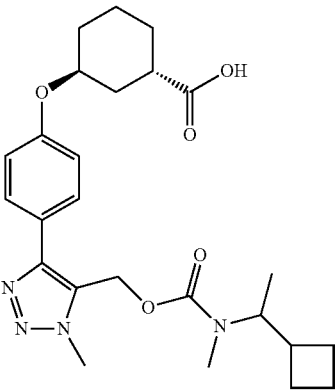 [SMILES: CC(C1CCC1)N(C)C(=O)OCc1c(-c2ccc(O[C@H]3CCC[C@H](C(=O)O)C3)cc2)nnn1C]<br>(1S,3S)-3-(4-(5-((((1-cyclobutylethyl)(methyl)carbamoyl)oxy)methyl)-1-methyl-1H-1,2,3-triazol-4-yl)phenoxy)cyclohexane-1-carboxylic acid (isomer 2) | LCMS, $[M + H]^+$ = 471.3<br>$^1$H NMR (400 MHz, CDCl$_3$) δ 7.85-7.62 (m, 2H), 7.03 (br d, J = 3.3 Hz, 2H), 5.32 (br d, J = 2.9 Hz, 2H), 4.87-4.56 (m, 1H), 4.19 (br s, 3H), 3.07-2.86 (m, 1H), 2.67 (br s, 3H), 2.49-1.49 (m, 16H), 1.05-0.93 (m, 3H)<br>hLPA1 IC$_{50}$ = 14 nM. | Example 1 |

TABLE 1-continued

| Example | Structure & Name | Analytical & Biology Data | Method |
|---|---|---|---|
| 50 | 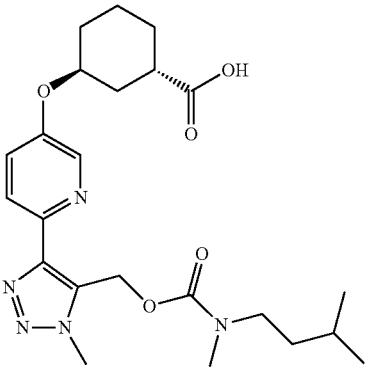 [SMILES: CC(C)CCN(C)C(=O)OCc1c(-c2ccc(O[C@H]3CCC[C@H](C(=O)O)C3)cn2)nnn1C]<br>(1S,3S)-3-((6-(5-(((isopentyl(methyl)carbamoyl)oxy)methyl)-1-methyl-1H-1,2,3-triazol-4-yl)pyridin-3-yl)oxy)cyclohexane-1-carboxylic acid | LCMS, [M + H]$^+$ = 460.2<br>$^1$H NMR (500 MHz, DMSO-d$_6$) δ 8.34 (br. s., 1H), 8.09-7.93 (m, 1H), 7.55 (d, J = 7.9 Hz, 1H), 5.62 (d, J = 16.8 Hz, 2H), 4.78 (br. s., 1H), 4.11 (br. s., 3H), 3.29-3.00 (m, 2H), 2.76 (d, J = 17.7 Hz, 3H), 2.64 (br. s., 1H), 1.97-1.45 (m, 8H), 1.40-1.14 (m, 2H), 0.88 (d, J = 4.9 Hz, 3H), 0.67 (d, J = 5.2 Hz, 3H)<br>hLPA1 IC$_{50}$ = 12 nM. | Example 1 |
| 51 | 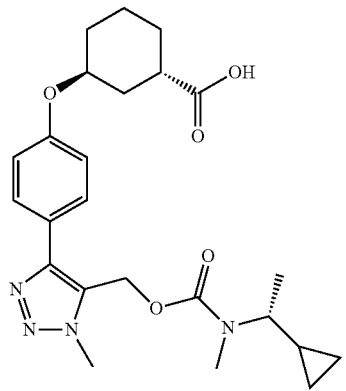 [SMILES: C[C@H](C1CC1)N(C)C(=O)OCc1c(-c2ccc(O[C@H]3CCC[C@H](C(=O)O)C3)cc2)nnn1C]<br>(1S,3S)-3-(4-(5-(((((R)-1-cyclopropylethyl)(methyl)carbamoyl)oxy)methyl)-1-methyl-1H-1,2,3-triazol-4-yl)phenoxy)cyclohexane-1-carboxylic acid | LCMS, [M + H]$^+$ = 457.3<br>$^1$H NMR (400 MHz, CD$_3$CN) δ 7.64-7.44 (m, 2H), 6.89 (d, J = 8.8 Hz, 2H), 5.10 (s, 2H), 4.61-4.49 (m, 1H), 3.94 (s, 3H), 2.70-2.52 (m, 4H), 1.96-1.85 (m, 1H), 1.75-1.35 (m, 8H), 0.97 (br. s., 3H), 0.75 (br. s., 1H), 0.44-0.25 (m, 4H)<br>hLPA1 IC$_{50}$ = 24 nM.<br>In vivo acute histamine assay: −73% histamine at a 3 mg/kg dose of Example 51 | Example 1 |
| 52 | 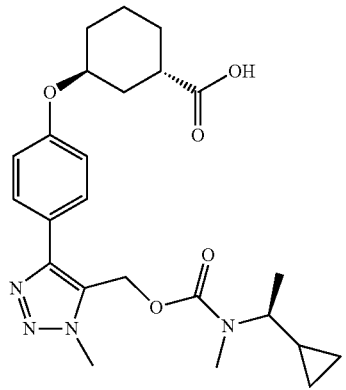 [SMILES: C[C@@H](C1CC1)N(C)C(=O)OCc1c(-c2ccc(O[C@H]3CCC[C@H](C(=O)O)C3)cc2)nnn1C]<br>(1S,3S)-3-(4-(5-(((((S)-1-cyclopropylethyl)(methyl)carbamoyl)oxy)methyl)-1-methyl-1H-1,2,3-triazol-4-yl)phenoxy)cyclohexane-1-carboxylic acid | LCMS, [M + H]$^+$ = 457.2<br>$^1$H NMR (500 MHz, DMSO-d$_6$) δ 7.54 (d, J = 8.2 Hz, 2H), 6.96 (d, J = 8.2 Hz, 2H), 5.18 (br. s., 2H), 4.59 (br. s., 1H), 3.99 (s, 3H), 2.62 (br. s., 3H), 2.51 (br. s., 1H), 1.74-1.31 (m, 8H), 1.06-0.90 (m, 3H), 0.87-0.71 (m, 1H), 0.43-−0.30 (m, 4H)<br>hLPA1 IC$_{50}$ = 197 nM. | Example 3 |

TABLE 1-continued

| Example | Structure & Name | Analytical & Biology Data | Method |
|---|---|---|---|
| 53 | (1S,3S)-3-(4-(5-((((isobutyl(methyl)carbamoyl)oxy)methyl)-1-methyl-1H-1,2,3-triazol-4-yl)phenoxy)cyclohexane-1-carboxylic acid (diastereomeric mixture) | LCMS, $[M + H]^+$ = 445.2<br>$^1$H NMR (500 MHz, DMSO-$d_6$) δ 7.68 (br. s., 2H), 7.08 (d, J = 8.2 Hz, 2H), 5.31 (s, 2H), 4.72 (br. s., 1H), 4.12 (s, 3H), 3.08-2.93 (m, 2H), 2.80 (d, J = 15.3 Hz, 3H), 2.67 (br. s., 1H), 2.03-1.48 (m, 9H), 0.88-0.64 (m, 6H)<br>hLPA1 IC$_{50}$ = 440 nM. | Example 1 |
| 54 | (1S,3S)-3-(4-(5-((((1-cyclobutylethyl)(methyl)carbamoyl)oxy)methyl)-1-methyl-1H-1,2,3-triazol-4-yl)phenoxy)cyclohexane-1-carboxylic acid (diastereomeric mixture) | LCMS, $[M + H]^+$ = 471.2<br>$^1$H NMR (400 MHz, CDCl$_3$) δ 7.60 (t, J = 9.4 Hz, 2H), 6.93 (d, J = 7.5 Hz, 2H), 5.21 (s, 2H), 4.61 (br. s., 1H), 4.10 (d, J = 2.2 Hz, 4H), 3.84 (dd, J = 10.3, 6.6 Hz, 1H), 2.98-2.76 (m, 1H), 2.69-2.53 (m, 3H), 2.34-2.19 (m, 1H), 2.08 (d, J = 13.9 Hz, 1H), 2.00-1.40 (m, 12H), 0.90 (dd, J = 17.7, 6.7 Hz, 3H)<br>hLPA1 IC$_{50}$ = 19 nM. | Example 2 |
| 55 | (rac)-trans-3-(4-(5-((((2-cyclopropylethyl)(methyl)carbamoyl)oxy)methyl)-1-methyl-1H-1,2,3-triazol-4-yl)phenoxy)cyclohexane-1-carboxylic acid | LCMS, $[M + H]^+$ = 457.2<br>$^1$H NMR (500 MHz, DMSO-$d_6$) δ 7.80 (br. s., 2H), 7.20 (d, J = 7.6 Hz, 2H), 5.43 (br. s., 2H), 4.83 (br. s., 1H), 4.24 (s, 3H), 3.54-3.30 (m, 3H), 2.93 (d, J = 9.2 Hz, 3H), 2.79 (br. s., 1H), 2.17-1.30 (m, 10H), 0.76--0.06 (m, 4H)<br>hLPA1 IC$_{50}$ = 41 nM. | Example 3 |

TABLE 1-continued

| Example | Structure & Name | Analytical & Biology Data | Method |
|---|---|---|---|
| 56 | 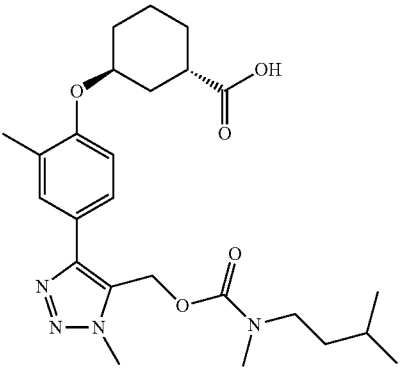<br>(1S,3S)-3-(4-(5-(((isopentyl(methyl)carbamoyl)oxy)methyl)-1-methyl-1H-1,2,3-triazol-4-yl)-2-methylphenoxy)cyclohexane-1-carboxylic acid | LCMS, [M + H]$^+$ = 473.2<br>$^1$H NMR (400 MHz, CD$_3$CN) δ 7.61 (d, J = 15.2 Hz, 2H), 7.05 (br. s., 1H), 5.33 (br. s., 2H), 4.79 (br. s., 1H), 4.14 (s, 3H), 3.35-3.13 (m, 2H), 2.91-2.72 (m, 4H), 2.36-2.26 (m, 3H), 2.14 (d, J = 13.4 Hz, 1H), 1.89-1.26 (m, 10H), 1.02-0.68 (m, 6H)<br>hLPA1 IC$_{50}$ = 3 nM. | Example 2 |
| 57 | 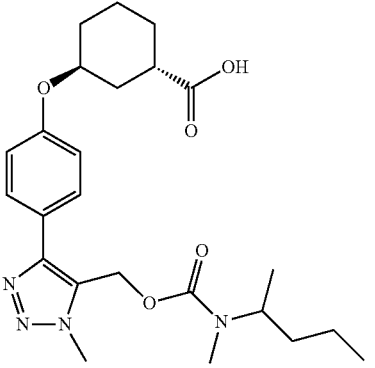 [SMILES: CCCC(C)N(C)C(=O)OCc1c(-c2ccc(O[C@H]3CCC[C@H](C(=O)O)C3)cc2)nnn1C]<br>trans-3-(4-(1-methyl-5-(((methyl(pentan-2-yl)carbamoyl)oxy)methyl)-1H-1,2,3-triazol-4-yl)phenoxy)cyclohexane-1-carboxylic acid (diastereomeric mixture) | LCMS, [M + H]$^+$ = 459.2<br>$^1$H NMR (500 MHz, DMSO-d$_6$) δ 7.67 (t, J = 9.6 Hz, 2H), 7.16-6.98 (m, 2H), 5.31 (s, 2H), 4.72 (br. s., 1H), 4.12 (s, 3H), 2.66 (d, J = 10.1 Hz, 1H), 2.04-1.47 (m, 10H), 1.46-1.28 (m, 3H), 1.19-0.65 (m, 9H)<br>hLPA1 IC$_{50}$ = 142 nM. | Example 2 |
| 58 | 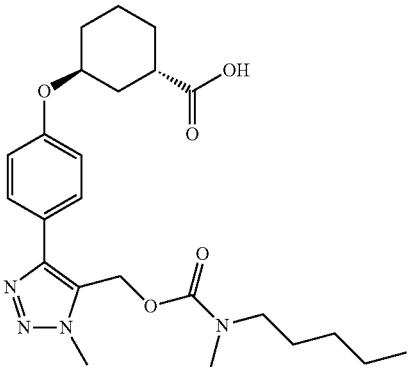 [SMILES: CCCCCN(C)C(=O)OCc1c(-c2ccc(O[C@H]3CCC[C@H](C(=O)O)C3)cc2)nnn1C]<br>(rac)-trans-3-(4-(1-methyl-5-(((methyl(pentyl)carbamoyl)oxy)methyl)-1H-1,2,3-triazol-4-yl)phenoxy)cyclohexane-1-carboxylic acid | LCMS, [M + H]$^+$ = 459.1<br>$^1$H NMR (500 MHz, DMSO-d$_6$) δ 7.70 (d, J = 8.2 Hz, 2H), 7.08 (d, J = 7.6 Hz, 2H), 5.31 (br. s., 2H), 4.72 (br. s., 1H), 4.12 (s, 3H), 3.23-3.08 (m, 2H), 2.79 (d, J = 13.7 Hz, 3H), 2.67 (br. s., 1H), 2.03-1.01 (m, 14H), 0.93-0.69 (m, 3H)<br>hLPA1 IC$_{50}$ = 250 nM. | Example 2 |

TABLE 1-continued

| Example | Structure & Name | Analytical & Biology Data | Method |
|---|---|---|---|
| 59 | 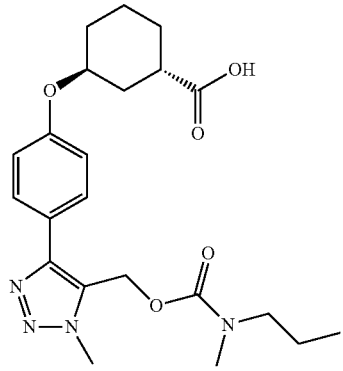 [SMILES: CCCN(C)C(=O)OCc1c(-c2ccc(O[C@H]3CCC[C@H](C(=O)O)C3)cc2)nnn1C]<br>(rac)-trans-3-(4-(1-methyl-5-(((methyl(propyl)carbamoyl)oxy)methyl)-1H-1,2,3-triazol-4-yl)phenoxy)cyclohexane-1-carboxylic acid | LCMS, [M + H]$^+$ = 431.1<br>$^1$H NMR (500 MHz, DMSO-d$_6$) δ 7.68 (br. s., 2H), 7.09 (d, J = 8.5 Hz, 2H), 5.31 (s, 2H), 4.72 (br. s., 1H), 4.12 (s, 3H), 3.20-3.07 (m, 2H), 2.80 (d, J = 9.8 Hz, 3H), 2.67 (br. s., 1H), 2.05-1.31 (m, 10H), 0.84-0.65 (m, 3H)<br>hLPA1 IC$_{50}$ = 1880 nM. | Example 2 |
| 60 | 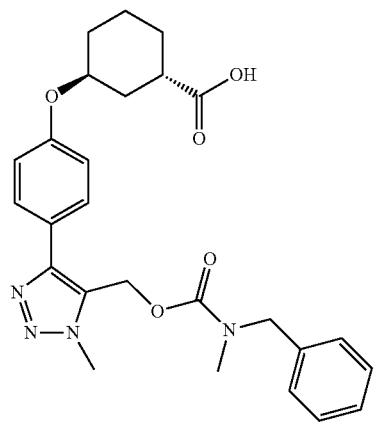 [SMILES: CN(Cc1ccccc1)C(=O)OCc1c(-c2ccc(O[C@H]3CCC[C@H](C(=O)O)C3)cc2)nnn1C]<br>(rac)-trans-3-(4-(5-(((benzyl(methyl)carbamoyl)oxy)methyl)-1-methyl-1H-1,2,3-triazol-4-yl)phenoxy)cyclohexane-1-carboxylic acid | LCMS, [M + H]$^+$ = 479.2<br>$^1$H NMR (500 MHz, DMSO-d$_6$) δ 7.80-7.55 (m, 2H), 7.44-6.96 (m, 7H), 5.48-5.16 (m, 2H), 4.70 (br. s., 1H), 4.41 (d, J = 12.8 Hz, 2H), 4.21-3.94 (m, 3H), 2.90-2.73 (m, 3H), 2.70-2.61 (m, 1H), 2.04-1.48 (m, 8H)<br>hLPA1 IC$_{50}$ = 130 nM. | Example 2 |
| 61 | 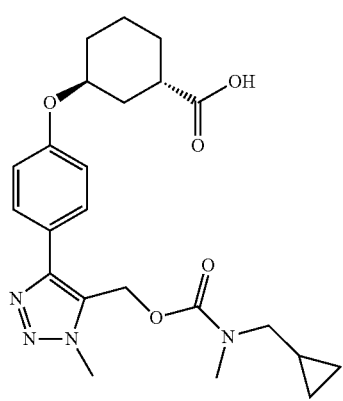 [SMILES: CN(CC1CC1)C(=O)OCc1c(-c2ccc(O[C@H]3CCC[C@H](C(=O)O)C3)cc2)nnn1C]<br>(rac)-trans-3-(4-(5-(((((cyclopropylmethyl)(methyl)carbamoyl)oxy)methyl)-1-methyl-1H-1,2,3-triazol-4-yl)phenoxy)cyclohexane-1-carboxylic acid | LCMS, [M + H]$^+$ = 443.2<br>$^1$H NMR (500 MHz, 1H NMR (500 MHz, DMSO-d$_6$) δ 7.66-7.46 (m, 2H), 7.08-6.86 (m, 2H), 5.28-5.11 (m, 2H), 4.68-4.59 (m, 1H), 4.10-3.94 (m, 3H), 3.08-2.91 (m, 3H), 2.85-2.71 (m, 3H), 2.65-2.54 (m, 1H), 1.97-1.39 (m, 8H), 0.96-0.67 (m, 1H), 0.46-0.22 (m, 2H), 0.16 to −0.08 (m, 2H)<br>hLPA1 IC$_{50}$ = 273 nM. | Example 2 |

TABLE 1-continued

| Example | Structure & Name | Analytical & Biology Data | Method |
|---|---|---|---|
| 62 | 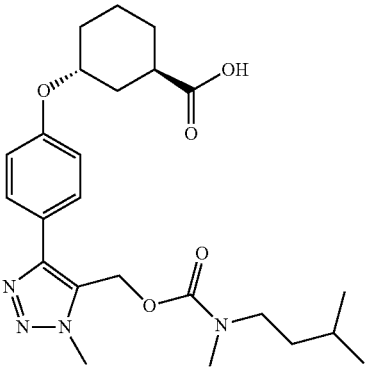 [SMILES: CC(C)CCN(C)C(=O)OCc1c(-c2ccc(O[C@@H]3CCC[C@@H](C(=O)O)C3)cc2)nnn1C]<br>(1R,3R)-3-(4-(5-(((isopentyl(methyl)carbamoyl)oxy)methyl)-1-methyl-1H-1,2,3-triazol-4-yl)phenoxy)cyclohexane-1-carboxylic acid | LCMS, [M + H]$^+$ = 459.2<br>$^1$H NMR (400 MHz, CD$_3$CN) δ 7.80-7.65 (m, 2H), 7.12-6.96 (m, 2H), 5.35-5.24 (m, 2H), 4.78-4.70 (m, 1H), 5.07-4.33 (m, 1H), 4.20-4.06 (m, 3H), 3.37-3.14 (m, 2H), 2.93-2.72 (m, 4H), 2.13-2.02 (m, 1H), 1.92-1.22 (m, 10H), 0.99-0.74 (m, 6H)<br>hLPA1 IC$_{50}$ = 1290 nM. | Example 2 |
| 63 | 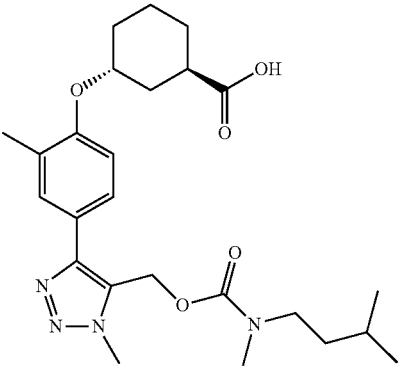 [SMILES: Cc1cc(-c2nnn(C)c2COC(=O)N(C)CCC(C)C)ccc1O[C@@H]1CCC[C@@H](C(=O)O)C1]<br>(1R,3R)-3-(4-(5-(((isopentyl(methyl)carbamoyl)oxy)methyl)-1-methyl-1H-1,2,3-triazol-4-yl)-2-methylphenoxy)cyclohexane-1-carboxylic acid | LCMS, [M + H]$^+$ = 473.2<br>$^1$H NMR (400 MHz, CD$_3$CN) δ 7.65-7.46 (m, 2H), 7.04 (d, J = 8.4 Hz, 1H), 5.29 (br. s., 2H), 4.78 (br. s., 1H), 4.13 (s, 3H), 3.30-3.19 (m, 2H), 2.88-2.74 (m, 4H), 2.30 (s, 3H), 2.18-2.09 (m, 1H), 1.80-1.25 (m, 11H), 0.96-0.70 (m, 6H)<br>hLPA1 IC$_{50}$ = 701 nM. | Example 2 |
| 64 | 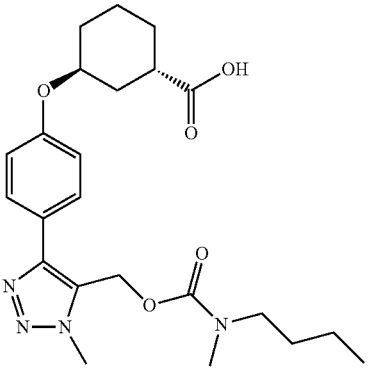 [SMILES: CCCCN(C)C(=O)OCc1c(-c2ccc(O[C@H]3CCC[C@H](C(=O)O)C3)cc2)nnn1C]<br>(rac)-trans-3-(4-(5-(((butyl(methyl)carbamoyl)oxy)methyl)-1-methyl-1H-1,2,3-triazol-4-yl)phenoxy)cyclohexane-1-carboxylic acid | LCMS, [M + H]$^+$ = 445.2<br>(500 MHz, DMSO-d$_6$) δ 7.76-7.57 (m, 2H), 7.17-6.94 (m, 2H), 5.42-5.23 (m, 2H), 4.77-4.62 (m, 1H), 4.19-4.04 (m, 3H), 3.28-3.06 (m, 2H), 2.88-2.75 (m, 3H), 2.71-2.59 (m, 1H), 2.01-1.03 (m, 13H), 0.92-0.68 (m, 3H)<br>hLPA1 IC$_{50}$ = 32 nM. | Example 1 |

TABLE 1-continued

| Example | Structure & Name | Analytical & Biology Data | Method |
|---|---|---|---|
| 65 | trans-3-(4-(5-((((1-cyclopropylethyl)(methyl)carbamoyl)oxy)methyl)-1-methyl-1H-1,2,3-triazol-4-yl)phenoxy)cyclohexane-1-carboxylic acid (diastereomeric mixture) | LCMS, [M + H]$^+$ = 457.2<br>$^1$H NMR (500 MHz, DMSO-d$_6$) δ 7.54 (d, J = 8.5 Hz, 2H), 6.96 (d, J = 8.2 Hz, 2H), 5.19 (br. s., 2H), 4.60 (br. s., 1H), 3.99 (s, 3H), 2.63 (br. s., 4H), 2.60-2.51 (m, 1H), 1.95-1.34 (m, 8H), 1.06-0.71 (m, 4H), 0.47-0.29 (m, 4H)<br>hLPA1 IC$_{50}$ = 80 nM. | Example 1 |
| 66 | (rac)-trans-3-(4-(5-(((((cyclobutylmethyl)(methyl)carbamoyl)oxy)methyl)-1-methyl-1H-1,2,3-triazol-4-yl)phenoxy)cyclohexane-1-carboxylic acid | LCMS, [M + H]$^+$ = 457.2<br>$^1$H NMR (500 MHz, DMSO-d$_6$) δ 7.70 (d, J = 7.9 Hz, 2H), 7.09 (d, J = 8.5 Hz, 2H), 5.31 (br. s., 2H), 4.72 (br. s., 1H), 4.12 (br. s., 3H), 3.31-3.13 (m, 2H), 2.78 (d, J = 11.0 Hz, 3H), 2.67 (br. s., 1H), 2.03-1.45 (m, 15H)<br>hLPA1 IC$_{50}$ = 68 nM. | Example 1 |
| 67 | trans-3-(4-(5-((((1-cyclobutylethyl)(methyl)carbamoyl)oxy)methyl)-1-methyl-1H-1,2,3-triazol-4-yl)phenoxy)cyclohexane-1-carboxylic acid (diastereomeric mixture) | LCMS, [M + H]$^+$ = 471.2<br>$^1$H NMR (500 MHz, DMSO-d$_6$) δ 7.81-7.58 (m, 2H), 7.12-7.03 (m, 2H), 5.43-5.17 (m, 2H), 4.71 (br. s., 1H), 4.12 (d, J = 12.2 Hz, 3H), 4.06-3.74 (m, 1H), 3.00 (s, 3H), 2.66 (br. s., 1H), 2.03-1.44 (m, 15H), 0.94-0.81 (m, 3H)<br>hLPA1 IC$_{50}$ = 109 nM. | Example 1 |

TABLE 1-continued

| Example | Structure & Name | Analytical & Biology Data | Method |
|---|---|---|---|
| 68 | (trans)-3-(4-(5-((((sec-butyl(methyl)carbamoyl)oxy)methyl)-1-methyl-1H-1,2,3-triazol-4-yl)phenoxy)cyclohexane-1-carboxylic acid (diastereomeric mixture) | LCMS, [M + H]$^+$ = 445.2<br>$^1$H NMR (500 MHz, DMSO-d$_6$) δ 7.75-7.60 (m, 2H), 7.08 (d, J = 8.9 Hz, 2H), 5.31 (s, 2H), 4.71 (br. s., 1H), 4.11 (s, 3H), 4.05-3.73 (m, 1H), 2.73-2.57 (m, 4H), 2.02-1.27 (m, 10H), 1.08-0.92 (m, 3H), 0.76-0.57 (m, 3H)<br>hLPA1 IC$_{50}$ = 320 nM. | Example 1 |
| 69 | (3S)-3-((6-(5-(((((cyclobutylmethyl)(methyl)carbamoyl)oxy)methyl)-1-methyl-1H-1,2,3-triazol-4-yl)-2-methylpyridin-3-yl)oxy)cyclohexane-1-carboxylic-1-d acid (homochiral) | LCMS, [M + H]$^+$ = 473.0<br>$^1$H NMR (500 MHz, DMSO-d$_6$) δ 7.83 (d, J = 8.5 Hz, 1H), 7.52 (d, J = 8.6 Hz, 1H), 5.62 (d, J = 19.4 Hz, 2H), 4.09 (d, J = 7.2 Hz, 3H), 3.33-3.04 (m, 2H), 2.82-2.67 (m, 3H), 2.36 (br. s., 3H), 2.45-2.16 (m, 1H), 2.08-1.15 (m, 14H)<br>hLPA1 IC$_{50}$ = 57 nM. | Example 2 (using intermediate 2) |
| 70 | (1S,3S)-3-(4-(5-(((((R)-1-cyclopropylethyl)(methyl)carbamoyl)oxy)methyl)-1-methyl-1H-1,2,3- | LCMS, [M + H]$^+$ = 475.3<br>$^1$H NMR (400 MHz, CDCl$_3$) δ 7.51-7.32 (m, 2H), 7.03 (t, J = 8.5 Hz, 1H), 5.28-5.12 (m, 2H), 4.62 (br. s., 1H), 4.11 (s, 3H), 3.41 (d, J = 9.0 Hz, 1H), 3.19 (br. s., 1H), 2.98-2.69 (m, 4H), 2.11 (d, J = 13.6 Hz, 1H), 2.01-1.67 (m, 4H), 1.65-1.49 (m, 3H), 1.11 (d, J = 6.6 Hz, 3H), 0.78 (br. s., 1H), 0.57--0.15 (m, 3H)<br>hLPA1 IC$_{50}$ = 10 nM. | Example 1 |

TABLE 1-continued

| Example | Structure & Name | Analytical & Biology Data | Method |
|---|---|---|---|
| | triazol-4-yl)-2-fluorophenoxy)cyclohexane-1-carboxylic acid | | |
| 71 | (rac)-trans-3-(4-(5-(((isopentyl(methyl)carbamoyl)oxy)methyl)-1-methyl-1H-1,2,3-triazol-4-yl)phenoxy)cyclohexane-1-carboxylic acid | LCMS, [M + H]$^+$ = 459.2<br>$^1$H NMR (500 MHz, DMSO-d$_6$) δ 7.88-7.56 (m, 2H), 7.08 (br. s., 2H), 5.31 (br. s., 2H), 4.71 (br. s., 1H), 4.12 (s, 3H), 3.29-3.05 (m, 2H), 2.79 (d, J = 17.1 Hz, 3H), 2.70-2.60 (m, 1H), 2.05-1.19 (m, 11H), 0.93-0.69 (m, 6H)<br>hLPA1 IC$_{50}$ = 13 nM. | Example 2 |
| 72 | (1-Methyl-4-(4-(((1R,3R)-3-((methylsulfonyl)carbamoyl)cyclohexyl)oxy)phenyl)-1H-1,2,3-triazol-5-yl)methyl cyclopentyl (methyl)carbamate | LCMS, [M + H]$^+$ = 534.4<br>$^1$H NMR (400 MHz, CD$_3$OD) δ 7.67 (d, J = 8.8 Hz, 2H), 7.09 (d, J = 8.8 Hz, 2H), 5.37 (s, 2H), 4.20 (s, 3H), 3.20 (s, 3H), 2.78-2.89 (m, 5H), 1.59-2.10 (m, 17H).<br>hLPA1 IC$_{50}$ = 2780 nM. | Example 7 |
| 73 | (1S,3S)-3-(4-(5-(((cyclobutyl(methyl)carbamoyl)oxy)methyl)-1-methyl-1H-1,2,3-triazol-4-yl)phenoxy)cyclohexane-1-carboxylic acid | LCMS, [M + H]$^+$ = 443.5<br>$^1$H NMR (400 MHz, CD$_3$OD) δ 7.64 (d, J = 8.00 Hz, 2H), 7.08 (d, J = 8.00 Hz, 2H), 5.33 (s, 2H), 4.72-4.74 (m, 1H), 4.18 (s, 3H), 2.78-2.84 (m, 4H), 2.08-2.14 (m, 5H), 1.82-1.93 (m, 3H), 1.41-1.79 (m, 7H).<br>hLPA1 IC$_{50}$ = 62 nM. | Example 10 |

TABLE 1-continued

| Example | Structure & Name | Analytical & Biology Data | Method |
|---|---|---|---|
| 74 | 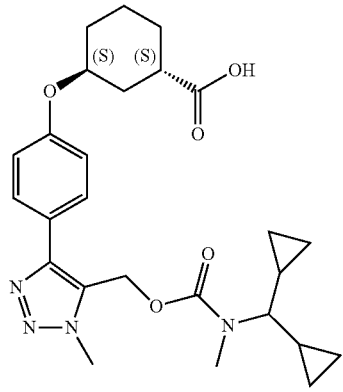<br>(1S,3S)-3-(4-(5-((((Dicyclopropylmethyl)(methyl)carbamoyl)oxy)methyl)-1-methyl-1H-1,2,3-triazol-4-yl)phenoxy)cyclohexanecarboxylic acid | LCMS, [M + H]$^+$ = 483.2<br>$^1$H NMR (400 MHz, CD$_3$OD) δ 7.66 (d, J = 8.80 Hz, 2H), 7.09 (d, J = 8.80 Hz, 2H), 5.36 (s, 2H), 4.83-4.89 (m, 1H), 4.19 (s, 3H), 2.90-2.97 (m, 3H), 2.70-2.87 (m, 2H), 2.08-2.15 (m, 1H), 1.90-1.99 (m, 3H), 1.62-1.74 (m, 4H), 1.05-1.09 (m, 2H), 0.50-0.70 (m, 2H), 0.12-0.43 (m, 6H).<br>hLPA1 IC$_{50}$ = 100 nM. | Example 3 |
| 75 | 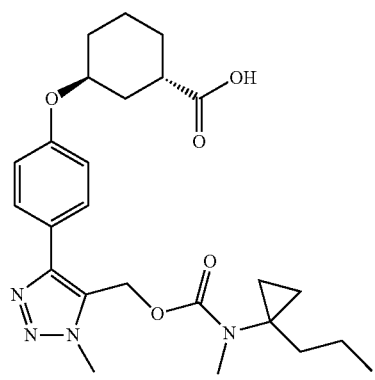 [SMILES: CCCC1(N(C)C(=O)OCc2c(-c3ccc(O[C@H]4CCC[C@H](C(=O)O)C4)cc3)nnn2C)CC1]<br>(1S,3S)-3-(4-(1-methyl-5-(((methyl(1-propylcyclopropyl)carbamoyl)oxy)methyl)-1H-1,2,3-triazol-4-yl)phenoxy)cyclohexane-1-carboxylic acid | LCMS, [M + H]$^+$ = 471.2<br>$^1$H NMR (400 MHz, CD$_3$OD) δ 7.70-7.80 (m, 1H), 7.60-7.70 (m, 1H), 7.08 (m, 2H), 5.30-5.39 (m, 2H), 4.81-4.83 (m, 1H), 4.18-4.21 (m, 3H), 2.89 (s, 3H), 2.79-2.82 (m, 1H), 2.06-2.12 (m, 1H), 1.80-2.00 (m, 3H), 1.60-1.80 (m, 4H), 1.20-1.50 (m, 4H), 0.80-0.90 (m, 2H), 0.70-0.80 (m, 3H), 0.60-0.70 (m, 2H).<br>hLPA1 IC$_{50}$ = 20 nM. | Example 3 |
| 76 | 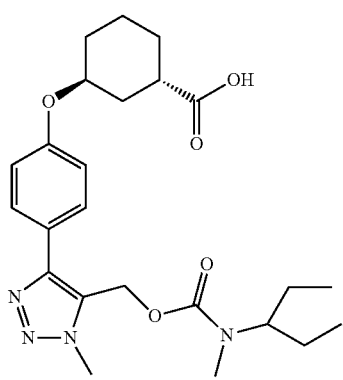 [SMILES: CCC(CC)N(C)C(=O)OCc1c(-c2ccc(O[C@H]3CCC[C@H](C(=O)O)C3)cc2)nnn1C]<br>(1S,3S)-3-(4-(1-methyl-5-(((methyl(pentan-3-yl)carbamoyl)oxy)methyl)-1H-1,2,3-triazol-4-yl)phenoxy)cyclohexane-1-carboxylic acid | LCMS, [M + H]$^+$ = 459.2<br>$^1$H NMR (400 MHz, CD$_3$OD) δ 7.60-7.70 (m, 2H), 7.10-7.00 (m, 2H), 5.37 (s, 2H), 4.70-4.80 (m, 1H), 4.18 (s, 3H), 2.75-2.85 (m, 1H), 2.60-2.70 (m, 3H), 2.08-2.15 (m, 1H), 1.90-2.00 (m, 3H), 1.60-1.75 (m, 5H), 1.40-1.50 (m, 4H), 0.71-0.81 (m, 6H).<br>hLPA1 IC$_{50}$ = 47 nM. | Example 3 |

TABLE 1-continued

| Example | Structure & Name | Analytical & Biology Data | Method |
|---|---|---|---|
| 77 | 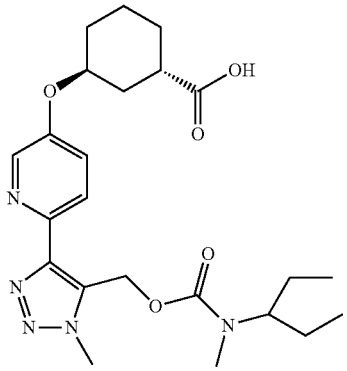 [SMILES: CCC(CC)N(C)C(=O)OCc1c(-c2ccc(O[C@H]3CCC[C@H](C(=O)O)C3)cn2)nnn1C]<br>(1S,3S)-3-((6-(1-methyl-5-(((methyl(pentan-3-yl)carbamoyl)oxy)methyl)-1H-1,2,3-triazol-4-yl)pyridin-3-yl)oxy)cyclohexane-1-carboxylic acid | LCMS, $[M + H]^+$ = 460.4<br>$^1$H NMR (400 MHz, CD$_3$OD) δ 8.30-8.46 (m, 1H), 7.90-7.97 (m, 1H), 7.51-7.65 (m, 1H), 5.70 (d, J = 10.8 Hz, 1H), 4.50-4.60 (m, 1H), 4.20 (s, 3H), 3.62-3.93 (m, 1H), 2.71-2.82 (m, 1H), 2.60-2.70 (m, 3H), 1.82-2.10 (m, 4H), 1.57-1.79 (m, 4H), 1.36-1.49 (m, 5H), 0.82 (t, J = 7.2 Hz, 3H), 0.67 (t, J = 7.6 Hz, 3H). | Example 1 |
| 78 | 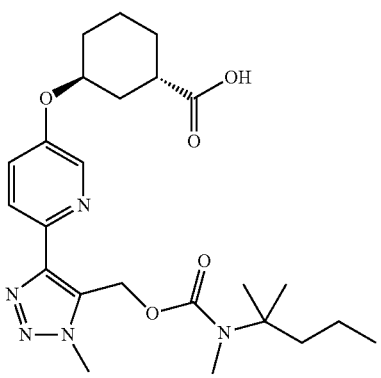 [SMILES: CCCC(C)(C)N(C)C(=O)OCc1c(-c2ccc(O[C@H]3CCC[C@H](C(=O)O)C3)cn2)nnn1C]<br>(1S,3S)-3-((6-(1-methyl-5-(((methyl(2-methylpentan-2-yl)carbamoyl)oxy)methyl)-1H-1,2,3-triazol-4-yl)pyridin-3-yl)oxy)cyclohexane-1-carboxylic acid | LCMS, $[M + H]^+$ = 474.4<br>$^1$H NMR (400 MHz, CD$_3$OD) δ 8.30-8.50 (m, 1H), 7.94-8.05 (m, 1H), 7.53 (d, J = 8.40 Hz, 1H), 5.66 (s, 2H), 4.82-4.86 (m, 1H), 4.20 (s, 3H), 2.75-2.90 (m, 4H), 1.90-2.20 (m, 4H), 1.60-1.90 (m, 6H), 1.31 (s, 6H), 1.15-1.21 (m, 2H), 0.80 (t, J = 6.40 Hz, 3H).<br>hLPA1 IC$_{50}$ = 27 nM. | Example 1 |
| 79 | 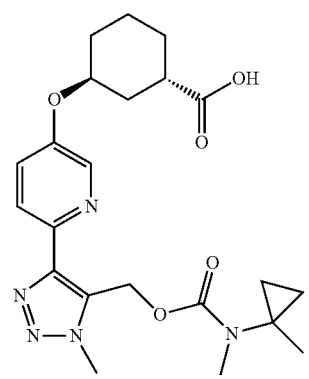 [SMILES: CN(C(=O)OCc1c(-c2ccc(O[C@H]3CCC[C@H](C(=O)O)C3)cn2)nnn1C)C1(C)CC1]<br>(1S,3S)-3-((6-(1-methyl-5-(((methyl(1-methylcyclopropyl)carbamoyl)oxy)methyl)-1H-1,2,3-triazol-4-yl)pyridin-3-yl)oxy)cyclohexane-1-carboxylic acid | LCMS, $[M + H]^+$ = 444.2<br>$^1$H NMR (400 MHz, CD$_3$OD) δ 8.35-8.40 (m, 1H), 7.97 (d, J = 9.20 Hz, 1H), 7.53 (dd, J = 8.8 & 2.8 Hz, 1H), 5.70 (s, 2H), 4.80-4.85 (m, 1H), 4.21 (d, J = 16.00 Hz, 3H), 2.81-2.87 (m, 4H), 1.91-2.11 (m, 4H), 1.63-1.87 (m, 4H), 1.12 (s, 3H), 0.56-0.87 (m, 4H).<br>hLPA1 IC$_{50}$ = 45 nM. | Example 1 |

TABLE 1-continued

| Example | Structure & Name | Analytical & Biology Data | Method |
|---|---|---|---|
| 80 | 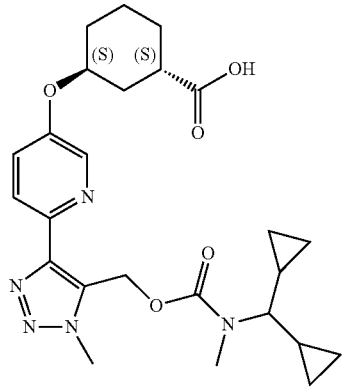<br>(1S,3S)-3-((6-(5-(((((Dicyclopropylmethyl)(methyl)carbamoyl)oxy)methyl)-1-methyl-1H-1,2,3-triazol-4-yl)pyridin-3-yl)oxy)cyclohexanecarboxylic acid | LCMS, [M + H]$^+$ = 484.4<br>$^1$H NMR (400 MHz, CD$_3$OD) δ 8.32-8.40 (m, 1H), 7.97-8.04 (m, 1H), 7.53 (d, J = 8.00 Hz, 1H), 5.60-5.80 (m, 2H), 4.82-4.87 (m, 1H), 4.19 (s, 3H), 2.91 (d, J = 14.80 Hz, 3H), 2.79-2.81 (m, 2H), 2.40-2.50 (m, 1H), 1.91-2.10 (m, 4H), 1.63-1.79 (m, 4H), 0.99-1.07 (m, 2H), 0.51-0.68 (m, 2H), 0.13-0.41 (m, 5H).<br>hLPA1 IC$_{50}$ = 60 nM. | Example 3 |
| 81 | 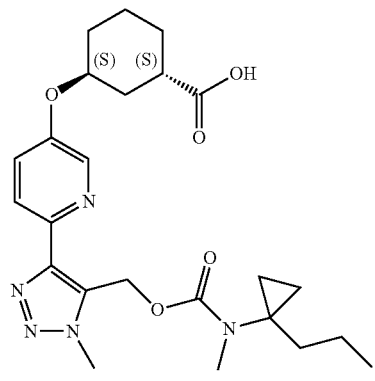<br>(1S,3S)-3-((6-(1-methyl-5-(((methyl(1-propylcyclopropyl)carbamoyl)oxy)methyl)-1H-1,2,3-triazol-4-yl)pyridin-3-yl)oxy)cyclohexane-1-carboxylic acid | LCMS, [M + H]$^+$ = 472.2<br>$^1$H NMR (400 MHz, CD$_3$OD) δ 8.31-8.39 (m, 1H), 7.94-8.02 (m, 1H), 7.52 (d, J = 8.40 Hz, 1H), 5.67-5.70 (m, 2H), 4.81-4.89 (m, 1H), 4.40-4.50, m, 1H), 4.20 (d, J = 16.40 Hz, 3H), 2.72-2.87 (m, 3H), 1.85-2.10 (m, 4H), 1.60-1.73 (m, 4H), 1.10-1.40 (m, 4H), 0.84-0.90 (m, 2H), 0.65-0.76 (m, 4H), 0.56-0.59 (m, 1H).<br>hLPA1 IC$_{50}$ = 61 nM. | Example 3 |
| 82 | 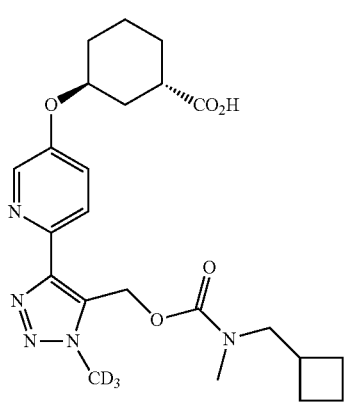 [SMILES: [2H]C([2H])([2H])n1nnc(-c2ccc(O[C@H]3CCC[C@H](C(=O)O)C3)cn2)c1COC(=O)N(C)CC1CCC1]<br>(1S,3S)-3-((6-(5-(((((cyclobutylmethyl)(methyl)carbamoyl)oxy)methyl)-1-(methyl-d3)-1H-1,2,3-triazol-4-yl)pyridin-3-yl)oxy)cyclohexane-1-carboxylic acid | LCMS, [M + H]$^+$ = 460.9<br>$^1$H NMR (500 MHz, DMSO-d$_6$) δ 8.35 (br. s., 1H), 7.99 (d, J = 8.7 Hz, 1H), 7.54 (d, J = 6.6 Hz, 1H), 5.85-5.40 (m, 2H), 4.78 (br. s., 1H), 3.59-2.83 (m, 2H), 2.79-2.60 (m, 4H), 2.03-1.36 (m, 14H), 1.16 (t, J = 7.2 Hz, 1H)<br>hLPA1 IC$_{50}$ = 28 nM. | Example 4 |

TABLE 1-continued

| Example | Structure & Name | Analytical & Biology Data | Method |
|---|---|---|---|
| 83 | 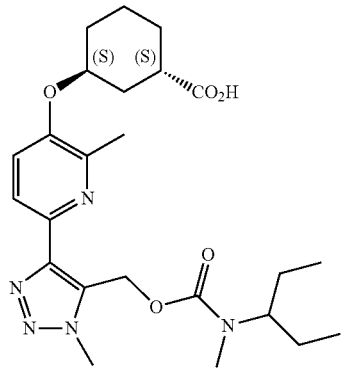<br>(1S,3S)-3-((2-Methyl-6-(1-methyl-5-(((methyl(pentan-3-yl)carbamoyl)oxy)methyl)-1H-1,2,3-triazol-4-yl)pyridin-3-yl)oxy)cyclohexanecarboxylic acid | LCMS, [M + H]$^+$ = 474.4<br>$^1$H NMR (400 MHz, CD$_3$OD) δ 7.68 (d, J = 8.0 Hz, 1H), 7.35-7.40 (m, 1H), 5.55-5.65 (m, 2H), 4.20-4.30 (m, 1H), 4.07 (s, 3H), 3.75-3.90 (m, 1H), 3.55-3.70 (m, 1H), 2.50-2.70 (m, 3H), 2.20-2.40 (m, 3H), 1.80-2.10 (m, 3H), 1.94 (s, 3H), 1.55-1.84 (m, 3H), 1.10-1.40 (m, 3H), 0.70 (t, J = 7.6 Hz, 3H), 0.55 (t, J = 7.2 Hz, 3H).<br>hLPA1 IC$_{50}$ = 92 nM. | Example 2 |
| 84 | 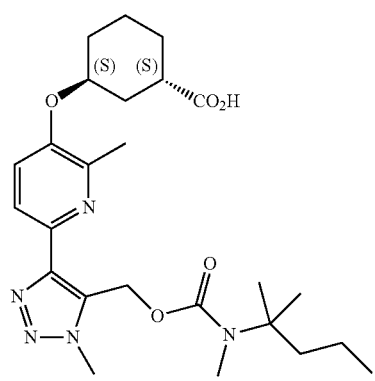<br>(1S,3S)-3-((2-methyl-6-(1-methyl-5-(((methyl(2-methylpentan-2-yl)carbamoyl)oxy)methyl)-1H-1,2,3-triazol-4-yl)pyridin-3-yl)oxy)cyclohexanecarboxylic acid | LCMS, [M + H]$^+$ = 488.2<br>$^1$H NMR (400 MHz, CD$_3$OD) δ 7.70 (d, J = 8.4, 1H), 7.32 (d, J = 8.4 Hz, 1H), 5.56 (s, 2H), 4.07 (s, 3H), 2.74 (s, 3H), 2.62-2.69 (m, 1H), 2.40 (s, 3H), 1.98-2.05 (m, 1H), 1.80-1.90 (m, 3H), 1.45-1.70 (m, 5H), 1.20 (s, 6H), 1.01-1.10 (m, 3H), 0.71-0.79 (m, 1H), 0.60-0.70 (m, 3H).<br>hLPA1 IC$_{50}$ = 69 nM. | Example 1 |
| 85 | 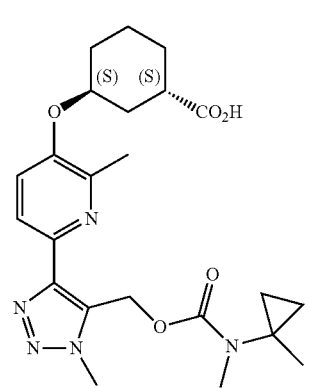<br>(1S,3S)-3-((2-methyl-6-(1-methyl-5-(((methyl(1-methylcyclopropyl)carbamoyl)oxy)methyl)-1H-1,2,3-triazol-4-yl)pyridin-3-yl)oxy)cyclohexane-1-carboxylic acid | LCMS, [M + H]$^+$ = 458.2<br>$^1$H NMR (400 MHz, CD$_3$OD) δ 7.81 (d, J = 8, 1H) 7.44 (d, J = 8 Hz, 1 H) 5.71 (s, 2 H) 4.79-4.81 (m, 1 H) 4.13-4.26 (m, 3H) 2.74-2.88 (m, 4 H) 2.51 (s, 3 H) 2.06-2.18 (m, 1 H) 1.86-1.96 (m, 3 H) 1.62-1.83 (m, 4 H) 1.11 (br. s., 3 H) 0.43-0.85 (m, 4 H)<br>hLPA1 IC$_{50}$ = 58 nM. | Example 1 |

TABLE 1-continued

| Example | Structure & Name | Analytical & Biology Data | Method |
|---|---|---|---|
| 86 | 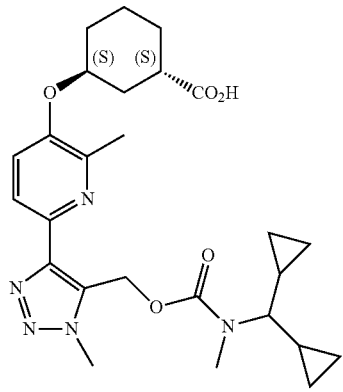<br>(1S,3S)-3-((6-(5-((((Dicyclopropylmethyl)(methyl)carbamoyl)oxy)methyl)-1-methyl-1H-1,2,3-triazol-4-yl)-2-methylpyridin-3-yl)oxy)cyclohexanecarboxylic acid | LCMS, [M + H]$^+$ = 498.3<br>$^1$H NMR (400 MHz, CD$_3$OD) δ 7.79 (d, J = 8.0 Hz, 1H), 7.42 (d, J = 8.0 Hz, 1H), 5.60-5.70 (m, 2H), 4.17 (s, 3H), 2.90 (d, J = 13.2 Hz, 3H), 2.60-2.80 (m, 3H), 2.49 (s, 3H), 2.40-2.55 (m, 3H), 2.05-2.15 (m, 1H), 1.60-1.80 (m, 4H), 1.20-1.40 (m, 2H), 0.90-1.10 (m, 2H), 0.45-0.65 (m, 2H), 0.30-0.40 (m, 2H), 0.10-0.30 (m, 2H).<br>hLPA1 IC$_{50}$ = 54 nM. | Example 1 |
| 87 | 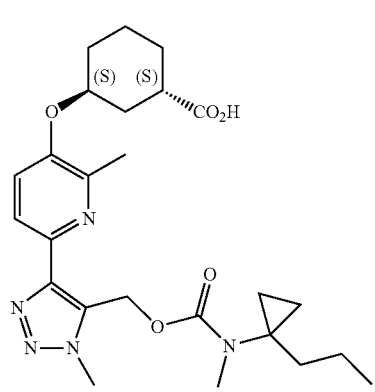<br>(1S,3S)-3-((2-methyl-6-(1-methyl-5-(((methyl(1-propylcyclopropyl)carbamoyl)oxy)methyl)-1H-1,2,3-triazol-4-yl)pyridin-3-yl)oxy)cyclohexane-1-carboxylic acid | LCMS, [M + H]$^+$ = 486.0<br>$^1$H NMR (400 MHz, CD$_3$OD) δ 7.77-7.86 (m, 1 H) 7.44 (d, J = 8.4 Hz, 1 H) 5.71 (d, J = 11.6 Hz, 2H) 4.81-4.84 (m, 1 H), 4.2 (d, J = 8.4 Hz, 1 H), 2.74-2.90 (m, 4H), 2.51 (s, 3H), 2.10-2.15 (m, 1H), 1.91-1.97 (m, 3H), 1.66-1.74 (m, 4H), 1.28-1.37 (m, 2H), 1.12-1.20 (m, 2H), 0.84-0.93 (m, 2H), 0.68-0.71 (m, 5H), 0.51-0.53 (m, 2H).<br>hLPA1 IC$_{50}$ = 36 nM. | Example 1 |
| 88 | 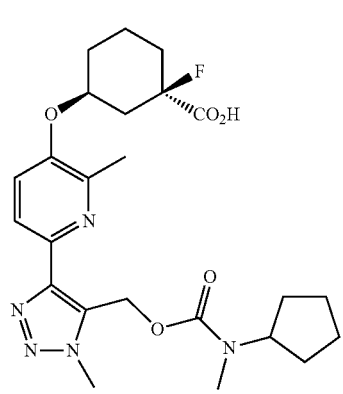 [SMILES: Cc1nc(-c2nnn(C)c2COC(=O)N(C)C2CCCC2)ccc1O[C@H]1CCC[C@](F)(C(=O)O)C1]<br>(rac)-trans-3-((6-(5-(((cyclopentyl(methyl)carbamoyl)oxy)methyl)-1-methyl-1H-1,2,3-triazol-4-yl)-2-methylpyridin-3-yl)oxy)-1-fluorocyclohexane-1-carboxylic acid | LCMS, [M + H]$^+$ = 490.3<br>$^1$H NMR (400 MHz, CDCl$_3$) δ 7.89 (d, J = 8.6 Hz, 1H), 7.24-7.17 (m, 1H), 5.71-5.62 (m, 2H), 4.71 (tt, J = 6.8, 3.7 Hz, 1H), 4.58-4.13 (m, 1H), 4.07 (s, 3H), 2.65 (br. s., 3H), 2.52-2.38 (m, 4H), 2.24-1.32 (m, 15H);<br>hLPA1 IC$_{50}$ = 32 nM. | Example 11 |

TABLE 1-continued

| Example | Structure & Name | Analytical & Biology Data | Method |
|---|---|---|---|
| 89 | 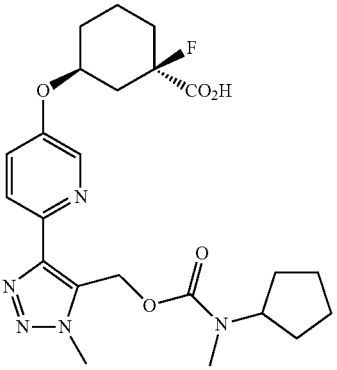 [SMILES: CN(C(=O)OCc1c(-c2ccc(O[C@H]3CCC[C@](F)(C(=O)O)C3)cn2)nnn1C)C1CCCC1]<br>(rac)-trans-3-((6-(5-(((cyclopentyl(methyl)carbamoyl)oxy)methyl)-1-methyl-1H-1,2,3-triazol-4-yl)pyridin-3-yl)oxy)-1-fluorocyclohexane-1-carboxylic acid | LCMS, [M + H]$^+$ = 476.3<br>$^1$H NMR (500 MHz, CDCl$_3$) δ 8.46 (d, J = 2.5 Hz, 1H), 8.05 (d, J = 8.8 Hz, 1H), 7.56 (dd, J = 8.9, 2.6 Hz, 1H), 5.50 (s, 2H), 4.89-4.75 (m, 1H), 4.55-4.44 (m, 1H), 4.10 (s, 3H), 2.64 (br. s., 3H), 2.56-2.37 (m, 4H), 2.19-1.37 (m, 15H)<br>hLPA1 IC$_{50}$ = 32 nM. | Example 11 |
| 90 | 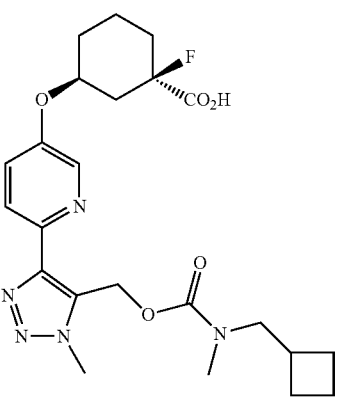 [SMILES: CN(CC1CCC1)C(=O)OCc1c(-c2ccc(O[C@H]3CCC[C@](F)(C(=O)O)C3)cn2)nnn1C]<br>(rac)-trans-3-((6-(5-((((cyclobutylmethyl)(methyl)carbamoyl)oxy)methyl)-1-methyl-1H-1,2,3-triazol-4-yl)pyridin-3-yl)oxy)-1-fluorocyclohexane-1-carboxylic acid | LCMS, [M + H]$^+$ = 476.3<br>$^1$H NMR (500 MHz, CDCl$_3$) δ 8.60 (d, J = 2.5 Hz, 1H), 8.18 (d, J = 8.5 Hz, 1H), 7.76 (d, J = 8.8 Hz, 1H), 5.56 (s, 2H), 4.92 (br. s., 1H), 4.65-4.50 (m, 1H), 4.21 (d, J = 3.0 Hz, 3H), 2.85 (d, J = 17.1 Hz, 3H), 2.66-2.41 (m, 4H), 2.29-1.48 (m, 15H)<br>hLPA1 IC$_{50}$ = 14 nM. | Example 11 |
| 91 | 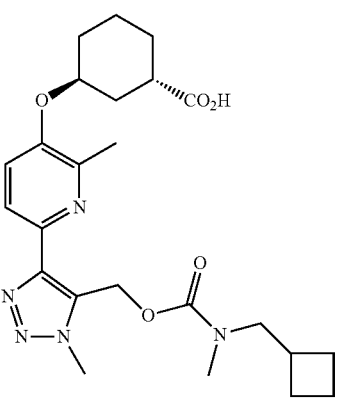 [SMILES: Cc1nc(-c2nnn(C)c2COC(=O)N(C)CC2CCC2)ccc1O[C@H]1CCC[C@H](C(=O)O)C1]<br>(rac)-trans-3-((6-(5-((((cyclobutylmethyl)(methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 473.4<br>$^1$H NMR (500 MHz, CDCl$_3$) δ 8.11 (d, J = 8.8 Hz, 1H), 7.80 (t, J = 8.9 Hz, 1H), 5.70-5.42 (m, 2H), 4.86 (br. s., 1H), 4.20 (d, J = 1.7 Hz, 3H), 3.39-3.26 (m, 3H), 2.90 (d, J = 7.7 Hz, 3H), 2.77-2.69 (m, 3H), 2.19-1.63 (m, 15H)<br>hLPA1 IC$_{50}$ = 18 nM. | Example 2 |

TABLE 1-continued

| Example | Structure & Name | Analytical & Biology Data | Method |
|---|---|---|---|
| 92 | 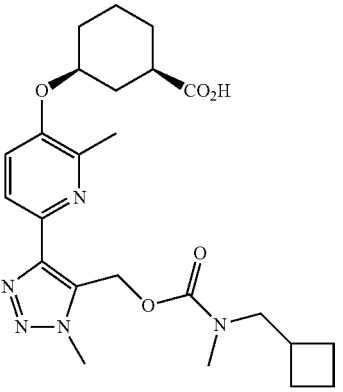 [SMILES: Cc1nc(-c2nnn(C)c2COC(=O)N(C)CC2CCC2)ccc1O[C@H]1CCC[C@@H](C(=O)O)C1]<br>(rac)-cis-3-((6-(5-(((((cyclobutylmethyl)(methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 472.3<br>$^1$H NMR (400 MHz, CDCl$_3$) δ 8.08 (d, J = 8.6 Hz, 1H), 7.66 (t, J = 8.6 Hz, 1H), 5.72 (d, J = 14.5 Hz, 1H), 5.47 (d, J = 14.3 Hz, 1H), 4.58 (br. s., 1H), 4.21 (s, 3H), 3.40-3.19 (m, 2H), 2.90 (s, 3H), 2.70 (d, J = 2.6 Hz, 3H), 2.64-2.46 (m, 2H), 2.31-1.48 (m, 14H)<br>hLPA1 IC$_{50}$ = 76 nM. | Example 2 |
| 93 | 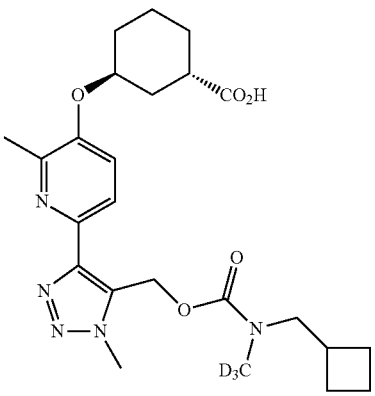 [SMILES: [2H]C([2H])([2H])N(CC1CCC1)C(=O)OCc1c(-c2ccc(O[C@H]3CCC[C@H](C(=O)O)C3)c(C)n2)nnn1C]<br>(1S,3S)-3-((6-(5-(((((cyclobutylmethyl)(methyl-d3)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 475.1<br>$^1$H NMR (500 MHz, CDCl$_3$) δ 8.10 (br. s., 1H), 7.87 (br. s., 1H), 5.90-5.21 (m, 2H), 4.21 (br. s., 3H), 3.30 (t, J = 8.0 Hz, 2H), 2.85 (br. s., 1H), 2.73 (br. s., 3H), 2.63-2.47 (m, 1H), 2.24-1.52 (m, 16H)<br>hLPA1 IC$_{50}$ = 20 nM. | Example 4 |
| 94 | 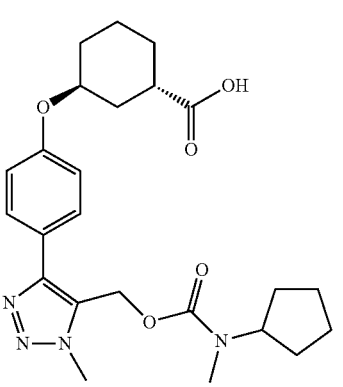<br>(1S,3S)-3-(4-(5-(1-((cyclopentyl(methyl)carbamoyl)oxy)ethyl)-1-methyl-1H-1,2,3-triazol-4-yl)phenoxy)cyclohexane-1-carboxylic acid | LCMS, [M + H]$^+$ = 471.3<br>$^1$H NMR (500 MHz, DMSO-d$_6$) δ 7.58 (br. S., 2H), 7.05 (d, J = 8.0 Hz, 2H), 6.00 (d, J = 6.9 Hz, 1H), 4.69 (br. S., 1H), 4.40-4.22 (m, 1H), 4.13 (s, 3H), 2.65 (br. S., 4H), 1.98-1.35 (m, 19H)<br>hLPA1 IC$_{50}$ = 241 nM. | Example 14 |

TABLE 1-continued

| Example | Structure & Name | Analytical & Biology Data | Method |
|---|---|---|---|
| 95 | (Cis)-3-((6-(5-((((cyclobutylmethyl)(methyl)carbamoyl)oxy)methyl)-1-methyl-1H-1,2,3-triazol-4-yl)-2-methylpyridin-3-yl)oxy)cyclohexane-1-carboxylic acid; Enantiomer A | LCMS, [M + H]$^+$ = 472.3 $^1$H NMR (400 MHz, CDCl$_3$) δ 7.91 (d, J = 8.1 Hz, 1H), 7.16 (dd, J = 8.3, 3.6 Hz, 1H), 5.74 (br. S., 2H), 4.32-4.18 (m, 1H), 4.13 (br. S., 3H), 3.35-3.11 (m, 2H), 2.92-2.75 (m, 3H), 2.56-2.24 (m, 5H), 2.17-1.35 (m, 15H) hLPA1 IC$_{50}$ = 1152 nM. | Example 1 |
| 96 | (Cis)-3-((6-(5-((((cyclobutylmethyl)(methyl)carbamoyl)oxy)methyl)-1-methyl-1H-1,2,3-triazol-4-yl)-2-methylpyridin-3-yl)oxy)cyclohexane-1-carboxylic acid Enantiomer B | LCMS, [M + H]$^+$ = 472.3 $^1$H NMR (400 MHz, CDCl$_3$) δ 7.86 (d, J = 8.6 Hz, 1H), 7.11 (d, J = 8.6 Hz, 1H), 5.67 (br. s., 2H), 4.23-4.12 (m, 1H), 4.06 (br. s., 3H), 3.31-3.01 (m, 2H), 2.86-2.65 (m, 3H), 2.42-2.30 (m, 4H), 2.16-1.31 (m, 15H) hLPA1 IC$_{50}$ = 20 nM. | Example 1 |
| 97 | | LCMS, [M + H]$^+$ = 472.3 $^1$H NMR (400 MHz, CDCl$_3$) δ 8.03-7.90 (m, 1H), 7.23 (d, J = 8.6 Hz, 1H), 5.77 (br d, J = 5.3 Hz, 2H), 4.72 (br s, 1H), 4.16 (br s, 3H), 3.38-3.15 (m, 2H), 2.90 (br s, 3H), 2.80 (br s, 2H), 2.59 (br s, 1H), 2.45-2.36 (m, 1H), 2.23-2.10 (m, 1H), 2.08-1.52 (m, 14H) hLPA1 IC$_{50}$ = 10 nM. | Example 1 |

| Example | Structure & Name | Analytical & Biology Data | Method |
|---|---|---|---|
| | (1R,3R)-3-((6-(5-(((((cyclobutylmethyl)(methyl)carbamoyl)oxy)methyl)-1-methyl-1H-1,2,3-triazol-4-yl)-2-methylpyridin-3-yl)oxy)cyclohexane-1-carboxylic acid | | |
| 98 | 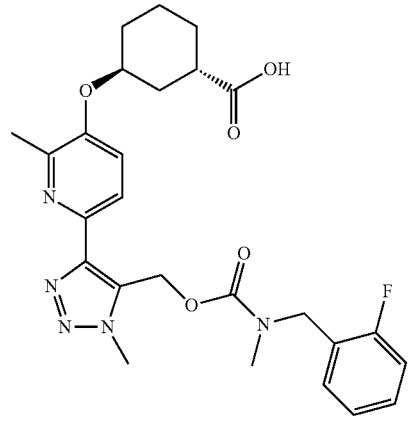<br>(1S,3S)-3-((6-(5-((((2-fluorobenzyl)(methyl)carbamoyl)oxy)methyl)-1-methyl-1H-1,2,3-triazol-4-yl)-2-methylpyridin-3-yl)oxy)cyclohexane-1-carboxylic acid | LCMS, $[M + H]^+$ = 512.3<br>$^1$H NMR (600 MHz, DMSO-$d_6$) δ 7.84 (d, J = 5.2 Hz, 1H), 7.46 (br. s., 1H), 7.41-6.79 (m, 4H), 5.87-5.59 (m, 2H), 4.78 (br. s., 1H), 4.51-4.26 (m, 2H), 4.15-3.91 (m, 3H), 3.53-3.37 (m, 1H), 2.87-2.69 (m, 3H), 2.67-2.58 (m, 1H), 2.46-2.30 (m, 3H), 2.07-1.44 (m, 8H)<br>hLPA1 IC$_{50}$ = 19 nM. | Example 1 |
| 99 | 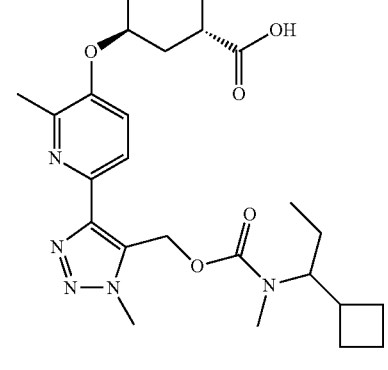<br>(1S,3S)-3-((6-(5-((((1-cyclobutylpropyl)(methyl)carbamoyl)oxy)methyl)-1-methyl-1H-1,2,3-triazol-4-yl)-2-methylpyridin-3-yl)oxy)cyclohexane-1-carboxylic acid<br>(diastereomeric mixture) | LCMS, $[M + H]^+$ = 486.3<br>$^1$H NMR (600 MHz, DMSO-$d_6$) δ 7.47 (d, J = 8.5 Hz, 1H), 6.98 (d, J = 9.1 Hz, 1H), 5.65 (br. s., 2H), 4.77 (br. s., 1H), 4.07 (s, 3H), 3.51 (br. s., 4H), 2.66-2.57 (m, 1H), 2.40 (br. s., 3H), 2.29-2.19 (m, 1H), 2.05-1.97 (m, 1H), 1.89-1.43 (m, 14H), 1.25 (d, J = 7.3 Hz, 3H), 0.76 (t, J = 7.3 Hz, 3H)<br>hLPA1 IC$_{50}$ = 144 nM. | Example 1 |

TABLE 1-continued

| Example | Structure & Name | Analytical & Biology Data | Method |
|---|---|---|---|
| 100 | 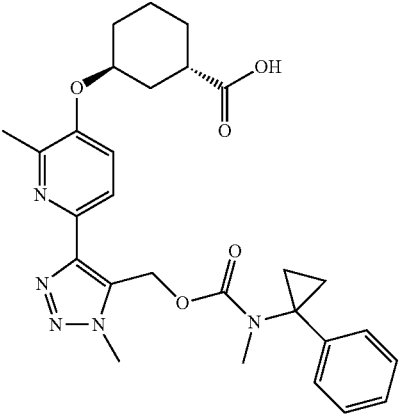 [SMILES: Cc1nc(-c2nnn(C)c2COC(=O)N(C)C2(c3ccccc3)CC2)ccc1O[C@H]1CCC[C@H](C(=O)O)C1]<br>(1S,3S)-3-((2-methyl-6-(1-methyl-5-(((methyl(1-phenylcyclopropyl)carbamoyl)oxy)methyl)-1H-1,2,3-triazol-4-yl)pyridin-3-yl)oxy)cyclohexane-1-carboxylic acid | LCMS, $[M + H]^+$ = 520.0<br>$^1$H NMR (400 MHz, CD$_3$OD) δ 7.60-7.69 (m, 1 H) 7.01-7.34 (m, 5 H) 6.78-6.88 (m, 1H) 5.60-5.68 (m, 2 H) 4.08-4.14 (m, 1 H) 3.76-3.86 (m, 3 H) 2.88-2.94 (m, 3 H) 2.80-2.83 (m, 1 H) 2.32-2.44 (m, 3H) 1.86-1.92 (m, 4 H) 1.54-1.67 (m, 4 H) 1.18-1.27 (m, 4 H)<br>hLPA1 IC$_{50}$ = 70 nM. | Example 5 |
| 101 | 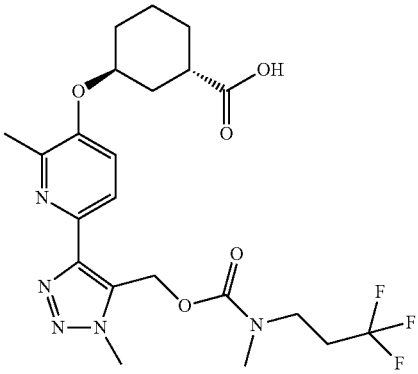 [SMILES: Cc1nc(-c2nnn(C)c2COC(=O)N(C)CCC(F)(F)F)ccc1O[C@H]1CCC[C@H](C(=O)O)C1]<br>(1S,3S)-3-((2-methyl-6-(1-methyl-5-(((methyl(3,3,3-trifluoropropyl)carbamoyl)oxy)methyl)-1H-1,2,3-triazol-4-yl)pyridin-3-yl)oxy)cyclohexane-1-carboxylic acid | LCMS, $[M + H]^+$ = 500.0<br>$^1$H NMR (400 MHz, CD$_3$OD) δ 7.60-7.69 (m, 1 H) 7.01-7.34 (m, 5 H) 6.78-6.88 (m, 1 H) 5.60-5.68 (m, 2 H) 4.08-4.14 (m, 1 H) 3.76-3.86 (m, 3 H) 2.88-2.94 (m, 3 H) 2.80-2.83 (m, 1 H) 2.32-2.44 (m, 3H) 1.86-1.92 (m, 4 H) 1.54-1.67 (m, 4 H) 1.18-1.27 (m, 4 H)<br>hLPA1 IC$_{50}$ = 49 nM. | Example 5 |
| 102 | 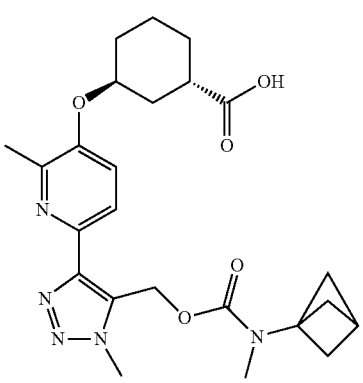 [SMILES: Cc1nc(-c2nnn(C)c2COC(=O)N(C)C23CC(C2)C3)ccc1O[C@H]1CCC[C@H](C(=O)O)C1] | LCMS, $[M + H]^+$ = 469.9<br>$^1$H NMR (500 MHz, DMSO-d$_6$) δ 7.83 (d, J = 8.4 Hz, 1H), 7.48 (d, J = 8.6 Hz, 1H), 5.61 (s, 2H), 4.87-4.69 (m, 1H), 4.10 (s, 3H), 2.71 (br. S., 3H), 2.55 (s, 3H), 2.40 (s, 3H), 2.07-1.47 (m, 15H)<br>hLPA1 IC$_{50}$ = 53 nM. | Example 1 |

TABLE 1-continued

| Example | Structure & Name | Analytical & Biology Data | Method |
|---|---|---|---|
| | (1S,3S)-3-((6-(5-(((bicyclo[1.1.1]pentan-1-yl(methyl)carbamoyl)oxy)methyl)-1-methyl-1H-1,2,3-triazol-4-yl)-2-methylpyridin-3-yl)oxy)cyclohexane-1-carboxylic acid | | |
| 103 | (1S,3S)-3-((2-methyl-6-(1-methyl-5-(((methyl(phenethyl)carbamoyl)oxy)methyl)-1H-1,2,3-triazol-4-yl)pyridin-3-yl)oxy)cyclohexane-1-carboxylic acid | LCMS, [M + H]$^+$ = 508.2<br>$^1$H NMR (400 MHz, CD$_3$OD) δ 7.84-7.88 (m, 1 H) 7.46 (br. s., 1 H) 7.12-7.31 (m, 4 H) 6.97-7.01 (m, 1 H) 5.60-5.73 (m, 2H) 4.80 (br. s., 1 H) 4.12 (br. s., 3 H) 3.46-3.53 (m, 3 H) 2.74-2.85 (m, 4 H) 2.63 (d, J = 7.03 Hz, 1 H) 2.46 (br. s., 3 H) 2.09 (br. s., 1 H) 1.94 (br. s., 3 H) 1.61-1.73 (m, 4 H)<br>hLPA1 IC$_{50}$ = 119 nM. | Example 5 |
| 104 | (1S,3S)-3-((2-methyl-6-(1-methyl-5-(((methyl(propyl)carbamoyl)oxy)methyl)-1H-1,2,3-triazol-4-yl)pyridin-3-yl)oxy)cyclohexane-1-carboxylic acid | LCMS, [M + H]$^+$ = 446.1<br>$^1$H NMR (400 MHz, CD$_3$OD) δ 7.81 (d, J = 8.53 Hz, 1 H) 7.44 (d, J = 8.53 Hz, 1 H) 5.71 (br. s., 2 H) 4.81 (br. s., 1 H) 4.19 (s, 3 H) 3.09-3.17 (m, 2 H) 2.81-2.90 (m, 4 H) 2.51 (s, 3 H) 2.14 (br. s., 1 H) 1.88-1.92 (m, 3 H) 1.68-1.71 (m, 4 H) 1.56 (br. s., 2 H) 0.88 (d, J = 7.03 Hz, 3 H)<br>hLPA1 IC$_{50}$ = 19 nM | Example 5 |
| 105 | | LCMS, [M + H]$^+$ = 456.3<br>hLPA1 IC$_{50}$ = 576 nM. | Example 3 |

TABLE 1-continued

| Example | Structure & Name | Analytical & Biology Data | Method |
|---|---|---|---|
| | (1S,3S)-3-((6-(5-((((bicyclo[1.1.1]pentan-1-ylcarbamoyl)oxy)methyl)-1-methyl-1H-1,2,3-triazol-4-yl)-2-methylpyridin-3-yl)oxy)cyclohexane-1-carboxylic acid | | |
| 106 | (1S,3S)-3-((6-(5-((((1,3-dimethylcyclobutyl)(methyl)carbamoyl)oxy)methyl)-1-methyl-1H-1,2,3-triazol-4-yl)-2-methylpyridin-3-yl)oxy)cyclohexane-1-carboxylic acid Enantiomer A | LCMS, [M + H]$^+$ = 486.1 $^1$H NMR (400 MHz, CD$_3$OD) δ 7.79 (d, J = 8.53 Hz, 1 H) 7.44 (d, J = 8.53 Hz, 1 H) 5.66 (s, 2 H) 4.19 (s, 3H) 2.68 (d, J = 6.02 Hz, 1 H) 2.52 (s, 3 H) 2.12 (d, J = 13.05 Hz, 3 H) 1.94 (br. s., 3H) 1.58-1.79 (m, 5H) 1.31 (br. s., 6 H) 1.13 (br. s., 3 H) 0.93-0.96 (m, 3 H) hLPA1 IC$_{50}$ = 67 nM. | Example 5 |
| 107 | (1S,3S)-3-((6-(5-((((1,3-dimethylcyclobutyl)(methyl)carbamoyl)oxy)methyl)-1-methyl-1H-1,2,3-triazol-4-yl)-2-methylpyridin-3-yl)oxy)cyclohexane-1-carboxylic acid Enantiomer B | LCMS, [M + H]$^+$ = 486.1 $^1$H NMR (400 MHz, CD$_3$OD) δ ppm 7.79 (d, J = 8.53 Hz, 1 H) 7.44 (d, J = 8.53 Hz, 1 H) 5.66 (s, 2 H) 4.19 (s, 3H) 2.68 (d, J = 6.02 Hz, 1 H) 2.52 (s, 3 H) 2.12 (d, J = 13.05 Hz, 3 H) 1.94 (br. s., 3H) 1.58-1.79 (m, 5H) 1.31 (br. s., 6 H) 1.13 (br. s., 3 H) 0.93-0.96 (m, 3 H) hLPA1 IC$_{50}$ = 70 nM. | Example 5 |

TABLE 1-continued

| Example | Structure & Name | Analytical & Biology Data | Method |
|---|---|---|---|
| 108 | 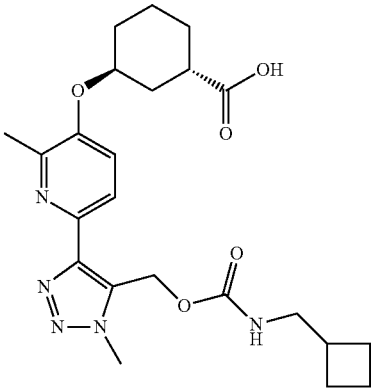 [SMILES: Cc1nc(-c2nnn(C)c2COC(=O)NCC2CCC2)ccc1O[C@H]1CCC[C@H](C(=O)O)C1]<br>(1S,3S)-3-((6-(5-((((cyclobutylmethyl)carbamoyl)oxy)methyl)-1-methyl-1H-1,2,3-triazol-4-yl)-2-methylpyridin-3-yl)oxy)cyclohexane-1-carboxylic acid | LCMS, $[M + H]^+$ = 458.0<br>$^1$H NMR (500 MHz, DMSO-$d_6$) δ 7.83 (d, J = 8.2 Hz, 1H), 7.58-7.37 (m, 1H), 7.29 (br. s., 1H), 5.64 (s, 2H), 4.77 (br. s., 1H), 4.07 (s, 3H), 3.01 (t, J = 6.0 Hz, 2H), 2.44-2.31 (m 4H), 2.05-1.40 (m, 15H)<br>hLPA1 $IC_{50}$ = 108 nM. | Example 1 |
| 109 | 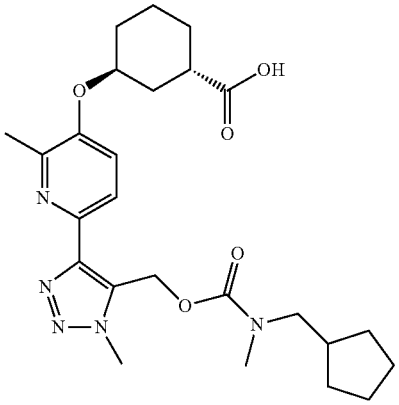 [SMILES: Cc1nc(-c2nnn(C)c2COC(=O)N(C)CC2CCCC2)ccc1O[C@H]1CCC[C@H](C(=O)O)C1]<br>(1S,3S)-3-((6-(5-((((cyclopentylmethyl)(methyl)carbamoyl)oxy)methyl)-1-methyl-1H-1,2,3-triazol-4-yl)-2-methylpyridin-3-yl)oxy)cyclohexane-1-carboxylic acid | LCMS, $[M + H]^+$ = 486.2<br>$^1$H NMR (400 MHz, DMSO-$d_6$) δ 6.97-7.04 (m, 1 H) 6.60-6.67 (m, 1 H) 4.89 (s, 2 H) 3.99-4.01 (m, 1 H) 3.38 (s, 3 H) 2.39-2.43 (m, 1 H) 2.26-2.30 (m, 1 H) 2.08 (s, 3 H) 1.70 (s, 3 H) 1.28-1.33 (m, 1 H) 1.10-1.19 (m, 4 H) 0.46-0.98 (m, 12 H) 0.39-0.42 (m, 1 H)<br>hLPA1 $IC_{50}$ = 22 nM. | Example 5 |
| 110 | 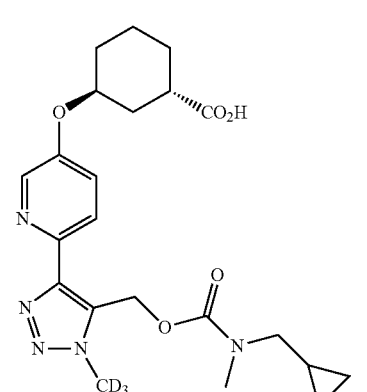 | LCMS, $[M + H]^+$ = 447.4<br>$^1$H NMR (500 MHz, DMSO-$d_6$) δ 8.34 (br. s., 1H), 7.98 (d, J = 7.7 Hz, 1H), 7.53 (d, J = 7.5 Hz, 1H), 7.36-6.86 (m, 1H), 6.03-5.43 (m, 2H), 4.77 (br. s., 1H), 3.26-2.57 (m, 6H), 2.19-1.31 (m, 8H), 1.07-0.65 (m, 1H), 0.62--0.21 (m, 4H)<br>hLPA1 $IC_{50}$ = 31 nM. | Example 4 |

TABLE 1-continued

| Example | Structure & Name | Analytical & Biology Data | Method |
|---|---|---|---|
|  | (1S,3S)-3-((6-(5-((((cyclopropylmethyl)(methyl)carbamoyl)oxy)methyl)-1-(methyl-d3)-1H-1,2,3-triazol-4-yl)pyridin-3-yl)oxy)cyclohexane-1-carboxylic acid |  |  |
| 111 | (1S,3S)-3-((6-(5-(((cyclopentyl(methyl)carbamoyl)oxy)methyl)-1-(methyl-d3)-1H-1,2,3-triazol-4-yl)pyridin-3-yl)oxy)cyclohexane-1-carboxylic acid | LCMS, [M + H]$^+$ = 461.2<br>$^1$H NMR (500 MHz, DMSO-d$_6$) δ 8.33 (d, J = 2.4 Hz, 1H), 7.98 (d, J = 8.8 Hz, 1H), 7.53 (d, J = 6.3 Hz, 1H), 5.60 (br. s., 2H), 4.77 (br. s., 1H), 3.59 (br. s., 1H), 2.63 (br. s., 4H), 1.94 (br. s., 1H), 1.86-1.69 (m, 3H), 1.68-1.25 (m, 12H)<br>hLPA1 IC$_{50}$ = 23 nM. | Example 4 |
| 112 | (1S,3S)-3-((6-(5-(((butyl(methyl)carbamoyl)oxy)methyl)-1-(methyl-d3)-1H-1,2,3-triazol-4-yl)pyridin-3-yl)oxy)cyclohexane-1-carboxylic acid | LCMS, [M + H]$^+$ = 449.4<br>$^1$H NMR (500 MHz, DMSO-d$_6$) δ 8.34 (d, J = 2.3 Hz, 1H), 7.98 (d, J = 8.8 Hz, 1H), 7.54 (d, J = 7.6 Hz, 1H), 5.83-5.25 (m, 2H), 4.77 (br. s., 1H), 3.29-2.97 (m, 2H), 2.85-2.59 (m, 4H), 1.94 (br. s., 1H), 1.88-1.71 (m, 3H), 1.68-1.33 (m, 5H), 1.31-1.14 (m, 2H), 1.08-0.55 (m, 4H)<br>hLPA1 IC$_{50}$ = 17 nM. | Example 4 |
| 113 |  | LC/MS: [M + H]$^+$ = 486.1<br>$^1$H NMR (500 MHz, DMSO-d$_6$) δ 7.99-7.72 (m, 1H), 7.48 (br d, J = 7.4 Hz, 1H), 5.62 (br s, 3H), 4.79 (br s, 1H), 4.10 (br s, 4H), 3.31-2.96 (m, 5H), 2.71-2.59 (m, 1H), 2.41 (br s, 3H), 1.97-1.77 (m, 6H), 1.59-1.34 (m, 6H), 1.07-0.76 (m, 4H)<br>hLPA1 IC$_{50}$ = 15 nM | Example 1 |

| Example | Structure & Name | Analytical & Biology Data | Method |
|---|---|---|---|
| | (1S,3S)-3-((6-(5-(((((cyclobutylmethyl)(ethyl)carbamoyl)oxy)methyl)-1-methyl-1H-1,2,3-triazol-4-yl)-2-methylpyridin-3-yl)oxy)cyclohexane-1-carboxylic acid | | |
| 114 | (1S,3S)-3-((2-methyl-6-(1-methyl-5-(((morpholine-4-carbonyl)oxy)methyl)-1H-1,2,3-triazol-4-yl)pyridin-3-yl)oxy)cyclohexane-1-carboxylic acid | LC/MS: [M + H]$^+$ = 460.2<br>$^1$H NMR (500 MHz, DMSO-d$_6$) δ 7.80 (br d, J = 8.6 Hz, 1H), 7.45 (br d, J = 8.7 Hz, 1H), 5.65 (s, 2H), 4.76 (br s, 1H), 4.06 (s, 2H), 3.93-3.84 (m, 2H), 3.61-3.17 (m, 7H), 2.66-2.58 (m, 1H), 2.39 (s, 3H), 2.12-1.29 (m, 8H)<br>hLPA1 IC$_{50}$ = 643 nM | Example 1 |
| 115 | (1S,3S)-3-((6-(5-(((((cyclopropylmethyl)(methyl)carbamoyl)oxy)methyl)-1-methyl-1H-1,2,3-triazol-4-yl)-2-methylpyridin-3-yl)oxy)cyclohexane-1-carboxylic acid | LC/MS: [M + H]$^+$ = 458.2<br>$^1$H NMR (500 MHz, DMSO-d$_6$) δ 7.84 (br d, J = 8.2 Hz, 1H), 7.48 (br d, J = 7.7 Hz, 1H), 5.86-5.45 (m, 2H), 4.78 (br s, 1H), 4.10 (s, 3H), 3.12-2.92 (m, 2H), 2.89-2.76 (m, 3H), 2.62 (br s, 1H), 2.41 (s, 3H), 2.09-1.42 (m, 8H), 0.97-0.64 (m, 1H), 0.55--0.10 (m, 4H)<br>hLPA1 IC$_{50}$ = 18 nM | Example 1 |
| 116 | | LC/MS: [M + H]$^+$ = 460.2<br>$^1$H NMR (500 MHz, DMSO-d$_6$) δ 8.03-7.74 (m, 1H), 7.47 (br d, J = 7.7 Hz, 1H), 6.06-5.43 (m, 2H), 4.78 (br s, 1H), 4.10 (s, 3H), 3.02 (br d, J = 6.8 Hz, 1H), 2.88 (br d, J = 6.9 Hz, 1H), 2.81-2.69 (m, 3H), 2.62 (br t, J = 10.2 Hz, 1H), 2.41 (s, 3H), 2.12-1.42 (m, 9H), 0.81 (br d, J = 6.1 Hz, 3H), 0.62 (br d, J = 5.8 Hz, 3H)<br>hLPA1 IC$_{50}$ = 29 nM | Example 1 |

TABLE 1-continued

| Example | Structure & Name | Analytical & Biology Data | Method |
|---|---|---|---|
| | (1S,3S)-3-((6-(5-(((isobutyl(methyl)carbamoyl)oxy)methyl)-1-methyl-1H-1,2,3-triazol-4-yl)-2-methylpyridin-3-yl)oxy)cyclohexane-1-carboxylic acid | | |
| 117 | (1S,3S)-3-((2-methyl-6-(1-methyl-5-(((methyl((tetrahydro-2H-pyran-4-yl)methyl)carbamoyl)oxy)methyl)-1H-1,2,3-triazol-4-yl)pyridin-3-yl)oxy)cyclohexane-1-carboxylic acid | LC/MS: [M + H]$^+$ = 502.1<br>$^1$H NMR (500 MHz, DMSO-d$_6$) δ 7.85 (br d, J = 6.1 Hz, 1H), 7.48 (br d, J = 8.6 Hz, 1H), 5.73-5.48 (m, 2H), 4.78 (br s, 1H), 4.10 (br d, J = 7.7 Hz, 3H), 3.82 (br d, J = 8.8 Hz, 1H), 3.62 (br d, J = 12.5 Hz, 1H), 3.24 (br s, 1H), 3.17 (s, 1H), 3.09 (br d, J = 6.3 Hz, 1H), 3.04-2.92 (m, 2H), 2.84-2.72 (m, 3H), 2.41 (s, 3H), 2.05-1.10 (m, 13H)<br>hLPA1 IC$_{50}$ = 17 nM | Example 1 |
| 118 | (1S,3S)-3-((2-methyl-6-(1-methyl-5-(((methyl(pyridin-2-ylmethyl)carbamoyl)oxy)methyl)-1H-1,2,3-triazol-4-yl)pyridin-3-yl)oxy)cyclohexane-1-carboxylic acid | LC/MS: [M + H]$^+$ = 495.0<br>$^1$H NMR (500 MHz, DMSO-d$_6$) δ 8.69-7.72 (m, 2H), 7.72-7.03 (m, 4H), 5.79-5.58 (m, 2H), 4.78 (br s, 1H), 4.45 (s, 2H), 4.27-3.82 (m, 2H), 3.17 (s, 1H), 2.97-2.75 (m, 3H), 2.63 (br s, 1H), 2.44-2.29 (m, 3H), 2.02 (br d, J = 12.7 Hz, 1H), 1.93-1.40 (m, 7H)<br>hLPA1 IC$_{50}$ = 211 nM | Example 1 |
| 119 | | LC/MS: [M + H]$^+$ = 432.1<br>$^1$H NMR (500 MHz, DMSO-d$_6$) δ 7.84 (d, J = 8.5 Hz, 1H), 7.48 (br d, J = 8.6 Hz, 1H), 5.64 (br d, J = 13.1 Hz, 2H), 4.78 (br s, 1H), 4.09 (s, 3H), 3.31-3.04 (m, 2H), 2.84-2.70 (m, 3H), 2.62 (br s, 1H), 2.41 (s, 3H), 2.01 (br d, J = 14.1 Hz, 1H), 1.92-1.72 (m, 3H), 1.69-1.43 (m, 4H), 1.08-0.78 (m, 3H)<br>hLPA1 IC$_{50}$ = 878 nM | Example 1 |

TABLE 1-continued

| Example | Structure & Name | Analytical & Biology Data | Method |
|---|---|---|---|
|  | (1S,3S)-3-((6-(5-(((ethyl(methyl)carbamoyl)oxy)methyl)-1-methyl-1H-1,2,3-triazol-4-yl)-2-methylpyridin-3-yl)oxy)cyclohexane-1-carboxylic acid | | |
| 120 | (1S,3S)-3-((2-methyl-6-(1-methyl-5-(((methyl(pyridin-3-ylmethyl)carbamoyl)oxy)methyl)-1H-1,2,3-triazol-4-yl)pyridin-3-yl)oxy)cyclohexane-1-carboxylic acid | LC/MS: [M + H]$^+$ = 495.1<br>$^1$H NMR (500 MHz, DMSO-d$_6$) δ 8.64-8.27 (m, 2H), 7.85 (d, J = 8.6 Hz, 1H), 7.70-7.31 (m, 2H), 6.59 (s, 1H), 5.81-5.57 (m, 2H), 4.79 (br s, 1H), 4.52-4.27 (m, 2H), 4.20-3.96 (m, 2H), 3.39 (br s, 1H), 2.98-2.70 (m, 3H), 2.63 (br d, J = 9.8 Hz, 1H), 2.38 (br d, J = 17.8 Hz, 2H), 2.10-1.96 (m, 1H), 1.91-1.04 (m, 8H)<br>hLPA1 IC$_{50}$ = 809 nM | Example 1 |
| 121 | (1S,3S)-3-((2-methyl-6-(1-methyl-5-(((methyl(pyrimidin-2-ylmethyl)carbamoyl)oxy)methyl)-1H-1,2,3-triazol-4-yl)pyridin-3-yl)oxy)cyclohexane-1-carboxylic acid | LC/MS: [M + H]$^+$ = 496.1<br>$^1$H NMR (500 MHz, DMSO-d$_6$) δ 8.76 (br d, J = 4.9 Hz, 1H), 8.61 (d, J = 4.9 Hz, 1H), 7.95-7.68 (m, 1H), 7.50-7.20 (m, 2H), 5.85-5.44 (m, 2H), 4.77 (br s, 1H), 4.67-4.49 (m, 2H), 4.13 (s, 1H), 2.95-2.75 (m, 4H), 2.64 (br s, 1H), 2.44-2.33 (m, 4H), 2.09-1.97 (m, 1H), 1.91-1.74 (m, 4H), 1.68-1.48 (m, 4H)<br>hLPA1 IC$_{50}$ = 1087 nM | Example 1 |

TABLE 1-continued

| Example | Structure & Name | Analytical & Biology Data | Method |
|---|---|---|---|
| 122 | 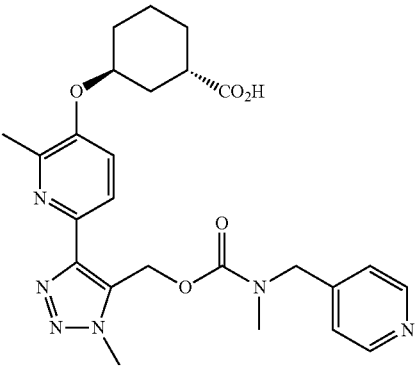 [SMILES: Cc1nc(-c2nnn(C)c2COC(=O)N(C)Cc2ccncc2)ccc1O[C@H]1CCC[C@H](C(=O)O)C1]<br>(1S,3S)-3-((2-methyl-6-(1-methyl-5-(((methyl(pyridin-4-ylmethyl)carbamoyl)oxy)methyl)-1H-1,2,3-triazol-4-yl)pyridin-3-yl)oxy)cyclohexane-1-carboxylic acid | LC/MS: $[M + H]^+$ = 495.0<br>$^1$H NMR (500 MHz, DMSO-$d_6$) δ 8.85-8.33 (m, 1H), 8.06-7.72 (m, 1H), 7.58-7.39 (m, 2H), 7.37-6.99 (m, 2H), 6.04-5.53 (m, 2H), 4.87-4.31 (m, 2H), 4.23-3.84 (m, 3H), 3.17 (s, 1H), 2.93-2.73 (m, 3H), 2.67-2.57 (m, 1H), 2.43-2.29 (m, 3H), 2.02 (br d, J = 13.9 Hz, 1H), 1.90-1.73 (m, 2H), 1.66-1.47 (m, 2H), 1.37-1.14 (m, 2H), 1.00 (br d, J = 6.1 Hz, 1H), 0.85 (br d, J = 6.3 Hz, 1H)<br>hLPA1 $IC_{50}$ = 873 nM | Example 1 |
| 123 | 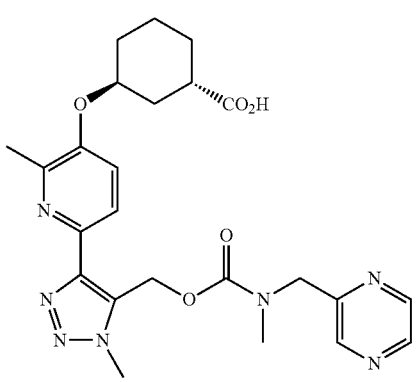 [SMILES: Cc1nc(-c2nnn(C)c2COC(=O)N(C)Cc2cnccn2)ccc1O[C@H]1CCC[C@H](C(=O)O)C1]<br>(1S,3S)-3-((2-methyl-6-(1-methyl-5-(((methyl(pyrazin-2-ylmethyl)carbamoyl)oxy)methyl)-1H-1,2,3-triazol-4-yl)pyridin-3-yl)oxy)cyclohexane-1-carboxylic acid | LC/MS: $[M + H]^+$ = 496.1<br>$^1$H NMR (500 MHz, DMSO-$d_6$) δ 8.63-8.51 (m, 1H), 8.47-8.30 (m, 1H), 7.96-7.59 (m, 1H), 7.56-7.27 (m, 1H), 6.05-5.37 (m, 2H), 4.77 (br s, 1H), 4.62-4.39 (m, 2H), 4.24-3.84 (m, 3H), 3.45 (br s, 1H), 2.98-2.76 (m, 3H), 2.63 (br s, 1H), 2.41-2.24 (m, 3H), 2.15-1.35 (m, 8H)<br>hLPA1 $IC_{50}$ δ 618 nM | Example 1 |
| 124 | 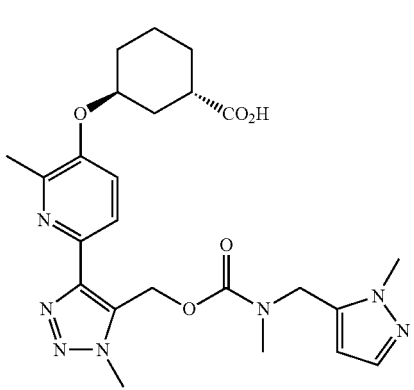 [SMILES: Cc1nc(-c2nnn(C)c2COC(=O)N(C)Cc2ccnn2C)ccc1O[C@H]1CCC[C@H](C(=O)O)C1]<br>(1S,3S)-3-((2-methyl-6-(1-methyl-5-(((methyl((1-methyl-1H-pyrazol-5-yl)methyl)carbamoyl)oxy)methyl)-1H-1,2,3-triazol-4-yl)pyridin-3-yl)oxy)cyclohexane-1-carboxylic acid | LC/MS: $[M + H]^+$ = 498.2<br>$^1$H NMR (500 MHz, DMSO-$d_6$) δ 7.83 (d, J = 8.5 Hz, 1H), 7.49 (d, J = 8.5 Hz, 1H), 7.41-7.12 (m, 1H), 6.14 (br s, 1H), 5.70 (br s, 2H), 5.13-3.29 (m, 7H), 2.71 (br s, 3H), 2.59-2.55 (m, 2H), 2.39 (s, 3H), 2.14-1.31 (m, 9H)<br>hLPA1 $IC_{50}$ = 982 nM | Example 1 |

TABLE 1-continued

| Example | Structure & Name | Analytical & Biology Data | Method |
|---|---|---|---|
| 125 | 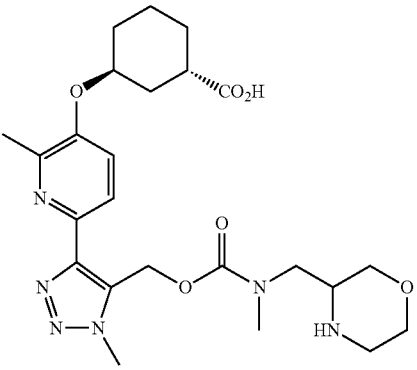 [SMILES: Cc1nc(-c2nnn(C)c2COC(=O)N(C)CC2COCCN2)ccc1O[C@H]1CCC[C@H](C(=O)O)C1]<br>(1S,3S)-3-((2-methyl-6-(1-methyl-5-(((methyl(morpholin-3-ylmethyl)carbamoyl)oxy)methyl)-1H-1,2,3-triazol-4-yl)pyridin-3-yl)oxy)cyclohexane-1-carboxylic acid | LC/MS: [M + H]$^+$ = 504.0<br>$^1$H NMR (500 MHz, DMSO-d$_6$) δ 7.83 (br d, J = 8.5 Hz, 2H), 7.49 (br d, J = 8.5 Hz, 1H), 6.00-5.25 (m, 3H), 4.75 (br s, 2H), 4.10 (br s, 4H), 2.90-2.72 (m, 3H), 2.41 (s, 4H), 2.14-1.31 (m, 13H)<br>hLPA1 IC$_{50}$ = 668 nM | Example 1 |
| 126 | 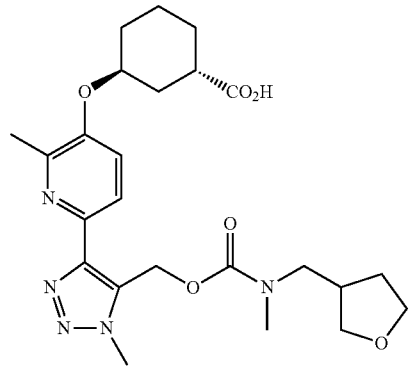 [SMILES: Cc1nc(-c2nnn(C)c2COC(=O)N(C)CC2CCOC2)ccc1O[C@H]1CCC[C@H](C(=O)O)C1]<br>(1S,3S)-3-((2-methyl-6-(1-methyl-5-(((methyl((tetrahydrofuran-3-yl)methyl)carbamoyl)oxy)methyl)-1H-1,2,3-triazol-4-yl)pyridin-3-yl)oxy)cyclohexane-1-carboxylic acid | LC/MS: [M + H]$^+$ = 488.1<br>$^1$H NMR (500 MHz, DMSO-d$_6$) δ 7.94 (br d, J = 8.9 Hz, 1H), 7.83 (d, J = 8.5 Hz, 1H), 7.48 (br d, J = 8.5 Hz, 1H), 6.52 (br d, J = 8.2 Hz, 1H), 5.65 (br s, 2H), 4.76 (br s, 1H), 4.09 (s, 3H), 3.55-2.96 (m, 3H), 2.85-2.70 (m, 3H), 2.60-2.56 (m, 1H), 2.40 (s, 3H), 2.33-2.23 (m, 1H), 2.03-1.19 (m, 11H)<br>hLPA1 IC$_{50}$ = 346 nM | Example 1 |
| 127 | 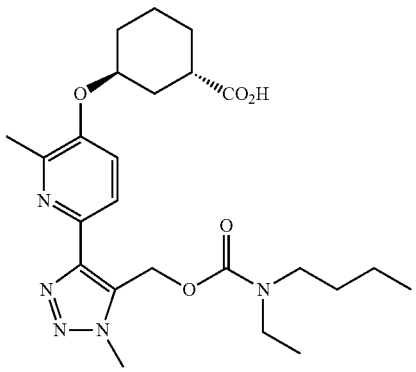 [SMILES: CCCCN(CC)C(=O)OCc1c(-c2ccc(O[C@H]3CCC[C@H](C(=O)O)C3)c(C)n2)nnn1C]<br>(1S,3S)-3-((6-(5-(((butyl(ethyl)carbamoyl)oxy)methyl)-1-methyl-1H-1,2,3-triazol-4-yl)-2-methylpyridin-3-yl)oxy)cyclohexane-1-carboxylic acid | LC/MS: [M + H]$^+$ = 474.2<br>$^1$H NMR (500 MHz, DMSO-d$_6$) δ 7.81 (br d, J = 8.5 Hz, 1H), 7.44 (br d, J = 8.5 Hz, 1H), 5.58 (s, 2H), 4.75 (br s, 1H), 4.08 (s, 3H), 3.23-2.91 (m, 4H), 2.60 (br s, 1H), 2.39 (s, 3H), 2.05-1.93 (m, 1H), 1.89-1.71 (m, 3H), 1.66-1.37 (m, 4H), 1.25-1.12 (m, 4H), 1.06-0.77 (m, 5H), 0.58 (br s, 2H)<br>hLPA1 IC$_{50}$ = 33 nM | Example 1 |

TABLE 1-continued

| Example | Structure & Name | Analytical & Biology Data | Method |
|---|---|---|---|
| 128 | 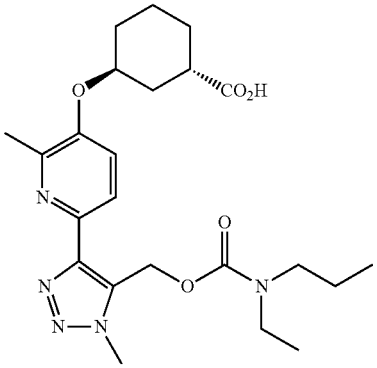 [SMILES: CCCN(CC)C(=O)OCc1c(-c2ccc(O[C@H]3CCC[C@H](C(=O)O)C3)c(C)n2)nnn1C]<br>(1S,3S)-3-((6-(5-((((ethyl(propyl)carbamoyl)oxy)methyl)-1-methyl-1H-1,2,3-triazol-4-yl)-2-methylpyridin-3-yl)oxy)cyclohexane-1-carboxylic acid | LC/MS: [M + H]$^+$ = 460.3<br>$^1$H NMR (500 MHz, DMSO-d$_6$) δ 7.83 (br d, J = 8.5 Hz, 1H), 7.47 (d, J = 8.5 Hz, 1H), 5.61 (s, 2H), 4.78 (br s, 1H), 4.09 (s, 3H), 3.42-3.33 (m, 1H), 3.23-2.96 (m, 4H), 2.62 (br t, J = 10.4 Hz, 1H), 2.41 (s, 3H), 2.01 (br d, J = 13.7 Hz, 1H), 1.91-1.73 (m, 3H), 1.68-1.41 (m, 5H), 1.28 (br s, 1H), 1.00 (br d, J = 6.1 Hz, 1H), 0.92-0.76 (m, 3H), 0.62 (br s, 1H)<br>hLPA1 IC$_{50}$ = 158 nM | Example 3 |
| 129 | 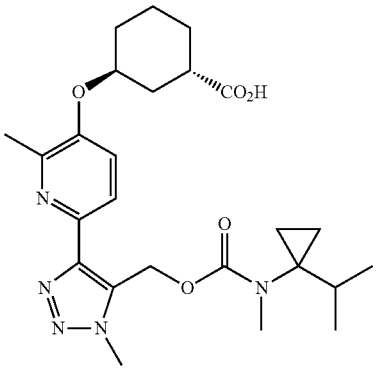 [SMILES: Cc1nc(-c2nnn(C)c2COC(=O)N(C)C2(C(C)C)CC2)ccc1O[C@H]1CCC[C@H](C(=O)O)C1]<br>(1S,3S)-3-((6-(5-((((1-isopropylcyclopropyl)(methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 486<br>$^1$H NMR (500 MHz, DMSO-d$_6$) δ 7.81 (br d, J = 8.2 Hz, 1H), 7.46 (br d, J = 8.5 Hz, 1H), 5.60 (br s, 2H), 4.78 (br s, 1H), 4.15-4.03 (m, 3H), 3.53 (br s, 1H), 2.80-2.70 (m, 3H), 2.65-2.57 (m, 1H), 2.41 (s, 3H), 2.05-1.96 (m, 1H), 1.89-1.72 (m, 3H), 1.66-1.46 (m, 4H), 0.86-0.82 (m, 2H), 0.76-0.48 (m, 8H)<br>hLPA1 IC$_{50}$ = 352 nM | Example 3 |
| 130 | 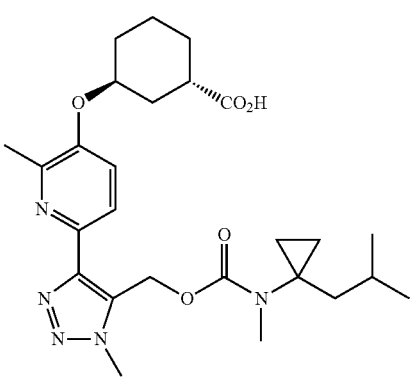<br>(1S,3S)-3-((6-(5-((((1-isobutylcyclopropyl)(methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 500<br>$^1$H NMR (500 MHz, DMSO-d$_6$) δ 7.82 (br d, J = 8.5 Hz, 1H), 7.46 (br d, J = 8.5 Hz, 1H), 5.59 (br s, 2H), 4.77 (br s, 1H), 4.15-4.02 (m, 3H), 3.59 (br s, 1H), 2.79-2.66 (m, 3H), 2.63-2.56 (m, 1H), 2.39 (s, 3H), 2.04-1.94 (m, 1H), 1.88-1.71 (m, 3H), 1.66-1.44 (m, 4H), 1.15-1.08 (m, 1H), 0.90-0.85 (m, 2H), 0.83-0.32 (m, 9H)<br>hLPA1 IC$_{50}$ = 243 nM | Example 10 |

TABLE 1-continued

| Example | Structure & Name | Analytical & Biology Data | Method |
|---|---|---|---|
| 131 | 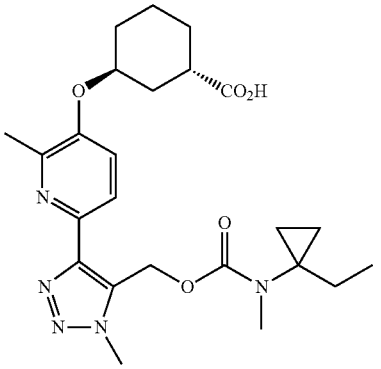 [SMILES: CCC1(N(C)C(=O)OCc2c(-c3ccc(O[C@H]4CCC[C@H](C(=O)O)C4)c(C)n3)nnn2C)CC1]<br>(1S,3S)-3-((6-(5-((((1-ethylcyclopropyl)(methyl)carbamoyl)oxy)methyl)-1-methyl-1H-1,2,3-triazol-4-yl)-2-methylpyridin-3-yl)oxy)cyclohexane-1-carboxylic acid | LCMS, $[M + H]^+ = 472$<br>$^1$H NMR (500 MHz, DMSO-$d_6$) δ 7.80 (br d, J = 7.9 Hz, 1H), 7.46 (br d, J = 8.2 Hz, 1H), 5.60 (s, 2H), 4.81-4.71 (m, 1H), 4.15-4.01 (m, 3H), 3.66 (br s, 3H), 2.78-2.66 (m, 3H), 2.61-2.55 (m, 1H), 2.40 (s, 3H), 2.02-1.93 (m, 1H), 1.85-1.73 (m, 3H), 1.64-1.44 (m, 5H), 0.85-0.76 (m, 1H), 0.67-0.57 (m, 4H), 0.44 (br s, 1H)<br>hLPA1 IC$_{50}$ = 187 nM | Example 10 |
| 132 | 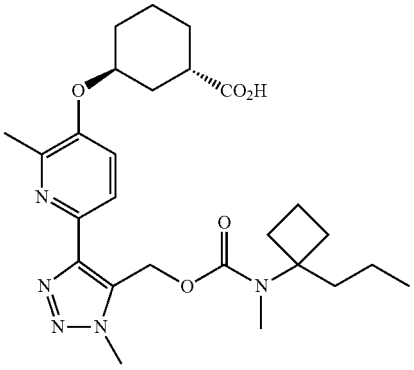<br>(1S,3S)-3-((2-methyl-6-(1-methyl-5-(((methyl(1-propylcyclobutyl)carbamoyl)oxy)methyl)-1H-1,2,3-triazol-4-yl)pyridin-3-yl)oxy)cyclohexane-1-carboxylic acid | LCMS, $[M + H]^+ = 500$<br>$^1$H NMR (500 MHz, DMSO-$d_6$) δ 8.01-7.78 (m, 1H), 7.49 (br d, J = 4.6 Hz, 1H), 5.58 (br s, 2H), 4.78 (br s, 1H), 4.09 (br s, 3H), 3.54-3.32 (m, 2H), 2.63-2.58 (m, 3H), 2.46-2.32 (m, 3H), 2.08-1.97 (m, 3H), 1.91-1.74 (m, 4H), 1.70-1.47 (m, 8H), 1.28-1.19 (m, 1H), 1.07-0.79 (m, 3H), 0.62-0.56 (m, 1H)<br>hLPA1 IC$_{50}$ = 180 nM | Example 10 |
| 133 | 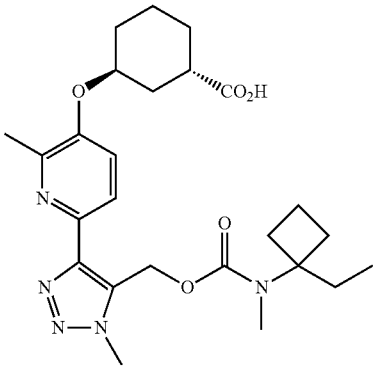 [SMILES: CCC1(N(C)C(=O)OCc2c(-c3ccc(O[C@H]4CCC[C@H](C(=O)O)C4)c(C)n3)nnn2C)CCC1]<br>(1S,3S)-3-((6-(5-((((1-ethylcyclobutyl)(methyl)carbamoyl)oxy)methyl)-1-methyl-1H-1,2,3-triazol-4-yl)-2-methylpyridin-3-yl)oxy)cyclohexane-1-carboxylic acid | LCMS, $[M + H]^+ = 486$<br>$^1$H NMR (500 MHz, DMSO-$d_6$) δ 7.81 (br d, J = 7.3 Hz, 1H), 7.48 (br d, J = 8.5 Hz, 1H), 5.57 (br s, 2H), 4.82-4.73 (m, 1H), 4.08 (s, 3H), 2.64-2.57 (m, 3H), 2.41 (s, 3H), 2.23-1.74 (m, 9H), 1.70-1.44 (m, 8H), 0.92-0.41 (m, 3H)<br>hLPA1 IC$_{50}$ = 174 nM | Example 10 |

| Example | Structure & Name | Analytical & Biology Data | Method |
|---|---|---|---|
| 134 | 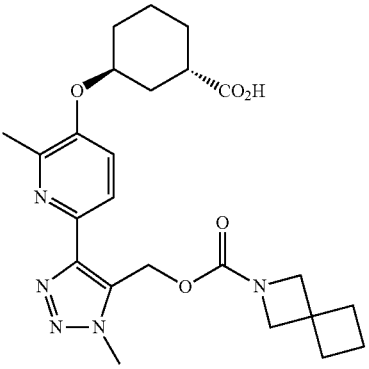 [SMILES: Cc1nc(-c2nnn(C)c2COC(=O)N2CC3(CCC3)C2)ccc1O[C@H]1CCC[C@H](C(=O)O)C1]<br>(1S,3S)-3-((6-(5-(((2-azaspiro[3.3]heptane-2-carbonyl)oxy)methyl)-1-methyl-1H-1,2,3-triazol-4-yl)-2-methylpyridin-3-yl)oxy)cyclohexane-1-carboxylic acid | LCMS, $[M + H]^+$ = 470<br>$^1$H NMR (500 MHz, DMSO-$d_6$) δ 7.83 (d, J = 8.5 Hz, 1H), 7.48 (d, J = 8.9 Hz, 1H), 5.62 (s, 2H), 4.77 (br s, 1H), 4.06 (s, 3H), 3.90 (s, 1H), 3.81 (br s, 3H), 2.64-2.58 (m, 1H), 2.41 (s, 3H), 2.10-1.97 (m, 5H), 1.88-1.75 (m, 3H), 1.74-1.50 (m, 6H)<br>hLPA1 $IC_{50}$ = 76 nM | Example 1 |
| 135 | 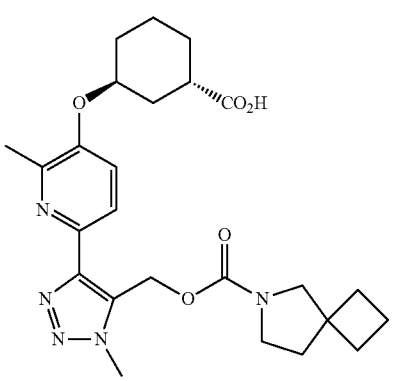 [SMILES: Cc1nc(-c2nnn(C)c2COC(=O)N2CCC3(CCC3)C2)ccc1O[C@H]1CCC[C@H](C(=O)O)C1]<br>(1S,3S)-3-((6-(5-(((6-azaspiro[3.4]octane-6-carbonyl)oxy)methyl)-1-methyl-1H-1,2,3-triazol-4-yl)-2-methylpyridin-3-yl)oxy)cyclohexane-1-carboxylic acid | LCMS, $[M + H]^+$ = 484<br>$^1$H NMR (500 MHz, DMSO-$d_6$) δ 7.79 (br d, J = 8.2 Hz, 1H), 7.44 (br d, J = 8.5 Hz, 1H), 5.62-5.56 (m, 2H), 4.74 (br s, 1H), 4.08-4.04 (m, 2H), 3.86-3.61 (m, 2H), 3.18 (s, 3H), 3.04 (s, 1H), 2.62-2.56 (m, 1H), 2.38 (s, 3H), 2.01-1.92 (m, 1H), 1.90-1.71 (m, 10H), 1.65-1.41 (m, 4H)<br>hLPA1 $IC_{50}$ = 47 nM | Example 1 |
| 136 | 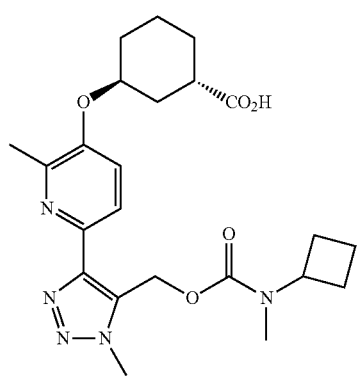 [SMILES: Cc1nc(-c2nnn(C)c2COC(=O)N(C)C2CCC2)ccc1O[C@H]1CCC[C@H](C(=O)O)C1]<br>(1S,3S)-3-((6-(5-(((cyclobutyl(methyl)carbamoyl)oxy)methyl)-1-methyl-1H-1,2,3-triazol-4-yl)-2-methylpyridin-3-yl)oxy)cyclohexane-1-carboxylic acid | LCMS, $[M + H]^+$ = 458<br>$^1$H NMR (500 MHz, CDCl$_3$) δ 7.98 (d, J = 8.5 Hz, 1H), 7.25 (d, J = 8.8 Hz, 1H), 5.77 (s, 2H), 4.76-4.71 (m, 1H), 4.17-4.13 (m, 4H), 2.93-2.82 (m, 3H), 2.53 (s, 3H), 2.07 (s, 10H), 1.68 (br s, 5H)<br>hLPA1 $IC_{50}$ = 36 nM | Example 1 |

TABLE 1-continued

| Example | Structure & Name | Analytical & Biology Data | Method |
|---|---|---|---|
| 137 | 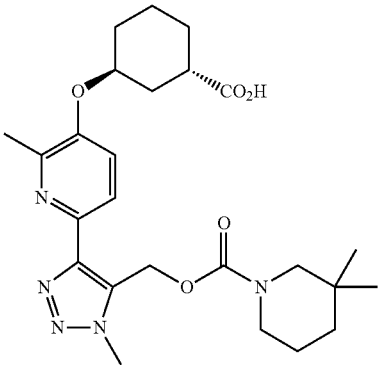<br>(1S,3S)-3-((6-(5-(((3,3-dimethylpiperidine-1-carbonyl)oxy)methyl)-1-methyl-1H-1,2,3-triazol-4-yl)-2-methylpyridin-3-yl)oxy)cyclohexane-1-carboxylic acid | LCMS, [M + H]$^+$ = 586<br>$^1$H NMR (500 MHz, DMSO-d$_6$) δ 7.83 (br d, J = 8.5 Hz, 1H), 7.47 (br d, J = 8.9 Hz, 1H), 5.62 (br s, 2H), 4.77 (br s, 1H), 4.09 (s, 3H), 3.30-2.86 (m, 4H), 2.61-2.57 (m, 1H), 2.41 (s, 3H), 2.03-1.92 (m, 1H), 1.88-1.72 (m, 3H), 1.62 (br d, J = 9.2 Hz, 5H), 1.31-1.19 (m, 4H) 0.89-0.75 (m, 3H), 0.73-0.60 (m, 3H)<br>hLPA1 IC$_{50}$ = 292 nM | Example 1 |
| 138 | 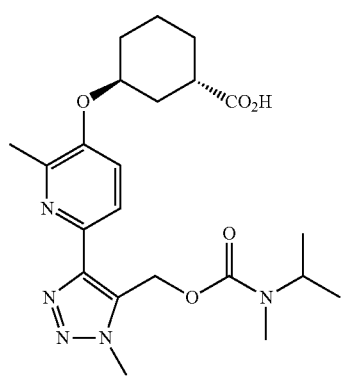 [SMILES: Cc1nc(-c2nnn(C)c2COC(=O)N(C)C(C)C)ccc1O[C@H]1CCC[C@H](C(=O)O)C1]<br>(1S,3S)-3-((6-(5-((((isopropylmethyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 446<br>$^1$H NMR (500 MHz, DMSO-d$_6$) δ 7.84 (br d, J = 8.3 Hz, 1H), 7.48 (br d, J = 8.6 Hz, 1H), 5.63 (br s, 2H), 4.79 (br s, 1H), 4.09 (s, 3H), 3.91-3.90 (m, 1H), 2.69-2.61 (m, 3H), 2.41 (s, 3H), 1.62 (br s, 9H), 1.03 (br s, 3H), 0.93 (br s, 3H)<br>hLPA1 IC$_{50}$ = 98 nM | Example 3 |
| 139 | 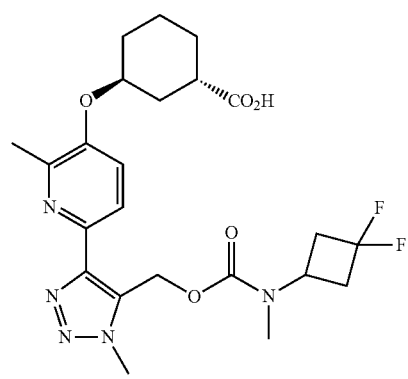 [SMILES: Cc1nc(-c2nnn(C)c2COC(=O)N(C)C2CC(F)(F)C2)ccc1O[C@H]1CCC[C@H](C(=O)O)C1]<br>(1S,3S)-3-((6-(5-((((3,3-difluorocyclobutyl)(methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 494<br>$^1$H NMR (500 MHz, DMSO-d$_6$) δ 7.85 (d, J = 8.2 Hz, 1H), 7.48 (d, J = 8.9 Hz, 1H), 5.66 (br s, 2H), 4.78 (br s, 1H), 4.10 (s, 3H), 2.82-2.68 (m, 5H), 2.67-2.59 (m, 2H), 2.41 (s, 3H), 2.06-1.97 (m, 1H), 1.94-1.71 (m, 3H), 1.68-1.42 (m, 4H), 1.24 (s, 2H)<br>hLPA1 IC$_{50}$ = 70 nM | Example 10 |

TABLE 1-continued

| Example | Structure & Name | Analytical & Biology Data | Method |
|---|---|---|---|
| 140 | 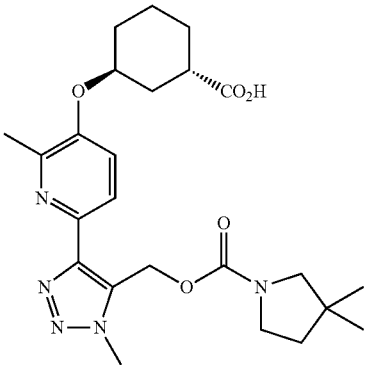<br>(1S,3S)-3-((6-(5-(((3,3-dimethylpyrrolidine-1-carbonyl)oxy)methyl)-1-methyl-1H-1,2,3-triazol-4-yl)-2-methylpyridin-3-yl)oxy)cyclohexane-1-carboxylic acid | LCMS, $[M + H]^+$ = 472<br>$^1$H NMR (500 MHz, DMSO-$d_6$) δ 7.83 (br d, J = 8.5 Hz, 1H), 7.47 (br d, J = 8.5 Hz, 1H), 5.65 (br d, J = 4.6 Hz, 2H), 4.78 (br s, 1H), 4.08 (br d, J = 4.6 Hz, 3H), 3.36-3.21 (m, 1H), 3.02 (s, 1H), 2.90 (s, 1H), 2.62 (br s, 1H), 2.41 (s, 3H), 2.06-1.96 (m, 1H), 1.80 (br s, 3H), 1.57 (br t, J = 7.2 Hz, 6H), 1.23 (s, 2H), 0.99 (s, 3H), 0.94 (s, 3H)<br>hLPA1 $IC_{50}$ = 148 nM | Example 1 |
| 141 | 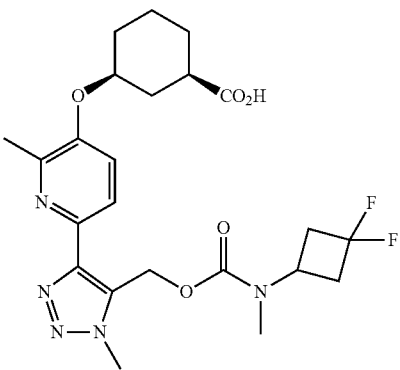 [SMILES: Cc1nc(-c2nnn(C)c2COC(=O)N(C)C2CC(F)(F)C2)ccc1O[C@H]1CCC[C@@H](C(=O)O)C1]<br>(1R,3S)-3-((6-(5-((((3,3-difluoro-cyclobutyl)(methyl)carbamoyl)oxy)methyl)-1-methyl-1H-1,2,3-triazol-4-yl)-2-methylpyridin-3-yl)oxy)cyclohexane-1-carboxylic acid; cis isomer from epimerization in final ester hydrolysis | LCMS, $[M + H]^+$ = 494<br>$^1$H NMR (500 MHz, DMSO-$d_6$) δ 7.84 (d, J = 8.2 Hz, 1H), 7.52 (d, J = 8.5 Hz, 1H), 5.65 (br s, 2H), 4.45-4.38 (m, 1H), 4.10 (s, 3H), 2.79-2.74 (m, 4H), 2.70-2.62 (m, 1H), 2.49-2.40 (m, J = 11.7, 11.7 Hz, 2H), 2.37-2.34 (m, 3H), 2.30-2.20 (m, 1H), 2.11-2.00 (m, 1H), 1.90-1.78 (m, 2H), 1.47-1.23 (m, 6H)<br>hLPA1 $IC_{50}$ = 283 nM | Example 10 |
| 142 | 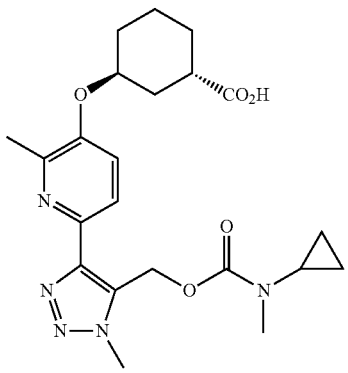 [SMILES: Cc1nc(-c2nnn(C)c2COC(=O)N(C)C2CC2)ccc1O[C@H]1CCC[C@H](C(=O)O)C1]<br>(1S,3S)-3-((6-(5-((((cyclopropyl(methyl)carbamoyl)oxy)methyl)-1-methyl-1H-1,2,3-triazol-4-yl)-2-methylpyridin-3-yl)oxy)cyclohexane-1-carboxylic acid | LCMS, $[M + H]^+$ = 444<br>$^1$H NMR (500 MHz, DMSO-$d_6$) δ 7.83 (br d, J = 8.5 Hz, 1H), 7.47 (br d, J = 8.2 Hz, 1H), 5.65 (s, 2H), 4.81-4.73 (m, 1H), 4.10 (s, 3H), 3.72-3.52 (m, 1H), 2.74 (br s, 3H), 2.65-2.57 (m, 1H), 2.41 (s, 3H), 2.04-1.94 (m, 1H), 1.92-1.70 (m, 3H), 1.68-1.41 (m, 4H), 0.57 (br s, 2H), 0.48 (br s, 2H)<br>hLPA1 $IC_{50}$ = 252 nM | Example 10 |

TABLE 1-continued

| Example | Structure & Name | Analytical & Biology Data | Method |
|---|---|---|---|
| 143 | 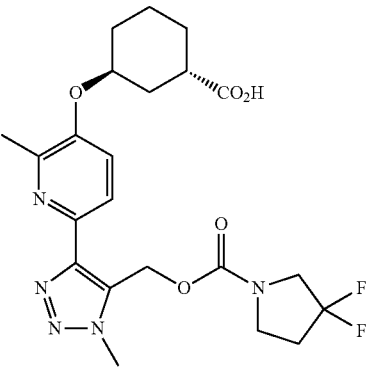 [SMILES: Cc1nc(-c2nnn(C)c2COC(=O)N2CCC(F)(F)C2)ccc1O[C@H]1CCC[C@H](C(=O)O)C1]<br>(1S,3S)-3-((6-(5-(((3,3-difluoro-pyrrolidine-1-carbonyl)oxy)methyl)-1-methyl-1H-1,2,3-triazol-4-yl)-2-methylpyridin-3-yl)oxy)cyclohexane-1-carboxylic acid | LCMS, [M + H]$^+$ = 480<br>$^1$H NMR (500 MHz, DMSO-d$_6$) δ 7.82 (br d, J = 7.6 Hz, 1H), 7.49 (br d, J = 7.6 Hz, 1H), 5.70 (s, 2H), 4.75 (br s, 1H), 4.09 (s, 3H), 3.73-3.54 (m, 1H), 2.42-2.38 (m, 3H), 2.38-2.31 (m, 2H), 1.99-1.46 (m, 8H), 1.23 (s, 2H)<br>hLPA1 IC$_{50}$ = 518 nM | Example 1 |
| 144 | 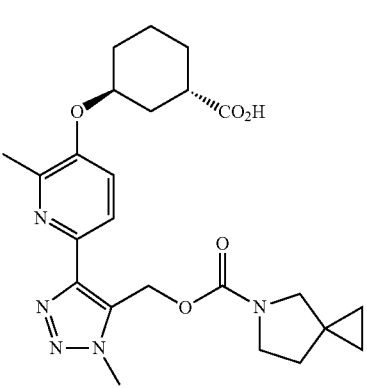 [SMILES: Cc1nc(-c2nnn(C)c2COC(=O)N2CCC3(CC3)C2)ccc1O[C@H]1CCC[C@H](C(=O)O)C1]<br>(1S,3S)-3-((6-(5-(((5-azaspiro[2.4]heptane-5-carbonyl)oxy)methyl)-1-methyl-1H-1,2,3-triazol-4-yl)-2-methylpyridin-3-yl)oxy)cyclohexane-1-carboxylic acid | LCMS, [M + H]$^+$ = 470<br>$^1$H NMR (500 MHz, DMSO-d$_6$) δ 7.84 (br d, J = 8.4 Hz, 1H), 7.47 (d, J = 8.6 Hz, 1H), 5.67 (s, 2H), 4.77 (br s, 1H), 4.09 (br s, 3H), 2.72-2.60 (m, 1H), 2.43 (s, 3H), 2.08-1.97 (m, 1H), 1.83 (br d, J = 10.9 Hz, 3H), 1.75-1.45 (m, 7H), 1.25 (s, 2H), 0.63-0.44 (m, 4H)<br>hLPA1 IC$_{50}$ = 89 nM | Example 1 |
| 145 | 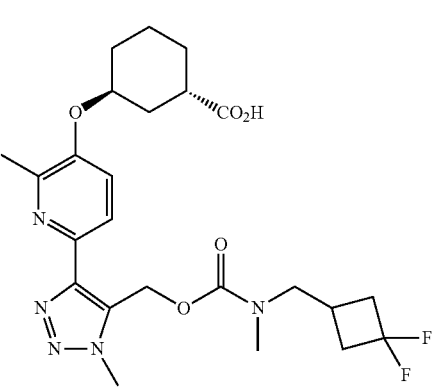 [SMILES: Cc1nc(-c2nnn(C)c2COC(=O)N(C)CC2CC(F)(F)C2)ccc1O[C@H]1CCC[C@H](C(=O)O)C1]<br>(1S,3S)-3-((6-(5-(((((3,3-difluoro-cyclobutyl)methyl)(methyl)carba-moyl)oxy)methyl)-1-methyl-1H-1,2,3-triazol-4-yl)-2-methylpyridin-3-yl)oxy)cyclohexane-1-carboxylic acid | LCMS, [M + H]$^+$ = 508<br>$^1$H NMR (500 MHz, DMSO-d$_6$) δ 7.84 (br d, J = 8.5 Hz, 1H), 7.46 (d, J = 8.7 Hz, 1H), 5.65 (br s, 2H), 4.77 (br s, 1H), 4.10 (s, 3H), 2.79 (br s, 3H), 2.70-2.62 (m, 1H), 2.43 (s, 3H), 2.39-2.19 (m, 4H), 2.09-1.97 (m, 2H), 1.92-1.76 (m, 3H), 1.71-1.60 (m, 2H), 1.59-1.47 (m, 2H), 1.25 (s, 2H)<br>hLPA1 IC$_{50}$ = 94 nM | Example 3 |

TABLE 1-continued

| Example | Structure & Name | Analytical & Biology Data | Method |
|---|---|---|---|
| 146 | (1R,3S)-3-((2-methyl-6-(1-methyl-5-(((methyl(spiro[2.3]hexan-1-yl)carbamoyl)oxy)methyl)-1H-1,2,3-triazol-4-yl)pyridin-3-yl)oxy)cyclohexane-1-carboxylic acid (cis isomer from epimerization in final ester hydrolysis) | LCMS, [M + H]$^+$ = 484<br>$^1$H NMR (500 MHz, DMSO-d$_6$) δ 7.83 (d, J = 8.2 Hz, 1H), 7.51 (d, J = 8.5 Hz, 1H), 5.98-5.48 (m, 2H), 4.45-4.36 (m, 1H), 4.13 (s, 3H), 3.53-3.14 (m, 1H), 2.72 (s, 2H), 2.47-2.39 (m, 1H), 2.35 (s, 3H), 2.27-2.20 (m, 1H), 2.08-1.99 (m, 1H), 1.93-1.58 (m, 7H), 1.50-1.20 (m, 6H), 0.75-0.65 (m, 1H), 0.58-0.50 (m, 1H)<br>hLPA1 IC$_{50}$ = 1816 nM | Example 3 |
| 147 | (1S,3S)-3-((2-methyl-6-(1-methyl-5-(((3-methylpyrrolidine-1-carbonyl)oxy)methyl)-1H-1,2,3-triazol-4-yl)pyridin-3-yl)oxy)cyclohexane-1-carboxylic acid (mixture of diastereomers) | LCMS, [M + H]$^+$ = 458<br>$^1$H NMR (500 MHz, DMSO-d$_6$) δ 7.83 (d, J = 8.6 Hz, 1H), 7.47 (d, J = 8.7 Hz, 1H), 5.65 (s, 2H), 4.81-4.74 (m, 1H), 4.08 (s, 3H), 3.82-3.59 (m, 1H), 3.45-3.10 (m, 3H), 2.81-2.66 (m, 1H), 2.65-2.58 (m, 1H), 2.41 (s, 3H), 2.08-1.95 (m, 1H), 1.93-1.73 (m, 4H), 1.67-1.33 (m, 5H), 1.26-1.18 (m, 1H), 0.99-0.86 (m, 3H)<br>hLPA1 IC$_{50}$ = 250 nM | Example 1 |
| 148 | (1S,3S)-3-((6-(5-(((-2-azabicyclo[2.2.1]heptane-2-carbonyl)oxy)methyl)-1-methyl-1H-1,2,3-triazol-4-yl)-2-methylpyridin-3-yl)oxy)cyclohexane-1-carboxylic acid (mixture of diastereomers) | LCMS, [M + H]$^+$ = 470<br>$^1$H NMR (500 MHz, DMSO-d$_6$) δ 7.85-7.78 (m, 1H), 7.46 (d, J = 8.7 Hz, 1H), 5.67-5.54 (m, 2H), 4.77 (br s, 1H), 4.13-4.03 (m, 3H), 3.98-3.85 (m, 1H), 3.77-3.66 (m, 1H), 3.20-3.05 (m, 1H), 2.93-2.77 (m, 1H), 2.66-2.57 (m, 1H), 2.48-2.42 (m, 1H), 2.40 (s, 3H), 2.04-1.96 (m, 1H), 1.88-1.72 (m, 3H), 1.65-1.52 (m, 4H), 1.50-1.44 (m, 2H), 1.37-1.24 (m, 3H)<br>hLPA1 IC$_{50}$ = 325 nM | Example 1 |

TABLE 1-continued

| Example | Structure & Name | Analytical & Biology Data | Method |
|---|---|---|---|
| 149 | (1S,3S)-3-((2-methyl-6-(1-methyl-5-(((octahydrocyclopenta[b]pyrrole-1-carbonyl)oxy)methyl)-1H-1,2,3-triazol-4-yl)pyridin-3-yl)oxy)cyclohexane-1-carboxylic acid (mixture of diastereomers) | LCMS, [M + H]$^+$ = 484<br>$^1$H NMR (500 MHz, DMSO-d$_6$) δ 7.83 (br d, J = 8.5 Hz, 1H), 7.47 (br d, J = 8.5 Hz, 1H), 5.68-5.57 (m, 2H), 4.78 (br s, 1H), 4.13-4.06 (m, 3H), 4.04-3.86 (m, 1H), 3.58-3.47 (m, 3H), 2.68-2.57 (m, 2H), 2.41 (s, 3H), 2.05-1.96 (m, 1H), 1.89-1.74 (m, 4H), 1.69-1.59 (m, 3H), 1.54-1.45 (m, 4H), 1.26-1.22 (m, 2H)<br>hLPA1 IC$_{50}$ = 180 nM | Example 1 |
| 150 | (1S,3S)-3-((6-(5-(((3-(cyclopropylmethyl)pyrrolidine-1-carbonyl)oxy)methyl)-1-methyl-1H-1,2,3-triazol-4-yl)-2-methylpyridin-3-yl)oxy)cyclohexane-1-carboxylic acid (mixture of diastereomers) | LCMS, [M + H]$^+$ = 498<br>$^1$H NMR (500 MHz, DMSO-d$_6$) δ 7.84 (br d, J = 8.2 Hz, 1H), 7.48 (br d, J = 8.5 Hz, 1H), 5.66 (br s, 2H), 4.82-4.75 (m, 1H), 4.09 (s, 3H), 3.63-3.33 (m, 1H), 3.32-3.08 (m, 2H), 2.97-2.72 (m, 1H), 2.68-2.60 (m, 1H), 2.42 (s, 3H), 2.20-2.08 (m, 1H), 2.07-1.98 (m, 1H), 1.98-1.90 (m, 1H), 1.90-1.73 (m, 3H), 1.68-1.38 (m, 5H), 1.29-1.11 (m, 2H), 0.70-0.54 (m, 1H), 0.42-0.30 (m, 2H), 0.04--0.11 (m, 2H)<br>hLPA1 IC$_{50}$ = 91 nM | Example 1 |
| 151 | (1S,3S)-3-((6-(5-(((3-isobutylpyrrolidine-1-carbonyl)oxy)methyl)-1-methyl-1H-1,2,3-triazol-4-yl)-2-methylpyridin-3-yl)oxy)cyclohexane-1-carboxylic acid (mixture of diastereomers) | LCMS, [M + H]$^+$ = 500<br>$^1$H NMR (500 MHz, DMSO-d$_6$) δ 7.84 (br d, J = 8.2 Hz, 1H), 7.47 (br d, J = 8.3 Hz, 1H), 5.66 (br s, 2H), 4.80-4.74 (m, 1H), 4.10 (s, 3H), 3.64-3.33 (m, 1H), 2.86-2.77 (m, 1H), 2.74-2.64 (m, 1H), 2.43 (s, 3H), 2.16-2.08 (m, 1H), 2.08-2.00 (m, 1H), 1.98-1.77 (m, 5H), 1.71-1.32 (m, 7H), 1.29-1.12 (m, 2H), 0.92-0.81 (m, 6H)<br>hLPA1 IC$_{50}$ = 101 nM | Example 1 |

TABLE 1-continued

| Example | Structure & Name | Analytical & Biology Data | Method |
|---|---|---|---|
| 152 | (1S,3S)-3-((6-(5-(((2-ethylpyrrolidine-1-carbonyl)oxy)methyl)-1-methyl-1H-1,2,3-triazol-4-yl)-2-methylpyridin-3-yl)oxy)cyclohexane-1-carboxylic acid (mixture of diastereomers) | LCMS, [M + H]$^+$ = 471<br>$^1$H NMR (500 MHz, DMSO-d$_6$) δ 7.83 (br s, 1H), 7.48 (br d, J = 8.5 Hz, 1H), 5.64 (br s, 2H), 4.79 (br s, 1H), 4.09 (br s, 3H), 3.61-3.12 (m, 3H), 2.67-2.59 (m, 1H), 2.42 (s, 3H), 2.06-1.94 (m, 1H), 1.92-1.42 (m, 12H), 0.86-0.75 (m, 2H), 0.64-0.54 (m 1H)<br>hLPA1 IC$_{50}$ = 157 nM | Example 1 |
| 153 | (1S,3S)-3-((6-(5-(((2-isobutylpyrrolidine-1-carbonyl)oxy)methyl)-1-methyl-1H-1,2,3-triazol-4-yl)-2-methylpyridin-3-yl)oxy)cyclohexane-1-carboxylic acid (mixture of diastereomers) | LCMS, [M + H]$^+$ = 500<br>$^1$H NMR (500 MHz, DMSO-d$_6$) δ 7.84 (br d, J = 8.5 Hz, 1H), 7.48 (br d, J = 7.3 Hz, 1H), 5.74-5.48 (m, 2H), 4.78 (br s, 1H), 4.10 (br s, 3H), 3.66-3.11 (m, 3H), 2.41 (br s, 3H), 2.09-1.41 (m, 14H), 1.36-1.07 (m, 2H), 0.89 (br s, 3H), 0.59-0.42 (m, 3H)<br>hLPA1 IC$_{50}$ = 163 nM | Example 1 |
| 154 | (1S,3S)-3-((2-methyl-6-(1-methyl-5-(((2-(trifluoromethyl)pyrrolidine-1-carbonyl)oxy)methyl)-1H-1,2,3-triazol-4-yl)pyridin-3-yl)oxy)cyclohexane-1-carboxylic acid (mixture of diastereomers) | LCMS, [M + H]$^+$ = 511<br>$^1$H NMR (500 MHz, DMSO-d$_6$) δ 7.83 (br d, J = 8.2 Hz, 1H), 7.55 (br d, J = 8.5 Hz, 1H), 5.82-5.65 (m, 2H), 4.78-4.68 (m, 1H), 4.10 (br s, 3H), 3.29-3.13 (m, 3H), 2.39 (s, 2H), 2.14-2.00 (m, 1H), 1.98-1.46 (m, 12H)<br>hLPA1 IC$_{50}$ = 321 nM | Example 1 |

TABLE 1-continued

| Example | Structure & Name | Analytical & Biology Data | Method |
|---|---|---|---|
| 155 | 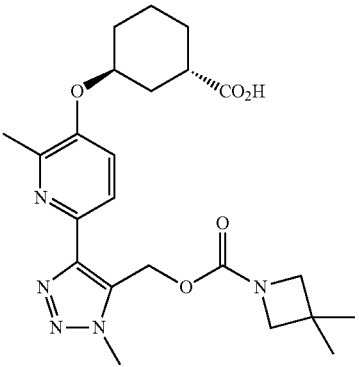<br>(1S,3S)-3-((6-(5-(((3,3-dimethylazetidine-1-carbonyl)oxy)methyl)-1-methyl-1H-1,2,3-triazol-4-yl)-2-methylpyridin-3-yl)oxy)cyclohexane-1-carboxylic acid | LCMS, [M + H]$^+$ = 458<br>$^1$H NMR (500 MHz, DMSO-d$_6$) δ 7.84 (br d, J = 8.2 Hz, 1H), 7.49 (d, J = 8.9 Hz, 1H), 5.64 (s, 2H), 4.79 (br s, 1H), 4.07 (s, 3H), 3.64-3.45 (m, 1H), 3.32-3.09 (m, 1H), 2.70-2.59 (m, 1H), 2.43 (s, 3H), 2.30-2.15 (m, 1H), 2.05-1.98 (m, 1H), 1.91-1.73 (m, 3H), 1.67-1.45 (m, 4H), 1.16 (s, 6H)<br>hLPA1 IC$_{50}$ = 175 nM | Example 1 |
| 156 | 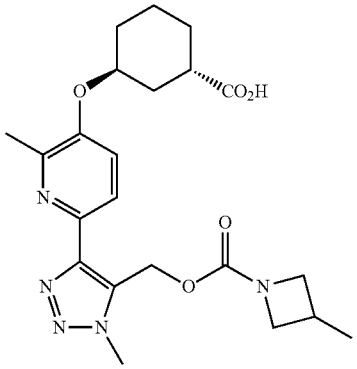<br>(1S,3S)-3-((2-methyl-6-(1-methyl-5-(((3-methylazetidine-1-carbonyl)oxy)methyl)-1H-1,2,3-triazol-4-yl)pyridin-3-yl)oxy)cyclohexane-1-carboxylic acid | LCMS, [M + H]$^+$ = 444<br>$^1$H NMR (500 MHz, DMSO-d$_6$) δ 7.84 (br d, J = 8.5 Hz, 1H), 7.48 (br d, J = 8.9 Hz, 1H), 5.64 (s, 2H), 4.79 (br s, 1H), 4.07 (s, 3H), 4.00-3.92 (m, 2H), 3.31-3.09 (m, 1H), 2.68-2.58 (m, 2H), 2.43 (s, 3H), 2.02 (br d, J = 13.4 Hz, 1H), 1.94-1.73 (m, 3H), 1.63 (br d, J = 10.1 Hz, 4H), 1.12 (d, J = 6.7 Hz, 3H)<br>hLPA1 IC$_{50}$ = 231 nM | Example 1 |
| 157 | 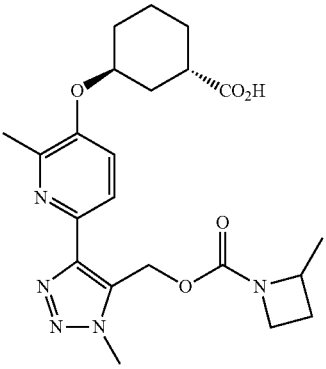<br>(1S,3S)-3-((2-methyl-6-(1-methyl-5-(((2-methylazetidine-1-carbonyl)oxy)methyl)-1H-1,2,3-triazol-4-yl)pyridine-3-yl)oxy)cyclohexane-1-carboxylic acid (mixture of diastereomers) | LCMS, [M + H]$^+$ = 444<br>$^1$H NMR (500 MHz, DMSO-d$_6$) δ 7.84 (br d, J = 8.5 Hz, 1H), 7.48 (d, J = 8.9 Hz, 1H), 5.63 (s, 2H), 4.79 (br s, 1H), 4.08 (s, 3H), 3.81-3.69 (m, 2H), 3.64-3.50 (m, 1H), 3.31-3.10 (m, 1H), 2.67-2.59 (m, 1H), 2.43 (s, 3H), 2.33-2.21 (m, 1H), 2.12-1.96 (m, 1H), 1.64 (br s, 7H), 1.00 (d, J = 6.1 Hz, 3H)<br>hLPA1 IC$_{50}$ = 529 nM | Example 1 |

TABLE 1-continued

| Example | Structure & Name | Analytical & Biology Data | Method |
|---|---|---|---|
| 158 | 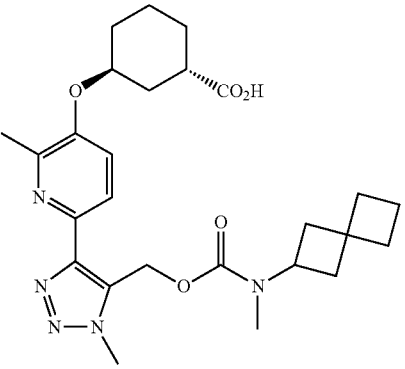 [SMILES: Cc1nc(-c2nnn(C)c2COC(=O)N(C)C2CC3(CCC3)C2)ccc1O[C@H]1CCC[C@H](C(=O)O)C1]<br>(1R,3S)-3-((2-methyl-6-(1-methyl-5-(((methyl(spiro[3.3]heptan-2-yl)carbamoyl)oxy)methyl)-1H-1,2,3-triazol-4-yl)pyridin-3-yl)oxy)cyclohexane-1-carboxylic acid | LCMS, [M + H]$^+$ = 498<br>$^1$H NMR (500 MHz, DMSO-d$_6$) δ 7.83 (d, J = 8.2 Hz, 1H), 7.48 (d, J = 8.5 Hz, 1H), 5.62 (br s, 2H), 4.78 (br s, 1H), 4.09 (s, 3H), 3.32-3.12 (m, 1H), 2.74-2.58 (m, 4H), 2.41 (s, 3H), 2.10-1.70 (m, 14H), 1.68-1.44 (m, 4H)<br>hLPA1 IC$_{50}$ = 32 nM | Example 10 |
| 159 | 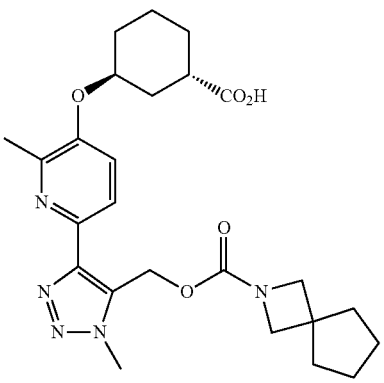 [SMILES: Cc1nc(-c2nnn(C)c2COC(=O)N2CC3(CCCC3)C2)ccc1O[C@H]1CCC[C@H](C(=O)O)C1]<br>(1S,3S)-3-((6-(5-(((2-azaspiro[3.4]octane-2-carbonyl)oxy)methyl)-1-methyl-1H-1,2,3-triazol-4-yl)-2-methylpyridin-3-yl)oxy)cyclohexane-1-carboxylic acid | LCMS, [M + H]$^+$ = 484<br>$^1$H NMR (500 MHz, DMSO-d$_6$) δ 7.83 (br d, J = 8.5 Hz, 1H), 7.48 (d, J = 8.5 Hz, 1H), 5.64 (s, 2H), 4.78 (br s, 1H), 4.07 (s, 3H), 3.69 (br s, 3H), 3.63-3.51 (m, 1H), 3.31-3.11 (m, 2H), 2.42 (s, 3H), 1.91-1.77 (m, 3H), 1.71-1.58 (m, 6H), 1.57-1.47 (m, 6H)<br>hLPA1 IC$_{50}$ = 162 nM | Example 1 |
| 160 | 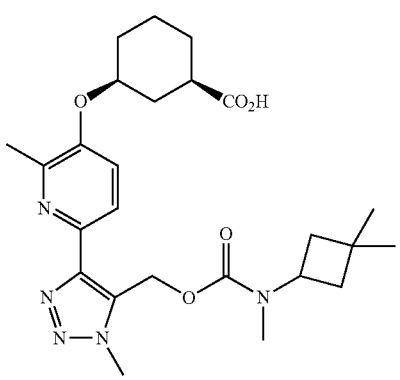<br>(1R,3S)-3-((6-(5-((((3,3-dimethylcyclobutyl)(methyl)carbamoyl)oxy)methyl)-1-methyl-1H-1,2,3-triazol-4-yl)-2-methylpyridin-3-yl)oxy)cyclohexane-1-carboxylic acid (cis isomer from epimerization in final ester hydrolysis step) | LCMS, [M + H]$^+$ = 486<br>$^1$H NMR (500 MHz, DMSO-d$_6$) δ 7.84 (d, J = 8.5 Hz, 1H), 7.53 (d, J = 8.5 Hz, 1H), 5.63 (br s, 2H), 4.49-4.36 (m, 1H), 4.10 (s, 3H), 2.77-2.69 (m, 3H), 2.48-2.39 (m, 1H), 2.37 (s, 3H), 2.31-2.23 (m, 1H), 2.12-2.02 (m, 1H), 1.92-1.59 (m, 6H), 1.50-1.20 (m, 4H), 1.14-0.95 (m, 6H)<br>hLPA1 IC$_{50}$ = 61 nM | Example 3 |

TABLE 1-continued

| Example | Structure & Name | Analytical & Biology Data | Method |
|---|---|---|---|
| 161 | 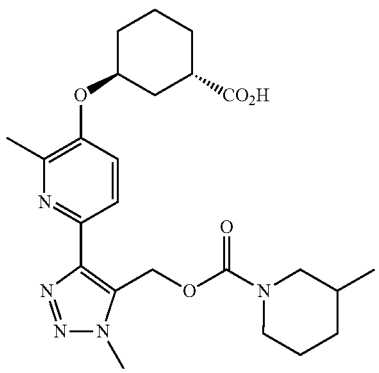<br>(1S,3S)-3-((2-methyl-6-(1-methyl-5-(((3-methylpiperidine-1-carbonyl)oxy)methyl)-1H-1,2,3-triazol-4-yl)pyridin-3-yl)oxy)cyclohexane-1-carboxylic acid (mixture of diastereomers) | LCMS, [M + H]$^+$ = 472<br>$^1$H NMR (500 MHz, DMSO-d$_6$) δ 7.84 (br d, J = 8.5 Hz, 1H), 7.46 (d, J = 8.7 Hz, 1H), 5.65 (s, 2H), 4.77 (br s, 1H), 4.09 (s, 3H), 3.81-3.66 (m, 1H), 2.82-2.70 (m, 1H), 2.69-2.62 (m, 1H), 2.43 (s, 3H), 2.06-1.97 (m, 1H), 1.92-1.76 (m, 3H), 1.66 (br s, 6H), 1.46-1.18 (m, 3H), 1.03 (s, 2H), 0.86-0.71 (m, 3H)<br>hLPA1 IC$_{50}$ = 178 nM | Example 1 |
| 162 | 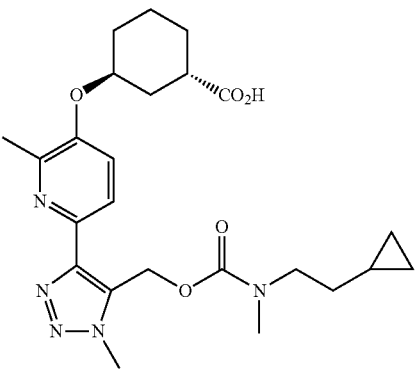 [SMILES: Cc1nc(-c2nnn(C)c2COC(=O)N(C)CCC2CC2)ccc1O[C@H]1CCC[C@H](C(=O)O)C1]<br>(1S,3S)-3-((6-(5-((((2-cyclopropylethyl)(methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 472<br>$^1$H NMR (500 MHz, DMSO-d$_6$) δ 7.83 (d, J = 8.6 Hz, 1H), 7.45 (d, J = 8.6 Hz, 1H), 5.63 (s, 2H), 4.82-4.71 (m, 1H), 4.09 (s, 3H), 3.62-3.53 (m, 2H), 3.34-3.18 (m, 1H), 2.79 (br s, 3H), 2.70-2.61 (m, 1H), 2.42 (s, 3H), 2.07-1.97 (m, 1H), 1.89-1.77 (m, 3H), 1.70-1.47 (m, 4H), 1.31-1.15 (m, 2H), 0.42-0.16 (m, 2H), 0.03--0.26 (m, 2H)<br>hLPA1 IC$_{50}$ = 34 nM | Example 1 |
| 163 | 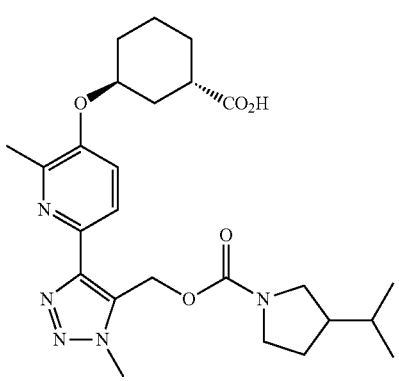 [SMILES: Cc1nc(-c2nnn(C)c2COC(=O)N2CCC(C(C)C)C2)ccc1O[C@H]1CCC[C@H](C(=O)O)C1]<br>(1S,3S)-3-((6-(5-(((3-isopropylpyrrolidine-1-carbonyl)oxy)methyl)-1-methyl-1H-1,2,3-triazol-4-yl)-2-methylpyridin-3-yl)oxy)cyclohexane-1-carboxylic acid (mixture of diastereomers) | LCMS, [M + H]$^+$ = 486<br>$^1$H NMR (500 MHz, DMSO-d$_6$) δ 7.84 (br d, J = 8.5 Hz, 1H), 7.48 (d, J = 8.5 Hz, 1H), 5.66 (br d, J = 9.5 Hz, 2H), 4.83-4.75 (m, 1H), 4.10 (s, 3H), 3.18 (br s, 1H), 2.93-2.81 (m, 1H), 2.74 (s, 1H), 2.68-2.60 (m, 1H), 2.42 (s, 3H), 2.07-1.98 (m, 1H), 1.94-1.73 (m, 6H), 1.67-1.34 (m, 6H), 0.93-0.75 (m, 6H)<br>hLPA1 IC$_{50}$ = 104 nM | Example 1 |

TABLE 1-continued

| Example | Structure & Name | Analytical & Biology Data | Method |
|---|---|---|---|
| 164 | (1S,3S)-3-((6-(5-(((3-cyclopropylpyrrolidine-1-carbonyl)oxy)methyl)-1-methyl-1H-1,2,3-triazol-4-yl)-2-methylpyridin-3-yl)oxy)cyclohexane-1-carboxylic acid (mixture of diastereomers) | LCMS, [M + H]$^+$ = 484<br>$^1$H NMR (500 MHz, DMSO-$d_6$) δ 7.82 (br d, J = 8.5 Hz, 1H), 7.46 (d, J = 8.5 Hz, 1H), 5.65 (br s, 2H), 4.80-4.74 (m, 1H), 4.08 (s, 3H), 3.33-3.08 (m, 2H), 2.88 (s, 2H), 2.65-2.58 (m, 1H), 2.40 (s, 3H), 2.04-1.95 (m, 1H), 1.90 (s, 4H), 1.62 (br s, 6H), 0.71-0.54 (m, 1H), 0.42-0.26 (m, 2H), 0.16-0.02 (m, 2H)<br>hLPA1 IC$_{50}$ = 83 nM | Example 1 |
| 165 | (1S,3S)-3-((6-(5-(((3-ethylpyrrolidine-1-carbonyl)oxy)methyl)-1-methyl-1H-1,2,3-triazol-4-yl)-2-methylpyridin-3-yl)oxy)cyclohexane-1-carboxylic acid (mixture of diastereomers) | LCMS, [M + H]$^+$ = 472<br>$^1$H NMR (500 MHz, DMSO-$d_6$) δ 7.84 (d, J = 8.5 Hz, 1H), 7.49 (d, J = 8.9 Hz, 1H), 5.67 (br s, 2H), 4.83-4.76 (m, 1H), 4.10 (s, 3H), 3.24-3.09 (m, 1H), 2.98-2.78 (m, 1H), 2.77-2.69 (m, 1H), 2.67-2.61 (m, 1H), 2.42 (s, 3H), 2.06-1.79 (m, 6H), 1.67-1.23 (m, 8H), 0.93-0.79 (m, 3H)<br>hLPA1 IC$_{50}$ = 102 nM | Example 1 |
| 166 | (1S,3S)-3-((2-methyl-6-(1-methyl-5-(((3-propylpyrrolidine-1-carbonyl)oxy)methyl)-1H-1,2,3-triazol-4-yl)pyridin-3-yl)oxy)cyclohexane-1-carboxylic acid (mixture of diastereomers) | LCMS, [M + H]$^+$ = 486<br>$^1$H NMR (500 MHz, DMSO-$d_6$) δ 7.84 (d, J = 8.5 Hz, 1H), 7.48 (d, J = 8.5 Hz, 1H), 5.66 (br s, 2H), 4.82-4.74 (m, 1H), 4.09 (s, 3H), 3.24-3.07 (m, 1H), 2.90 (s, 1H), 2.76-2.67 (m, 1H), 2.67-2.60 (m, 1H), 2.42 (s, 3H), 2.10-1.97 (m, 2H), 1.92 (s, 5H), 1.68-1.34 (m, 5H), 1.32-1.19 (m, 4H), 0.92-0.80 (m, 3H)<br>hLPA1 IC$_{50}$ = 109 nM | Example 1 |

TABLE 1-continued

| Example | Structure & Name | Analytical & Biology Data | Method |
|---|---|---|---|
| 167 | (1S,3S)-3-((6-(5-(((-7-azabicyclo[2.2.1]heptane-7-carbonyl)oxy)methyl)-1-methyl-1H-1,2,3-triazol-4-yl)-2-methylpyridin-3-yl)oxy)cyclohexane-1-carboxylic acid | LCMS, [M + H]$^+$ = 470<br>$^1$H NMR (500 MHz, DMSO-d$_6$) δ 7.85 (d, J = 8.5 Hz, 1H), 7.50 (d, J = 8.5 Hz, 1H), 5.64 (s, 2H), 4.79 (br s, 1H), 4.09 (s, 3H), 3.31-3.13 (m, 1H), 2.67-2.59 (m, 1H), 2.42 (s, 3H), 2.06-1.98 (m, 1H), 1.91-1.74 (m, 3H), 1.67-1.46 (m, 8H), 1.39-1.33 (m, 4H)<br>hLPA1 IC$_{50}$ = 317 nM | Example 1 |
| 168 | (1S,3S)-3-((6-(5-((((3,3-dimethylcyclobutyl)(methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 486<br>$^1$H NMR (500 MHz, DMSO-d$_6$) δ 7.84 (d, J = 8.5 Hz, 1H), 7.48 (d, J = 8.5 Hz, 1H), 5.63 (br s, 2H), 4.78 (br s, 1H), 4.10 (s, 3H), 2.72 (br s, 3H), 2.68-2.58 (m, 1H), 2.41 (s, 3H), 2.00 (br s, 1H), 1.93-1.71 (m, 6H), 1.64 (br s, 5H), 1.07-0.95 (m, 6H)<br>hLPA1 IC$_{50}$ = 29 nM | Example 3 |
| 169 | (1S,3S)-3-((2-methyl-6-(1-methyl-5-(((3-phenylpyrrolidine-1-carbonyl)oxy)methyl)-1H-1,2,3-triazol-4-yl)pyridin-3-yl)oxy)cyclohexane-1-carboxylic acid (mixture of diastereomers) | LCMS, [M + H]$^+$ = 520<br>$^1$H NMR (500 MHz, DMSO-d$_6$) δ 7.91-7.81 (m, 1H), 7.52-7.45 (m, 1H), 7.37-7.19 (m, 5H), 5.72 (br s, 2H), 4.83-4.75 (m, 1H), 4.11 (br d, J = 13.7 Hz, 3H), 3.81-3.63 (m, 1H), 3.39-3.10 (m, 3H), 2.67-2.61 (m, 1H), 2.43 (br d, J = 4.9 Hz, 3H), 2.24-2.16 (m, 1H), 2.07-1.99 (m, 1H), 1.97-1.73 (m, 4H), 1.70-1.47 (m, 4H)<br>hLPA1 IC$_{50}$ = 336 nM | Example 1 |

TABLE 1-continued

| Example | Structure & Name | Analytical & Biology Data | Method |
|---|---|---|---|
| 170 | 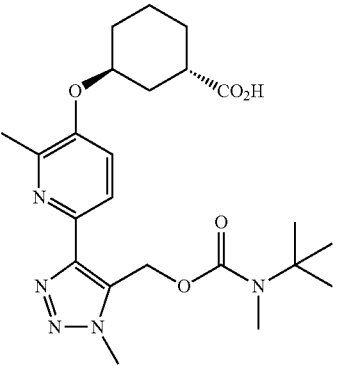 [SMILES: Cc1nc(-c2nnn(C)c2COC(=O)N(C)C(C)(C)C)ccc1O[C@H]1CCC[C@H](C(=O)O)C1]<br>(1S,3S)-3-((6-(5-(((tert-butyl (methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]⁺ = 460<br>¹H NMR (500 MHz, DMSO-d₆) δ 7.84 (br d, J = 8.5 Hz, 1H), 7.48 (br d, J = 8.5 Hz, 1H), 5.60 (s, 2H), 4.79 (br s, 1H), 4.10 (s, 3H), 2.77 (s, 3H), 2.68-2.58 (m, 1H), 2.42 (s, 3H), 2.09-1.97 (m, 1H), 1.93-1.73 (m, 3H), 1.69-1.43 (m, 4H), 1.27 (s, 9H)<br>hLPA1 IC₅₀ = 183 nM | Example 1 |
| 171 | 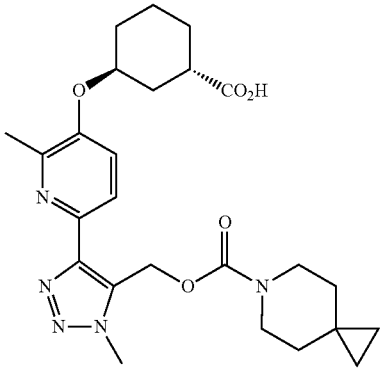 [SMILES: Cc1nc(-c2nnn(C)c2COC(=O)N2CCC3(CC2)CC3)ccc1O[C@H]1CCC[C@H](C(=O)O)C1]<br>(1S,3S)-3-((6-(5-(((6-azaspiro [2.5]octane-6-carbonyl)oxy)methyl)-1-methyl-1H-1,2,3-triazol-4-yl)-2-methylpyridin-3-yl)oxy)cyclohexane-1-carboxylic acid | LCMS, [M + H]⁺ = 484<br>¹H NMR (500 MHz, DMSO-d₆) δ 7.84 (d, J = 8.5 Hz, 1H), 7.48 (d, J = 8.5 Hz, 1H), 5.66 (s, 2H), 4.79 (br s, 1H), 4.09 (s, 3H), 3.59-3.16 (m, 2H), 2.69-2.60 (m, 1H), 2.42 (s, 3H), 2.06-1.95 (m, 1H), 1.91-1.71 (m, 3H), 1.68-1.44 (m, 4H), 1.31-1.11 (m, 4H), 0.28 (s, 4H)<br>hLPA1 IC₅₀ = 162 nM | Example 1 |
| 172 | 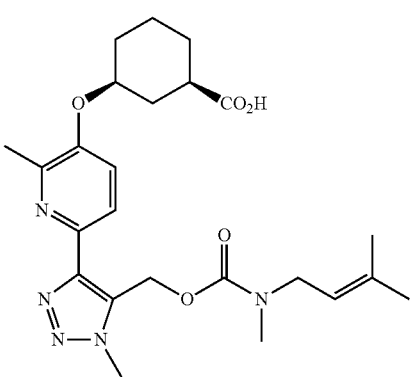 [SMILES: CC(C)=CCN(C)C(=O)OCc1c(-c2ccc(O[C@H]3CCC[C@@H](C(=O)O)C3)c(C)n2)nnn1C]<br>(1R,3S)-3-((2-methyl-6-(1-methyl-5-(((methyl(3-methylbut-2-en-1-yl)carbamoyl)oxy)methyl)-1H-1,2,3-triazol-4-yl)pyridin-3-yl)oxy) cyclohexane-1-carboxylic acid (cis isomer from epimerization during final hydrolysis step) | LCMS, [M + H]⁺ = 472<br>¹H NMR (500 MHz, DMSO-d₆) δ 7.84 (d, J = 8.5 Hz, 1H), 7.53 (d, J = 8.5 Hz, 1H), 5.68-5.59 (m, 2H), 5.16-4.91 (m, 1H), 4.47-4.36 (m, 1H), 4.09 (s, 3H), 3.87-3.60 (m, 2H), 2.80-2.64 (m, 3H), 2.45-2.39 (m, 1H), 2.37 (s, 3H), 2.30-2.22 (m, 1H), 2.09-2.02 (m, 1H), 1.93-1.78 (m, 3H), 1.72-1.49 (m, 4H), 1.47-1.28 (m, 5H)<br>hLPA1 IC₅₀ = 312 nM | Example 3 |

TABLE 1-continued

| Example | Structure & Name | Analytical & Biology Data | Method |
|---|---|---|---|
| 173 | 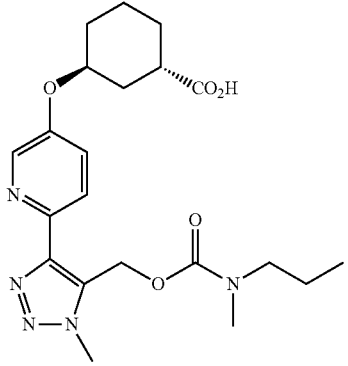 [SMILES: CCCN(C)C(=O)OCc1c(-c2ccc(O[C@H]3CCC[C@H](C(=O)O)C3)cn2)nnn1C]<br>(1S,3S)-3-((6-(1-methyl-5-(((methyl(propyl)carbamoyl)oxy)methyl)-1H-1,2,3-triazol-4-yl)pyridin-3-yl)oxy)cyclohexane-1-carboxylic acid | LCMS, [M + H]$^+$ = 432<br>$^1$H NMR (500 MHz, DMSO-d$_6$) δ 8.35 (d, J = 2.4 Hz, 1H), 7.99 (br d, J = 8.2 Hz, 1H), 7.58-7.52 (m, 1H), 5.67-5.58 (m, 2H), 4.79 (br s, 1H), 4.10 (s, 3H), 3.20-3.01 (m, 2H), 2.77 (br d, J = 15.9 Hz, 3H), 2.71-2.62 (m, 1H), 2.00-1.72 (m, 4H), 1.72-1.41 (m, 5H), 1.40-1.28 (m, 1H), 0.86-0.61 (m, 3H)<br>hLPA1 IC$_{50}$ = 131 nM | Example 1 |
| 174 | 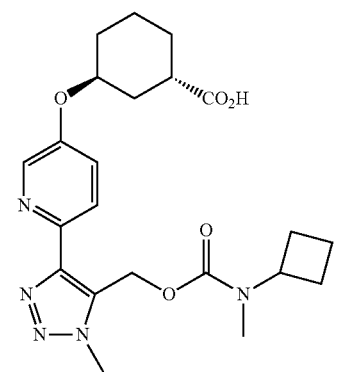 [SMILES: CN(C(=O)OCc1c(-c2ccc(O[C@H]3CCC[C@H](C(=O)O)C3)cn2)nnn1C)C1CCC1]<br>(1S,3S)-3-((6-(5-(((cyclobutyl(methyl)carbamoyl)oxy)methyl)-1-methyl-1H-1,2,3-triazol-4-yl)pyridin-3-yl)oxy)cyclohexane-1-carboxylic acid | LCMS, [M + H]$^+$ = 444<br>$^1$H NMR (500 MHz, DMSO-d$_6$) δ 8.35 (d, J = 2.4 Hz, 1H), 8.00 (d, J = 8.9 Hz, 1H), 7.55 (dd, J = 8.9, 2.7 Hz, 1H), 5.63 (s, 2H), 4.79 (br s, 1H), 4.57-4.17 (m, 1H), 4.10 (s, 3H), 2.80-2.63 (m, 4H), 2.12-1.94 (m, 4H), 1.90-1.74 (m, 4H), 1.72-1.48 (m, 5H)<br>hLPA1 IC$_{50}$ = 58 nM | Example 1 |
| 175 | 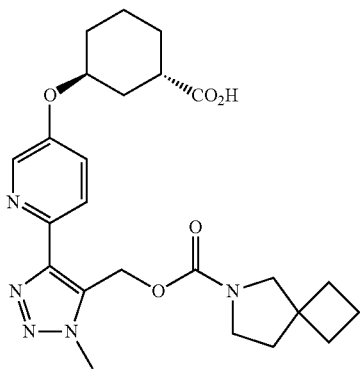 [SMILES: Cn1nnc(-c2ccc(O[C@H]3CCC[C@H](C(=O)O)C3)cn2)c1COC(=O)N1CCC2(CCC2)C1]<br>(1S,3S)-3-((6-(5-(((6-azaspiro[3.4]octane-6-carbonyl)oxy)methyl)-1-methyl-1H-1,2,3-triazol-4-yl)pyridin-3-yl)oxy)cyclohexane-1-carboxylic acid | LCMS, [M + H]$^+$ = 470<br>$^1$H NMR (500 MHz, DMSO-d$_6$) δ 8.43-8.26 (m, 1H), 8.08-7.91 (m, 1H), 7.64-7.44 (m, 1H), 5.63 (br s, 2H), 4.78 (br s, 1H), 4.08 (br s, 3H), 3.30-3.11 (m, 3H), 2.71-2.60 (m, 1H), 2.00-1.88 (m, 2H), 1.88-1.73 (m, 9H), 1.70-1.44 (m, 4H)<br>hLPA1 IC$_{50}$ = 703 nM | Example 1 |

TABLE 1-continued

| Example | Structure & Name | Analytical & Biology Data | Method |
|---|---|---|---|
| 176 | 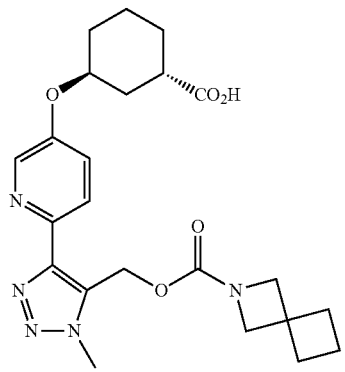 [SMILES: Cn1nnc(-c2ccc(O[C@H]3CCC[C@H](C(=O)O)C3)cn2)c1COC(=O)N1CC2(CCC2)C1]<br>(1S,3S)-3-((6-(5-(((2-azaspiro[3.3]heptane-2-carbonyl)oxy)methyl)-1-methyl-1H-1,2,3-triazol-4-yl)pyridin-3-yl)oxy)cyclohexane-1-carboxylic acid | LCMS, [M + H]$^+$ = 456<br>$^1$H NMR (500 MHz, DMSO-d$_6$) δ 8.35 (d, J = 2.4 Hz, 1H), 8.00 (d, J = 8.9 Hz, 1H), 7.55 (dd, J = 8.7, 2.6 Hz, 1H), 5.60 (s, 2H), 4.79 (br s, 1H), 4.08 (s, 3H), 3.84 (s, 4H), 2.72-2.63 (m, 1H), 2.13-2.02 (m, 4H), 2.01-1.92 (m, 1H), 1.90-1.76 (m, 3H), 1.76-1.60 (m, 4H), 1.60-1.48 (m, 2H)<br>hLPA1 IC$_{50}$ = 400 nM | Example 1 |
| 177 | 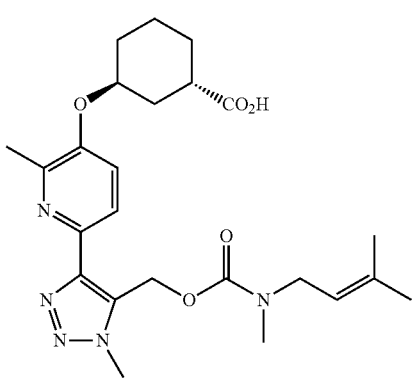 [SMILES: CC(C)=CCN(C)C(=O)OCc1c(-c2ccc(O[C@H]3CCC[C@H](C(=O)O)C3)c(C)n2)nnn1C]<br>(1S,3S)-3-((2-methyl-6-(1-methyl-5-(((methyl(3-methylbut-2-en-1-yl)carbamoyl)oxy)methyl)-1H-1,2,3-triazol-4-yl)pyridin-3-yl)oxy)cyclohexane-1-carboxylic acid | LCMS, [M + H]$^+$ = 472<br>$^1$H NMR (500 MHz, DMSO-d$_6$) δ 7.85 (d, J = 8.5 Hz, 1H), 7.49 (d, J = 8.5 Hz, 1H), 5.69-5.61 (m, 2H), 5.17-4.91 (m, 1H), 4.78 (br s, 1H), 4.09 (s, 3H), 3.85-3.61 (m, 2H), 2.80-2.66 (m, 3H), 2.65-2.59 (m, 1H), 2.41 (s, 3H), 2.06-1.96 (m, 1H), 1.90-1.74 (m, 3H), 1.73-1.60 (m, 4H), 1.59-1.47 (m, 4H), 1.46-1.37 (m, 2H)<br>hLPA1 IC$_{50}$ = 21 nM | Example 3 |
| 178 | 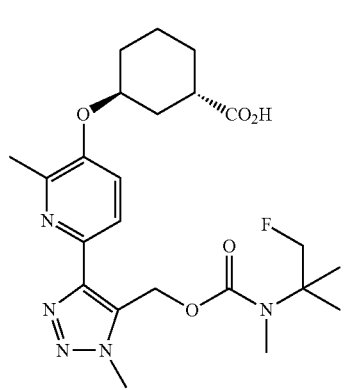 [SMILES: Cc1nc(-c2nnn(C)c2COC(=O)N(C)C(C)(C)CF)ccc1O[C@H]1CCC[C@H](C(=O)O)C1]<br>(1S,3S)-3-((6-(5-((((1-fluoro-2-methylpropan-2-yl)(methyl)carbamoyl)oxy)methyl)-1-methyl-1H-1,2,3-triazol-4-yl)-2-methyl-pyridin-3-yl)oxy)cyclohexane-1-carboxylic acid | LCMS, [M + H]$^+$ = 478<br>$^1$H NMR (500 MHz, DMSO-d$_6$) δ 7.85 (d, J = 8.5 Hz, 1H), 7.49 (d, J = 8.5 Hz, 1H), 5.62 (s, 2H), 4.81-4.74 (m, 1H), 4.57 (s, 1H), 4.47 (s, 1H), 4.11 (s, 3H), 2.82 (s, 3H), 2.65-2.58 (m, 1H), 2.42 (s, 3H), 2.05-1.96 (m, 1H), 1.89-1.74 (m, 3H), 1.64 (br s, 4H), 1.28 (br s, 6H)<br>hLPA1 IC$_{50}$ = 156 nM | Example 3 |

TABLE 1-continued

| Example | Structure & Name | Analytical & Biology Data | Method |
|---|---|---|---|
| 179 | (1S,3S)-3-((2-methyl-6-(1-methyl-5-(((methyl(spiro[2.3]hexan-5-yl)carbamoyl)oxy)methyl)-1H-1,2,3-triazol-4-yl)pyridin-3-yl)oxy)cyclohexane-1-carboxylic acid | LCMS, [M + H]$^+$ = 484<br>$^1$H NMR (500 MHz, DMSO-d$_6$) δ 7.82 (d, J = 8.5 Hz, 1H), 7.45 (d, J = 8.6 Hz, 1H), 5.63 (s, 2H), 4.75 (br s, 1H), 4.09 (s, 3H), 2.88-2.72 (m, 3H), 2.70-2.59 (m, 1H), 2.41 (s, 3H), 2.38-2.28 (m, 2H), 2.08-1.75 (m, 7H), 1.70-1.45 (m, 4H), 0.47-0.26 (m, 4H)<br>hLPA1 IC$_{50}$ = 14 nM | Example 3 |
| 180 | (1S,3S)-3-((6-(1-methyl-5-(((methyl(spiro[3.3]heptan-2-yl)carbamoyl)oxy)methyl)-1H-1,2,3-triazol-4-yl)pyridin-3-yl)oxy)cyclohexane-1-carboxylic acid | LCMS, [M + H]$^+$ = 484<br>$^1$H NMR (500 MHz, DMSO-d$_6$) δ 8.34 (br s, 1H), 7.99 (br d, J = 8.9 Hz, 1H), 7.59-7.51 (m, 1H), 5.60 (br s, 2H), 4.82-4.74 (m, 1H), 4.09 (s, 3H), 2.72-2.61 (m, 4H), 2.05-1.70 (m, 15H), 1.70-1.60 (m, 2H), 1.60-1.44 (m, 2H)<br>hLPA1 IC$_{50}$ = 62 nM | Example 10 |
| 181 | (1S,3S)-3-((6-(5-((((3,3-dimethylcyclobutyl)(methyl)carbamoyl)oxy)methyl)-1-methyl-1H-1,2,3-triazol-4-yl)pyridin-3-yl)oxy)cyclohexane-1-carboxylic acid | LCMS, [M + H]$^+$ = 472<br>$^1$H NMR (500 MHz, DMSO-d$_6$) δ 8.34 (br d, J = 2.1 Hz, 1H), 7.98 (br d, J = 8.5 Hz, 1H), 7.54 (dd, J = 8.9, 2.7 Hz, 1H), 5.60 (br s, 2H), 4.78 (br s, 1H), 4.61-4.23 (m, 1H), 4.10 (s, 3H), 2.71 (s, 3H), 2.68-2.61 (m, 1H), 2.08-1.71 (m, 7H), 1.66 (br d, J = 8.9 Hz, 2H), 1.60-1.46 (m, 2H), 1.14-0.90 (m, 6H)<br>hLPA1 IC$_{50}$ = 101 nM | Example 10 |

TABLE 1-continued

| Example | Structure & Name | Analytical & Biology Data | Method |
|---|---|---|---|
| 182 | (1S,3S)-3-((6-(5-((((3-fluorocyclobutyl)(methyl)carbamoyl)oxy)methyl)-1-methyl-1H-1,2,3-triazol-4-yl)-2-methylpyridin-3-yl)oxy)cyclohexane-1-carboxylic acid (mixture of diastereomers) | LCMS, [M + H]$^+$ = 476<br>$^1$H NMR (500 MHz, DMSO-d$_6$) δ 7.83 (d, J = 8.5 Hz, 1H), 7.46 (d, J = 8.6 Hz, 1H), 5.63 (s, 2H), 5.17-4.99 (m, 1H), 4.79-4.71 (m, 1H), 4.09 (s, 3H), 3.69-3.51 (m, 1H), 3.46 (br s, 1H), 2.75 (s, 3H), 2.67-2.57 (m, 1H), 2.41 (s, 4H), 2.32-2.17 (m, 2H), 2.03-1.95 (m, 1H), 1.88-1.75 (m, 3H), 1.69-1.45 (m, 4H)<br>hLPA1 IC$_{50}$ = 61 nM | Example 10 |
| 183 | (1S,3S)-3-((6-(1-methyl-5-(((methyl(spiro[2.3]hexan-5-yl)carbamoyl)oxy)methyl)-1H-1,2,3-triazol-4-yl)pyridin-3-yl)oxy)cyclohexane-1-carboxylic acid | LCMS, [M + H]$^+$ = 470<br>$^1$H NMR (500 MHz, CHLOROFORM-d) δ 8.34 (d, J = 2.5 Hz, 1H), 8.13 (d, J = 8.8 Hz, 1H), 7.36 (dd, J = 8.8, 2.8 Hz, 1H), 5.76 (s, 2H), 4.79-4.69 (m, 1H), 4.16 (s, 3H), 3.01-2.82 (m, 4H), 2.47-2.32 (m, 2H), 2.18-1.87 (m, 7H), 1.85-1.56 (m, 4H), 0.61-0.27 (m, 4H)<br>hLPA1 IC$_{50}$ = 20 nM | Example 3 |
| 184 | (1S,3S)-3-((6-(5-(((((2,2-dimethylcyclopropyl)methyl)(methyl)carbamoyl)oxy)methyl)-1-methyl-1H-1,2,3-triazol-4-yl)-2-methylpyridin-3-yl)oxy)cyclohexane-1-carboxylic acid (mixture of diastereomers) | LCMS, [M + H]$^+$ = 486<br>$^1$H NMR (500 MHz, DMSO-d$_6$) δ 7.94-7.76 (m, 1H), 7.55-7.40 (m, 1H), 5.75-5.53 (m, 2H), 4.77 (br s, 1H), 4.09 (s, 3H), 3.30-3.02 (m, 1H), 2.90-2.72 (m, 3H), 2.70-2.58 (m, 1H), 2.45-2.32 (m, 3H), 2.06-1.94 (m, 1H), 1.90-1.72 (m, 3H), 1.67-1.43 (m, 4H), 1.08-0.93 (m, 3H), 0.92-0.77 (m, 3H), 0.75-0.49 (m, 1H), 0.46-0.14 (m, 1H), 0.14 to −0.15 (m, 1H)<br>hLPA1 IC$_{50}$ = 37 nM | Example 3 |

TABLE 1-continued

| Example | Structure & Name | Analytical & Biology Data | Method |
|---|---|---|---|
| 185 | (1S,3S)-3-((6-(5-(((((2,2-dimethylcyclopropyl)methyl)(methyl)carbamoyl)oxy)methyl)-1-methyl-1H-1,2,3-triazol-4-yl)pyridin-3-yl)oxy)cyclohexane-1-carboxylic acid (mixture of diastereomers) | LCMS, $[M + H]^+$ = 472<br>$^1$H NMR (500 MHz, DMSO-$d_6$) δ 8.34 (br s, 1H), 7.99 (br d, J = 8.7 Hz, 1H), 7.53 (dd, J = 8.6, 2.5 Hz, 1H), 5.63 (s, 2H), 4.84-4.73 (m, 1H), 4.11 (s, 3H), 2.82 (br s, 3H), 2.73-2.63 (m, 1H), 2.03-1.93 (m, 1H), 1.91-1.74 (m, 3H), 1.72-1.49 (m, 4H), 1.26 (s, 1H), 0.97 (br s, 6H), 0.66 (br s, 1H), 0.38 (br s, 1H), 0.02 (br s, 1H)<br>hLPA1 $IC_{50}$ = 86 nM | Example 3 |
| 186 | (1S,3S)-3-((6-(5-(((((2,2-difluorocyclopropyl)methyl)(methyl)carbamoyl)oxy)methyl)-1-methyl-1H-1,2,3-triazol-4-yl)pyridin-3-yl)oxy)cyclohexane-1-carboxylic acid (mixture of diastereomers) | LCMS, $[M + H]^+$ = 480<br>$^1$H NMR (500 MHz, DMSO-$d_6$) δ 8.34 (d, J = 2.3 Hz, 1H), 7.99 (d, J = 8.7 Hz, 1H), 7.53 (dd, J = 8.7, 2.7 Hz, 1H), 5.64 (br s, 2H), 4.82-4.73 (m, 1H), 4.10 (s, 3H), 2.83 (br s, 3H), 2.72-2.64 (m, 1H), 2.01-1.93 (m, 1H), 1.90-1.73 (m, 4H), 1.71-1.48 (m, 5H), 1.25 (s, 1H), 1.23-1.09 (m, 1H)<br>hLPA1 $IC_{50}$ = 67 nM | Example 3 |
| 187 | (1S,3S)-3-((6-(5-((((3-fluoro-3-methylbutyl)(methyl)carbamoyl)oxy)methyl)-1-methyl-1H-1,2,3-triazol-4-yl)-2-methylpyridin-3-yl)oxy)cyclohexane-1-carboxylic acid | LCMS, $[M + H]^+$ = 492<br>$^1$H NMR (500 MHz, DMSO-$d_6$) δ 7.90-7.73 (m, 1H), 7.51-7.42 (m, 1H), 5.64-5.58 (m, 2H), 4.76 (br s, 1H), 4.08 (br s, 3H), 3.81-3.74 (m, 2H), 3.31-3.22 (m, 1H), 3.15-3.09 (m, 1H), 2.66-2.57 (m, 1H), 2.38 (br s, 3H), 1.98-1.72 (m, 5H), 1.67-1.39 (m, 6H), 1.32-1.24 (m, 3H), 1.09-1.01 (m, 3H)<br>hLPA1 $IC_{50}$ = 50 nM | Example 3 |

TABLE 1-continued

| Example | Structure & Name | Analytical & Biology Data | Method |
|---|---|---|---|
| 188 | 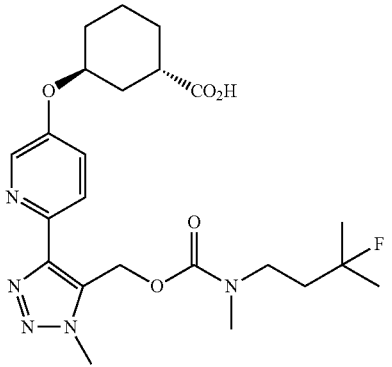 [SMILES: CN(CCC(C)(C)F)C(=O)OCc1c(-c2ccc(O[C@H]3CCC[C@H](C(=O)O)C3)cn2)nnn1C]<br>(1S,3S)-3-((6-(5-((((3-fluoro-3-methylbutyl)(methyl)carbamoyl)oxy)methyl)-1-methyl-1H-1,2,3-triazol-4-yl)pyridin-3-yl)oxy)cyclohexane-1-carboxylic acid | LCMS, $[M + H]^+ = 478$<br>$^1$H NMR (500 MHz, DMSO-$d_6$) δ 8.39-8.25 (m, 1H), 8.08-7.93 (m, 1H), 7.54 (br s, 1H), 5.66-5.53 (m, 2H), 4.76 (br s, 1H), 4.09 (br s, 2H), 3.86-3.74 (m, 2H), 3.31-3.24 (m, 1H), 3.16-3.12 (m, 1H), 2.68-2.60 (m, 1H), 1.97-1.73 (m, 5H), 1.63 (br s, 6H), 1.33-1.25 (m, 3H), 1.14-1.07 (m, 3H)<br>hLPA1 $IC_{50}$ = 32 nM | Example 3 |
| 189 | 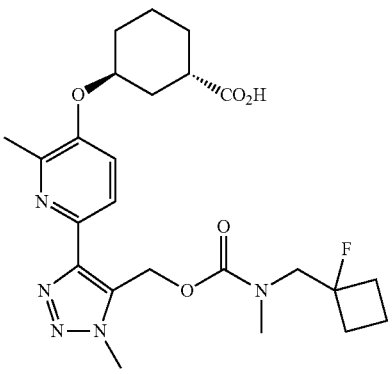 [SMILES: Cc1nc(-c2nnn(C)c2COC(=O)N(C)CC2(F)CCC2)ccc1O[C@H]1CCC[C@H](C(=O)O)C1]<br>(1S,3S)-3-((6-(5-(((((1-fluorocyclobutyl)methyl)(methyl)carbamoyl)oxy)methyl)-1-methyl-1H-1,2,3-triazol-4-yl)-2-methylpyridin-3-yl)oxy)cyclohexane-1-carboxylic acid | LCMS, $[M + H]^+ = 490$<br>$^1$H NMR (500 MHz, DMSO-$d_6$) δ 7.84 (br d, J = 8.4 Hz, 1H), 7.46 (br d, J = 8.6 Hz, 1H), 5.69 (s, 2H), 4.77 (br s, 1H), 4.11 (s, 3H), 3.72-3.23 (m, 1H), 2.85 (br s, 3H), 2.72-2.60 (m, 1H), 2.42 (s, 3H), 2.20-1.73 (m, 9H), 1.65 (br d, J = 9.8 Hz, 5H)<br>hLPA1 $IC_{50}$ = 120 nM | Example 3 |
| 190 | 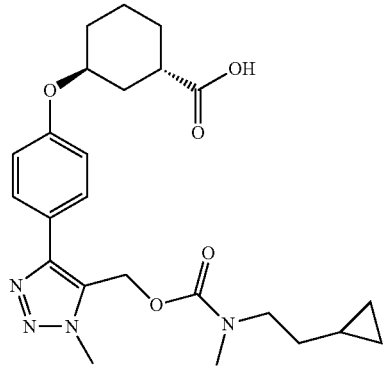<br>(1S,3S)-3-((6-(5-((((3-fluoropropyl)(methyl)carbamoyl)oxy)methyl)-1-methyl-1H-1,2,3-triazol-4-yl)-2-methylpyridin-3-yl)oxy)cyclohexane-1-carboxylic acid | LCMS, $[M + H]^+ = 464.1$<br>$^1$H NMR (500 MHz, CDCl$_3$) δ8.12 (d, J = 8.8 Hz, 1H), 7.86 (br t, J = 7.8 Hz, 1H), 5.64-5.57 (m, 1H), 5.55-5.47 (m, 1H), 4.86 (br s, 1H), 4.53 (dt, J = 10.4, 5.4 Hz, 1H), 4.43 (dt, J = 10.5, 5.3 Hz, 1H), 4.22 (s, 3H), 3.45 (q, J = 7.1 Hz, 2H), 2.97 (d, J = 12.9 Hz, 3H), 2.88 (br s, 1H), 2.74 (d, J = 2.2 Hz, 3H), 2.18-1.76 (m, 9H), 1.68 (br d, J = 6.3 Hz, 1H)<br>$^{19}$F-NMR: −221.9 ppm<br>hLPA1 $IC_{50}$ = 81 nM | |

TABLE 1-continued

| Example | Structure & Name | Analytical & Biology Data | Method |
|---|---|---|---|
| 191 | (1S,3S)-3-((6-(5-((((4-fluorobutyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 464.1<br>$^1$H NMR (500 MHz, DMSO-d$_6$) δ 7.84 (d, J = 8.5 Hz, 1H), 7.48 (d, J = 8.7 Hz, 1H), 7.33 (br t, J = 5.6 Hz, 1H), 5.64 (s, 2H), 4.79 (br s, 1H), 4.47 (t, J = 6.1 Hz, 1H), 4.37 (t, J = 6.0 Hz, 1H), 4.08 (s, 3H), 3.02 (q, J = 6.0 Hz, 2H), 2.71-2.59 (m, 1H), 2.42 (s, 3H), 2.11-1.98 (m, 1H), 1.90-1.75 (m, 3H), 1.72-1.41 (m, 8H)<br>hLPA1 IC$_{50}$ = 553 nM | |
| 192 | (1S,3S)-3-((6-(5-((((4-fluorobutyl)(methyl)carbamoyl)oxy)methyl)-1-methyl-1H-1,2,3-triazol-4-yl)-2-methylpyridin-3-yl)oxy)cyclohexane-1-carboxylic acid | LCMS, [M + H]$^+$ = 478.4<br>$^1$H NMR (400 MHz, CDCl$_3$) δ 11.11 (br s, 1H), 8.18 (d, J = 8.8 Hz, 1H), 8.00 (d, J = 8.8 Hz, 1H), 5.58-5.39 (m, 2H), 4.90 (br s, 1H), 4.57-4.49 (m, 1H), 4.46-4.35 (m, 1H), 4.23 (d, J = 4.2 Hz, 3H), 3.35 (br d, J = 7.0 Hz, 2H), 3.03-2.69 (m, 7H), 2.24-1.57 (m, 12H)<br>$^{19}$F NMR: 219 ppm<br>hLPA1 IC$_{50}$ = 36 nM | |
| 193 | (1R,3R)-3-((2-methyl-6-(1-methyl-5-((((methyl(propyl)carbamoyl)oxy)methyl)-1H-1,2,3-triazol-4-yl)pyridin-3-yl)oxy)cyclohexane-1-carboxylic acid | LCMS, [M + H]$^+$ = 446.1<br>$^1$H NMR (400 MHz, CDCl$_3$) δ 7.95 (d, J = 8.6 Hz, 1H), 7.20 (d, J = 8.6 Hz, 1H), 5.77 (br d, J = 5.3 Hz, 2H), 4.38-4.21 (m, 1H), 4.15 (s, 3H), 3.34-3.06 (m, 2H), 2.98-2.79 (m, 3H), 2.60-2.38 (m, 5H), 2.21-1.94 (m, 3H), 1.81-1.66 (m, 1H), 1.63-1.33 (m, 7H), 0.97-0.70 (m, 2H)<br>hLPA1 IC$_{50}$ = 1696 nM | |

The following analogs were synthesized according to the methods described for the preparation of Example 1 except that the intermediate 3 was used (instead of Example 1F).

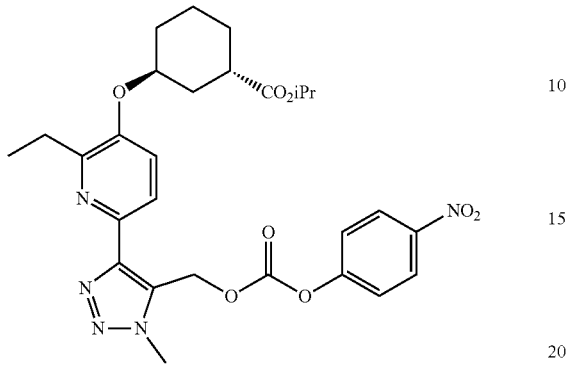

Intermediate 3

Intermediate 3 was prepared from 2,5-dibromo-6-ethyl-pyridine using the same synthetic sequence as described for the preparation of Example 1.

| Example | Structure & Name | Analytical & Biology Data | Method |
|---|---|---|---|
| 194 | (1S,3S)-3-((6-(5-((((cyclopropylmethyl)(methyl)carbamoyl)oxy)methyl)-1-methyl-1H-1,2,3-triazol-4-yl)-2-ethylpyridin-3-yl)oxy)cyclohexane-1-carboxylic acid | LCMS, [M + H]$^+$ = 472.0<br>$^1$H NMR (500 MHz, DMSO-d$_6$) δ 7.87 (br d, J = 7.9 Hz, 1H), 7.50 (br d, J = 8.5 Hz, 1H), 5.69 (br d, J = 16.2 Hz, 2H), 4.81 (br s, 1H), 4.14 (s, 3H), 3.56 (br s, 1H), 3.10 (br s, 1H), 2.99 (br s, 1H), 2.89-2.78 (m, 5H), 2.10-2.02 (m, 1H), 1.90 (br d, J = 11.6 Hz, 1H), 1.86-1.78 (m, 2H), 1.69-1.48 (m, 4H), 1.31-1.20 (m, 3H), 1.03-0.86 (m, 1H), 0.85-0.66 (m, 1H), 0.45 (br s, 1H), 0.28 (br s, 1H), 0.22 (br s, 1H), 0.00 (br s, 1H)<br>hLPA1 IC$_{50}$ = 14 nM | Example 1 |
| 195 | | LCMS, [M + H]+ = 485.9<br>$^1$H NMR (500 MHz, DMSO-d$_6$) δ 7.94-7.76 (m, 1H), 7.60-7.41 (m, 1H), 5.66 (s, 2H), 4.88-4.62 (m, 1H), 2.80 (q, J = 7.3 Hz, 2H), 2.64 (br s, 3H), 2.01-1.92 (m, 1H), 1.92-1.86 (m, 1H), 1.85-1.72 (m, 4H), 1.67-1.58 (m, 5H), 1.54 (br s, 5H), 1.43 (br s, 5H), 1.24 (br t, J = 7.4 Hz, 3H)<br>hLPA1 IC$_{50}$ = 11 nM | |

| Example | Structure & Name | Analytical & Biology Data | Method |
|---|---|---|---|
| | (1S,3S)-3-((6-(5-((((cyclopentyl(methyl)carbamoyl)oxy)methyl)-1-methyl-1H-1,2,3-triazol-4-yl)-2-ethylpyridin-3-yl)oxy)cyclohexane-1-carboxylic acid | | |
| 196 | (1S,3S)-3-((6-(5-((((cyclobutylmethyl(methyl)carbamoyl)oxy)methyl)-1-methyl-1H-1,2,3-triazol-4-yl)-2-ethylpyridin-3-yl)oxy)cyclohexane-1-carboxylic acid | LCMS, [M + H]+ = 486.2<br>$^1$H NMR (500 MHz, DMSO-$d_6$) δ 7.83 (br d, J = 8.2 Hz, 1H), 7.50 (br d, J = 8.6 Hz, 1H), 5.66 (br d, J = 16.0 Hz, 2H), 4.75 (br s, 1H), 4.10 (br d, J = 9.4 Hz, 3H), 2.80 (br d, J = 6.4 Hz, 2H), 2.73 (br d, J = 17.7 Hz, 3H), 1.91 (br d, J = 14.9 Hz, 2H), 1.84 (s, 6H), 1.76 (s, 4H), 1.71-1.57 (m, 4H), 1.54 (br s, 2H), 1.43 (br d, J = 8.1 Hz, 1H), 1.25 (br d, J = 6.8 Hz, 3H)<br>hLPA1 IC$_{50}$ = 12 nM | |
| 197 | (1S,3S)-3-((2-ethyl-6-(5-((((isobutyl(methyl)carbamoyl)oxy)methyl)-1-methyl-1H-1,2,3-triazol-4-yl)pyridin-3-yl)oxy)cyclohexane-1-carboxylic acid | LCMS, [M + H]$^+$ = 474.1<br>$^1$H NMR (500 MHz, DMSO-$d_6$) δ 7.80 (br t, J =8.1 Hz, 1H), 7.45 (br d, J = 8.2 Hz, 1H), 5.63 (br d, J = 18.3 Hz, 2H), 4.75 (br s, 1H), 4.08 (br s, 3H), 2.99 (br d, J = 7.0 Hz, 1H), 2.85 (br d, J = 6.7 Hz, 1H), 2.81-2.70 (m, 5H), 1.97 (br d, J = 13.7 Hz, 1H), 1.86 (s, 1H), 1.79 (br d, J = 12.5 Hz, 3H), 1.60 (br d, J = 8.9 Hz, 3H), 1.57-1.45 (m, 2H), 1.23 (br d, J = 7.6 Hz, 3H), 0.78 (br d, J = 5.5 Hz, 3H), 0.59-0.54 (m, 3H)<br>hLPA1 IC$_{50}$ = 27 nM | |
| 198 | | LCMS, [M + H]$^+$ = 494.0<br>$^1$H NMR (500 MHz, DMSO-$d_6$) δ 7.84 (br d, J = 8.3 Hz, 2H), 7.47 (br d, J = 8.5 Hz, 1H), 7.32-7.27 (m, 2H), 7.22 (br d, J = 7.2 Hz, 3H), 5.69 (s, 2H), 4.76 (br s, 1H), 4.18 (br d, J = 5.9 Hz, 2H), 4.08 (s, 3H), 3.50 (br s, 1H), 2.78 (q, J = 7.3 Hz, 2H), 1.98 (br d, J = 13.0 Hz, 1H), 1.80 (br d, J = 11.8 Hz, 3H), 1.61 (br s, 2H), 1.54 (br s, 1H), 1.50 (br s, 1H), 1.22 (br t, J = 7.4 Hz, 3H)<br>hLPA1 IC$_{50}$ = 46 nM | |

| Example | Structure & Name | Analytical & Biology Data | Method |
|---|---|---|---|
| | (1S,3S)-3-((6-(5-(((benzylcarbamoyl)oxy)methyl)-1-methyl-1H-1,2,3-triazol-4-yl)-2-ethylpyridin-3-yl)oxy)cyclohexane-1-carboxylic acid | | |
| 199 | 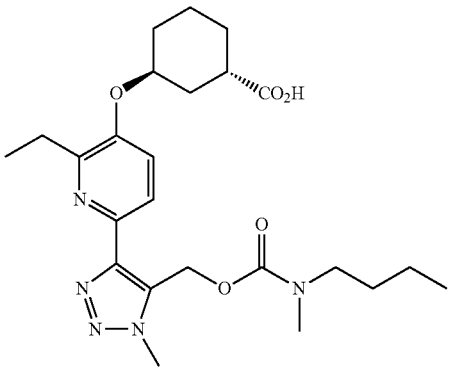 [SMILES: CCCCN(C)C(=O)OCc1c(-c2ccc(O[C@H]3CCC[C@H](C(=O)O)C3)c(CC)n2)nnn1C]<br>(1S,3S)-3-((6-(5-(((butyl(methyl)carbamoyl)oxy)methyl)-1-methyl-1H-1,2,3-triazol-4-yl)-2-ethylpyridin-3-yl)oxy)cyclohexane-1-carboxylic acid | LCMS, [M + H]$^+$ = 474.1<br>$^1$H NMR (500 MHz, DMSO-d$_6$) δ 7.83 (br d, J = 8.3 Hz, 1H), 7.46 (br d, J = 8.3 Hz, 1H), 5.64 (br d, J = 12.4 Hz, 2H), 4.76 (br s, 1H), 4.09 (br s, 3H), 3.53 (br s, 1H), 3.17 (br s, 1H), 3.03 (br s, 1H), 2.82-2.69 (m, 5H), 1.98 (br d, J = 13.8 Hz, 1H), 1.79 (br d, J = 11.0 Hz, 3H), 1.60 (br s, 2H), 1.57-1.45 (m, 2H), 1.41 (br s, 1H), 1.26-1.16 (m, 5H), 1.01-0.93 (m, 1H), 0.86 (br s, 1H), 0.61 (br s, 2H)<br>hLPA1 IC$_{50}$ = 7 nM | |
| 200 | 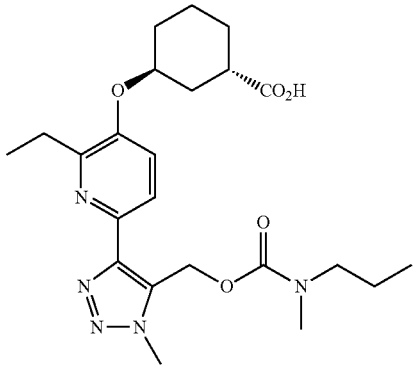 [SMILES: CCCN(C)C(=O)OCc1c(-c2ccc(O[C@H]3CCC[C@H](C(=O)O)C3)c(CC)n2)nnn1C]<br>(1S,3S)-3-((2-ethyl-6-(1-methyl-5-(((methyl(propyl)carbamoyl)oxy)methyl)-1H-1,2,3-triazol-4-yl)pyridin-3-yl)oxy)cyclohexane-1-carboxylic acid | LCMS, [M + H]$^+$ = 460.1<br>$^1$H NMR (500 MHz, DMSO-d$_6$) δ 7.92-7.70 (m, 1H), 7.62-7.30 (m, 1H), 5.80-5.48 (m, 2H), 4.89-4.58 (m, 1H), 4.24-3.82 (m, 3H), 3.60-3.25 (m, 1H), 3.21-2.93 (m, 2H), 2.85-2.67 (m, 5H), 2.66-2.56 (m, 1H), 2.07-1.94 (m, 1H), 1.90-1.69 (m, 3H), 1.68-1.36 (m, 5H), 1.33-1.14 (m, 3H), 0.86-0.67 (m, 2H), 0.67-0.40 (m, 2H)<br>hLPA1 IC$_{50}$ = 11 nM | |
| 201 | 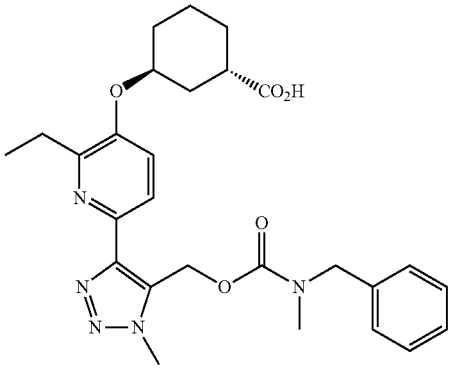 | LCMS, [M + H]$^+$ = 474.1<br>$^1$H NMR (500 MHz, DMSO-d$_6$) δ 7.83 (br d, J = 8.3 Hz, 1H), 7.46 (br d, J = 8.3 Hz, 1H), 5.64 (br d, J = 12.4 Hz, 2H), 4.76 (br s, 1H), 4.09 (br s, 3H), 3.53 (br s, 1H), 3.17 (br s, 1H), 3.03 (br s, 1H), 2.82-2.69 (m, 5H), 1.98 (br d, J = 13.8 Hz, 1H), 1.79 (br d, J = 11.0 Hz, 3H), 1.60 (br s, 2H), 1.57-1.45 (m, 2H), 1.41 (br s, 1H), 1.26-1.16 (m, 5H), 1.01-0.93 (m, 1H), 0.86 (br s, 1H), 0.61 (br s, 2H)<br>hLPA1 IC$_{50}$ = 25 nM | |

| Example | Structure & Name | Analytical & Biology Data | Method |
|---|---|---|---|
| | (1S,3S)-3-((6-(5-(((benzyl(methyl)carbamoyl)oxy)methyl)-1-methyl-1H-1,2,3-triazol-4-yl)-2-ethylpyridin-3-yl)oxy)cyclohexane-1-carboxylic acid | | |
| 202 | (1S,3S)-3-((2-ethyl-6-(5-(((ethyl(methyl)carbamoyl)oxy)methyl)-1-methyl-1H-1,2,3-triazol-4-yl)pyridin-3-yl)oxy)cyclohexane-1-carboxylic acid | LCMS, $[M + H]^+ = 446.1$<br>$^1$H NMR (500 MHz, DMSO-$d_6$) δ 7.84 (br d, J = 8.5 Hz, 1H), 7.47 (br d, J = 8.5 Hz, 1H), 5.66 (br s, 2H), 4.76 (br s, 1H), 4.09 (s, 3H), 3.56-3.37 (m, 1H), 3.19 (br d, J = 18.6 Hz, 1H), 3.11 (br s, 1H), 2.82-2.75 (m, 3H), 2.73 (br s, 2H), 2.60-2.53 (m, 1H), 1.98 (br d, J = 13.4 Hz, 1H), 1.80 (br d, J = 11.0 Hz, 2H), 1.61 (br s, 2H), 1.53 (br d, J = 16.5 Hz, 2H), 1.24 (t, J = 7.5 Hz, 3H), 1.00 (br d, J = 6.1 Hz, 2H), 0.86 (br s, 2H)<br>hLPA1 IC$_{50}$ = 160 nM | |
| 203 | (1S,3S)-3-((6-(5-(((cyclobutyl(methyl)carbamoyl)oxy)methyl)-1-methyl-1H-1,2,3-triazol-4-yl)-2-ethylpyridin-3-yl)oxy)cyclohexane-1-carboxylic acid | LCMS, $[M + H]^+ = 472.1$<br>$^1$H NMR (500 MHz, DMSO-$d_6$) δ 7.81 (br d, J = 8.2 Hz, 1H), 7.46 (br d, J = 8.9 Hz, 1H), 5.62 (s, 2H), 4.74 (br s, 1H), 4.07 (s, 3H), 3.77-3.70 (m, 4H), 2.77 (q, J = 7.3 Hz, 2H), 2.70 (br s, 2H), 2.03 (br s, 1H), 1.93 (br d, J = 13.1 Hz, 2H), 1.88-1.72 (m, 5H), 1.63-1.41 (m, 6H), 1.21 (br t, J = 7.3 Hz, 3H)<br>hLPA1 IC$_{50}$ = 8 nM | |
| 204 | | LCMS, $[M + H]^+ = 472.1$<br>$^1$H NMR (500 MHz, DMSO-$d_6$) δ 7.81 (br d, J = 8.5 Hz, 1H), 7.46 (br d, J = 8.5 Hz, 1H), 5.62 (s, 2H), 4.74 (br s, 1H), 4.05 (s, 3H), 3.79-3.70 (m, 4H), 2.78 (q, J = 7.3 Hz, 2H), 1.91 (br s, 1H), 1.86-1.73 (m, 5H), 1.64-1.44 (m, 4H), 1.22 (t, J = 7.5 Hz, 3H), 1.13 (s, 6H)<br>hLPA1 IC$_{50}$ = 102 nM | |

| Example | Structure & Name | Analytical & Biology Data | Method |
|---|---|---|---|
| 205 | (1S,3S)-3-((6-(5-(((3,3-dimethylazetidine-1-carbonyl)oxy)methyl)-1-methyl-1H-1,2,3-triazol-4-yl)-2-ethylpyridin-3-yl)oxy)cyclohexane-1-carboxylic acid<br>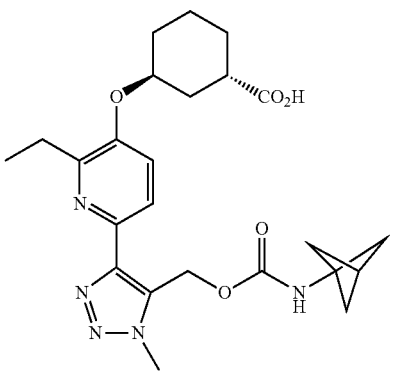 [SMILES: CCc1nc(-c2nnn(C)c2COC(=O)NC23CC(C2)C3)ccc1O[C@H]1CCC[C@H](C(=O)O)C1] | LCMS, [M + H]+ = 470.1<br>1H NMR (500 MHz, DMSO-d6) δ 7.82 (br d, J = 7.3 Hz, 1H), 7.48 (br s, 1H), 5.62 (br s, 2H), 4.99-4.53 (m, 1H), 4.07 (br s, 2H), 3.58 (br s, 1H), 3.17 (s, 1H), 2.89 (s, 1H), 2.82 (br s, 1H), 2.73 (s, 1H), 2.35 (br s, 1H), 2.05 (br s, 1H), 1.90 (br s, 7H), 1.64 (br s, 4H), 1.25 (br s, 3H), 1.00 (d, J = 6.1 Hz, 1H)<br>hLPA1 IC50 = 842 nM | |
| 206 | (1S,3S)-3-((6-(5-(((bicyclo[1.1.1]pentan-1-ylcarbamoyl)oxy)methyl)-1-methyl-1H-1,2,3-triazol-4-yl)-2-ethylpyridin-3-yl)oxy)cyclohexane-1-carboxylic acid<br>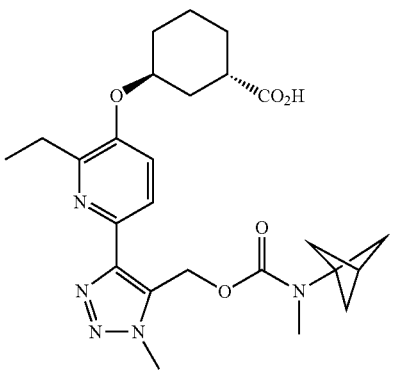<br>(1S,3S)-3-((6-(5-(((bicyclo[1.1.1]pentan-1-yl(methyl)carbamoyl)oxy)methyl)-1-methyl-1H-1,2,3-triazol-4-yl)-2-ethylpyridin-3-yl)oxy)cyclohexane-1-carboxylic acid | LCMS, [M + H]+ = 484.1<br>1H NMR (500 MHz, DMSO-d6) δ 7.88-7.75 (m, J = 8.2 Hz, 1H), 7.54-7.41 (m, J = 8.2 Hz, 1H), 5.63 (s, 2H), 4.88-4.67 (m, 1H), 4.09 (s, 2H), 3.69-3.53 (m, 1H), 3.17 (s, 1H), 2.89 (s, 1H), 2.80 (br d, J = 7.3 Hz, 2H), 2.76-2.63 (m, 3H), 2.05 (br s, 1H), 1.79 (br s, 8H), 1.61 (br s, 4H), 1.22 (br t, J = 7.3 Hz, 3H), 1.00 (d, J = 6.4 Hz, 1H)<br>hLPA1 IC50 = 34 nM | |

| Example | Structure & Name | Analytical & Biology Data | Method |
|---|---|---|---|
| 207 | 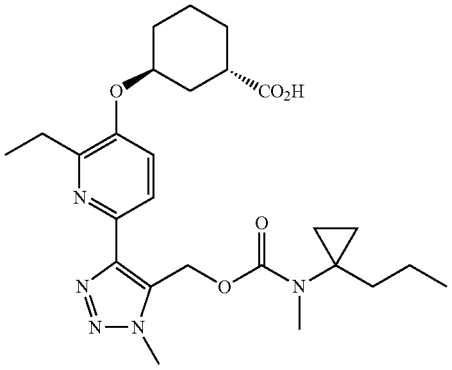 [SMILES: CCCC1(N(C)C(=O)OCc2c(-c3ccc(O[C@H]4CCC[C@H](C(=O)O)C4)c(CC)n3)nnn2C)CC1]<br>(1S,3S)-3-((2-ethyl-6-(1-methyl-5-(((methyl(1-propylcyclopropyl)carbamoyl)oxy)methyl)-1H-1,2,3-triazol-4-yl)pyridin-3-yl)oxy)cyclohexane-1-carboxylic acid | LCMS, $[M + H]^+$ = 500.4<br>$^1$H NMR (500 MHz, DMSO-$d_6$) δ 7.83 (br d, J = 8.5 Hz, 1H), 7.47 (br d, J = 8.5 Hz, 1H), 5.64 (br d, J = 8.5 Hz, 2H), 4.78 (br s, 1H), 4.12 (s, 2H), 4.08 (br s, 1H), 2.83-2.73 (m, 4H), 2.73-2.65 (m, 1H), 2.60 (br s, 1H), 2.12-1.94 (m, 1H), 1.86 (br d, J = 12.2 Hz, 1H), 1.82-1.70 (m, 2H), 1.66-1.52 (m, 3H), 1.52-1.37 (m, 2H), 1.31-1.22 (m, 4H), 1.20 (br s, 1H), 1.06 (br d, J = 8.2 Hz, 1H), 1.00 (d, J = 6.1 Hz, 1H), 0.84 (br s, 1H), 0.74 (br s, 1H), 0.68-0.54 (m, 4H), 0.44 (br s, 1H)<br>hLPA1 IC$_{50}$ = 133 nM | |
| 208 | 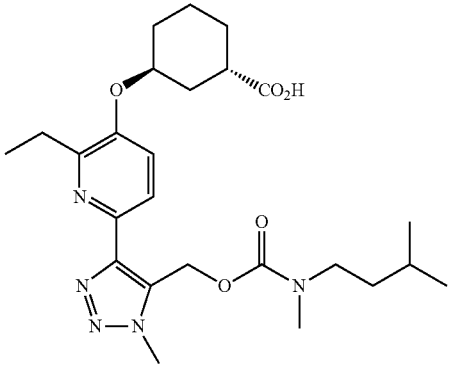 [SMILES: CCc1nc(-c2nnn(C)c2COC(=O)N(C)CCC(C)C)ccc1O[C@H]1CCC[C@H](C(=O)O)C1]<br>(1S,3S)-3-((2-ethyl-6-(5-(((isopentyl(methyl)carbamoyl)oxy)methyl)-1-methyl-1H-1,2,3-triazol-4-yl)pyridin-3-yl)oxy)cyclohexane-1-carboxylic acid | LCMS, $[M + H]^+$ = 488.3<br>$^1$H NMR (500 MHz, DMSO-$d_6$) δ 7.89-7.77 (m, J = 8.5 Hz, 1H), 7.53-7.41 (m, J = 8.5 Hz, 1H), 5.64 (br s, 2H), 4.76 (br s, 1H), 4.09 (s, 3H), 3.27-3.10 (m, 1H), 3.04 (br s, 1H), 2.89 (s, 1H), 2.82-2.67 (m, 5H), 1.98 (br d, J = 12.8 Hz, 1H), 1.89 (s, 3H), 1.80 (br d, J = 11.6 Hz, 2H), 1.61 (br d, J = 8.5 Hz, 2H), 1.54 (br s, 1H), 1.49 (br d, J = 11.3 Hz, 1H), 1.30 (br d, J = 5.8 Hz, 1H), 1.24 (br t, J = 7.5 Hz, 3H), 1.12 (br s, 1H), 0.86 (br s, 3H), 0.60 (br s, 3H)<br>hLPA1 IC$_{50}$ = 26 nM | |
| 209 | 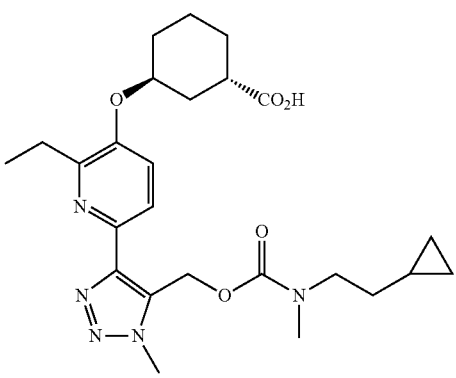 [SMILES: CCc1nc(-c2nnn(C)c2COC(=O)N(C)CCC2CC2)ccc1O[C@H]1CCC[C@H](C(=O)O)C1]<br>(1S,3S)-3-((6-(5-((((2-cyclopropylethyl)(methyl)carbamoyl)oxy)methyl)-1-methyl-1H-1,2,3-triazol-4-yl)-2-ethylpyridin-3-yl)oxy)cyclohexane-1-carboxylic acid | LCMS, $[M + H]^+$ = 486.4<br>$^1$H NMR (500 MHz, DMSO-$d_6$) δ 7.83 (br d, J = 7.6 Hz, 1H), 7.46 (br d, J = 8.5 Hz, 1H), 5.65 (br d, J = 10.7 Hz, 2H), 4.77 (br s, 1H), 4.09 (br s, 3H), 3.24 (br s, 1H), 3.12 (br s, 1H), 2.95-2.85 (m, 1H), 2.83-2.71 (m, 5H), 2.61 (br t, J = 10.5 Hz, 1H), 2.08-1.95 (m, 1H), 1.92-1.82 (m, 2H), 1.82-1.73 (m, 2H), 1.66-1.45 (m, 4H), 1.33 (br s, 1H), 1.28-1.11 (m, 4H), 0.35 (br s, 1H), 0.16 (br s, 1H), -0.01 (br s, 1H), -0.27 (br s, 1H)<br>hLPA1 IC$_{50}$ = 22 nM | |

| Example | Structure & Name | Analytical & Biology Data | Method |
|---|---|---|---|
| 210 | 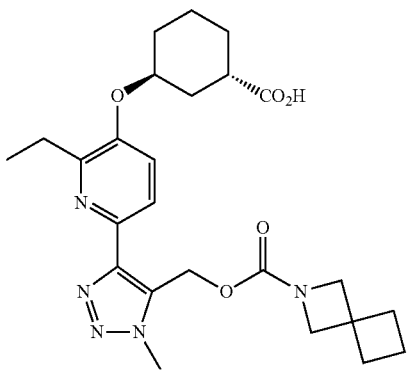 [SMILES: CCc1nc(-c2nnn(C)c2COC(=O)N2CC3(CCC3)C2)ccc1O[C@H]1CCC[C@H](C(=O)O)C1]<br><br>(1S,3S)-3-((6-(5-(((2-azaspiro[3.3]heptane-2-carbonyl)oxy)methyl)-1-methyl-1H-1,2,3-triazol-4-yl)-2-ethylpyridin-3-yl)oxy)cyclohexane-1-carboxylic acid | LCMS, [M + H]+ = 484.4<br>$^1$H NMR (500 MHz, DMSO-$d_6$) δ 7.83 (d, J = 8.5 Hz, 1H), 7.46 (d, J = 8.5 Hz, 1H), 5.64 (s, 2H), 4.77 (br s, 1H), 4.07 (s, 3H), 2.93-2.86 (m, 1H), 2.80 (q, J = 7.3 Hz, 2H), 2.73 (s, 1H), 2.61 (br t, J = 10.7 Hz, 1H), 2.09-1.99 (m, 5H), 1.93-1.82 (m, 3H), 1.82-1.67 (m, 4H), 1.65-1.52 (m, 3H), 1.50 (br s, 1H), 1.28-1.14 (m, 3H)<br>hLPA1 $IC_{50}$ = 67 nM | |
| 211 | 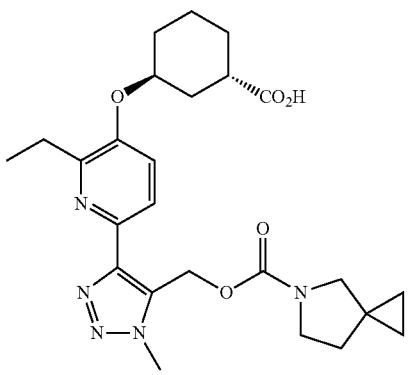 [SMILES: CCc1nc(-c2nnn(C)c2COC(=O)N2CCC3(CC3)C2)ccc1O[C@H]1CCC[C@H](C(=O)O)C1]<br><br>(1S,3S)-3-((6-(5-(((5-azaspiro[2.4]heptane-5-carbonyl)oxy)methyl)-1-methyl-1H-1,2,3-triazol-4-yl)-2-ethylpyridin-3-yl)oxy)cyclohexane-1-carboxylic acid | LCMS, [M + H]+ = 484.4<br>$^1$H NMR (500 MHz, DMSO-$d_6$) δ 7.87-7.80 (m, 1H), 7.46 (br d, J = 8.9 Hz, 1H), 5.69 (br d, J = 5.8 Hz, 2H), 4.77 (br s, 1H), 4.09 (br d, J = 15.3 Hz, 3H), 3.15 (s, 1H), 3.07 (s, 1H), 2.89 (s, 1H), 2.80 (q, J = 7.6 Hz, 2H), 2.73 (s, 1H), 2.61 (br t, J = 10.5 Hz, 1H), 2.16-1.96 (m, 1H), 1.91-1.74 (m, 3H), 1.70 (t, J = 6.9 Hz, 2H), 1.65-1.45 (m, 4H), 1.29-1.14 (m, 3H), 0.55 (br s, 1H), 0.53-0.45 (m, 3H)<br>hLPA1 $IC_{50}$ = 47 nM | |

The following analogs were synthesized according to the methods described for the preparation of Example 1 except that the intermediate 4 was used (instead of Example 1F).

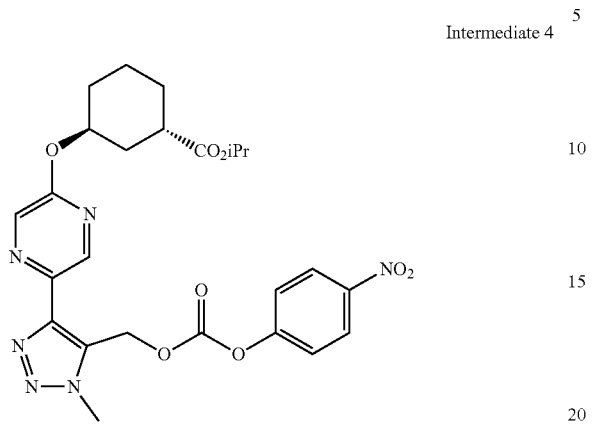

Intermediate 4

Intermediate 3 was prepared from 2,5-dibromo-pyrazine using the same synthetic sequence as described for the preparation of Example 1.

| Example | Structure & Name | Analytical & Biology Data | Method |
|---|---|---|---|
| 212 | (1S,3S)-3-((5-(5-(((butyl(methyl)carbamoyl)oxy)methyl)-1-methyl-1H-1,2,3-triazol-4-yl)pyrazin-2-yl)oxy)cyclohexane-1-carboxylic acid | LCMS, [M + H]+ = 447.1<br>$^1$H NMR (500 MHz, DMSO-$d_6$) δ 8.77 (s, 1H), 8.34 (s, 1H), 5.53 (br d, J = 15.0 Hz, 2H), 5.36 (br s, 1H), 4.12 (s, 3H), 3.16 (br s, 1H), 3.06 (br s, 1H), 2.74 (br d, J = 11.6 Hz, 3H), 2.66 (br t, J = 10.1 Hz, 1H), 2.07 (br d, J = 13.1 Hz, 1H), 1.87-1.79 (m, 3H), 1.66 (br t, J = 13.0 Hz, 2H), 1.60-1.48 (m, 2H), 1.41 (br s, 1H), 1.22 (br s, 2H), 1.06-0.99 (m, 1H), 0.86 (br s, 1H), 0.68 (br s, 2H)<br>hLPA1 $IC_{50}$ = 40 nM | Example 1 |
| 213 | | LCMS, [M + H]+ = 445.1<br>$^1$H NMR (500 MHz, DMSO-$d_6$) δ 8.80-8.73 (m, 1H), 8.37-8.30 (m, 1H), 5.54 (br d, J = 13.1 Hz, 2H), 5.40-5.31 (m, 1H), 4.12 (s, 3H), 3.12-3.02 (m, 1H), 3.02-2.92 (m, 1H), 2.83 (br s, 3H), 2.70-2.60 (m, 1H), 2.12-2.01 (m, 1H), 1.86-1.79 (m, 3H), 1.71-1.61 (m, 2H), 1.59-1.48 (m, 2H), 0.98-0.85 (m, 1H), 0.85-0.70 (m, 1H), 0.49-0.36 (m, 1H), 0.36-0.23 (m, 1H), 0.23-0.09 (m, 1H), 0.09--0.07 (m, 1H)<br>hLPA1 $IC_{50}$ = 1070 nM | Example 1 |

| Example | Structure & Name | Analytical & Biology Data | Method |
|---|---|---|---|
| | (1S,3S)-3-((5-(5-((((cyclopropylmethyl)(methyl)carbamoyl)oxy)methyl)-1-methyl-1H-1,2,3-triazol-4-yl)pyrazin-2-yl)oxy)cyclohexane-1-carboxylic acid | | |
| 214 | 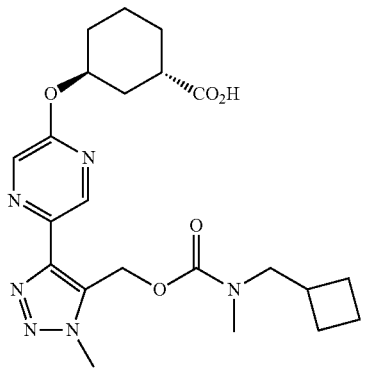 [SMILES: CN(CC1CCC1)C(=O)OCc1c(-c2cnc(O[C@H]3CCC[C@H](C(=O)O)C3)cn2)nnn1C] | LCMS, [M + H]+ = 459.0<br>$^1$H NMR (500 MHz, DMSO-$d_6$) δ 8.75 (s, 1H), 8.33 (br s, 1H), 5.51 (br d, J = 16.5 Hz, 2H), 5.34 (br s, 1H), 4.12 (br s, 3H), 3.56 (br s, 1H), 3.18 (br d, J = 10.4 Hz, 1H), 3.08 (br d, J = 5.5 Hz, 1H), 2.71 (br d, J = 9.5 Hz, 3H), 2.64 (br s, 1H), 2.34-2.19 (m, 1H), 2.08-2.02 (m, 1H), 1.90 (br s, 1H), 1.86-1.78 (m, 3H), 1.75 (br s, 1H), 1.71 (br s, 1H), 1.64 (br d, J = 13.4 Hz, 3H), 1.59-1.46 (m, 3H), 1.40 (br s, 1H)<br>hLPA1 IC$_{50}$ = 68 nM | Example 1 |
| | (1S,3S)-3-((5-(5-((((cyclobutylmethyl)(methyl)carbamoyl)oxy)methyl)-1-methyl-1H-1,2,3-triazol-4-yl)pyrazin-2-yl)oxy)cyclohexane-1-carboxylic acid | | |
| 215 | 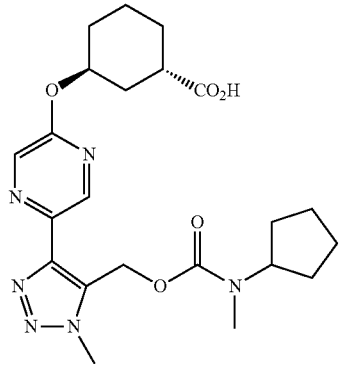 [SMILES: CN(C(=O)OCc1c(-c2cnc(O[C@H]3CCC[C@H](C(=O)O)C3)cn2)nnn1C)C1CCCC1] | LCMS, [M + H]+ = 459.3<br>$^1$H NMR (500 MHz, DMSO-$d_6$) δ 8.76 (s, 1H), 8.34 (s, 1H), 5.54 (s, 2H), 5.35 (br s, 1H), 4.47-4.22 (m, 1H), 4.11 (s, 3H), 3.53-3.31 (m, 1H), 2.63 (br s, 4H), 2.10-2.03 (m, 1H), 1.87-1.76 (m, 3H), 1.73-1.60 (m, 3H), 1.57 (br s, 3H), 1.51 (br d, J = 12.2 Hz, 2H), 1.43 (br s, 4H)<br>hLPA1 IC$_{50}$ = 84 nM | Example 1 |
| | (1S,3S)-3-((5-(5-(((cyclopentyl(methyl)carbamoyl)oxy)methyl)-1-methyl-1H-1,2,3-triazol-4-yl)pyrazin-2-yl)oxy)cyclohexane-1-carboxylic acid | | |

Example 216

(1S,3S)-3-((3-methyl-5-(1-methyl-5-(((methyl(propyl)carbamoyl)oxy)methyl)-1H-1,2,3-triazol-4-yl)pyrazin-2-yl)oxy)cyclohexane-1-carboxylic Acid

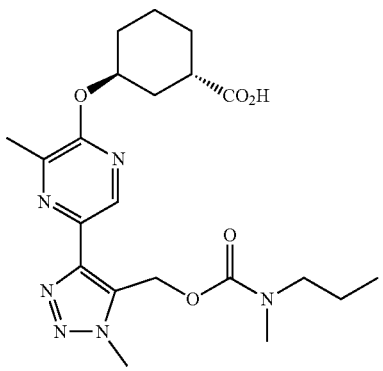 [SMILES: CCCN(C)C(=O)OCc1c(-c2cnc(O[C@H]3CCC[C@H](C(=O)O)C3)c(C)n2)nnn1C]

216A. Methyl 3-bromo-6-(3-hydroxyprop-1-yn-1-yl)pyrazine-2-carboxylate

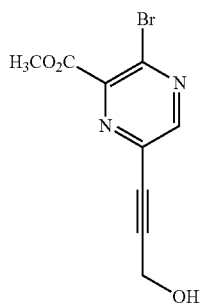 [SMILES: COC(=O)c1nc(C#CCO)cnc1Br]

A mixture of methyl 3,6-dibromopyrazine-2-carboxylate (16.5 g, 55.8 mmol), propargyl alcohol (3.33 mL, 55.8 mmol), and TEA (46.6 mL, 335 mmol) in MeCN (100 mL) was degassed with $N_2$ and then CuI (0.531 g, 2.79 mmol) and bis(triphenylphosphine)Palladium(II) chloride (1.96 g, 2.79 mmol) were successively added. The reaction mixture was degassed with $N_2$ for 3 cycles & stirred at rt for 18 h, then was filtered through a pad of Celite. The filtrate was concentrated in vacuo. The crude oil was chromatographed (120 g $SiO_2$ eluted with EtOAc/hexane using a continuous gradient from 0% to 80% over 25 min) to give the title product (5.40 g, 19.9 mmol, 35.7% yield) as a brownish oil. $^1$H NMR (500 MHz, $CDCl_3$) δ 8.53 (s, 1H), 4.56 (d, J=6.3 Hz, 2H), 4.04 (s, 3H), 2.09-2.00 (m, 1H)

216B. Methyl 3-bromo-6-(5-(hydroxymethyl)-1-methyl-1H-1,2,3-triazol-4-yl)pyrazine-2-carboxylate

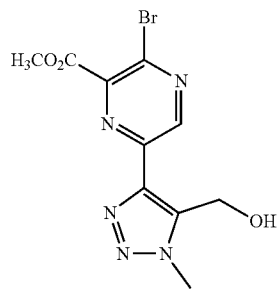 [SMILES: COC(=O)c1nc(-c2nnn(C)c2CO)cnc1Br]

To a solution of Example 216A (2.7 g, 9.96 mmol) in 1,4-dioxane (100 mL) were successively added $TMSCH_2N_3$ (1.48 mL, 9.96 mmol), chloro(pentamethylcyclopenta-dienyl)bis(triphenylphosphine)Ruthenium(II) (0.397 g, 0.498 mmol), and CuI (0.095 g, 0.498 mmol). The mixture was degassed with $N_2$ for 3 cycles. The resulting homogenous mixture was then heated at 50° C. (oil bath) for 16 h, then was cooled to rt and concentrated in vacuo. The residue was dissolved in THF (40 mL) and cooled to 0° C.; TBAF (19.9 mL of a 1 M solution in THF, 19.9 mmol) was added at 0° C. The reaction mixture was allowed to warm to rt and stirred at rt for 60 min, after which sat. aq. $NaHCO_3$ aqueous solution (20 mL) was added. The mixture was stirred for 1 h and filtered. The filtrate was concentrated in vacuo. The crude brown oily product was chromatographed ($SiO_2$; 80 g; elution with EtOAc/Hexane—continuous gradient from 0% to 80% over 25 min) to give title product (1.5 g, 4.57 mmol, 45.9% yield) as a light brownish solid. $^1$H NMR (400 MHz, $CDCl_3$) δ 9.42 (s, 1H), 4.90-4.85 (m, 3H), 4.15 (s, 3H), 4.07 (s, 3H)

216C. Methyl 3-bromo-6-(1-methyl-5-(((tetrahydro-2H-pyran-2-yl)oxy)methyl)-1H-1,2,3-triazol-4-yl)pyrazine-2-carboxylate

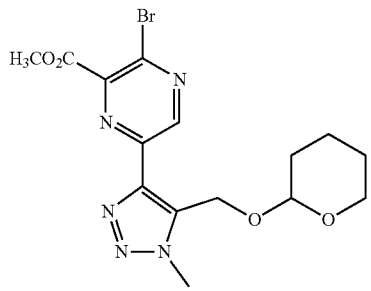 [SMILES: COC(=O)c1nc(-c2nnn(C)c2COC2CCCCO2)cnc1Br]

p-TsOH.$H_2O$ (0.087 g, 0.457 mmol) was added to a solution of Example 216B (3.0 g, 9.14 mmol) and 3,4-dihydro-2H-pyran (2.502 mL, 27.4 mmol) in DCM (10 mL) at 0° C. The reaction mixture was stirred overnight at rt and neutralized with satd aq. $NaHCO_3$ to pH 7 at 0° C. The mixture was partitioned between $CH_2Cl_2$ (10 mL) and water (10 mL), and the aqueous layer was extracted with DCM (3×10 mL). The combined organic extracts were dried ($MgSO_4$), filtered, and concentrated in vacuo. The crude oil was chromatographed (40 g $SiO_2$; elution with EtOAc/Hexane—continuous gra-

216D. 3-Bromo-6-(1-methyl-5-(((tetrahydro-2H-pyran-2-yl)oxy)methyl)-1H-1,2,3-triazol-4-yl)pyrazine-2-carboxylic Acid

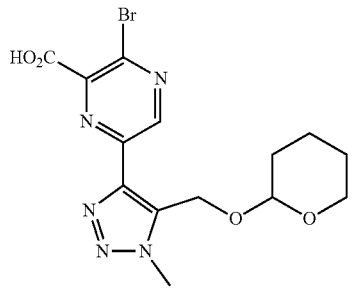 [SMILES: Cn1nnc(-c2cnc(Br)c(C(=O)O)n2)c1COC1CCCCO1]

A solution of LiOH.H₂O (0.484 g, 11.53 mmol) in water (6 mL) was added dropwise to a stirred solution of Example 216C (1.0 g, 2.43 mmol) in THF (6 mL) at 0° C. The reaction mixture was allowed to warm to rt and stirred at rt for 60 min, then was quenched carefully with 1N aq. HCl to pH~5 at 0° C. and extracted with DCM (20×5 mL). The combined organic extracts were washed with brine and dried over Na₂SO₄. Volatiles were removed in vacuo to afford the title compound (0.80 g, 2.01 mmol, 83% yield) as a light yellowish solid.

[M-THP+H]⁺=313.9/315.9; ¹H NMR (500 MHz, CDCl₃) δ 9.46 (s, 1H), 5.42 (d, J=13.5 Hz, 1H), 4.90 (d, J=13.8 Hz, 1H), 4.24 (s, 3H), 3.87 (td, J=10.9, 2.6 Hz, 1H), 3.73 (d, J=11.3 Hz, 1H), 1.93-1.50 (m, 7H)

217E. 3-Bromo-6-(1-methyl-5-(((tetrahydro-2H-pyran-2-yl)oxy)methyl)-1H-1,2,3-triazol-4-yl)pyrazine-2-carbonyl chloride

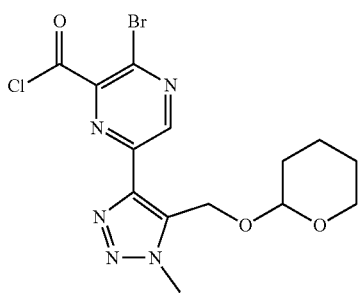 [SMILES: Cn1nnc(-c2cnc(Br)c(C(=O)Cl)n2)c1COC1CCCCO1]

A mixture of Example 217D (228 mg, 0.573 mmol) and 1-chloro-N,N,2-trimethylprop-1-en-1-amine (0.114 mL, 0.859 mmol) in DCM (2 mL) was stirred at rt for 1 h. The reaction mixture was concentrated in vacuo to give the title compound (239 mg, 0.574 mmol, 100% yield) as yellowish oil which was used in the next reaction without further purification.

218F. (3-Bromo-6-(1-methyl-5-(((tetrahydro-2H-pyran-2-yl)oxy)methyl)-1H-1,2,3-triazol-4-yl)pyrazin-2-yl)methanol

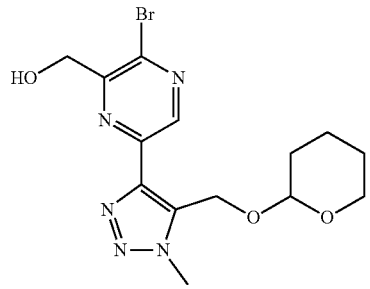 [SMILES: Cn1nnc(-c2cnc(Br)c(CO)n2)c1COC1CCCCO1]

A solution of Example 218E (3.14 g, 7.54 mmol) in THF (20 mL) was added dropwise to a suspension of NaBH₄ (0.656 g, 17.33 mmol) in EtOH (20 mL) at −78° C. The reaction was stirred at −78° C. for 1 h. Aq. HCl (9.80 mL of a 1.0 N solution, 9.80 mmol) was added cautiously to the reaction to make it weakly acidic at −78° C. The mixture was then basified with sat'd aq. NaHCO₃ to pH~8 and extracted with EtOAc (4×20 mL). The combined organic extracts were dried (MgSO₄) and concentrated in vacuo. The crude oily product was chromatographed (40 g SiO₂; elution with EtOAc/Hexane (continuous gradient from 0% to 80% over 25 min) to give the title compound (2.50 g, 6.51 mmol, 86% yield) as a light yellowish solid.

¹H NMR (500 MHz, CDCl₃) δ 9.13 (s, 1H), 5.47 (d, J=13.2 Hz, 1H), 4.98 (d, J=13.2 Hz, 1H), 4.89-4.85 (m, 2H), 4.76 (t, J=2.9 Hz, 1H), 4.69 (t, J=5.6 Hz, 1H), 4.19 (s, 3H), 3.93-3.81 (m, 1H), 3.62 (dt, J=10.9, 3.9 Hz, 1H), 1.86-1.47 (m, 6H)

218G. 2-Bromo-3-(chloromethyl)-5-(1-methyl-5-(((tetrahydro-2H-pyran-2-yl)oxy)methyl)-1H-1,2,3-triazol-4-yl)pyrazine

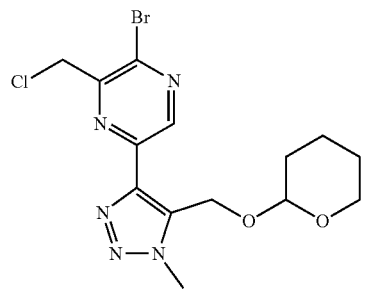 [SMILES: Cn1nnc(-c2cnc(Br)c(CCl)n2)c1COC1CCCCO1]

To a solution of Example 218F (190 mg, 0.494 mmol) in CHCl₃ (3 mL) was added methanesulfonyl chloride (0.057 mL, 0.74 mmol), iPr₂NEt (0.259 mL, 1.48 mmol) and DMAP (6.0 mg, 0.049 mmol) at 0° C. After the addition was complete, the reaction mixture was stirred at rt for 30 min. after which LiCl (105 mg, 2.472 mmol) and DMF (3 mL) were successively added. The mixture was stirred at rt for 1 h and then concentrated in vacuo. The residue was partitioned between water and EtOAc (10 mL each). The organic phase was washed with brine, dried (MgSO₄) and concentrated in vacuo. The crude oily product was chromato- (dient from 0% to 50% over 25 min) to give the title compound (3.50 g, 8.49 mmol, 93% yield) as light brownish oil. [M-THP+H]⁺=328.1/330.1; ¹H NMR (400 MHz, CDCl₃) δ 9.31 (s, 1H), 5.28-5.09 (m, 2H), 4.75-4.71 (m, 1H), 4.19 (s, 3H), 4.03 (s, 3H), 3.82-3.75 (m, 1H), 3.53-3.45 (m, 1H), 1.85-1.44 (m, 6H)

graphed (12 g SiO₂; elution with EtOAc/Hexane (continuous gradient from 0% to 50% over 10 min) to give the title compound (175 mg, 0.435 mmol, 88% yield) as a white solid.

¹H NMR (400 MHz, CDCl₃) δ 9.14 (s, 1H), 5.33-5.19 (m, 2H), 4.84 (s, 2H), 4.75 (t, J=3.4 Hz, 1H), 4.19 (s, 3H), 3.88-3.75 (m, 1H), 3.59-3.47 (m, 1H), 1.87-1.46 (m, 6H)

218H. 2-Bromo-3-methyl-5-(1-methyl-5-(((tetrahydro-2H-pyran-2-yl)oxy)methyl)-1H-1,2,3-triazol-4-yl)pyrazine

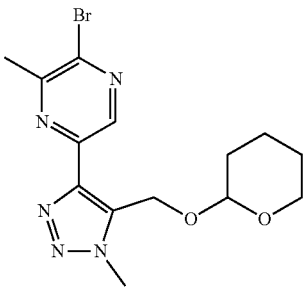 [SMILES: Cc1nc(-c2nnn(C)c2COC2CCCCO2)cnc1Br]

To a 0° C. solution of NaBH₄ (286 mg, 7.55 mmol) in EtOH (20 mL) was added dropwise a solution of Example 218G (760 mg, 1.89 mmol) in THF (20 mL). After the addition was complete, the reaction was stirred at rt for 6 h. LCMS indicated the reaction was still not complete, so additional NaBH₄ (286 mg, 7.55 mmol) was added and the reaction mixture was stirred for 3 days, then cautiously quenched with water at 0° C. The mixture was extracted with EtOAc (3×5 mL). The combined organic extracts were washed with brine, dried (Na₂SO₄), and concentrated in vacuo. The crude oily product was chromatographed (24 g SiO₂; elution with EtOAc/Hexane (continuous gradient from 0% to 50% over 10 min) to give the title compound (600 mg, 1.63 mmol, 86% yield) as a white solid.

¹H NMR (500 MHz, CDCl₃) δ 9.04 (s, 1H), 5.29-5.20 (m, 2H), 4.75 (t, J=3.4 Hz, 1H), 4.20 (s, 3H), 3.86 (ddd, J=11.3, 8.3, 3.0 Hz, 1H), 3.59-3.50 (m, 1H), 2.72 (s, 3H), 1.85-1.49 (m, 6H)

218I. 3-Methyl-5-(1-methyl-5-(((tetrahydro-2H-pyran-2-yl)oxy)methyl)-1H-1,2,3-triazol-4-yl)pyrazin-2-ol

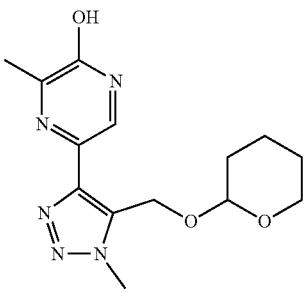 [SMILES: Cc1nc(-c2nnn(C)c2COC2CCCCO2)cnc1O]

A mixture of Example 218H (600 mg, 1.63 mmol) KOH (1.00 mL of a 7 M aq. solution, 7.0 mmol) in water (5 mL) and dioxane (5 mL) was degassed under N₂ and then tBuXphos (83 mg, 0.196 mmol) and Pd₂(dba)₃ (44.8 mg, 0.049 mmol) were added. The reaction mixture was degassed under N₂ again and then stirred at 80° C. overnight. The reaction was cooled to rt, then was acidified to pH 5 with 1N aq. HCl at 0° C. and partitioned between water and EtOAc. The organic phase was separated, dried (MgSO₄), and concentrated in vacuo. The crude oily product was chromatographed (12 g SiO₂; elution with EtOAc/Hexane (continuous gradient from 0% to 100% over 7 min) to give the title compound (340 mg, 1.11 mmol, 68.3% yield) as a light yellowish solid. [M-THP+H]⁺=222.2; ¹H NMR (500 MHz, CDCl₃) δ 8.04 (s, 1H), 5.24-5.15 (m, 2H), 4.88-4.72 (m, 1H), 4.16 (s, 3H), 3.90 (ddd, J=11.2, 8.2, 3.2 Hz, 1H), 3.72-3.52 (m, 1H), 2.55 (s, 3H), 1.90-1.44 (m, 7H)

218J. Isopropyl (1S,3S)-3-((3-methyl-5-(1-methyl-5-(((tetrahydro-2H-pyran-2-yl)oxy)methyl)-1H-1,2,3-triazol-4-yl)pyrazin-2-yl)oxy)cyclohexane-1-carboxylate

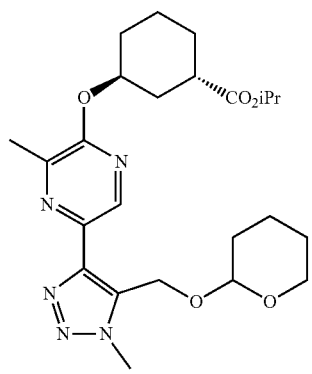

To a mixture of Example 218I (340 mg, 1.11 mmol)), ((1S,3R)-isopropyl 3-hydroxycyclo-hexane carboxylate (373 mg, 2.00 mmol) in THF (5 mL) were successively added n-Bu₃P (0.556 mL, 2.227 mmol) and (E)-diazene-1,2-diylbis(piperidin-1-ylmethanone) (562 mg, 2.23 mmol). The reaction mixture was then stirred at 80° C. for 18 h, then was cooled to rt and concentrated in vacuo. The crude oily product was chromatographed (24 g SiO₂; elution with EtOAc/Hexane (continuous gradient from 0% to 50% over 10 min) to give the title compound (527 mg, 1.11 mmol, 100% yield) as a clear oil. [M+H]⁺=474.2

218K. Isopropyl (1S,3S)-3-((5-(5-(hydroxymethyl)-1-methyl-1H-1,2,3-triazol-4-yl)-3-methylpyrazin-2-yl)oxy)cyclohexane-1-carboxylate

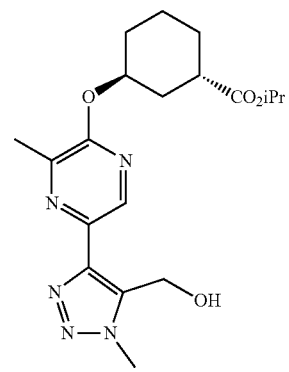

A mixture of Example 218J (527 mg, 1.11 mmol) and pyridinium p-toluenesulfonate (28 mg, 0.11 mmol) in MeOH (10 mL) was stirred at rt for 3 days and then concentrated in vacuo. The crude oily product was chromatographed (24 g SiO$_2$; elution with EtOAc/Hexane (continuous gradient from 0% to 100% over 10 min) to give the title compound (277 mg, 0.711 mmol, 63.9% yield) as a clear oil.

[M+H]$^+$=390.2; $^1$H NMR (500 MHz, CDCl$_3$) δ 8.89 (s, 1H), 5.54 (br s, 1H), 5.04 (dt, J=12.4, 6.3 Hz, 1H), 4.83 (s, 2H), 4.16-4.10 (m, 3H), 2.74 (tt, J=11.1, 3.9 Hz, 1H), 2.56 (s, 3H), 2.23 (br d, J=14.0 Hz, 1H), 2.01 (br dd, J=8.8, 4.1 Hz, 2H), 1.89 (ddd, J=13.9, 11.4, 2.8 Hz, 1H), 1.82-1.47 (m, 5H), 1.26 (dd, J=6.3, 2.8 Hz, 6H)

218L. Isopropyl (1S,3S)-3-((3-methyl-5-(1-methyl-5-(((((4-nitrophenoxy)carbonyl)oxy)methyl)-1H-1,2,3-triazol-4-yl)pyrazin-2-yl)oxy)cyclohexane-1-carboxylate

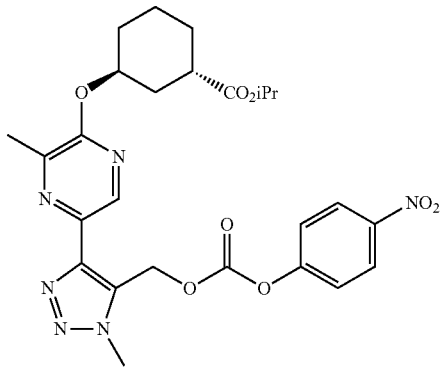

A solution of 4-nitrophenyl chloroformate (172 mg, 0.854 mmol) in DCM (1 mL) was added dropwise to a solution of Example 218K (277 mg, 0.711 mmol) and pyridine (0.288 mL, 3.56 mmol) in DCM (5 mL) over 1 h at 0° C. The reaction was then stirred at rt for 18 h, then was concentrated in vacuo. The crude oily product was chromatographed (12 g SiO$_2$; elution with EtOAc/Hexane (continuous gradient from 0% to 50% over 10 min) to give the title compound (366 mg, 0.66 mmol, 93% yield) as a light yellowish oil.

[M+H]$^+$=555.2; $^1$H NMR (500 MHz, CDCl$_3$) δ 8.79 (s, 1H), 8.33-8.28 (m, 2H), 7.44-7.37 (m, 2H), 6.02-5.94 (m, 2H), 5.52 (br s, 1H), 5.03 (dt, J=12.6, 6.2 Hz, 1H), 4.23 (s, 3H), 2.74 (tt, J=11.1, 3.9 Hz, 1H), 2.52 (s, 3H), 2.22 (br d, J=14.0 Hz, 1H), 2.03-1.96 (m, 2H), 1.93-1.83 (m, 1H), 1.81-1.52 (m, 4H), 1.30-1.22 (m, 6H)

Example 218

To a solution of Example 218L (8 mg, 0.014 mmol) in DCM (1 mL) was added N-methyl propan-1-amine (1.8 µL; 0.017 mmol) and DIPEA (7.6 µL, 0.043 mmol). The reaction mixture was stirred at rt for 2 h, then was concentrated in vacuo. The crude oil was (4 g SiO$_2$; elution with EtOAc/Hexane (continuous gradient from 0% to 30% over 10 min) to give the corresponding carbamate-isopropyl ester Example as a clear oil. This ester intermediate was stirred with 1N aq. NaOH (0.2 mL) in THF (1 mL) and MeOH (0.2 mL) at rt for 18 h and then acidified to pH=~2 with TFA. The reaction mixture was purified by preparative HPLC (Sunfire C18 30×100 mm-regenerated column; detection at 220 nm; flow rate=40 mL/min; continuous gradient from 20% B to 100% B over 10 min+2 min hold time at 100% B, where A=90:10:0.1 H$_2$O:MeCN:TFA and B=90:10:0.1 MeCN:H$_2$O:TFA) to give Example 218 (5 mg, 11.0 µmol, 76% yield) as a clear oil. [M+H]$^+$=447.3; $^1$H NMR (500 MHz, CDCl$_3$) δ 8.72 (s, 1H), 5.69 (br d, J=7.4 Hz, 2H), 5.53 (br s, 1H), 4.18 (s, 3H), 3.26 (br t, J=7.2 Hz, 1H), 3.13 (br t, J=7.2 Hz, 1H), 2.97-2.79 (m, 4H), 2.52 (s, 3H), 2.32 (br d, J=14.0 Hz, 1H), 2.16-1.99 (m, 2H), 1.93-1.37 (m, 7H), 0.98-0.71 (m, 3H). hLPA IC$_{50}$=194 nM

| Example | Structure & Name | Analytical & Biology Data | Method |
|---|---|---|---|
| 219 | 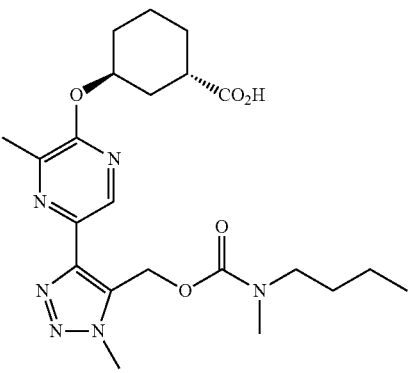 [SMILES: CCCCN(C)C(=O)OCc1c(-c2cnc(O[C@H]3CCC[C@H](C(=O)O)C3)c(C)n2)nnn1C]<br>(1S,3S)-3-((5-(5-(((butyl(methyl)carbamoyl)oxy)methyl)-1-methyl-1H-1,2,3-triazol-4-yl)-3-methylpyrazin-2-yl)oxy)cyclohexane-1-carboxylic acid | LCMS, [M + H]$^+$ = 461.4; $^1$H NMR (500 MHz, CDCl$_3$) δ 8.69 (s, 1H), 5.68 (br. s., 2H), 5.53 (br. s., 1H), 4.19 (s, 3H), 3.36-3.10 (m, 2H), 2.97-2.79 (m, 4H), 2.53 (s, 3H), 2.32 (d, J = 14.0 Hz, 1H), 2.14-1.97 (m, 2H), 1.94-1.12 (m, 9H), 1.02-0.74 (m, 3H)<br>hLPA1 IC$_{50}$ = 21 nM | Example 218 |

| Example | Structure & Name | Analytical & Biology Data | Method |
|---|---|---|---|
| 220 | 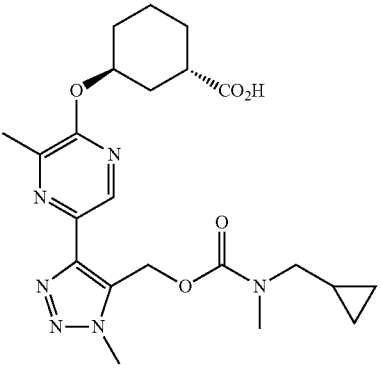 [SMILES: Cc1nc(-c2nnn(C)c2COC(=O)N(C)CC2CC2)cnc1O[C@H]1CCC[C@H](C(=O)O)C1]<br>(1S,3S)-3-((5-(5-((((cyclopropyl-methyl)(methyl)carbamoyl)oxy)methyl)-1-methyl-1H-1,2,3-triazol-4-yl)-3-methyl-pyrazin-2-yl)oxy)cyclohexane-1-carboxylic acid | LCMS, $[M + H]^+ = 458.9$.<br>$^1$H NMR (500 MHz, DMSO-$d_6$): δ 8.57 (s, 1H), 5.54 (d, J = 19.1 Hz, 2H), 5.38 (s, 1H), 4.10 (s, 3H), 3.05 (br s, 1H), 2.93 (br s, 1H), 2.85-2.76 (m, 2H), 2.54 (s, 3H), 2.44 (s, 3H), 2.41-2.12 (m, 8H). 0.40 (br s, 1H), 0.24 (br s, 1H), 0.16 (br s, 1H), −0.04 (br s, 1H).<br>hLPA1 $IC_{50}$ = 149 nM | Example 218 |
| 221 | 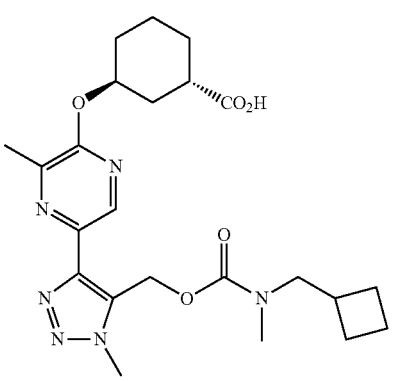 [SMILES: Cc1nc(-c2nnn(C)c2COC(=O)N(C)CC2CCC2)cnc1O[C@H]1CCC[C@H](C(=O)O)C1]<br>(1S,3S)-3-((5-(5-((((cyclobutylmethyl)(methyl)carbamoyl)oxy)methyl)-1-methyl-1H-1,2,3-triazol-4-yl)-3-methylpyrazin-2-yl)oxy)cyclohexane-1-carboxylic acid | LCMS, $[M + H]^+ = 473.2$.<br>$^1$H NMR (500 MHz, CDCl$_3$): δ 8.66 (s, 1H), 5.64 (br s, 2H), 5.51 (s, 1H), 4.17 (s, 3H), 3.31 (d, J = 7.5 Hz, 1H), 3.17 (d, J = 7.3 Hz, 1H), 2.91-2.77 (m, 4H), 2.61-2.35 (m, 1H), 2.50 (s, 3H), 2.29 (d, J = 14.1 Hz, 1H), 2.10-1.50 (m, 13H).<br>hLPA1 $IC_{50}$ = 23 nM | Example 218 |
| 222 | 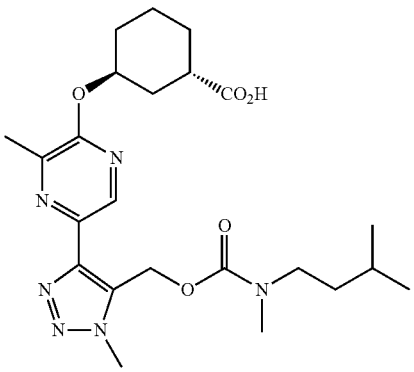 [SMILES: Cc1nc(-c2nnn(C)c2COC(=O)N(C)CCC(C)C)cnc1O[C@H]1CCC[C@H](C(=O)O)C1]<br>(1S,3S)-3-((5-(5-(((isopentyl(methyl)carbamoyl)oxy)methyl)-1-methyl-1H-1,2,3-triazol-4-yl)-3-methylpyrazin-2-yl)oxy)cyclohexane-1-carboxylic acid | LCMS; $[M + H]^+ = 475.4$;<br>$^1$H NMR (500 MHz, DMSO-$d_6$) δ 8.58 (br s, 1H), 5.54 (br d, J = 13.0 Hz, 2H), 5.38 (br s, 1H), 4.12 (br s, 3H), 3.18 (br d, J = 9.2 Hz, 1H), 3.03 (br s, 1H), 2.80-2.58 (m, 4H), 2.44 (br s, 3H), 2.09 (br d, J = 13.6 Hz, 1H), 1.94-1.03 (m, 10H), 0.92-0.55 (m, 6H)<br>hLPA1 $IC_{50}$ = 19 nM | Example 218 |

-continued

| Example | Structure & Name | Analytical & Biology Data | Method |
|---|---|---|---|
| 223 | 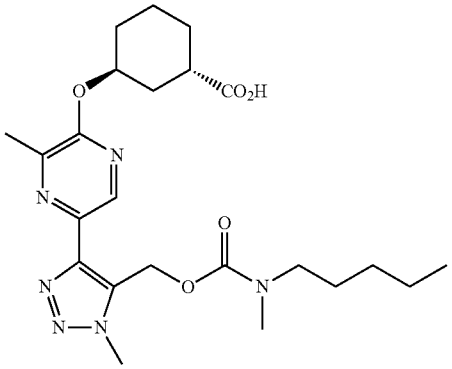 [SMILES: CCCCCN(C)C(=O)OCc1c(-c2cnc(O[C@H]3CCC[C@H](C(=O)O)C3)c(C)n2)nnn1C]<br>(1S,3S)-3-((3-methyl-5-(1-methyl-5-(((methyl(pentyl)carbamoyl)oxy)methyl)-1H-1,2,3-triazol-4-yl)pyrazin-2-yl)oxy)cyclohexane-1-carboxylic acid | LCMS; $[M + H]^+$ = 475.4; $^1$H NMR (500 MHz, DMSO-$d_6$) δ 8.58 (s, 1H), 5.54 (br d, J = 15.9 Hz, 2H), 5.37 (br s, 1H), 4.11 (br s, 2H), 3.22-2.99 (m, 2H), 2.80-2.67 (m, 3H), 2.62-2.53 (m, 4H), 2.44 (s, 2H), 2.13-1.96 (m, 1H), 1.90-0.59 (m, 15H)<br>hLPA1 $IC_{50}$ = 56 nM | Example 218 |
| 224 | 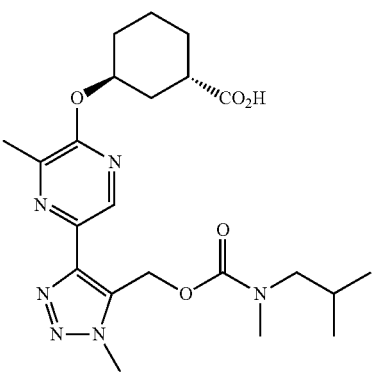 [SMILES: Cc1nc(-c2nnn(C)c2COC(=O)N(C)CC(C)C)cnc1O[C@H]1CCC[C@H](C(=O)O)C1]<br>(1S,3S)-3-((5-(5-(((isobutyl(methyl)carbamoyl)oxy)methyl)-1-methyl-1H-1,2,3-triazol-4-yl)-3-methylpyrazin-2-yl)oxy)cyclohexane-1-carboxylic acid | LCMS; $[M + H]^+$ = 461.2; $^1$H NMR (500 MHz, CDCl$_3$): δ 8.72 (s, 1H), 5.69 (br d, J = 14.3 Hz, 2H), 5.53 (br s, 1H), 4.18 (s, 3H), 3.12 (br d, J = 7.4 Hz, 1H), 3.03-2.77 (m, 6H), 2.53 (s, 3H), 2.32 (br d, J = 14.0 Hz, 1H), 2.18-1.53 (m, 7H), 0.99-0.74 (m, 6H)<br>hLPA1 $IC_{50}$ = 121 nM | Example 218 |
| 225 | 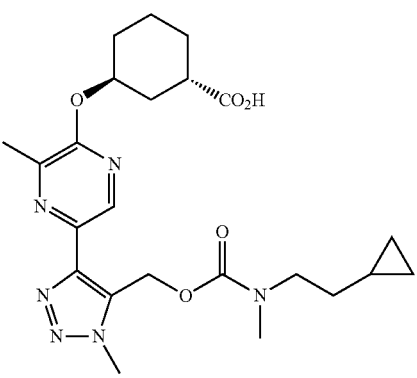 [SMILES: Cc1nc(-c2nnn(C)c2COC(=O)N(C)CCC2CC2)cnc1O[C@H]1CCC[C@H](C(=O)O)C1]<br>(1S,3S)-3-((5-(5-((((2-cyclopropylethyl)(methyl)carbamoyl)oxy)methyl)-1-methyl-1H-1,2,3-triazol-4-yl)-3-methylpyrazin-2-yl)oxy)cyclohexane-1-carboxylic acid | LCMS; $[M + H]^+$ = 473.4; $^1$H NMR (500 MHz, DMSO-$d_6$) δ 8.57 (s, 1H), 5.54 (br d, J = 14.4 Hz, 2H), 5.38 (br s, 1H), 4.11 (br s, 3H), 3.29-3.07 (m, 2H), 2.82-2.70 (m, 3H), 2.57 (br d, J = 11.3 Hz, 1H), 2.43 (s, 3H), 2.16-1.97 (m, 1H), 1.93-1.01 (m, 9H), 0.70-0.12 (m, 3H), 0.06--0.40 (m, 2H)<br>hLPA1 $IC_{50}$ = 70 nM | Example 218 |

| Example | Structure & Name | Analytical & Biology Data | Method |
|---|---|---|---|
| 226 | 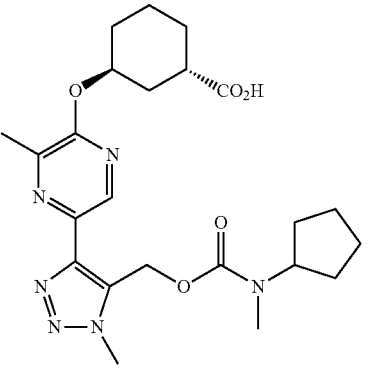 [SMILES: Cc1nc(-c2nnn(C)c2COC(=O)N(C)C2CCCC2)cnc1O[C@H]1CCC[C@H](C(=O)O)C1]<br>(1S,3S)-3-((5-(5-((((cyclopentyl(methyl)carbamoyl)oxy)methyl)-1-methyl-1H-1,2,3-triazol-4-yl)-3-methylpyrazin-2-yl)oxy)cyclohexane-1-carboxylic acid | LCMS; $[M + H]^+$ = 473.5;<br>$^1$H NMR (500 MHz, DMSO-$d_6$) δ 8.56 (s, 1H), 5.53 (s, 2H), 5.38 (br s, 1H), 4.10 (s, 3H), 3.64 (br s, 1H), 2.62 (br s, 4H), 2.44 (s, 3H), 2.19-2.02 (m, 1H), 1.95-1.24 (m, 15H)<br>hLPA1 IC$_{50}$ = 49 nM | Example 218 |
| 227 | 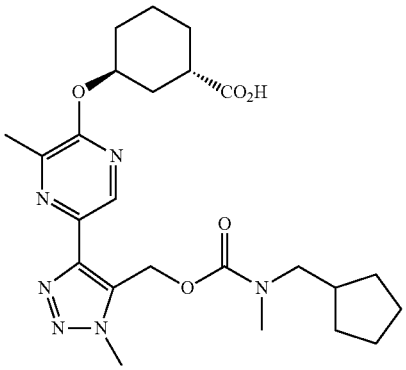 [SMILES: Cc1nc(-c2nnn(C)c2COC(=O)N(C)CC2CCCC2)cnc1O[C@H]1CCC[C@H](C(=O)O)C1]<br>(1S,3S)-3-((5-(5-(((((cyclopentylmethyl)(methyl)carbamoyl)oxy)methyl)-1-methyl-1H-1,2,3-triazol-4-yl)-3-methylpyrazin-2-yl)oxy)cyclohexane-1-carboxylic acid | LCMS; $[M + H]^+$ = 487.5;<br>$^1$H NMR (500 MHz, DMSO-$d_6$) δ 8.58 (s, 1H), 5.61-5.48 (m, 2H), 5.40 (br s, 1H), 4.12 (br s, 3H), 3.20-2.91 (m, 2H), 2.84-2.69 (m, 3H), 2.64 (br s, 1H), 2.48-2.42 (m, 3H), 2.10 (br d, J = 13.1 Hz, 1H), 1.96-1.07 (m, 15H), 0.89 (br s, 1H)<br>hLPA1 IC$_{50}$ = 18 nM | Example 218 |
| 228 | 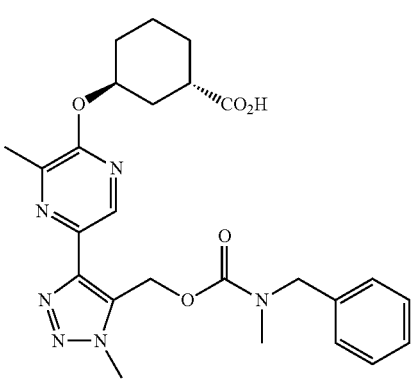 [SMILES: Cc1nc(-c2nnn(C)c2COC(=O)N(C)Cc2ccccc2)cnc1O[C@H]1CCC[C@H](C(=O)O)C1]<br>(1S,3S)-3-((5-(5-(((benzyl(methyl)carbamoyl)oxy)methyl)-1-methyl-1H-1,2,3-triazol-4-yl)-3-methylpyrazin-2-yl)oxy)cyclohexane-1-carboxylic acid | LCMS; $[M + H]^+$ = 495.3;<br>$^1$H NMR (500 MHz, DMSO-$d_6$) δ 8.56 (br s, 1H), 7.38-7.04 (m, 4H), 6.96 (br s, 1H), 5.68-5.47 (m, 2H), 5.37 (br s, 1H), 4.47-4.21 (m, 2H), 4.19-3.97 (m, 3H), 2.83-2.66 (m, 3H), 2.62 (br t, J = 11.0 Hz, 1H), 2.46-2.32 (m, 3H), 2.13-2.04 (m, 1H), 1.95-1.40 (m, 7H)<br>hLPA1 IC$_{50}$ = 60 nM | Example 218 |

| Example | Structure & Name | Analytical & Biology Data | Method |
|---|---|---|---|
| 229 | 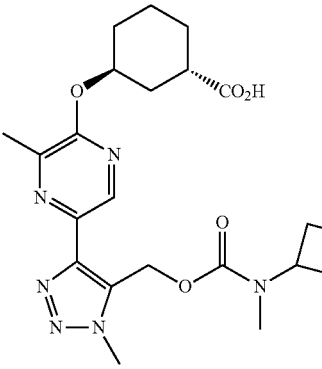<br>(1S,3S)-3-((5-(5-(((cyclobutyl(methyl)carbamoyl)oxy)methyl)-1-methyl-1H-1,2,3-triazol-4-yl)-3-methylpyrazin-2-yl)oxy)cyclohexane-1-carboxylic acid | LCMS; $[M + H]^+$ = 459.0; $^1$H NMR (500 MHz, DMSO-$d_6$) δ 8.58-8.57 (m, 1H), 5.54 (br s, 2H), 5.39 (br s, 1H), 4.10 (s, 4H), 2.82-2.57 (m, 4H), 2.47-2.39 (m, 3H), 2.18-1.31 (m, 14H)<br>hLPA1 $IC_{50}$ = 76 nM | |
| 230 | 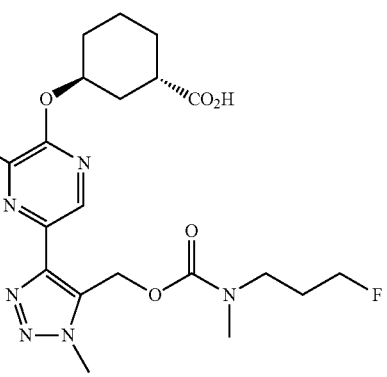<br>(1S,3S)-3-((5-(5-((((3-fluoropropyl)(methyl)carbamoyl)oxy)methyl)-1-methyl-1H-1,2,3-triazol-4-yl)-3-methylpyrazin-2-yl)oxy)cyclohexane-1-carboxylic acid | LCMS; $[M + H]^+$ = 465.4; $^1$H NMR (500 MHz, DMSO-$d_6$) δ 8.58 (s, 1H), 5.56 (br s, 2H), 5.39 (br s, 1H), 4.54-4.17 (m, 2H), 4.11 (s, 3H), 3.39-3.14 (m, 2H), 2.89-2.69 (m, 3H), 2.64 (br t, J = 10.8 Hz, 1H), 2.45 (s, 3H), 2.10 (br d, J = 13.7 Hz, 1H), 1.94-1.41 (m, 9H)<br>hLPA1 $IC_{50}$ = 390 nM | |
| 231 | 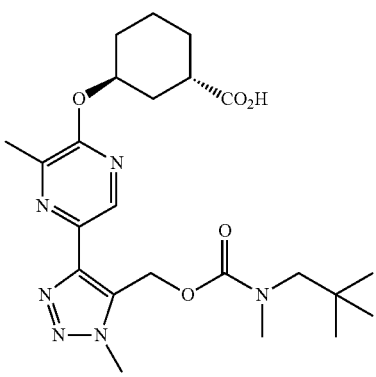 [SMILES: Cc1nc(-c2nnn(C)c2COC(=O)N(C)CC(C)(C)C)cnc1O[C@H]1CCC[C@H](C(=O)O)C1]<br>(1S,3S)-3-((3-methyl-5-(1-methyl-5-(((methyl(neopentyl)carbamoyl)oxy)methyl)-1H-1,2,3-triazol-4-yl)pyrazin-2-yl)oxy)cyclohexane-1-carboxylic acid | LCMS; $[M + H]^+$ = 475.2; $^1$H NMR (500 MHz, CHLOROFORM-d) δ 8.71 (s, 1H), 5.68 (br d, J = 12.1 Hz, 2H), 5.54 (br s, 1H), 4.23-4.16 (m, 3H), 3.14 (s, 1H), 3.04-2.96 (m, 3H), 2.93-2.81 (m, 2H), 2.53 (s, 3H), 2.32 (br d, J = 14.0 Hz, 1H), 2.16-1.97 (m, 2H), 1.94-1.84 (m, 1H), 1.83-1.55 (m, 4H), 1.04-0.72 (m, 9H)<br>hLPA1 $IC_{50}$ = 88 nM | |

| Example | Structure & Name | Analytical & Biology Data | Method |
|---|---|---|---|
| 232 | 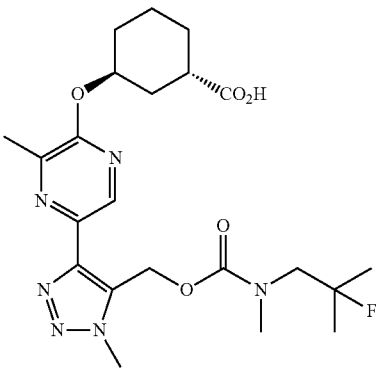<br>(1S,3S)-3-((5-(5-((((2-fluoro-2-methylpropyl)(methyl)carbamoyl)oxy)methyl)-1-methyl-1H-1,2,3-triazol-4-yl)-3-methylpyrazin-2-yl)oxy)cyclohexane-1-carboxylic acid | LCMS; $[M + H]^+ = 479.2$;<br>$^1$H NMR (500 MHz, CDCl$_3$): δ 8.67 (s, 1H), 5.80-5.57 (m, 2H), 5.54 (br s, 1H), 4.26-4.16 (m, 3H), 3.57-3.27 (m, 2H), 3.10-2.77 (m, 4H), 2.59-2.46 (m, 3H), 2.32 (br d, J = 13.8 Hz, 1H), 2.13-1.97 (m, 2H), 1.95-1.53 (m, 5H), 1.42-1.13 (m, 6H); $^{19}$F NMR (471 MHz, CDCl$_3$): δ -139.12 (s, 1F)<br>hLPA1 IC$_{50}$ = 191 nM | |
| 233 | 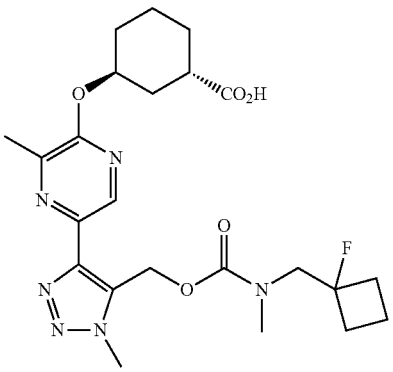 [SMILES: Cc1nc(-c2nnn(C)c2COC(=O)N(C)CC2(F)CCC2)cnc1O[C@H]1CCC[C@H](C(=O)O)C1]<br>(1S,3S)-3-((5-(5-(((((1-fluoro-cyclobutyl)methyl)(methyl)carbamoyl)oxy)methyl)-1-methyl-1H-1,2,3-triazol-4-yl)-3-methylpyrazin-2-yl)oxy)cyclohexane-1-carboxylic acid | LCMS; $[M + H]^+ = 491.2$;<br>$^1$H NMR (400 MHz, CDCl$_3$): δ 8.70 (s, 1H), 5.69 (br d, J = 5.1 Hz, 2H), 5.51 (br s, 1H), 4.16 (s, 3H), 3.72-3.34 (m, 2H), 3.04-2.75 (m, 4H), 2.49 (br d, J = 4.6 Hz, 3H), 2.33-1.49 (m, 14H); $^{19}$F NMR (377 MHz, CDCl$_3$): δ -130.34 (br s, 1F)<br>hLPA1 IC$_{50}$ = 122 nM | |
| 234 | 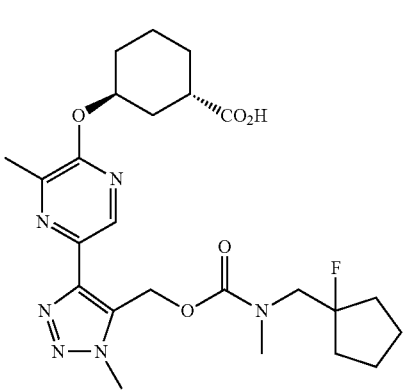 [SMILES: Cc1nc(-c2nnn(C)c2COC(=O)N(C)CC2(F)CCCC2)cnc1O[C@H]1CCC[C@H](C(=O)O)C1]<br>(1S,3S)-3-((5-(5-(((((1-fluorocyclopentyl)methyl)(methyl)carbamoyl)oxy)methyl)-1-methyl-1H-1,2,3-triazol-4-yl)-3-methylpyrazin-2-yl)oxy)cyclohexane-1-carboxylic acid | LCMS; $[M + H]^+ = 505.2$;<br>$^1$H NMR (400 MHz, CDCl$_3$): δ 8.64 (s, 1H), 5.71-5.61 (m, 2H), 5.52 (br s, 1H), 4.19 (s, 3H), 3.68-3.37 (m, 2H), 3.07-2.91 (m, 3H), 2.84 (tt, J = 11.2, 3.7 Hz, 1H), 2.51 (d, J = 3.5 Hz, 3H), 2.29 (br d, J = 13.9 Hz, 1H), 2.12-1.96 (m, 2H), 1.94-1.35 (m, 13H); $^{19}$F NMR (377 MHz, CDCl$_3$): δ -139.45 to -147.94 (m, 1F)<br>hLPA1 IC$_{50}$ = 72 nM | |

| Example | Structure & Name | Analytical & Biology Data | Method |
|---|---|---|---|
| 235 | 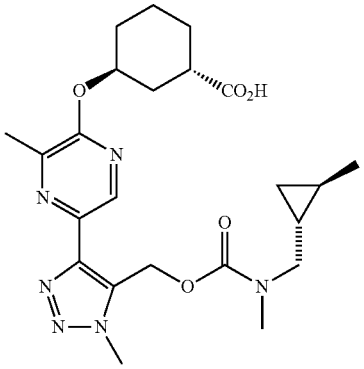<br>(1S,3S)-3-((3-methyl-5-(1-methyl-5-((((methyl(((1R,2R)-2-methylcyclopropyl)methyl)carbamoyl)oxy)methyl)-1H-1,2,3-triazol-4-yl)pyrazin-2-yl)oxy)cyclohexane-1-carboxylic acid | LCMS; $[M + H]^+$ = 473.0;<br>$^1$H NMR (500 MHz, CDCl$_3$): δ 8.72 (s, 1H), 5.82-5.56 (m, 2H), 5.53 (br s, 1H), 4.17 (s, 3H), 3.29-2.80 (m, 6H), 2.52 (s, 3H), 2.31 (br d, J = 14.0 Hz, 1H), 2.14-1.97 (m, 2H), 1.91-1.54 (m, 5H), 1.10-0.90 (m, 3H), 0.75-0.11 (m, 4H)<br>hLPA1 IC$_{50}$ = 70 nM | |
| 236 | 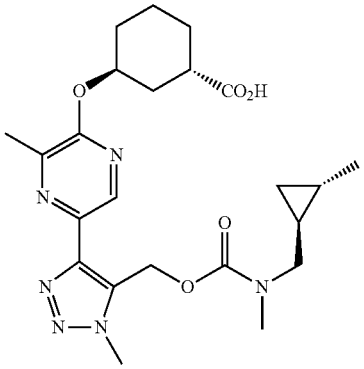<br>(1S,3S)-3-((3-methyl-5-(1-methyl-5-((((methyl(((1S,2S)-2-methylcyclopropyl)methyl)carbamoyl)oxy)methyl)-1H-1,2,3-triazol-4-yl)pyrazin-2-yl)oxy)cyclohexane-1-carboxylic acid | LCMS; $[M + H]^+$ = 473.0;<br>$^1$H NMR (500 MHz, CDCl$_3$): δ 8.72 (s, 5H), 5.69 (br d, J = 6.9 Hz, 2H), 5.52 (br s, 1H), 4.17 (s, 3H), 3.28-2.80 (m, 6H), 2.58-2.46 (m, 3H), 2.31 (br d, J = 13.8 Hz, 1H), 2.12-1.97 (m, 2H), 1.93-1.54 (m, 5H), 1.10-0.89 (m, 3H), 0.74-0.11 (m, 4H)<br>hLPA1 IC$_{50}$ = 46 nM | |

Example 237

(1S,3 S)-3-((5-(5-(((((cyclopropylmethyl)(methyl)carbamoyl)oxy)methyl)-1-methyl-1H-1,2,3-triazol-4-yl)-3-(trifluoromethyl)pyridin-2-yl)oxy)cyclohexane-1-carboxylic Acid

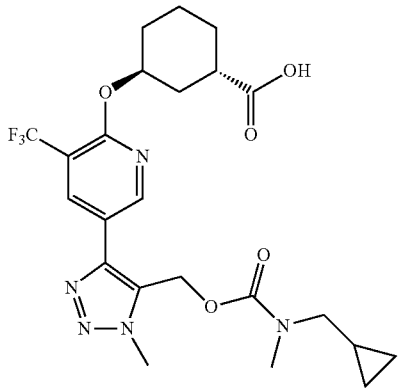 [SMILES: CN(CC1CC1)C(=O)OCc1c(-c2cnc(O[C@H]3CCC[C@H](C(=O)O)C3)c(C(F)(F)F)c2)nnn1C]

237A. Isopropyl (1S,3S)-3-((5-bromo-3-(trifluoromethyl)pyridin-2-yl)oxy)cyclohexane-1-carboxylate

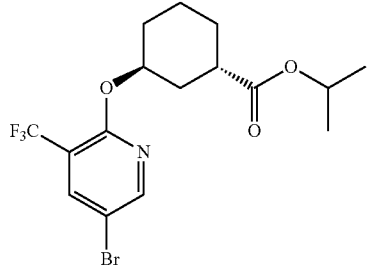 [SMILES: CC(C)OC(=O)[C@H]1CCC[C@H](Oc2ncc(Br)cc2C(F)(F)F)C1]

To a N₂-flushed, 50 mL round bottom flask was added (E)-diazene-1,2-diylbis (piperidin-1-ylmethanone) (2.11 g, 8.35 mmol), toluene (15 mL) and n-Bu₃P (2.1 mL, 8.35 mmol); the dark orange solution became a light yellow solution after the addition of n-Bu₃P. The solution was stirred at rt for 30 min, then 5-bromo-3-(trifluoromethyl)pyridin-2-ol (1.01 g, 4.17 mmol) and (1S,3R)-isopropyl 3-hydroxycyclohexanecarboxylate (1.40 g, 7.51 mmol) were successively added. The reaction mixture was heated to 80° C. for 16 h, then was cooled to rt. EtOAc (10 mL) and water (5 mL) were added, and the mixture was stirred for 10 min and the organic layer was separated. The aqueous layer was back-extracted with EtOAc (2×10 mL). The combined organic extracts were washed with brine (10 mL), dried (MgSO₄), and concentrated in vacuo to give the crude product. This crude material was chromatographed (SiO₂, 120 g; elution with EtOAc/hexanes (continuous gradient from 0 to 100%) to afford the title compound (1.7 g, 4.14 mmol, 99% yield) as a colorless oil. ¹H NMR (500 MHz, CDCl₃): δ 8.32 (d, J=2.4 Hz, 1H), 7.93 (d, J=2.5 Hz, 1H), 5.52 (br s, 1H), 5.06-4.94 (m, 1H), 2.69 (tt, J=11.6, 3.9 Hz, 1H), 2.23-2.17 (m, 1H), 2.03-1.93 (m, 2H), 1.82-1.43 (m, 5H), 1.22 (d, J=6.3 Hz, 6H). LCMS, [M+H]⁺=410.

237B. Isopropyl (1S,3 S)-3-((5-(3-hydroxyprop-1-yn-1-yl)-3-(trifluoromethyl)pyridin-2-yl)oxy)cyclohexane-1-carboxylate

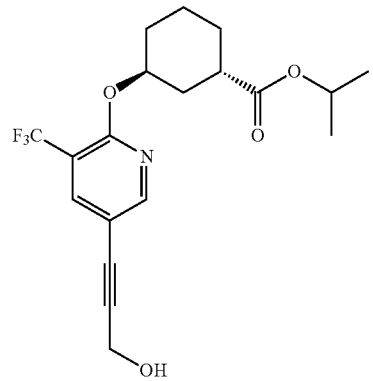 [SMILES: CC(C)OC(=O)[C@H]1CCC[C@H](Oc2ncc(C#CCO)cc2C(F)(F)F)C1]

To a 100 mL round bottom flask containing Example 237A (1.7 g, 4.1 mmol) and prop-2-yn-1-ol (0.70 g, 12.4 mmol) in MeCN (21 ml) was added Et₃N (2.89 mL, 20.7 mmol). The solution was quickly degassed (evacuation under vacuum, then refill with N₂ (3x)). Trans-dichlorobis (triphenylphosphine) palladium (II) chloride (0.29 g, 0.41 mmol) and CuI (0.039 g, 0.21 mmol) were added. The solution degassed (evacuation under vacuum, then refill with N₂ (3x)). The reaction was heated to reflux at 80° C. for 24 h, then was cooled to rt. The reaction mixture was filtered through a Celite® plug, which was washed with EtOAc (2×10 mL). The combined filtrates were concentrated in vacuo and the residue was chromatographed (40 g SiO₂; continuous gradient from 0% to 100% EtOAc in Hexanes for 20 min) to give the title compound as a white solid (1.13 g, 2.93 mmol, 71% yield). ¹H NMR (400 MHz, CDCl₃) δ 8.35 (d, J=2.4 Hz, 1H), 7.88 (d, J=2.5 Hz, 1H), 5.58 (br s, 1H), 5.06-4.97 (m, 1H), 4.50 (d, J=6.2 Hz, 2H), 2.70 (tt, J=11.6, 3.9 Hz, 1H), 2.24-2.17 (m, 1H), 2.03-1.93 (m, 2H), 1.82-1.43 (m, 5H), 1.22 (d, J=6.3 Hz, 6H). LCMS, [M+H]⁺=386.2.

237C. Isopropyl (1S,3S)-3-((5-(5-(hydroxymethyl)-1-methyl-1H-1,2,3-triazol-4-yl)-3-(trifluoromethyl)pyridin-2-yl)oxy)cyclohexane-1-carboxylate

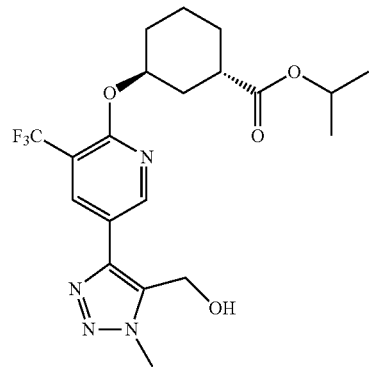 [SMILES: CC(C)OC(=O)[C@H]1CCC[C@H](Oc2ncc(-c3nnn(C)c3CO)cc2C(F)(F)F)C1]

To a solution of Example 237B (1.13 g, 2.9 mmol) in 1,4-dioxane (20 mL) was added TMSCH₂N₃ (0.68 g, 5.3 mmol), chloro(pentamethylcyclopentadienyl)bis(triphenylphosphine)Ruthenium(II) (0.12 g, 0.15 mmol), and CuI (0.028 g, 0.15 mmol). The mixture was quickly evacuated and backfilled with N$_2$ (this sequence was repeated three times). The resulting homogenous mixture was then heated in a 50° C. oil bath for 16 h (when the external and internal temp. are between 49 to 50° C.), then was cooled to rt and concentrated on a rotary evaporator to dryness (the waste trap content was collected, labeled as azide-containing hazardous waste and disposed accordingly). The residue was dissolved in THF (20 mL). TBAF (5.86 mL of a 1 M solution in THF, 5.86 mmol) was added and the mixture was stirred at rt for 60 min. The reaction was quenched with sat'd aq. NaHCO$_3$ (20 mL) and extracted with EtOAc (4×20 mL). The combined organic extracts were washed with brine (20 mL), dried (MgSO$_4$) and concentrated in vacuo. The crude was chromatographed (continuous gradient from 0% to 70% EtOAc/hexanes over 27 min, then gradient from 70 to 100% in 8 min; 80 g Gold ISCO SiO$_2$ column) and then preparative HPLC under the following conditions: Column: Phenomenex Luna 5u C18 100A 30×250 mm; Mobile Phase A: 10:90 MeCN:H$_2$O with 0.1% TFA; Mobile Phase B: 90:10 MeCN:H$_2$O with 0.1% TFA; Gradient: 0-100% B over 20 min, then a 5-min hold at 100% B; Flow: 30 mL/min. Fractions containing the desired product were combined and dried via centrifugal evaporation to afford the title compound (0.50 g, 1.13 mmol, 38.5% yield) (the later eluting fraction). $^1$H NMR (400 MHz, CDCl$_3$) δ 8.55 (d, J=2.5 Hz, 1H), 8.25 (d, J=2.5 Hz, 1H), 5.62 (br s, 1H), 5.06-4.99 (m, 1H), 4.86 (s, 2H), 4.18 (s, 3H), 2.73 (tt, J=11.5, 3.8 Hz, 1H), 2.28-2.22 (m, 1H), 2.05-1.98 (m, 2H), 1.85-1.45 (m, 5H), 1.22 (d, J=6.2 Hz, 6H). The regiochemistry of this desired product was determined by 1D-NoE NMR experiments. LCMS, [M+H]$^+$=443.2.

237D. Isopropyl (1S,3S)-3-((5-(1-methyl-5-((((4-nitrophenoxy)carbonyl)oxy)methyl)-1H-1,2,3-triazol-4-yl)-3-(trifluoromethyl)pyridin-2-yl)oxy)cyclohexane-1-carboxylate

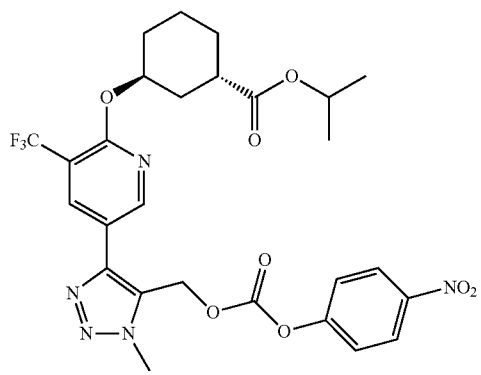 [SMILES: CC(C)OC(=O)[C@H]1CCC[C@H](Oc2ncc(-c3nnn(C)c3COC(=O)Oc3ccc([N+](=O)[O-])cc3)cc2C(F)(F)F)C1]

To a solution of Example 237C (116 mg, 0.26 mmol) and 4-nitrophenyl chloroformate (106 mg, 0.52 mmol) in DCM (3 mL) was added pyridine (0.085 mL, 1.05 mmol) at rt. A white solid was formed. The reaction mixture was stirred at rt for 16 h, after which the solid was filtered off and washed with DCM. The combined filtrate and washes were evaporated in vacuo. The crude product was chromatographed (12 g SiO$_2$, elution with continuous gradient from 0 to 100% EtOAc in DCM) to give the title compound (114 mg, 0.19 mmol, 71.6% yield) as a white solid. $^1$H NMR (500 MHz, CDCl$_3$) δ 8.65 (d, J=2.2 Hz, 1H), 8.35 (d, J=2.1 Hz, 1H), 8.31 (d, J=9.1 Hz, 2H), 7.40 (d, J=9.1 Hz, 2H), 5.64 (br s, 1H), 5.45 (s, 2H), 5.06-4.99 (m, 1H), 4.25 (s, 3H), 2.74 (t, J=11.7 Hz, 1H), 2.29-2.22 (m, 1H), 2.05-1.98 (m, 2H), 1.86-1.45 (m, 5H), 1.22 (d, J=6.2 Hz, 6H). LCMS, [M+H]$^+$=608.3.

Example 237

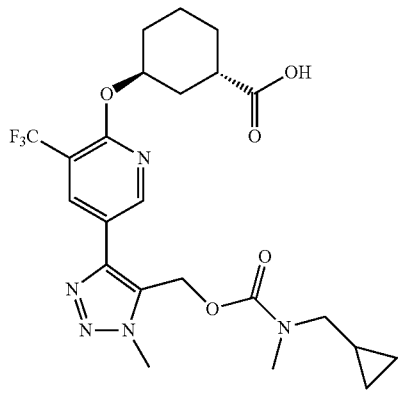 [SMILES: CN(CC1CC1)C(=O)OCc1c(-c2cnc(O[C@H]3CCC[C@H](C(=O)O)C3)c(C(F)(F)F)c2)nnn1C]

To a solution of Example 237D (5.4 mg, 8.9 µmol) and 1-cyclopropyl-N-methylmethanamine (2.0 µL, 0.018 mmol) in THF (0.4 mL) was added N-ethyl-N-isopropyl-propan-2-amine (5 µL, 0.027 mmol). The mixture was stirred at rt for 1 h, after which a solution of LiOH.H$_2$O (3.7 mg, 0.088 mmol) in water (0.4 mL) and MeOH (0.2 mL) was added. The reaction mixture was stirred at rt for 48 h, then was acidified to pH=4 with 1N aq. HCl and extracted with EtOAc (3×5 mL). The combined organic extracts were dried (MgSO$_4$) and concentrated in vacuo. The crude product was purified via preparative LC/MS with the following conditions: Column: XBridge C18, 19×200 mm, 5-µm particles; Mobile Phase A: 5:95 MeCN: H$_2$O with 10 mM NH$_4$OAc; Mobile Phase B: 95:5 MeCN:H$_2$O with 10 mM NH$_4$OAc; Continuous gradient: 20-60% B over 20 min, then a 4-min hold at 100% B; Flow: 20 mL/min. Fractions containing the desired product were combined and dried via centrifugal evaporation to afford the title compound (2.4 mg, 51% yield).

The following compounds were prepared by the general synthetic scheme for Example 237.

| Example | Structure & Name | Analytical & Biology Data | Method |
|---|---|---|---|
| 237 | (1S,3S)-3-((5-(5-(((((cyclopropylmethyl)(methyl)carbamoyl)oxy)methyl)-1-methyl-1H-1,2,3-triazol-4-yl)-3-(trifluoromethyl)pyridin-2-yl)oxy)cyclohexane-1-carboxylic acid | LCMS, [M + H]⁺ = 512.0. ¹H NMR (500 MHz, DMSO-d₆) δ 8.75 (s, 1H), 8.32 (s, 1H), 5.55 (br s, 1H), 5.33 (s, 2H), 4.12 (s, 3H), 2.71 (s, 3H), 2.66-2.58 (m, 1H), 2.54 (s, 2H), 2.41-2.12 (m, 9H). 0.41 (br s, 1H), 0.25 (br s, 1H), 0.18 (br s, 1H), −0.01 (br s, 1H). hLPA1 IC₅₀ = 2400 nM | Example 237 |
| 238 | (1S,3S)-3-((5-(5-(((cyclopentyl(methyl)carbamoyl)oxy)methyl)-1-methyl-1H-1,2,3-triazol-4-yl)-3-(trifluoromethyl)pyridin-2-yl)oxy)cyclohexane-1-carboxylic acid | LCMS, [M + H]⁺ = 526.0. ¹H NMR (500 MHz, DMSO-d₆) δ 8.56 (s, 1H), 8.12 (s, 1H), 5.32 (br s, 1H), 5.15 (s, 1H), 5.11 (s, 1H), 3.91 (s, 3H), 3.0-2.85 m, 3H), 2.50 (s, 3H), 1.88-1.13 (m, 15H). hLPA1 IC₅₀ = 174 nM | |
| 239 | | LCMS, [M + H]⁺ = 512.5. ¹H NMR (500 MHz, DMSO-d₆) δ 8.76 (s, 1H), 8.34 (s, 1H), 5.55 (br s, 1H), 5.33 (s, 2H), 4.12 (s, 3H), 2.71 (s, 3H), 2.54 (s, 2H), 2.12-1.36 (m, 14H). hLPA1 IC₅₀ = 440 nM | |

| Example | Structure & Name | Analytical & Biology Data | Method |
|---|---|---|---|
| 240 | (1S,3S)-3-((5-(5-((((cyclobutylmethyl)(methyl)carbamoyl)oxy)methyl)-1-methyl-1H-1,2,3-triazol-4-yl)-3-(trifluoromethyl)pyridin-2-yl)oxy)cyclohexane-1-carboxylic acid<br><br>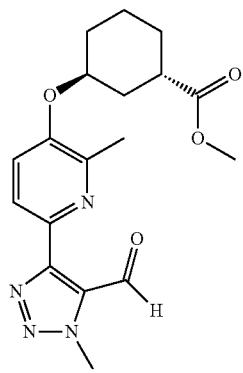<br><br>(1S,3S)-3-((5-(5-(((cyclobutyl(methyl)carbamoyl)oxy)methyl)-1-methyl-1H-1,2,3-triazol-4-yl)-3-(trifluoromethyl)pyridin-2-yl)oxy)cyclohexane-1-carboxylic acid | LCMS, [M + H]$^+$ = 526.0. $^1$H NMR (500 MHz, DMSO-d$_6$) δ 8.79 (s, 1H), 8.36 (s, 1H), 5.57 (br s, 1H), 5.37 (br s, 2H), 4.14 (s, 3H), 2.64 (s, 3H), 2.59-2.52 (m, 2H), 2.15-1.32 (m, 16H).<br>hLPA1 IC$_{50}$ = 1207 nM | |

Example 241

(1S,3S)-3-((6-(5-(2-(((Cyclobutylmethyl)(methyl)carbamoyl)oxy)ethyl)-1-methyl-1H-1,2,3-triazol-4-yl)-2-methylpyridin-3-yl)oxy)cyclohexane-1-carboxylic Acid

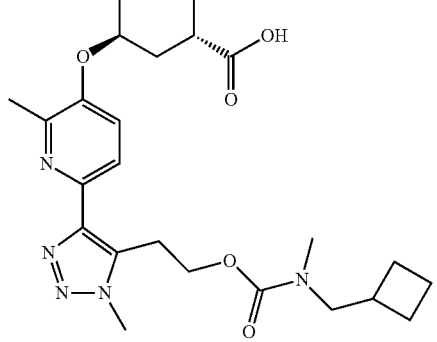

241A. Methyl (S, 3S)-3-((6-(5-formyl-1-methyl-1H-1,2,3-triazol-4-yl)-2-methylpyridin-3-yl)oxy)cyclohexane-1-carboxylate To a stirred solution of methyl (1S,3S)-3-((6-(5-(hydroxymethyl)-1-methyl-1H-1,2,3-triazol-4-yl)-2-methylpyridin-3-yl)oxy)cyclohexane-1-carboxylate (3.28 g, 9.10 mmol) in CH$_2$Cl$_2$ (45.5 ml) were added NaHCO$_3$ (3.82 g, 45.5 mmol) and Dess-Martin periodinane (4.63 g, 10.9 mmol) and the reaction mixture was stirred at rt for 1 h. The white solid was filtered off through Celite® and rinsed with EtOAc. The combined filtrates were washed with sat. aq. NaHCO$_3$, water, brine, dried over Na$_2$SO$_4$, filtered and concentrated in vacuo. The crude product was chromatographed (120 g Redisep® SiO$_2$ column; isocratic 60% EtOAc in Hex) to afford the title compound as a clear, colorless oil (3.10 g, 95%). LC-MS, [M+H]$^+$=359.1. $^1$H NMR (500 MHz, CDCl$_3$) δ 10.96 (s, 1H), 8.09 (d, J=8.5 Hz, 1H), 7.24 (d, J=8.5 Hz, 1H), 4.77-4.72 (m, 1H), 4.36 (s, 3H), 3.70 (s, 3H), 2.87-2.80 (m, 1H), 2.51 (s, 3H), 2.20-2.08 (m, 1H), 2.02-1.91 (m, 3H), 1.80-1.59 (m, 4H).

241B Methyl (1S,3S)-3-((2-methyl-6-(1-methyl-5-vinyl-1H-1,2,3-triazol-4-yl)pyridin-3-yl)oxy)cyclohexane-1-carboxylate

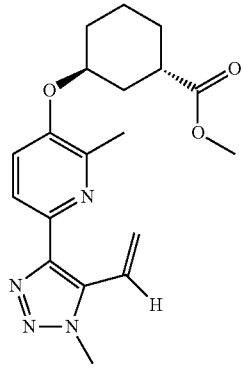 [SMILES: C=Cc1c(-c2ccc(O[C@H]3CCC[C@H](C(=O)OC)C3)c(C)n2)nnn1C]

To a cooled (0° C.) suspension of methyltriphenylphosphonium bromide (3.77 g, 10.55 mmol) in THF (70.3 mL) was added KOtBu (0.947 g, 8.44 mmol), and the reaction mixture was stirred at 0° C. for 30 min. To this reaction mixture was added a solution of Example 241A (2.52 g, 7.03 mmol) in THF (10 mL). The reaction was stirred at 0° C. for 30 min, then was allowed to warm to rt. After 1 h at rt, the reaction was quenched with sat. aq. NH$_4$Cl, then was diluted with EtOAc. The aqueous layer was extracted with EtOAc (2×25 mL). The combined organic extracts were washed with brine, dried (Na$_2$SO$_4$), and concentrated in vacuo. The crude product was chromatographed (220 g Redisep® SiO$_2$ column; continuous gradient from 0-60% EtOAc in Hex) to afford the title compound as a white gum (2.2 g, 88%). LC-MS, [M+H]$^+$=357.0. $^1$H NMR (500 MHz, CDCl$_3$) δ 7.91 (d, J=8.5 Hz, 1H), 7.42 (dd, J=18.3, 12.0 Hz, 1H), 7.20 (d, J=8.5 Hz, 1H), 5.93-5.88 (m, 1H), 5.70-5.66 (m, 1H), 4.71 (br s, 1H), 4.15 (s, 3H), 3.70 (s, 3H), 2.84 (tt, J=10.5, 3.9 Hz, 1H), 2.53 (s, 3H), 2.16 (br d, J=13.8 Hz, 1H), 2.02-1.87 (m, 3H), 1.87-1.71 (m, 1H), 1.71-1.54 (m, 3H).

241C Methyl (1S,3S)-3-((6-(5-(2-hydroxyethyl)-1-methyl-1H-1,2,3-triazol-4-yl)-2-methylpyridin-3-yl)oxy)cyclohexane-1-carboxylate

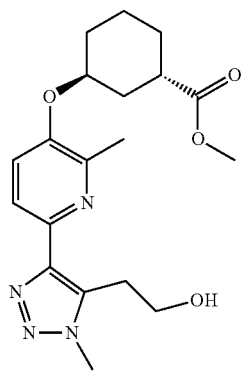 [SMILES: COC(=O)[C@H]1CCC[C@H](Oc2ccc(-c3nnn(C)c3CCO)nc2C)C1]

To a cooled (0° C.) solution of Example 241B (1.45 g, 4.07 mmol) in THF (13.6 ml) was added dropwise 9-BBN (17.9 mL of a 0.5M solution in THF; 8.95 mmol). The ice bath was then removed and the reaction was warmed to 65° C. After 4 h at 65° C., the reaction mixture was cooled to 0° C. and a solution of sodium perborate tetrahydrate (2.50 g, 16.3 mmol) in water (10 mL) was added. The reaction was then warmed to rt and stirred at rt for 18 h; water was then added. The aqueous layer was extracted with EtOAc (2×20 mL). The combined organic extracts were washed with brine, dried (MgSO$_4$) and concentrated in vacuo. The crude product was chromatographed (120 g Redisep® SiO$_2$ column; continuous gradient from 0-100% EtOAc in Hex) to afford the title compound as a colorless oil (0.37 g, 24%). LC-MS, [M+H]$^+$=375.1. $^1$H NMR (400 MHz, CDCl$_3$) δ 7.92 (d, J=8.6 Hz, 1H), 7.30-7.25 (m, 1H), 6.71-6.42 (m, 1H), 4.74-4.68 (m, 1H), 4.06-3.98 (m, 5H), 3.70 (s, 3H), 3.26 (td, J=5.6, 1.4 Hz, 2H), 2.83 (tt, J=10.3, 3.9 Hz, 1H), 2.51 (s, 3H), 2.14 (dt, J=13.9, 4.3 Hz, 1H), 2.02-1.87 (m, 3H), 1.82-1.56 (m, 4H).

241D. Methyl (1S,3S)-3-((2-methyl-6-(1-methyl-5-(2-(((4-nitrophenoxy)carbonyl)oxy)ethyl)-1H-1,2,3-triazol-4-yl)pyridin-3-yl)oxy)cyclohexane-1-carboxylate

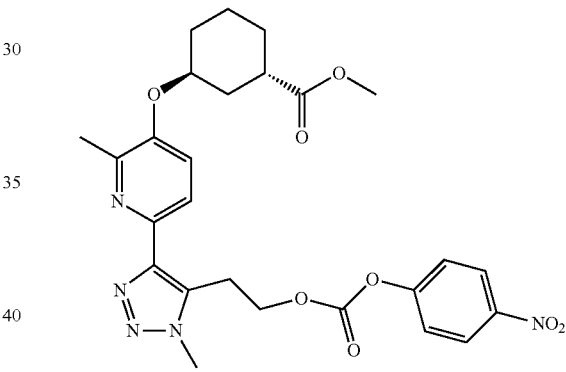

To a solution of Example 241C (370 mg, 0.988 mmol) and 4-nitrophenyl chloroformate (299 mg, 1.48 mmol) in THF (9.9 mL) was added pyridine (0.24 mL, 2.96 mmol). The reaction mixture was stirred at rt for 3 h, then was concentrated in vacuo. The crude product was chromatographed (120 g Redisep® SiO$_2$ column; continuous gradient from 0-100% EtOAc in Hex) to afford the title compound as a white solid (387 mg, 72.6%). LC-MS, [M+H]$^+$=540.1. $^1$H NMR (500 MHz, CDCl$_3$) δ 8.30 (d, J=9.4 Hz, 2H), 8.03 (d, J=8.5 Hz, 1H), 7.34 (d, J=9.4 Hz, 2H), 7.24 (d, J=8.5 Hz, 1H), 4.75-4.69 (m, 3H), 4.14 (s, 3H), 3.72 (s, 3H), 3.66 (t, J=6.3 Hz, 2H), 2.89-2.83 (m, 1H), 2.50 (s, 3H), 2.17 (br d, J=14.0 Hz, 1H), 2.04-1.89 (m, 3H), 1.87-1.72 (m, 1H), 1.70-1.59 (m, 3H).

Example 241

To a solution of Example 241D (11 mg, 0.020 mmol) and iPr$_2$NEt (7.1 µl, 0.041 mmol) in THF (1 mL) was added 1-cyclobutyl-N-methylmethanamine (2.0 mg, 0.020 mmol). The reaction was stirred at rt for 1 h. Water (0.5 mL) was added, followed by aq. LiOH.H$_2$O (0.05 mL of a 2N solution, 0.10 mmol). The reaction was stirred at rt for 18 h, then was acidified with 1N aq. HCl to pH~4 and extracted with EtOAc (3×5 mL). The combined organic extracts were washed with brine, dried (MgSO$_4$) and concentrated in vacuo. The crude material was purified by preparative HPLC (Column: XBridge C18, 19×200 mm, 5-μm particles; Mobile Phase A: 5:95 MeCN: water with 10 mM NH$_4$OAc; Mobile Phase B: 95:5 MeCN: water with 10 mM NH$_4$OAc; continuous gradient: 15-55% B over 25 min, then a 4-min hold at 100% B; Flow: 20 mL/min). Fractions containing the desired product were combined and dried via centrifugal evaporation to afford the title compound (5.7 mg, 58.7%). LC-MS, [M+H]$^+$=486.0. $^1$H NMR (500 MHz, DMSO-d$_6$) δ 7.84 (br s, 1H), 7.48 (br d, J=8.5 Hz, 1H), 4.76 (br s, 1H), 4.30 (br s, 2H), 4.02 (s, 3H), 3.53 (br s, 2H), 3.21-3.11 (m, 1H), 3.03-2.93 (m, 1H), 2.71 (br s, 3H), 2.63-2.56 (m, 1H), 2.42 (s, 3H), 2.33-2.24 (m, 1H), 2.02-1.37 (m, 14H). hLPA1 IC$_{50}$=41 nM.

The following examples were prepared according to the synthetic scheme described for Example 241.

| Example | Structure & Name | Analytical & Biology Data | Method |
|---|---|---|---|
| 242 | (1S,3S)-3-((2-Methyl-6-(1-methyl-5-(2-((methyl(propyl)carbamoyl)oxy)-ethyl)-1H-1,2,3-triazol-4-yl)pyridin-3-yl)oxy)cyclohexane-1-carboxylic acid, TFA salt | LC-MS, [M + H]$^+$ = 460.2 $^1$H NMR (500 MHz, DMSO-d$_6$) δ 7.83 (d, J = 8.5 Hz, 1H), 7.47 (d, J = 8.5 Hz, 1H), 4.78 (br s, 1H), 4.30 (br s, 2H), 4.03 (s, 3H), 3.56-3.46 (m, 2H), 3.11-2.85 (m, 2H), 2.76-2.61 (m, 4H), 2.43 (s, 3H), 2.06-1.99 (m, 1H), 1.92-1.74 (m, 3H), 1.69-1.20 (m, 6H), 0.86-0.57 (m, 3H). hLPA1 IC$_{50}$ = 319 nM | Example 241 |
| 243 | (1S,3S)-3-((6-(5-(2-((Cyclopentyl-(methyl)carbamoyl)oxy)ethyl)-1-methyl-1H-1,2,3-triazol-4-yl)-2-methylpyridin-3-yl)oxy)cyclohexane-1-carboxylic acid | LC-MS, [M + H]$^+$ = 486.0 $^1$H NMR (500 MHz, DMSO-d$_6$) δ 7.83 (d, J = 8.5 Hz, 1H), 7.46 (br d, J = 8.7 Hz, 1H), 4.73 (br s, 1H), 4.32 (br t, J = 6.1 Hz, 2H), 4.23-4.11 (m, 1H), 4.01 (s, 3H), 3.53 (br t, J = 6.0 Hz, 2H), 2.60-2.55 (m, 4H), 2.42 (s, 3H), 1.99-1.22 (m, 16H). hLPA1 IC$_{50}$ = 72 nM. | Example 241 |

| Example | Structure & Name | Analytical & Biology Data | Method |
|---|---|---|---|
| 244 | (1S,3S)-3-((6-(5-(2-((Benzyl(methyl)-carbamoyl)oxy)ethyl)-1-methyl-1H-1,2,3-triazol-4-yl)-2-methylpyridin-3-yl)oxy)cyclohexane-1-carboxylic acid | LC-MS, [M + H]$^+$ = 508.0<br>$^1$H NMR (500 MHz, DMSO-d$_6$) δ 7.82 (br d, J = 8.2 Hz, 1H), 7.48 (br d, J = 4.9 Hz, 1H), 7.36-7.24 (m, 3H), 7.15 (br d, J = 5.2 Hz, 1H), 7.04 (br s, 1H), 4.74 (br s, 1H), 4.43-4.30 (m, 3H), 4.17 (br s, 1H), 4.05-3.92 (m, 3H), 3.56-3.49 (m, 2H), 2.71 (s, 3H), 2.60-2.54 (m, 1H), 2.44-2.36 (m, 3H), 1.98-1.48 (m, 8H).<br>hLPA1 IC$_{50}$ = 54 nM. | Example 241 |
| 245 | (1S,3S)-3-((6-(5-(2-((Isobutyl-(methyl)carbamoyl)oxy)ethyl)-1-methyl-1H-1,2,3-triazol-4-yl)-2-methylpyridin-3-yl)oxy)cyclohexane-1-carboxylic acid | LC-MS, [M + H]$^+$ = 474.2<br>$^1$H NMR (500 MHz, DMSO-d$_6$) δ 7.83 (br d, J = 8.5 Hz, 1H), 7.46 (br d, J = 8.6 Hz, 1H), 4.75 (br s, 1H), 4.31 (br s, 2H), 4.02 (s, 3H), 3.56-3.47 (m, 2H), 2.93-2.55 (m, 7H), 2.43 (s, 3H), 2.04-1.48 (m, 8H), 0.71 (br d, J = 10.8 Hz, 6H).<br>hLPA1 IC$_{50}$ = 69 nM. | Example 241 |
| 246 | (2S,3S)-3-((2-Methyl-6-(1-methyl-5-(2-((pyrrolidine-1-carbonyl)oxy)-ethyl)-1H-1,2,3-triazol-4-yl)pyridin-3-yl)oxy)cyclohexane-1-carboxylic acid, TFA salt | LC-MS, [M + H]$^+$ = 458.3<br>$^1$H NMR (500 MHz, DMSO-d$_6$) δ 7.84 (br s, 1H), 7.45 (br d, J = 8.6 Hz, 1H), 4.75 (br s, 1H), 4.31 (t, J = 6.1 Hz, 2H), 4.03 (s, 3H), 3.51 (br t, J = 6.0 Hz, 2H), 3.21-2.62 (m, 5H), 2.42 (br s, 3H), 2.08-1.95 (m, 1H), 1.91-1.74 (m, 3H), 1.72-1.50 (m, 8H).<br>hLPA1 IC$_{50}$ = 210 nM. | Example 241 |

| Example | Structure & Name | Analytical & Biology Data | Method |
|---|---|---|---|
| 247 | 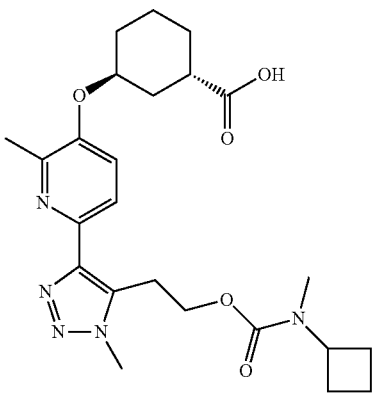 [SMILES: Cc1nc(-c2nnn(C)c2CCOC(=O)N(C)C2CCC2)ccc1O[C@H]1CCC[C@H](C(=O)O)C1]<br>(1S,3S)-3-((6-(5-(2-(((Cyclobutyl(methyl)carbamoyl)oxy)ethyl)-1-methyl-1H-1,2,3-triazol-4-yl)-2-methylpyridin-3-yl)oxy)cyclohexane-1-carboxylic acid, TFA salt | LC-MS, [M + H]$^+$ = 472.1<br>$^1$H NMR (500 MHz, DMSO-d$_6$) δ 7.83 (d, J = 8.5 Hz, 1H), 7.44 (d, J = 8.6 Hz, 1H), 4.75 (br s, 1H), 4.31 (br t, J = 6.2 Hz, 2H), 4.02 (s, 3H), 3.52 (br t, J = 5.7 Hz, 2H), 3.24-3.15 (m, 1H), 2.68-2.56 (m, 4H), 2.43 (s, 3H), 2.08-1.38 (m, 14H).<br>hLPA1 IC$_{50}$ = 41 nM. | Example 241 |
| 248 | 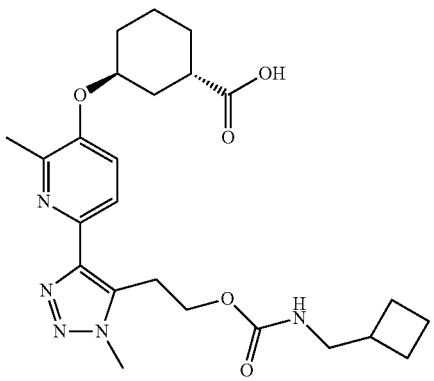 [SMILES: Cc1nc(-c2nnn(C)c2CCOC(=O)NCC2CCC2)ccc1O[C@H]1CCC[C@H](C(=O)O)C1]<br>(1S,3S)-3-((6-(5-(2-(((Cyclobutylmethyl)carbamoyl)oxy)ethyl)-1-methyl-1H-1,2,3-triazol-4-yl)-2-methylpyridin-3-yl)oxy)cyclohexane-1-carboxylic acid, TFA salt | LC-MS, [M + H]$^+$ = 472.1<br>$^1$H NMR (500 MHz, DMSO-d$_6$) δ 7.49 (br s, 1H), 7.01 (br s, 1H), 4.75 (br s, 1H), 4.29 (br s, 2H), 4.02 (s, 3H), 3.54-3.24 (m, 2H), 3.00-2.94 (m, 2H), 2.71-2.63 (m, 2H), 2.35 (br s, 3H), 2.09-1.45 (m, 14H).<br>hLPA1 IC$_{50}$ = 144 nM. | Example 241 |

Example 249

(1S,3S)-3-((6-(5-(3-(((Benzyl(methyl)carbamoyl)oxy)propyl)-1-methyl-1H-1,2,3-triazol-4-yl)-2-methylpyridin-3-yl)oxy)cyclohexane-1-carboxylic Acid

249B. Methyl (1S,3S)-3-((6-(5-(3-(benzyloxy)prop-1-en-1-yl)-1-methyl-1H-1,2,3-triazol-4-yl)-2-methylpyridin-3-yl)oxy)cyclohexane-1-carboxylate

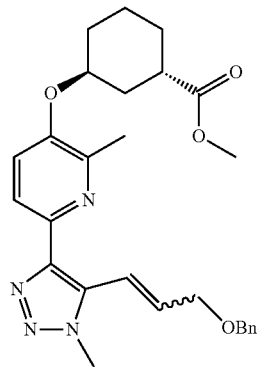

In a sealed tube was placed Example 249A (0.116 g, 0.243 mmol), Example 241A (0.058 g, 0.162 mmol), K₂CO₃ (0.067 g, 0.485 mmol), and THF (1.6 mL). The reaction was stirred at 115° C. for 2 h, then was cooled to rt. The mixture was diluted with EtOAc, washed with brine, dried (MgSO₄), and concentrated in vacuo. The crude product was chromatographed (12 g Redisep® SiO₂ column, eluting with 0-100% EtOAc in Hex) to afford the title compound as a yellow solid (35 mg, 45%) as a mixture of cis/trans isomers.

249C Methyl (1S,3S)-3-((6-(5-(3-(benzyloxy)propyl)-1-methyl-1H-1,2,3-triazol-4-yl)-2-methyl pyridine-3-yl)oxy)cyclohexane-1-carboxylate

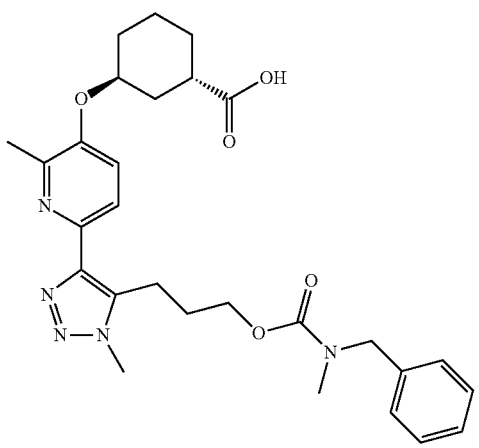 [SMILES: Cc1nc(-c2nnn(C)c2CCCOC(=O)N(C)Cc2ccccc2)ccc1O[C@H]1CCC[C@H](C(=O)O)C1]

249A (2-(Benzyloxy)ethyl)triphenylphosphonium bromide

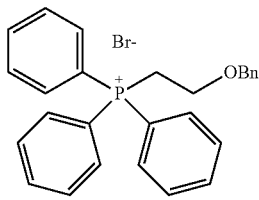

Benzyl 2-bromoethyl ether (0.78 mL, 4.96 mmol) was added to a solution of Ph₃P (1 g, 3.81 mmol) in toluene (7.63 mL) and the reaction was stirred at 105° C. for 18 h, then was cooled to rt. Diethyl ether (50 mL) was added, and the mixture was stirred for 15 min at rt; the precipitated product was collected by filtration, rinsed with ether and air-dried to afford the title product (1.46 g, 80%) as a white solid. LC-MS, [M]⁺=397.1. ¹H NMR (500 MHz, CDCl₃) δ 7.87-7.73 (m, 9H), 7.63 (td, J=7.8, 3.3 Hz, 6H), 7.27-7.19 (m, 3H), 6.92 (d, J=6.6 Hz, 2H), 4.36 (dt, J=11.7, 5.7 Hz, 2H), 4.27 (s, 2H), 4.11-4.01 (m, 2H).

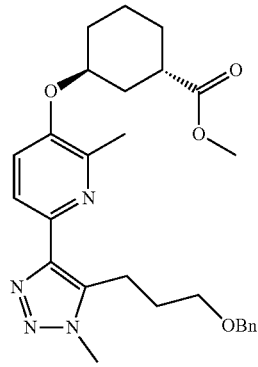 [SMILES: COC(=O)[C@H]1CCC[C@H](Oc2ccc(-c3nnn(C)c3CCCOCc3ccccc3)nc2C)C1]

To a solution of Example 249B (35 mg, 0.073 mmol) in MeOH (20 mL) under Ar was added 20% Pd(OH)₂ on carbon (10.31 mg, 0.015 mmol) and ammonium formate (93 mg, 1.47 mmol). The reaction mixture was stirred in a sealed tube at 65° C. for 18 h, then was cooled to rt. The reaction was filtered through a pad of Celite®, rinsed with MeOH, and the filtrate was concentrated in vacuo. The crude material was purified by preparative HPLC using the following conditions: Column: Sunfire Prep C18 OBD 5 um 30×100 mm; Mobile Phase A: 10:90 MeCN: water with 0.1% TFA; Mobile Phase B: 90:10 MeCN: water with 0.1% TFA; Gradient: 20-100% B over 12 min; Flow: 40 mL/min. Fractions containing the desired product were combined and dried via centrifugal evaporation to afford the title compound (40 mg, 92%) as a yellow solid. LC-MS, [M+H]⁺=479.3.

249D. Methyl (1S,3S)-3-((6-(5-(3-hydroxypropyl)-1-methyl-1H-1,2,3-triazol-4-yl)-2-methyl-pyridin-3-yl)oxy)cyclohexane-1-carboxylate

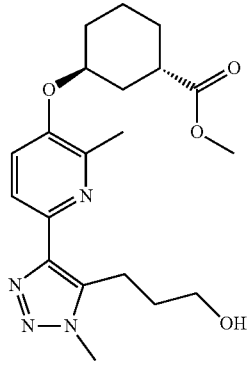 [SMILES: COC(=O)[C@H]1CCC[C@H](Oc2ccc(-c3nnn(C)c3CCCO)nc2C)C1]

To a solution of Example 249C (40 mg, 0.067 mmol) in EtOH (2 mL) and AcOH (1 mL) was added 10% Pd/C (7.2 mg, 6.8 μmol), and H₂ gas was bubbled through the reaction mixture for a few minutes; the reaction was then stirred under H₂-balloon for 72 h. The reaction mixture was filtered through a pad of Celite®, rinsed with MeOH, and the combined filtrate/rinses were concentrated in vacuo. The crude material was purified by preparative HPLC using the following conditions: Column: Sunfire Prep C18 OBD 5u 30×100 mm; Mobile Phase A: 10:90 MeCN: water with 0.1% TFA; Mobile Phase B: 90:10 MeCN: water with 0.1% TFA; Gradient: 20-100% B over 12 min; Flow: 40 mL/min. Fractions containing the desired product were combined and dried via centrifugal evaporation to afford the title compound 246D (23 mg, 68%) as a colorless solid. LC-MS, [M+H]⁺=389.2. ¹H NMR (500 MHz, CD₃OD) δ 8.10-7.98 (m, 2H), 5.02-4.96 (m, 1H), 4.15 (s, 3H), 3.71 (s, 3H), 3.62 (br t, J=5.6 Hz, 2H), 3.18 (br t, J=7.2 Hz, 2H), 2.91-2.83 (m, 1H), 2.71 (s, 3H), 2.20-2.10 (m, 1H), 2.07-1.90 (m, 5H), 1.85-1.65 (m, 4H).

249E Methyl(1S,3S)-3-((2-methyl-6-(1-methyl-5-(3-(((4-nitrophenoxy)carbonyl)oxy)propyl)-1H-1,2,3-triazol-4-yl)pyridin-3-yl)oxy)cyclohexane-1-carboxylate

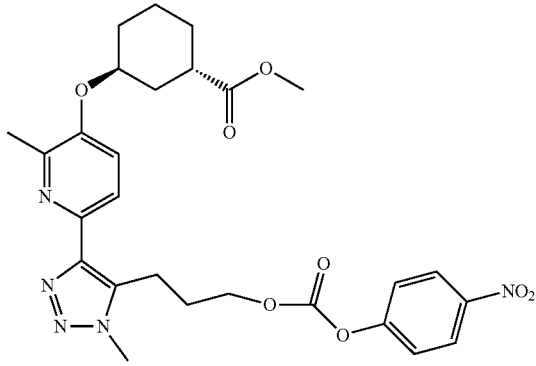 [SMILES: COC(=O)[C@H]1CCC[C@H](Oc2ccc(-c3nnn(C)c3CCCOC(=O)Oc3ccc([N+](=O)[O-])cc3)nc2C)C1]

To a solution of Example 249D (21 mg, 0.042 mmol) and 4-nitrophenyl chloroformate (12.6 mg, 0.063 mmol) in THF (1 mL) was added pyridine (10 μl, 0.13 mmol). The reaction was stirred at rt for 18 h, then was concentrated in vacuo. The crude product was chromatographed (4 g Redisep® SiO₂ column, eluting with 0-100% EtOAc in Hex) to afford the title compound (10 mg, 43%) as a white solid. LC-MS, [M+H]⁺=554.2.

Example 249

To a solution of Example 249E (10 mg, 0.018 mmol) and DIEA (6.31 μl, 0.036 mmol) in THF (1 mL) was added N-methyl-1-phenylmethanamine (2.2 mg, 0.018 mmol). After 1 h, water (0.5 mL) was added, followed by aq. LiOH (0.070 mL of a 2M solution, 0.139 mmol). The reaction mixture was stirred at rt for 18 h, after which the pH was adjusted with 1N aq. HCl to ~4 and the mixture was extracted with EtOAc (3×). The combined organic extracts were washed with brine, dried (MgSO₄) and concentrated in vacuo. The crude material was purified by preparative HPLC using the following conditions: Column: Sunfire Prep C18 OBD 5u 30×100 mm; Mobile Phase A: 10:90 MeCN: water with 0.1% TFA; Mobile Phase B: 90:10 MeCN: water with 0.1% TFA; Gradient: 20-100% B over 12 min; Flow: 40 mL/min. Fractions containing the desired product were combined and dried via centrifugal evaporation, then re-purified by preparative HPLC using the following conditions: Column: Sunfire Prep C18 OBD 5u 30×100 mm; Mobile Phase A: 10:90 MeOH: water with 0.1% TFA; Mobile Phase B: 90:10 MeOH: water with 0.1% TFA; Gradient: 20-100% B over 12 min; Flow: 40 mL/min. Fractions containing the desired product were combined and dried via centrifugal evaporation to afford the title compound (2.1 mg, 18%) as a white solid. LC-MS, [M+H]⁺=522.3. ¹H NMR (400 MHz, 60° C., CD₃OD) δ 7.65 (br d, J=8.4 Hz, 1H), 7.32 (br d, J=8.8 Hz, 1H), 7.23-7.05 (m, 5H), 4.69-4.61 (m, 1H), 4.30 (s, 2H), 4.09 (t, J=5.6 Hz, 2H), 3.90 (br s, 3H), 3.16-3.08 (m, 2H), 2.75-2.63 (m, 4H), 2.39 (s, 3H), 2.04-1.89 (m, 3H), 1.89-1.75 (m, 3H), 1.72-1.49 (m, 4H). hLPA1 IC₅₀=122 nM.

Synthesis of Amine Intermediate for the Preparation of Example 250

Intermediate 5. N-methyl-2-propoxyethan-1-amine

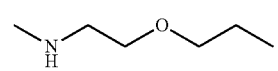

Intermediate 5A.
N-benzyl-N-methyl-2-propoxyethan-1-amine

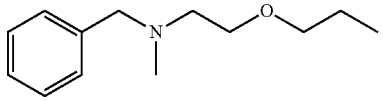

To a solution of 2-(benzyl(methyl)amino)ethan-1-ol (1 mL, 6.15 mmol) in dry DMF (5 mL) was added 60% NaH in mineral oil (0.369 g, 9.23 mmol) at 0° C. After 1 h, 1-chloropropane (0.813 mL, 9.23 mmol) was added. The reaction mixture was stirred overnight at rt, then was quenched with ice water and extracted with EtOAc. The organic phase was washed with water and brine, dried (Na$_2$SO$_4$) and concentrated in vacuo. The crude oily product was chromatographed (24 g SiO$_2$; elution with EtOAc/Hexane (continuous gradient from 0% to 100% over 10 min)) to give the free amine as an oil. This oil was treated with 2.0 M HCl in ether to give N-benzyl-N-methyl-2-propoxyethan-1-amine HCl salt (1.2 g, 4.92 mmol, 80% yield) as a clear oil. $^1$H NMR (400 MHz, CDCl$_3$) δ 7.67-7.61 (m, 2H), 7.47-7.43 (m, 3H), 4.34-4.20 (m, 2H), 4.04-3.93 (m, 2H), 3.46 (t, J=6.6 Hz, 2H), 3.34-3.27 (m, 1H), 3.14-3.06 (m, 1H), 2.74 (d, J=5.1 Hz, 3H), 1.65-1.59 (m, 2H), 0.93 (t, J=7.4 Hz, 3H)

Intermediate 5

A mixture of Intermediate 5A (1.2 g, 4.92 mmol) and 20% Pd(OH)2-C (0.346 g, 2.461 mmol) in EtOH (5 mL) was stirred at 60° C. under 1 atmosphere H$_2$ for 2 h, then was filtered and concentrated in vacuo to provide the title intermediate as the HCl salt (0.72 g, 4.69 mmol, 95% yield) as a white solid. $^1$H NMR (500 MHz, CDCl$_3$) δ 9.41 (br s, 2H), 3.81 (t, J=4.8 Hz, 2H), 3.44 (t, J=6.6 Hz, 2H), 3.24-3.11 (m, 2H), 2.77 (br t, J=5.0 Hz, 3H), 1.60 (sxt, J=7.1 Hz, 2H), 0.90 (t, J=7.4 Hz, 3H).

Synthesis of Amine Intermediate 6 for Examples 254 & 255:

Intermediate 6. 2-fluoro-N-methylbutan-1-amine

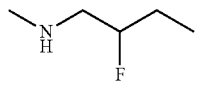

Intermediate 6A.
1-(benzyl(methyl)amino)butan-2-ol

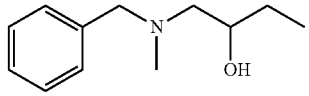

A solution of N-methyl-1-phenylmethanamine (6.09 mL, 46.4 mmol) and 1,2-epoxybutane (1.0 mL, 11.6 mmol) in EtOH (50 mL) was stirred under reflux for 8 h, then was cooled to rt and concentrated in vacuo. The crude residue was chromatographed (80 g SiO$_2$; elution with MeOH/DCM (continuous gradient from 0% to 10% over 20 min) to give the title compound (500 mg, 2.59 mmol, 22.3% yield) as a clear oil. $^1$H NMR (500 MHz, CDCl$_3$) δ 7.35-7.24 (m, 5H), 3.72-3.41 (m, 4H), 2.42-2.32 (m, 2H), 2.23 (s, 3H), 1.50-1.36 (m, 2H), 0.97 (t, J=7.6 Hz, 3H); [M+H]$^+$=194.3

Intermediate 6B.
N-benzyl-2-fluoro-N-methylbutan-1-amine

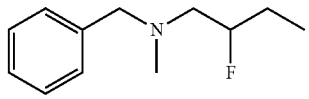

DAST (0.697 mL in THF, 5.28 mmol) was added to a solution of Intermediate 6A (0.51 g, 2.64 mmol) in DCM (3 mL) at −78° C. and the reaction was stirred for 5 h at −78° C. and for 18 h at rt. Volatiles were concentrated in vacuo and the residue was carefully quenched with water (2 mL). The aqueous solution containing product was purified by prepHPLC (Sunfire C18 30×100 mm-regenerated column; detection at 220 nm; flow rate=40 mL/min; continuous gradient from 0% B to 100% B over 10 min+2 min hold time at 100% B, where A=90:10:0.1 H$_2$O:MeCN:TFA and B=90:10:0.1 MeCN:H$_2$O:TFA) and appropriate fractions were concentrated to obtain an oil. The residue was treated with 2.0 M HCl in ether (3.61 mL, 7.22 mmol) to give the HCl salt of the title compound (0.22 g, 1.127 mmol, 42.7% yield) as a clear oil. $^1$H NMR (500 MHz, CD$_3$OD) δ 7.54 (s, 5H), 5.12-4.91 (m, 1H), 4.68-4.22 (m, 2H), 3.56-3.41 (m, 2H), 3.01-2.83 (m, 3H), 1.84-1.60 (m, 2H), 1.06 (q, J=7.7 Hz, 3H); $^{19}$F NMR (471 MHz, METHANOL-d4) δ −186.78 (s), −188.25 (s); [M+H]$^+$=196.3

Intermediate 6

A mixture of Intermediate 6B (0.22 g, 0.95 mmol) and 20% Pd(OH)$_2$—C (0.067 g, 0.475 mmol) in EtOH (5 mL) was stirred at 60° C. under 1 atmosphere of H$_2$ for 2 h. The mixture was filtered and concentrated in vacuo to provide the title compound as the HCl salt (0.099 g, 9.41 mmol, 99% yield) as a white solid. $^1$H NMR (400 MHz, CDCl$_3$) δ 10.06-9.40 (m, 2H), 5.34-4.94 (m, 1H), 3.38-3.02 (m, 2H), 2.81 (br s, 3H), 1.75 (br d, J=1.5 Hz, 2H), 1.04 (br t, J=6.2 Hz, 3H); $^{19}$F NMR (377 MHz, CDCl$_3$) δ: −185.22 (br s, F).

Intermediate 7. 4-fluoro-N-methylpentan-1-amine
(for the Synthesis of Example 256)

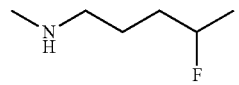

7A. N-benzyl-4-hydroxy-N-methylpentanamide

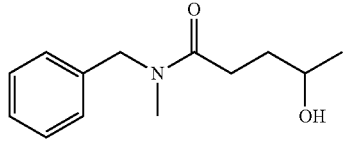 [SMILES: CC(O)CCC(=O)N(C)Cc1ccccc1]

N-methyl-1-phenylmethanamine (5.78 mL, 44.9 mmol) was added to a mixture of 5-methyl dihydrofuran-2(3H)-one (1.426 mL, 14.98 mmol) and toluene (20 mL), and NaOMe solution (sodium (1.033 g, 44.9 mmol) added to MeOH (15 mL)) was added dropwise at 20 to 30° C., followed by stirring for 18 h at rt. The reaction was quenched by addition of ice water (20 mL) and HOAc (3.43 mL, 60 mmol) was added dropwise. The aqueous layer was extracted with EtOAc (2×20 mL). The combined organic extracts were washed with water and concentrated in vacuo. The crude oily product was chromatographed (40 g SiO$_2$; elution with EtOAc/Hexane (continuous gradient from 0% to 100% over 10 min)) to give the title compound (1.5 g, 6.78 mmol, 45.2% yield) as a clear oil. $^1$H NMR (400 MHz, CDCl$_3$) δ

7.41-7.13 (m, 5H), 4.63-4.53 (m, 2H), 3.85 (dddd, J=14.0, 8.0, 6.2, 4.2 Hz, 1H), 3.02 (dd, J=7.4, 4.5 Hz, 1H), 2.98-2.91 (m, 3H), 2.66-2.45 (m, 2H), 1.97-1.70 (m, 2H), 1.21 (dd, J=17.6, 6.4 Hz, 3H)); [M+H]⁺=222.2.

7B. 5-(benzyl(methyl)amino)pentan-2-ol

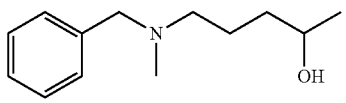

Intermediate 7A (1.5 g, 6.78 mmol) was added to a suspension of LAH (4.07 mL of a 2.0 M solution in THF; 8.13 mmol) in THF (50 mL). The mixture was heated at reflux for 18 h, then was cooled to 0° C. Brine (~1 mL) was carefully added until no more gas was generated. The solids were filtered off, and the filtrate was concentrated in vacuo. The crude residue was chromatographed (12 g SiO₂; elution with MeOH/DCM (continuous gradient from 0% to 10% over 20 min) to give the title compound (1.35 g, 6.51 mmol, 96% yield) as a clear oil. ¹H NMR (500 MHz, CDCl₃) δ 7.40-7.25 (m, 5H), 3.84-3.73 (m, 1H), 3.56 (q, J=12.7 Hz, 2H), 2.59-2.51 (m, 1H), 2.49-2.39 (m, 1H), 2.18 (s, 3H), 1.82-1.67 (m, 3H), 1.50-1.40 (m, 1H), 1.22 (d, J=6.3 Hz, 3H); [M+H]⁺=208.3.

7C. N-benzyl-4-fluoro-N-methylpentan-1-amine

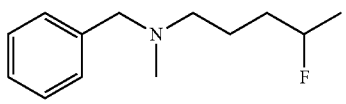

DAST (1.03 mL in THF, 7.81 mmol) was added to a solution of Intermediate 7B (0.81 g, 3.91 mmol) in DCM (3 mL) at −78° C. and the reaction was stirred for 5 h at −78° C. and for 18 h at rt. The reaction was concentrated in vacuo and carefully quenched with water (2 mL). The aqueous solution was purified by preparative HPLC (Sunfire C18 30×100 mm-regenerated column; detection at 220 nm; flow rate=40 mL/min; continuous gradient from 0% B to 100% B over 10 min+2 min hold time at 100% B, where A=90:10:0.1 H₂O:MeCN:TFA and B=90:10:0.1 MeCN:H₂O:TFA) and appropriate fractions were concentrated to give an oil. The residue was treated with 2.0 M HCl in ether (3.61 mL, 7.22 mmol) to give the title compound as the HCl salt (0.12 g, 0.488 mmol, 12.50% yield) as a clear oil. ¹H NMR (400 MHz, CDCl₃) δ 12.21 (br s, 1H), 7.62 (br s, 2H), 7.50-7.41 (m, 3H), 4.80-4.55 (m, 1H), 4.32-4.15 (m, 2H), 3.23-2.83 (m, 2H), 2.81-2.64 (m, 3H), 2.21-1.94 (m, 2H), 1.78-1.55 (m, 2H), 1.40-1.27 (m, 3H); ¹⁹F NMR (377 MHz, CDCl₃) δ −173.65 (d, J=38.9 Hz, F); [M+H]⁺=210.2

Intermediate 7

A mixture of Intermediate 7C (0.12 g, 0.488 mmol) and 20% Pd(OH)₂—C (0.034 g, 0.24 mmol) in EtOH (5 mL) was stirred at 60° C. under 1 atmosphere H₂ for 2 h. The reaction was filtered and concentrated in vacuo to provide the title compound as the HCl salt (0.05 g, 0.321 mmol, 65.8% yield) as a white solid. ¹H NMR (500 MHz, CDCl₃) δ 9.51 (br s, 2H), 4.83-4.62 (m, 1H), 3.01 (br s, 2H), 2.70 (br s, 3H), 2.13-1.94 (m, 2H), 1.81-1.65 (m, 2H), 1.41-1.29 (m, 3H); ¹⁹F NMR (471 MHz; CDCl₃) δ −173.53 (s, 1F).

| Example | Structure & Name | Analytical & Biology Data | Method |
|---|---|---|---|
| 250 | 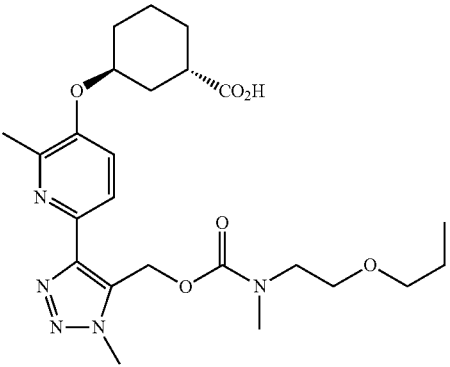<br>(1S,3S)-3-((2-methyl-6-(1-methyl-5-(((methyl(2-propoxyethyl)carbamoyl)oxy)methyl)-1H-1,2,3-triazol-4-yl)pyridin-3-yl)oxy)cyclohexane-1-carboxylic acid | LCMS; [M + H]⁺ = 490.3; ¹H NMR (500 MHz, DMSO-d₆) δ 7.85 (br s, 1H), 7.47 (d, J = 8.6 Hz, 1H), 5.66 (br s, 2H), 4.77 (br s, 1H), 4.10 (s, 3H), 2.83 (br s, 3H), 2.71-2.61 (m, 1H), 2.43 (s, 3H), 2.08-1.98 (m, 1H), 1.91-1.76 (m, 3H), 1.72-1.34 (m, 6H), 0.79 (br s, 3H), 6 protons are in water suppression area LPA1 IC₅₀ = 314 nM | Example 1 |

| Example | Structure & Name | Analytical & Biology Data | Method |
|---|---|---|---|
| 251 | 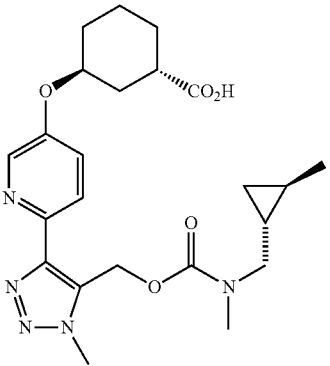<br>(1S,3S)-3-((6-(1-methyl-5-(((methyl(((1R,2R)-2-methylcyclopropyl)methyl)carbamoyl)oxy)methyl)-1H-1,2,3-triazol-4-yl)pyridin-3-yl)oxy)cyclohexane-1-carboxylic acid | LCMS; [M + H]$^+$ = 458.1;<br>$^1$H NMR (500 MHz, CDCl$_3$) δ 8.64 (d, J = 2.5 Hz, 1H), 8.24 (d, J = 8.8 Hz, 1H), 7.89-7.79 (m, 1H), 5.54 (s, 2H), 4.84 (br s, 1H), 4.23 (br s, 3H), 3.23-3.15 (m, 1H), 3.14-2.98 (m, 1H), 2.94 (br s, 4H), 2.19-2.01 (m, 2H), 1.98-1.75 (m, 5H), 1.73-1.61 (m, 1H), 1.03 (br s, 3H), 0.70-0.51 (m, 2H), 0.42-0.22 (m, 2H)<br>LPA1 IC$_{50}$ = 27 nM | Example 3 |
| 252 | 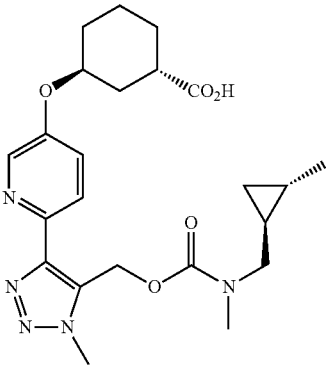 [SMILES: C[C@H]1C[C@@H]1CN(C)C(=O)OCc1c(-c2ccc(O[C@H]3CCC[C@H](C(=O)O)C3)cn2)nnn1C]<br>(1S,3S)-3-((6-(1-methyl-5-(((methyl(((1S,2S)-2-methylcyclopropyl)methyl)carbamoyl)oxy)methyl)-1H-1,2,3-triazol-4-yl)pyridin-3-yl)oxy)cyclohexane-1-carboxylic acid | LCMS; [M + H]$^+$ = 458.1;<br>$^1$H NMR (500 MHz, CDCl$_3$) δ 8.64 (d, J = 1.9 Hz, 1H), 8.23 (d, J = 8.8 Hz, 1H), 7.82 (br d, J = 8.0 Hz, 1H), 5.54 (s, 2H), 4.84 (br s, 1H), 4.23 (br s, 3H), 3.24-3.14 (m, 1H), 3.14-2.97 (m, 1H), 2.93 (br s, 4H), 2.19-2.00 (m, 2H), 1.98-1.61 (m, 6H), 1.02 (br s, 3H), 0.69-0.50 (m, 2H), 0.42-0.20 (m, 2H)<br>LPA1 IC$_{50}$ = 29 nM | Example 3 |
| 253 | 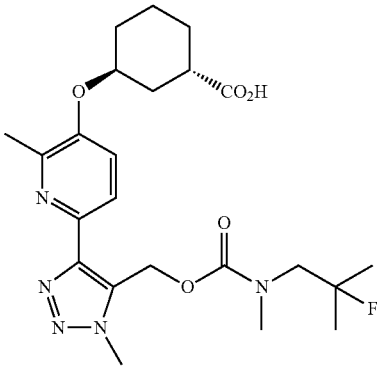 [SMILES: Cc1nc(-c2nnn(C)c2COC(=O)N(C)CC(C)(C)F)ccc1O[C@H]1CCC[C@H](C(=O)O)C1]<br>(1S,3S)-3-((6-(5-((((2-fluoro-2-methylpropyl)(methyl)carbamoyl)oxy)methyl)-1-methyl-1H-1,2,3-triazol-4-yl)-2-methylpyridin-3-yl)oxy)cyclohexane-1-carboxylic acid | LCMS; [M + H]$^+$ = 478.1;<br>$^1$H NMR (500 MHz, DMSO-d$_6$) δ 7.84 (br d, J = 8.5 Hz, 1H), 7.47 (br d, J = 8.6 Hz, 1H), 5.67 (br s, 4H), 4.77 (br s, 2H), 4.10 (s, 4H), 2.86 (br s, 2H), 2.65 (br t, J = 10.1 Hz, 1H), 2.42 (s, 3H), 2.08-1.99 (m, 1H), 1.91-1.75 (m, 3H), 1.73-1.44 (m, 4H), 1.37-0.97 (m, 6H)<br>3 protons are in water suppression area<br>LPA1 IC$_{50}$ = 134 nM | Example 1 |

| Example | Structure & Name | Analytical & Biology Data | Method |
|---|---|---|---|
| 254 | (1S,3S)-3-((5-(5-((((2-fluorobutyl)(methyl)carbamoyl)oxy)methyl)-1-methyl-1H-1,2,3-triazol-4-yl)-3-methylpyrazin-2-yl)oxy)cyclohexane-1-carboxylic acid; mixture of diastereomers | LCMS; [M + H]$^+$ = 479.1; $^1$H NMR (500 MHz, DMSO-d$_6$) δ 8.59 (s, 1H), 5.71-5.48 (m, 2H), 5.39 (br s, 1H), 4.73-4.21 (m, 1H), 4.11 (s, 3H), 3.57-3.19 (m, 2H), 2.90-2.74 (m, 3H), 2.64 (br t, J = 11.1 Hz, 1H), 2.45 (s, 3H), 2.19-2.04 (m, 1H), 1.96-1.72 (m, 3H), 1.70-1.24 (m, 6H), 0.97-0.60 (m, 3H); $^{19}$F NMR (471 MHz, DMSO-d$_6$) δ −73.42 (br s, TFA), −185.33 (br d, J = 97.1 Hz, F) LPA1 IC$_{50}$ = 132 nM | |
| 255 | (1S,3S)-3-((6-(5-((((2-fluorobutyl)(methyl)carbamoyl)oxy)methyl)-1-methyl-1H-1,2,3-triazol-4-yl)-2-methylpyridin-3-yl)oxy)cyclohexane-1-carboxylic acid; mixture of diastereomers | LCMS; [M + H]$^+$ = 478.2; $^1$H NMR (500 MHz, DMSO-d$_6$) δ 7.85 (br s, 1H), 7.47 (br d, J = 8.2 Hz, 1H), 5.76-5.51 (m, 2H), 4.77 (br s, 1H), 4.69-4.20 (m, 1H), 4.09 (s, 3H), 3.60-3.20 (m, 2H), 2.94-2.73 (m, 3H), 2.62 (br s, 1H), 2.40 (br s, 3H), 2.07-1.19 (m, 10H), 0.98-0.55 (m, 3H); $^{19}$F NMR (471 MHz, DMSO-d$_6$) δ −73.54 (s, TFA), −185.49 (s) LPA1 IC$_{50}$ = 57 nM | Example 1 |
| 256 | (1S,3S)-3-((6-(5-((((4-fluoropentyl)(methyl)carbamoyl)oxy)methyl)-1-methyl-1H-1,2,3-triazol-4-yl)-2-methylpyridin-3-yl)oxy)cyclohexane-1-carboxylic acid | LCMS; [M + H]$^+$ = 492.3; $^1$H NMR (500 MHz, DMSO-d$_6$) δ 7.83 (br d, J = 8.5 Hz, 1H), 7.45 (br d, J = 8.5 Hz, 1H), 5.62 (br d, J = 13.7 Hz, 2H), 4.85-4.29 (m, 2H), 4.08 (s, 3H), 3.25-3.03 (m, 2H), 2.83-2.68 (m, 3H), 2.62 (br t, J = 10.2 Hz, 1H), 2.40 (s, 3H), 1.99 (br d, J = 13.7 Hz, 1H), 1.90-0.97 (m, 11H), 0.84 (br t, J = 7.2 Hz, 3H); $^{19}$F NMR (471 MHz, DMSO-d$_6$) δ −73.75 (s, TFA), −170.59 (br d, J = 65.9 Hz, F) LPA1 IC$_{50}$ = 17 nM | Example 1 |

Example 257

(1S,3S)-3-((2-methyl-6-(1-methyl-5-(((methyl(((1R,2R)-2-methylcyclopropyl)methyl) carbamoyl)oxy)methyl)-1H-1,2,3-triazol-4-yl)pyridin-3-yl)oxy)cyclohexane-1-carboxylic Acid

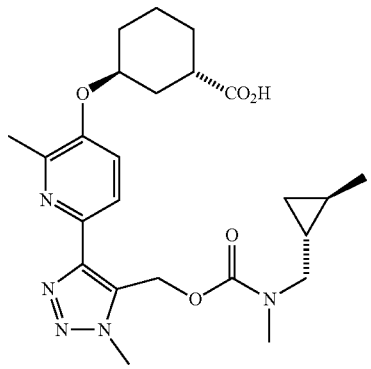

257A. (E)-N-benzylbut-2-enamide

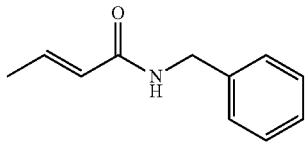

EDC (36.7 g, 192 mmol) was added portionwise to a solution of crotonic acid (15.0 g, 174 mmol), benzyl amine (21.0 mL, 192 mmol) and DIPEA (33.5 mL, 192 mmol) in DCM (300 mL). The reaction mixture was stirred overnight and then poured onto 10% aq. KHSO$_4$ (250 mL) and extracted with EtOAc (100 mL). The organic layer was washed once again with 10% aq. KHSO$_4$ followed by brine (150 mL), dried (Na$_2$SO$_4$) and concentrated in vacuo to give the title compound as a white solid (25 g, 143 mmol, 82% yield). [M+H]$^+$=176.2; $^1$H NMR (500 MHz, CDCl$_3$) δ 7.40-7.20 (m, 5H), 6.98-6.82 (m, 1H), 5.84 (br dd, J=15.1, 1.7 Hz, 2H), 4.52 (d, J=5.8 Hz, 2H), 1.87 (dd, J=6.9, 1.7 Hz, 3H)

257B. N-benzyl-2-methylcyclopropanecarboxamide

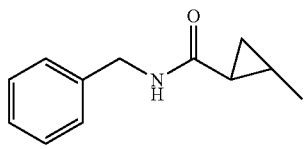

In an Erlenmeyer flask containing Et$_2$O (50 mL) and aq. 40% KOH (5 mL) was added N-methyl-N'-nitro-N-nitrosoguanidine (504 mg, 3.42 mmol) portionwise (with vigorous stirring) over 15 min at 0° C. Upon complete addition, stirring was stopped and the aqueous layer was separated. The ether layer was dried with KOH pellets and allowed to stand for 5 min, then decanted into a third flask with KOH pellets and then poured onto a THF solution (2 mL) containing Example 257A (300 mg, 1.712 mmol). Pd(OAc)$_2$ (3.84 mg, 0.017 mmol) was subsequently added and the reaction allowed to warm to rt and stirred for 1 h at rt. The reaction was concentrated in vacuo, and the crude oil was chromatographed (12 g SiO$_2$; elution with EtOAc/Hexane (continuous gradient from 0% to 50% over 20 min) to give the title compound (310 mg, 1.61 mmol, 94% yield) as a white solid. [M+H]$^+$=190.2; $^1$H NMR (400 MHz, CDCl$_3$) δ 7.37-7.26 (m, 5H), 5.82 (br s, 1H), 4.44 (dd, J=5.6, 2.3 Hz, 2H), 1.46-1.32 (m, 1H), 1.22-1.15 (m, 1H), 1.12-1.03 (m, 4H), 0.57 (ddd, J=7.9, 6.2, 3.7 Hz, 1H)

257C (1R,2R)—N-benzyl-2-methylcyclopropane-1-carboxamide and 257D (1S,2S)—N-benzyl-2-methylcyclopropane-1-carboxamide

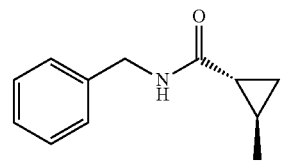

(1R,2R)

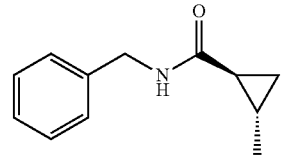

(1S,2S)

Example 257B (2.0 g, 10.6 mmol) was separated by chiral preparative HPLC (Instrument: Berger MG II (CTR-L409-PSFC1), Column: Chiralpak ID, 21×250 mm, 5 micron, Mobile Phase: 15% IPA/85% CO$_2$, Flow Conditions: 45 mL/min, 150 Bar, 40° C., Detector Wavelength: 220 nm, Injection Details: 0.25 mL of an ~200 mg/mL in IPA) to give Example 257C (0.9 g, 4.76 mmol, 45.0% yield, 99.0% ee) and Example 257D (0.9 g, 4.76 mmol, 45.0% yield, 99.0% ee) as white solids. The absolute stereochemistry of these two isomers was previously determined in the literature reference *Bioorg. Med. Chem. Lett.* 2007, 17, 1788.

257E. N-benzyl-1-((1R,2R)-2-methylcyclopropyl)methanamine

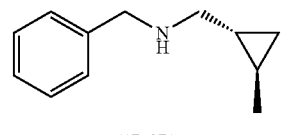

(1R,2R)

To a solution of Example 257C (0.90 g, 4.76 mmol) in THF (50 mL) was added BH$_3$.THF (23.8 mL of a 1M solution in THF, 23.8 mmol) dropwise. Upon completion of the addition (10 min), the mixture was heated at reflux for 5 h, then cooled to rt and quenched via successive addition of MeOH (2 mL) and 1N aq. HCl dropwise (10 mL). The resulting solution was stirred at 50° C. for 1 h and then partitioned between water and Et₂O (50 mL each). The aqueous layer was neutralized with 7N aq. KOH and extracted with DCM (3×10 mL). The organic layers were dried (Na₂SO₄) and concentrated in vacuo. The oily product was diluted with EtOAc and treated with HCl gas. The resulting solids were filtered, washed with hexane and dried to give the title compound (HCl salt; 0.9 g, 4.25 mmol, 89% yield) as a white solid.

[M+H]⁺=176.2; ¹H NMR (400 MHz, CD₃OD) δ 7.56-7.43 (m, 5H), 4.21 (s, 2H), 3.02-2.90 (m, 2H), 1.12 (d, J=5.5 Hz, 3H), 0.93-0.73 (m, 2H), 0.59 (dt, J=8.0, 5.0 Hz, 1H), 0.50 (dt, J=7.8, 5.3 Hz, 1H)

257F. N-benzyl-N-methyl-1-((1R,2R)-2-methylcyclopropyl)methanamine

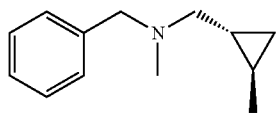

(1R,2R)

A solution of Example 257E (0.90 g, 5.13 mmol), 36% aq. formaldehyde solution (1.97 mL, 25.7 mmol), and HOAc (3 mL, 52.4 mmol) in MeOH (10 mL) was stirred at rt for 5 min. NaBH(OAc)₃ (2.177 g, 10.27 mmol) was then added. The reaction mixture was stirred at rt for 20 min and then concentrated in vacuo and the residue was partitioned between DCM (20 mL) and 1N NaOH (50 mL). The organic layer was dried (MgSO₄) and concentrated in vacuo. The residue was treated with 2.0 M HCl in ether (3 mL, 6.0 mmol) to give the title compound (HCl salt; 0.97 g, 4.30 mmol, 84% yield) as a white solid. [M+H]⁺=176.2; ¹H NMR (400 MHz, CD₃OD) δ 7.55-7.51 (m, 5H), 4.49 (dd, J=13.0, 7.3 Hz, 1H), 4.24 (br d, J=13.2 Hz, 1H), 3.22-3.14 (m, 1H), 3.02 (dt, J=13.3, 7.8 Hz, 1H), 2.85 (d, J=5.9 Hz, 3H), 1.15 (d, J=5.7 Hz, 3H), 0.94-0.79 (m, 2H), 0.66-0.53 (m, 2H)

257G. N-methyl-1-((1R,2R)-2-methylcyclopropyl)methanamine

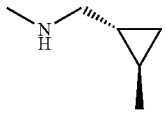

(1R,2R)

A mixture of Example 257F HCl salt (0.97 g, 4.30 mmol) and 20% Pd(OH)₂—C (0.1 g, 0.712 mmol) in EtOH (40 mL) was stirred at 60° C. under 1 atmosphere of H₂ for 2 h. The reaction was filtered and concentrated in vacuo to provide the title compound (HCl salt, 0.54 g, 3.98 mmol, 93% yield) as a white solid. ¹H NMR (400 MHz, CD₃OD) δ 2.91 (d, J=7.3 Hz, 2H), 2.71 (s, 3H), 1.12 (d, J=5.9 Hz, 3H), 0.92-0.75 (m, 2H), 0.59 (dt, J=8.4, 4.9 Hz, 1H), 0.48 (dt, J=8.0, 5.1 Hz, 1H)

Example 257

To a solution of Example 1F (30 mg, 0.054 mmol) in DCM (1 mL) was added Example 257G HCl salt (7.4 mg, 0.054 mmol) and DIPEA (0.028 mL, 0.163 mmol). The reaction mixture was stirred at rt for 2 h and then concentrated in vacuo. The residue was stirred with 1.0 M aq. NaOH (0.54 mL, 0.54 mmol) in THF (1 mL)/MeOH (0.2 mL) at rt for 18 h, then concentrated in vacuo and purified by preparative HPLC (Xbridge C18 5u OBD 19×100 mm column; detection at 220 nm; flow rate=20 mL/min; continuous gradient from 15% B to 100% B over 10 min+2 min hold time at 100% B, where A=90:10:0.1 H₂O:MeCN:TFA and B=90:10:0.1 MeCN:H₂O:TFA) to give the title compound (TFA salt; 26 mg, 0.044 mmol, 81% yield) as a yellowish oil. [M+H]⁺=472.1; ¹H NMR (400 MHz, CDCl₃) δ 8.05 (d, J=8.8 Hz, 1H), 7.66 (br t, J=9.9 Hz, 1H), 5.67-5.53 (m, 2H), 4.80 (br s, 1H), 4.18 (s, 3H), 3.28-2.91 (m, 5H), 2.86 (br s, 1H), 2.66 (s, 3H), 2.15-1.56 (m, 8H), 1.01 (br dd, J=12.1, 5.1 Hz, 3H), 0.72-0.46 (m, 2H), 0.43-0.13 (m, 2H); ¹⁹F NMR (377 MHz, CDCl₃) δ −75.88 (s, TFA). hLPA1 IC₅₀=18 nM Example 258

(1R,3S)-3-((2-methyl-6-(1-methyl-5-(((methyl(((1S,2S)-2-methylcyclopropyl)methyl) carbamoyl)oxy) methyl)-1H-1,2,3-triazol-4-yl)pyridin-3-yl)oxy)cyclohexane-1-carboxylic Acid

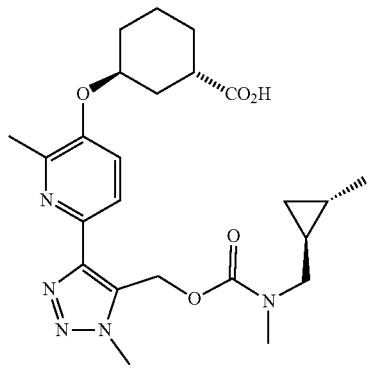

258A. N-methyl-1-((1S,2S)-2-methylcyclopropyl)methanamine

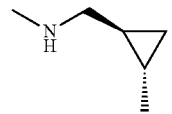

(1S,2S)

The same synthetic sequence to prepare Example 257G (from Example 257C) was used to prepare Example 258A from Example 257D (HCl salt; 0.53 g, 3.91 mmol, 91% yield) as a white solid. ¹H NMR (400 MHz, CD₃OD) δ 2.91 (d, J=7.3 Hz, 2H), 2.75-2.70 (m, 3H), 1.12 (d, J=5.7 Hz, 3H), 0.95-0.76 (m, 2H), 0.59 (dt, J=8.5, 4.9 Hz, 1H), 0.48 (dt, J=8.2, 5.1 Hz, 1H)

Example 258

To a solution of Example 1F (30 mg, 0.054 mmol) in DCM (1 mL) added Example 258A HCl salt (7.35 mg, 0.054 mmol) and DIPEA (0.028 mL, 0.163 mmol). The reaction mixture was stirred at rt for 2 h, then was concentrated in vacuo. The residue was stirred with 1.0 M aq. NaOH (0.542 mL, 0.542 mmol) in THF (1 mL)/MeOH (0.2 mL) at rt for 18 h and then purified by preparative HPLC (Xbridge C18 5u OBD 19×100 mm column; detection at 220 nm; flow rate=20 mL/min; continuous gradient from 30% B to 100% B over 10 min+2 min hold time at 100% B, where A=90: 10:0.1 H$_2$O:MeCN:TFA and B=90:10:0.1 MeCN:H$_2$O:TFA) to give the title compound (TFA salt, 27 mg, 0.046 mmol, 84% yield) as a yellowish oil. [M+H]$^+$=472.1; $^1$H NMR (400 MHz, CDCl$_3$) δ 8.04 (d, J=8.8 Hz, 1H), 7.63 (br t, J=9.6 Hz, 1H), 5.72-5.51 (m, 2H), 4.79 (br d, J=3.1 Hz, 1H), 4.18 (s, 3H), 3.29-2.80 (m, 6H), 2.65 (s, 3H), 2.11-1.98 (m, 2H), 1.97-1.56 (m, 6H), 1.01 (br dd, J=13.4, 5.1 Hz, 3H), 0.69-0.16 (m, 4H). hLPA1 IC$_{50}$=19 nM Example 259

(1S,3 S)-3-((6-(5-((((2,2-difluoropropyl)(methyl) carbamoyl)oxy)methyl)-1-methyl-1H-1,2,3-triazol-4-yl)-2-methylpyridin-3-yl)oxy)cyclohexane-1-carboxylic Acid

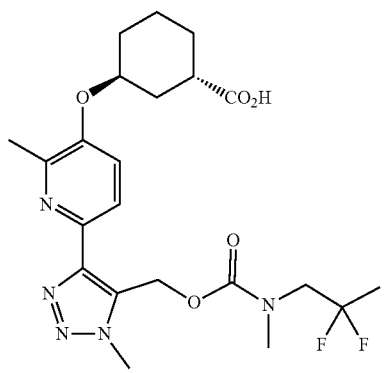 [SMILES: Cc1nc(-c2nnn(C)c2COC(=O)N(C)CC(C)(F)F)ccc1O[C@H]1CCC[C@H](C(=O)O)C1]

259A.
N-benzyl-2,2-difluoro-N-methylpropan-1-amine

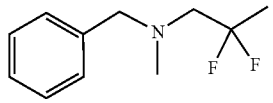

To a solution of 1-(benzyl(methyl)amino)propan-2-one (1.28 g, 7.22 mmol) and DAST (2.86 mL, 21.66 mmol) in DCM (12 ml) was added CsF (0.329 g, 2.166 mmol) portionwise, followed by a few drops of TFA at rt. The reaction mixture was stirred for 18 h at rt, then was quenched with satd aq. NaHCO$_3$. The aqueous layer was extracted with DCM (50 mL×3). The combined organic extracts were washed with water, brine, dried (MgSO$_4$) and concentrated in vacuo. The crude oily product was chromatographed (12 g SiO$_2$; elution with EtOAc/Hexane (continuous gradient from 0% to 50% over 10 min) and then further purified by preparative HPLC to give a clear oil. This material was treated with 2.0 M HCl in ether (3.61 mL, 7.22 mmol) to give the title compound (HCl salt, 334 mg, 1.417 mmol, 19.6% yield) as a white solid.

[M+H]$^+$=482.3; $^1$H NMR (400 MHz, CDCl$_3$) δ 7.68 (dt, J=3.8, 2.8 Hz, 2H), 7.55-7.38 (m, 3H), 4.56-4.18 (m, 2H), 3.65-3.15 (m, 2H), 2.94 (s, 3H), 1.80 (t, J=19.3 Hz, 3H); $^{19}$F NMR (377 MHz, CDCl$_3$) δ −87.77 to −91.55 (m, F)

259B. 2,2-difluoro-N-methylpropan-1-amine

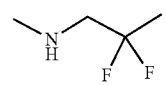

A mixture of Example 259A (HCl salt; 0.33 g, 1.40 mmol) and 20% Pd(OH)$_2$—C (0.10 g, 0.712 mmol) in EtOH (40 mL) was stirred at 60° C. under 1 atmosphere H$_2$ for 2 h. Filtration and concentration in vacuo provided 2,2-difluoro-N-methylpropan-1-amine (HCl salt, 200 mg, 1.37 mmol, 98% yield) as a white solid.

$^1$H NMR (500 MHz, CD$_3$OD) δ 3.63 (t, J=14.9 Hz, 2H), 2.81 (s, 3H), 1.79 (t, J=19.1 Hz, 3H); $^{19}$F NMR (471 MHz, CD$_3$OD) δ −98.01 (s)

Example 259

To a solution of Example 1F (30 mg, 0.054 mmol) in DCM (1 mL) added Example 259B (HCl salt; 15.78 mg, 0.108 mmol) and DIPEA (0.047 mL, 0.271 mmol). The reaction mixture was stirred at 50° C. for 18 h and then concentrated in vacuo. The residue was stirred with 1.0 M aq. NaOH (0.271 mL, 0.271 mmol) in THF (1 mL)/MeOH (0.2 mL) at rt for 18 h and then purified by preparative LC/MS (Column: XBridge C18, 19×200 mm, 5-μm particles; Mobile Phase A: 5:95 MeCN:H$_2$O with 10-mM NH$_4$OAc; Mobile Phase B: 95:5 MeCN:H$_2$O with 10-mM NH$_4$OAc; Gradient: 15-55% B over 20 min, then a 4-min hold at 100% B; Flow: 20 mL/min) to give the title compound (TFA salt; 9.3 mg, 0.015 mmol, 27.4% yield) as a yellowish oil. [M+H]$^+$=482.3; $^1$H NMR (500 MHz, DMSO-d$_6$) δ 7.85 (br d, J=7.9 Hz, 1H), 7.49 (br d, J=8.5 Hz, 1H), 5.70 (br d, J=18.3 Hz, 2H), 4.79 (br s, 1H), 4.11 (br s, 3H), 3.76-3.52 (m, 1H), 2.95-2.78 (m, 3H), 2.64 (br t, J=10.4 Hz, 1H), 2.42 (s, 3H), 2.03 (br d, J=13.7 Hz, 1H), 1.92-1.74 (m, 3H), 1.69-1.34 (m, 8H); $^{19}$F NMR (471 MHz, DMSO-d$_6$) δ −73.67 (s, TFA), −93.07 (br d, J=64.2 Hz). hLPA1 IC$_{50}$=134 nM

Example 260

(1S,3S)-3-((6-(5-((((3-fluorobutyl)(methyl)carbamoyl)oxy)methyl)-1-methyl-1H-1,2,3-triazol-4-yl)-2-methylpyridin-3-yl)oxy)cyclohexane-1-carboxylic Acid

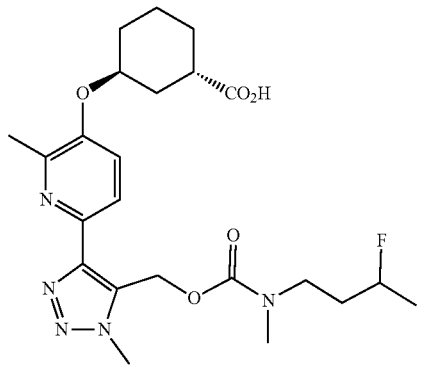 [SMILES: Cc1nc(-c2nnn(C)c2COC(=O)N(C)CCC(C)F)ccc1O[C@H]1CCC[C@H](C(=O)O)C1]

260A. 4-(benzyl(methyl)amino)butan-2-one

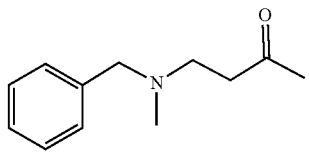

A mixture of N-methyl-1-phenylmethanamine (2.57 mL, 20 mmol), paraformaldehyde (0.901 g, 30.0 mmol) and conc. HCl (1.67 mL, 20.0 mmol) in iPrOH (2 mL) and acetone (50 mL) was stirred under reflux overnight and then concentrated in vacuo. The residue was diluted with water, basified to pH 14 with 1 N aq. NaOH solution (33.4 mL, 33.4 mmol) and extracted with ether. The organic phase was dried ($Na_2SO_4$) and concentrated in vacuo to give the title compound (4.0 g, 20.9 mmol, 94% yield), which was used directly in the next reaction. [M+H]$^+$=192.2; $^1$H NMR (400 MHz, CDCl$_3$) δ 7.34-7.22 (m, 5H), 3.49 (s, 2H), 2.74-2.67 (m, 2H), 2.66-2.58 (m, 2H), 2.19 (s, 3H), 2.14 (s, 3H)

260B. 4-(benzyl(methyl)amino)butan-2-ol

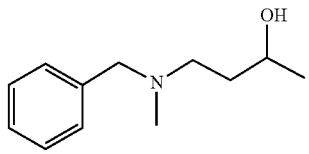

NaBH$_4$ (2.37 g, 62.7 mmol) was added to a solution of Example 260A (4.0 g, 20.9 mmol) in MeOH (90 mL) at 0° C. under N$_2$. The reaction mixture was stirred for 1 h at 0° C.; water was then added at 0° C. and the mixture was concentrated in vacuo. The residue was dissolved in EtOAc, washed with water, dried (Na$_2$SO$_4$) and concentrated in vacuo. The residue was chromatographed (SiO$_2$; elution with isocratic 10% EtOH/CHCl$_3$) to give the title compound (3.5 g, 18.11 mmol, 87% yield) as a light yellowish oil. [M+H]$^+$=194.2; $^1$H NMR (400 MHz, CDCl$_3$) δ 7.35-7.27 (m, 5H), 3.99-3.86 (m, 1H), 3.72-3.31 (m, 2H), 2.76 (td, J=12.0, 3.3 Hz, 1H), 2.59-2.48 (m, 1H), 2.22 (s, 3H), 1.72-1.61 (m, 1H), 1.54-1.45 (m, 1H), 1.15 (d, J=6.2 Hz, 3H)

260C. N-benzyl-3-fluoro-N-methylbutan-1-amine

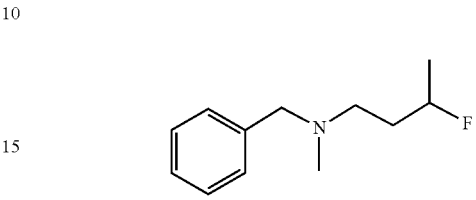

DAST (1.367 mL, 10.35 mmol) was added to a solution of Example 260B (1.0 g, 5.17 mmol) in DCM (5 mL) at −78° C. and the reaction was stirred for 5 h at −78° C. and 18 h at rt, after which it was quenched with sat. aq. NaHCO$_3$ (50 mL). The aqueous layer was extracted with DCM (20 mL×3), and the combined organic extracts were dried (MgSO$_4$) and concentrated in vacuo. The crude oil was purified by preparative HPLC (Sunfire C18 30×100 mm-regenerated column; detection at 220 nm; flow rate=40 mL/min; continuous gradient from 0% B to 100% B over 10 min+2 min hold time at 100% B, where A=90:10:0.1 H$_2$O:MeCN:TFA and B=90:10:0.1 MeCN:H$_2$O:TFA) and appropriate fractions were concentrated in vacuo to give an oil. This product was treated with 2.0 M HCl in ether (3.61 mL, 7.22 mmol) to give the title compound (HCl salt; 0.15 g, 0.647 mmol, 12.5% yield) as a white solid. [M+H]$^+$=196.2; $^1$H NMR (400 MHz, CDCl$_3$) δ 7.69-7.54 (m, 2H), 7.50-7.34 (m, 3H), 4.97-4.57 (m, 1H), 4.39-3.96 (m, 2H), 3.38-3.21 (m, 1H), 3.08-2.88 (m, 1H), 2.77-2.64 (m, 3H), 2.57-1.96 (m, 2H), 1.54-1.29 (m, 3H); $^{19}$F NMR (377 MHz, CDCl$_3$) δ −176.04 (s), −176.11 (s)

260D.

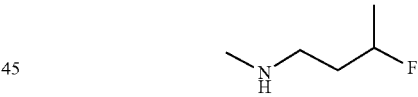

A mixture of Example 260C (HCl salt; 0.15 g, 0.647 mmol) and 20% Pd(OH)$_2$—C (0.045 g, 0.324 mmol) in EtOH (5 mL) was stirred at 60° C. under 1 atmosphere H$_2$ for 2 h. Filtration and concentration in vacuo provided the title compound (HCl salt; 0.075 g, 0.530 mmol, 82% yield) as a white solid.

$^1$H NMR (400 MHz, CDCl$_3$) δ 5.01-4.71 (m, 1H), 3.13 (br s, 2H), 2.72 (br s, 3H), 2.33-2.06 (m, 2H), 1.53-1.25 (m, 3H); $^{19}$F NMR (377 MHz, CDCl$_3$) δ −175.47 (s, 1F)

Example 260

To a solution of Example 1F (30 mg, 0.054 mmol) in DCM (1 mL) was added Example 260D (HCl salt; 15.4 mg, 0.11 mmol) and DIPEA (0.047 mL, 0.271 mmol). The reaction mixture was stirred at rt for 1 h, then was concentrated in vacuo. The residue was stirred with 1.0 M aq. NaOH (0.271 mL, 0.271 mmol) in THF (1 mL)/MeOH (0.2 mL) at rt for 18 h and then was purified by preparative HPLC (Sunfire C18 30×100 mm-regenerated column; detection at 220 nm; flow rate=40 mL/min; continuous gradient from 30% B to 100% B over 10 min+2 min hold time at 100% B, where A=90:10:0.1 H$_2$O:MeCN:TFA and B=90:10:0.1 MeCN:H$_2$O: TFA) to give the title compound (TFA salt; 24 mg, 0.040 mmol, 73.4% yield) as a yellowish oil.

[M+H]$^+$=478.1; $^1$H NMR (500 MHz, CDCl$_3$) δ 8.18 (br d, J=8.5 Hz, 1H), 8.00 (br d, J=8.0 Hz, 1H), 5.57-5.42 (m, 2H), 4.90 (br s, 1H), 4.78-4.51 (m, 1H), 4.23 (s, 3H), 3.55-3.41 (m, 2H), 3.04-2.93 (m, 3H), 2.91-2.82 (m, 1H), 2.82-2.75 (m, 4H), 2.23-2.06 (m, 1H), 2.06-1.95 (m, 1H), 1.95-1.77 (m, 6H), 1.69 (br s, 1H), 1.42-1.31 (m, 3H); $^{19}$F NMR (471 MHz, CDCl$_3$) δ −76.03 (br s, TFA), −176.02 (dd, J=135.2, 9.3 Hz, F). hLPA1 IC$_{50}$=50 nM.

| Example | Structure & Name | Analytical & Biology Data | Method |
|---|---|---|---|
| 261 | 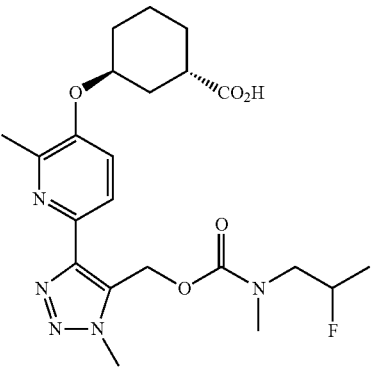 [SMILES: Cc1nc(-c2nnn(C)c2COC(=O)N(C)CC(C)F)ccc1O[C@H]1CCC[C@H](C(=O)O)C1]<br>(1S,3S)-3-((6-(5-((((2-fluoropropyl)(methyl)carbamoyl)oxy)methyl)-1-methyl-1H-1,2,3-triazol-4-yl)-2-methylpyridin-3-yl)oxy)cyclohexane-1-carboxylic acid | LCMS; [M + H]$^+$ = 464.0; $^1$H NMR (500 MHz, CDCl$_3$) δ 8.18-8.05 (m, 1H), 7.82-7.68 (m, 1H), 5.73-5.46 (m, 2H), 4.96-4.69 (m, 2H), 4.22 (br d, J = 12.9 Hz, 3H), 3.03 (br d, J = 7.2 Hz, 3H), 2.96-2.84 (m, 1H), 2.78-2.63 (m, 3H), 2.21-1.53 (m, 9H), 1.41-1.22 (m, 4H); $^{19}$F NMR (471 MHz, CDCl$_3$) δ −75.91 (br s, TFA), −175.36 to −181.71 (m, 1F) LPA1 IC$_{50}$ = 145 nM | Example 1 |
| 262 | 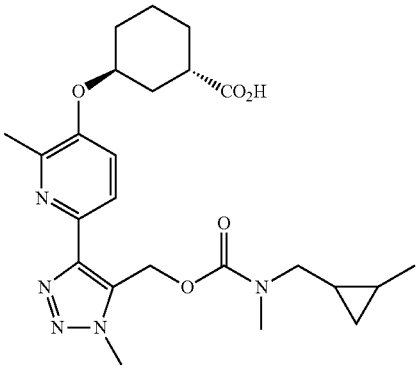<br>(1S,3S)-3-((2-methyl-6-(1-methyl-5-(((methyl((2-methylcyclopropyl)methyl)carbamoyl)oxy)methyl)-1H-1,2,3-triazol-4-yl)pyridin-3-yl)oxy)cyclohexane-1-carboxylic acid; mixture of diastereomers | LCMS; [M + H]$^+$ = 472.2; $^1$H NMR (400 MHz, CDCl$_3$) δ 8.16 (d, J = 8.8 Hz, 1H), 7.94 (br d, J = 9.0 Hz, 1H), 5.57-5.40 (m, 2H), 4.87 (br s, 1H), 4.21 (d, J = 6.4 Hz, 3H), 3.27-3.06 (m, 2H), 3.04-2.94 (m, 3H), 2.86 (br d, J = 3.5 Hz, 1H), 2.76 (d, J = 4.6 Hz, 3H), 2.20-1.56 (m, 8H), 1.09-1.01 (m, 3H), 0.73-0.23 (m, 4H) LPA1 IC$_{50}$ = 29 nM | |
| 263 | 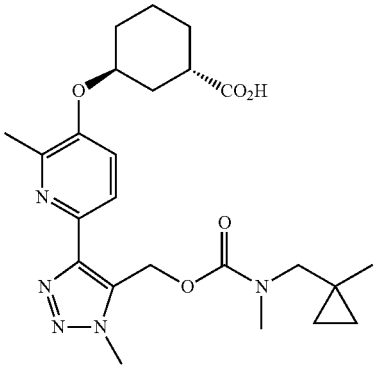 | LCMS; [M + H]$^+$ = 474.3; $^1$H NMR (500 MHz, DMSO-d$_6$) δ 7.83 (br d, J = 8.5 Hz, 1H), 7.46 (br d, J = 8.9 Hz, 1H), 5.64 (br s, 2H), 4.77 (br s, 1H), 4.09 (s, 3H), 3.18-2.95 (m, 2H), 2.90-2.72 (m, 3H), 2.63 (br d, J = 10.4 Hz, 1H), 2.40 (s, 3H), 2.05-1.40 (m, 8H), 0.97-0.66 (m, 3H), 0.43-0.07 (m, 4H) LPA1 IC$_{50}$ = 76 nM | |

| Example | Structure & Name | Analytical & Biology Data | Method |
|---|---|---|---|
| 264 | 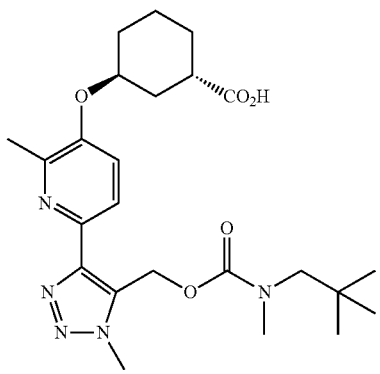 [SMILES: Cc1nc(-c2nnn(C)c2COC(=O)N(C)CC(C)(C)C)ccc1O[C@H]1CCC[C@H](C(=O)O)C1]<br>(1S,3S)-3-((2-methyl-6-(1-methyl-5-(((methyl((1-methylcyclopropyl)methyl)carbamoyl)oxy)methyl)-1H-1,2,3-triazol-4-yl)pyridin-3-yl)oxy)cyclohexane-1-carboxylic acid | LCMS; [M + H]$^+$ = 474.4; $^1$H NMR (500 MHz, DMSO-d$_6$) δ 7.84 (br s, 1H), 7.48 (br s, 1H), 5.63 (br d, J = 17.1 Hz, 2H), 4.79 (br s, 1H), 4.11 (s, 3H), 3.57 (br dd, J = 12.1, 6.0 Hz, 2H), 3.26 (dd, J = 10.4, 5.8 Hz, 1H), 3.20-3.11 (m, 1H), 3.06 (br s, 1H), 2.93 (br s, 1H), 2.90-2.76 (m, 3H), 2.63 (br s, 1H), 2.09-1.43 (m, 8H), 0.92-0.64 (m, 9H) LPA1 IC$_{50}$ = 76 nM | |

(1S,3S)-3-((2-methyl-6-(1-methyl-5-(((methyl(neopentyl)carbamoyl)oxy)methyl)-1H-1,2,3-triazol-4-yl)pyridin-3-yl)oxy)cyclohexane-1-carboxylic acid

Example 265

(1S,3S)-3-((6-(5-((((cyclobutylmethyl)(methyl)carbamoyl)oxy)methyl)-1-methyl-1H-1,2,3-triazol-4-yl)-2-(hydroxymethyl)pyridin-3-yl)oxy)cyclohexane-1-carboxylic Acid

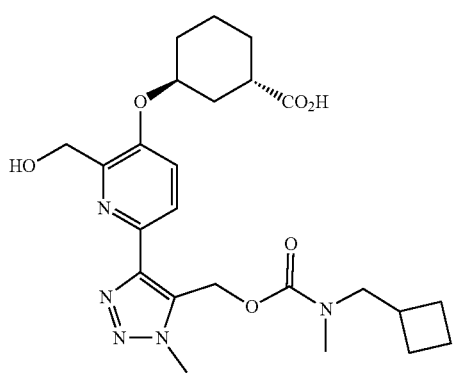 [SMILES: CN(CC1CCC1)C(=O)OCc1c(-c2ccc(O[C@H]3CCC[C@H](C(=O)O)C3)c(CO)n2)nnn1C]

265A. 3,6-dibromo-2-(((tetrahydro-2H-pyran-2-yl)oxy)methyl)pyridine

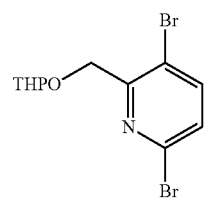

A solution of ethyl 3,6-dibromopicolinate (3.0 g, 9.71 mmol) in THF (50 mL) was stirred at 0° C., then LiBH$_4$ (7.28 mL of a 2M solution in THF, 14.57 mmol) was added portionwise over 5-10 min. Vigorous gas evolution ensued. The reaction mixture was stirred at rt overnight, then was quenched with 1N aq. HCl slowly, adjusting the pH to ~7. The mixture was partitioned between EtOAc and water (50 mL each) and extracted with EtOAc (3×). The combined organic extracts were dried (MgSO$_4$) and concentrated in vacuo. The residue was chromatographed (24 g SiO$_2$) to provide 3,6-dibromopyridin-2-yl)methanol (1.89 g, 7.08 mmol, 72.9% yield).

To a solution of (3,6-dibromopyridin-2-yl)methanol (2.46 g, 9.22 mmol) in CH$_2$Cl$_2$ (12 mL) was added 3,4-dihydro-2H-pyran (2.52 mL, 27.6 mmol) and pyridinium p-toluenesulfonate (0.116 g, 0.461 mmol). The reaction was stirred overnight at rt, then quenched with water and extracted with DCM, washed with water, brine, dried (MgSO$_4$) and concentrated in vacuo. The residue was chromatographed (24 g SiO$_2$, continuous gradient from 0-100% EtOAc/hexanes over 20 min) to give the title compound (3.4 g, 9.40 mmol, 100% yield). 1H NMR (500 MHz, CDCl$_3$) δ 7.72 (d, J=8.53 Hz, 1H), 7.32 (d, J=8.25 Hz, 1H), 4.94 (d, J=11.83 Hz, 1H), 4.88 (t, J=3.30 Hz, 1H), 4.69 (d, J=11.83 Hz, 1H), 3.94-4.09 (m, 1H), 3.49-3.70 (m, 1H), 1.49-2.00 (m, 8H)

265B. 3-(5-Bromo-6-(((tetrahydro-2H-pyran-2-yl)oxy)methyl)pyridin-2-yl)prop-2-yn-1-ol

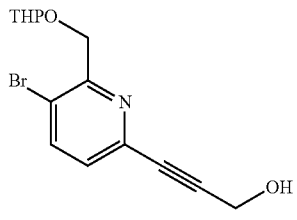

To a solution of Example 265A (3.4 g, 9.69 mmol) and prop-2-yn-1-ol (0.677 mL, 11.62 mmol) in MeCN (30 mL) was added Et$_3$N (6.00 mL). The solution was degassed with N$_2$ for 5 mins, after which Pd(Ph$_3$)$_2$Cl$_2$ (0.340 g, 0.484 mmol) and CuI (0.092 g, 0.484 mmol) were added. The reaction mixture was degassed with N$_2$ for 5 min, then was stirred at rt for 16 h under N$_2$. LCMS indicated at this time indicated that the reaction was complete. The reaction mixture was filtered through a pad of Celite and washed with EtOAc (4×30 mL). The filtrate was concentrated in vacuo and the residue was chromatographed (80 g SiO$_2$, elution by continuous gradient from 0% to 100% EtOAc/Hex over 80 min at 35 mL/min) to give the title compound (2.90 g, 8.89 mmol, 92% yield). $^1$H NMR (500 MHz, CDCl$_3$) δ 7.86 (d, J=8.25 Hz, 1H), 7.26 (d, J=8.25 Hz, 1H), 4.98 (d, J=11.55 Hz, 1H), 4.88 (t, J=3.30 Hz, 1H), 4.69 (d, J=11.55 Hz, 1H), 4.53 (d, J=6.05 Hz, 2H), 3.99 (dt, J=2.75, 10.45 Hz, 1H), 3.53-3.65 (m, 1H), 1.47-1.95 (m, 6H)

265C. (4-(5-Bromo-6-(((tetrahydro-2H-pyran-2-yl)oxy)methyl)pyridin-2-yl)-1-((trimethylsilyl)methyl)-1H-1,2,3-triazol-5-yl)methanol

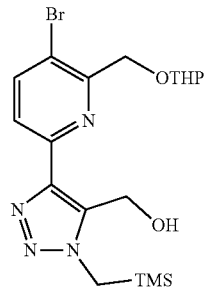

To a solution of Example 265B (2.9 g, 8.89 mmol) in dioxane (40 mL) was added CuI (0.068 g, 0.356 mmol), chloro(pentamethylcyclopentadienyl)bis(triphenylphosphine)Ruthenium(II) (0.283 g, 0.356 mmol). The resulting suspension was degassed with N$_2$ for 3 min, after which trimethylsilylmethyl azide (1.404 g, 9.78 mmol) was added. The mixture was degassed with N$_2$ for another 5 min, then was heated in an oil bath at 50° C. for 20 h under N$_2$, then was cooled to rt. The mixture was filtered through Celite; the filtrate was concentrated in vacuo, and chromatographed (120 g SiO$_2$; elution with continuous gradient from 0 to 60% EtOAc/Hex over 65 min at 120 mL/min) to give the title compound (2.30 g, 5.05 mmol, 56.8% yield). $^1$H NMR (500 MHz, CDCl$_3$) δ 8.10 (d, J=8.25 Hz, 1H), 7.97 (d, J=8.53 Hz, 1H), 6.41 (t, J=7.57 Hz, 1H), 5.05 (d, J=14.30 Hz, 1H), 4.86 (t, J=3.30 Hz, 1H), 4.80 (dd, J=1.38, 7.43 Hz, 2H), 4.76 (d, J=14.03 Hz, 1H), 3.86-3.97 (m, 1H), 3.83 (s, 2H), 3.53-3.64 (m, 1H), 1.51-2.02 (m, 8H), 0.18-0.27 (m, 9H)

265D. (4-(5-Bromo-6-(((tetrahydro-2H-pyran-2-yl)oxy)methyl)pyridin-2-yl)-1-methyl-1H-1,2,3-triazol-5-yl)methyl (cyclobutylmethyl)(methyl)carbamate

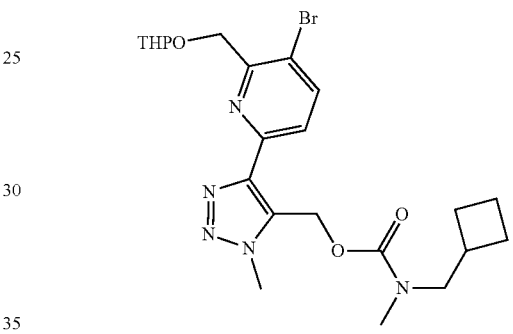

TBAF (5.56 mL of a 1M solution in THF, 5.56 mmol) was added dropwise to a solution of Example 265C (2.3 g, 5.05 mmol) in THF (15 mL) and the reaction mixture was stirred at rt overnight, then was quenched with satd aq. NaHCO$_3$ (50 mL) and stirred for 20 min at rt. The mixture was extracted with EtOAc (2×100 mL); the combined organic extracts were dried with Na$_2$SO$_4$, filtered and concentrated in vacuo. The crude product was chromatographed (40 g SiO$_2$; continuous gradient from 0% to 100% EtOAc over 30 min, at 20 mL/min) to give (4-(5-bromo-6-(((tetrahydro-2H-pyran-2-yl)oxy)methyl)pyridin-2-yl)-1-methyl-1H-1,2,3-triazol-5-yl)methanol (1.69 g, 4.41 mmol, 87% yield). To a solution of this material (0.41 g, 1.07 mmol) and pyridine (0.433 mL, 5.35 mmol) in DCM (5 mL) was added 4-nitrophenyl chloroformate (0.431 g, 2.140 mmol) in DCM (2 mL). The reaction mixture was stirred at rt overnight, then (cyclobutylmethyl)methylamine (0.318 g, 3.21 mmol) was added, followed by Et$_3$N (1.49 mL, 10.7 mmol). The reaction was stirred at rt for 3 h, then was partitioned between DCM and sat'd aq. NaHCO$_3$. The organic layer was washed with brine and concentrated in vacuo. The residue was chromatographed (40 g SiO$_2$; continuous gradient from 0% to 100% EtOAc over 30 min, at 20 ml/min) to give the title compound (0.52 g, 0.921 mmol, 86% yield). $^1$H NMR (500 MHz, CDCl$_3$) δ 8.05 (d, J=8.3 Hz, 1H), 7.96 (d, J=8.3 Hz, 1H), 5.83 (br d, J=16.0 Hz, 2H), 5.01 (d, J=11.8 Hz, 1H), 4.93 (t, J=3.2 Hz, 1H), 4.77 (d, J=12.1 Hz, 1H), 4.10-4.24 (m, 3H), 3.90-4.07 (m, 1H), 3.53-3.70 (m, 1H), 3.10-3.42 (m, 2H), 2.70-2.98 (m, 3H), 1.46-2.05 (m, 13H)

265E. (4-(5-hydroxy-6-(((tetrahydro-2H-pyran-2-yl)oxy)methyl)pyridin-2-yl)-1-methyl-1H-1,2,3-triazol-5-yl)methyl (cyclobutylmethyl)(methyl)carbamate

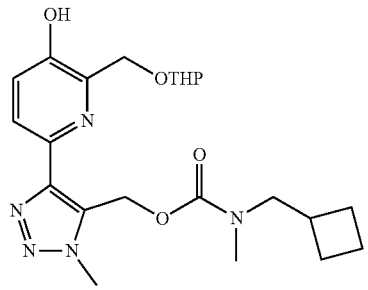

To a degassed solution of Example 265D (510 mg, 1.00 mmol), 4,4,4',4',5,5,5',5'-octamethyl-2,2'-bi(1,3,2-dioxaborolane) (509 mg, 2.01 mmol) and KOAc (295 mg, 3.01 mmol) in THF (4013 µl) was added PdCl₂(dppf) (36.7 mg, 0.050 mmol). The vial was purged with N₂, sealed and stirred at 80° C. overnight, then was cooled to rt. The mixture was diluted with EtOAc and filtered; the filtrate was concentrated in vacuo, re-dissolved in THF (5 mL) and this crude pinacol boronate product was used in the next step without further purification. To the solution of this crude pinacol boronate product in THF (5 mL) was added aq. NaOH (2.01 mL of a 1 M solution, 2.01 mmol), followed by aq. H₂O₂ (0.830 mL, 10.03 mmol). The reaction mixture was stirred at rt for 2 h, after which satd. aq. Na₂S₂O₃ (1 mL) was added; the mixture was stirred at rt for 10 min, then was extracted with EtOAc (3×10 mL). The combined organic extracts were dried (Na₂SO₄) and concentrated in vacuo. The residue was chromatographed (24 g SiO₂; continuous gradient from 0 to 100% EtOAc/Hex over 20 min at 20 mL/min) to give the title compound (379 mg, 0.851 mmol, 85% yield). ¹H NMR (500 MHz, CDCl₃) δ 8.22 (br s, 1H), 8.07 (d, J=8.53 Hz, 1H), 7.30 (d, J=8.53 Hz, 1H), 5.73 (br d, J=9.08 Hz, 2H), 5.14 (d, J=12.93 Hz, 1H), 4.92 (d, J=12.65 Hz, 1H), 4.77-4.86 (m, 1H), 4.15 (br d, J=5.23 Hz, 3H), 3.96-4.06 (m, 1H), 3.60-3.73 (m, 1H), 3.34 (br d, J=7.43 Hz, 1H), 3.18 (br d, J=6.88 Hz, 1H), 2.74-2.99 (m, 3H), 1.60-1.98 (m, 13H)

265E. Isopropyl (1S,3 S)-3-((6-(5-(((((cyclobutylmethyl)(methyl)carbamoyl)oxy)methyl)-1-methyl-1H-1,2,3-triazol-4-yl)-2-(hydroxymethyl)pyridin-3-yl)oxy)cyclohexane-1-carboxylate

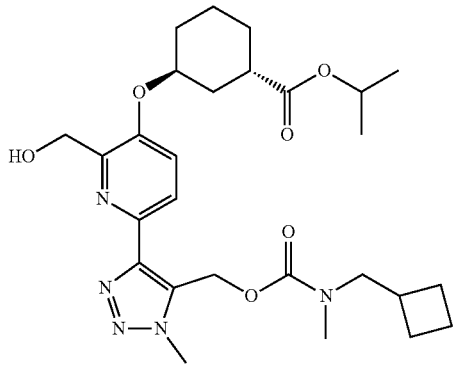 [SMILES: CC(C)OC(=O)[C@H]1CCC[C@H](Oc2ccc(-c3nnn(C)c3COC(=O)N(C)CC3CCC3)nc2CO)C1]

To a solution of Example 265D (275 mg, 0.617 mmol), Example 1F (610 mg, 1.54 mmol) in t-AmOH (5 mL) was added Cs₂CO₃ (603 mg, 1.85 mmol); the reaction was stirred at 65° C. for 24 h. Then more Example 1F (244 mg, 0.617 mmol) and Cs₂CO₃ (241 mg, 0.741 mmol) were added to the reaction, which was heated at 65° C. for another 24 h, then cooled to rt. Water (5 mL) was added and the mixture was stirred at rt for 10 min, then was extracted with EtOAc (3×10 mL). The combined organic extracts were dried (Na₂SO₄) and concentrated in vacuo. The residue was chromatographed (24 g SiO₂, continuous gradient from 0 to 100% EtOAc/Hex over 18 min at 15 mL/min) to give (1S,3S)-isopropyl 3-((6-(5-(((((cyclobutylmethyl) (methyl)carbamoyl)oxy)methyl)-1-methyl-1H-1,2,3-triazol-4-yl)-2-(((tetrahydro-2H-pyran-2-yl)oxy)methyl)pyridin-3-yl)oxy)cyclohexanecarboxylate (290 mg, 0.402 mmol, 65.1% yield).

A mixture of this THP ether (330 mg, 0.468 mmol) and PPTS (23.5 mg, 0.094 mmol) in MeOH (4 mL) was heated at 60° C. overnight, then was cooled to rt. Volatiles were removed in vacuo and the residue was partitioned between DCM and satd aq. NaHCO₃. The organic extract was dried (Na₂SO₄) was concentrated in vacuo. The crude product was chromatographed (24 g SiO₂; continuous gradient from 0 to 100% EtOAc/Hex over 20 min at 20 mL/min and then at 100% EtOAc for 10 min) to give the title compound (274 mg, 0.491 mmol, 100% yield). ¹H NMR (500 MHz, CDCl₃) δ 8.13 (br dd, J=3.71, 8.12 Hz, 1H), 7.32 (d, J=8.53 Hz, 1H), 5.70 (s, 2H), 4.99-5.14 (m, 1H), 4.78-4.90 (m, 1H), 4.75 (br s, 1H), 4.24 (s, 3H), 3.20-3.34 (m, 2H), 2.82-2.96 (m, 3H), 2.67-2.79 (m, 1H), 2.33-2.63 (m, 1H), 1.46-2.15 (m, 16H), 1.07-1.32 (m, 6H)

Example 265

To a solution of 265E (17 mg, 0.032 mmol) in THF (0.5 mL) was added 4 drops of MeOH at rt, after which LiOH.H₂O (0.080 mL, 0.321 mmol) was added. The reaction mixture was stirred at rt overnight, then was purified by preparative HPLC ((PHENOMENEX®, Axia 5µ C18 30×100 mm column; detection at 220 nm; flow rate=40 mL/min; continuous gradient from 0% B to 100% B over 10 min+2 min hold time at 100% B, where A=90:10:0.1 H₂O:MeOH:TFA and B=90:10:0.1 MeOH:H₂O:TFA)) to give the title compound (15 mg, 0.024 mmol, 75% yield). ¹H NMR (500 MHz, CDCl₃) δ 8.19 (br d, J=8.25 Hz, 1H), 7.65 (br d, J=8.53 Hz, 1H), 5.51-5.66 (m, 2H), 4.90-5.12 (m, 2H), 4.84 (br s, 1H), 4.24 (s, 3H), 3.29 (br dd, J=7.15, 16.78 Hz, 2H), 2.88 (br s, 4H), 2.38-2.68 (m, 1H), 1.49-2.22 (m, 15H). LCMS, [M+H]⁺=488.3. hLPA1 IC₅₀=68 nM

Example 266

(1S,3S)-3-((6-(5-(((((cyclobutylmethyl)(methyl)carbamoyl)oxy)methyl)-1-methyl-1H-1,2,3-triazol-4-yl)-2-(fluoromethyl)pyridin-3-yl)oxy)cyclohexane-1-carboxylic Acid

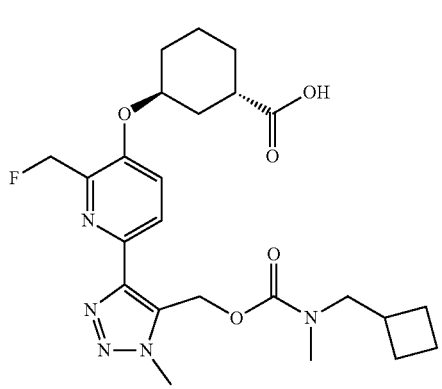 [SMILES: CN(CC1CCC1)C(=O)OCc1c(-c2ccc(O[C@H]3CCC[C@H](C(=O)O)C3)c(CF)n2)nnn1C]

To a solution of Example 265E (50 mg, 0.094 mmol) in DCM (1 mL) at 0° C., was added bis(2-methoxyethyl)aminosulfur trifluoride (0.061 mL, 0.283 mmol) dropwise under $N_2$. The reaction mixture was gradually warmed to rt and stirred at rt for 2 h, then was slowly quenched by addition of satd aq. $NaHCO_3$ followed by DCM. The organic layer was dried using a stream of $N_2$ and the crude product (1S,3S)-isopropyl 3-((6-(5-(((((cyclobutylmethyl)(methyl)carbamoyl)oxy)methyl)-1-methyl-1H-1,2,3-triazol-4-yl)-2-(fluoromethyl)pyridin-3-yl)oxy) cyclohexanecarboxylate) was used in the next step without further purification. To a solution of the crude isopropyl ester (50 mg, 0.094 mmol) in THF (0.5 mL) was added 4 drops of MeOH at rt, followed by aq. LiOH (0.235 mL, 0.941 mmol). The reaction mixture was stirred at rt overnight, then was filtered.

The crude product was purified by preparative HPLC (PHENOMENEX®, Axia 5 μC18 30×100 mm column; detection at 220 nm; flow rate=40 mL/min; continuous gradient from 0% B to 100% B over 10 min+2 min hold time at 100% B, where A=90:10:0.1 $H_2O$:MeOH:TFA and B=90:10:0.1 MeOH:$H_2O$:TFA to give the title compound (25 mg, 0.039 mmol, 41.8% yield). $^1H$ NMR (500 MHz, $CDCl_3$) δ 8.19 (br d, J=8.53 Hz, 1H), 7.62-7.71 (m, 1H), 5.49-5.77 (m, 4H), 4.84 (br s, 1H), 4.22 (br d, J=4.40 Hz, 3H), 3.16-3.44 (m, 2H), 2.80-2.98 (m, 4H), 1.26-2.68 (m, 16H). LCMS, [M+H]$^+$=490.3. hLPA1 $IC_{50}$=27 nM.

Example 267

(1S,3S)-3-((6-(5-(((((cyclobutylmethyl)(methyl)carbamoyl)oxy)methyl)-1-methyl-1H-1,2,3-triazol-4-yl)-2-(difluoromethyl)pyridin-3-yl)oxy)cyclohexane-1-carboxylic Acid

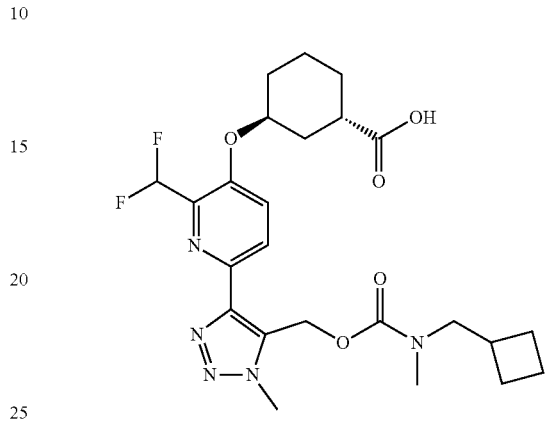

To a mixture of Example 265E (80 mg, 0.151 mmol) and 75 mg of Celite in DCM (1.5 mL) was added pyridinium dichromate (73.9 mg, 0.196 mmol). The reaction mixture was stirred at rt for 90 min, after which more pyridinium dichromate (73.9 mg; 0.196 mmol) was added, and the reaction was stirred overnight at rt. EtOAc was added and the mixture was filtered through Celite. The filtrate was concentrated in vacuo, and the crude product was chromatographed (4 g $SiO_2$, continuous gradient from 0 to 100% EtOAc/Hex over 12 min at 8 mL/min) to give (1S,3S)-isopropyl 3-((6-(5-(((((cyclobutylmethyl)(methyl)carbamoyl)oxy) methyl)-1-methyl-1H-1,2,3-triazol-4-yl)-2-formylpyridin-3-yl)oxy)cyclohexanecarboxylate (15 mg, 0.028 mmol, 18% yield). To a RT solution of the above aldehyde (15 mg, 0.028 mmol) in DCM (0.3 mL) was added bis(2-methoxyethyl)aminosulfur trifluoride (0.032 mL, 0.148 mmol) in one portion. The mixture was stirred at rt for 2 h; volatiles were removed via an $N_2$ stream, and the crude difluoromethyl product (1S,3S)-isopropyl 3-((6-(5-(((((cyclobutylmethyl)(methyl) carbamoyl)oxy)methyl)-1-methyl-1H-1,2,3-triazol-4-yl)-2-(difluoromethyl)pyridin-3-yl)oxy) cyclohexanecarboxylate was directly in the next step without further purification. To a solution of this isopropyl ester (13 mg, 0.024 mmol) in THF (0.5 mL) was added aq. LiOH (0.118 mL, 0.473 mmol) and 4 drops of MeOH. The reaction mixture was stirred at rt for 2 days, filtered and the crude product was purified by preparative HPLC, (PHENOMENEX®, Axia 5μ C18 30×100 mm column; detection at 220 nm; flow rate=40 mL/min; continuous gradient from 0% B to 100% B over 10 min+2 min hold time at 100% B, where A=90:10:0.1 $H_2O$:MeOH:TFA and B=90:10:0.1 MeOH:$H_2O$:TFA) to give the title compound (2 mg, 3.19 μmol, 13.5% yield). $^1H$ NMR (400 MHz, $CDCl_3$) δ 8.28 (d, J=8.80 Hz, 1H), 7.37-7.65 (m, 1H), 6.62-7.05 (m, 1H), 5.71 (br s, 2H), 4.80 (br d, J=2.64 Hz, 1H), 4.17 (br d, J=7.92 Hz, 3H), 3.09-3.45 (m, 2H), 2.72-3.02 (m, 4H), 1.36-2.65 (m, 15H). LCMS, [M+H]$^+$=508.2. hLPA $IC_{50}$=30 nM Alternatively, the title compound can also be synthesized as follows.

267A. (3,6-Dibromopyridin-2-yl)methanol

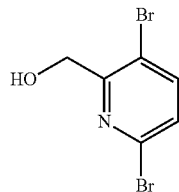

To a 0° C. solution of ethyl 3,6-dibromopicolinate (5.0 g, 16.2 mmol) in THF (30 mL) was added LiBH$_4$ in THF (12.14 mL of a 2 M solution, 24.28 mmol) portionwise over 10 min. Vigorous gas evolution ensued. After 1 h at rt, the reaction mixture was slowly quenched with satd aq., stirred for 10 min, then was extracted with EtOAc. The pH of the aqueous phase was adjusted to 7-8 by addition of 1N aq. HCl, then was extracted again with EtOAc. The combined organic extracts were dried (Na$_2$SO$_4$) and concentrated in vacuo. The crude material was chromatographed (40 g SiO$_2$; EtOAc/Hexane; continuous gradient from 0% to 100% EtOAc over 30 min, at 20 mL/min) to give the title compound (3.0 g, 11.24 mmol, 69.4% yield), 1H NMR (500 MHz, CDCl$_3$) δ 7.72 (d, J=7.98 Hz, 1H), 7.35 (d, J=7.98 Hz, 1H), 4.77 (d, J=4.95 Hz, 2H), 3.78 (t, J=5.09 Hz, 1H)

267B. 3,6-Dibromo-2-(difluoromethyl)pyridine

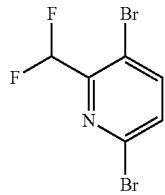 [SMILES: FC(F)c1nc(Br)ccc1Br]

Anhydrous DMSO (4.04 mL, 56.9 mmol) was added dropwise to a solution of (COCl)$_2$ (2.277 mL, 26.0 mmol) in DCM (25 mL) at −78° C. After stirring at −78° C. for 15 min, a solution of Example 267A (2.17 g, 8.13 mmol) in DCM (25 mL) was added dropwise. After stirring for 15 min at −78° C., TEA (10.2 mL, 73.2 mmol) was added dropwise. The reaction was allowed to warm to rt over 1 h (the reaction mixture became cloudy); more DCM (50 mL) was added and the mixture was stirred for 2 h at rt. The reaction was quenched with brine (20 mL) and extracted with DCM (2×50 mL). The combined organic extracts were dried (Na$_2$SO$_4$) and concentrated in vacuo. The crude oil was chromatographed (80 g SiO$_2$; elution with EtOAc/Hexane (continuous gradient from 0% to 60% over 20 min) to give 3,6-dibromopicolinaldehyde (1.92 g, 7.25 mmol, 89% yield) as a light yellowish oil. To a solution of the 3,6-dibromopicolin-aldehyde (1.5 g, 5.66 mmol) in DCM (6 mL) at rt was added bis(2-methoxyethyl)aminosulfur trifluoride (1.46 mL, 6.79 mmol) in one portion. The mixture was stirred at rt for 1 h, then was carefully quenched with sat'd aq. NaHCO$_3$, adjusted to pH=7-8 and extracted with DCM (2×). The combined organic extracts were concentrated in vacuo. The residue was chromatographed (EtOAc/Hexane; continuous gradient from 0% to 100% EtOAc over 20 min, at 15 mL/min) to give the title compound (1.48 g, 5.16 mmol, 91% yield). $^1$H NMR (500 MHz, CDCl$_3$) δ 7.83 (d, J=8.53 Hz, 1H), 7.51 (d, J=8.53 Hz, 1H), 6.65-7.00 (m, 1H)

Example 267B can then be used as the starting material for the synthesis of Example 267. The synthetic sequence is analogous to that used for the synthesis of Example 1 (i.e. regioselective Sonogashira coupling of the less hindered bromide of Example 267B with propargyl alcohol, followed by Ru-mediated [3+2] cycloaddition with trimethylsilyl azide to form the 1,2,3-triazole, etc.).

Example 267

1H NMR (400 MHz, CDCl$_3$) δ 8.28 (d, J=8.80 Hz, 1H), 7.37-7.65 (m, 1H), 6.62-7.05 (m, 1H), 5.71 (br s, 2H), 4.80 (br d, J=2.64 Hz, 1H), 4.17 (br d, J=7.92 Hz, 3H), 3.09-3.45 (m, 2H), 2.72-3.02 (m, 4H), 1.36-2.65 (m, 15H). LCMS, [M+H]$^+$=508.2 hLPA1 IC$_{50}$=30 nM

Example 268

(1S,3 S)-3-((6-(5-((((cyclobutylmethyl)(methyl)carbamoyl)oxy)methyl)-1-methyl-1H-1,2,3-triazol-4-yl)-2-(methoxymethyl)pyridin-3-yl)oxy)cyclohexane-1-carboxylic Acid

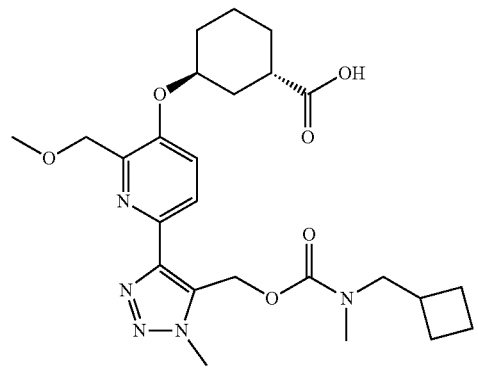 [SMILES: COCc1nc(-c2nnn(C)c2COC(=O)N(C)CC2CCC2)ccc1O[C@H]1CCC[C@H](C(=O)O)C1]

268A. 3,6-Dibromo-2-(methoxymethyl)pyridine

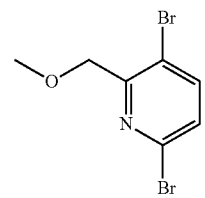

A solution of (3,6-dibromopyridin-2-yl)methanol (1.67 g, 6.26 mmol) in anhydrous THF (29 mL) was slowly added to a stirring suspension of NaH (0.30 g, 7.51 mmol) in anhydrous THF (5 ml) at 0-5° C. under N$_2$. After gas evolution stopped, MeI (0.587 mL, 9.38 mmol) was added slowly dropwise and the reaction was warmed to rt over 1 h. Brine (10 mL) was added slowly to the reaction, which was then extracted with EtOAc (2×50 mL). The combined organic extracts were dried (Na$_2$SO$_4$) and concentrated in vacuo. The crude material was chromatographed (24 g SiO$_2$; EtOAc/Hexane; continuous gradient from 0% to 100%

EtOAc over 30 min, at 10 mL/min) to give the title compound (1.70 g, 6.05 mmol, 97% yield). $^1$H NMR (500 MHz, CDCl$_3$) δ 7.72 (d, J=8.25 Hz, 1H), 7.34 (d, J=8.25 Hz, 1H), 4.66 (s, 2H), 3.52 (s, 3H).

Example 268B was then used for the synthesis of Example 268. The synthetic sequence is analogous to that used for the synthesis of Example 1 (i.e. regioselective Sonogashira coupling of the less hindered bromide of Example 268B with propargyl alcohol, followed by Ru-mediated [3+2] cycloaddition with trimethylsilyl azide to form the 1,2,3-triazole, etc.).

Example 268

$^1$H NMR (500 MHz, DMSO-d$_6$) δ 7.95 (br d, J=8.24 Hz, 1H), 7.60 (br d, J=8.85 Hz, 1H), 5.63 (br d, J=12.82 Hz, 2H), 4.81 (br s, 1H), 4.53 (br s, 2H), 4.10 (br s, 3H), 3.03-3.27 (m, 2H), 2.68-2.82 (m, 3H), 2.59 (br d, J=10.38 Hz, 1H), 2.56 (s, 3H), 1.32-2.36 (m, 16H); LCMS, [M+H]$^+$=502.3; hLPA1 IC$_{50}$=103 nM

Example 269

(1S,3S)-3-((6-(5-(((((cyclobutylmethyl)(methyl)carbamoyl)oxy)methyl)-1-methyl-1H-1,2,3-triazol-4-yl)-2-(trifluoromethyl)pyridin-3-yl)oxy)cyclohexane-1-carboxylic Acid

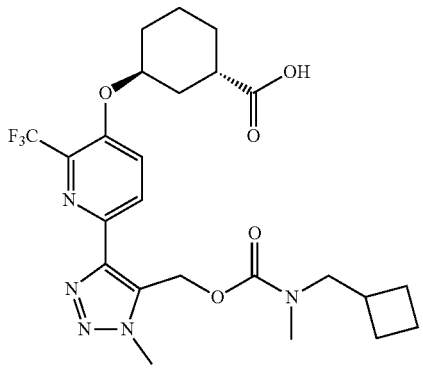 [SMILES: CN(CC1CCC1)C(=O)OCc1c(-c2ccc(O[C@H]3CCC[C@H](C(=O)O)C3)c(C(F)(F)F)n2)nnn1C]

Example 269 was synthesized using commercially available 3,6-dibromo-2-(trifluoromethyl) pyridine, using the same synthetic sequence as for the preparation of Example 1.

Example 269

$^1$H NMR (500 MHz, CDCl$_3$) δ 8.39 (br d, J=8.80 Hz, 1H), 7.54 (d, J=9.08 Hz, 1H), 5.71 (br s, 1H), 4.86 (br s, 1H), 4.21 (br d, J=13.76 Hz, 3H), 3.12-3.40 (m, 2H), 2.89-2.99 (m, 1H), 2.74-2.89 (m, 3H), 2.35-2.66 (m, 1H), 2.17-2.37 (m, 1H), 1.42-2.29 (m, 14H)

LCMS, [M+H]$^+$=526.2; hLPA1 IC$_{50}$=10 nM.

Example 270

(1S,3S)-3-((2-cyano-6-(1-methyl-5-(((methyl(propyl)carbamoyl)oxy)methyl)-1H-1,2,3-triazol-4-yl)pyridin-3-yl)oxy)cyclohexane-1-carboxylic acid

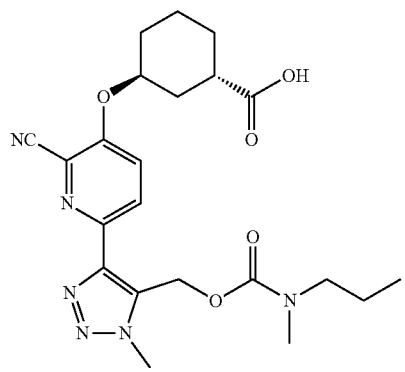 [SMILES: CCCN(C)C(=O)OCc1c(-c2ccc(O[C@H]3CCC[C@H](C(=O)O)C3)c(C#N)n2)nnn1C]

270A. 3,6-Dibromopicolinonitrile

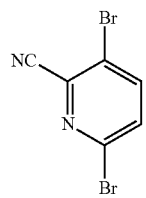

To a suspension of 3,6-dibromopicolinic acid (0.5 g, 1.780 mmol), NH$_4$Cl (0.381 g, 7.12 mmol) and Et$_3$N (1.985 ml, 14.24 mmol) in THF (7.12 mL) was added 1-propanephosphonic anhydride (4.24 mL, 7.12 mmol) dropwise at 0° C. The reaction was slowly warmed to rt, then was heated to 80° C. for 48 h, then was cooled to rt. The mixture was partitioned between water and EtOAc (10 mL each) and extracted with EA (2×10 mL). The combined organic extracts were dried (Na$_2$SO$_4$) and concentrated in vacuo. The residue was chromatographed (40 g SiO$_2$; EtOAc/Hexane; continuous gradient from 0% to 100% EtOAc over 30 min, at 20 mL/min) to give the title compound (0.32 g, 1.22 mmol, 68.6% yield) as a white solid. $^1$H NMR (500 MHz, CDCl$_3$) δ 7.88 (d, J=8.53 Hz, 1H), 7.60 (d, J=8.53 Hz, 1H).

Example 270 was synthesized using Example 270A, using the same synthetic sequence as for the preparation of Example 1 (except that N-methyl, N-propylamine was used to generate the carbamate of Example 270 rather than the N-methyl, N-cyclobutylmethylamine that was used in Example 1).

Example 270

$^1$H NMR (500 MHz, DMSO-d$_6$) δ 8.30 (d, J=9.16 Hz, 1H), 7.98 (d, J=9.16 Hz, 1H), 5.54 (br d, J=19.53 Hz, 2H), 5.01 (br s, 1H), 4.14 (s, 3H), 3.00-3.25 (m, 2H), 2.77 (br d, J=9.16 Hz, 3H), 2.63 (br t, J=10.22 Hz, 1H), 1.15-2.21 (m, 10H), 0.58-0.96 (m, 3H) LCMS, [M+H]$^+$=457.1; hLPA1 IC$_{50}$=11 nM

Example 271

(1S,3 S)-3-((6-(5-((((cyclobutylmethyl)(methyl)carbamoyl)oxy)methyl)-1-methyl-1H-1,2,3-triazol-4-yl)-2-(2-hydroxypropan-2-yl)pyridin-3-yl)oxy)cyclohexane-1-carboxylic Acid

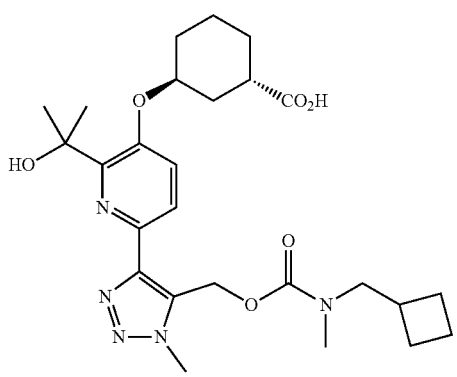 [SMILES: CN(CC1CCC1)C(=O)OCc1c(-c2ccc(O[C@H]3CCC[C@H](C(=O)O)C3)c(C(C)(C)O)n2)nnn1C]

271A. Ethyl 3-bromo-6-(1-methyl-5-(((tetrahydro-2H-pyran-2-yl)oxy)methyl)-1H-1,2,3-triazol-4-yl)picolinate

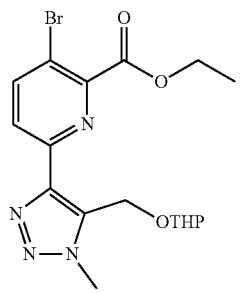

This compound was synthesized from commercially available ethyl 3,6-dibromopicolinate, using the same synthetic sequence as for Example 265. $^1$H NMR (500 MHz, CDCl$_3$) δ 8.20 (d, J=8.53 Hz, 1H), 8.05 (d, J=8.53 Hz, 1H), 5.26-5.40 (m, 2H), 4.76 (t, J=3.44 Hz, 1H), 4.50 (q, J=7.15 Hz, 2H), 4.19 (s, 3H), 3.83 (ddd, J=3.03, 8.05, 11.21 Hz, 1H), 3.46-3.62 (m, 1H), 1.51-1.88 (m, 6H), 1.48 (t, J=7.15 Hz, 3H)

271B. Ethyl 3-hydroxy-6-(1-methyl-5-(((tetrahydro-2H-pyran-2-yl)oxy)methyl)-1H-1,2,3-triazol-4-yl)picolinate

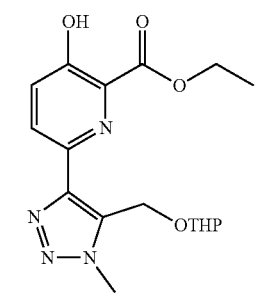

To a degassed solution of Example 271A (433 mg, 1.02 mmol), 4,4,4',4',5,5,5',5'-octamethyl-2,2'-bi(1,3,2-dioxaborolane) (517 mg, 2.036 mmol) and KOAc (300 mg, 3.05 mmol) in THF (4.07 mL) was added PdCl$_2$(dppf) (37.2 mg, 0.051 mmol). The vial was purged with N$_2$, sealed and stirred at 80° C. overnight, then was cooled to rt. The mixture was filtered and the filtrate (crude pinacol boronate) was used directly in the next step without further purification To a solution of the above crude boronate product (397 mg, 1.018 mmol) in EtOAc (7 mL) and THF (2 mL) was added H$_2$O$_2$ (0.946 mL, 10.2 mmol). The reaction was stirred at rt for 3 h, then was extracted with EtOAc. To the aqueous phase was added satd aq. Na$_2$S$_2$O$_3$ (3 mL) and 2 drops of 1N aq. NaOH; the mixture was stirred for 5 min and extracted again with EtOAc (2×5 mL). The combined organic extracts were concentrated in vacuo. The residue was chromatographed (40 g SiO$_2$; EtOAc/Hexane-continuous gradient from 0% to 100% EtOAc over 30 min, at 20 mL/min) to give the title compound (328 mg, 88% yield). $^1$H NMR (500 MHz, CDCl$_3$) δ 10.74 (s, 1H), 8.35 (d, J=8.80 Hz, 1H), 7.46 (d, J=8.80 Hz, 1H), 5.22-5.57 (m, 2H), 4.81 (t, J=3.58 Hz, 1H), 4.52 (dq, J=2.06, 7.11 Hz, 2H), 4.19 (s, 3H), 3.93 (br s, 1H), 3.84 (ddd, J=2.61, 8.32, 11.07 Hz, 1H), 3.43-3.60 (m, 1H), 1.48-2.06 (m, 9H)

271C. 2-(2-hydroxypropan-2-yl)-6-(1-methyl-5-(((tetrahydro-2H-pyran-2-yl)oxy)methyl)-1H-1,2,3-triazol-4-yl)pyridin-3-ol

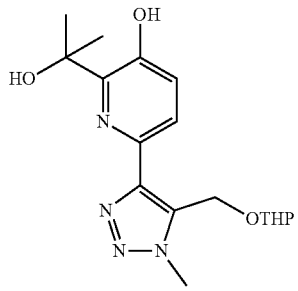

To a solution of Example 271B (0.3 g, 0.828 mmol) in THF (7 mL) was added dropwise CH₃MgBr (1.95 mL of a 3.5 M solution in THF, 6.62 mmol) at 0° C. The resulted mixture was allowed to warm to rt and stirred at rt for 3 h. Satd aq. NH₄Cl was then carefully added to quench the reaction, which was extracted with EtOAc. The aqueous layer was carefully adjusted to pH 6 by using 1 N aq. HCl, then extracted again with EtOAc (2×). The combined organic extracts were dried (Na₂SO₄) and concentrated in vacuo. The crude product was chromatographed (24 g SiO₂; EtOAc/Hexane-continuous gradient from 0% to 100% EtOAc over 30 min, at 10 mL/min) to give the title compound (110 mg, 0.316 mmol, 38.1% yield).

Example 271

Example 271C was converted to Example 271 by a similar sequence used to convert Example 1C to Example 1.
¹H NMR (500 MHz, DMSO-d₆) δ 7.96 (d, J=8.54 Hz, 1H), 7.59 (br d, J=8.54 Hz, 1H), 5.49 (s, 2H), 4.85 (br s, 1H), 4.13 (br s, 2H), 3.79 (br d, J=16.78 Hz, 1H), 3.07-3.26 (m, 2H), 2.88 (s, 1H), 2.68-2.75 (m, 2H), 2.55 (s, 3H), 1.19-2.16 (m, 20H). LCMS, [M+H]⁺=516.3.
hLPA1 IC₅₀=225 nM Example 272

(1S,3 S)-3-((2-Methoxy-6-(1-methyl-5-(((methyl (propyl)carbamoyl)oxy)methyl)-1H-1,2,3-triazol-4-yl)pyridin-3-yl)oxy)cyclohexane-1-carboxylic Acid

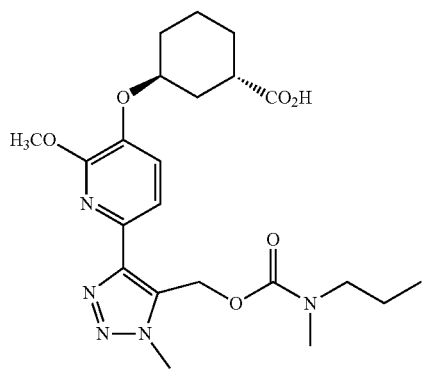 [SMILES: CCCN(C)C(=O)OCc1c(-c2ccc(O[C@H]3CCC[C@H](C(=O)O)C3)c(OC)n2)nnn1C]

Example 272 was synthesized from 3,6-dibromo-2-(methoxy)pyridine using the same synthetic sequence as for the preparation of Example 1 from 3,6-dibromopyridine. LCMS, [M+H]⁺=462.1; ¹H NMR (500 MHz, CDCl₃) δ 7.81 (d, J=8.0 Hz, 1H), 7.33-7.30 (m, 1H), 5.79 (br s, 2H), 4.72-4.67 (m, 1H), 4.18 (s, 3H), 4.04 (s, 3H), 3.25 (br t, J=7.3 Hz, 1H), 3.18-3.07 (m, 1H), 3.06-2.95 (m, 1H), 2.92 (s, 1.5H), 2.83 (s, 1.5H), 2.16-2.07 (m, 2H), 2.05-1.83 (m, 4H), 1.79-1.68 (m, 2H), 1.68-1.52 (m, 2H), 1.50-1.33 (m, 1H), 0.95-0.85 (m, 1.5H), 0.76 (br t, J=7.2 Hz, 1.5H) hLPA1 IC₅₀=4 nM The following examples were synthesized according to the procedures described above.

| Example | Structure & Name | Analytical & Biology Data | Method |
|---|---|---|---|
| 273 | ![structure] (1S,3S)-3-((6-(5-((((cyclopropylmethyl)(methyl)carbamoyl)oxy)methyl)-1-methyl-1H-1,2,3-triazol-4-yl)-2-(trifluoromethyl)pyridin-3-yl)oxy)cyclohexane-1-carboxylic acid | LCMS, [M + H]+ = 512.4 1H NMR (500 MHz, DMSO-d₆) δ 8.33 (br d, J = 8.85 Hz, 1H), 7.87-8.11 (m, 1H), 5.62 (br d, J = 17.09 Hz, 2H), 5.06 (br s, 1H), 4.18 (s, 2H), 2.69-3.38 (m, 6H), 2.11 (br d, J = 13.43 Hz, 1H), 1.78-2.02 (m, 3H), 1.44-1.76 (m, 3H), 1.14-1.35 (m, 1H), 1.05 (d, J = 6.10 Hz, 1H), 0.71-0.97 (m, 1H), 0.47 (br s, 1H), 0.30 (br s, 2H), 0.13-0.26 (m, 1H) hLPA1 IC₅₀ = 7 nM. | Example 269 |

| Example | Structure & Name | Analytical & Biology Data | Method |
|---------|------------------|---------------------------|--------|
| 274 | 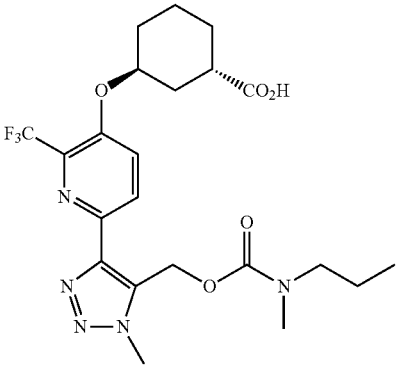 [SMILES: CCCN(C)C(=O)OCc1c(-c2ccc(O[C@H]3CCC[C@H](C(=O)O)C3)c(C(F)(F)F)n2)nnn1C]<br>(1S,3S)-3-((6-(1-methyl-5-(((methyl(propyl)carbamoyl)oxy)methyl)-1H-1,2,3-triazol-4-yl)-2-(trifluoromethyl)pyridin-3-yl)oxy)cyclohexane-1-carboxylic acid | 1H NMR (500 MHz, DMSO-d6) δ 8.27 (br d, J = 8.54 Hz, 1H), 7.95 (br d, J = 8.85 Hz, 1H), 5.57 (br d, J = 13.43 Hz, 2H), 5.01 (br s, 1H), 4.13 (s, 2H), 2.97-3.21 (m, 2H), 2.93 (q, J = 7.22 Hz, 2H), 2.65-2.79 (m, 3H), 1.21-2.13 (m, 8H), 1.17 (t, J = 7.17 Hz, 3H), 0.50-0.85 (m, 2H)<br>LCMS, [M + H]+ = 499.9<br>hLPA1 IC$_{50}$ = 28 nM. | Example 269 |
| 275 | 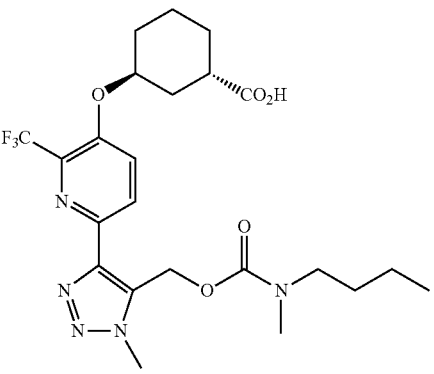 [SMILES: CCCCN(C)C(=O)OCc1c(-c2ccc(O[C@H]3CCC[C@H](C(=O)O)C3)c(C(F)(F)F)n2)nnn1C]<br>(1S,3S)-3-((6-(5-(((butyl(methyl)carbamoyl)oxy)methyl)-1-methyl-1H-1,2,3-triazol-4-yl)-2-(trifluoromethyl)pyridin-3-yl)oxy)cyclohexane-1-carboxylic acid | 1H NMR (500 MHz, DMSO-d6) δ 8.27 (br d, J = 8.85 Hz, 1H), 7.94 (br d, J = 8.85 Hz, 1H), 5.55 (br d, J = 12.82 Hz, 2H), 5.00 (br s, 1H), 4.13 (br s, 3H), 2.99-3.23 (m, 2H), 2.92 (q, J = 7.32 Hz, 1H), 2.74 (br s, 1H), 2.70 (br s, 2H), 1.33-2.13 (m, 10H), 1.08-1.27 (m, 3H), 0.91-1.00 (m, 1H), 0.85 (br s, 1H), 0.61 (br s, 2H)<br>LCMS, [M + H]+ = 514.1<br>hLPA1 IC$_{50}$ = 5.6 nM. | Example 269 |
| 276 | 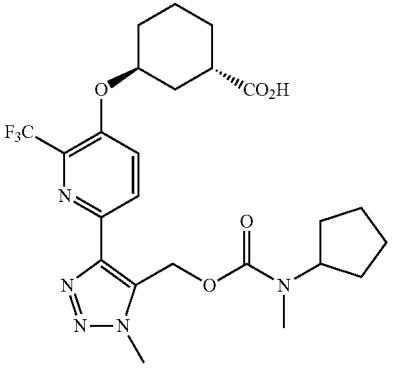 [SMILES: CN(C(=O)OCc1c(-c2ccc(O[C@H]3CCC[C@H](C(=O)O)C3)c(C(F)(F)F)n2)nnn1C)C1CCCC1]<br>(1S,3S)-3-((6-(5-(((cyclopentyl(methyl)carbamoyl)oxy)methyl)-1-methyl-1H-1,2,3-triazol-4-yl)-2-(trifluoromethyl)pyridin-3-yl)oxy)cyclohexane-1-carboxylic acid | 1H NMR (500 MHz, DMSO-d6) δ 8.27 (d, J = 8.84 Hz, 1H), 7.96 (d, J = 9.00 Hz, 1H), 5.56 (br s, 2H), 5.01 (br s, 1H), 4.13 (s, 3H), 3.65 (m, 1H), 2.54-2.70 (m, 4H), 1.73-2.14 (m, 4H), 1.25-1.71 (m, 12H)<br>LCMS, [M + H]+ = 526.5<br>hLPA1 IC$_{50}$ = 15 nM. | Example 269 |

| Example | Structure & Name | Analytical & Biology Data | Method |
|---|---|---|---|
| 277 | (1S,3S)-3-((2-(difluoromethyl)-6-(1-methyl-5-(((methyl(propyl)carbamoyl)oxy)methyl)-1H-1,2,3-triazol-4-yl)pyridin-3-yl)oxy)cyclohexane-1-carboxylic acid | 1H NMR (500 MHz, DMSO-d6) δ 8.16 (br d, J = 8.24 Hz, 1H), 7.82 (br d, J = 8.85 Hz, 1H), 7.01-7.34 (m, 1H), 5.62 (br d, J = 13.12 Hz, 2H), 4.94 (br s, 1H), 4.13 (s, 3H), 2.95-3.22 (m, 2H), 2.75 (br d, J = 16.78 Hz, 3H), 2.66 (br t, J = 10.68 Hz, 1H), 2.06 (br d, J = 13.43 Hz, 1H), 1.39-1.95 (m, 8H), 1.18-1.34 (m, 2H), 0.52-0.88 (m, 3H)<br>LCMS, [M + H]+ = 482.2<br>hLPA1 IC$_{50}$ = 35 nM | Example 267 |
| 278 | (1S,3S)-3-((6-(5-(((butyl(methyl)carbamoyl)oxy)methyl)-1-methyl-1H-1,2,3-triazol-4-yl)-2-(difluoromethyl)pyridin-3-yl)oxy)cyclohexane-1-carboxylic acid | 1H NMR (500 MHz, DMSO-d6) δ 8.16 (d, J = 8.85 Hz, 1H), 7.82 (br d, J = 8.85 Hz, 1H), 6.87-7.22 (m, 1H), 5.62 (br d, J = 10.99 Hz, 2H), 4.93 (br s, 1H), 4.13 (br s, 3H), 2.96-3.29 (m, 2H), 2.61-2.87 (m, 4H), 0.52-2.18 (m, 15H)<br>LCMS, [M + H]$^+$ = 496.2<br>hLPA1 IC$_{50}$ = 22 nM | Example 267 |
| 279 | (1S,3S)-3-((6-(5-((((cyclopropylmethyl)(methyl)carbamoyl)oxy)methyl)-1-methyl-1H-1,2,3-triazol-4-yl)-2-(difluoromethyl)pyridin-3-yl)oxy)cyclohexane-1-carboxylic acid | 1H NMR (500 MHz, DMSO-d6) δ 8.16 (d, J = 8.75 Hz, 1H), 7.80 (d, J = 8.92 Hz, 1H), 6.84-7.23 (m, 1H), 5.63 (s, 2H), 4.92 (br s, 1H), 4.13 (s, 3H), 2.83 (s, 2H), 2.61-2.74 (m, 1H), 2.55 (s, 3H), 2.01-2.17 (m, 1H), 1.40-1.95 (m, 7H), 1.25 (s, 1H), −0.16-0.98 (m, 5H)<br>LCMS, [M + H]+ = 494.2<br>hLPA1 IC$_{50}$ = 21 nM | Example 267 |

| Example | Structure & Name | Analytical & Biology Data | Method |
|---|---|---|---|
| 280 | 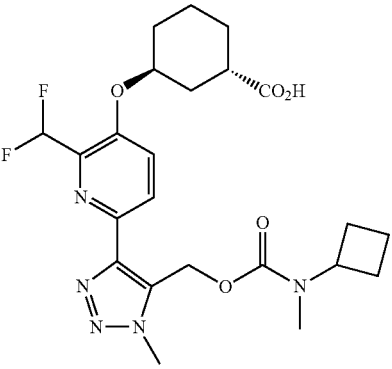 [SMILES: CN(C(=O)OCc1c(-c2ccc(O[C@H]3CCC[C@H](C(=O)O)C3)c(C(F)F)n2)nnn1C)C1CCC1]<br>(1S,3S)-3-((6-(5-(((cyclobutyl(methyl)carbamoyl)oxy)methyl)-1-methyl-1H-1,2,3-triazol-4-yl)-2-(difluoromethyl)pyridin-3-yl)oxy)cyclohexane-1-carboxylic acid | 1H NMR (500 MHz, DMSO-d6) δ 8.16 (d, J = 8.75 Hz, 1H), 7.80 (d, J = 8.92 Hz, 1H), 6.89-7.22 (m, 1H), 5.62 (s, 2H), 4.92 (br s, 1H), 2.74 (s, 3H), 2.60-2.72 (m, 1H), 2.55 (s, 3H), 1.79 (d, J = 123.19 Hz, 15H)<br>LCMS, [M + H]+ = 494.2<br>hLPA1 IC$_{50}$ = 22 nM | Example 267 |
| 281 | 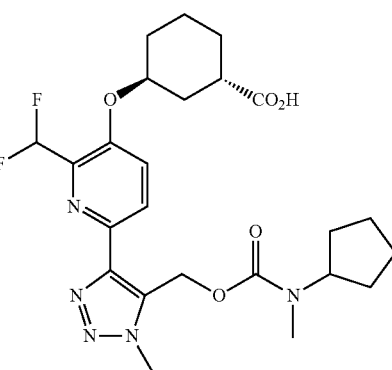<br>(1S,3S)-3-((6-(5-(((cyclopentyl(methyl)carbamoyl)oxy)methyl)-1-methyl-1H-1,2,3-triazol-4-yl)-2-(difluoromethyl)pyridin-3-yl)oxy)cyclohexane-1-carboxylic acid | 1H NMR (500 MHz, DMSO-d6) δ 8.16 (d, J = 8.85 Hz, 1H), 7.82 (br d, J = 8.85 Hz, 1H), 6.88-7.19 (m, 1H), 5.62 (br d, J = 10.99 Hz, 2H), 4.93 (br s, 1H), 4.02-4.24 (m, 3H), 2.97-3.34 (m, 2H), 2.60-2.85 (m, 4H), −0.24-2.48 (m, 16H)<br>LCMS, [M + H]+ = 508.2<br>hLPA1 IC$_{50}$ = 35 nM | Example 267 |
| 282 | 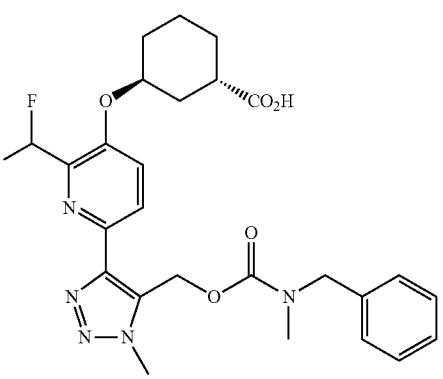<br>(1S,3S)-3-((6-(5-(((benzyl(methyl)carbamoyl)oxy)methyl)-1-methyl-1H-1,2,3-triazol-4-yl)-2-(difluoromethyl)pyridin-3-yl)oxy)cyclohexane-1-carboxylic acid | 1H NMR (500 MHz, DMSO-d6) δ 8.16 (br d, J = 8.75 Hz, 1H), 7.80 (br d, J = 8.84 Hz, 1H), 6.85-7.47 (m, 6H), 5.69 (br s, 2H), 4.91 (br s, 1H), 4.37 (br s, 2H), 4.07 (br d, J = 14.22 Hz, 3H), 2.61-2.89 (m, 4H), 1.42-2.16 (m, 8H)<br>LCMS, [M + H]+ = 530.9<br>hLPA1 IC$_{50}$ = 19 nM | Example 267 |

| Example | Structure & Name | Analytical & Biology Data | Method |
|---|---|---|---|
| 283 | (1S,3S)-3-((2-(methoxymethyl)-6-(1-methyl-5-(((methyl(propyl)carbamoyl)oxy)methyl)-1H-1,2,3-triazol-4-yl)pyridin-3-yl)oxy)cyclohexane-1-carboxylic acid | 1H NMR (500 MHz, DMSO-d6) δ 7.97 (br d, J = 7.02 Hz, 1H), 7.61 (br d, J = 8.54 Hz, 1H), 5.66 (br d, J = 8.54 Hz, 2H), 4.84 (br s, 2H), 4.54 (br d, J = 2.75 Hz, 2H), 4.11 (s, 3H), 3.34 (s, 1H), 2.97-3.22 (m, 2H), 2.71-2.86 (m, 3H), 2.62-2.70 (m, 1H), 1.23-2.13 (m, 10H), 1.01 (d, J = 6.41 Hz, 1H), 0.56-0.87 (m, 3H) LCMS, [M + H]+ = 476.2 hLPA1 IC$_{50}$ = 475 nM | Example 268 |
| 284 | (1S,3S)-3-((6-(5-4(butyl(methyl)carbamoyl)oxy)methyl)-1-methyl-1H-1,2,3-triazol-4-yl)-2-(methoxymethyl)pyridin-3-yl)oxy)cyclohexane-1-carboxylic acid | 1H NMR (500 MHz, DMSO-d6) δ 7.98 (br d, J = 8.85 Hz, 1H), 7.61 (br d, J = 8.85 Hz, 1H), 5.66 (br d, J = 8.85 Hz, 2H), 4.84 (br s, 1H), 4.54 (d, J = 2.44 Hz, 2H), 4.11 (s, 3H), 3.00-3.28 (m, 2H), 2.61-2.85 (m, 4H), 0.57-2.16 (m, 18H) LCMS, [M + H]+ = 490.3 hLPA1 IC$_{50}$ = 48 nM | Example 268 |
| 285 | (1S,3S)-3-((6-(5-((((cyclopropylmethyl)(methyl)carbamoyl)oxy)methyl)-1-methyl-1H-1,2,3-triazol-4-yl)-2-(methoxymethyl)pyridin-3-yl)oxy)cyclohexane-1-carboxylic acid | 1H NMR (500 MHz, DMSO-d6) δ 7.98 (br d, J = 8.54 Hz, 1H), 7.60 (br d, J = 8.54 Hz, 1H), 5.66 (br d, J = 12.82 Hz, 2H), 4.82 (br s, 1H), 4.42-4.65 (m, 2H), 4.12 (s, 3H), 2.92-3.22 (m, 2H), 2.61-2.89 (m, 4H), 0.64-2.16 (m, 14H), −0.11-0.53 (m, 4H) LCMS, [M + H]+ = 488.3 hLPA1 IC$_{50}$ = 1008 nM | Example 268 |

| Example | Structure & Name | Analytical & Biology Data | Method |
|---|---|---|---|
| 286 | 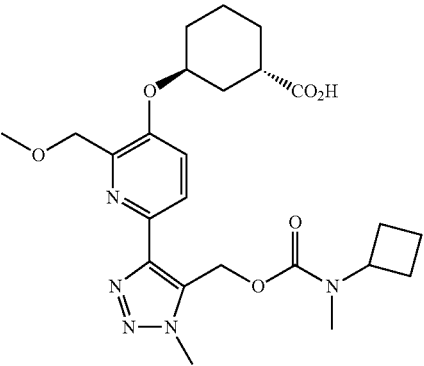 [SMILES: COCc1nc(-c2nnn(C)c2COC(=O)N(C)C2CCC2)ccc1O[C@H]1CCC[C@H](C(=O)O)C1]<br>(1S,3S)-3-((6-(5-(((cyclobutyl(methyl)carbamoyl)oxy)methyl)-1-methyl-1H-1,2,3-triazol-4-yl)-2-(methoxymethyl) pyridin-3-yl)oxy)cyclohexane-1-carboxylic acid | 1H NMR (500 MHz, DMSO-d6) δ 7.96 (br d, J = 8.54 Hz, 1H), 7.60 (br d, J = 8.85 Hz, 1H), 5.63 (s, 2H), 4.82 (br s, 1H), 4.52 (br s, 2H), 4.09 (s, 3H), 3.32 (s, 3H), 2.59-2.81 (m, 4H), 1.26-2.24 (m, 15H)<br>LCMS, [M + H]+ = 488.3<br>hLPA1 IC$_{50}$ = 92 nM | Example 268 |
| 287 | 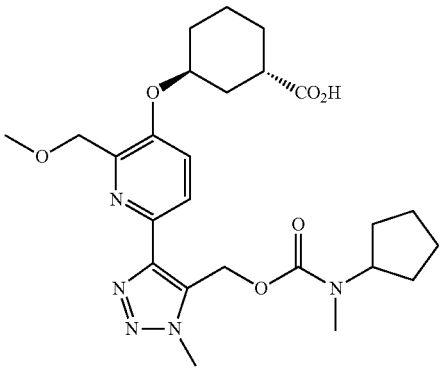 [SMILES: COCc1nc(-c2nnn(C)c2COC(=O)N(C)C2CCCC2)ccc1O[C@H]1CCC[C@H](C(=O)O)C1]<br>(1S,3S)-3-((6-(5-((((cyclopentyl(methyl)carbamoyl)oxy)methyl)-1-methyl-1H-1,2,3-triazol-4-yl)-2-(methoxymethyl)pyridin-3-yl)oxy)cyclohexane-1-carboxylic acid | 1H NMR (500 MHz, DMSO-d6) δ 7.98 (d, J = 8.54 Hz, 1H), 7.61 (d, J = 8.85 Hz, 1H), 5.66 (s, 2H), 4.84 (br s, 1H), 4.54 (d, J = 2.75 Hz, 2H), 4.11 (s, 3H), 3.91 (s, 1H), 2.73-2.92 (m, 1H), 2.65 (br s, 3H), 2.56 (s, 1H), 1.24-2.12 (m, 17H)<br>LCMS, [M + H]+ = 502.3<br>hLPA1 IC$_{50}$ = 118 nM | Example 268 |
| 288 | 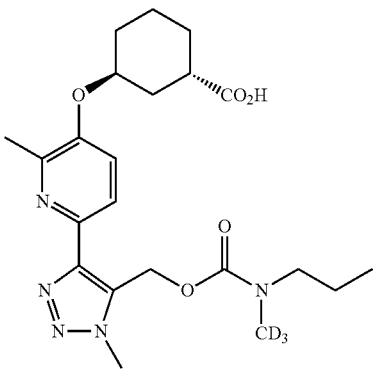 [SMILES: [2H]C([2H])([2H])N(CCC)C(=O)OCc1c(-c2ccc(O[C@H]3CCC[C@H](C(=O)O)C3)c(C)n2)nnn1C]<br>(1S,3S)-3-((2-methyl-6-(1-methyl-5-(((((methyl-d3)(propyl)carbamoyl)oxy)methyl)-1H-1,2,3-triazol-4-yl)pyridin-3-yl)oxy)cyclohexane-1-carboxylic acid | 1H NMR (500 MHz, CDCl$_3$) δ 8.12 (br d, J = 8.53 Hz, 1H), 7.95 (br s, 1H), 5.39-5.59 (m, 2H), 4.87 (br s, 1H), 4.20 (br s, 3H), 3.23 (br s, 2H), 2.84 (br s, 1H), 2.68-2.79 (m, 3H), 1.46-2.19 (m, 10H), 0.88 (br s, 3H)<br>LCMS, [M + H]+ = 449.1<br>hLPA1 IC$_{50}$ = 29 nM | Example 93 |

-continued

| Example | Structure & Name | Analytical & Biology Data | Method |
|---|---|---|---|
| 289 | 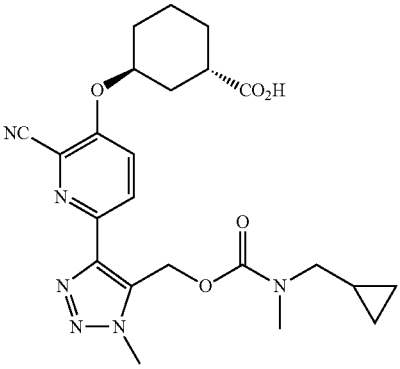 [SMILES: CN(CC1CC1)C(=O)OCc1c(-c2ccc(O[C@H]3CCC[C@H](C(=O)O)C3)c(C#N)n2)nnn1C]<br>(1S,3S)-3-((2-cyano-6-(5-((((cyclopropylmethyl)(methyl)carbamoyl)oxy)methyl)-1-methyl-1H-1,2,3-triazol-4-yl)pyridin-3-yl)oxy)cyclohexane-1-carboxylic acid | 1H NMR (500 MHz, DMSO-d6) δ 8.29 (d, J = 8.85 Hz, 1H), 7.98 (br d, J = 9.16 Hz, 1H), 5.45-5.65 (m, 2H), 4.99 (br s, 1H), 4.12 (s, 3H), 2.91-3.14 (m, 2H), 2.83 (br s, 3H), 2.56-2.69 (m, 1H), 1.41-2.04 (m, 8H), 0.71-1.03 (m, 1H), −0.08-0.50 (m, 4H)<br>LCMS, [M + H]+ = 469.1<br>hLPA1 IC$_{50}$ = 40 nM | Example 270 |
| 290 | 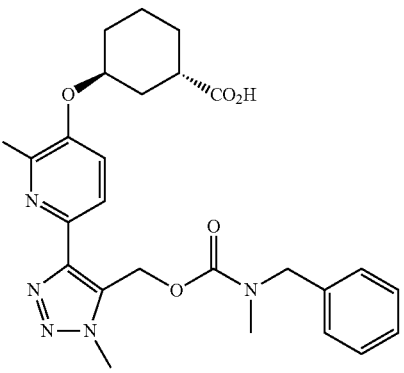<br>(1S,3S)-3-((6-(5-(((benzyl(methyl)carbamoyl)oxy)methyl)-1-methyl-1H-1,2,3-triazol-4-yl)-2-cyanopyridin-3-yl)oxy)cyclohexane-1-carboxylic acid | $^1$H NMR (500 MHz, DMSO-d$_6$) δ 8.30 (br s, 1H), 7.92 (br d, J = 9.77 Hz, 1H), 6.91-7.38 (m, 5H), 5.47-5.72 (m, 2H), 5.00 (br s, 1H), 4.25-4.50 (m, 3H), 3.94-4.20 (m, 2H), 2.60-2.88 (m, 4H), 1.37-2.18 (m, 8H)<br>LCMS, [M + H]+ = 505.3<br>hLPA1 IC$_{50}$ = 2 nM | Example 270 |
| 291 | 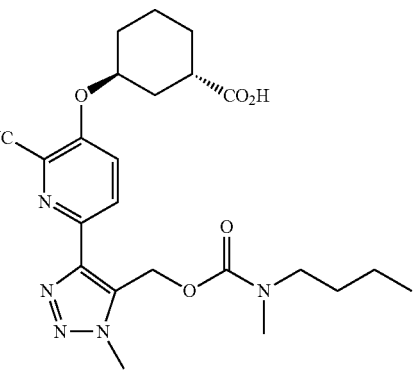<br>(1S,3S)-3-((6-(5-(((butyl(methyl)carbamoyl)oxy)methyl)-1-methyl-1H-1,2,3-triazol-4-yl)-2-cyanopyridin-3-yl)oxy)cyclohexane-1-carboxylic acid | 1H NMR (500 MHz, DMSO-d6) δ 8.30 (br d, J = 8.85 Hz, 1H), 7.98 (d, J = 9.16 Hz, 1H), 5.40-5.65 (m, 2H), 5.00 (br s, 1H), 4.13 (br s, 3H), 2.99-3.29 (m, 2H), 2.70-2.83 (m, 3H), 2.62 (br t, J = 9.92 Hz, 1H), 0.59-2.17 (m, 15H)<br>LCMS, [M + H]+ = 471.3<br>hLPA1 IC$_{50}$ = 15 nM | Example 270 |

-continued

| Example | Structure & Name | Analytical & Biology Data | Method |
|---|---|---|---|
| 292 | 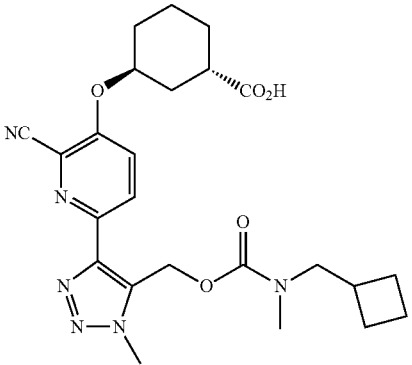 [SMILES: CN(CC1CCC1)C(=O)OCc1c(-c2ccc(O[C@H]3CCC[C@H](C(=O)O)C3)c(C#N)n2)nnn1C]<br>(1S,3S)-3-((2-cyano-6-(5-(((((cyclobutylmethyl)(methyl)carbamoyl)oxy)methyl)-1-methyl-1H-1,2,3-triazol-4-yl)pyridin-3-yl)oxy)cyclohexane-1-carboxylic acid | 1H NMR (500 MHz, DMSO-d6) δ 8.24-8.45 (m, 1H), 8.30 (br d, J = 8.67 Hz, 1H), 7.97 (br d, J = 9.09 Hz, 1H), 5.43-5.68 (m, 2H), 5.01 (br s, 1H), 4.05-4.22 (m, 3H), 3.56 (br s, 1H), 3.05-3.30 (m, 2H), 2.66-2.83 (m, 3H), 1.09-2.37 (m, 15H)<br>LCMS, [M + H]+ = 483.2<br>hLPA1 IC$_{50}$ = 20 nM | Example 270 |
| 293 | 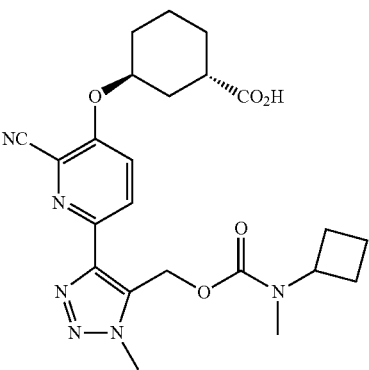 [SMILES: CN(C(=O)OCc1c(-c2ccc(O[C@H]3CCC[C@H](C(=O)O)C3)c(C#N)n2)nnn1C)C1CCC1]<br>(1S,3S)-3-((2-cyano-6-(5-((((cyclobutyl(methyl)carbamoyl)oxy)methyl)-1-methyl-1H-1,2,3-triazol-4-yl)pyridin-3-yl)oxy)cyclohexane-1-carboxylic acid | 1H NMR (500 MHz, DMSO-d6) δ 8.30 (d, J = 9.16 Hz, 1H), 7.97 (br d, J = 9.16 Hz, 1H), 5.52 (br s, 2H), 5.00 (br s, 1H), 4.12 (s, 3H), 3.40-3.67 (m, 1H), 2.74 (br s, 3H), 2.57-2.66 (m, 1H), 1.29-2.22 (m, 14H)<br>LCMS, [M + H]+ = 469.3<br>hLPA1 IC$_{50}$ = 23 nM | Example 270 |
| 294 | 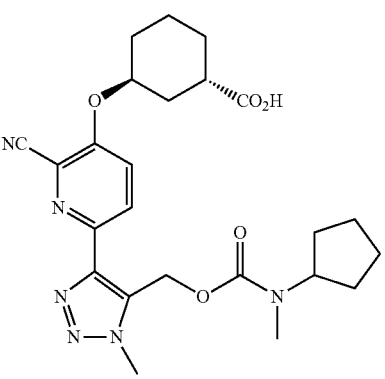 [SMILES: CN(C(=O)OCc1c(-c2ccc(O[C@H]3CCC[C@H](C(=O)O)C3)c(C#N)n2)nnn1C)C1CCCC1]<br>(1S,3S)-3-((2-cyano-6-(5-(((cyclopentyl(methyl)carbamoyl)oxy)methyl)-1-methyl-1H-1,2,3-triazol-4-yl)pyridin-3-yl)oxy)cyclohexane-1-carboxylic acid | 1H NMR (500 MHz, DMSO-d6) δ 8.29 (d, J = 8.85 Hz, 1H), 7.97 (br d, J = 9.16 Hz, 1H), 5.52 (br s, 2H), 5.00 (br s, 1H), 4.12 (s, 3H), 3.50-3.69 (m, 1H), 2.65 (br s, 3H), 2.60 (br s, 1H), 1.22-2.11 (m, 16H)<br>LCMS, [M + H]+ = 483.3<br>hLPA1 IC$_{50}$ = 15 nM | Example 270 |

What is claimed is:

1. A method of treating a disease, disorder, or condition in a mammal comprising administering a therapeutically effective amount of a compound, or a stereoisomer or pharmaceutically acceptable salt thereof, to the mammal in need thereof; wherein the disease, disorder or condition is selected from pulmonary fibrosis, asthma, chronic obstructive pulmonary disease (COPD), hepatic fibrosis, renal fibrosis, arterial fibrosis, systemic sclerosis, liver fibrosis, skin fibrosis, fibrosis of the gut, and ocular fibrosis, and the compound is represented by Formula (III):

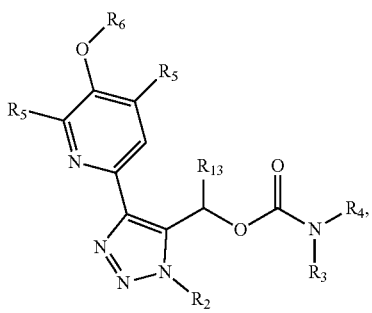

(III)

$R_2$ is independently selected from $CH_3$ and $CD_3$;
$R_{13}$ is independently selected from H and $C_{1-4}$ alkyl;
$R_3$ is independently selected from H and $C_{1-4}$ alkyl;
$R_4$ is independently selected from $C_{1-6}$ alkyl substituted with 1-3 $R_9$, —$(CR_7R_7)_r$—$C_{3-6}$ cycloalkyl substituted with 1-3 $R_8$, and —$(CR_7R_7)_r$-aryl substituted with 1-3 $R_8$;
$R_5$ is independently selected from H, F, Cl, CN and $C_{1-4}$ alkyl; provided one of $R_5$ is H;
$R_6$ is

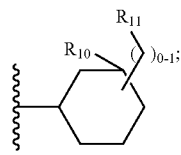

$R_7$ is independently selected from H, $C_{1-4}$ alkyl, and $C_{3-6}$ cycloalkyl; or $R_7$ and $R_7$, together with the carbon atom to which they both attach, form a $C_{3-6}$ cycloalkyl ring;
$R_8$ is independently selected from H, $C_{1-6}$ alkyl substituted with 1-5 $R_9$, $C_{3-6}$ cycloalkyl, F, Cl, Br, CN, =O, and COOH;
$R_9$ is independently selected from H, F, Cl, $NH_2$, OH, $OC_{1-5}$alkyl, $C_{1-5}$alkyl, $C_{3-6}$ cycloalkyl, and phenyl, wherein when $R_9$ is Cl, $NH_2$ or OH, it is not substituted on $C_1$ of the alkyl to which it is attached;
$R_{10}$ is independently selected from H, D, $C_{1-4}$ alkyl, and F;
$R_{11}$ is independently selected from CN, C(=O)$R_{12}$, and tetrazolyl;
$R_{12}$ is independently selected from OH, $OC_{1-4}$ alkyl, $NH_2$, and $NHSO_2C_{1-4}$ alkyl; and
r is independently selected from zero, 1, 2, 3, and 4.

2. The method of claim 1, wherein the disease, disorder, or condition is pulmonary fibrosis, hepatic fibrosis, renal fibrosis, arterial fibrosis, or systemic sclerosis.

3. The method of claim 1, wherein the disease, disorder, or condition is idiopathic pulmonary fibrosis (IPF).

4. The method of claim 1, wherein the disease, disorder, or condition is non-alcoholic steatohepatitis (NASH).

5. The method of claim 1, wherein the compound is represented by Formula (IV):

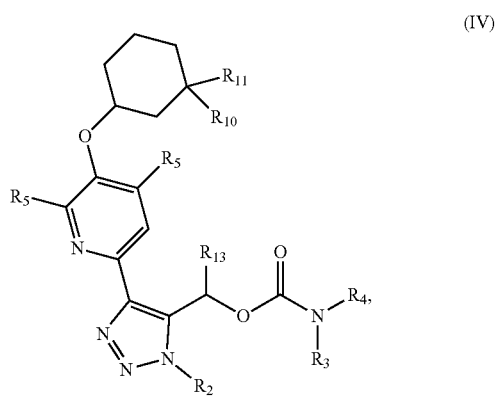

(IV)

$R_2$ is independently selected from $CH_3$ and $CD_3$;
$R_{13}$ is independently selected from H and $C_{1-4}$ alkyl;
$R_3$ is independently selected from H and $C_{1-4}$ alkyl;
$R_4$ is independently selected from $C_{1-6}$ alkyl,

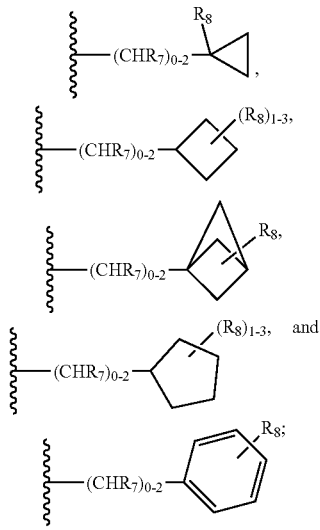

$R_5$ is independently selected from H, F, Cl, and $C_{1-4}$ alkyl; provided one of $R_5$ is H;
$R_7$ is independently selected from H, $C_{1-4}$ alkyl, and $C_{3-6}$ cycloalkyl;
$R_8$ is independently selected from H, $C_{1-6}$ alkyl substituted with 1-5 $R_9$, $C_{3-6}$ cycloalkyl, F, Cl, Br, CN, =O, and COOH;
$R_9$ is independently selected from H, F, Cl, $NH_2$, OH, $OC_{1-5}$alkyl, $C_{1-5}$alkyl, $C_{3-6}$ cycloalkyl, and phenyl, wherein when $R_9$ is Cl, $NH_2$ or OH, it is not substituted on $C_1$ of the alkyl to which it is attached;
$R_{10}$ is independently selected from H, D, $C_{1-4}$ alkyl, and F;

$R_{11}$ is independently selected from CN, C(=O)$R_{12}$, and

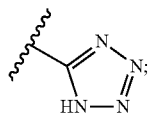 [SMILES: *c1nnn[nH]1]

and $R_{12}$ is independently selected from OH and NHSO$_2$C$_{1-4}$alkyl.

6. The method of claim 5, wherein the compound is represented by Formula (IV), wherein:

$R_4$ is independently selected from

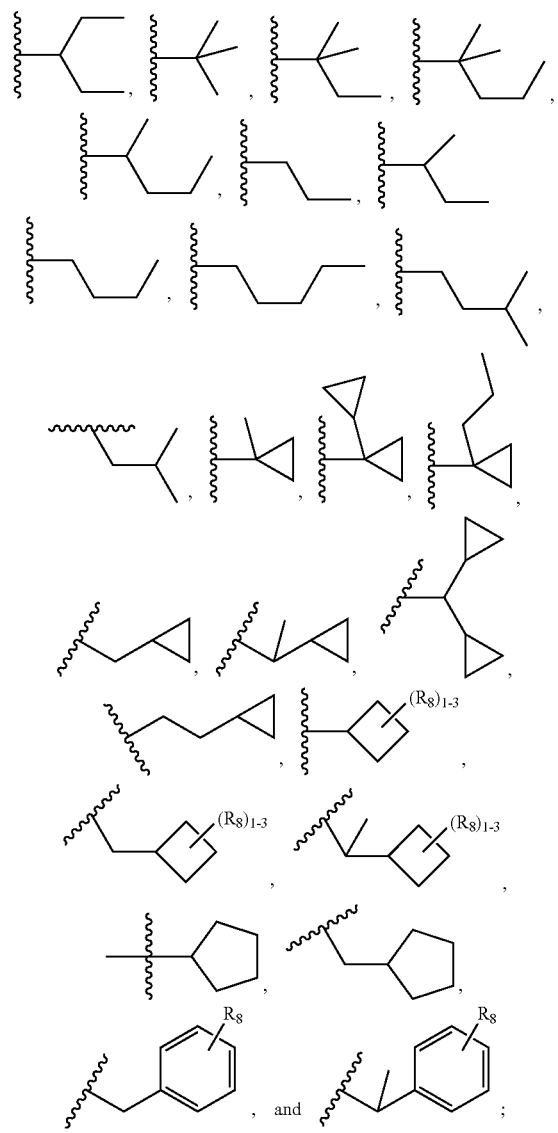

and $R_8$ is independently selected from H, F, Cl, Br, CN, and C$_{1-4}$ alkyl.

7. The method of claim 6, wherein the compound is represented by Formula (V):

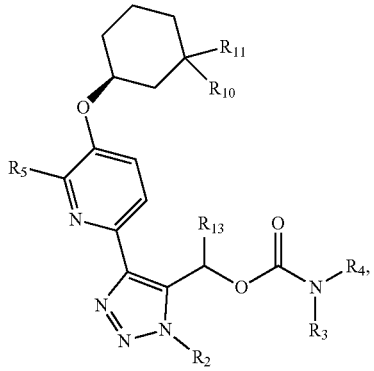

(V)

$R_2$ is independently selected from CH$_3$ and CD$_3$;
$R_{13}$ is independently selected from H and CH$_3$;
$R_3$ is independently selected from H and CH$_3$;
$R_4$ is independently selected from

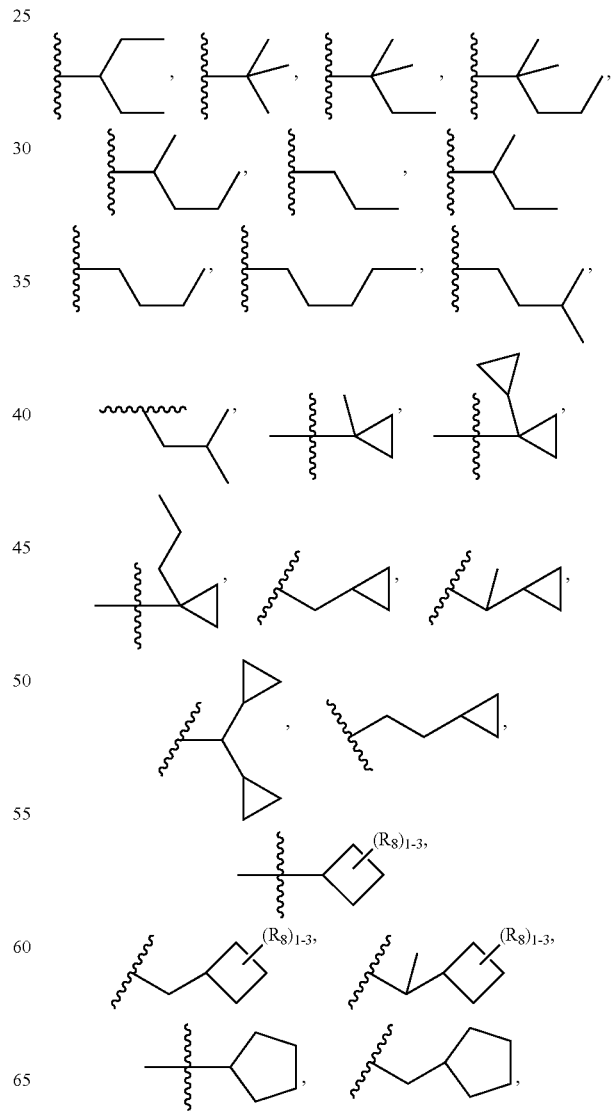

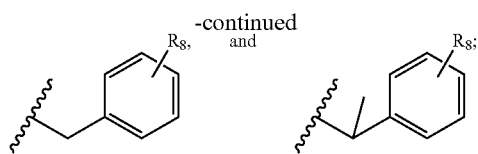
R$_5$ is independently selected from H, F, and C$_{1-4}$ alkyl;
R$_8$ is independently selected from H, F, Cl, Br, CN, and C$_{1-4}$ alkyl;
R$_{10}$ is independently selected from H, D, and F; and
R$_{11}$ is independently selected from —C(=O)OH, and —C(=O)NHSO$_2$Me.
8. The method of claim 1, wherein the compound is selected from:
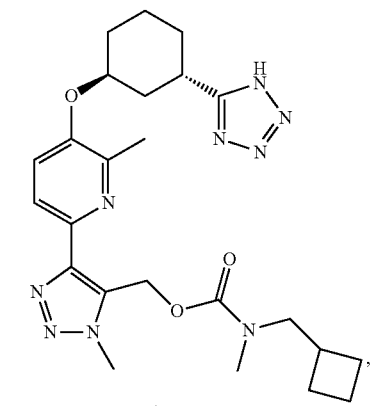
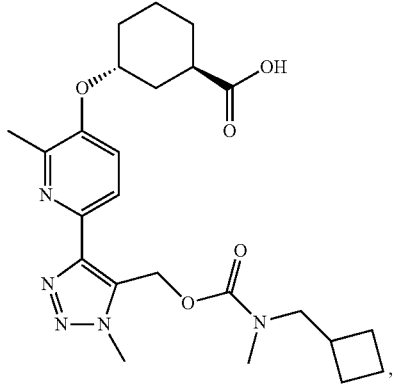
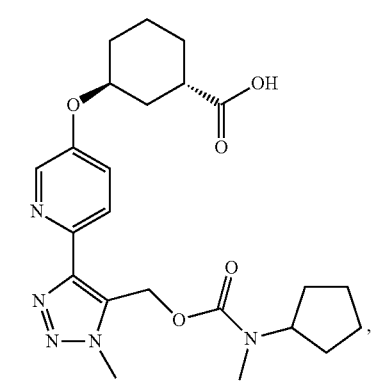
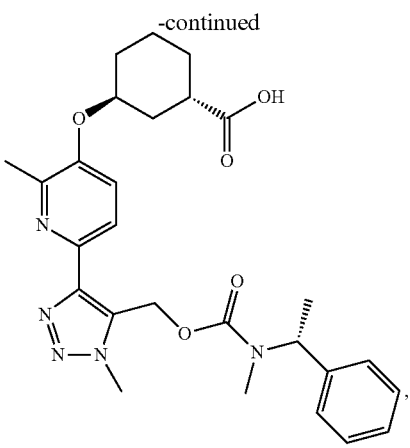
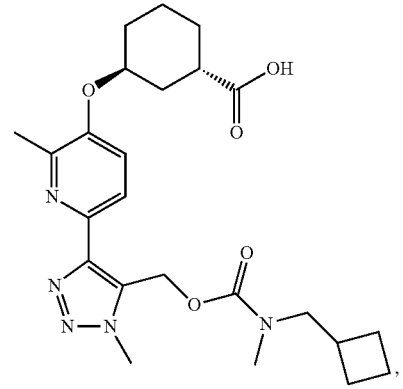
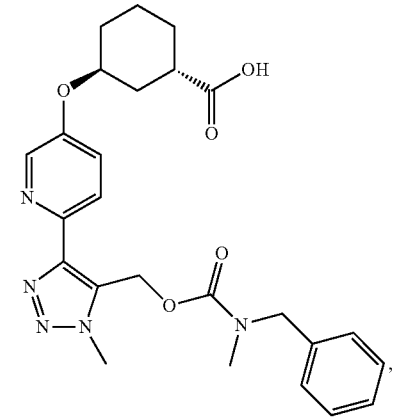

371
-continued

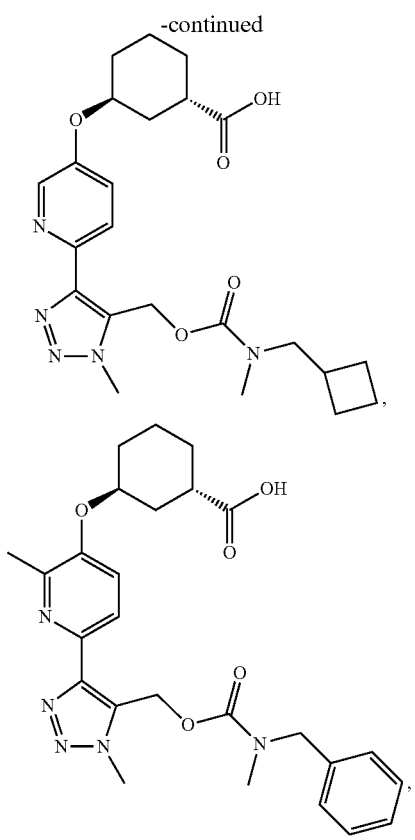

, and

372
-continued

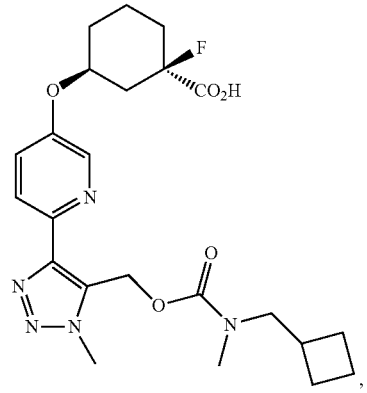

, or a stereoisomer or a pharmaceutically acceptable salt thereof.

9. The method of claim 1, wherein the stereoisomer is an enantiomer or a diastereomer.

10. A method of treating idiopathic pulmonary fibrosis (IPF) in a mammal comprising administering a therapeutically effective amount of a compound, or a stereoisomer or pharmaceutically acceptable salt thereof, to the mammal in need thereof, wherein the compound is represented by formula:

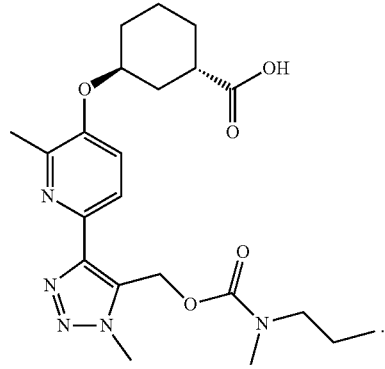 [SMILES: CCCN(C)C(=O)OCc1c(-c2ccc(O[C@H]3CCC[C@H](C(=O)O)C3)c(C)n2)nnn1C]

.

11. A method of treating idiopathic pulmonary fibrosis (IPF) in a mammal comprising administering a therapeutically effective amount of a compound, or a stereoisomer or pharmaceutically acceptable salt thereof, to the mammal in need thereof, wherein the compound is represented by formula:

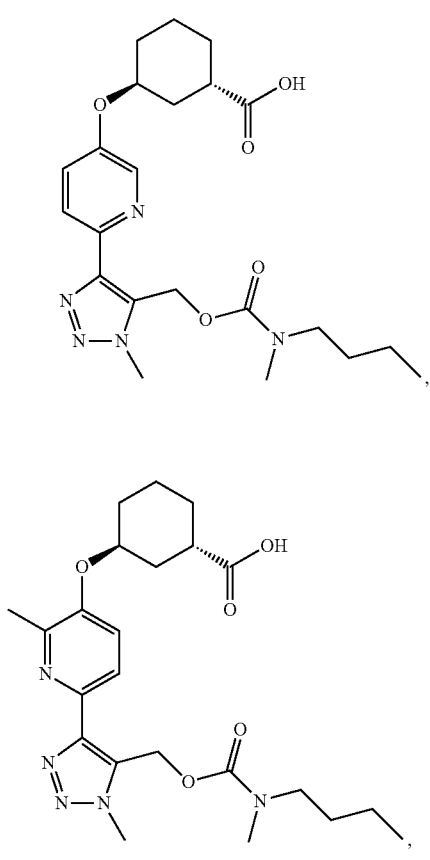

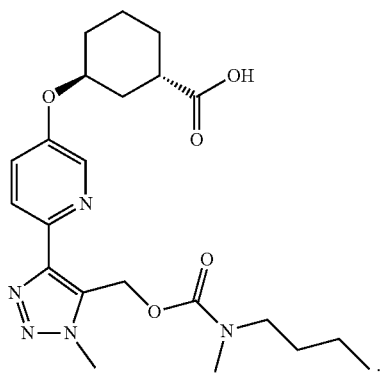

12. A method of treating idiopathic pulmonary fibrosis (IPF) in a mammal comprising administering a therapeutically effective amount of a compound, or a stereoisomer or pharmaceutically acceptable salt thereof, to the mammal in need thereof, wherein the compound is represented by formula:

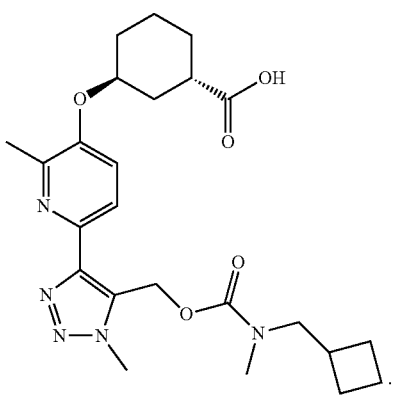 [SMILES: Cc1nc(-c2nnn(C)c2COC(=O)N(C)CC2CCC2)ccc1O[C@H]1CCC[C@H](C(=O)O)C1]

13. A method of treating idiopathic pulmonary fibrosis (IPF) in a mammal comprising administering a therapeutically effective amount of a compound, or a stereoisomer or pharmaceutically acceptable salt thereof, to the mammal in need thereof, wherein the compound is represented by formula:

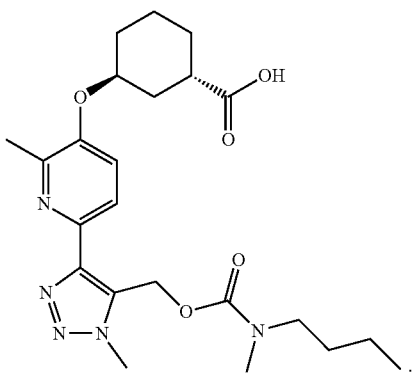 [SMILES: CCCCN(C)C(=O)OCc1c(-c2ccc(O[C@H]3CCC[C@H](C(=O)O)C3)c(C)n2)nnn1C]

14. A method of treating idiopathic pulmonary fibrosis (IPF) in a mammal comprising administering a therapeutically effective amount of a compound to the mammal in need thereof, wherein the compound is represented by formula:

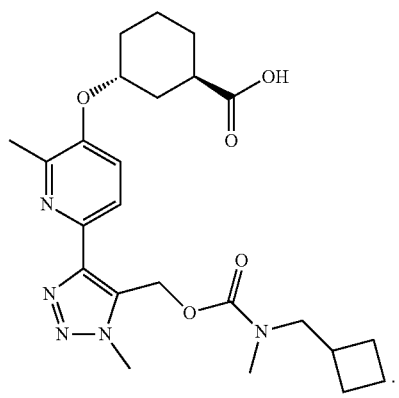 [SMILES: Cc1nc(-c2nnn(C)c2COC(=O)N(C)CC2CCC2)ccc1O[C@@H]1CCC[C@@H](C(=O)O)C1]

15. A method of treating idiopathic pulmonary fibrosis (IPF) in a mammal comprising administering a therapeutically effective amount of a compound to the mammal in need thereof, wherein the compound is represented by formula:

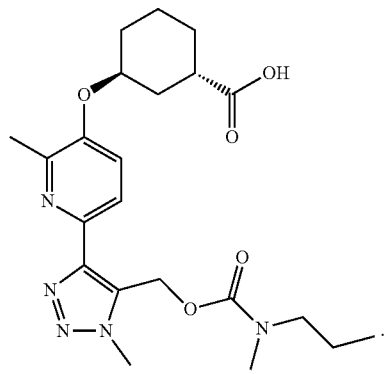 [SMILES: CCCN(C)C(=O)OCc1c(-c2ccc(O[C@H]3CCC[C@H](C(=O)O)C3)c(C)n2)nnn1C]

16. A method of treating idiopathic pulmonary fibrosis (IPF) in a mammal comprising administering a therapeutically effective amount of a compound to the mammal in need thereof, wherein the compound is represented by formula:

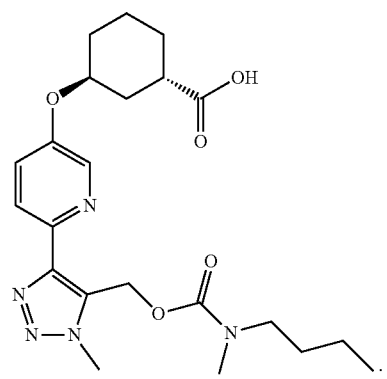 [SMILES: CCCCN(C)C(=O)OCc1c(-c2ccc(O[C@H]3CCC[C@H](C(=O)O)C3)cn2)nnn1C]

17. A method of treating idiopathic pulmonary fibrosis (IPF) in a mammal comprising administering a therapeutically effective amount of a compound to the mammal in need thereof, wherein the compound is represented by formula:
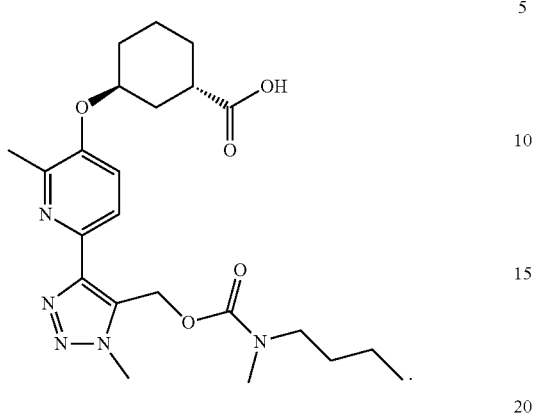
18. The method of any one of claims 10, 11, 12, and 13, wherein the stereoisomer is an enantiomer or a diastereomer.
* * * * *